United States Patent
KC et al.

(10) Patent No.: US 10,285,983 B2
(45) Date of Patent: May 14, 2019

(54) 3-(1H-PYRROLO[2,3-B]PYRIDIN-2-YL)-1H-PYRAZOLO[3,4-B] PYRIDINES AND THERAPEUTIC USES THEREOF

(71) Applicant: Samumed, LLC, San Diego, CA (US)

(72) Inventors: Sunil Kumar KC, San Diego, CA (US); David Mark Wallace, San Diego, CA (US); Jianguo Cao, San Diego, CA (US); Chandramouli Chiruta, San Diego, CA (US); John Hood, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 15/749,727

(22) PCT Filed: Aug. 3, 2016

(86) PCT No.: PCT/US2016/045283
§ 371 (c)(1),
(2) Date: Feb. 1, 2018

(87) PCT Pub. No.: WO2017/023996
PCT Pub. Date: Feb. 9, 2017

(65) Prior Publication Data
US 2018/0228783 A1 Aug. 16, 2018

Related U.S. Application Data

(60) Provisional application No. 62/356,133, filed on Jun. 29, 2016, provisional application No. 62/200,301, filed on Aug. 3, 2015.

(51) Int. Cl.
| | |
|---|---|
| C07D 471/04 | (2006.01) |
| A61K 31/437 | (2006.01) |
| A61P 19/02 | (2006.01) |
| A61P 11/00 | (2006.01) |
| A61P 19/08 | (2006.01) |
| A61P 35/00 | (2006.01) |
| C07D 519/00 | (2006.01) |

(52) U.S. Cl.
CPC ............ *A61K 31/437* (2013.01); *A61P 11/00* (2018.01); *A61P 19/02* (2018.01); *A61P 19/08* (2018.01); *A61P 35/00* (2018.01); *C07D 519/00* (2013.01)

(58) Field of Classification Search
CPC .......................... C07D 471/04; A61K 31/437
USPC ........................................ 546/119; 514/303
See application file for complete search history.

(56) References Cited

U.S. PATENT DOCUMENTS

| | | | |
|---|---|---|---|
| 4,164,559 A | 8/1979 | Miyata et al. | |
| 4,474,752 A | 10/1984 | Haslam et al. | |
| 4,603,139 A | 7/1986 | King | |
| 5,037,844 A | 8/1991 | Hamminga et al. | |
| 5,922,733 A | 7/1999 | Forbes et al. | |
| 6,120,484 A | 9/2000 | Silverstein | |
| 6,358,978 B1 | 3/2002 | Ritzeler et al. | |
| 6,377,849 B1 | 4/2002 | Lenarz et al. | |
| 6,440,102 B1 | 8/2002 | Arenberg et al. | |
| 6,555,539 B2 | 4/2003 | Reich et al. | |
| 6,648,873 B2 | 11/2003 | Arenberg et al. | |
| 6,831,175 B2 | 12/2004 | Li et al. | |
| 6,884,890 B2 | 4/2005 | Kania et al. | |
| 6,897,208 B2 | 5/2005 | Edwards et al. | |
| 6,911,211 B2 | 6/2005 | Eini et al. | |
| 6,919,461 B2 | 7/2005 | Reich et al. | |
| 7,008,953 B2 | 3/2006 | Kephart et al. | |
| 7,064,215 B2 | 6/2006 | Renhowe et al. | |
| 7,232,912 B2 | 6/2007 | Reich et al. | |
| 7,285,565 B2 | 10/2007 | Zhu et al. | |
| 7,390,815 B2 | 6/2008 | Davies et al. | |
| 7,429,609 B2 | 9/2008 | Ohi et al. | |
| 7,452,993 B2 | 11/2008 | Arnold et al. | |
| 7,468,376 B2 | 12/2008 | Rosales et al. | |
| 7,482,342 B2 | 1/2009 | D'Orchymont et al. | |
| 7,488,737 B2 | 2/2009 | Xie et al. | |
| 7,491,710 B2 | 2/2009 | Cherrier et al. | |
| 7,541,367 B2 | 6/2009 | Chiu et al. | |
| 7,626,021 B2 | 12/2009 | Arnold et al. | |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application of Hamish Christopher Swan Wood, Norman Whittaker, Irene Stirling and Kyuji Ohta.," 582 F.2d 638 (Fed. Cir. 1978), 2 pages.

Adaimy et al., "Mutation in WNT10A Is Associated with an Autosomal Recessive Ectodermal Dysplasia: The Odonto-onycho-dermal Dysplasia," *Am. J. Hum. Genet.*, (Oct. 2007), 81(4), 821-828.

Anastas and Moon, "WNT signalling pathways as therapeutic targets in cancer," *Nat Rev Cancer*, 13(1):11-26, Jan. 2013.

Andres, "Molecular genetics and animal models in autistic disorder," *Brain Research Bulletin*, (2002), 57(1), 109-119.

Barker and Clevers, "Mining the Wnt pathway for cancer therapeutics," *Nat Rev Drug Discov.*, 5(12):997-1014, Dec. 2006.

(Continued)

*Primary Examiner* — Charanjit Aulakh
(74) *Attorney, Agent, or Firm* — Fish & Richardson P.C.

(57) ABSTRACT

7-Azaindazole compounds for treating various diseases and pathologies are disclosed. More particularly, the present disclosure concerns the use of a 7-azaindazole compound or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

30 Claims, No Drawings

(56) References Cited

U.S. PATENT DOCUMENTS

| | | |
|---|---|---|
| 7,642,278 B2 | 1/2010 | Jansen et al. |
| 7,666,867 B2 | 2/2010 | Makriyannis et al. |
| 7,812,043 B2 | 10/2010 | Lau et al. |
| 7,829,558 B2 | 11/2010 | Arnold et al. |
| 7,842,711 B2 | 11/2010 | D'Orchymont et al. |
| 7,902,217 B2 | 3/2011 | Xie et al. |
| 7,943,616 B2 | 5/2011 | Cox et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |
| 8,987,298 B2 | 3/2015 | Hood et al. |
| 9,012,472 B2 | 4/2015 | Hood et al. |
| 9,056,874 B2 | 6/2015 | Adams et al. |
| 9,067,939 B2 | 6/2015 | Hood et al. |
| 9,090,613 B2 | 7/2015 | Hood et al. |
| 9,174,967 B2 | 11/2015 | Körber et al. |
| 9,199,991 B2 | 12/2015 | Hood et al. |
| 9,221,793 B2 | 12/2015 | Hood et al. |
| 9,233,104 B2 | 1/2016 | Hood et al. |
| 9,381,192 B2 | 7/2016 | Hood et al. |
| 9,538,272 B2 | 1/2017 | Auclair et al. |
| 9,540,398 B2 | 1/2017 | KC et al. |
| 9,586,977 B2 | 3/2017 | Hood et al. |
| 9,745,271 B2 | 8/2017 | Hood et al. |
| 9,763,927 B2 | 9/2017 | Hood et al. |
| 9,763,951 B2 | 9/2017 | KC et al. |
| 9,802,916 B2 | 10/2017 | Hood et al. |
| 9,815,854 B2 | 11/2017 | KC et al. |
| 9,828,372 B2 | 11/2017 | Kumar KC et al. |
| 9,844,536 B2 | 12/2017 | KC et al. |
| 9,855,272 B2 | 1/2018 | Hood et al. |
| 9,889,140 B2 | 2/2018 | KC et al. |
| 9,908,867 B2 | 3/2018 | Kumar KC et al. |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0070546 A1 | 3/2005 | Arrington et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0132495 A1 | 6/2008 | Berdini et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0082144 A1 | 4/2011 | Lau et al. |
| 2011/0178075 A1 | 7/2011 | Xie et al. |
| 2011/0190290 A1 | 8/2011 | Hood et al. |
| 2011/0034497 A1 | 10/2011 | Hood et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0267548 A1 | 10/2013 | Follmann et al. |
| 2014/0194441 A1 | 7/2014 | K.C. et al. |
| 2014/0364451 A1 | 12/2014 | John et al. |
| 2015/0087687 A1 | 3/2015 | Brown et al. |
| 2015/0111872 A1 | 4/2015 | Desroy et al. |
| 2016/0068529 A1 | 3/2016 | K.C. et al. |
| 2016/0068547 A1 | 3/2016 | K.C. et al. |
| 2016/0068548 A1 | 3/2016 | K.C. et al. |
| 2016/0068549 A1 | 3/2016 | K.C. et al. |
| 2016/0068550 A1 | 3/2016 | K.C. et al. |
| 2016/0068551 A1 | 3/2016 | K.C. et al. |
| 2016/0075701 A1 | 3/2016 | KC |
| 2016/0090380 A1 | 3/2016 | KC |
| 2016/0101092 A1 | 4/2016 | Hood et al. |
| 2016/0297812 A1 | 10/2016 | Hood et al. |
| 2017/0333409 A1 | 11/2017 | Hood et al. |
| 2017/0349584 A1 | 12/2017 | KC et al. |
| 2018/0086754 A1 | 3/2018 | KC et al. |
| 2018/0133199 A1 | 5/2018 | Dellamary |
| 2018/0141963 A1 | 5/2018 | KC et al. |
| 2018/0148444 A1 | 5/2018 | KC et al. |
| 2018/0153873 A1 | 6/2018 | Hood et al. |
| 2018/0162840 A1 | 6/2018 | KC et al. |
| 2018/0177787 A1 | 6/2018 | KC et al. |
| 2018/0185343 A1 | 7/2018 | Deshmukh et al. |
| 2018/0201624 A1 | 7/2018 | KC et al. |
| 2018/0207141 A1 | 7/2018 | KC et al. |
| 2018/0214427 A1 | 8/2018 | KC et al. |
| 2018/0214428 A1 | 8/2018 | KC et al. |
| 2018/0214429 A1 | 8/2018 | KC et al. |
| 2018/0215753 A1 | 8/2018 | KC et al. |
| 2018/0221341 A1 | 8/2018 | KC et al. |
| 2018/0221350 A1 | 8/2018 | KC et al. |
| 2018/0221351 A1 | 8/2018 | KC et al. |
| 2018/0221352 A1 | 8/2018 | KC et al. |
| 2018/0221353 A1 | 8/2018 | KC et al. |
| 2018/0221354 A1 | 8/2018 | KC et al. |
| 2018/0222891 A1 | 8/2018 | KC et al. |
| 2018/0222923 A1 | 8/2018 | KC et al. |
| 2018/0228780 A1 | 8/2018 | KC et al. |
| 2018/0228781 A1 | 8/2018 | KC et al. |
| 2018/0228782 A1 | 8/2018 | KC et al. |
| 2018/0228784 A1 | 8/2018 | KC et al. |
| 2018/0228785 A1 | 8/2018 | KC et al. |
| 2018/0230142 A1 | 8/2018 | KC et al. |

(56) References Cited

U.S. PATENT DOCUMENTS

| | | | |
|---|---|---|---|
| 2018/0237416 A1 | 8/2018 | Hood et al. | |
| 2018/0250269 A1 | 9/2018 | KC et al. | |
| 2018/0256588 A1 | 9/2018 | Hood et al. | |

FOREIGN PATENT DOCUMENTS

| | | |
|---|---|---|
| CN | 1829713 | 9/2006 |
| CN | 101440092 | 5/2009 |
| KZ | 20122 | 10/2008 |
| RU | 2331640 | 8/2008 |
| RU | 2416610 | 4/2011 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2007147874 | 12/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO2010064875 | 6/2010 |
| WO | WO2010107765 | 9/2010 |
| WO | WO2010111060 | 9/2010 |
| WO | WO2010132725 | 11/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013113722 | 8/2013 |
| WO | WO2017079765 | 5/2017 |

OTHER PUBLICATIONS

Beyer et al., "Extended report: β-catenin is a central mediator of pro-fibrotic Wnt signaling in systemic sclerosis," *Ann Rheum Dis*, 71:761-767, online Feb. 2012.

Biason-Lauber et al., "A WNT4 Mutation Associated with Müllerian-Duct Regression and Virilization in a 46,XX Woman," *N. Engl. J. Med.*, (Aug. 2004), 351(8), 792-798.

Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.

Blom et al., "Involvement of the Wnt signaling pathway in experimental and human osteoarthritis: prominent role of Wnt-induced signaling protein 1," *Arthritis Rheum.*, 60(2):501-512, Feb. 2009.

Boyden et al., "High Bone Density Due to a Mutation in LDL-Receptor-Related Protein 5," *N. Engl. J. Med.*, (May 2002), 346(20):1513-1521.

Brack et al., "Increased Wnt signaling during aging alters muscle stem cell fate and increases fibrosis," *Science.*, 317(5839):807-810, Aug. 2007.

Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.

Chilosi et al., "The pathogenesis of COPD and IPF: Distinct horns of the same devil?," *Respiratory Research*, 13:3, 2012.

Chockalingam et al., "Elevated aggrecanase activity in a rat model of joint injury is attenuated by an aggrecanase specific inhibitor," *Osteoarthritis Cartilage*, Mar. 2011, 19(3): 315-323.

Chou and Talalay, "Quantitative analysis of dose-effect relationships: the combined effects of multiple drugs or enzyme inhibitors," *Advances in Enzyme Regulation* (1984), 22, 27-55.

Chou, "Drug combination studies and their synergy quantification using the Chou-Talalay method," *Cancer Res.*, 70(2):440-446, Jan. 2010.

Chou, "Graphic rule for drug metabolism systems," *Current Drug Metabolism*, (May 2010) 11(4): 369-378.

Christodoulides et al., "WNT10B mutations in human obesity," *Diabetologia*, (2006) 49(4):678-684.

Clevers and Nusse, "Wnt/β-catenin signaling and disease," *Cell*, (Jun. 2012), 149(6):1192-1205.

Clevers, "Wnt/beta-catenin signaling in development and disease," *Cell*, (Nov. 2006), 127(3), 469-480.

Corr, "Wnt-beta-catenin signaling in the pathogenesis of osteoarthritis," *Nat Clin Pract Rheumatol*, 4(10):550-556, Oct. 2008.

D'Alessio et al., "Benzodipyrazoles: a new class of potent CDK2 inhibitors," *Bioorganic & Medicinal Chemistry Letters* (2005), 15(5), 1315-1319.

Dann et al., "Insights into Wnt binding and signaling from the structures of two Frizzled cysteine-rich domains," Nature, (Jul. 2001), 412, pp. 86-90.

Datta et al., "Novel therapeutic approaches for pulmonary fibrosis," *Br J Pharmacol.*, 163(1):141-172, May 2011.

Davidson et al., "Emerging links between CDK cell cycle regulators and Wnt signaling," Trends Cell Biol., Aug. 2010, 20(8):453-460.

De Ferrari and Inestrosa, "Wnt signaling function in Alzheimer's disease," *Brain Research Reviews*, (2000), 33(1): 1-12.

De Ferrari and Moon, "The ups and downs of Wnt signaling in prevalent neurological disorders," Oncogene, (2006) 25(57): 7545-7553.

De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.

(56) References Cited

OTHER PUBLICATIONS

Dermer, "Another Anniversary for the War on Cancer," *Nature Biotechnology*, 12:320 (1994).
Dessalew et al., "3D-QSAR CoMFA and CoMSIA study on benzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
du Bois, "Strategies for treating idiopathic pulmonary fibrosis," *Nature Reviews Drug Discovery*, 9(2): 129-140 (Feb. 2010).
Edamoto et al., "Alterations of RB1, p53 and Wnt pathways in hepatocellular carcinomas associated with hepatitis C, hepatitis B and alcoholic liver cirrhosis," *Int J Cancer.*, 106(3):334-341, Sep. 1, 2003.
Egloff et al., "Gastrin-releasing peptide receptor expression in non-cancerous bronchial epithelia is associated with lung cancer: a case-control study," *Respiratory Research*, 13:9, Feb. 2012.
Espada et al., "Wnt signalling and cancer stem cells," *Clin. Transl. Oncol.*, (2009), 11(7), 411-27.
Ewan et al., "A useful approach to identify novel small-molecule inhibitors of Wnt-dependent transcription," *Cancer Res.* (2010), 70(14), 5963-5973.
Florez et al., "TCF7L2 Polymorphisms and Progression to Diabetes in the Diabetes Prevention Program," *N. Engl. J. Med.*, (Jul. 2006), 355(3):241-250.
Freese et al., "Wnt signaling in development and disease," *Neurobiology of Disease*, (2010) 38(2): 148-153.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," *Biochim Biophys Acta.*, 1653(1):1-24, Jun. 2003.
Handeli and Simon, "A small-molecule inhibitor of Tcf/beta-catenin signaling down-regulates PPARgamma and PPARdelta activities," *Mol Cancer Ther.*, 7(3):521-529, Mar. 2008.
Henderson Jr. et al., "Inhibition of Wnt/beta-catenin/CREB binding protein (CBP) signaling reverses pulmonary fibrosis," *Proc Natl Acad Sci U S A.*, 107(32):14309-14314, Epub Jul. 2010.
Hu et al., "Discovery of indazoles as inhibitors of Tpl2 kinase," *Bioorganic & Medicinal Chemistry Letters*, (Aug. 2011) 21(16): 4758-4761.
Huang et al., "Tankyrase inhibition stabilizes axin and antagonizes Wnt signaling," *Nature*, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.
Hübner et al., "Standardized quantification of pulmonary fibrosis in histological samples," *Biotechniques*, 44(4):507-511, 514-517, Apr. 2008.
Im et al., "Wnt inhibitors enhance chondrogenesis of human mesenchymal stem cells in a long-term pellet culture," *Biotechnol Lett.*, 33(5):1061-1068, Epub Jan. 2011.
Inestrosa and Toledo, "The role of Wnt signaling in neuronal dysfunction in Alzheimer's Disease," *Mol Neurodegener*, 3:9, doi:10.1186/1750-1326-3-9, 13 pages, Jul. 2008.
International Preliminary Report on Patentability for International Application No. PCT/US2016/45283, dated Feb. 15, 2018, 7 pages.
International Search Report and Written Opinion for International Application No. PCT/US2016/45283, dated Oct. 4, 2016, 13 pages.
Janssens et al., "The Wnt-dependent signaling pathways as target in oncology drug discovery," *Invest New Drugs.*, 24(4):263-280, Jul. 2006.
Jenkins et al., "Germline mutations in WTX cause a sclerosing skeletal dysplasia but do not predispose to tumorigenesis," *Nat. Genet.* (Jan. 2009), 41(1), 95-100.
Jessen et al., "Peripheral white blood cell toxicity induced by broad spectrum cyclin-dependent kinase inhibitors," *Journal of Applied Toxicology* (Jan. 2007), 27(2), 133-142.
Johnson et al., "A stem cell-based approach to cartilage repair," *Science*., 336(6082):717-721, Epub Apr. 5, 2012.
Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.
Karlberg et al., "Structural basis for the interaction between tankyrase-2 and a potent Wnt-signaling inhibitor," *J. Med. Chem.* (2010), 53(14), 5352-5.
Kibar et al., "Mutations in VANGL1 Associated with Neural-Tube Defects," *N. Engl. J. Med.*, (Apr. 2007), 356(14):1432-1437.
King et al., "BUILD-3: a randomized, controlled trial of bosentan in idiopathic pulmonary fibrosis," *Am J Respir Crit Care Med.*, 184(1):92-99, Epub Apr. 2011.
Kishimoto et al: "Wnt/Beta-Catenin Signaling Suppresses Expressions of Ses, Mkx and Tnmd in Tendon-Derived Cells," PLOS ONE, Jul. 27, 2017, 12(7), E0182051, pp. 1-17.
Kuwajima et al., "Necdin Promotes GABAergic Neuron Differentiation in Cooperation with Dlx Homeodomain Proteins," *Journal of Neuroscience* (May 2006), 26(20), 5383-5392.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3): 605-619.
Lammi et al., "Mutations in AXIN2 Cause Familial Tooth Agenesis and Predispose to Colorectal Cancer," *Am. J. Hum. Genet.* (2004), 74(5), 1043-1050.
Leyns et al., "Frzb-1 Is a Secreted Antagonist of Wnt Signaling Expressed in the Spemann Organizer," *Cell* (Mar. 1997), 88(6), 747-756.
Li et al., "Artesunate attenuates the growth of human colorectal carcinoma and inhibits hyperactive Wnt/beta-catenin pathway," *Int J Cancer.*, 121(6):1360-1365, Sep. 2007.
Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.
Liu, et.al., "Fibrotic lung fibroblasts show blunted inhibition by cAMP due to deficient cAMP response element-binding protein phosphorylation," *J Pharmacol Exp Ther.*, 315(2):678-687, Epub Aug. 3, 2005.
Lories et al., "To Wnt or not to Wnt: the bone and joint health dilemma," *Nat Rev Rheumatol.*, 9(6):328-339, Epub Mar. 2013.
Low et al., "Phenotypic fingerprinting of small molecule cell cycle kinase inhibitors for drug discovery," *Curr Chem Genomics.*, 3:13-21, Mar. 2009.
Lu et al., "Structure-activity relationship studies of small-molecule inhibitors of Wnt response," *Bioorganic & Medicinal Chemistry Letters*, (Jul. 2009), 19(14):3825-3827.
Lui: "Histopathological Changes in Tendinopathypotential Roles of BMPs?" Rheumatology, May 2013, 52:2116-2126.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et al., "Wnt/beta-catenin signaling pathway as a novel cancer drug target," *Curr Cancer Drug Targets.*, 4(8):653-671, Dec. 2004.
Luyten et al., "Wnt signaling and osteoarthritis," *Bone*, 44(4):522-527, Epub Dec. 14, 2008.
MacDonald et al., "Wnt/beta-catenin signaling: components, mechanisms, and diseases," *Dev. Cell* (Jul. 2009), 17(1), 9-26.
Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.

(56) References Cited

OTHER PUBLICATIONS

McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
Misra et al., "1H-Pyrazolo[3,4-b]pyridine inhibitors of cyclin-dependent kinases: highly potent 2,6-Difluorophenacyl analogues," *Bioorganic & Medicinal Chemistry Letters*, (2003), 13:2405-2408.
Morrisey, "Wnt signaling and pulmonary fibrosis," *Am J Pathol.*, 162(5):1393-1397, May 2003.
Muddassar et al., "Elucidation of binding mode and three dimensional quantitative structure-activity relationship studies of a novel series of protein kinase B/Akt inhibitors," *Journal of Molecular Modeling*, (2009), 15(2): 183-192.
Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science*, (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.
Okerlund and Cheyette, "Synaptic Wnt signaling—a contributor to major psychiatric disorders?" *J Neurodev Disord.*, (2011) 3(2):162-174.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Polakis, "Wnt signaling and cancer," *Genes Dev.*, 14: 1837-1851, 2000.
PUBCHEM. Substance Record for SID 164345938. Deposit Date: Nov. 4, 2013. [retrieved on Nov. 16, 2015]. Retrieved from the Internet. <URL: https://pubchem.ncbi.nlm.nih.gov/substance/164345938#section=Top>, 5 pages.
Qin et al. "Complexity of the genotype-phenotype correlation in familial exudative vitreoretinopathy with mutations in the LRP5 and/or FZD4 genes," *Hum. Mutat.* (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," *Science*, (Feb. 2007), 315(5812):642-645, published online Jan. 4, 2007.
Robitaille et al., "Mutant frizzled-4 disrupts retinal angiogenesis in familial exudative vitreoretinopathy," *Nat. Genet.*, (Sep. 2002), 32(2):326-330.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.

Salinas, "Wnt signaling in the vertebrate central nervous system: from axon guidance to synaptic function," *Cold Spring Harb Perspect Biol.*, (2012) 4(2). pii: a008003, 15 pages.
Sato, "Upregulation of the Wnt/beta-catenin pathway induced by transforming growth factor-beta in hypertrophic scars and keloids," *Acta Derm Venereol.*, 86(4):300-307, 2006.
Seah et al., "Neuronal Death Resulting from Targeted Disruption of the Snf2 Protein ATRX Is Mediated by p53," *Journal of Neuroscience* (Nov. 2008), 28(47), 12570-12580.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Staines et al., "Cartilage development and degeneration: a Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2):242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Thompson et al., "WNT/beta-catenin signaling in liver health and disease," *Hepatology.*, 45(5):1298-1305, May 2007.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci U S A.* 108(15):5929-5930, Epub Mar. 2011.
Watts et.al., "RhoA signaling modulates cyclin D1 expression in human lung fibroblasts; implications for idiopathic pulmonary fibrosis," *Respir Res.*, 7:88, Jun. 15, 2006.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.

(56) References Cited

OTHER PUBLICATIONS

Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yardy and Brewster, "Wnt signalling and prostate cancer," *Prostate Cancer Prostatic Dis*, 8(2):119-126, 2005.
Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zhong et al., "Characterization of in vitro and in vivo metabolism of AG-024322, a novel cyclin-dependent kinase (CDK) inhibitor," *Health* (2009), 1(4): 249-262.
Zhu et al. "Design and synthesis of pyridine-pyrazolopyridine-based inhibitors of protein kinase B/Akt," Bioorganic & Medicinal Chemistry, Mar. 2007, 15(6):2441-2452.
Ai et al., "Optimal Method to Stimulate Cytokine Producti on and Its Use in Immunotoxicity Assessment," Int J Environ Res Public Health, Sep. 2013, 10(9):3834-3842.
Cecil Textbook of Medicine, edited by Bennet, J.C., and Plum F., 20th edition, vol. 1, 1004-1010, 1996.
Chanput et.al., "Transcription profiles of LPS-stimulated THP-1 monocytes and macrophages: a tool to study inflammation modulating effects of food-derived compounds," Food Funct, Dec. 2010, 1(3):254-61.
clinicaltrials.gov' [online]. ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retreived on Aug. 1, 2018]. Retreived from the Internet: URL<https://clinicaltrials.gov/ct2/show/NCT02095548?term=NCT02095548&rank=1>, 7 pages.
clinicaltrials.gov' [online]. ClinicalTrials.gov Identifier: NCT02536833, "A Study Evaluating the Safety, Tolerability, and Efficacy of SM04690 Injected in the Target Knee Joint of Moderately to Severely Symptomatic Osteoarthritis Subjects," Sep. 1, 2015, [retreived on Aug. 1, 2018]. Retreived from the Internet: URL<https://clinicaltrials.gov/ct2/show/NCT02536833?term=NCT02536833&rank=1>, X pages.
Dermer et al., "Another Anniversary for the War on Cancer," Bio/Technology, Mar. 1994, 12:320.
Freshney et al., Culture of Animal Cells, A Manual of Basic Technique, Alan R. Liss, Inc., 1983, New York, p. 1-6.
Gitter et al., "Characteristics of human synovial fibroblast activation by IL-1 beta and TNF alpha," Immunology, Feb. 1989, 66(2):196-200.
Golub et al., "Molecular Classification of Cancer: Class Discovery and Class Prediction by Gene Expression Monitoring," Science, Oct. 1999, 286(5439):531-537.
Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.
Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.
Monner et al., "Induction of lymphokine synthesis in peripheral blood mononuclear cells with phorbol ester and calcium ionophore allows precise measurement of individual variations in capacity to produce IL 2," Lymphokine Res. 1986;5 Suppl 1:S67-73.
Ngkelo et. al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.
Park et. al., "Optimized THP-1 differentiation is required for the detection of responses to weak stimuli," Inflamm Res, Jan. 2007, 56(1):45-50.
Pritzker et al., "Osteoarthritis cartilage histopathology: grading and staging," Osteoarthr. Cartil., Jan. 2006, 14(1):13-29.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.

Yamada et al., "Emergence of TNIK inhibitors in cancer therapeutics," Cancer Sci, May 2017, 108(5):818-823.
Adult Brain Tumors Treatment, National Cancer Institute, pp. 1-21 (Jan. 24, 2013), 21 pages.
Barroga et al., "Discovery of an Intra-Articular Injection Small Molecule Inhibitor of the Wnt Pathway (SM04690) As a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of-the-wnt-pathway-sm04690-as-a-potential-disease-modifying-treatment-for-knee-osteoarthritis/>, 3 pages.
Bass, "Why the difference between tendinitis and tendinosis matters," International Journal of Therapeutic Massage and Bodywork, vol. 5, No. 1, Mar. 2012.
Bone fractures—https://my.clevelandclinic.org/health/diseases/15241-bone-fractures—Jun. 2018, 5 pages.
Cancer definition in MedicineNet.com—2005, 1 page.
Cancer Drug Design and Discovery Neidle, Stephen, ed. (Elsevier/Academic Press, 2008), 5 pages.
Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):18-27.
Enzo et al., "The Wnt/β-catenin pathway in human fibrotic-like diseases and its eligibility as a therapeutic target," Molecular and Cellular Therapies, 2015, 3(1), 13 pages.
Forestier et al., "Prevalence of generalized osteoarthritis in a population with knee osteoarthritis," Joint Bone Spine, May 2011, 78(3):275-278.
GastricMALTLynnphonna—LynnphonnaAssociation—2011, 10 pages.
Hayami et al., "Characterization of articular cartilage and subchondral bone changes in the rat anterior cruciate ligament transection and meniscectomized models of osteoarthritis," Bone, Feb. 2006, 38(2):234-243.
Lala and Orucevic, "Role of nitric oxide in tumor progression: lessons from experimental tumors," Cancer and Metastasi Review, vol. 17, Mar. 1998, pp. 91-106.
MedlinePlus, [online] "Cancer," [retrieved on Jul. 6, 2007]. Retrieved from the internet, URL http://www.nInn.nih.govinnedlineplus/cancer.html>.
Osteoarthritis, https://www.rnayoclinic.org/diseases-conditions/osteoarthritis/diagnosis-treatrnent/drc-20351930—Sep. 2018, 8 pages.
Exhibit A: *Otsuka Pharmaceutical Co., Ltd., v. Sandoz, Inc., Sun Pharmaceutical Industries, Ltd., Synton BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc.*, Decision on Appeal, 2011-1126, -1127, May 7, 2012, 33 pages.
Patani and Lavoie, "Bioisosterism: A Rational Approach in Drug Design," Chem. Rev, Jul. 25, 1996, vol. 96, p. 3147-3176.
Stomach cancer—Mayoclinic.com—Apr. 9, 2011, 8 pages.
Types of Brain Cancer at http://www.cancercenter.corn/brain-cancer/types-of-brain-cancer.cfrn (Mar. 12, 2013), 3 pages.
Types of Breast Cancer, published in breastcancer.org (Sep. 30, 2012), 1 page.
Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.

3-(1H-PYRROLO[2,3-B]PYRIDIN-2-YL)-1H-PYRAZOLO[3,4-B] PYRIDINES AND THERAPEUTIC USES THEREOF

RELATED APPLICATIONS

This application is a National Stage application under 35 U.S.C. § 371 of International Application No. PCT/US2016/045283, having an International Filing Date of Aug. 3, 2016, which claims the benefit of U.S. Provisional Application Nos. 62/200,301, filed Aug. 3, 2015, and 62/356,133, filed Jun. 29, 2016, which are incorporated herein by reference in their entirety.

BACKGROUND

Technical Field

This disclosure relates to inhibitors of one or more proteins in the Wnt pathway, including inhibitors of one or more Wnt proteins, and compositions comprising the same. More particularly, it concerns the use of a 7-azaindazole compound or salts or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

SUMMARY

The present disclosure provides methods and reagents, involving contacting a cell with an agent, such as a 7-azaindazole compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing a 7-azaindazole core. Other embodiments disclosed herein include pharmaceutical compositions and methods of treatment using these compounds.

One embodiment disclosed herein includes a compound having the structure of Formula I:

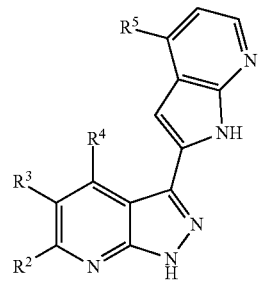

as well as prodrugs and pharmaceutically acceptable salts thereof.

In some embodiments of Formula (I):
$R^2$ and $R^4$ are independently selected from the group consisting of H and halide;
$R^3$ is selected from the group consisting of -heteroaryl optionally substituted with 1-4 $R^6$ and -heterocyclyl optionally substituted with 1-10 $R^7$;
$R^5$ is selected from the group consisting of H, -heteroaryl optionally substituted with 1-4 $R^8$, -heterocyclyl optionally substituted with 1-10 $R^9$, and -aryl optionally substituted with 1-5 $R^{10}$;
each $R^6$ is independently selected from the group consisting of halide, —($C_{1-6}$ alkyl), —($C_{2-6}$ alkenyl), —($C_{2-6}$ alkynyl), —($C_{1-4}$ alkylene)$_p$heterocyclyl optionally substituted with 1-10 $R^{11}$, —($C_{2-4}$ alkenylene)$_p$heterocyclyl optionally substituted with 1-10 $R^{11}$, —($C_{2-4}$ alkynylene)$_p$heterocyclyl optionally substituted with 1-10 $R^{11}$, —($C_{1-4}$ alkylene)$_p$carbocyclyl optionally substituted with 1-12 $R^{12}$, —($C_{2-4}$ alkenylene)$_p$carbocyclyl optionally substituted with 1-12 $R^{12}$, —($C_{2-4}$ alkynylene)$_p$carbocyclyl optionally substituted with 1-12 $R^{12}$, —($C_{1-4}$ alkylene)$_p$aryl optionally substituted with 1-5 $R^{13}$, —($C_{2-4}$ alkenylene)$_p$aryl optionally substituted with 1-5 $R^{13}$, —($C_{2-4}$ alkynylene)$_p$aryl optionally substituted with 1-5 $R^{13}$, —NHC(=O)$R^{14}$, —$NR^{15}R^{16}$, —($C_{1-6}$ alkylene)$NR^{17}R^{18}$, —($C_{2-6}$ alkenylene)$NR^{17}R^{18}$, —($C_{2-6}$ alkynylene)$NR^{17}R^{18}$, and —($C_{1-4}$ alkylene)$_p OR^{24}$;
each $R^7$ is independently selected from the group consisting of —($C_{1-4}$ alkyl), —($C_{2-4}$ alkenyl), —($C_{2-4}$ alkynyl), halide, —$CF_3$, and —CN;
each $R^8$ is independently selected from the group consisting of —($C_{1-6}$ alkyl), —($C_{2-6}$ alkenyl), —($C_{2-6}$ alkynyl), halide, —$CF_3$, —$OCH_3$, —CN, and —C(=O)$R^{19}$;
each $R^9$ is independently selected from the group consisting of —($C_{1-6}$ alkyl), —($C_{2-6}$ alkenyl), —($C_{2-6}$ alkynyl), halide, —$CF_3$, —CN, and —$OCH_3$;
each $R^{10}$ is independently selected from the group consisting of —($C_{1-6}$ alkyl), —($C_{2-6}$ alkenyl), —($C_{2-6}$ alkynyl), halide, —$CF_3$, —CN, —($C_{1-6}$ alkylene)$_p NHSO_2R^{19}$, —($C_{2-6}$ alkenylene)$_p NHSO_2R^{19}$, —($C_{2-6}$ alkynylene)$_p NHSO_2R^{19}$, —$NR^{15}$($C_{1-6}$ alkylene)$NR^{15}R^{16}$, —$NR^{15}$($C_{2-6}$ alkenylene)$NR^{15}R^{16}$, —$NR^{15}$($C_{2-6}$ alkynylene)$NR^{15}R^{16}$, —($C_{1-6}$ alkylene)$_p NR^{15}R^{16}$, —($C_{2-6}$ alkenylene)$_p NR^{15}R^{16}$, —($C_{2-6}$ alkynylene)$_p NR^{15}R^{16}$, and —$OR^{27}$;
each $R^{11}$ is independently selected from the group consisting of amino, —($C_{1-4}$ alkyl), —($C_{2-4}$ alkenyl), —($C_{2-4}$ alkynyl), halide, —$CF_3$, and —CN;

each $R^{12}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{13}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{14}$ is independently selected from the group consisting of —$(C_{1-9}$ alkyl), —$(C_{1-4}$ haloalkyl), —$(C_{2-9}$ alkenyl), —$(C_{2-9}$ alkynyl), -heteroaryl optionally substituted with 1-4 $R^{20}$, -aryl optionally substituted with 1-5 $R^{21}$, —$CH_2$aryl optionally substituted with 1-5 $R^{21}$, -carbocyclyl optionally substituted with 1-12 $R^{22}$, —$CH_2$carbocyclyl optionally substituted with 1-12 $R^{22}$, —$(C_{1-4}$ alkylene$)_p NR^{25}R^{26}$, —$(C_{2-4}$ alkenylene$)_p NR^{25}R^{26}$, —$(C_{2-4}$ alkynylene$)_p NR^{25}R^{26}$, -heterocyclyl optionally substituted with 1-10 $R^{23}$, and —$CH_2$heterocyclyl optionally substituted with 1-10 $R^{23}$;

each $R^{15}$ is independently selected from the group consisting of H, —$(C_{1-6}$ alkyl), —$(C_{2-6}$ alkenyl), and —$(C_{2-6}$ alkynyl);

each $R^{16}$ is independently selected from the group consisting of H, —$(C_{1-6}$ alkyl), —$(C_{2-6}$ alkenyl), —$(C_{2-6}$ alkynyl), —$CH_2$aryl optionally substituted with 1-5 $R^{21}$, and —$CH_2$carbocyclyl optionally substituted with 1-12 $R^{22}$;

each $R^{17}$ is independently selected from the group consisting of H, —$(C_{1-6}$ alkyl), —$(C_{2-6}$ alkenyl), and —$(C_{2-6}$ alkynyl);

each $R^{18}$ is independently selected from the group consisting of H, —$(C_{1-6}$ alkyl), —$(C_{2-6}$ alkenyl), —$(C_{2-6}$ alkynyl), —$CH_2$aryl optionally substituted with 1-5 $R^{21}$ and —$CH_2$carbocyclyl optionally substituted with 1-12 $R^{22}$;

each $R^{19}$ is independently selected from the group consisting of —$(C_{1-6}$ alkyl), —$(C_{2-6}$ alkenyl), and —$(C_{2-6}$ alkynyl);

each $R^{20}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{21}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{22}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{23}$ is independently selected from the group consisting of —$(C_{1-4}$ alkyl), —$(C_{2-4}$ alkenyl), —$(C_{2-4}$ alkynyl), halide, —$CF_3$, and —CN;

$R^{24}$ is selected from the group consisting of H, —$(C_{1-6}$ alkyl), —$(C_{2-6}$ alkenyl), —$(C_{2-6}$ alkynyl), —$(C_{1-4}$ alkylene$)_p$heterocyclyl optionally substituted with 1-10 $R^{23}$, —$(C_{2-4}$ alkenylene$)_p$heterocyclyl optionally substituted with 1-10 $R^{23}$, —$(C_{2-4}$ alkynylene$)_p$heterocyclyl optionally substituted with 1-10 $R^{23}$, —$(C_{1-4}$ alkylene$)_p$carbocyclyl optionally substituted with 1-12 $R^{22}$, —$(C_{2-4}$ alkenylene$)_p$carbocyclyl optionally substituted with 1-12 $R^{22}$, —$(C_{2-4}$ alkynylene$)_p$carbocyclyl optionally substituted with 1-12 $R^{22}$, —$(C_{1-4}$ alkylene$)_p$aryl optionally substituted with 1-5 $R^{21}$, —$(C_{2-4}$ alkenylene$)_p$aryl optionally substituted with 1-5 $R^{21}$, —$(C_{2-4}$ alkynylene$)_p$aryl optionally substituted with 1-5 $R^{21}$, —$(C_{1-6}$ alkylene$)_p NR^{25}R^{26}$, —$(C_{2-4}$ alkenylene$)_p NR^{25}R^{26}$, and —$(C_{2-4}$ alkynylene$)_p NR^{25}R^{26}$;

each $R^{25}$ is independently selected from the group consisting of H, —$(C_{1-6}$ alkyl), —$(C_{2-6}$ alkenyl), and —$(C_{2-6}$ alkynyl);

each $R^{26}$ is independently selected from the group consisting of H, —$(C_{1-6}$ alkyl), —$(C_{2-6}$ alkenyl), and —$(C_{2-6}$ alkynyl);

$R^{27}$ is selected from the group consisting of H, —$(C_{1-6}$ alkyl), —$(C_{2-6}$ alkenyl), —$(C_{2-6}$ alkynyl), —$(C_{1-4}$ alkylene$)_p$heterocyclyl optionally substituted with 1-10 $R^{23}$, —$(C_{2-4}$ alkenylene$)_p$heterocyclyl optionally substituted with 1-10 $R^{23}$, —$(C_{2-4}$ alkynylene$)_p$heterocyclyl optionally substituted with 1-10 $R^{23}$, —$(C_{1-6}$ alkylene$)_p NR^{25}R^{26}$, —$(C_{2-6}$ alkenylene$)_p NR^{25}R^{26}$, and —$(C_{2-6}$ alkynylene$)NR^{25}R^{26}$; and each p is independently an integer of 0 or 1.

In some embodiments of Formula (I):

$R^2$ and $R^4$ are independently selected from the group consisting of H and halide;

$R^3$ is selected from the group consisting of -heteroaryl optionally substituted with 1-4 $R^6$ and -heterocyclyl optionally substituted with 1-10 $R^7$;

$R^5$ is selected from the group consisting of H, -heteroaryl optionally substituted with 1-4 $R^8$, -heterocyclyl optionally substituted with 1-10 $R^9$, and -aryl optionally substituted with 1-5 $R^{10}$;

each $R^6$ is independently selected from the group consisting of halide, —$(C_{1-6}$ alkyl), —$(C_{2-6}$ alkenyl), —$(C_{2-6}$ alkynyl), —$(C_{1-4}$ alkylene$)_p$heterocyclyl optionally substituted with 1-10 $R^{11}$, —$(C_{2-4}$ alkenylene$)_p$heterocyclyl optionally substituted with 1-10 $R^{11}$, —$(C_{2-4}$ alkynylene$)_p$heterocyclyl optionally substituted with 1-10 $R^{11}$, —$(C_{1-4}$ alkylene$)_p$carbocyclyl optionally substituted with 1-12 $R^{12}$, —$(C_{2-4}$ alkenylene$)_p$carbocyclyl optionally substituted with 1-12 $R^{12}$, —$(C_{2-4}$ alkynylene$)_p$carbocyclyl optionally substituted with 1-12 $R^{12}$, —$(C_{1-4}$ alkylene$)_p$aryl optionally substituted with 1-5 $R^{13}$, —$(C_{2-4}$ alkenylene$)_p$aryl optionally substituted with 1-5 $R^{13}$, —$(C_{2-4}$ alkynylene$)_p$aryl optionally substituted with 1-5 $R^{13}$, —NHC(=O)$R^{14}$, —$NR^{15}R^{16}$, —$(C_{1-6}$ alkylene)$NR^{17}R^{18}$, —$(C_{2-6}$ alkenylene)$NR^{17}R^{18}$, and —$(C_{2-6}$ alkynylene)$NR^{17}R^{18}$, —$OR^{24}$;

each $R^7$ is independently selected from the group consisting of —$(C_{1-4}$ alkyl), —$(C_{2-4}$ alkenyl), —$(C_{2-4}$ alkynyl), halide, —$CF_3$, and —CN;

each $R^8$ is independently selected from the group consisting of —$(C_{1-6}$ alkyl), —$(C_{2-6}$ alkenyl), —$(C_{2-6}$ alkynyl), halide, —$CF_3$, —$OCH_3$, —CN, and —C(=O)$R^{19}$;

each $R^9$ is independently selected from the group consisting of —$(C_{1-6}$ alkyl), —$(C_{2-6}$ alkenyl), —$(C_{2-6}$ alkynyl), halide, —$CF_3$, —CN, and —$OCH_3$;

each $R^{10}$ is independently selected from the group consisting of —$(C_{1-6}$ alkyl), —$(C_{2-6}$ alkenyl), —$(C_{2-6}$ alkynyl), halide, —$CF_3$, —CN, —$(C_{1-6}$ alkylene$)_p NHSO_2 R^{19}$, —$(C_{2-6}$ alkenylene$)_p NHSO_2 R^{19}$, —$(C_{2-6}$ alkynylene$)_p NHSO_2 R^{19}$, —$NR^{15}(C_{1-6}$ alkylene)$NR^{15}R^{16}$, —$NR^{15}(C_{2-6}$ alkenylene)$NR^{15}R^{16}$, —$NR^{15}(C_{2-6}$ alkynylene)$NR^{15}R^{16}$, —$(C_{1-6}$ alkylene$)_p NR^{15}R^{16}$, —$(C_{2-6}$ alkenylene$)_p NR^{15}R^{16}$, —$(C_{2-6}$ alkynylene$)_p NR^{15}R^{16}$, and —$OR^{27}$;

each $R^{11}$ is independently selected from the group consisting of amino, —$(C_{1-4}$ alkyl), —$(C_{2-4}$ alkenyl), —$(C_{2-4}$ alkynyl), halide, —$CF_3$, and —CN;

each $R^{12}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{13}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{14}$ is independently selected from the group consisting of —$(C_{1-9}$ alkyl), —$(C_{2-9}$ alkenyl), —$(C_{2-9}$ alkynyl), -heteroaryl optionally substituted with 1-4 $R^{20}$, -aryl optionally substituted with 1-5 $R^{21}$, —$CH_2$aryl optionally substituted with 1-5 $R^{21}$, -carbocyclyl optionally substituted with 1-12 $R^{22}$, —$CH_2$carbocyclyl optionally substituted with 1-12 $R^{22}$, —$(C_{1-4}$ alkylene$)_pNR^{25}R^{26}$, —$(C_{2-4}$ alkenylene$)_p$ $NR^{25}R^{26}$, —$(C_{2-4}$ alkynylene$)_pNR^{25}R^{26}$, -heterocyclyl optionally substituted with 1-10 $R^{23}$, and —$CH_2$heterocyclyl optionally substituted with 1-10 $R^{23}$;

each $R^{15}$ is independently selected from the group consisting of H, —$(C_{1-6}$ alkyl), —$(C_{2-6}$ alkenyl), and —$(C_{2-6}$ alkynyl);

each $R^{16}$ is independently selected from the group consisting of H, —$(C_{1-6}$ alkyl), —$(C_{2-6}$ alkenyl), —$(C_{2-6}$ alkynyl), —$CH_2$aryl optionally substituted with 1-5 $R^{21}$, and —$CH_2$carbocyclyl optionally substituted with 1-12 $R^{22}$;

each $R^{17}$ is independently selected from the group consisting of H, —$(C_{1-6}$ alkyl), —$(C_{2-6}$ alkenyl), and —$(C_{2-6}$ alkynyl);

each $R^{18}$ is independently selected from the group consisting of H, —$(C_{1-6}$ alkyl), —$(C_{2-6}$ alkenyl), —$(C_{2-6}$ alkynyl), —$CH_2$aryl optionally substituted with 1-5 $R^{21}$ and —$CH_2$carbocyclyl optionally substituted with 1-12 $R^{22}$;

each $R^{19}$ is independently selected from the group consisting of —$(C_{1-6}$ alkyl), —$(C_{2-6}$ alkenyl), and —$(C_{2-6}$ alkynyl);

each $R^{20}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{21}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{22}$ is independently selected from the group consisting of —$(C_{1-4}$ alkyl), —$(C_{2-4}$ alkenyl), —$(C_{2-4}$ alkynyl), halide, —$CF_3$, and —CN;

each $R^{23}$ is independently selected from the group consisting of —$(C_{1-4}$ alkyl), —$(C_{2-4}$ alkenyl), —$(C_{2-4}$ alkynyl), halide, —$CF_3$, and —CN;

$R^{24}$ is selected from the group consisting of H, —$(C_{1-6}$ alkyl), —$(C_{2-6}$ alkenyl), —$(C_{2-6}$ alkynyl), —$(C_{1-4}$ alkylene$)_p$heterocyclyl optionally substituted with 1-10 $R^{23}$, —$(C_{2-4}$ alkenylene$)_p$heterocyclyl optionally substituted with 1-10 $R^{23}$, —$(C_{2-4}$ alkynylene$)_p$heterocyclyl optionally substituted with 1-10 $R^{23}$, —$(C_{1-4}$ alkylene$)_p$carbocyclyl optionally substituted with 1-12 $R^{22}$, —$(C_{2-4}$ alkenylene$)_p$carbocyclyl optionally substituted with 1-12 $R^{22}$, —$(C_{2-4}$ alkynylene$)_p$carbocyclyl optionally substituted with 1-12 $R^{22}$, —$(C_{1-4}$ alkylene$)_p$aryl optionally substituted with 1-5 $R^{21}$, —$(C_{2-4}$ alkenylene$)_p$aryl optionally substituted with 1-5 $R^{21}$, —$(C_{2-4}$ alkynylene$)_p$aryl optionally substituted with 1-5 $R^{21}$, —$(C_{1-6}$ alkylene$)_pNR^{25}R^{26}$, —$(C_{2-4}$ alkenylene$)_p$ $NR^{25}R^{26}$, and —$(C_{2-4}$ alkynylene$)NR^{25}R^{26}$;

each $R^{25}$ is independently selected from the group consisting of H, —$(C_{1-6}$ alkyl), —$(C_{2-6}$ alkenyl), and —$(C_{2-6}$ alkynyl);

each $R^{26}$ is independently selected from the group consisting of H, —$(C_{1-6}$ alkyl), —$(C_{2-6}$ alkenyl), and —$(C_{2-6}$ alkynyl);

$R^{27}$ is selected from the group consisting of H, —$(C_{1-6}$ alkyl), —$(C_{2-6}$ alkenyl), —$(C_{2-6}$ alkynyl), —$(C_{1-4}$ alkylene$)_p$heterocyclyl optionally substituted with 1-10 $R^{23}$, —$(C_{2-4}$ alkenylene$)_p$heterocyclyl optionally substituted with 1-10 $R^{23}$, —$(C_{2-4}$ alkynylene$)_p$heterocyclyl optionally substituted with 1-10 $R^{23}$, —$(C_{1-6}$ alkylene$)_pNR^{25}R^{26}$, —$(C_{2-6}$ alkenylene$)_pNR^{25}R^{26}$, and —$(C_{2-6}$ alkynylene$)_pNR^{25}R^{26}$; and each p is independently an integer of 0 or 1.

Some embodiments include stereoisomers and pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the disclosure, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 12/852,706; 12/968,505; 13/552,188; 13/800,963; 13/855,874; 13/887,177 13/938,691; 13/938,692; 14/019,103; 14/019,147; 14/019,940; 14/149,948; 14/178,749; 14/331,427; 14/334,005; and 14/664,517 and U.S. Provisional Application Ser. Nos. 61/232,603; 61/288,544; 61/305,459; 61/620,107; 61/642,915; 61/750,221; 61/968,350; 62/047, 324; 62/047,371; 62/047,395; 62/047,401; 62/047,406; 62/047,438; 62/047,509; 62/047,575; 62/047,567, all of which are incorporated by reference in their entirety herein.

Some embodiments provided herein relate to a method for treating a disease or disorder including, but not limited to, cancers, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, osteoarthritis, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressiva, fibrous dysplasia, giant cell tumor of bone, hip labral tear, meniscal tears, bone/osteoporotic (wrist, spine, shoulder and hip) fractures, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

"Exocyclic double bond" means a carbon-carbon double bond connected to and hence external to, a ring structure.

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C═C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c] pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —$NH(C_{1-3}$ alkyl), and —$N(C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12*th* Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and a compound as provided herein or a salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds of Formula I:

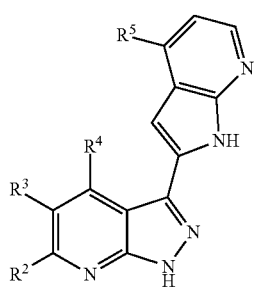

I or salts, pharmaceutically acceptable salts, or prodrugs thereof.

In some embodiments, $R^2$ and $R^4$ are independently selected from the group consisting of H and halide (e.g., F, Cl, Br, I).

In some embodiments, $R^2$ is H, and $R^4$ is F.
In some embodiments, $R^2$ is F, and $R^4$ is H.
In some embodiments, $R^2$ and $R^4$ are both H.
In some embodiments, $R^2$ and $R^4$ are both F.
In some embodiments, $R^3$ is selected from the group consisting of -heteroaryl optionally substituted with 1-4 (e.g., 1-3, 1-2, 1) $R^6$ and -heterocyclyl optionally substituted with 1-10 (e.g., 1-9, 1-8, 1-7, 1-6, 1-5, 1-4, 1-3, 1-2, 1) $R^7$.

In some embodiments, $R^3$ is selected from the group consisting of -heteroaryl optionally substituted with 1-2 (e.g., 1) $R^6$ and -heterocyclyl optionally substituted with 1-2 (e.g., 1) $R^7$.

In some embodiments, the heteroaryl of $R^3$ is selected from the group consisting of -pyridinyl, -pyrimidinyl, -pyrazolyl, -imidazolyl, -thiazolyl, and -oxazolyl.

In some embodiments, the heteroaryl of $R^3$ is selected from the group consisting of -pyridin-3-yl, -pyrimidin-5-yl, -pyrazol-4-yl, -imidazol-5-yl, -thiazol-2-yl, -thiazol-5-yl, -oxazol-2-yl, and -oxazol-5-yl.

In some embodiments, the -heterocyclyl of $R^3$ is selected from the group consisting of -tetrahydropyridinyl and -piperidinyl.

In some embodiments, the -heterocyclyl of $R^3$ is selected from the group consisting of -1,2,3,6-tetrahydropyridinyl and -piperidin-4-yl.

In some embodiments, $R^3$ is -pyridinyl optionally substituted with 1 $R^6$.

In some embodiments, $R^3$ is -pyridin-3-yl optionally substituted with 1 $R^6$.

In some embodiments, $R^3$ is -pyrimidinyl optionally substituted with 1 $R^6$.

In some embodiments, $R^3$ is -pyrimidin-5-yl optionally substituted with 1 $R^6$.

In some embodiments, $R^3$ is -pyrazolyl optionally substituted with 1 $R^6$.

In some embodiments, $R^3$ is -pyrazolyl substituted with 1 $R^6$.

In some embodiments, $R^3$ is -pyrazolyl substituted with 1 methyl.

In some embodiments, $R^3$ is -pyrazolyl optionally substituted with 2 $R^6$.

In some embodiments, $R^3$ is -pyrazolyl substituted with 2 $R^6$.

In some embodiments, $R^3$ is -pyrazolyl substituted with 1 methyl and 1 —CH$_2$OH.

In some embodiments, $R^3$ is -pyrazol-4-yl optionally substituted with 1 $R^6$.

In some embodiments, $R^3$ is -pyrazol-4-yl substituted with 1 $R^6$.

In some embodiments, $R^3$ is -pyrazol-4-yl substituted with 1 methyl.

In some embodiments, $R^3$ is -pyrazol-4-yl optionally substituted with 2 $R^6$.

In some embodiments, $R^3$ is -pyrazol-4-yl substituted with 2 $R^6$.

In some embodiments, $R^3$ is -pyrazol-4-yl substituted with 1 methyl and 1 —CH$_2$OH.

In some embodiments, $R^3$ is -imidazolyl optionally substituted with 1-2 $R^6$.

In some embodiments, $R^3$ is -imidazolyl substituted with 1-2 $R^6$.

In some embodiments, $R^3$ is -imidazolyl substituted with 1-2 methyls.

In some embodiments, $R^3$ is -imidazolyl substituted with 1 methyl.

In some embodiments, $R^3$ is -imidazolyl substituted with 2 methyls.

In some embodiments, $R^3$ is -imidazol-5-yl optionally substituted with 1-2 $R^6$.

In some embodiments, $R^3$ is -imidazol-5-yl substituted with 1-2 $R^6$.

In some embodiments, $R^3$ is -imidazol-5-yl substituted with 1-2 methyls.

In some embodiments, $R^3$ is -imidazol-5-yl substituted with 1 methyl.

In some embodiments, $R^3$ is -imidazol-5-yl substituted with 2 methyls.

In some embodiments, $R^3$ is -thiazolyl optionally substituted with 1 $R^6$.

In some embodiments, $R^3$ is -thiazol-2-yl optionally substituted with 1 $R^6$.

In some embodiments, $R^3$ is thiazol-5-yl optionally substituted with 1 $R^6$.

In some embodiments, $R^3$ is -oxazolyl optionally substituted with 1 $R^6$.

In some embodiments, $R^3$ is -oxazol-2-yl optionally substituted with 1 $R^6$.

In some embodiments, $R^3$ is -oxazol-5-yl optionally substituted with 1 $R^6$.

In some embodiments, $R^5$ is selected from the group consisting of H, -heteroaryl optionally substituted with 1-4 (e.g., 1-3, 1-2, 1) $R^8$, -heterocyclyl optionally substituted with 1-10 (e.g., 1-9, 1-8, 1-7, 1-6, 1-5, 1-4, 1-3, 1-2, 1) $R^9$, and -aryl optionally substituted with 1-5 (e.g., 1-4, 1-3, 1-2, 1) $R^{10}$.

In some embodiments, $R^5$ is selected from the group consisting of H, -heteroaryl optionally substituted with 1-2 (e.g., 1) $R^8$, -heterocyclyl optionally substituted with 1-2 (e.g., 1) $R^9$, and -phenyl optionally substituted with 1-2 (e.g., 1) $R^{10}$.

In some embodiments, $R^5$ is H.

In some embodiments, $R^5$ is -heteroaryl optionally substituted with 1-2 (e.g., 1) $R^8$.

In some embodiments, $R^5$ is -heterocyclyl optionally substituted with 1-2 (e.g., 1) $R^9$.

In some embodiments, $R^5$ is -piperidinyl optionally substituted with 1-2 (e.g., 1) $R^9$.

In some embodiments, $R^5$ is -piperazinyl optionally substituted with 1-2 (e.g., 1) $R^9$.

In some embodiments, $R^5$ is -aryl optionally substituted with 1-2 (e.g., 1) $R^{10}$.

In some embodiments, $R^5$ is -phenyl optionally substituted with 1-2 (e.g., 1) $R^{10}$.

In some embodiments, $R^5$ is -pyridinyl optionally substituted with 1-2 (e.g., 1) $R^8$.

In some embodiments, $R^5$ is -pyridin-3-yl optionally substituted with 1-2 (e.g., 1) $R^8$.

In some embodiments, $R^5$ is -pyridin-4-yl optionally substituted with 1-2 (e.g., 1) $R^8$.

In some embodiments, $R^5$ is -pyridin-5-yl optionally substituted with 1-2 (e.g., 1) $R^8$.

In some embodiments, $R^5$ is -imidazolyl optionally substituted with 1-2 (e.g., 1) $R^8$.

In some embodiments, $R^5$ is -imidazolyl substituted with 1-2 (e.g., 1) $R^8$.

In some embodiments, $R^5$ is -imidazolyl substituted with 1 $R^8$.

In some embodiments, $R^5$ is -imidazolyl substituted with 1 methyl.

In some embodiments, $R^5$ is -imidazol-1-yl optionally substituted with 1-2 (e.g., 1) $R^8$.

In some embodiments, $R^5$ is -imidazol-1-yl substituted with 1-2 (e.g., 1) $R^8$.

In some embodiments, $R^5$ is -imidazol-1-yl substituted with 1 $R^8$.

In some embodiments, $R^5$ is -imidazol-1-yl substituted with 1 methyl.

In some embodiments, $R^5$ is -furanyl optionally substituted with 1-2 (e.g., 1) $R^8$.

In some embodiments, $R^5$ is -furan-2-yl optionally substituted with 1-2 (e.g., 1) $R^8$.

In some embodiments, $R^5$ is -furan-3-yl optionally substituted with 1-2 (e.g., 1) $R^8$.

In some embodiments, $R^5$ is -thiophenyl optionally substituted with 1-2 (e.g., 1) $R^8$.

In some embodiments, $R^5$ is -thiophen-2-yl optionally substituted with 1-2 (e.g., 1) $R^8$.

In some embodiments, $R^5$ is -thiophen-2-yl optionally substituted with 1-2 (e.g., 1) $R^8$, and each $R^8$ is independently halide.

In some embodiments, $R^5$ is -thiophen-2-yl optionally substituted with 1-2 (e.g., 1) F.

In some embodiments, $R^5$ is -thiophen-2-yl optionally substituted with 1-2 (e.g., 1) Cl.

In some embodiments, $R^5$ is -thiophen-2-yl optionally substituted with 1-2 (e.g., 1) $R^8$, and each $R^8$ is independently —($C_{1-6}$ alkyl).

In some embodiments, $R^5$ is -thiophen-2-yl optionally substituted with 1-2 (e.g., 1) $R^8$, and each $R^8$ is independently —($C_{1-2}$ alkyl).

In some embodiments, $R^5$ is -thiophen-2-yl optionally substituted with 1-2 (e.g., 1) methyls.

In some embodiments, $R^5$ is -thiophen-2-yl optionally substituted with 1-2 (e.g., 1) —$CF_3$.

In some embodiments, $R^5$ is -thiophen-2-yl optionally substituted with 1-2 (e.g., 1) —CN.

In some embodiments, $R^5$ is -thiophen-2-yl optionally substituted with 1 —C(=O)$R^9$.

In some embodiments, $R^5$ is -thiophen-2-yl optionally substituted with 1 —C(=O)$R^{19}$, and $R^{19}$ is —($C_{1-6}$ alkyl).

In some embodiments, $R^5$ is -thiophen-2-yl optionally substituted with 1 —C(=O)$R^{19}$, and $R^{19}$ is —($C_{1-4}$ alkyl).

In some embodiments, $R^5$ is -thiophen-2-yl optionally substituted with 1 —C(=O)$R^{19}$, and $R^{19}$ is —($C_{1-2}$ alkyl).

In some embodiments, $R^5$ is -thiophen-2-yl optionally substituted with 1 —C(=O)$R^{19}$, and $R^{19}$ is methyl.

In some embodiments, $R^5$ is -thiophen-3-yl optionally substituted with 1-2 (e.g., 1) $R^8$.

In some embodiments, $R^5$ is -thiophen-3-yl optionally substituted with 1-2 (e.g., 1) $R^8$ and each $R^8$ is independently halide.

In some embodiments, $R^5$ is -thiophen-3-yl optionally substituted with 1-2 (e.g., 1) F.

In some embodiments, $R^5$ is -thiophen-3-yl optionally substituted with 1-2 (e.g., 1) Cl.

In some embodiments, $R^5$ is -thiophen-3-yl optionally substituted with 1-2 (e.g., 1) $R^8$, and each $R^8$ is independently —($C_{1-6}$ alkyl).

In some embodiments, $R^5$ is -thiophen-3-yl optionally substituted with 1-2 (e.g., 1) $R^8$, and each $R^8$ is independently —($C_{1-2}$ alkyl).

In some embodiments, $R^5$ is -thiophen-3-yl optionally substituted with 1-2 (e.g., 1) methyls.

In some embodiments, $R^5$ is -thiophen-3-yl optionally substituted with 1-2 (e.g., 1) —$CF_3$.

In some embodiments, $R^5$ is -thiophen-3-yl optionally substituted with 1-2 (e.g., 1) —CN.

In some embodiments, $R^5$ is -thiophen-3-yl optionally substituted with 1 —C(=O)$R^9$.

In some embodiments, $R^5$ is -thiophen-3-yl optionally substituted with 1 —C(=O)$R^{19}$, and $R^{19}$ is —($C_{1-6}$ alkyl).

In some embodiments, $R^5$ is -thiophen-3-yl optionally substituted with 1 —C(=O)$R^{19}$, and $R^{19}$ is —($C_{1-4}$ alkyl).

In some embodiments, $R^5$ is -thiophen-3-yl optionally substituted with 1 —C(=O)$R^{19}$, and $R^{19}$ is —($C_{1-2}$ alkyl).

In some embodiments, $R^5$ is -thiophen-3-yl optionally substituted with 1 —C(=O)$R^{19}$, and $R^{19}$ is methyl.

In some embodiments, $R^5$ is selected from the group consisting of:

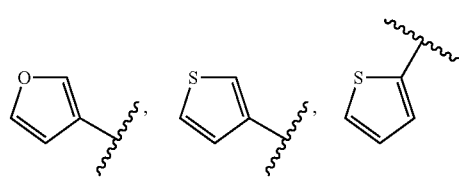

-continued

[structures: 5-fluoro-thiophen-2-yl, 5-chloro-thiophen-2-yl, 5-methyl-thiophen-2-yl, 5-acetyl-thiophen-2-yl, and 4-methyl-imidazol-1-yl]

In some embodiments, $R^5$ is -phenyl optionally substituted with 1-2 (e.g., 1) $R^{10}$, and each $R^{10}$ is independently halide.

In some embodiments, $R^5$ is -phenyl optionally substituted with 1-2 (e.g., 1) F.

In some embodiments, $R^5$ is -phenyl optionally substituted with 2 $R^{10}$, one $R^{10}$ is halide and the other $R^{10}$ is —($C_{1-6}$ alkylene)NHSO$_2R^{19}$.

In some embodiments, $R^5$ is -phenyl optionally substituted with 2 $R^{10}$, one $R^{10}$ is halide and the other $R^{10}$ is —($C_{1-4}$ alkylene)NHSO$_2R^{19}$.

In some embodiments, $R^5$ is -phenyl optionally substituted with 2 $R^{10}$, one $R^{10}$ is halide and the other $R^{10}$ is —($C_{1-2}$ alkylene)NHSO$_2R^{19}$.

In some embodiments, $R^5$ is -phenyl optionally substituted with 2 $R^{10}$, one $R^{10}$ is halide and the other $R^{10}$ is —CH$_2$NHSO$_2R^{19}$.

In some embodiments, $R^5$ is -phenyl optionally substituted with 2 $R^{10}$, one $R^{10}$ is halide and the other $R^{10}$ is —CH$_2$NHSO$_2R^{19}$, $R^{19}$ is —($C_{1-4}$ alkyl).

In some embodiments, $R^5$ is -phenyl optionally substituted with 2 $R^{10}$, one $R^{10}$ is halide and the other $R^{10}$ is —CH$_2$NHSO$_2R^{19}$, $R^{19}$ is —($C_{1-2}$ alkyl).

In some embodiments, $R^5$ is -phenyl optionally substituted with 2 $R^{10}$, one $R^{10}$ is halide and the other $R^{10}$ is —CH$_2$NHSO$_2R^{19}$, $R^{19}$ is methyl.

In some embodiments, $R^5$ is -phenyl optionally substituted with 2 $R^{10}$, one $R^{10}$ is F and the other $R^{10}$ is —CH$_2$NHSO$_2R^{19}$, $R^{19}$ is —($C_{1-2}$ alkyl).

In some embodiments, $R^5$ is -phenyl optionally substituted with 2 $R^{10}$, one $R^{10}$ is F and the other $R^{10}$ is —CH$_2$NHSO$_2R^{19}$, $R^{19}$ is methyl.

In some embodiments, $R^5$ is -phenyl optionally substituted with 2 $R^{10}$, one $R^{10}$ is halide and the other $R^{10}$ is —NR$^{15}$(C$_{1-6}$ alkylene)NR$^{15}R^{16}$.

In some embodiments, $R^5$ is -phenyl optionally substituted with 2 $R^{10}$, one $R^{10}$ is halide and the other $R^{10}$ is —NR$^{15}$(C$_{1-5}$ alkylene)NR$^{15}R^{16}$.

In some embodiments, $R^5$ is -phenyl optionally substituted with 2 $R^{10}$, one $R^{10}$ is halide and the other $R^{10}$ is —NR$^{15}$(C$_{1-4}$ alkylene)NR$^{15}R^{16}$.

In some embodiments, $R^5$ is -phenyl optionally substituted with 2 $R^{10}$, one $R^{10}$ is halide and the other $R^{10}$ is —NR$^{15}$(C$_{1-3}$ alkylene)NR$^{15}R^{16}$.

In some embodiments, $R^5$ is -phenyl optionally substituted with 2 $R^{10}$, one $R^{10}$ is halide and the other $R^{10}$ is —NR$^5$CH$_2$CH$_2$NR$^{15}R^{16}$.

In some embodiments, $R^5$ is -phenyl optionally substituted with 2 $R^{10}$, one $R^{10}$ is halide and the other $R^{10}$ is —NHCH$_2$CH$_2$NR$^{15}R^{16}$.

In some embodiments, $R^5$ is -phenyl optionally substituted with 2 $R^{10}$, one $R^{10}$ is halide and the other $R^{10}$ is —NHCH$_2$CH$_2$NR$^{15}R^{16}$, and $R^{15}$ and $R^{16}$ are independently selected from —(C$_{1-6}$ alkyl).

In some embodiments, $R^5$ is -phenyl optionally substituted with 2 $R^{10}$, one $R^{10}$ is halide and the other $R^{10}$ is —NHCH$_2$CH$_2$NR$^{15}R^{16}$, and $R^{15}$ and $R^{16}$ are independently selected from —(C$_{1-4}$ alkyl).

In some embodiments, $R^5$ is -phenyl optionally substituted with 2 $R^{10}$, one $R^{10}$ is halide and the other $R^{10}$ is —NHCH$_2$CH$_2$NR$^{15}R^{16}$, and $R^{15}$ and $R^{16}$ are independently selected from —(C$_{1-2}$ alkyl).

In some embodiments, $R^5$ is -phenyl optionally substituted with 2 $R^{10}$, one $R^{10}$ is halide and the other $R^{10}$ is —NHCH$_2$CH$_2$NR$^{15}R^{16}$, and both $R^{15}$ and $R^{16}$ are methyls.

In some embodiments, $R^5$ is -phenyl optionally substituted with 2 $R^{10}$, one $R^{11}$ is F and the other $R^{10}$ is —NHCH$_2$CH$_2$NR$^{15}R^{16}$, and $R^{15}$ and $R^{16}$ are independently selected from —(C$_{1-2}$ alkyl).

In some embodiments, $R^5$ is -phenyl optionally substituted with 2 $R^{10}$, one $R^{11}$ is F and the other $R^{10}$ is —NHCH$_2$CH$_2$NR$^{15}R^{16}$, and both $R^{15}$ and $R^{16}$ are methyls.

In some embodiments, $R^5$ is -phenyl optionally substituted with 2 $R^{10}$, one $R^{10}$ is halide and the other $R^{10}$ is —OR$^{27}$.

In some embodiments, $R^5$ is -phenyl optionally substituted with 2 $R^{10}$, one $R^{10}$ is halide and the other $R^{10}$ is —OCH$_2$CH$_2$NR$^{25}R^{26}$.

In some embodiments, $R^5$ is -phenyl optionally substituted with 2 $R^{10}$, one $R^{10}$ is halide and the other $R^{10}$ is —OCH$_2$CH$_2$NR$^{25}R^{26}$, and $R^{25}$ and $R^{26}$ are independently —(C$_{1-2}$ alkyl).

In some embodiments, $R^5$ is -phenyl optionally substituted with 2 $R^{10}$, one $R^{10}$ is halide and the other $R^{10}$ is —OCH$_2$CH$_2$NR$^{25}R^{26}$, and $R^{25}$ and $R^{26}$ are both methyl.

In some embodiments, $R^5$ is -phenyl optionally substituted with 2 $R^{10}$, one $R^{11}$ is F and the other $R^{10}$ is —OCH$_2$CH$_2$NR$^{25}R^{26}$, and $R^{25}$ and $R^{26}$ are both methyl.

In some embodiments, $R^5$ is -phenyl optionally substituted with 2 $R^{10}$, one $R^{10}$ is halide and the other $R^{10}$ is —OCH$_2$CH$_2$heterocyclyl optionally substituted with 1-2 (e.g., 1) $R^{23}$.

In some embodiments, $R^5$ is -phenyl optionally substituted with 2 $R^{10}$, one $R^{10}$ is F and the other $R^{10}$ is —OCH$_2$CH$_2$heterocyclyl optionally substituted with 1-2 (e.g., 1) $R^{23}$.

In some embodiments, $R^5$ is -phenyl optionally substituted with 2 $R^{10}$, one $R^{10}$ is halide and the other $R^{10}$ is —OH.

In some embodiments, $R^5$ is -phenyl optionally substituted with 2 $R^{10}$, one $R^{10}$ is halide and the other $R^{10}$ is —OMe.

In some embodiments, $R^5$ is -phenyl optionally substituted with 1 —OMe.

In some embodiments, $R^5$ is selected from the group consisting of:

[structures: 3-fluorophenyl, 4-fluorophenyl, 2-fluorophenyl]

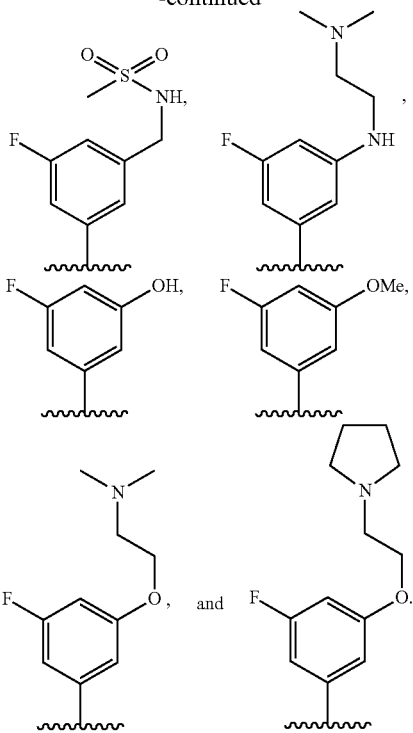

In some embodiments, R⁵ is -piperidin-1-yl optionally substituted with 1-2 (e.g., 1) R⁹.

In some embodiments, R⁵ is -piperidin-1-yl optionally substituted with 1-2 (e.g., 1) R⁹, and each R⁹ is independently halide.

In some embodiments, R⁵ is -piperazin-1-yl optionally substituted with 1-2 (e.g., 1) R⁹.

In some embodiments, R⁵ is -piperazin-1-yl optionally substituted with 1 C$_{1-3}$ alkyl.

In some embodiments, R⁵ is -piperazin-1-yl optionally substituted with 1 methyl.

In some embodiments, R⁵ is -morpholinyl optionally substituted with 1-2 (e.g., 1) R⁹.

In some embodiments, R⁵ is -morpholin-1-yl optionally substituted with 1-2 (e.g., 1) R⁹.

In some embodiments, R⁵ is selected from the group consisting of:

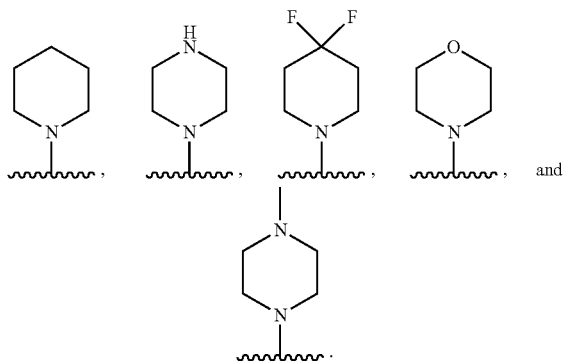

In some embodiments, each R⁶ is independently selected from the group consisting of halide, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 (e.g., 1-9, 1-8, 1-7, 1-6, 1-5, 1-4, 1-3, 1-2, 1) R¹¹, —(C$_{2-4}$ alkenylene)$_p$heterocyclyl optionally substituted with 1-10 (e.g., 1-9, 1-8, 1-7, 1-6, 1-5, 1-4, 1-3, 1-2, 1) R¹¹, —(C$_{2-4}$ alkynylene)$_p$heterocyclyl optionally substituted with 1-10 (e.g., 1-9, 1-8, 1-7, 1-6, 1-5, 1-4, 1-3, 1-2, 1) R¹¹, —(C$_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{2-4}$ alkenylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{2-4}$ alkynylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{1-4}$ alkylene)$_p$aryl optionally substituted with 1-5 (e.g., 1-4, 1-3, 1-2, 1) R¹³, —(C$_{2-4}$ alkenylene)$_p$aryl optionally substituted with 1-5 (e.g., 1-4, 1-3, 1-2, 1) R¹³, —(C$_{2-4}$ alkynylene)$_p$aryl optionally substituted with 1-5 (e.g., 1-4, 1-3, 1-2, 1) R¹³, —NHC(=O)R¹⁴, —NR¹⁵R¹⁶, —(C$_{1-6}$ alkylene)NR¹⁷R¹⁸, —(C$_{2-6}$ alkenylene)NR¹⁷R¹⁸, —(C$_{2-6}$ alkynylene)NR¹⁷R¹⁸, and —OR²⁴.

In some embodiments, each R⁶ is independently selected from the group consisting of halide, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 (e.g., 1-9, 1-8, 1-7, 1-6, 1-5, 1-4, 1-3, 1-2, 1) R¹¹, —(C$_{2-4}$ alkenylene)$_p$heterocyclyl optionally substituted with 1-10 (e.g., 1-9, 1-8, 1-7, 1-6, 1-5, 1-4, 1-3, 1-2, 1) R¹¹, —(C$_{2-4}$ alkynylene)$_p$heterocyclyl optionally substituted with 1-10 (e.g., 1-9, 1-8, 1-7, 1-6, 1-5, 1-4, 1-3, 1-2, 1) R¹¹, —(C$_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{2-4}$ alkenylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{2-4}$ alkynylene)$_p$carbocyclyl optionally substituted with 1-12 (e.g., 1-11, 1-10, 1-9, 1-8, 1-7, 1-6, 1-5, 1-4, 1-3, 1-2, 1) R¹², —(C$_{1-4}$ alkylene)$_p$aryl optionally substituted with 1-5 (e.g., 1-4, 1-3, 1-2, 1) R¹³, —(C$_{2-4}$ alkenylene)$_p$aryl optionally substituted with 1-5 (e.g., 1-4, 1-3, 1-2, 1) R¹³, —(C$_{2-4}$ alkynylene)$_p$aryl optionally substituted with 1-5 (e.g., 1-4, 1-3, 1-2, 1) R¹³, —NHC(=O)R¹⁴, —NR¹⁵R¹⁶, —(C$_{1-6}$ alkylene)NR¹⁷R¹⁸, —(C$_{2-6}$ alkenylene)NR¹⁷R¹⁸, —(C$_{2-6}$ alkynylene)NR¹⁷R¹⁸, and —(C$_{1-4}$ alkylene)$_p$OR²⁴.

In some embodiments, each R⁶ is independently selected from the group consisting of F, Cl, —(C$_{1-3}$ alkyl), -heterocyclyl optionally substituted with 1-2 (e.g., 1) R¹¹, —CH$_2$heterocyclyl optionally substituted with 1-2 (e.g., 1) R¹¹, -carbocyclyl optionally substituted with 1-2 (e.g., 1) R¹², —CH$_2$carbocyclyl optionally substituted with 1-2 (e.g., 1) R¹², -aryl optionally substituted with 1-2 (e.g., 1) R¹³, —CH$_2$aryl optionally substituted with 1-2 (e.g., 1) R¹³, —NHC(=O)R¹⁴, —NR¹⁵R¹⁶, —CH$_2$NR¹⁷R¹⁸, and —OR²⁴.

In some embodiments, each R⁶ is independently selected from the group consisting of F, Cl, —(C$_{1-3}$ alkyl), -heterocyclyl optionally substituted with 1-2 (e.g., 1) R¹¹, —CH$_2$heterocyclyl optionally substituted with 1-2 (e.g., 1) R¹¹, -carbocyclyl optionally substituted with 1-2 (e.g., 1) R¹², —CH$_2$carbocyclyl optionally substituted with 1-2 (e.g., 1) R¹², -aryl optionally substituted with 1-2 (e.g., 1) R¹³, —CH$_2$aryl optionally substituted with 1-2 (e.g., 1) R¹³, —NHC(=O)R¹⁴, —NR¹⁵R¹⁶, —CH$_2$NR¹⁷R¹⁸, —CH$_2$OR²⁴, and —OR²⁴.

In some embodiments, each R⁶ is independently selected from the group consisting of F, -Me, -heterocyclyl optionally substituted with 1-2 (e.g., 1) halides, -heterocyclyl optionally substituted with 1-2 (e.g., 1) methyls, —CH$_2$heterocyclyl optionally substituted with with 1-2 (e.g., 1) halides, —CH$_2$heterocyclyl optionally substituted with 1-2 (e.g., 1) methyls, -carbocyclyl optionally substituted with 1-2 (e.g., 1) halides, —CH$_2$carbocyclyl optionally substituted with 1-2 (e.g., 1) halides, -aryl optionally substituted with 1-2 (e.g., 1) halides, —CH$_2$aryl optionally substituted with 1-2 (e.g., 1) halides, —NHC(=O)R$^4$, —NH$_2$, —NHMe, —NHEt, —NHPr, —NMe$_2$, —CH$_2$NMe$_2$, —CH$_2$NHMe, —CH$_2$NHEt, —CH$_2$NHCH$_2$phenyl, —CH$_2$NHCH$_2$carbocylyl, —CH$_2$OH, and —OR$^{24}$.

In some embodiments, R$^6$ is selected from the group consisting of —(C$_{1-3}$ alkyl), —CH$_2$heterocyclyl optionally substituted with 1-2 R$^{11}$, —NHC(=O)R$^4$, —NR$^{15}$R$^{16}$, —CH$_2$NR$^{17}$R$^{18}$, —CH$_2$OH, and —OR$^{24}$.

In some embodiments, at least one R$^6$ is —(C$_{1-3}$ alkyl).
In some embodiments, at least one R$^6$ is —(C$_{1-2}$ alkyl).
In some embodiments, at least one R$^6$ is -Me.
In some embodiments, at least one R$^6$ is halide.
In some embodiments, at least one R$^6$ is F.
In some embodiments, at least one R$^6$ is —(C$_{1-4}$ alkylene)heterocyclyl optionally substituted with 1-2 R$^{11}$.
In some embodiments, at least one R$^6$ is —(C$_{1-3}$ alkylene)heterocyclyl optionally substituted with 1-2 R$^{11}$.
In some embodiments, at least one R$^6$ is —(C$_{1-2}$ alkylene)heterocyclyl optionally substituted with 1-2 R$^{11}$.
In some embodiments, at least one R$^6$ is —CH$_2$pyrrolidinyl optionally substituted with 1-2 R$^{11}$.
In some embodiments, R$^6$ is —CH$_2$pyrrolidinyl optionally substituted with 1-2 R$^{11}$.
In some embodiments, R$^6$ is —CH$_2$pyrrolidinyl optionally substituted with 1-2 R$^{11}$, and each R$^{11}$ is independently halide.
In some embodiments, R$^6$ is —CH$_2$pyrrolidinyl optionally substituted with 1-2 F.
In some embodiments, R$^6$ is —CH$_2$pyrrolidinyl substituted with 1-2 F.
In some embodiments, R$^6$ is —CH$_2$pyrrolidinyl substituted with 2 F.
In some embodiments, at least one R$^6$ is —CH$_2$piperidinyl optionally substituted with 1-2 R$^{11}$.
In some embodiments, R$^6$ is —CH$_2$piperidinyl optionally substituted with 1-2 R$^{11}$.
In some embodiments, R$^6$ is —CH$_2$piperidinyl optionally substituted with 1-2 R$^{11}$, and each R$^{11}$ is independently halide.
In some embodiments, R$^6$ is —CH$_2$piperidinyl optionally substituted with 1-2 F.
In some embodiments, R$^6$ is

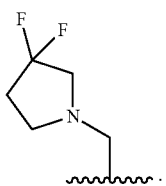 [SMILES: *CN1CCC(F)(F)C1]

In some embodiments, at least one R$^6$ is —(C$_{1-4}$ alkylene)carbocyclyl optionally substituted with 1-2 (e.g., 1) R$^{12}$.
In some embodiments, at least one R$^6$ is —(C$_{1-3}$ alkylene)carbocyclyl optionally substituted with 1-2 (e.g., 1) R$^{12}$.
In some embodiments, at least one R$^6$ is —(C$_{1-2}$ alkylene)carbocyclyl optionally substituted with 1-2 (e.g., 1) R$^{12}$.
In some embodiments, at least one R$^6$ is —CH$_2$carbocyclyl optionally substituted with 1-2 (e.g., 1) R$^{12}$.

In some embodiments, R$^6$ is —CH$_2$carbocyclyl optionally substituted with 1-2 (e.g., 1) R$^{12}$.
In some embodiments, at least one R$^6$ is —CH$_2$aryl optionally substituted with 1-2 (e.g., 1) R$^{13}$.
In some embodiments, at least one R$^6$ is —CH$_2$phenyl optionally substituted with 1-2 (e.g., 1) R$^{13}$.
In some embodiments, R$^6$ is —CH$_2$phenyl optionally substituted with 1-2 (e.g., 1) R$^{13}$.
In some embodiments, at least one R$^6$ is —NHC(=O)R$^{14}$.
In some embodiments, R$^6$ is —NHC(=O)R$^{14}$.
In some embodiments, at least one R$^6$ is —NHC(=O)R$^{14}$ and R$^{14}$ is —(C$_{1-9}$ alkyl).
In some embodiments, at least one R$^6$ is —NHC(=O)R$^{14}$ and R$^{14}$ is —(C$_{1-8}$ alkyl).
In some embodiments, at least one R$^6$ is —NHC(=O)R$^{14}$ and R$^{14}$ is —(C$_{1-7}$ alkyl).
In some embodiments, at least one R$^6$ is —NHC(=O)R$^{14}$ and R$^{14}$ is —(C$_{1-6}$ alkyl).
In some embodiments, at least one R$^6$ is —NHC(=O)R$^{14}$ and R$^{14}$ is —(C$_{1-5}$ alkyl).
In some embodiments, R$^6$ is —NHC(=O)R$^{14}$ and R$^{14}$ is —(C$_{1-5}$ alkyl).
In some embodiments, at least one R$^6$ is —NHC(=O)R$^{14}$ and R$^{14}$ is —(C$_{1-4}$ alkyl).
In some embodiments, R$^6$ is —NHC(=O)R$^{14}$ and R$^{14}$ is —(C$_{1-4}$ alkyl).
In some embodiments, at least one R$^6$ is —NHC(=O)R$^{14}$ and R$^{14}$ is —(C$_{1-3}$ alkyl).
In some embodiments, R$^6$ is —NHC(=O)R$^{14}$ and R$^{14}$ is —(C$_{1-3}$ alkyl).
In some embodiments, R$^6$ is —NHC(=O)R$^{14}$ and R$^{14}$ is —(C$_{1-2}$ alkyl).
In some embodiments, R$^6$ is —NHC(=O)R$^{14}$ and R$^{14}$ is —(C$_{1-2}$ alkyl).
In some embodiments, R$^6$ is —NHC(=O)R$^{14}$ and R$^{14}$ is —CF$_3$.
In some embodiments, at least one R$^6$ is —NHC(=O)R$^{14}$ and R$^{14}$ is —(C$_{2-5}$ alkyl).
In some embodiments, R$^6$ is —NHC(=O)R$^{14}$ and R$^{14}$ is —(C$_{2-5}$ alkyl).
In some embodiments, at least one R$^6$ is —NHC(=O)R$^{14}$ and R$^{14}$ is —(C$_{3-4}$ alkyl).
In some embodiments, at least one R$^6$ is —NHC(=O)R$^{14}$, R$^{14}$ is -aryl optionally substituted with 1-2 (e.g., 1) R$^{21}$.
In some embodiments, at least one R$^6$ is —NHC(=O)R$^{14}$, R$^{14}$ is -phenyl optionally substituted with 1-2 (e.g., 1) R$^{21}$.
In some embodiments, at least one R$^6$ is —NHC(=O)R$^{14}$, R$^{14}$ is —CH$_2$aryl optionally substituted with 1-2 (e.g., 1) R$^{21}$.
In some embodiments, at least one R$^6$ is —NHC(=O)R$^{14}$, R$^{14}$ is —CH$_2$phenyl optionally substituted with 1-2 (e.g., 1) R$^{21}$.
In some embodiments, at least one R$^6$ is —NHC(=O)R$^{14}$, R$^{14}$ is -heteroaryl optionally substituted with 1-2 (e.g., 1) R$^{20}$.
In some embodiments, at least one R$^6$ is —NHC(=O)R$^{14}$, R$^{14}$ is -carbocyclyl optionally substituted with 1-2 (e.g., 1) R$^{22}$.
In some embodiments, at least one R$^6$ is —NHC(=O)R$^{14}$, R$^{14}$ is -cyclopropyl optionally substituted with 1-2 (e.g., 1) R$^{22}$.
In some embodiments, at least one R$^6$ is —NHC(=O)R$^{14}$, R$^{14}$ is -cyclobutyl optionally substituted with 1-2 (e.g., 1) R$^{22}$.

In some embodiments, at least one $R^6$ is —NHC(=O)$R^{14}$, $R^{14}$ is -cyclopentyl optionally substituted with 1-2 (e.g., 1) $R^{22}$.

In some embodiments, at least one $R^6$ is —NHC(=O)$R^{14}$, $R^{14}$ is -cyclohexyl optionally substituted with 1-2 (e.g., 1) $R^{22}$.

In some embodiments, at least one $R^6$ is —NHC(=O)$R^{14}$, $R^4$ is —CH$_2$carbocyclyl optionally substituted with 1-2 (e.g., 1) $R^{22}$.

In some embodiments, at least one $R^6$ is —NHC(=O)$R^{14}$, $R^{14}$ is —CH$_2$cyclopropyl optionally substituted with 1-2 (e.g., 1) $R^{22}$.

In some embodiments, at least one $R^6$ is —NR$^{15}$R$^{16}$.

In some embodiments, at least one $R^6$ is —NR$^{15}$R$^{16}$, and $R^{15}$ and $R^{16}$ are independently selected from the group consisting of H and —(C$_{1-6}$ alkyl).

In some embodiments, at least one $R^6$ is —NR$^{15}$R$^{16}$, and $R^{15}$ and $R^{16}$ are independently selected from the group consisting of H and —(C$_{1-5}$ alkyl).

In some embodiments, at least one $R^6$ is —NR$^{15}$R$^{16}$, and $R^{15}$ and $R^{16}$ are independently selected from the group consisting of H and —(C$_{1-4}$ alkyl).

In some embodiments, at least one $R^6$ is —NR$^{15}$R$^{16}$, and $R^{15}$ and $R^{16}$ are independently selected from the group consisting of H and —(C$_{1-3}$ alkyl).

In some embodiments, at least one $R^6$ is —NR$^{15}$R$^{16}$, and $R^{15}$ and $R^{16}$ are independently selected from the group consisting of H and —(C$_{1-2}$ alkyl).

In some embodiments, at least one $R^6$ is —NR$^{15}$R$^{16}$, and $R^{15}$ and $R^{16}$ are independently selected from the group consisting of H and methyl.

In some embodiments, at least one $R^6$ is —NH$_2$.

In some embodiments, $R^6$ is —NH$_2$.

In some embodiments, at least one $R^6$ is —NHR$^{16}$ and $R^{16}$ is —(C$_{1-4}$ alkyl).

In some embodiments, at least one $R^6$ is —NHR$^{16}$ and $R^{16}$ is —(C$_{1-3}$ alkyl).

In some embodiments, at least one $R^6$ is —NHR$^{16}$ and $R^{16}$ is —(C$_{1-2}$ alkyl).

In some embodiments, $R^6$ is —NHR$^{16}$ and $R^{16}$ is —(C$_{1-2}$ alkyl).

In some embodiments, at least one $R^6$ is —NHR$^{16}$ and $R^{16}$ is —CH$_2$aryl optionally substituted with 1-2 (e.g., 1) $R^{21}$.

In some embodiments, at least one $R^6$ is —NHR$^{16}$ and $R^{16}$ is —CH$_2$phenyl optionally substituted with 1-2 (e.g., 1) $R^{21}$.

In some embodiments, at least one $R^6$ is —NHR$^{16}$ and $R^{16}$ is —CH$_2$carbocyclyl optionally substituted with 1-2 (e.g., 1) $R^{22}$.

In some embodiments, at least one $R^6$ is —NHR$^{16}$ and $R^{16}$ is —CH$_2$cyclopropyl optionally substituted with 1-2 (e.g., 1) $R^{22}$.

In some embodiments, at least one $R^6$ is —NHR$^{16}$ and $R^{16}$ is —CH$_2$cyclobutyl optionally substituted with 1-2 (e.g., 1) $R^{22}$.

In some embodiments, at least one $R^6$ is —NHR$^{16}$ and $R^{16}$ is —CH$_2$cyclopentyl optionally substituted with 1-2 (e.g., 1) $R^{22}$.

In some embodiments, at least one $R^6$ is —NHR$^{16}$ and $R^{16}$ is —CH$_2$cyclohexyl optionally substituted with 1-2 (e.g., 1) $R^{22}$.

In some embodiments, at least one $R^6$ is —(C$_{1-6}$ alkylene)NR$^{17}$R$^{18}$.

In some embodiments, at least one $R^6$ is —(C$_{1-5}$ alkylene)NR$^{17}$R$^{18}$.

In some embodiments, at least one $R^6$ is —(C$_{1-4}$ alkylene)NR$^{17}$R$^{18}$.

In some embodiments, at least one $R^6$ is —(C$_{1-3}$ alkylene)NR$^{17}$R$^{18}$.

In some embodiments, at least one $R^6$ is —(C$_{1-2}$ alkylene)NR$^{17}$R$^{18}$.

In some embodiments, at least one $R^6$ is —CH$_2$NR$^{17}$R$^{18}$.

In some embodiments, $R^6$ is —CH$_2$NR$^{17}$R$^{18}$.

In some embodiments, at least one $R^6$ is —CH$_2$NR$^{17}$R$^{18}$, and $R^{17}$ and $R^{18}$ are independently selected from the group consisting of H and —(C$_{1-6}$ alkyl).

In some embodiments, at least one $R^6$ is —CH$_2$NR$^{17}$R$^{18}$, and $R^{17}$ and $R^{18}$ are independently selected from the group consisting of H and —(C$_{1-5}$ alkyl).

In some embodiments, at least one $R^6$ is —CH$_2$NR$^{17}$R$^{18}$, and $R^{17}$ and $R^{18}$ are independently selected from the group consisting of H and —(C$_{1-4}$ alkyl).

In some embodiments, at least one $R^6$ is —CH$_2$NR$^{17}$R$^{18}$, and $R^{17}$ and $R^{18}$ are independently selected from the group consisting of H and —(C$_{1-3}$ alkyl).

In some embodiments, at least one $R^6$ is —CH$_2$NR$^{17}$R$^{18}$, and $R^{17}$ and $R^{18}$ are independently selected from the group consisting of H and —(C$_{1-2}$ alkyl).

In some embodiments, at least one $R^6$ is —CH$_2$NR$^{17}$R$^{18}$, and $R^{17}$ and $R^{18}$ are independently selected from the group consisting of H and methyl.

In some embodiments, $R^6$ is —CH$_2$NR$^{17}$R$^{18}$, and $R^{17}$ and $R^{18}$ are independently selected from the group consisting of H and methyl.

In some embodiments, at least one $R^6$ is —CH$_2$NH$_2$.

In some embodiments, $R^6$ is —CH$_2$NH$_2$.

In some embodiments, at least one $R^6$ is —CH$_2$NMe$_2$.

In some embodiments, $R^6$ is —CH$_2$NMe$_2$.

In some embodiments, at least one $R^6$ is —CH$_2$NHR$^{18}$ and $R^{18}$ is —(C$_{1-4}$ alkyl).

In some embodiments, at least one $R^6$ is —CH$_2$NHR$^{18}$ and $R^{18}$ is —(C$_{1-3}$ alkyl).

In some embodiments, at least one $R^6$ is —CH$_2$NHR$^{18}$ and $R^{18}$ is —(C$_{1-2}$ alkyl).

In some embodiments, $R^6$ is —CH$_2$NHR$^{18}$ and $R^{18}$ is —(C$_{1-2}$ alkyl).

In some embodiments, at least one $R^6$ is —CH$_2$NHR$^{18}$ and $R^{18}$ is —CH$_2$aryl optionally substituted with 1-2 (e.g., 1) $R^{21}$.

In some embodiments, at least one $R^6$ is —CH$_2$NHR$^{18}$ and $R^{18}$ is —CH$_2$phenyl optionally substituted with 1-2 (e.g., 1) $R^{21}$.

In some embodiments, $R^6$ is —CH$_2$NHR$^{18}$ and $R^{18}$ is —CH$_2$phenyl optionally substituted with 1-2 (e.g., 1) $R^{21}$.

In some embodiments, at least one $R^6$ is —CH$_2$NHR$^{18}$ and $R^{18}$ is —CH$_2$carbocyclyl optionally substituted with 1-2 (e.g., 1) $R^{22}$.

In some embodiments, at least one $R^6$ is —CH$_2$NHR$^{18}$ and $R^{18}$ is —CH$_2$cyclopropyl optionally substituted with 1-2 (e.g., 1) $R^{22}$.

In some embodiments, $R^6$ is —CH$_2$NHR$^{18}$ and $R^{18}$ is —CH$_2$cyclopropyl optionally substituted with 1-2 (e.g., 1) $R^{22}$.

In some embodiments, at least one $R^6$ is —CH$_2$NHR$^{18}$ and $R^{18}$ is —CH$_2$cyclobutyl optionally substituted with 1-2 (e.g., 1) $R^{22}$.

In some embodiments, $R^6$ is —CH$_2$NHR$^{18}$ and $R^{18}$ is —CH$_2$cyclobutyl optionally substituted with 1-2 (e.g., 1) $R^{22}$.

In some embodiments, at least one $R^6$ is —CH$_2$NHR$^{18}$ and $R^{18}$ is —CH$_2$cyclopentyl optionally substituted with 1-2 (e.g., 1) $R^{22}$.

In some embodiments, $R^6$ is —$CH_2NHR^{18}$ and $R^{18}$ is —$CH_2$cyclopentyl optionally substituted with 1-2 (e.g., 1) $R^{22}$.

In some embodiments, at least one $R^6$ is —$CH_2NHR^{18}$ and $R^{18}$ is —$CH_2$cyclohexyl optionally substituted with 1-2 (e.g., 1) $R^{22}$.

In some embodiments, $R^6$ is —$CH_2NHR^{18}$ and $R^{18}$ is —$CH_2$cyclohexyl optionally substituted with 1-2 (e.g., 1) $R^{22}$.

In some embodiments, at least one $R^6$ is —$OR^{24}$.
In some embodiments, at least one $R^6$ is —OH.
In some embodiments, $R^6$ is —OH.
In some embodiments, at least one $R^6$ is —($C_{1-4}$ alkylene)$OR^{24}$.
In some embodiments, $R^6$ is —($C_{1-4}$ alkylene)$OR^{24}$.
In some embodiments, $R^6$ is —($C_{1-3}$ alkylene)$OR^{24}$.
In some embodiments, $R^6$ is —($C_{1-2}$ alkylene)$OR^{24}$.
In some embodiments, $R^6$ is —$CH_2OR^{24}$.
In some embodiments, $R^6$ is —$CH_2OH$.
In some embodiments, at least one $R^6$ is —$OR^{24}$ and $R^{24}$ is —($C_{1-3}$ alkyl).
In some embodiments, at least one $R^6$ is —$OR^{24}$ and $R^{24}$ is —($C_{1-2}$ alkyl).
In some embodiments, at least one $R^6$ is —OMe.
In some embodiments, $R^6$ is —OMe.
In some embodiments, at least one $R^6$ is —$OR^{24}$ and $R^{24}$ is -heterocyclyl optionally substituted with 1-2 (e.g., 1) $R^{23}$.
In some embodiments, $R^6$ is —$OR^{24}$ and $R^{24}$ is -heterocyclyl optionally substituted with 1-2 (e.g., 1) $R^{23}$.
In some embodiments, at least one $R^6$ is —$OR^{24}$ and $R^{24}$ is -carbocyclyl optionally substituted with 1-2 (e.g., 1) $R^{22}$.
In some embodiments, $R^6$ is —$OR^{24}$ and $R^{24}$ is -carbocyclyl optionally substituted with 1-2 (e.g., 1) $R^{22}$.
In some embodiments, at least one $R^6$ is —$OR^{24}$ and $R^{24}$ is —($C_{1-4}$ alkylene)heterocyclyl optionally substituted with 1-2 (e.g., 1) $R^{23}$.
In some embodiments, at least one $R^6$ is —$OR^{24}$ and $R^{24}$ is —($CH_2CH_2$)heterocyclyl optionally substituted with 1-2 (e.g., 1) $R^{23}$.
In some embodiments, $R^6$ is —$OR^{24}$ and $R^{24}$ is —($CH_2CH_2$)heterocyclyl optionally substituted with 1-2 (e.g., 1) $R^{23}$.
In some embodiments, at least one $R^6$ is —$OR^{24}$ and $R^{24}$ is —($C_{1-4}$ alkylene)$NR^{25}R^{26}$ and $R^{25}$ and $R^{26}$ are independently —($C_{1-4}$ alkyl).
In some embodiments, at least one $R^6$ is —$OR^{24}$ and $R^{24}$ is —($CH_2CH_2$)$NR^{25}R^{26}$ and $R^{25}$ and $R^{26}$ are independently —($C_{1-2}$ alkyl).
In some embodiments, at least one $R^6$ is —$OR^{24}$ and $R^{24}$ is —($CH_2CH_2$)$NMe_2$.
In some embodiments, $R^6$ is —$OR^{24}$ and $R^{24}$ is —($CH_2CH_2$)$NMe_2$.
In some embodiments, at least one $R^6$ is —$OR^{24}$ and $R^{24}$ is —($C_{1-4}$ alkylene)aryl optionally substituted with 1-2 (e.g., 1) $R^{21}$, and each $R^{21}$ is independently halide.
In some embodiments, at least one $R^6$ is —$OR^{24}$ and $R^{24}$ is —($CH_2CH_2$)phenyl optionally substituted with 1-2 (e.g., 1) $R^{21}$, and each $R^{21}$ is independently halide.
In some embodiments, $R^6$ is —$OR^{24}$ and $R^{24}$ is —($CH_2CH_2$)phenyl optionally substituted with 1-2 (e.g., 1) $R^{21}$, and each $R^{21}$ is independently halide.
In some embodiments, at least one $R^6$ is —$OR^{24}$ and $R^{24}$ is —($CH_2$)phenyl optionally substituted with 1-2 (e.g., 1) $R^{21}$, and each $R^{21}$ is independently halide.
In some embodiments, $R^6$ is —$OR^{24}$ and $R^{24}$ is —($CH_2$)phenyl optionally substituted with 1-2 (e.g., 1) $R^{21}$, and each $R^{21}$ is independently halide.

In some embodiments, each $R^7$ is independently selected from the group consisting of —($C_{1-4}$ alkyl), —($C_{2-4}$ alkenyl), —($C_{2-4}$ alkynyl), halide, —$CF_3$, and —CN.
In some embodiments, each $R^7$ is independently selected from the group consisting of methyl, F, Cl, —$CF_3$, and —CN.
In some embodiments, at least one $R^7$ is —($C_{1-4}$ alkyl).
In some embodiments, at least one $R^7$ is —($C_{1-3}$ alkyl).
In some embodiments, at least one $R^7$ is —($C_{1-2}$ alkyl).
In some embodiments, at least one $R^7$ is methyl.
In some embodiments, at least one $R^7$ is halide.
In some embodiments, at least one $R^7$ is F.
In some embodiments, each $R^8$ is independently selected from the group consisting of —($C_{1-6}$ alkyl), —($C_{2-6}$ alkenyl), —($C_{2-6}$ alkynyl), halide, —$CF_3$, —$OCH_3$, —CN, and —C(=O)$R^{19}$.
In some embodiments, each $R^8$ is independently selected from the group consisting of methyl, F, Cl, —$CF_3$, —$OCH_3$, —CN, and —C(=O)Me.
In some embodiments, at least one $R^8$ is halide.
In some embodiments, at least one $R^8$ is F.
In some embodiments, at least one $R^8$ is —($C_{1-4}$ alkyl).
In some embodiments, at least one $R^8$ is —($C_{1-3}$ alkyl).
In some embodiments, at least one $R^8$ is —($C_{1-2}$ alkyl).
In some embodiments, at least one $R^8$ is methyl.
In some embodiments, $R^8$ is methyl.
In some embodiments, at least one $R^8$ is —C(=O)($C_{1-3}$ alkyl).
In some embodiments, at least one $R^8$ is —C(=O)Me.
In some embodiments, $R^8$ is —C(=O)Me.
In some embodiments, each $R^9$ is independently selected from the group consisting of —($C_{1-6}$ alkyl), —($C_{2-6}$ alkenyl), —($C_{2-6}$ alkynyl), halide, —$CF_3$, —CN, and —$OCH_3$.
In some embodiments, each $R^9$ is independently selected from the group consisting of methyl, F, Cl, —$CF_3$, —CN, and —$OCH_3$.
In some embodiments, each $R^{10}$ is independently selected from the group consisting of —($C_{1-6}$ alkyl), —($C_{2-6}$ alkenyl), —($C_{2-6}$ alkynyl), halide, —$CF_3$, —CN, —($C_{1-6}$ alkylene)$_p$$NHSO_2R^{19}$, —($C_{2-6}$ alkenylene)$_p$$NHSO_2R^{19}$, —($C_{2-6}$ alkynylene)$_p$$NHSO_2R^{19}$, —$NR^{15}$($C_{1-6}$ alkylene)$NR^{15}R^{16}$, —$NR^{15}$($C_{2-6}$ alkenylene)$NR^{15}R^{16}$, —$NR^{15}$($C_{2-6}$ alkynylene)$NR^{15}R^{16}$, —($C_{1-6}$ alkylene)$_p$$NR^{15}R^{16}$, —($C_{2-6}$ alkenylene)$_p$$NR^{15}R^{16}$, —($C_2$-alklkynylene)$_p$$NR^{15}R^{16}$, and —$OR^{27}$.
In some embodiments, each $R^{11}$ is independently selected from the group consisting of amino, —($C_{1-4}$ alkyl), —($C_{2-4}$ alkenyl), —($C_{2-4}$ alkynyl), halide, —$CF_3$, and —CN.
In some embodiments, each $R^{11}$ is independently selected from the group consisting of amino, methyl, F, Cl, —$CF_3$, and —CN.
In some embodiments, each $R^{12}$ is independently selected from the group consisting of —($C_{1-4}$ alkyl), —($C_{2-4}$ alkenyl), —($C_{2-4}$ alkynyl), halide, —$CF_3$, and —CN.
In some embodiments, each $R^{12}$ is independently selected from the group consisting of methyl, F, Cl, —$CF_3$, and —CN.
In some embodiments, each $R^{13}$ is independently selected from the group consisting of —($C_{1-4}$ alkyl), —($C_{2-4}$ alkenyl), —($C_{2-4}$ alkynyl), halide, —$CF_3$, and —CN.
In some embodiments, each $R^{13}$ is independently selected from the group consisting of methyl, F, Cl, —$CF_3$, and —CN.
In some embodiments, each $R^{14}$ is independently selected from the group consisting of —($C_{1-9}$ alkyl), —($C_{1-4}$ haloalkyl), —($C_{2-9}$ alkenyl), —($C_{2-9}$ alkynyl), -heteroaryl optionally substituted with 1-4 (e.g., 1-3, 1-2, 1) $R^{20}$, -aryl optionally substituted with 1-5 (e.g., 1-4, 1-3, 1-2, 1) $R^{21}$, —CH$_2$aryl optionally substituted with 1-5 (e.g., 1-4, 1-3, 1-2, 1) $R^{21}$, -carbocyclyl optionally substituted with 1-12 (e.g., 1-11, 1-10, 1-9, 1-8, 1-7, 1-6, 1-5, 1-4, 1-3, 1-2, 1) $R^{22}$, —CH$_2$carbocyclyl optionally substituted with 1-12 (e.g., 1-11, 1-10, 1-9, 1-8, 1-7, 1-6, 1-5, 1-4, 1-3, 1-2, 1) $R^{22}$, —(C$_{1-4}$ alkylene)$_p$NR$^{25}$R$^{26}$, —(C$_{2-4}$ alkenylene)$_p$NR$^{25}$R$^{26}$, —(C$_{2-4}$ alkynylene)$_p$NR$^{25}$R$^{26}$, -heterocyclyl optionally substituted with 1-10 (e.g., 1-9, 1-8, 1-7, 1-6, 1-5, 1-4, 1-3, 1-2, 1) $R^{23}$, and —CH$_2$heterocyclyl optionally substituted with 1-10 (e.g., 1-9, 1-8, 1-7, 1-6, 1-5, 1-4, 1-3, 1-2, 1) $R^{23}$.

In some embodiments, each $R^{15}$ is independently selected from the group consisting of H, —(C$_{1-6}$ alkyl), —(C$_{2-6}$ alkenyl), and —(C$_{2-6}$ alkynyl).

In some embodiments, each $R^{16}$ is independently selected from the group consisting of H, —(C$_{1-6}$ alkyl), —(C$_{2-6}$ alkenyl), —(C$_{2-6}$ alkynyl), —CH$_2$aryl optionally substituted with 1-5 (e.g., 1-4, 1-3, 1-2, 1) $R^{21}$, and —CH$_2$carbocyclyl optionally substituted with 1-12 (e.g., 1-11, 1-10, 1-9, 1-8, 1-7, 1-6, 1-5, 1-4, 1-3, 1-2, 1) $R^{22}$.

In some embodiments, each $R^{17}$ is independently selected from the group consisting of H, —(C$_{1-6}$ alkyl), —(C$_{2-6}$ alkenyl), and —(C$_{2-6}$ alkynyl).

In some embodiments, each $R^{18}$ is independently selected from the group consisting of H, —(C$_{1-6}$ alkyl), —(C$_{2-6}$ alkenyl), —(C$_{2-6}$ alkynyl), —CH$_2$aryl optionally substituted with 1-5 (e.g., 1-4, 1-3, 1-2, 1) $R^{21}$ and —CH$_2$carbocyclyl optionally substituted with 1-12 (e.g., 1-11, 1-10, 1-9, 1-8, 1-7, 1-6, 1-5, 1-4, 1-3, 1-2, 1) $R^{22}$.

In some embodiments, each $R^{19}$ is independently selected from the group consisting of —(C$_{1-6}$ alkyl), —(C$_{2-6}$ alkenyl), and —(C$_{2-6}$ alkynyl).

In some embodiments, each $R^{20}$ is independently selected from the group consisting of —(C$_{1-4}$ alkyl), —(C$_{2-4}$ alkenyl), —(C$_{2-4}$ alkynyl), halide, —CF$_3$, and —CN.

In some embodiments, each $R^{20}$ is independently selected from the group consisting of methyl, F, Cl, —CF$_3$, and —CN.

In some embodiments, each $R^{21}$ is independently selected from the group consisting of —(C$_{1-4}$ alkyl), —(C$_{2-4}$ alkenyl), —(C$_{2-4}$ alkynyl), halide, —CF$_3$, and —CN.

In some embodiments, each $R^{21}$ is independently selected from the group consisting of methyl, F, Cl, —CF$_3$, and —CN.

In some embodiments, each $R^{22}$ is independently selected from the group consisting of —(C$_{1-4}$ alkyl), —(C$_{2-4}$ alkenyl), —(C$_{2-4}$ alkynyl), halide, —CF$_3$, and —CN.

In some embodiments, each $R^{22}$ is independently selected from the group consisting of methyl, F, Cl, —CF$_3$, and —CN.

In some embodiments, each $R^{23}$ is independently selected from the group consisting of —(C$_{1-4}$ alkyl), —(C$_{2-4}$ alkenyl), —(C$_{2-4}$ alkynyl), halide, —CF$_3$, and —CN.

In some embodiments, each $R^{23}$ is independently selected from the group consisting of methyl, F, Cl, —CF$_3$, and —CN.

In some embodiments, $R^{24}$ is selected from the group consisting of H, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 (e.g., 1-9, 1-8, 1-7, 1-6, 1-5, 1-4, 1-3, 1-2, 1) $R^{23}$, —(C$_{2-4}$ alkenylene)$_p$heterocyclyl optionally substituted with 1-10 (e.g., 1-9, 1-8, 1-7, 1-6, 1-5, 1-4, 1-3, 1-2, 1) $R^{23}$, —(C$_{2-4}$ alkynylene)$_p$heterocyclyl optionally substituted with 1-10 (e.g., 1-9, 1-8, 1-7, 1-6, 1-5, 1-4, 1-3, 1-2, 1) $R^{23}$, —(C$_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{22}$, —(C$_{2-4}$ alkenylene)$_p$carbocyclyl optionally substituted with 1-12 (e.g., 1-11, 1-10, 1-9, 1-8, 1-7, 1-6, 1-5, 1-4, 1-3, 1-2, 1) $R^{22}$, —(C$_{2-4}$ alkynylene)$_p$carbocyclyl optionally substituted with 1-12 (e.g., 1-11, 1-10, 1-9, 1-8, 1-7, 1-6, 1-5, 1-4, 1-3, 1-2, 1) $R^{22}$, —(C$_{1-4}$ alkylene)$_p$aryl optionally substituted with 1-5 (e.g., 1-4, 1-3, 1-2, 1) $R^{21}$, —(C$_{2-4}$ alkenylene)$_p$aryl optionally substituted with 1-5 (e.g., 1-4, 1-3, 1-2, 1) $R^{21}$, —(C$_{2-4}$ alkynylene)$_p$aryl optionally substituted with 1-5 (e.g., 1-4, 1-3, 1-2, 1) $R^{21}$, —(C$_{1-6}$ alkylene)$_p$NR$^{25}$R$^{26}$, —(C$_{2-4}$ alkenylene)$_p$NR$^{25}$R$^{26}$, and —(C$_{2-4}$ alkynylene)$_p$NR$^{25}$R$^{26}$.

In some embodiments, each $R^{25}$ is independently selected from the group consisting of H, —(C$_{1-6}$ alkyl), —(C$_{2-6}$ alkenyl), and —(C$_{2-6}$ alkynyl).

In some embodiments, each $R^{26}$ is independently selected from the group consisting of H, —(C$_{1-6}$ alkyl), —(C$_{2-6}$ alkenyl), and —(C$_{2-6}$ alkynyl).

In some embodiments, $R^{27}$ is selected from the group consisting of H, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 (e.g., 1-9, 1-8, 1-7, 1-6, 1-5, 1-4, 1-3, 1-2, 1) $R^{23}$, —(C$_{2-4}$ alkenylene)$_p$heterocyclyl optionally substituted with 1-10 (e.g., 1-9, 1-8, 1-7, 1-6, 1-5, 1-4, 1-3, 1-2, 1) $R^{23}$, —(C$_{2-4}$ alkynylene)$_p$heterocyclyl optionally substituted with 1-10 (e.g., 1-9, 1-8, 1-7, 1-6, 1-5, 1-4, 1-3, 1-2, 1) $R^{23}$, —(C$_{1-6}$ alkylene)$_p$NR$^{25}$R$^{26}$, —(C$_{2-6}$ alkenylene)NR$^{25}$R$^{26}$, and —(C$_{2-6}$ alkynylene)NR$^{25}$R$^{26}$.

In some embodiments, each p is independently an integer of 0 or 1.

In some embodiments, p is 0.

In some embodiments, p is 1.

Illustrative compounds of Formula (I) are shown in Table 1.

TABLE 1

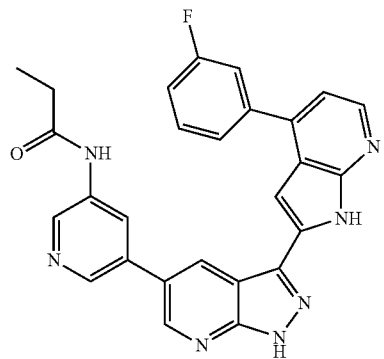 [SMILES: CCC(=O)Nc1cncc(-c2cnc3[nH]nc(-c4cc5c(-c6cccc(F)c6)ccnc5[nH]4)c3c2)c1]

1

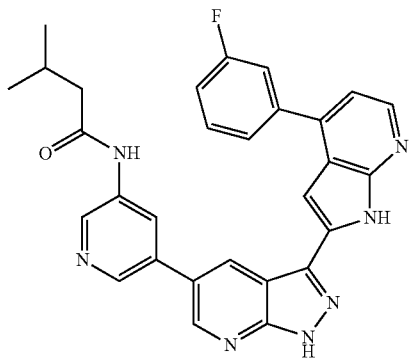 [SMILES: CC(C)CC(=O)Nc1cncc(-c2cnc3[nH]nc(-c4cc5c(-c6cccc(F)c6)ccnc5[nH]4)c3c2)c1]

2

TABLE 1-continued
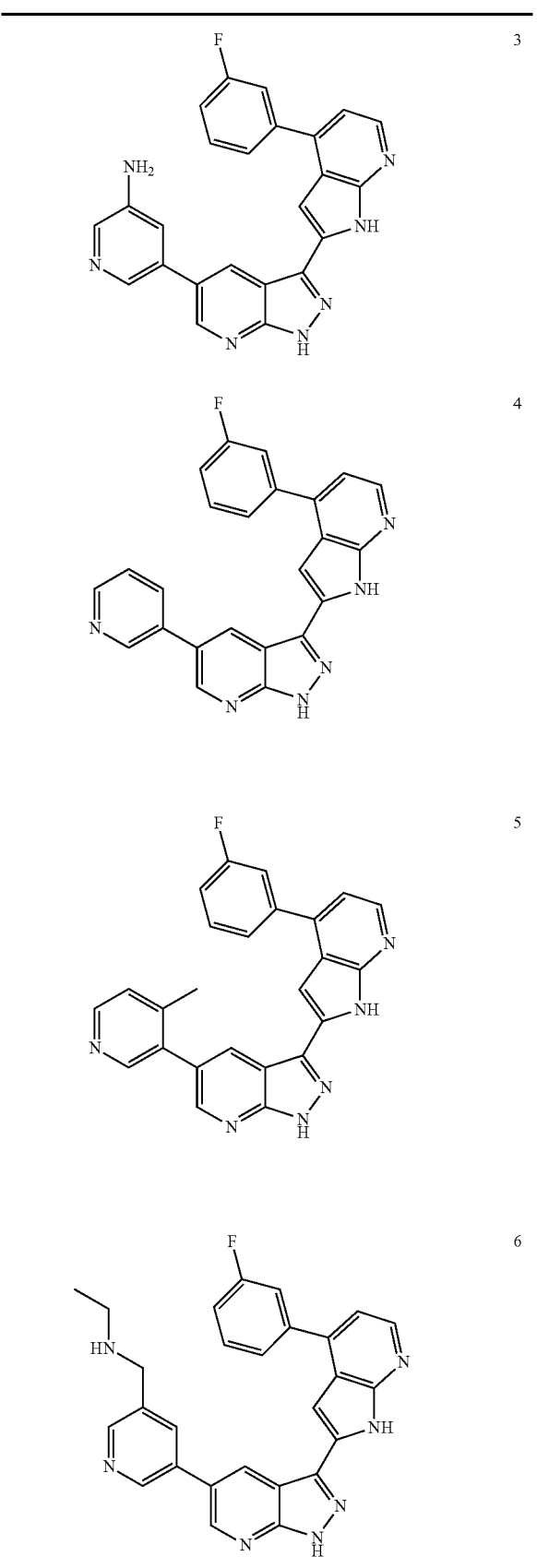
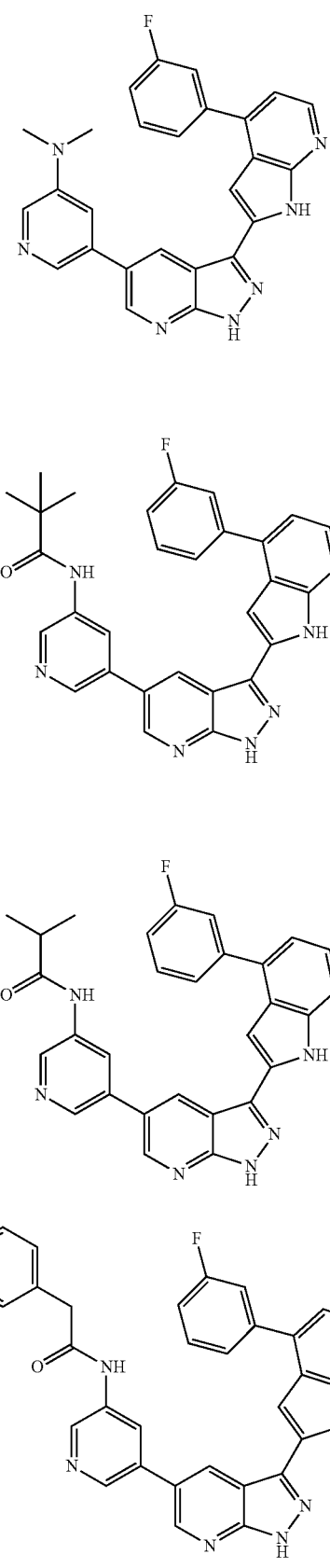

TABLE 1-continued
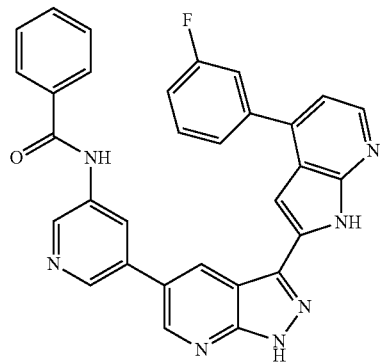 [SMILES: O=C(Nc1cncc(-c2cnc3[nH]nc(-c4cc5c(-c6cccc(F)c6)ccnc5[nH]4)c3c2)c1)c1ccccc1]
11
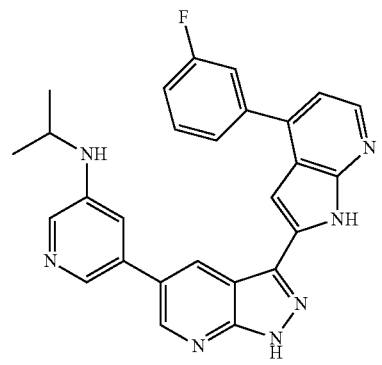 [SMILES: CC(C)Nc1cncc(-c2cnc3[nH]nc(-c4cc5c(-c6cccc(F)c6)ccnc5[nH]4)c3c2)c1]
12
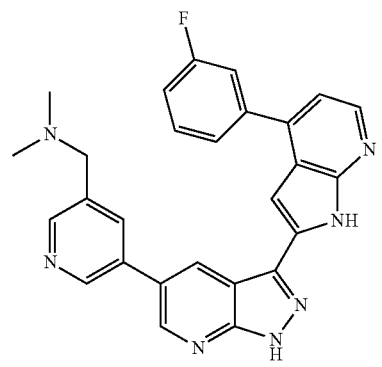 [SMILES: CN(C)Cc1cncc(-c2cnc3[nH]nc(-c4cc5c(-c6cccc(F)c6)ccnc5[nH]4)c3c2)c1]
13
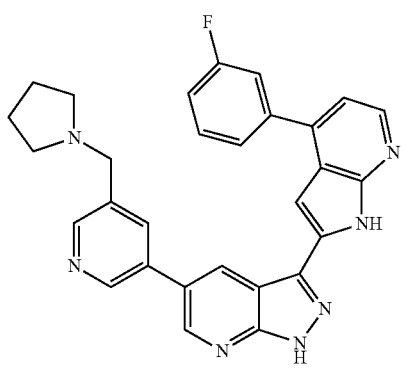 [SMILES: Fc1cccc(-c2ccnc3[nH]c(-c4n[nH]c5ncc(-c6cncc(CN7CCCC7)c6)cc45)cc23)c1]
14
TABLE 1-continued
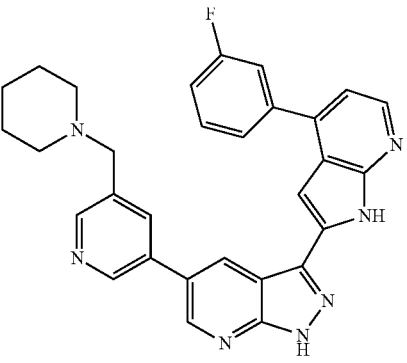
15
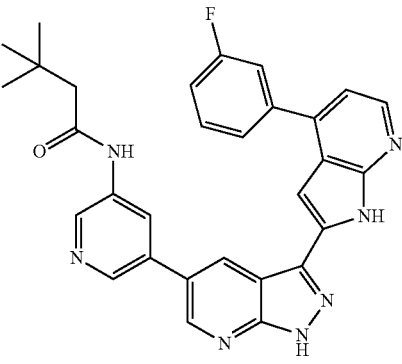 [SMILES: CC(C)(C)CC(=O)Nc1cncc(-c2cnc3[nH]nc(-c4cc5c(-c6cccc(F)c6)ccnc5[nH]4)c3c2)c1]
16
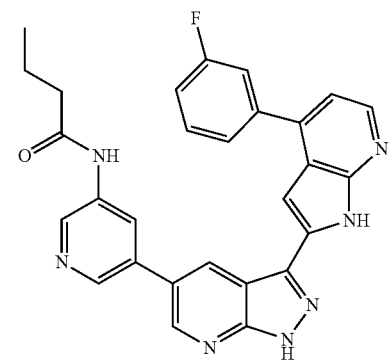 [SMILES: CCCC(=O)Nc1cncc(-c2cnc3[nH]nc(-c4cc5c(-c6cccc(F)c6)ccnc5[nH]4)c3c2)c1]
17
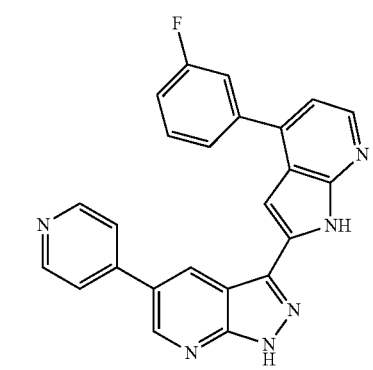 [SMILES: Fc1cccc(-c2ccnc3[nH]c(-c4n[nH]c5ncc(-c6ccncc6)cc45)cc23)c1]
18

TABLE 1-continued
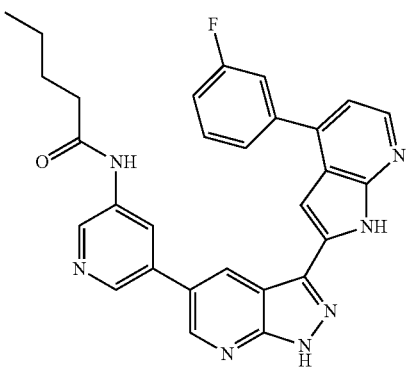 [SMILES: CCCCC(=O)Nc1cncc(-c2cnc3[nH]nc(-c4cc5c(-c6cccc(F)c6)ccnc5[nH]4)c3c2)c1] 19
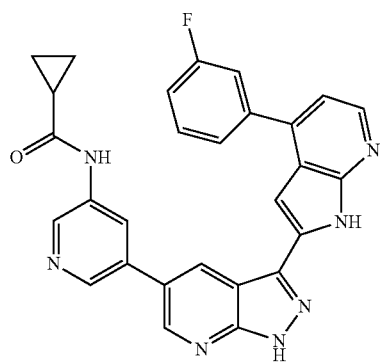 [SMILES: O=C(Nc1cncc(-c2cnc3[nH]nc(-c4cc5c(-c6cccc(F)c6)ccnc5[nH]4)c3c2)c1)C1CC1] 20
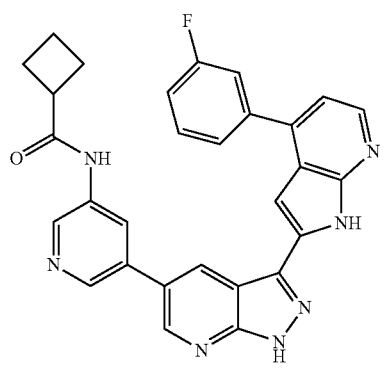 [SMILES: O=C(Nc1cncc(-c2cnc3[nH]nc(-c4cc5c(-c6cccc(F)c6)ccnc5[nH]4)c3c2)c1)C1CCC1] 21
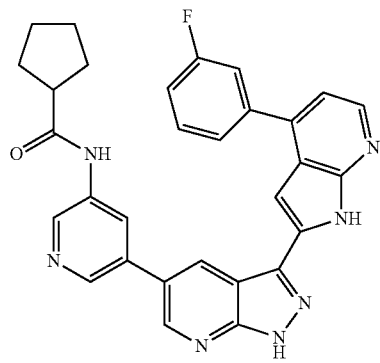 [SMILES: O=C(Nc1cncc(-c2cnc3[nH]nc(-c4cc5c(-c6cccc(F)c6)ccnc5[nH]4)c3c2)c1)C1CCCC1] 22
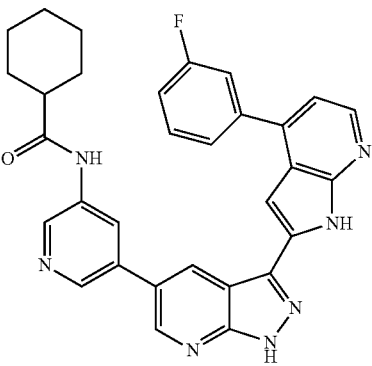 [SMILES: O=C(Nc1cncc(-c2cnc3[nH]nc(-c4cc5c(-c6cccc(F)c6)ccnc5[nH]4)c3c2)c1)C1CCCCC1] 23
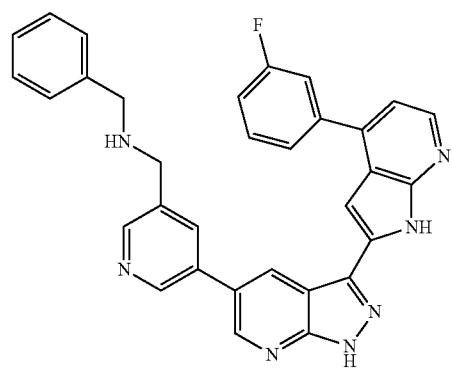 [SMILES: Fc1cccc(-c2ccnc3[nH]c(-c4n[nH]c5ncc(-c6cncc(CNCc7ccccc7)c6)cc45)cc23)c1] 24
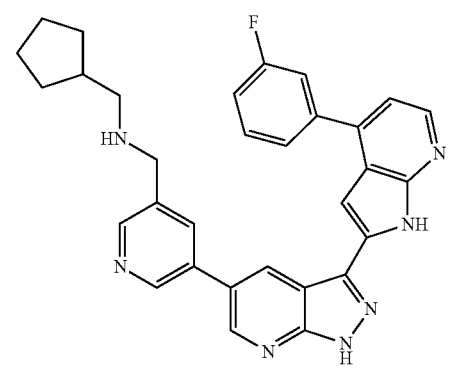 [SMILES: Fc1cccc(-c2ccnc3[nH]c(-c4n[nH]c5ncc(-c6cncc(CNCC7CCCC7)c6)cc45)cc23)c1] 25
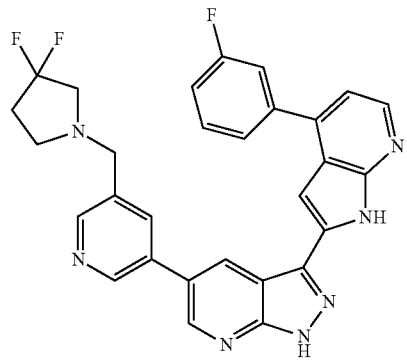 [SMILES: Fc1cccc(-c2ccnc3[nH]c(-c4n[nH]c5ncc(-c6cncc(CN7CCC(F)(F)C7)c6)cc45)cc23)c1] 26

TABLE 1-continued
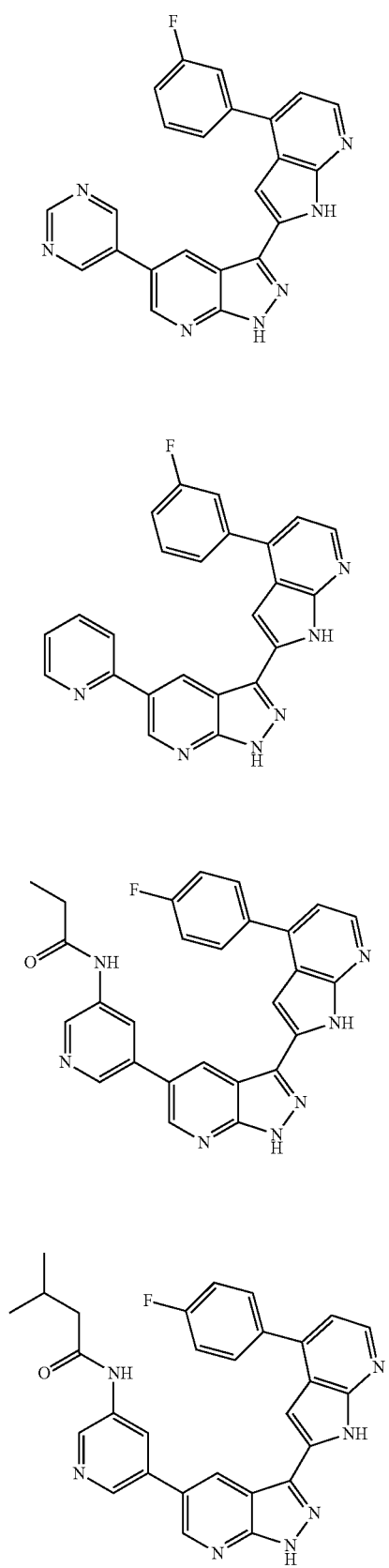
TABLE 1-continued
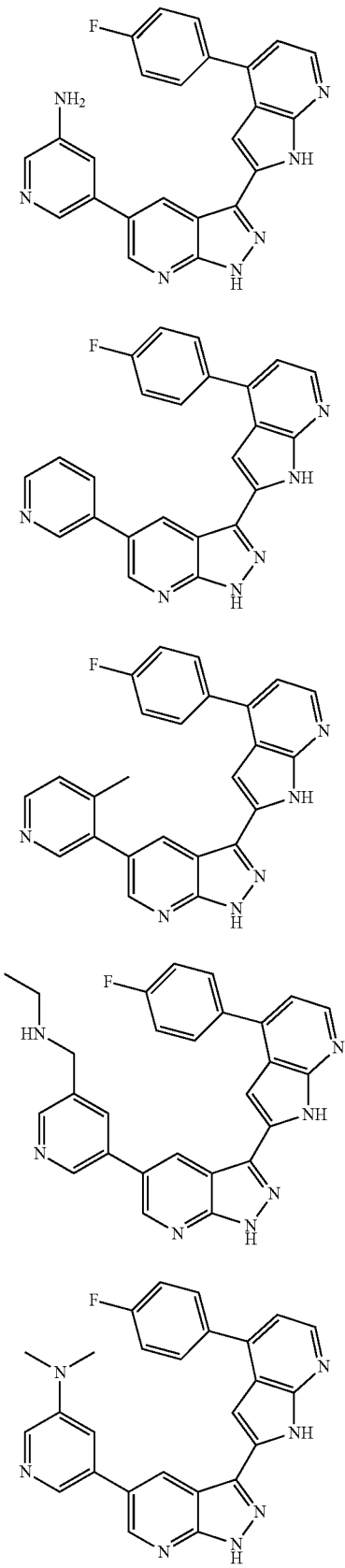

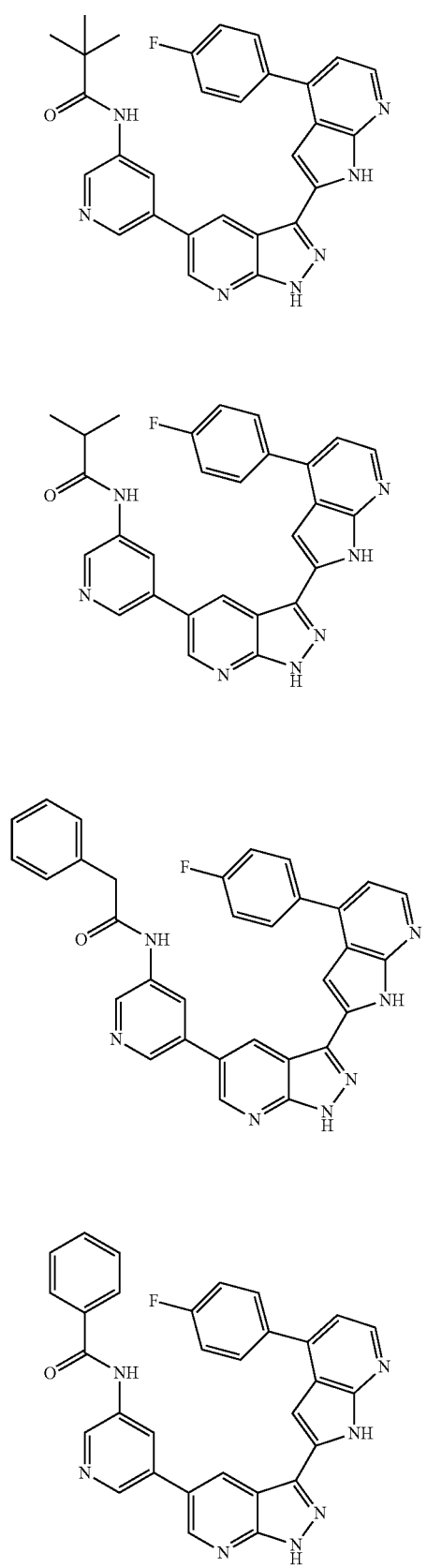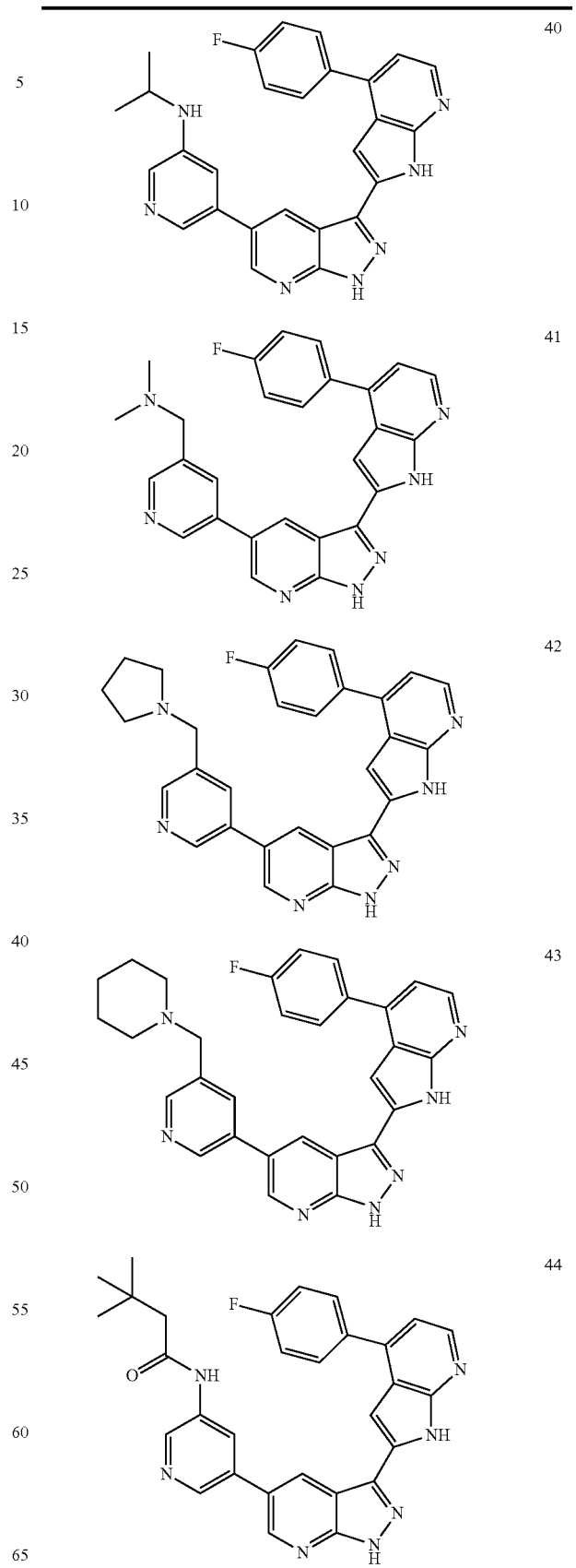

TABLE 1-continued
| | |
|---|---|
| 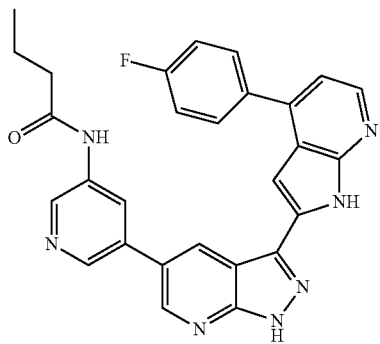 [SMILES: CCCC(=O)Nc1cncc(-c2cnc3[nH]nc(-c4cc5c(-c6ccc(F)cc6)ccnc5[nH]4)c3c2)c1] 45 | 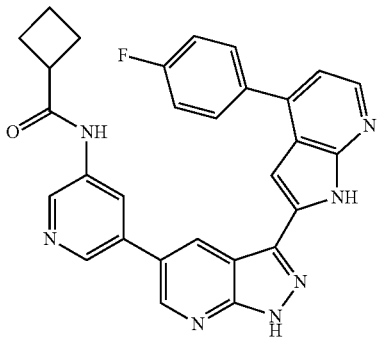 49 |
| 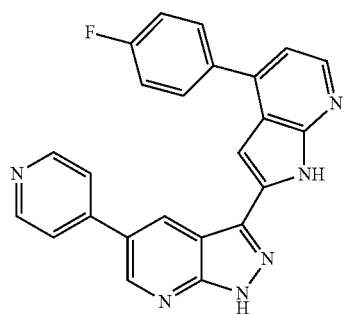 [SMILES: Fc1ccc(-c2ccnc3[nH]c(-c4n[nH]c5ncc(-c6ccncc6)cc45)cc23)cc1] 46 | 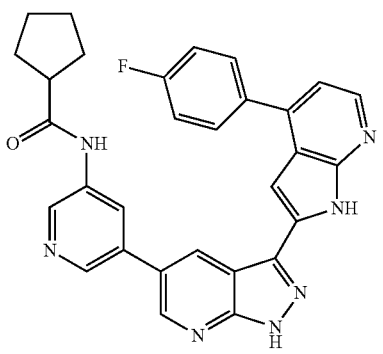 50 |
| 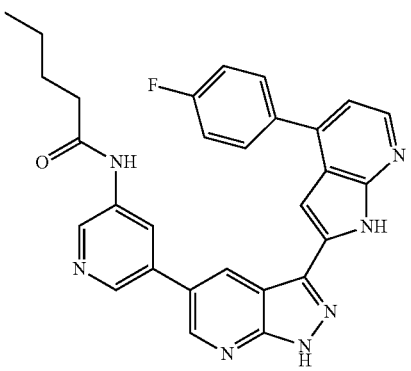 [SMILES: CCCCC(=O)Nc1cncc(-c2cnc3[nH]nc(-c4cc5c(-c6ccc(F)cc6)ccnc5[nH]4)c3c2)c1] 47 | 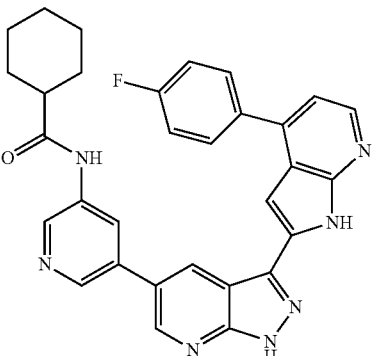 51 |
| 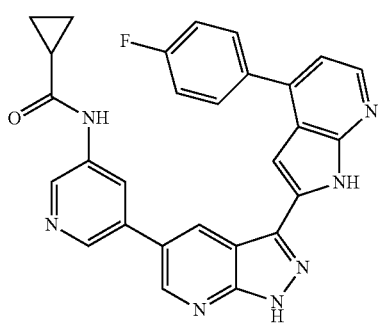 [SMILES: O=C(Nc1cncc(-c2cnc3[nH]nc(-c4cc5c(-c6ccc(F)cc6)ccnc5[nH]4)c3c2)c1)C1CC1] 48 | 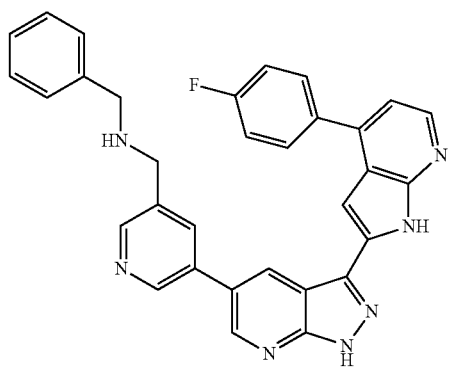 [SMILES: Fc1ccc(-c2ccnc3[nH]c(-c4n[nH]c5ncc(-c6cncc(CNCc7ccccc7)c6)cc45)cc23)cc1] 52 |

TABLE 1-continued
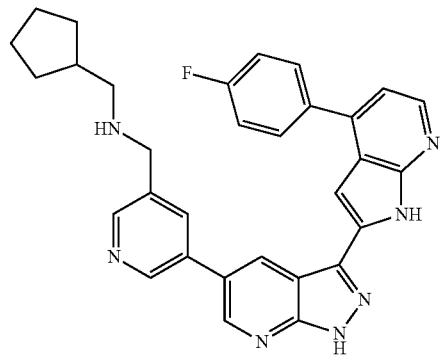 [SMILES: Fc1ccc(-c2ccnc3[nH]c(-c4n[nH]c5ncc(-c6cncc(CNCC7CCCC7)c6)cc45)cc23)cc1]
53
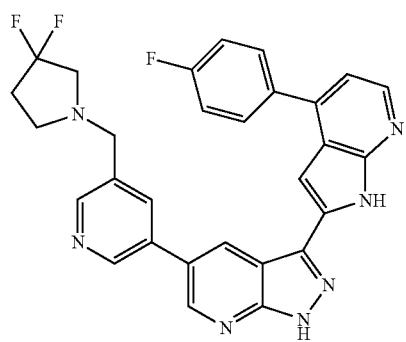 [SMILES: Fc1ccc(-c2ccnc3[nH]c(-c4n[nH]c5ncc(-c6cncc(CN7CCC(F)(F)C7)c6)cc45)cc23)cc1]
54
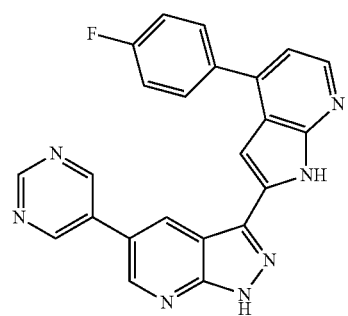 [SMILES: Fc1ccc(-c2ccnc3[nH]c(-c4n[nH]c5ncc(-c6cncnc6)cc45)cc23)cc1]
55
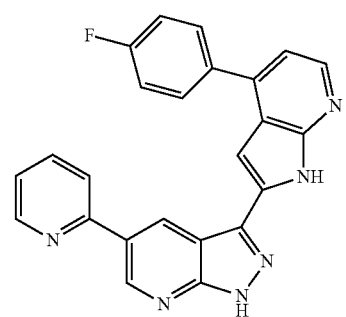 [SMILES: Fc1ccc(-c2ccnc3[nH]c(-c4n[nH]c5ncc(-c6ccccn6)cc45)cc23)cc1]
56
TABLE 1-continued
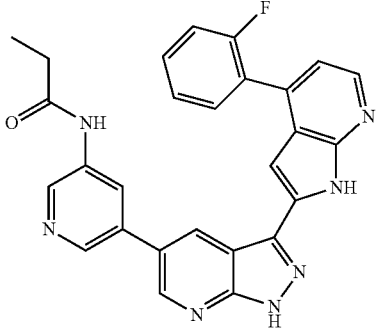 [SMILES: CCC(=O)Nc1cncc(-c2cnc3[nH]nc(-c4cc5c(-c6ccccc6F)ccnc5[nH]4)c3c2)c1]
57
58
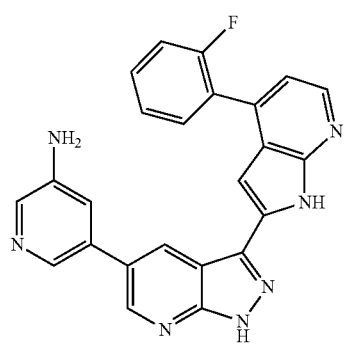 [SMILES: Nc1cncc(-c2cnc3[nH]nc(-c4cc5c(-c6ccccc6F)ccnc5[nH]4)c3c2)c1]
59
60

TABLE 1-continued
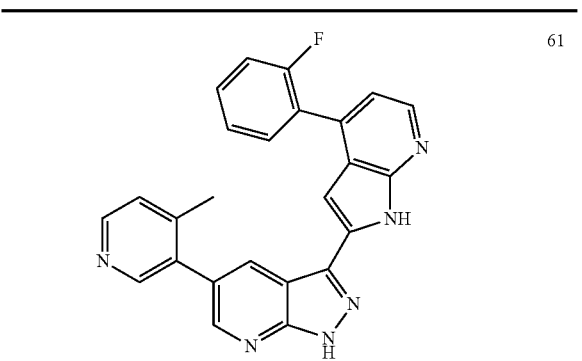
61
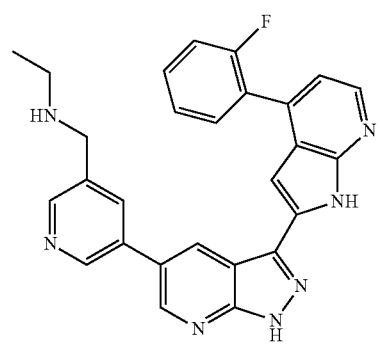 [SMILES: CCNCc1cncc(-c2cnc3[nH]nc(-c4cc5c(-c6ccccc6F)ccnc5[nH]4)c3c2)c1]
62
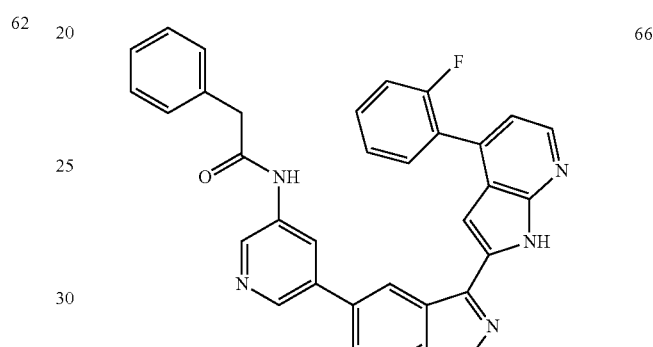
65
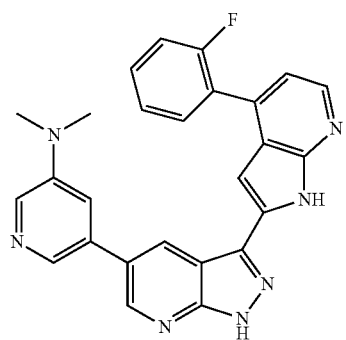 [SMILES: CN(C)c1cncc(-c2cnc3[nH]nc(-c4cc5c(-c6ccccc6F)ccnc5[nH]4)c3c2)c1]
63
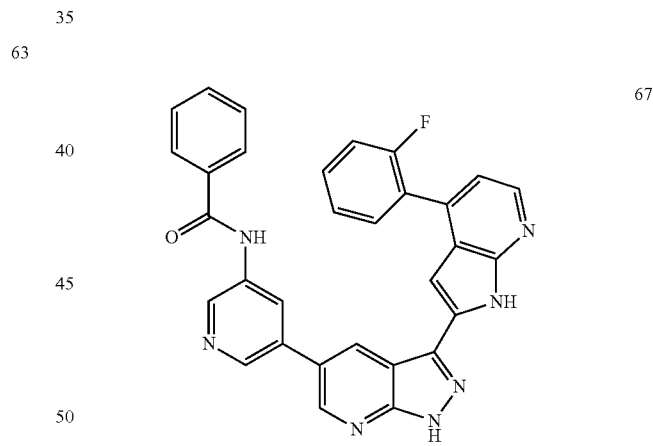
66
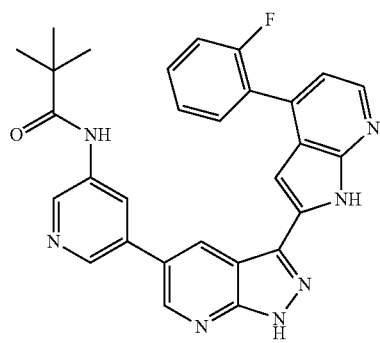 [SMILES: CC(C)(C)C(=O)Nc1cncc(-c2cnc3[nH]nc(-c4cc5c(-c6ccccc6F)ccnc5[nH]4)c3c2)c1]
64
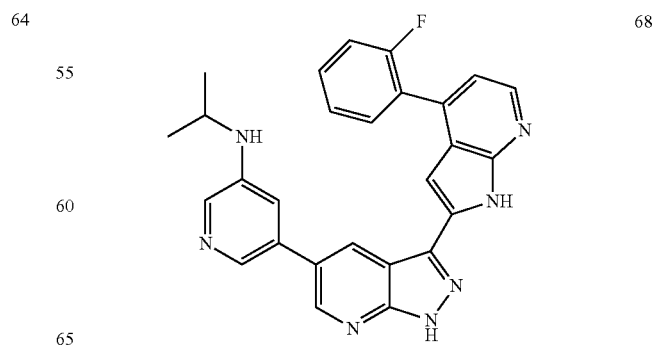
67
68

TABLE 1-continued
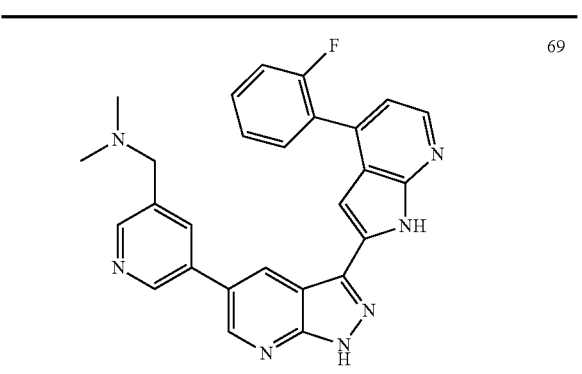
69
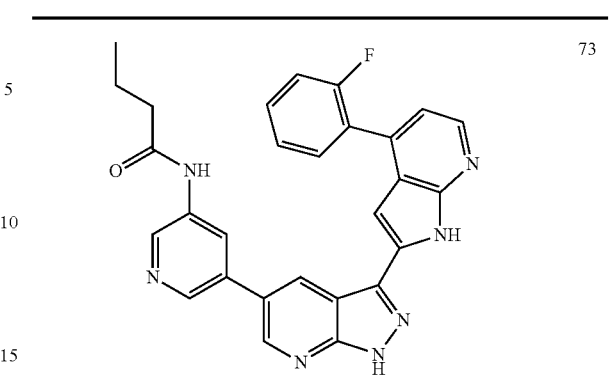
73
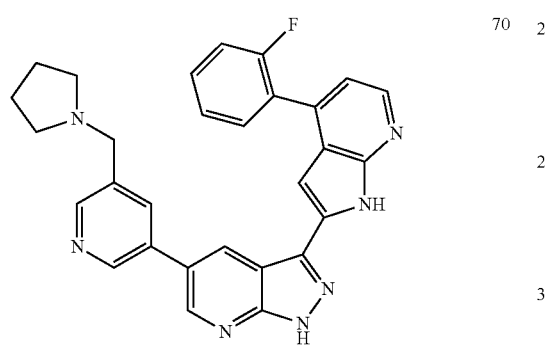
70
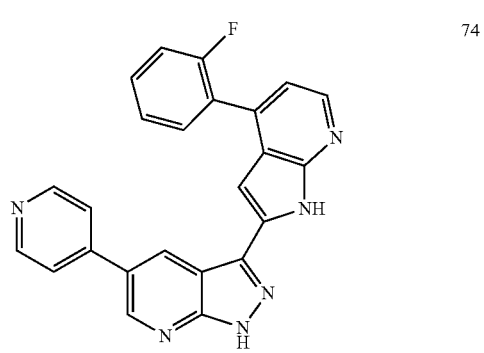
74
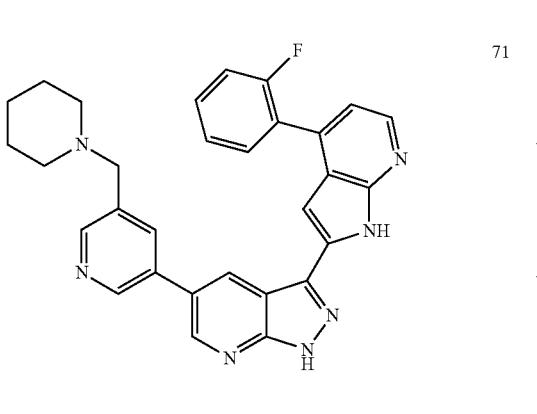
71
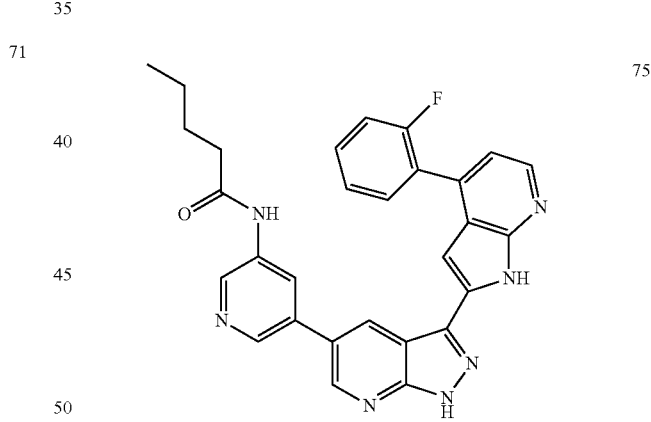
75
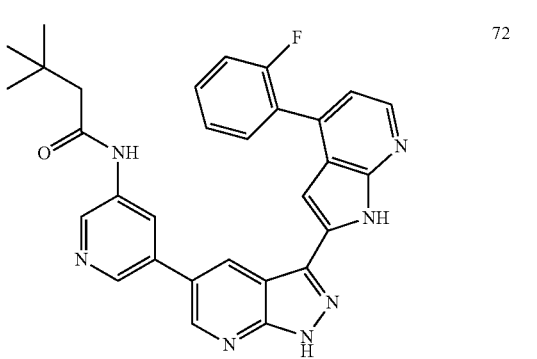
72
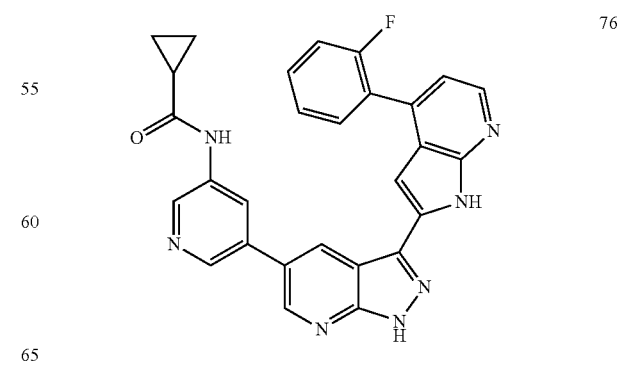
76

TABLE 1-continued
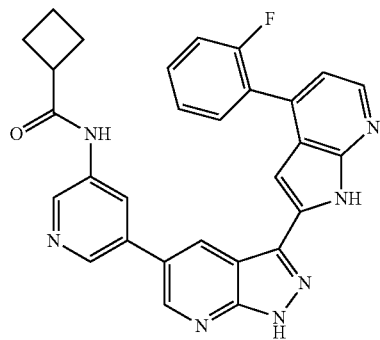 [SMILES: O=C(Nc1cncc(-c2cnc3[nH]nc(-c4cc5c(-c6ccccc6F)ccnc5[nH]4)c3c2)c1)C1CCC1]
77
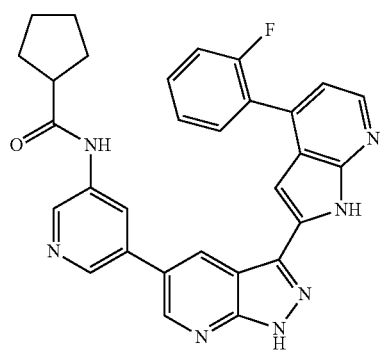 [SMILES: O=C(Nc1cncc(-c2cnc3[nH]nc(-c4cc5c(-c6ccccc6F)ccnc5[nH]4)c3c2)c1)C1CCCC1]
78
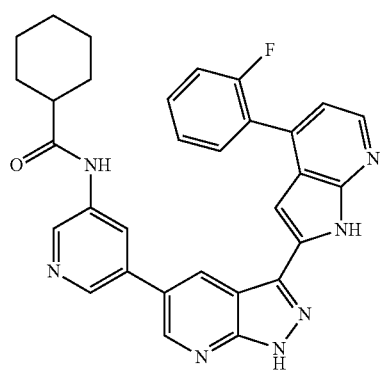 [SMILES: O=C(Nc1cncc(-c2cnc3[nH]nc(-c4cc5c(-c6ccccc6F)ccnc5[nH]4)c3c2)c1)C1CCCCC1]
79
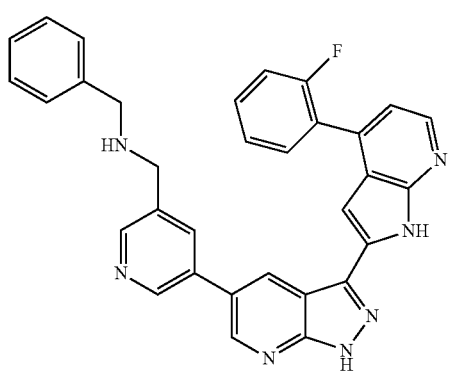 [SMILES: Fc1ccccc1-c1ccnc2[nH]c(-c3n[nH]c4ncc(-c5cncc(CNCc6ccccc6)c5)cc34)cc12]
80
TABLE 1-continued
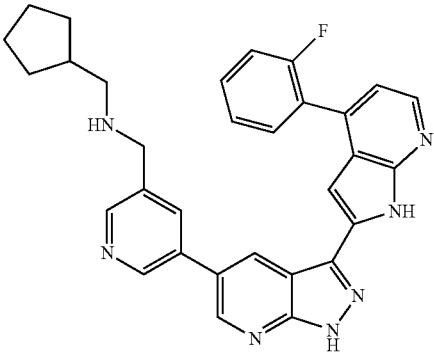 [SMILES: Fc1ccccc1-c1ccnc2[nH]c(-c3n[nH]c4ncc(-c5cncc(CNCC6CCCC6)c5)cc34)cc12]
81
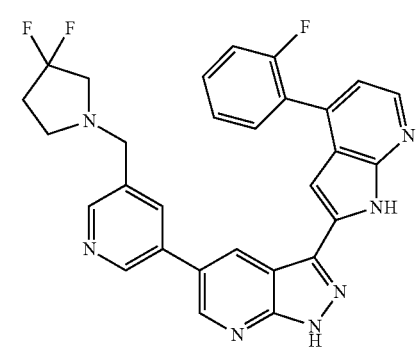 [SMILES: Fc1ccccc1-c1ccnc2[nH]c(-c3n[nH]c4ncc(-c5cncc(CN6CCC(F)(F)C6)c5)cc34)cc12]
82
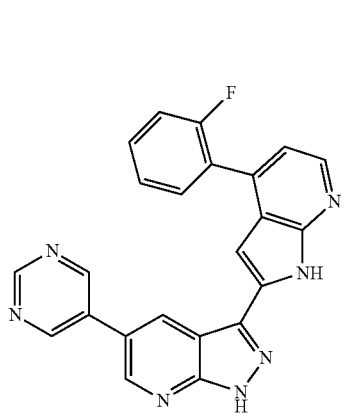 [SMILES: Fc1ccccc1-c1ccnc2[nH]c(-c3n[nH]c4ncc(-c5cncnc5)cc34)cc12]
83
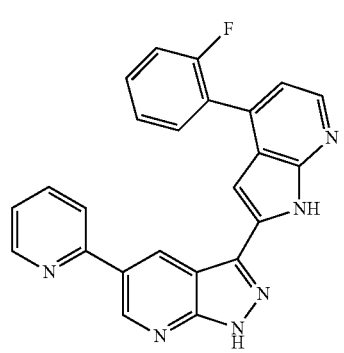 [SMILES: Fc1ccccc1-c1ccnc2[nH]c(-c3n[nH]c4ncc(-c5ccccn5)cc34)cc12]
84

TABLE 1-continued
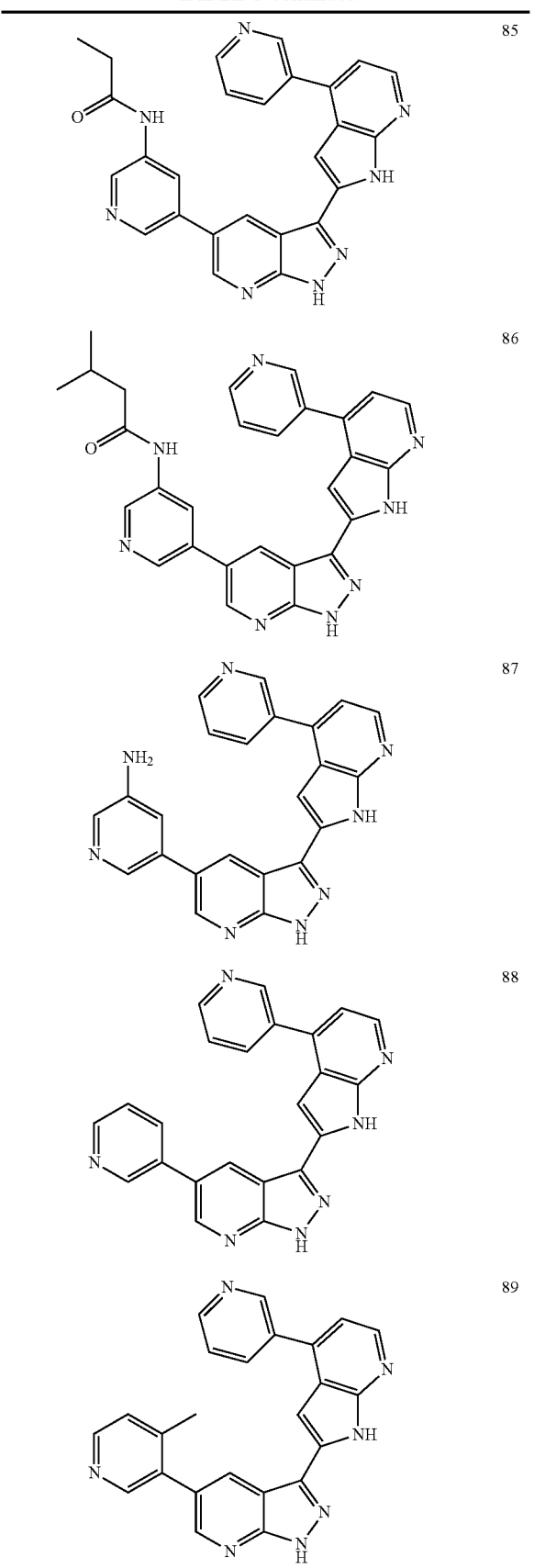
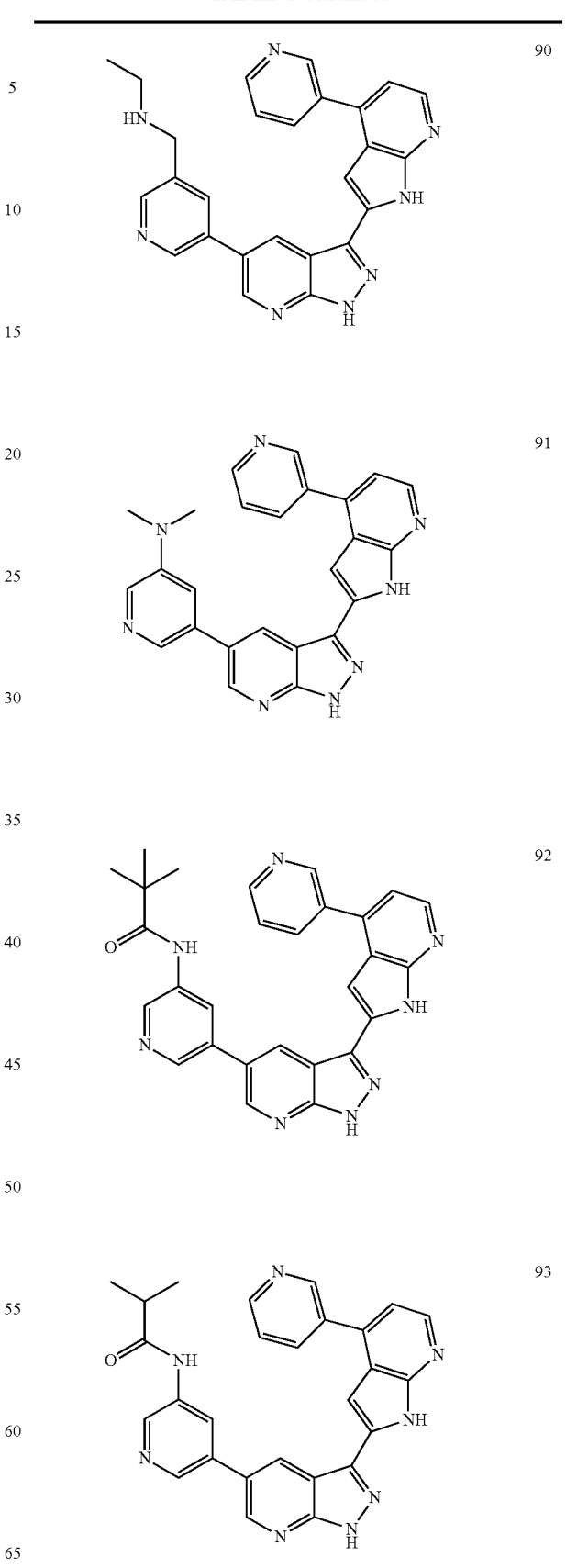

TABLE 1-continued
94 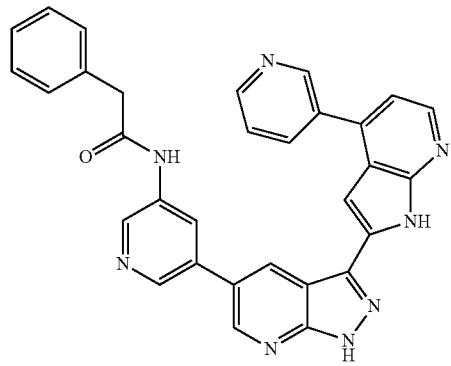 [SMILES: O=C(Cc1ccccc1)Nc1cncc(-c2cnc3[nH]nc(-c4cc5c(-c6cccnc6)ccnc5[nH]4)c3c2)c1]
95 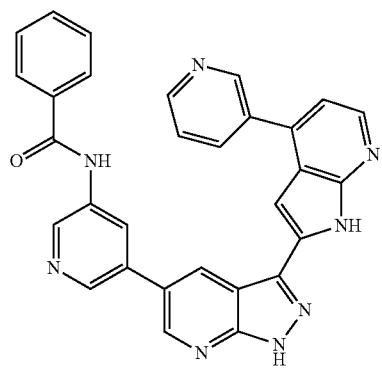 [SMILES: O=C(Nc1cncc(-c2cnc3[nH]nc(-c4cc5c(-c6cccnc6)ccnc5[nH]4)c3c2)c1)c1ccccc1]
96 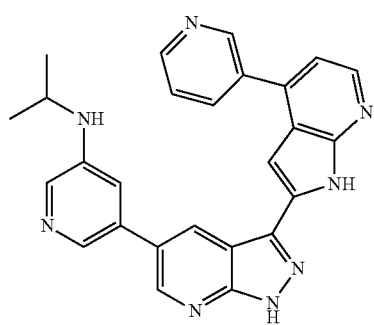 [SMILES: CC(C)Nc1cncc(-c2cnc3[nH]nc(-c4cc5c(-c6cccnc6)ccnc5[nH]4)c3c2)c1]
97 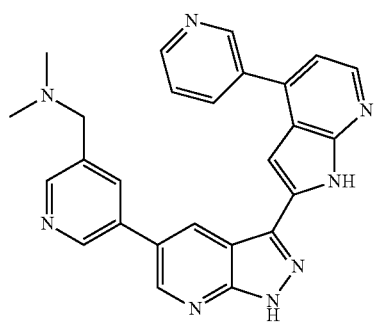 [SMILES: CN(C)Cc1cncc(-c2cnc3[nH]nc(-c4cc5c(-c6cccnc6)ccnc5[nH]4)c3c2)c1]
TABLE 1-continued
98 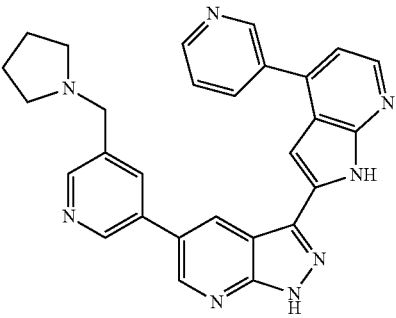 [SMILES: c1cncc(-c2ccnc3[nH]c(-c4n[nH]c5ncc(-c6cncc(CN7CCCC7)c6)cc45)cc23)c1]
99 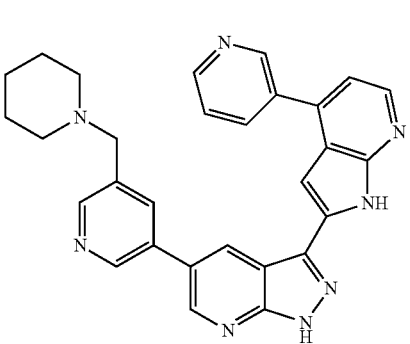 [SMILES: c1cncc(-c2ccnc3[nH]c(-c4n[nH]c5ncc(-c6cncc(CN7CCCCC7)c6)cc45)cc23)c1]
100 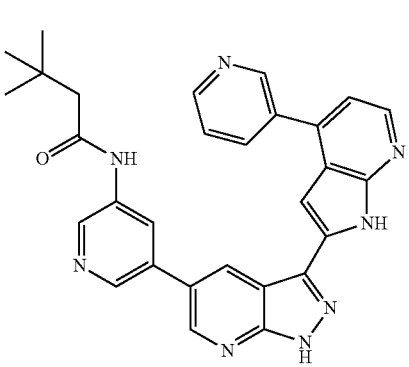 [SMILES: CC(C)(C)CC(=O)Nc1cncc(-c2cnc3[nH]nc(-c4cc5c(-c6cccnc6)ccnc5[nH]4)c3c2)c1]
101 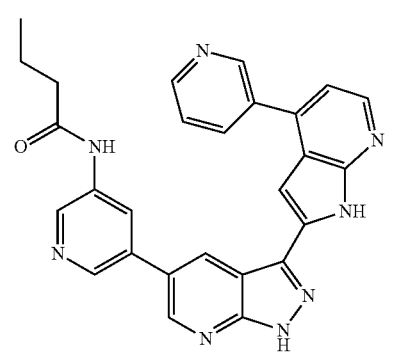 [SMILES: CCCC(=O)Nc1cncc(-c2cnc3[nH]nc(-c4cc5c(-c6cccnc6)ccnc5[nH]4)c3c2)c1]

TABLE 1-continued
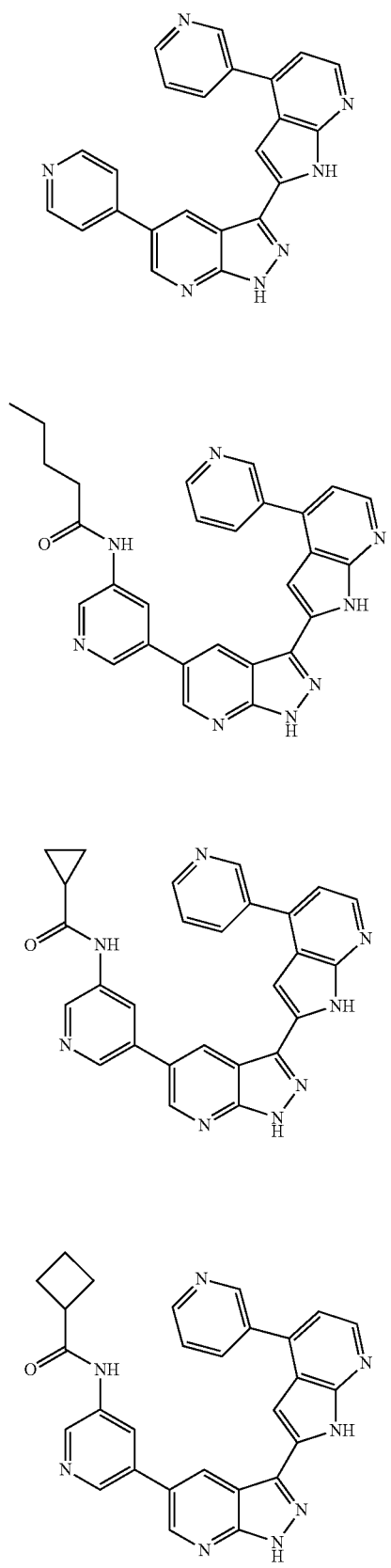
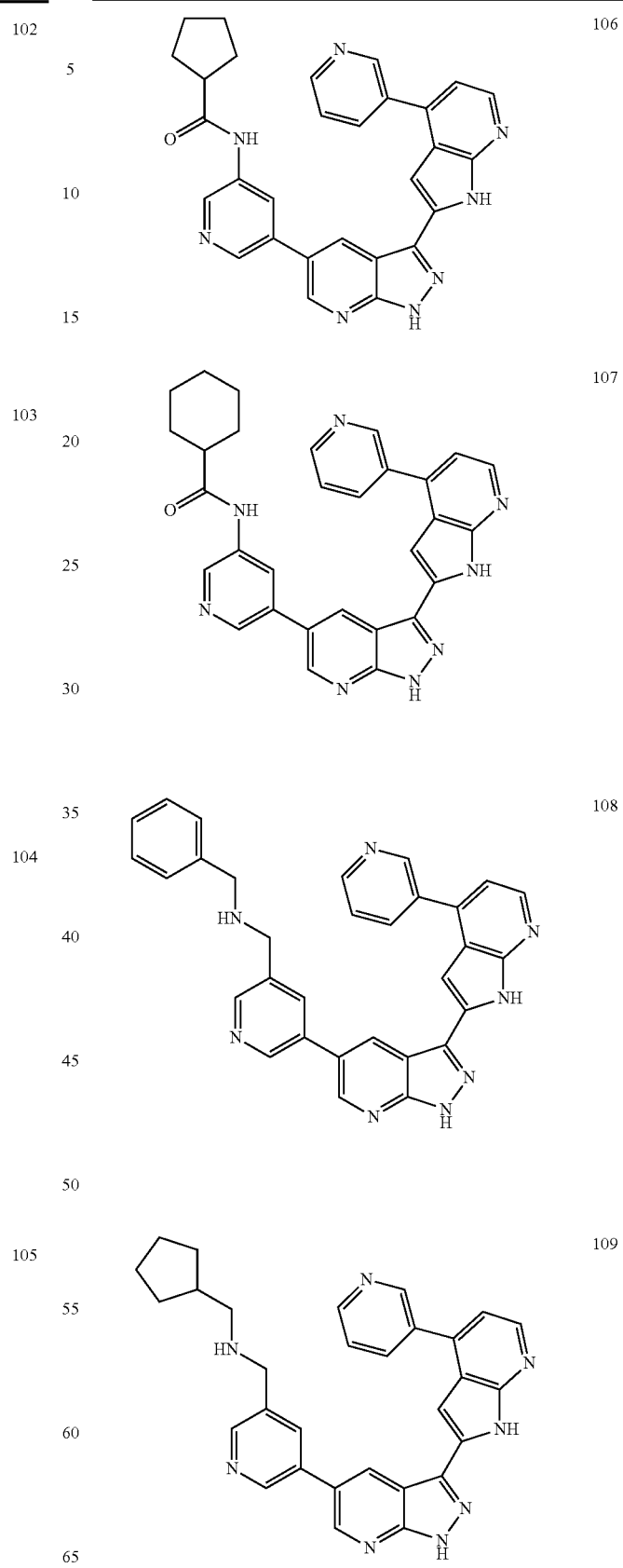

TABLE 1-continued
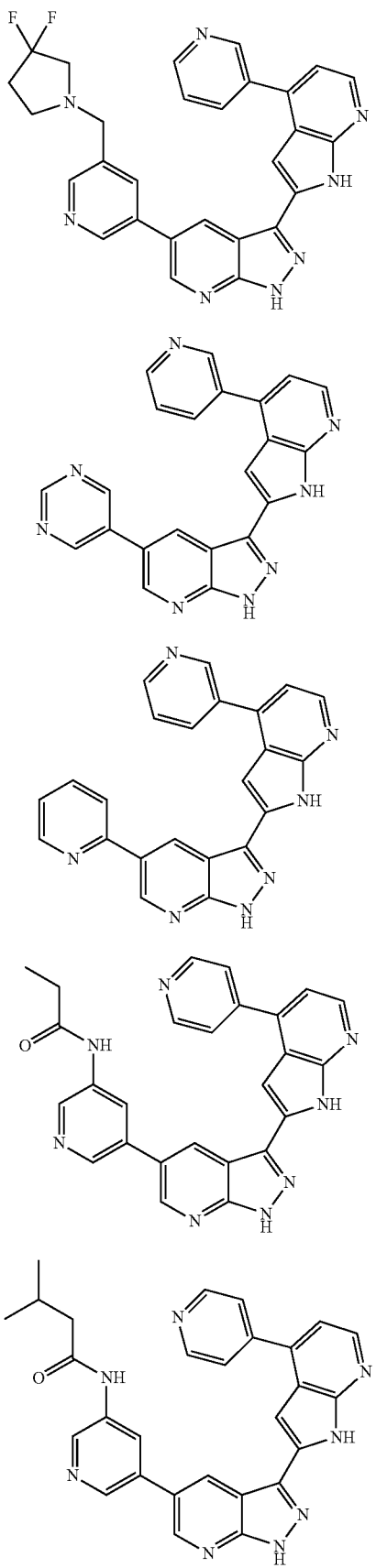
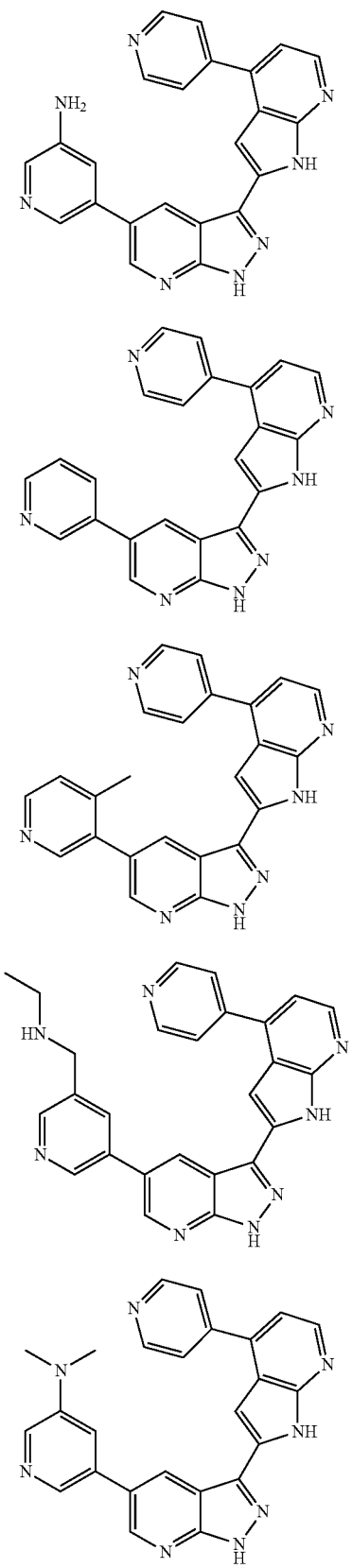

TABLE 1-continued
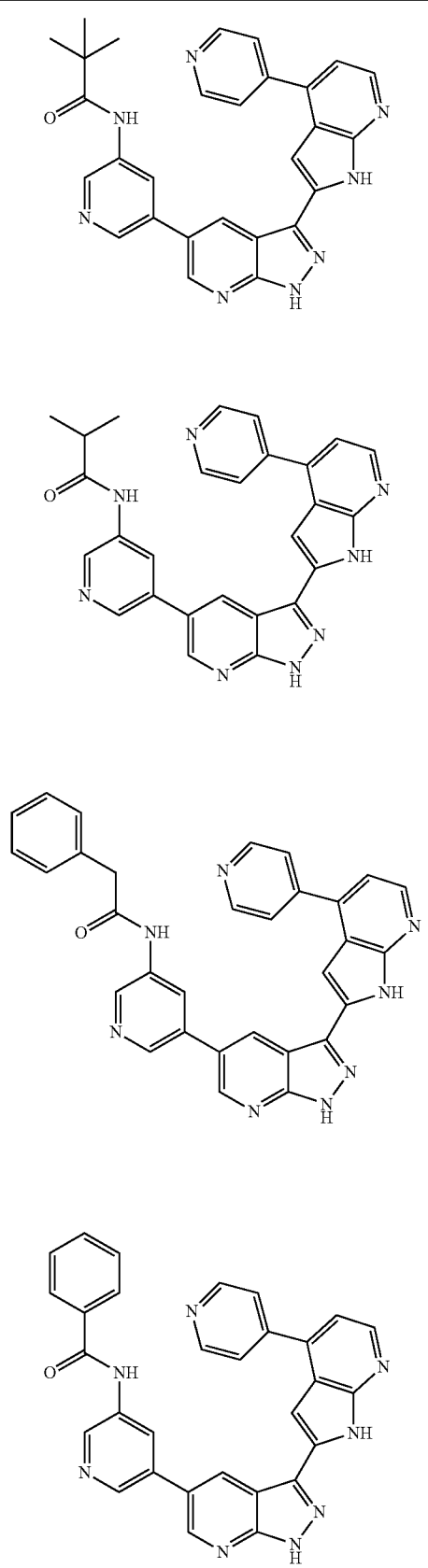
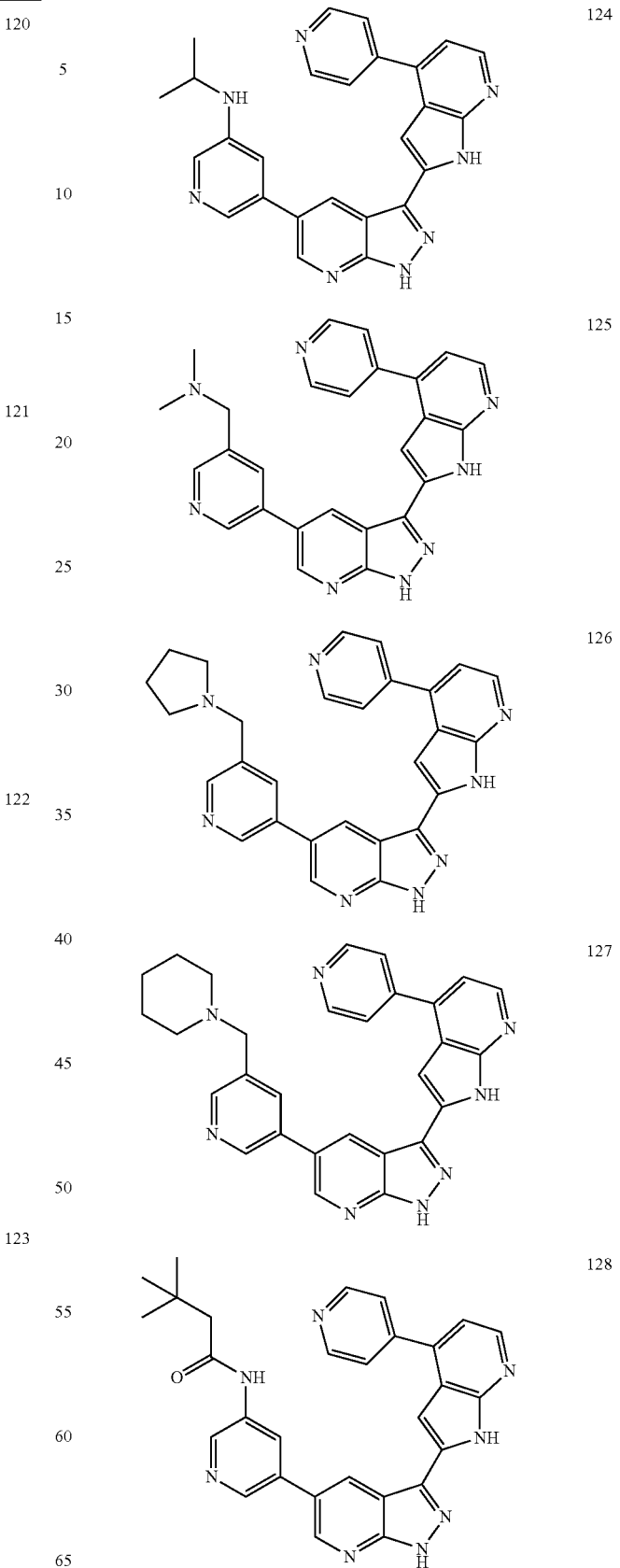

TABLE 1-continued
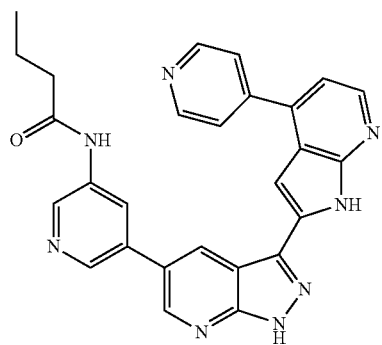
129
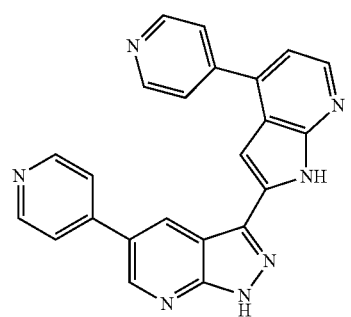 [SMILES: c1cc(-c2cnc3[nH]nc(-c4cc5c(-c6ccncc6)ccnc5[nH]4)c3c2)ccn1]
130
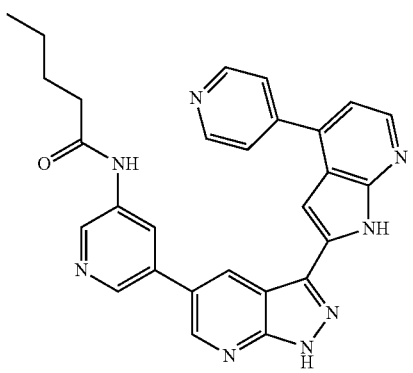 [SMILES: CCCCC(=O)Nc1cncc(-c2cnc3[nH]nc(-c4cc5c(-c6ccncc6)ccnc5[nH]4)c3c2)c1]
131
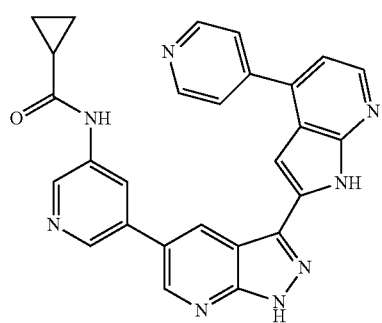 [SMILES: O=C(Nc1cncc(-c2cnc3[nH]nc(-c4cc5c(-c6ccncc6)ccnc5[nH]4)c3c2)c1)C1CC1]
132
TABLE 1-continued
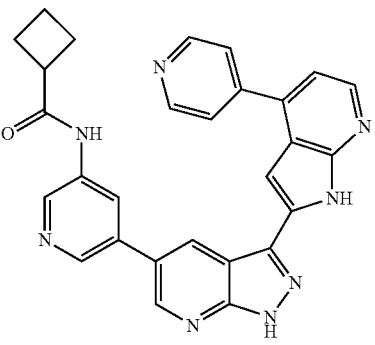 [SMILES: O=C(Nc1cncc(-c2cnc3[nH]nc(-c4cc5c(-c6ccncc6)ccnc5[nH]4)c3c2)c1)C1CCC1]
133
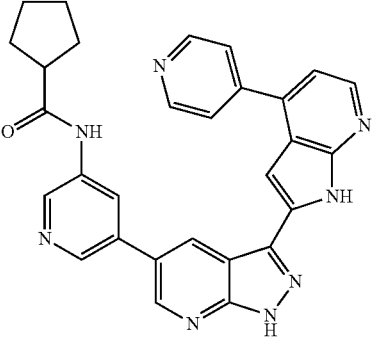 [SMILES: O=C(Nc1cncc(-c2cnc3[nH]nc(-c4cc5c(-c6ccncc6)ccnc5[nH]4)c3c2)c1)C1CCCC1]
134
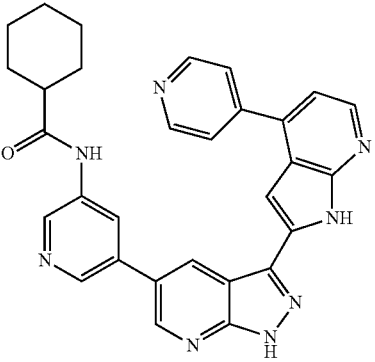 [SMILES: O=C(Nc1cncc(-c2cnc3[nH]nc(-c4cc5c(-c6ccncc6)ccnc5[nH]4)c3c2)c1)C1CCCCC1]
135
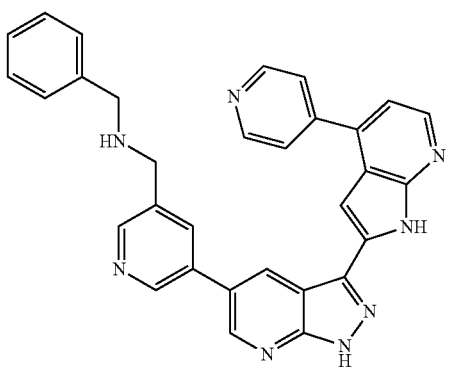 [SMILES: c1ccc(CNCc2cncc(-c3cnc4[nH]nc(-c5cc6c(-c7ccncc7)ccnc6[nH]5)c4c3)c2)cc1]
136

TABLE 1-continued
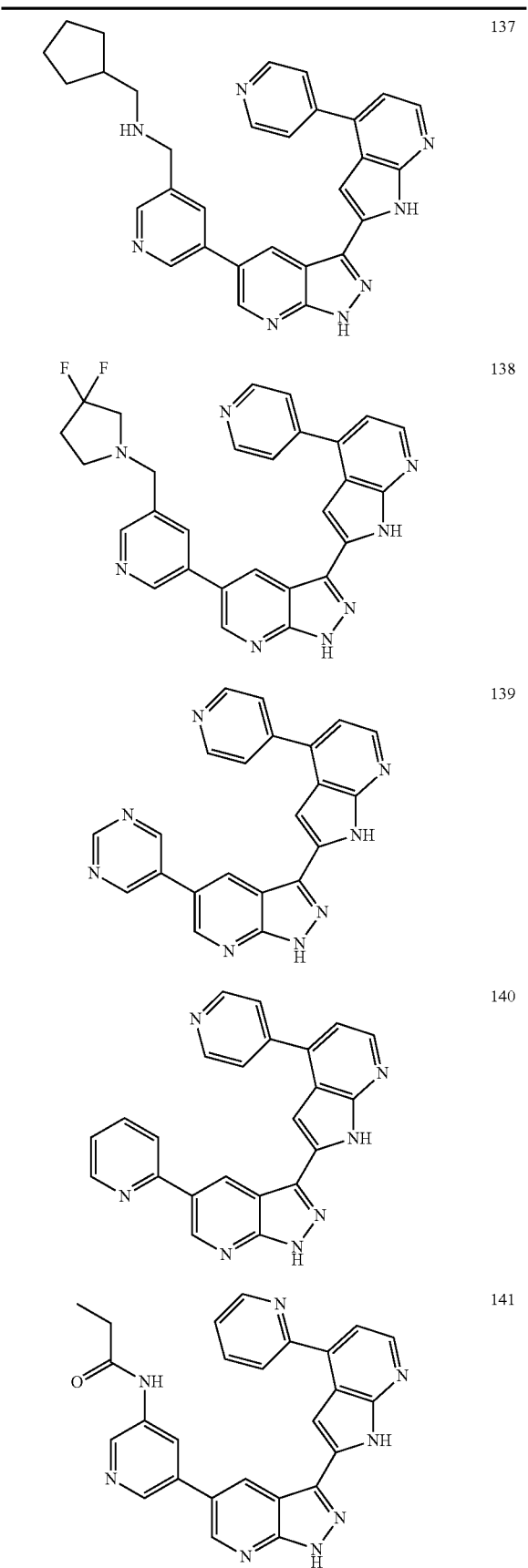

TABLE 1-continued
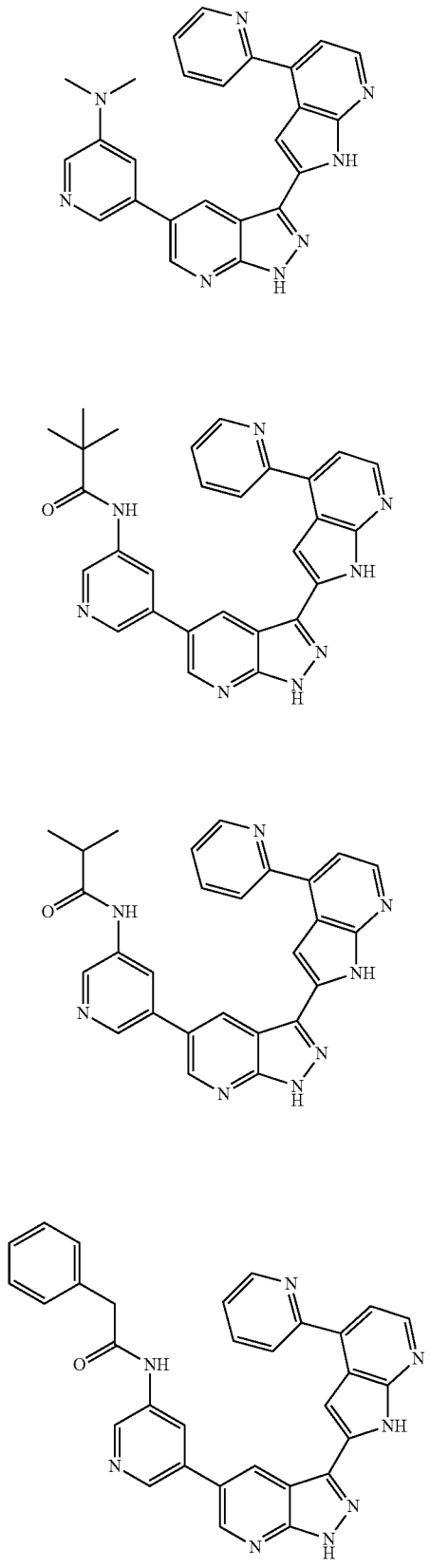
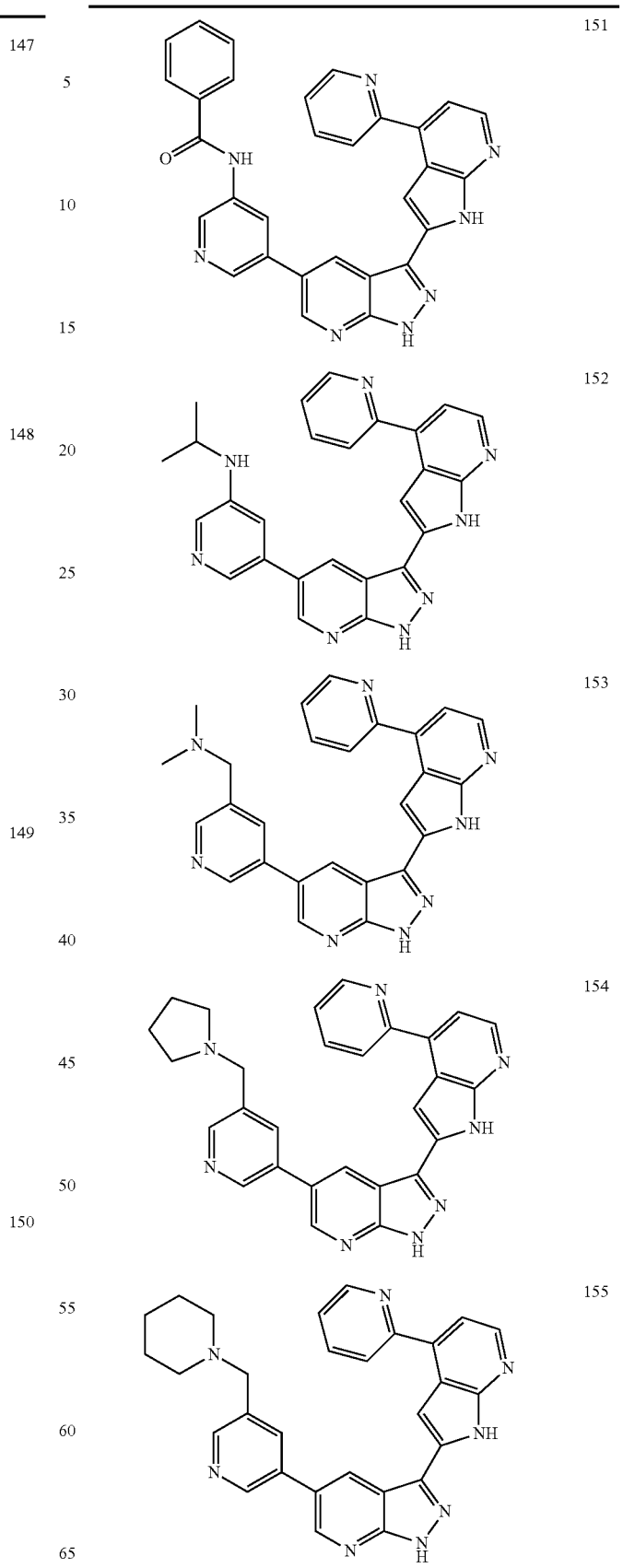

TABLE 1-continued
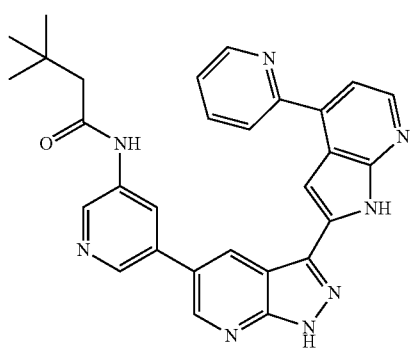 [SMILES: CC(C)(C)CC(=O)Nc1cncc(-c2cnc3[nH]nc(-c4cc5c(-c6ccccn6)ccnc5[nH]4)c3c2)c1] 156
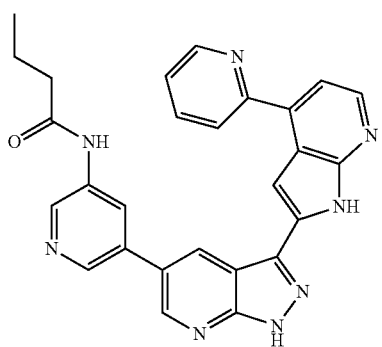 [SMILES: CCCC(=O)Nc1cncc(-c2cnc3[nH]nc(-c4cc5c(-c6ccccn6)ccnc5[nH]4)c3c2)c1] 157
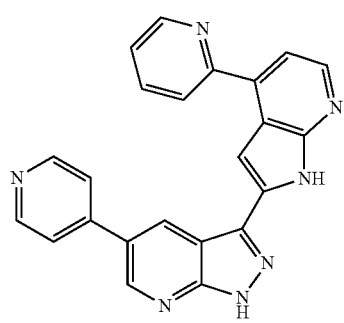 [SMILES: c1ccc(-c2ccnc3[nH]c(-c4n[nH]c5ncc(-c6ccncc6)cc45)cc23)nc1] 158
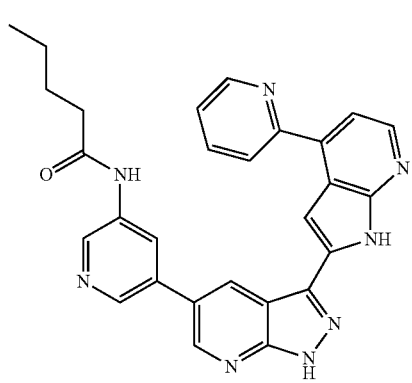 [SMILES: CCCCC(=O)Nc1cncc(-c2cnc3[nH]nc(-c4cc5c(-c6ccccn6)ccnc5[nH]4)c3c2)c1] 159
TABLE 1-continued
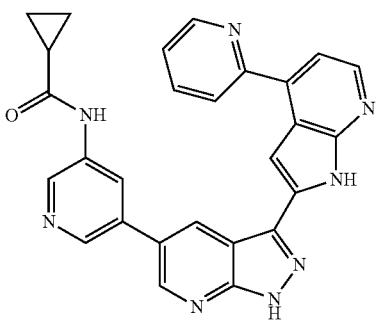 [SMILES: O=C(Nc1cncc(-c2cnc3[nH]nc(-c4cc5c(-c6ccccn6)ccnc5[nH]4)c3c2)c1)C1CC1] 160
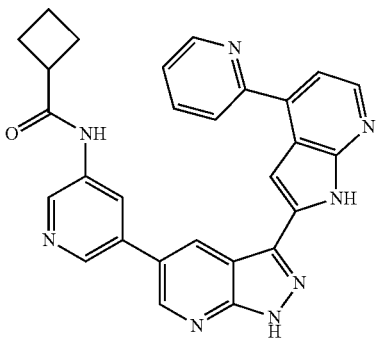 [SMILES: O=C(Nc1cncc(-c2cnc3[nH]nc(-c4cc5c(-c6ccccn6)ccnc5[nH]4)c3c2)c1)C1CCC1] 161
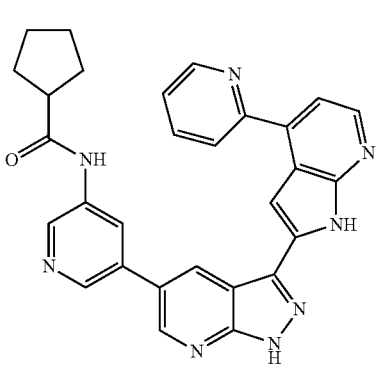 [SMILES: O=C(Nc1cncc(-c2cnc3[nH]nc(-c4cc5c(-c6ccccn6)ccnc5[nH]4)c3c2)c1)C1CCCC1] 162
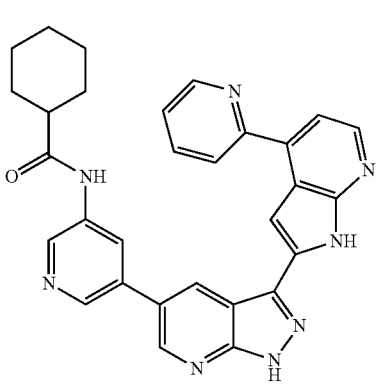 [SMILES: O=C(Nc1cncc(-c2cnc3[nH]nc(-c4cc5c(-c6ccccn6)ccnc5[nH]4)c3c2)c1)C1CCCCC1] 163

TABLE 1-continued
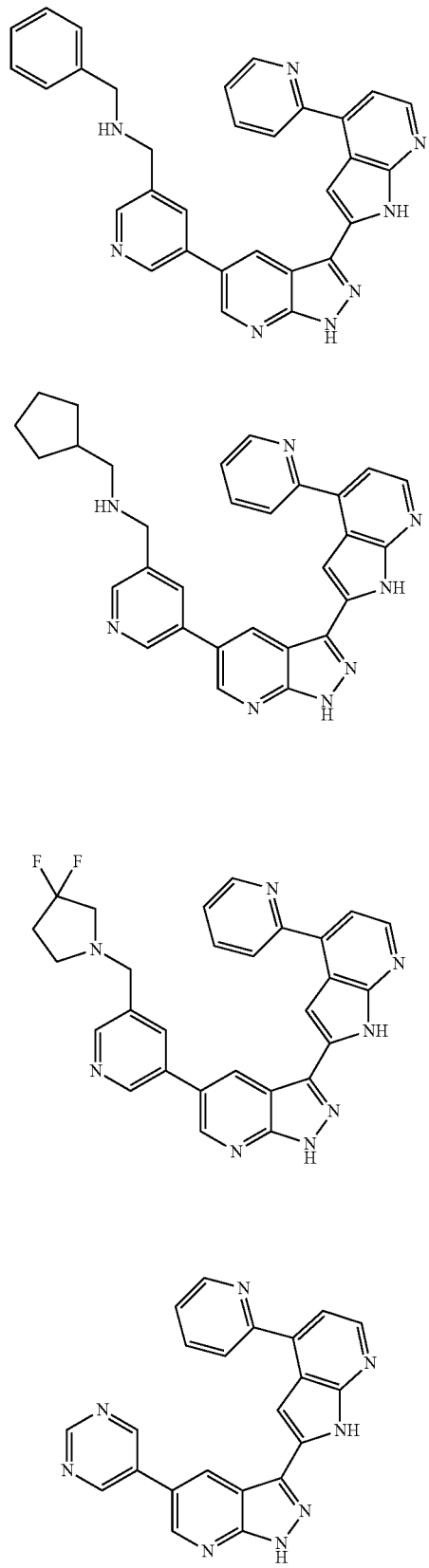
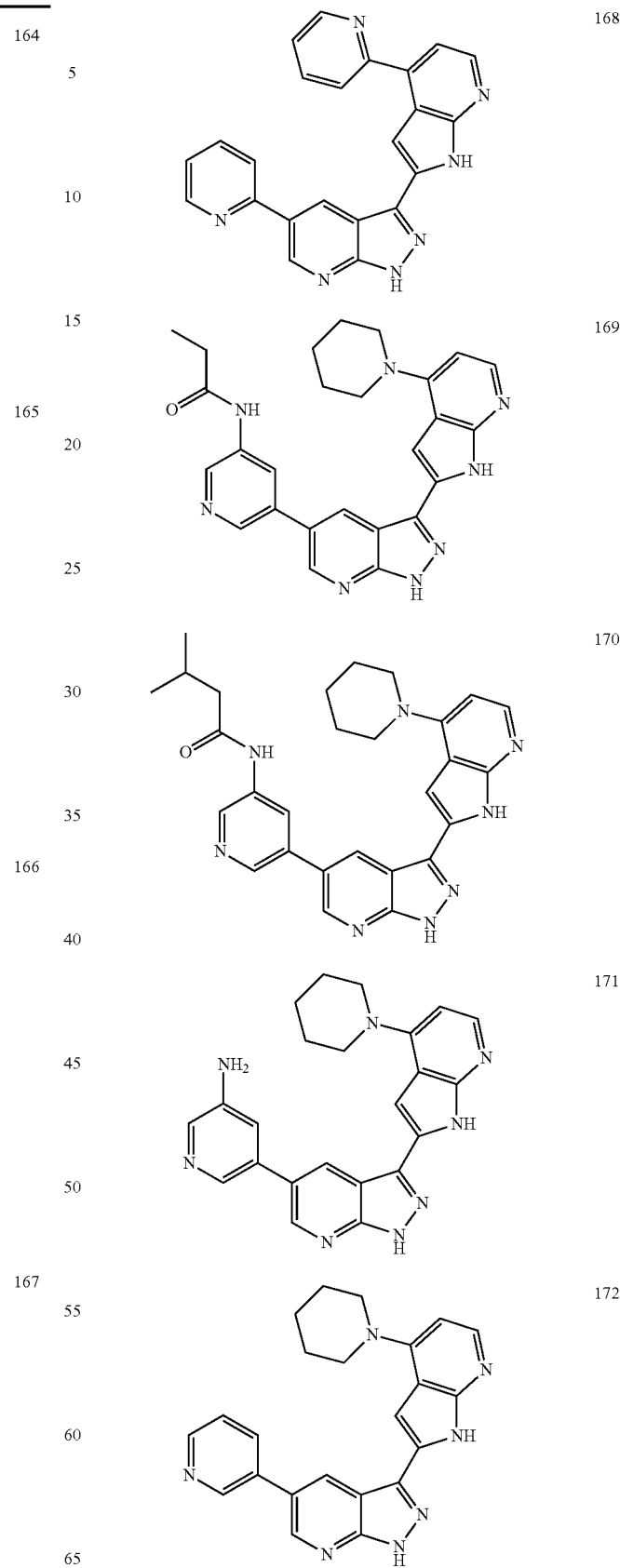

TABLE 1-continued
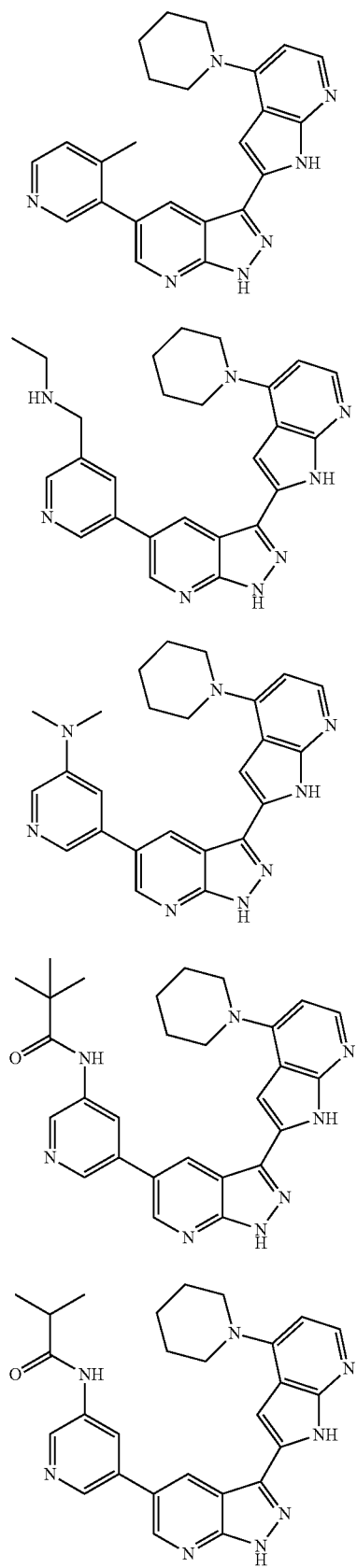
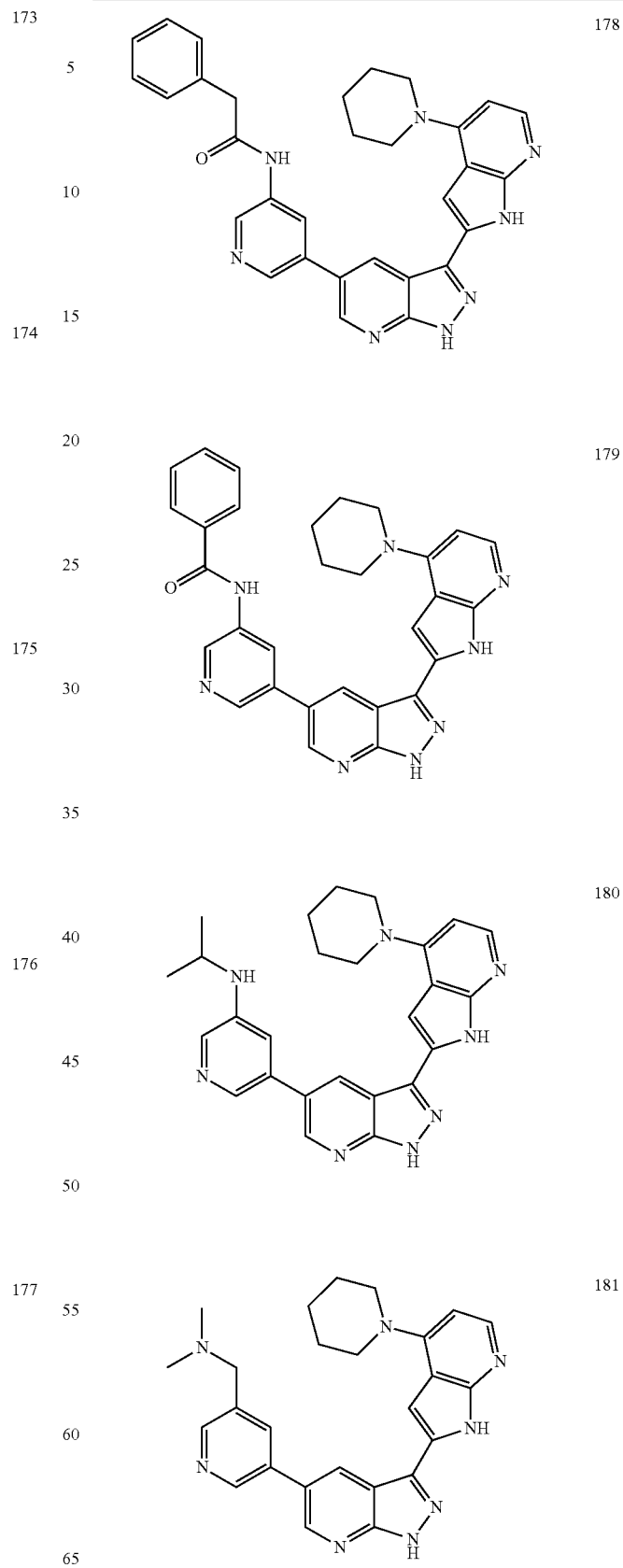

TABLE 1-continued
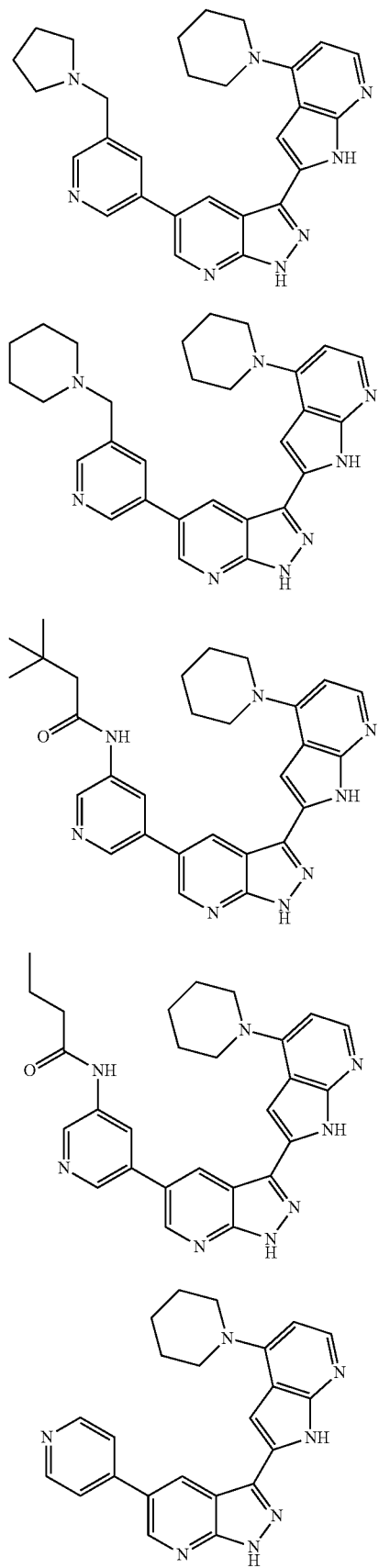
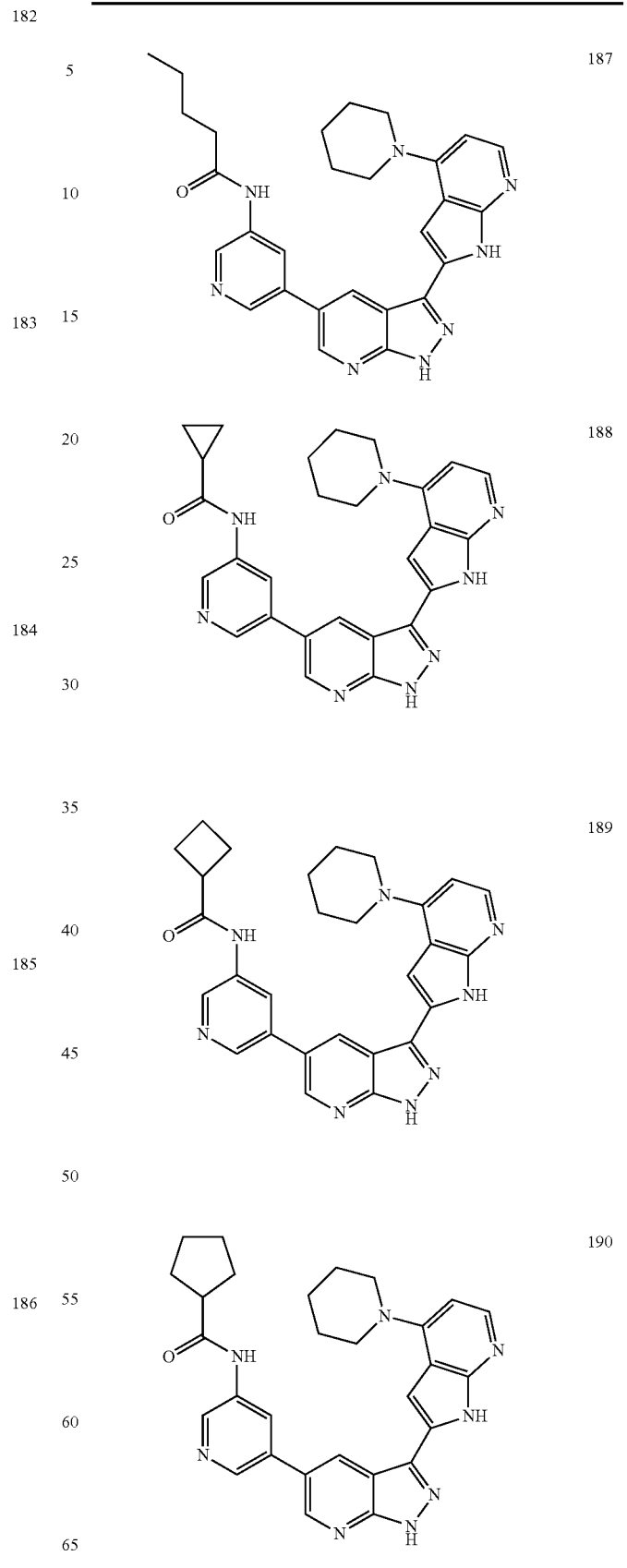

TABLE 1-continued
191
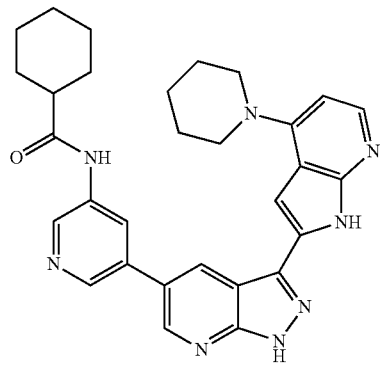 [SMILES: O=C(Nc1cncc(-c2cnc3[nH]nc(-c4cc5c(N6CCCCC6)ccnc5[nH]4)c3c2)c1)C1CCCCC1]
192
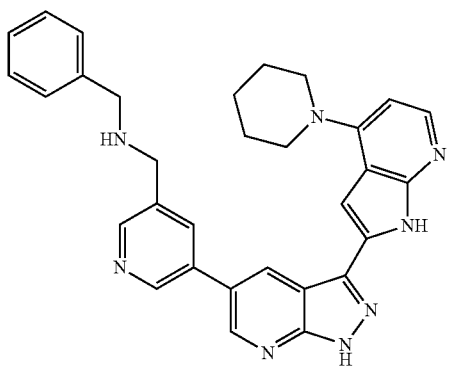 [SMILES: c1ccc(CNCc2cncc(-c3cnc4[nH]nc(-c5cc6c(N7CCCCC7)ccnc6[nH]5)c4c3)c2)cc1]
193
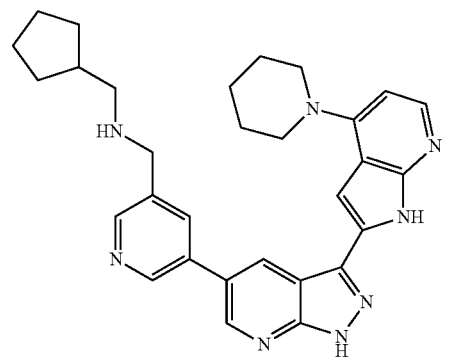 [SMILES: c1cc(N2CCCCC2)c2cc(-c3n[nH]c4ncc(-c5cncc(CNCC6CCCC6)c5)cc34)[nH]c2n1]
194
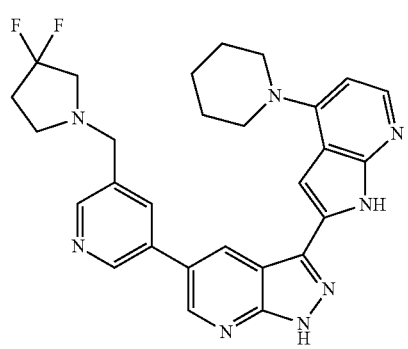 [SMILES: FC1(F)CCN(Cc2cncc(-c3cnc4[nH]nc(-c5cc6c(N7CCCCC7)ccnc6[nH]5)c4c3)c2)C1]
TABLE 1-continued
195
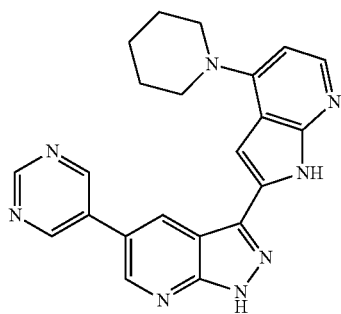 [SMILES: c1ncc(-c2cnc3[nH]nc(-c4cc5c(N6CCCCC6)ccnc5[nH]4)c3c2)cn1]
196
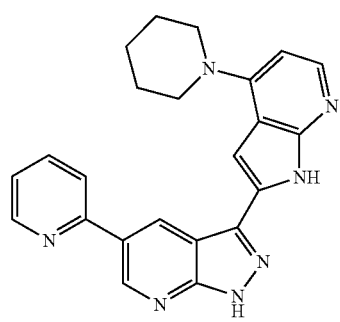 [SMILES: c1ccc(-c2cnc3[nH]nc(-c4cc5c(N6CCCCC6)ccnc5[nH]4)c3c2)nc1]
197
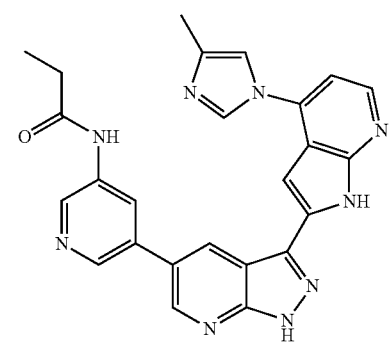 [SMILES: CCC(=O)Nc1cncc(-c2cnc3[nH]nc(-c4cc5c(-n6cnc(C)c6)ccnc5[nH]4)c3c2)c1]
198
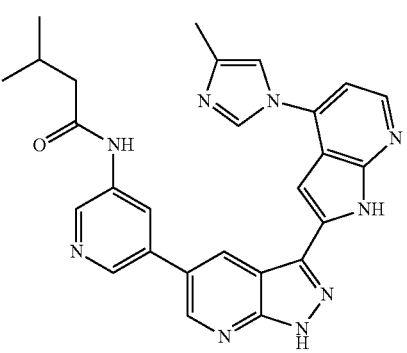 [SMILES: Cc1cn(-c2ccnc3[nH]c(-c4n[nH]c5ncc(-c6cncc(NC(=O)CC(C)C)c6)cc45)cc23)cn1]

TABLE 1-continued
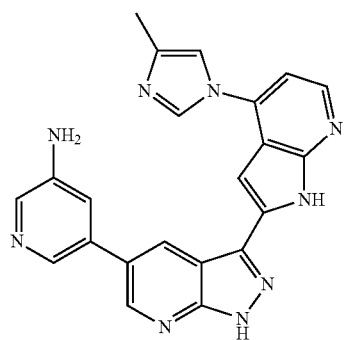 199
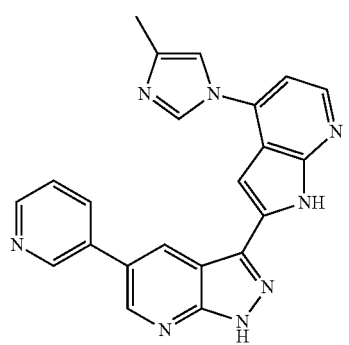 [SMILES: Cc1cn(-c2ccnc3[nH]c(-c4n[nH]c5ncc(-c6cccnc6)cc45)cc23)cn1] 200
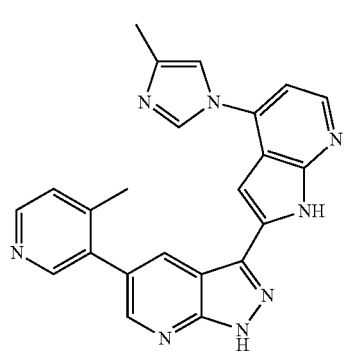 [SMILES: Cc1cn(-c2ccnc3[nH]c(-c4n[nH]c5ncc(-c6cnccc6C)cc45)cc23)cn1] 201
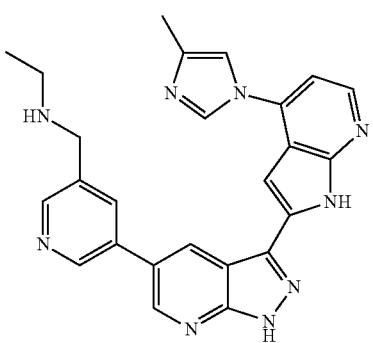 [SMILES: CCNCc1cncc(-c2cnc3[nH]nc(-c4cc5c(-n6cnc(C)c6)ccnc5[nH]4)c3c2)c1] 202
TABLE 1-continued
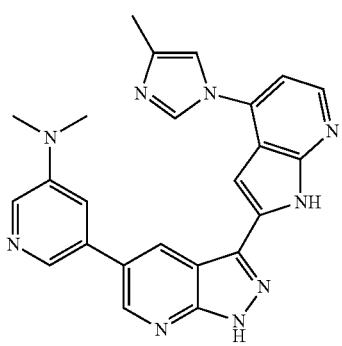 [SMILES: Cc1cn(-c2ccnc3[nH]c(-c4n[nH]c5ncc(-c6cncc(N(C)C)c6)cc45)cc23)cn1] 203
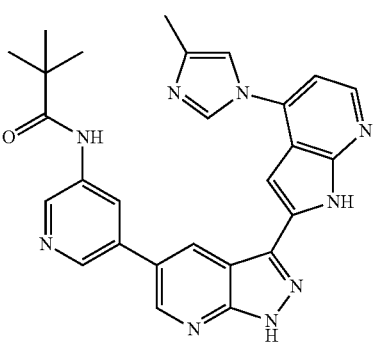 [SMILES: Cc1cn(-c2ccnc3[nH]c(-c4n[nH]c5ncc(-c6cncc(NC(=O)C(C)(C)C)c6)cc45)cc23)cn1] 204
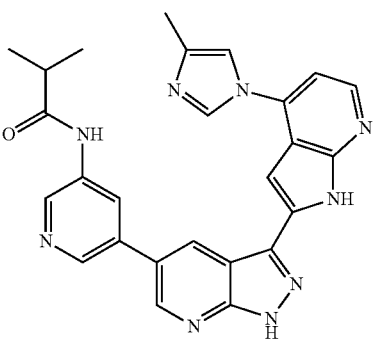 [SMILES: Cc1cn(-c2ccnc3[nH]c(-c4n[nH]c5ncc(-c6cncc(NC(=O)C(C)C)c6)cc45)cc23)cn1] 205
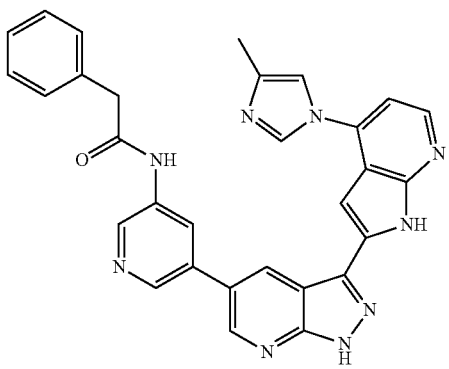 [SMILES: Cc1cn(-c2ccnc3[nH]c(-c4n[nH]c5ncc(-c6cncc(NC(=O)Cc7ccccc7)c6)cc45)cc23)cn1] 206

TABLE 1-continued
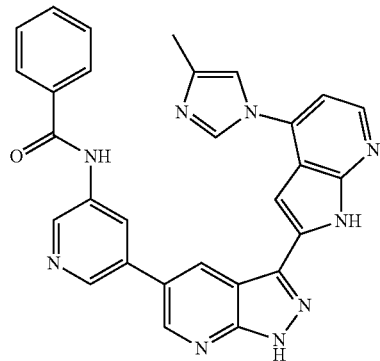 [SMILES: Cc1cn(-c2ccnc3[nH]c(-c4n[nH]c5ncc(-c6cncc(NC(=O)c7ccccc7)c6)cc45)cc23)cn1] 207
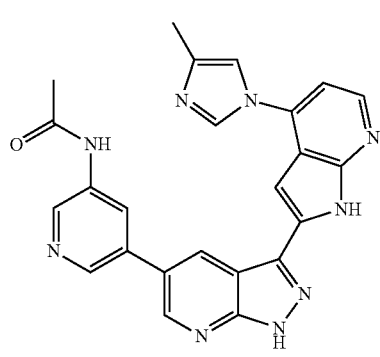 [SMILES: CC(=O)Nc1cncc(-c2cnc3[nH]nc(-c4cc5c(-n6cnc(C)c6)ccnc5[nH]4)c3c2)c1] 208
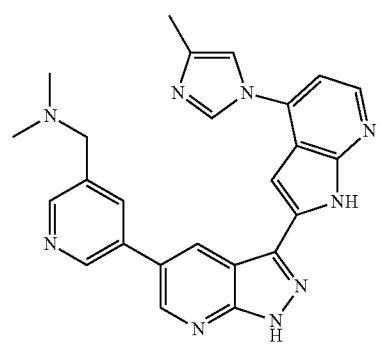 [SMILES: Cc1cn(-c2ccnc3[nH]c(-c4n[nH]c5ncc(-c6cncc(CN(C)C)c6)cc45)cc23)cn1] 209
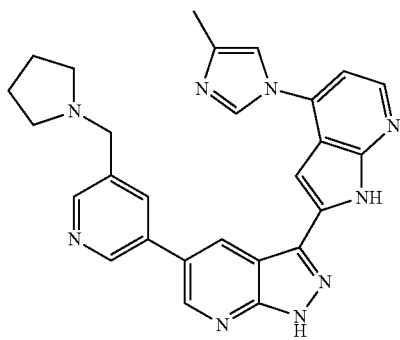 [SMILES: Cc1cn(-c2ccnc3[nH]c(-c4n[nH]c5ncc(-c6cncc(CN7CCCC7)c6)cc45)cc23)cn1] 210
TABLE 1-continued
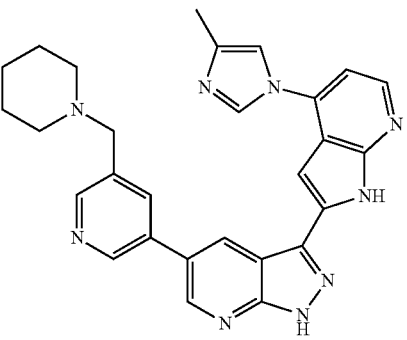 211
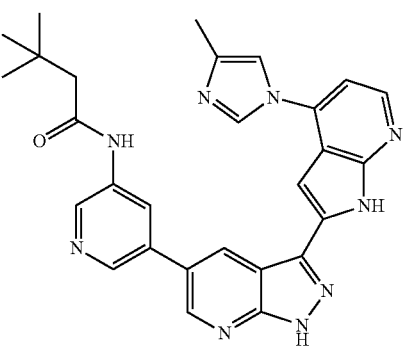 [SMILES: Cc1cn(-c2ccnc3[nH]c(-c4n[nH]c5ncc(-c6cncc(NC(=O)CC(C)(C)C)c6)cc45)cc23)cn1] 212
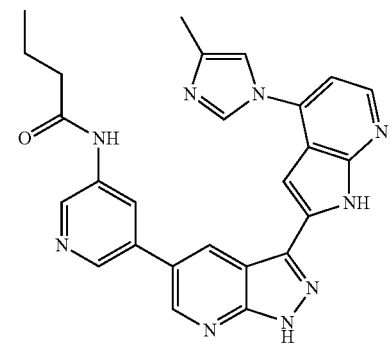 [SMILES: CCCC(=O)Nc1cncc(-c2cnc3[nH]nc(-c4cc5c(-n6cnc(C)c6)ccnc5[nH]4)c3c2)c1] 213
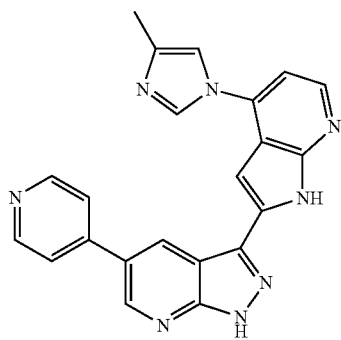 [SMILES: Cc1cn(-c2ccnc3[nH]c(-c4n[nH]c5ncc(-c6ccncc6)cc45)cc23)cn1] 214

TABLE 1-continued
215 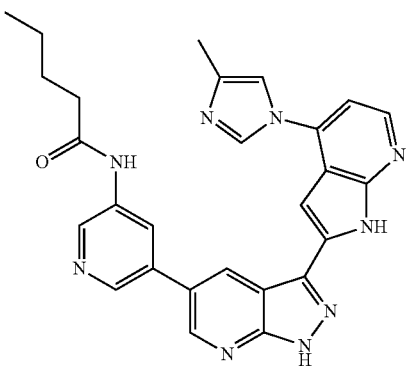 [SMILES: CCCCC(=O)Nc1cncc(-c2cnc3[nH]nc(-c4cc5c(-n6cnc(C)c6)ccnc5[nH]4)c3c2)c1]
216 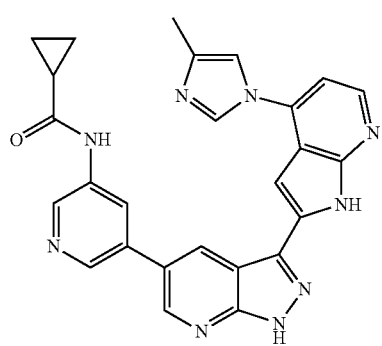 [SMILES: Cc1cn(-c2ccnc3[nH]c(-c4n[nH]c5ncc(-c6cncc(NC(=O)C7CC7)c6)cc45)cc23)cn1]
217 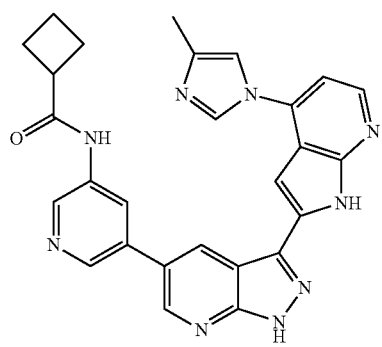 [SMILES: Cc1cn(-c2ccnc3[nH]c(-c4n[nH]c5ncc(-c6cncc(NC(=O)C7CCC7)c6)cc45)cc23)cn1]
218 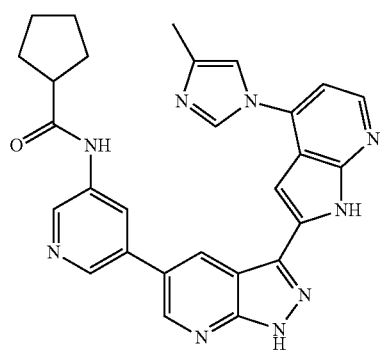 [SMILES: Cc1cn(-c2ccnc3[nH]c(-c4n[nH]c5ncc(-c6cncc(NC(=O)C7CCCC7)c6)cc45)cc23)cn1]
TABLE 1-continued
219 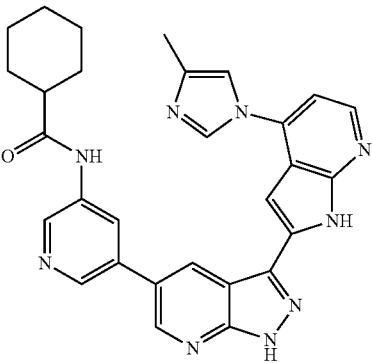 [SMILES: Cc1cn(-c2ccnc3[nH]c(-c4n[nH]c5ncc(-c6cncc(NC(=O)C7CCCCC7)c6)cc45)cc23)cn1]
220 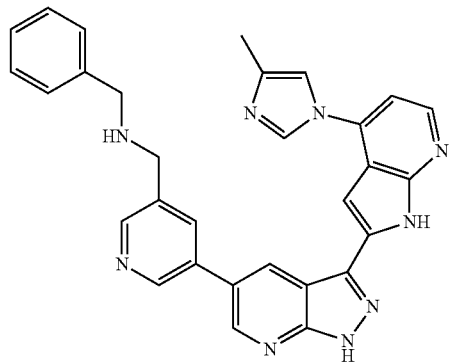 [SMILES: Cc1cn(-c2ccnc3[nH]c(-c4n[nH]c5ncc(-c6cncc(CNCc7ccccc7)c6)cc45)cc23)cn1]
221 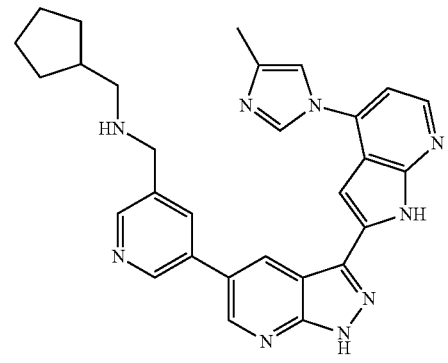 [SMILES: Cc1cn(-c2ccnc3[nH]c(-c4n[nH]c5ncc(-c6cncc(CNCC7CCCC7)c6)cc45)cc23)cn1]
222 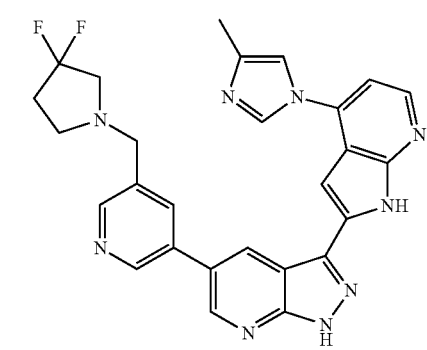 [SMILES: Cc1cn(-c2ccnc3[nH]c(-c4n[nH]c5ncc(-c6cncc(CN7CCC(F)(F)C7)c6)cc45)cc23)cn1]

TABLE 1-continued
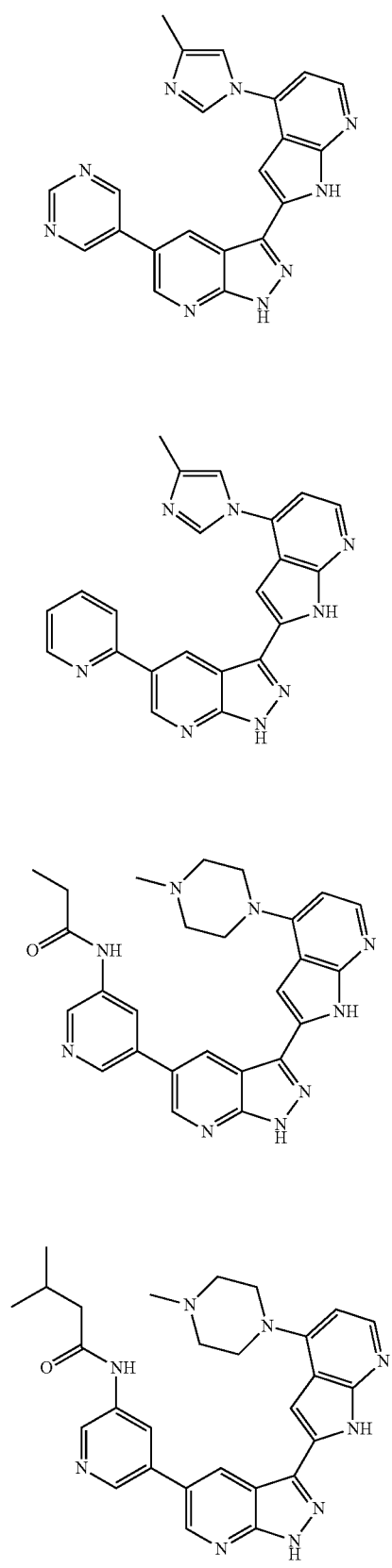
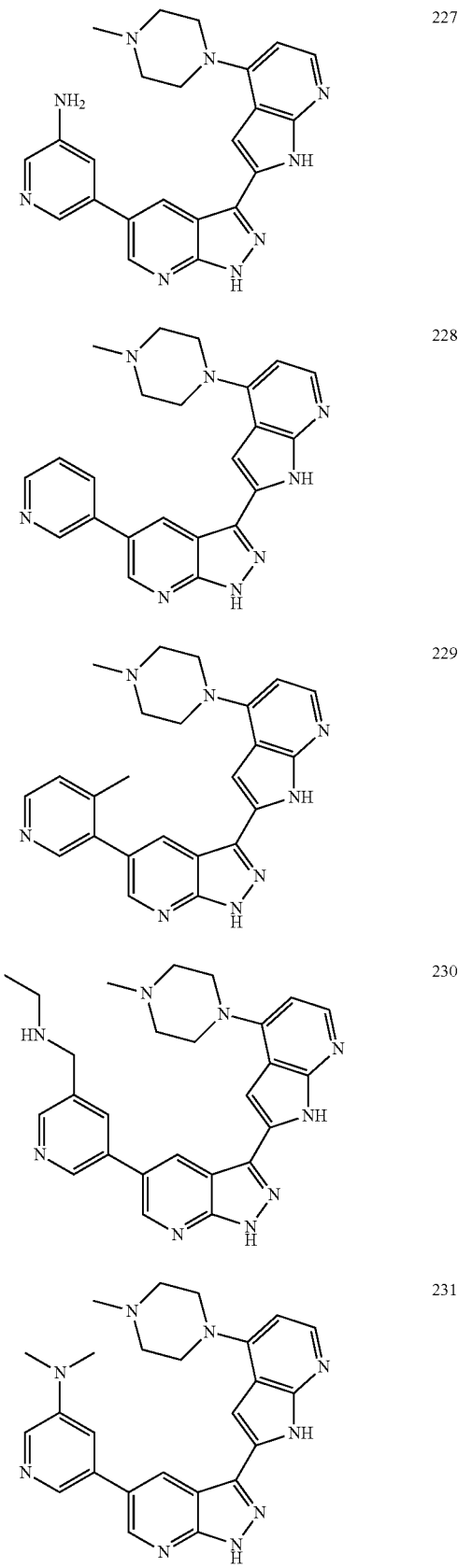

TABLE 1-continued
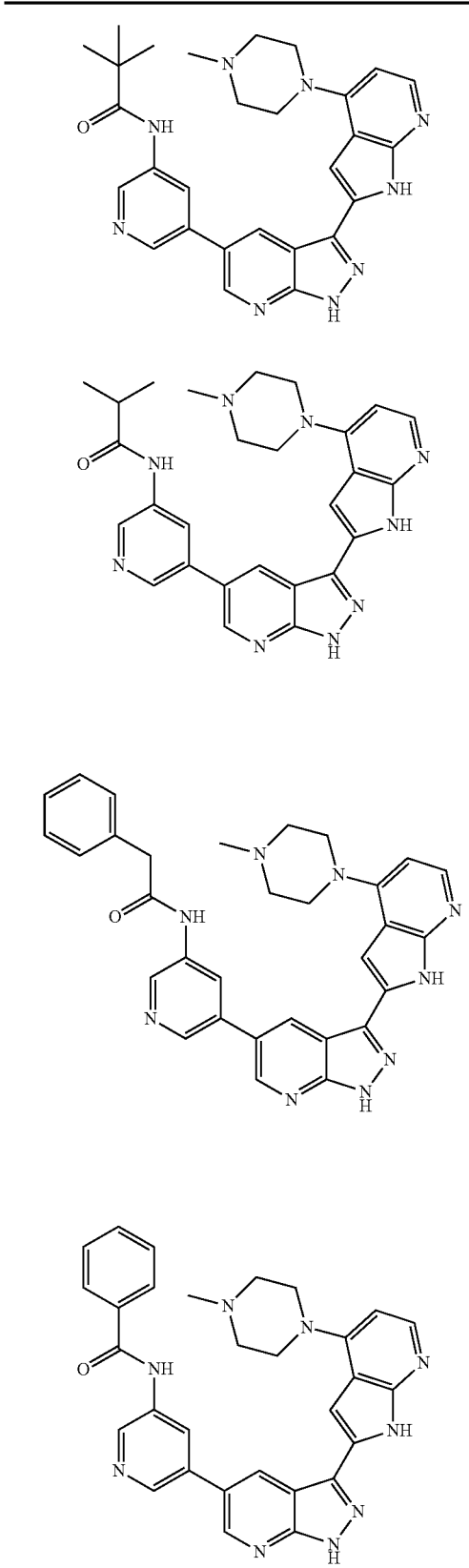
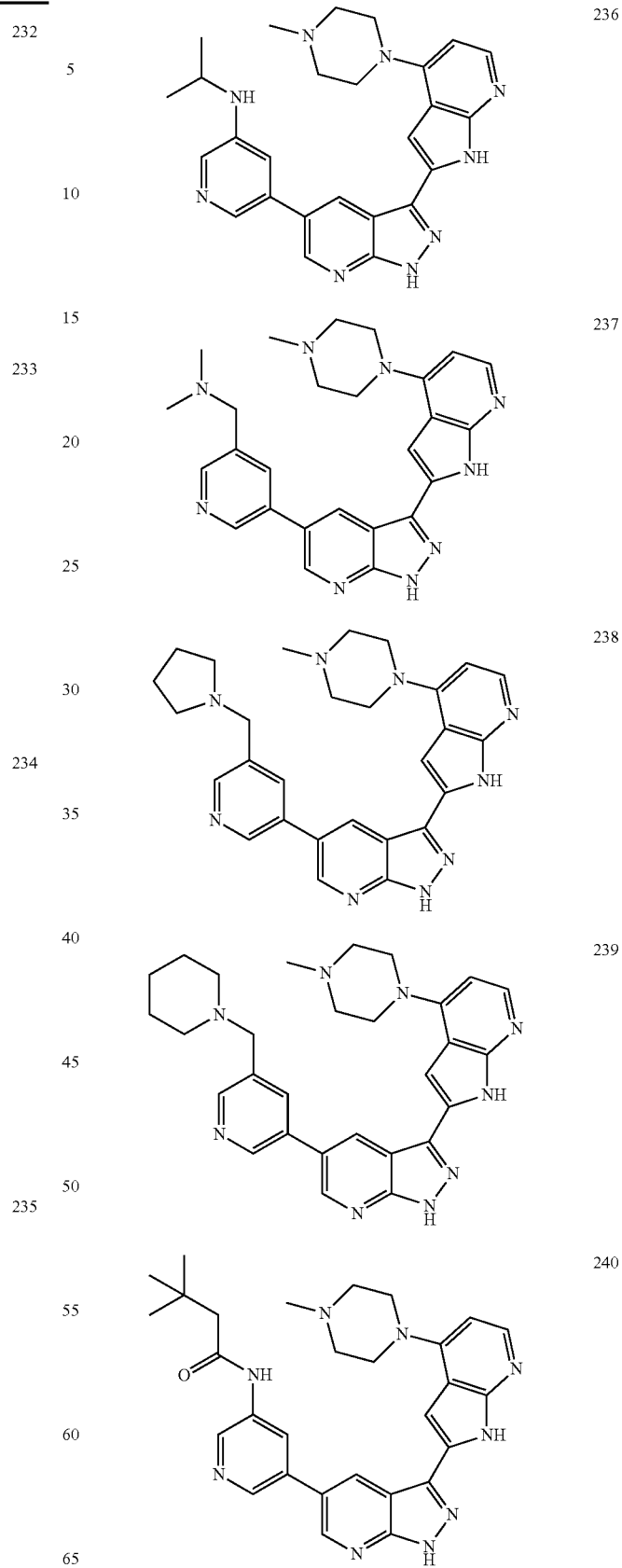

TABLE 1-continued
241
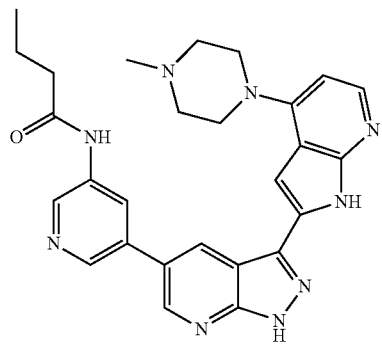 [SMILES: CCCC(=O)Nc1cncc(-c2cnc3[nH]nc(-c4cc5c(N6CCN(C)CC6)ccnc5[nH]4)c3c2)c1]
242
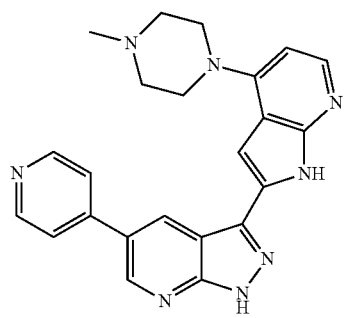 [SMILES: CN1CCN(c2ccnc3[nH]c(-c4n[nH]c5ncc(-c6ccncc6)cc45)cc23)CC1]
243
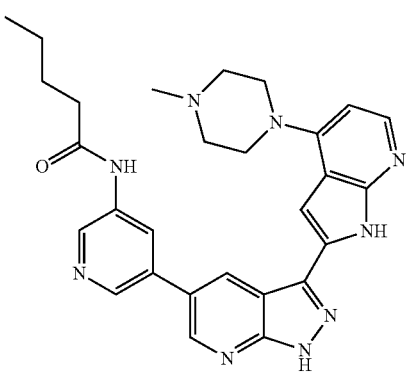 [SMILES: CCCCC(=O)Nc1cncc(-c2cnc3[nH]nc(-c4cc5c(N6CCN(C)CC6)ccnc5[nH]4)c3c2)c1]
244
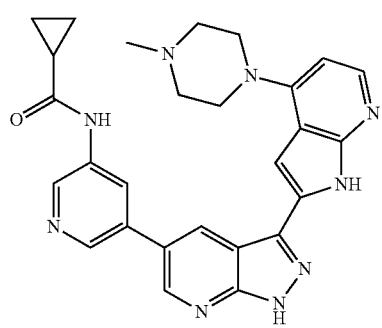 [SMILES: CN1CCN(c2ccnc3[nH]c(-c4n[nH]c5ncc(-c6cncc(NC(=O)C7CC7)c6)cc45)cc23)CC1]
TABLE 1-continued
245
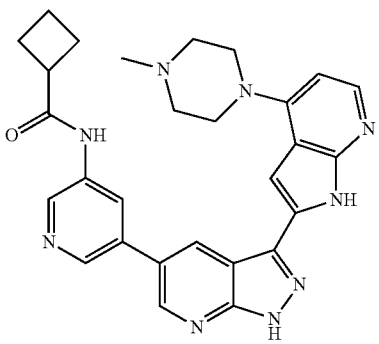 [SMILES: CN1CCN(c2ccnc3[nH]c(-c4n[nH]c5ncc(-c6cncc(NC(=O)C7CCC7)c6)cc45)cc23)CC1]
246
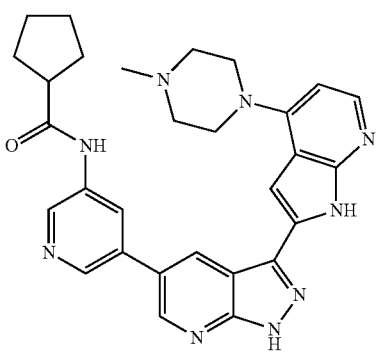 [SMILES: CN1CCN(c2ccnc3[nH]c(-c4n[nH]c5ncc(-c6cncc(NC(=O)C7CCCC7)c6)cc45)cc23)CC1]
247
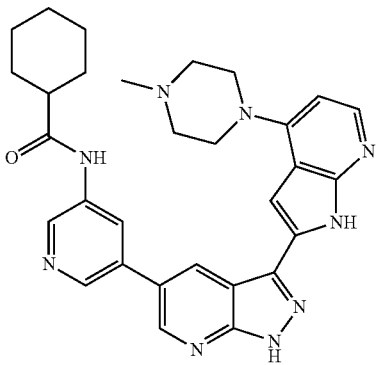 [SMILES: CN1CCN(c2ccnc3[nH]c(-c4n[nH]c5ncc(-c6cncc(NC(=O)C7CCCCC7)c6)cc45)cc23)CC1]
248
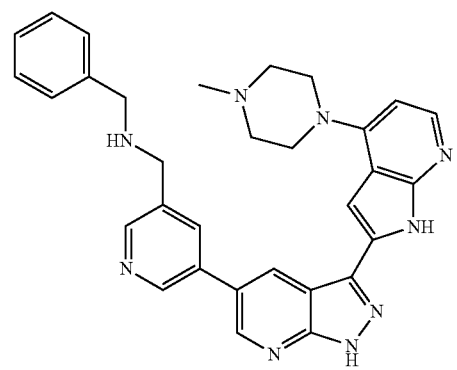 [SMILES: CN1CCN(c2ccnc3[nH]c(-c4n[nH]c5ncc(-c6cncc(CNCc7ccccc7)c6)cc45)cc23)CC1]

TABLE 1-continued
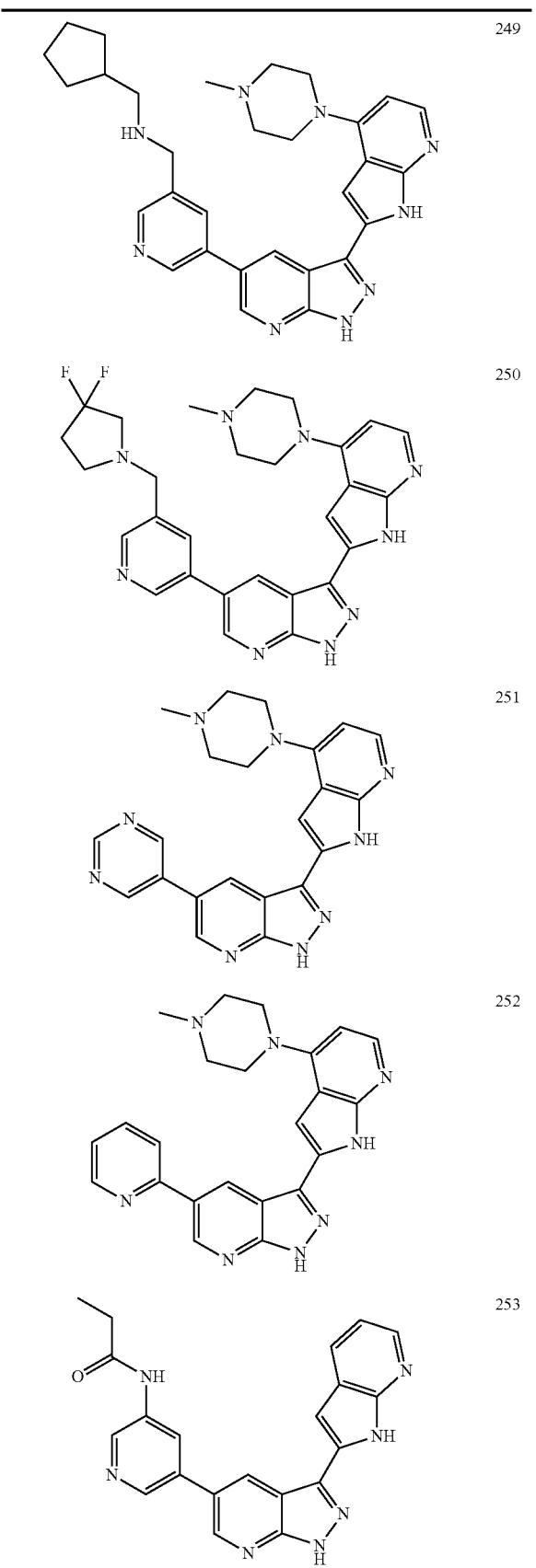
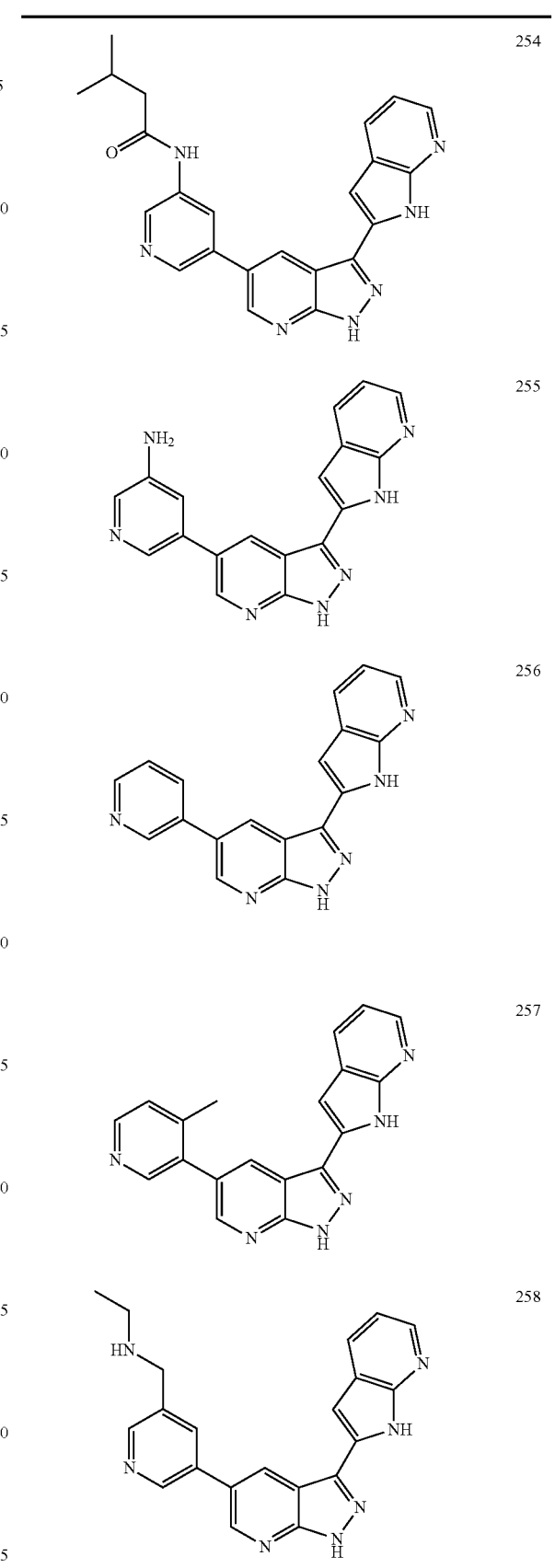

TABLE 1-continued
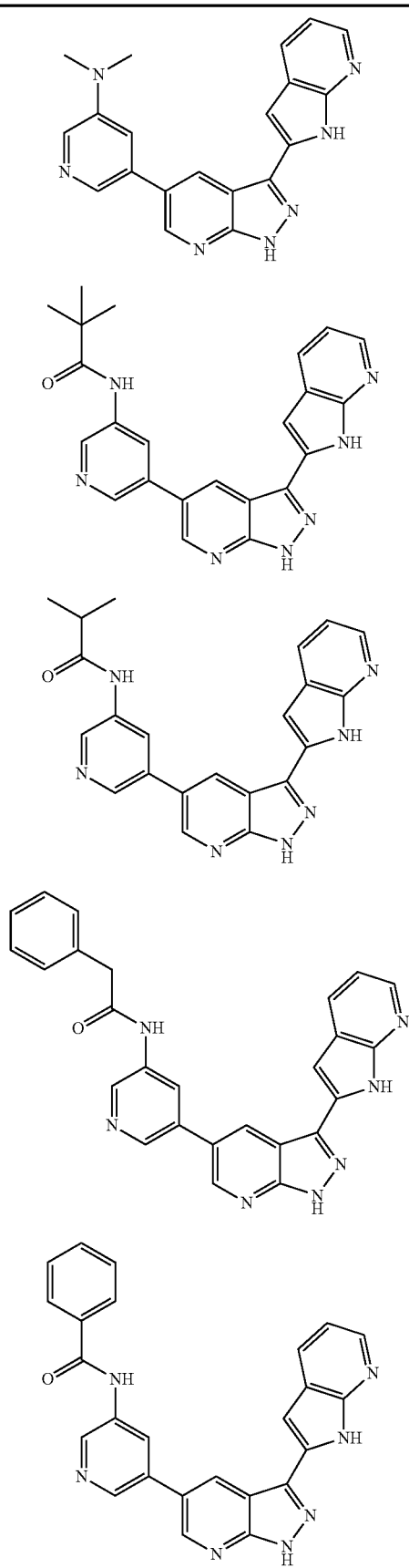
TABLE 1-continued
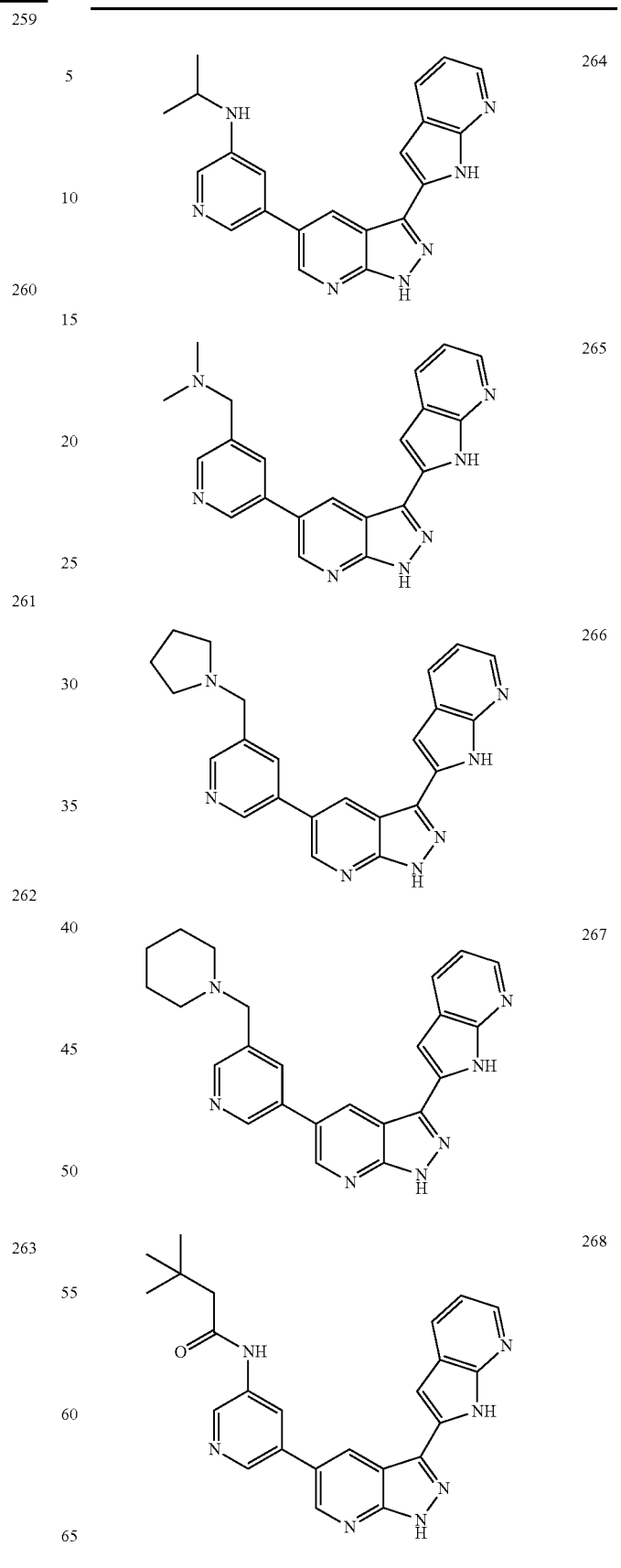

TABLE 1-continued
269
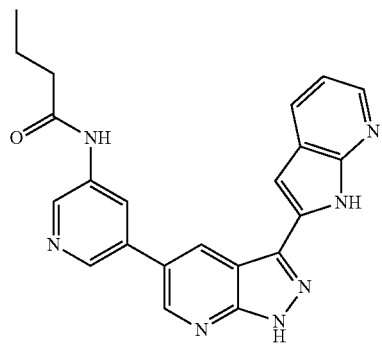 [SMILES: CCCC(=O)Nc1cncc(-c2cnc3[nH]nc(-c4cc5cccnc5[nH]4)c3c2)c1]
270
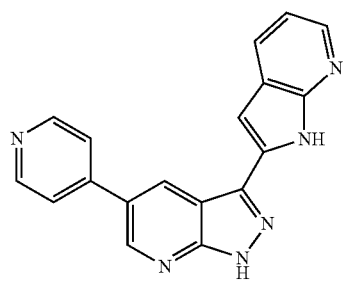 [SMILES: c1cnc2[nH]c(-c3n[nH]c4ncc(-c5ccncc5)cc34)cc2c1]
271
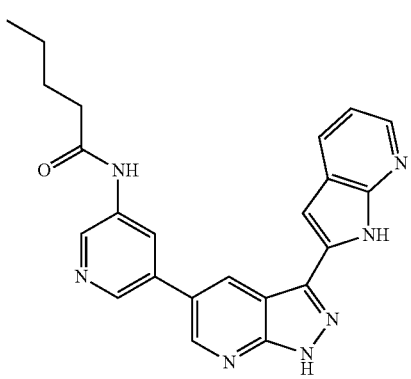 [SMILES: CCCCC(=O)Nc1cncc(-c2cnc3[nH]nc(-c4cc5cccnc5[nH]4)c3c2)c1]
272
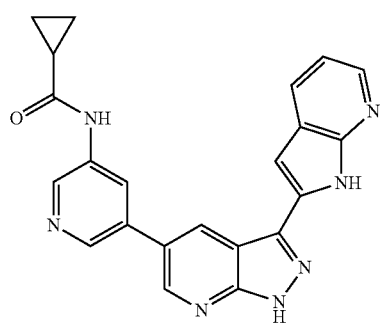 [SMILES: O=C(Nc1cncc(-c2cnc3[nH]nc(-c4cc5cccnc5[nH]4)c3c2)c1)C1CC1]
TABLE 1-continued
273
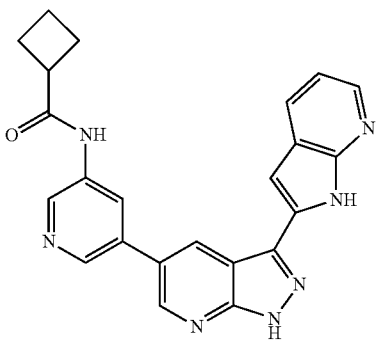 [SMILES: O=C(Nc1cncc(-c2cnc3[nH]nc(-c4cc5cccnc5[nH]4)c3c2)c1)C1CCC1]
274
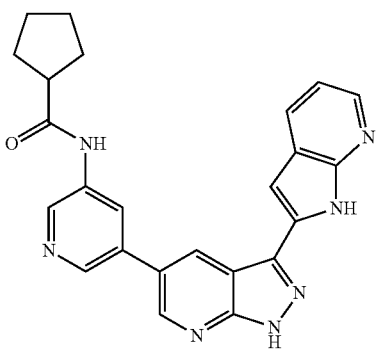 [SMILES: O=C(Nc1cncc(-c2cnc3[nH]nc(-c4cc5cccnc5[nH]4)c3c2)c1)C1CCCC1]
275
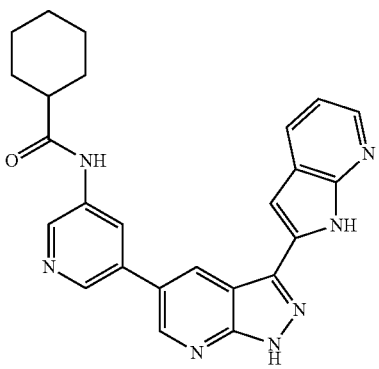 [SMILES: O=C(Nc1cncc(-c2cnc3[nH]nc(-c4cc5cccnc5[nH]4)c3c2)c1)C1CCCCC1]
276
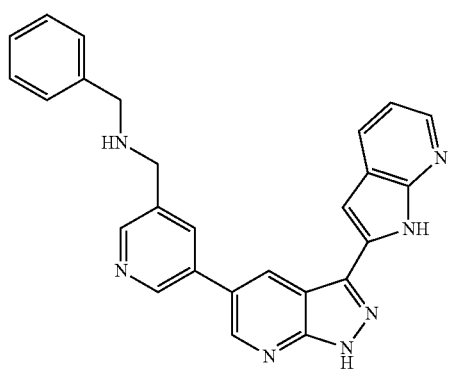 [SMILES: c1ccc(CNCc2cncc(-c3cnc4[nH]nc(-c5cc6cccnc6[nH]5)c4c3)c2)cc1]

TABLE 1-continued
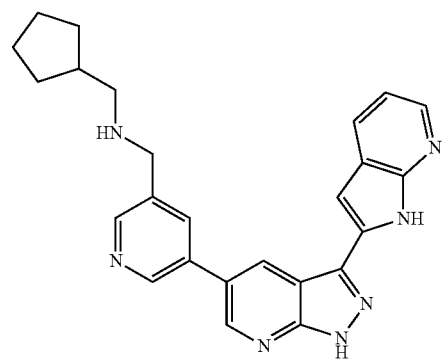 [SMILES: c1cnc2[nH]c(-c3n[nH]c4ncc(-c5cncc(CNCC6CCCC6)c5)cc34)cc2c1] 277
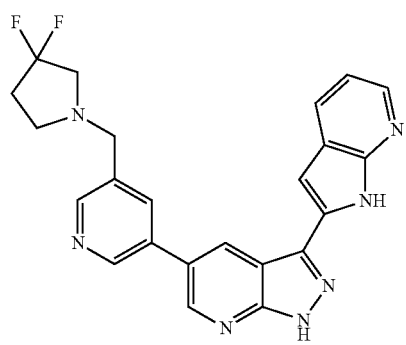 [SMILES: FC1(F)CCN(Cc2cncc(-c3cnc4[nH]nc(-c5cc6cccnc6[nH]5)c4c3)c2)C1] 278
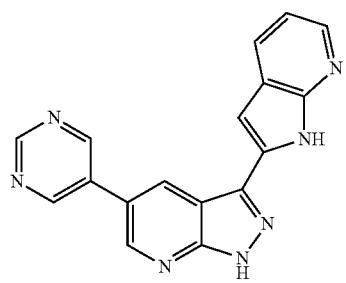 [SMILES: c1cnc2[nH]c(-c3n[nH]c4ncc(-c5cncnc5)cc34)cc2c1] 279
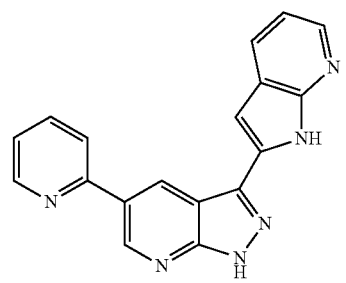 [SMILES: c1ccc(-c2cnc3[nH]nc(-c4cc5cccnc5[nH]4)c3c2)nc1] 280
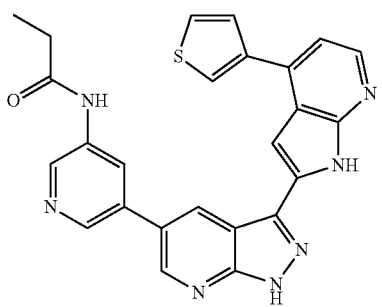 [SMILES: CCC(=O)Nc1cncc(-c2cnc3[nH]nc(-c4cc5c(-c6ccsc6)ccnc5[nH]4)c3c2)c1] 281
TABLE 1-continued
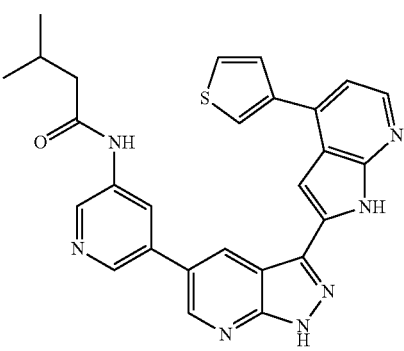 282
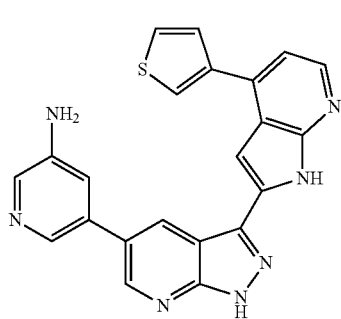 283
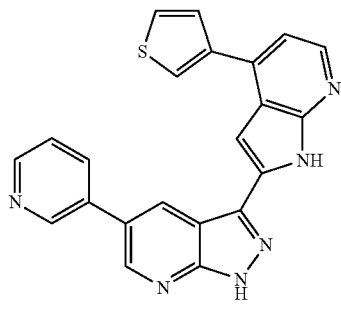 284
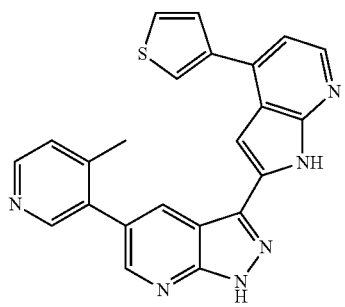 [SMILES: Cc1ccncc1-c1cnc2[nH]nc(-c3cc4c(-c5ccsc5)ccnc4[nH]3)c2c1] 285
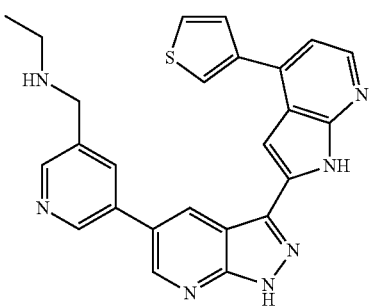 286

TABLE 1-continued
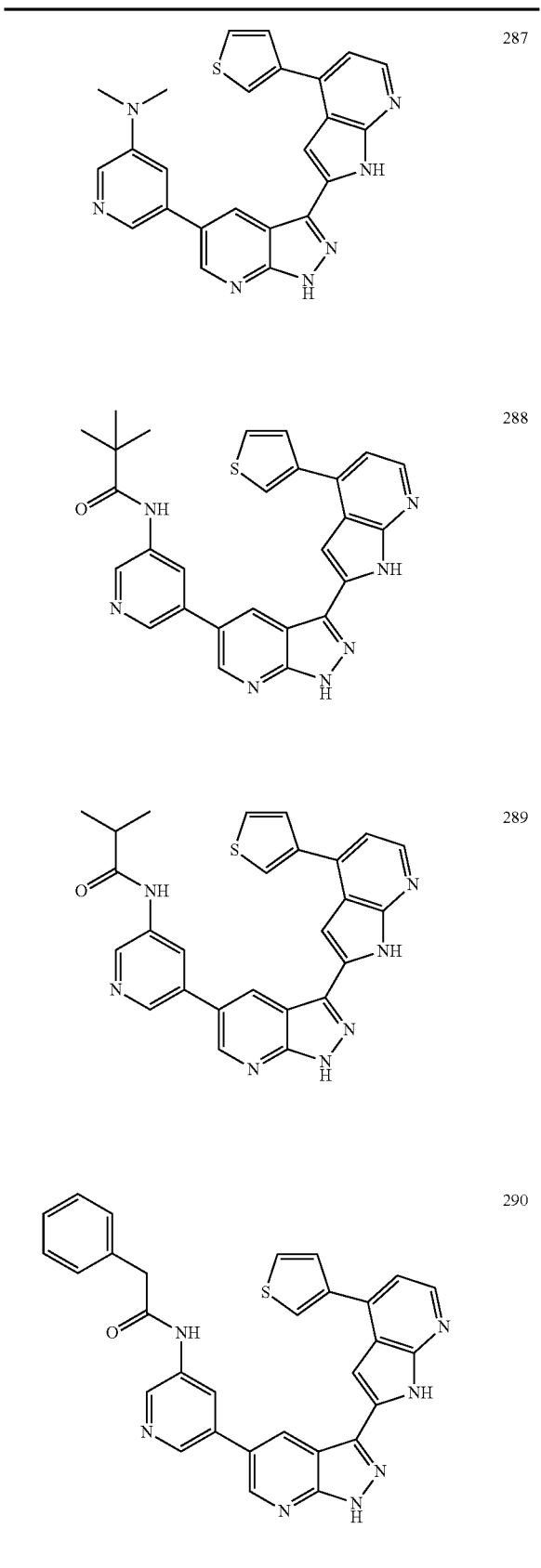
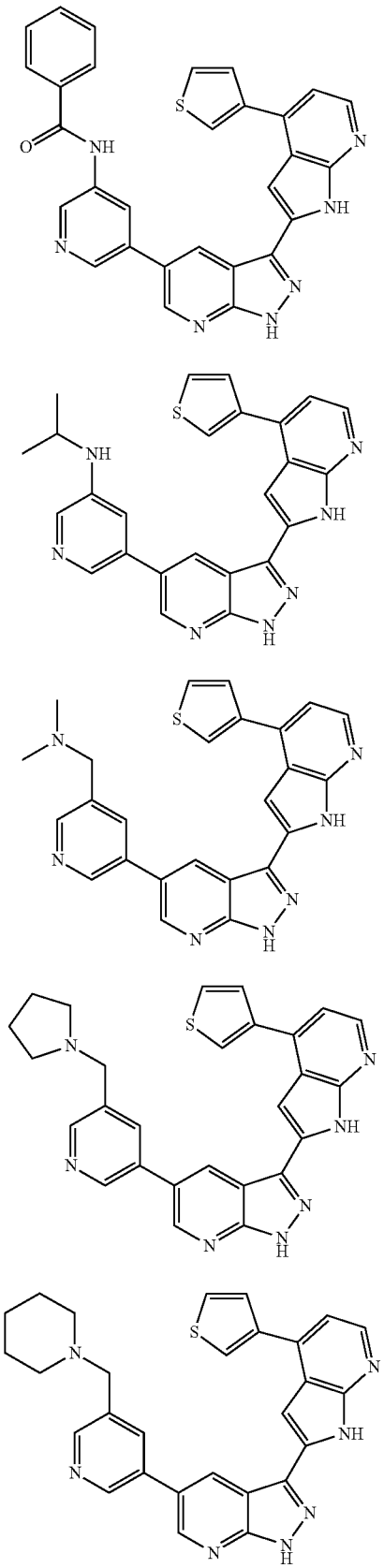

TABLE 1-continued
296
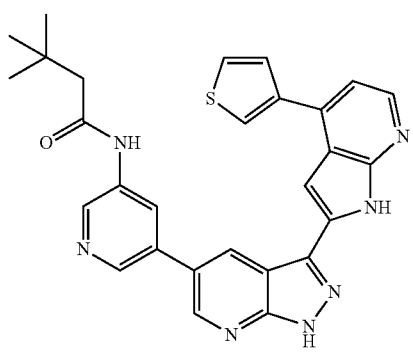 [SMILES: CC(C)(C)CC(=O)Nc1cncc(-c2cnc3[nH]nc(-c4cc5c(-c6ccsc6)ccnc5[nH]4)c3c2)c1]
297
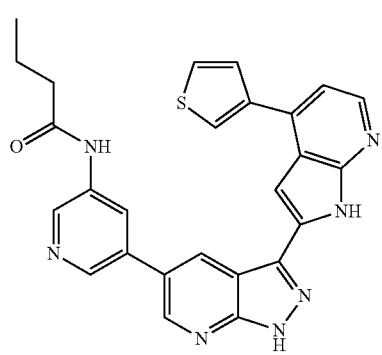
298
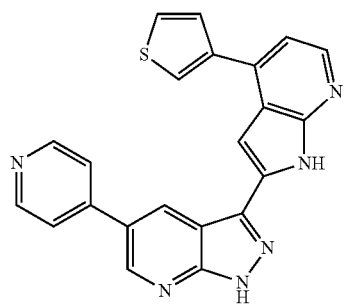 [SMILES: c1cc(-c2cnc3[nH]nc(-c4cc5c(-c6ccsc6)ccnc5[nH]4)c3c2)ccn1]
299
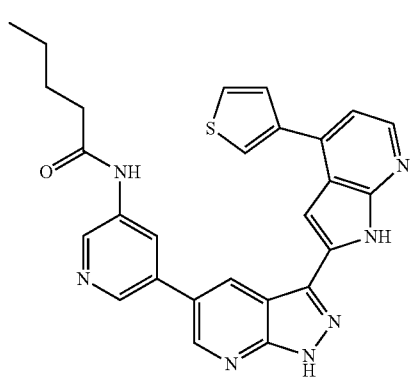
TABLE 1-continued
300
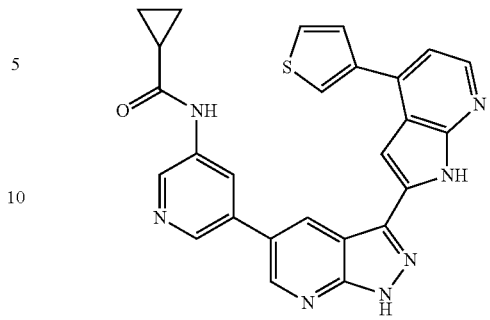
301
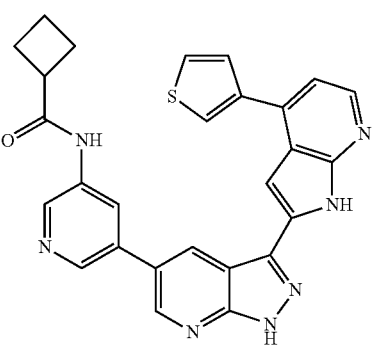
302
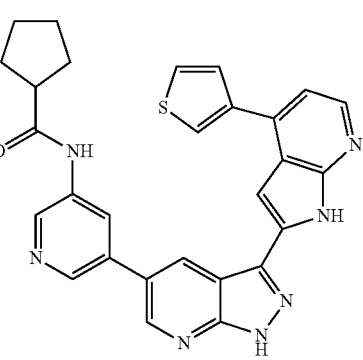
303
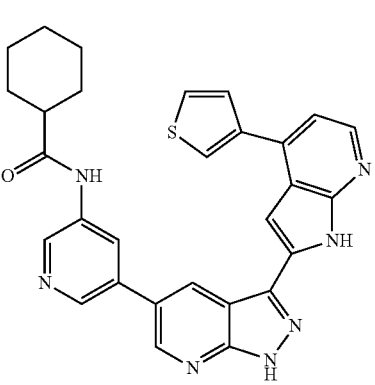 [SMILES: O=C(Nc1cncc(-c2cnc3[nH]nc(-c4cc5c(-c6ccsc6)ccnc5[nH]4)c3c2)c1)C1CCCCC1]

TABLE 1-continued
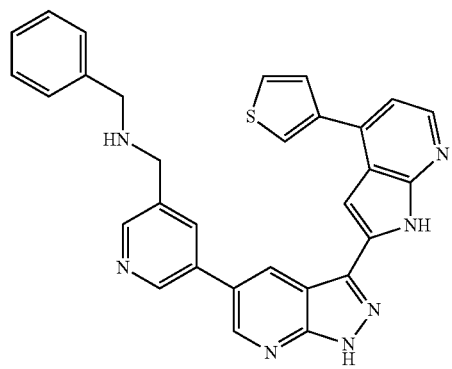 304
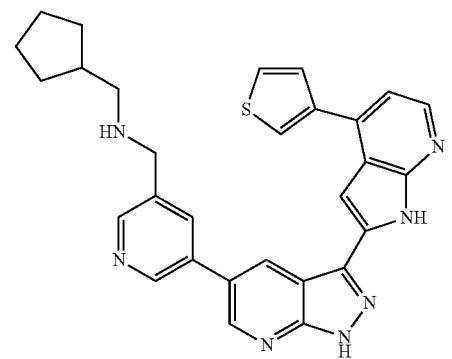 305
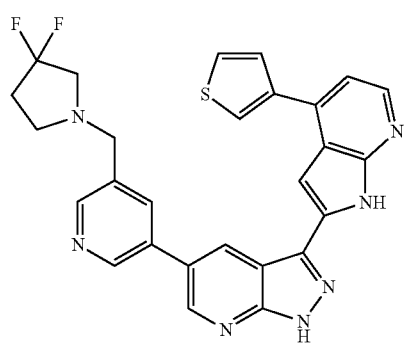 306
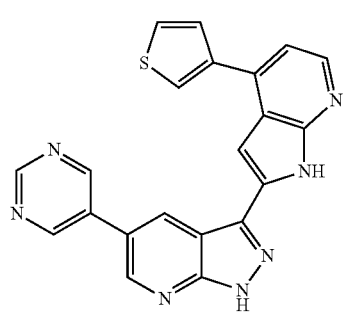 [SMILES: c1ncc(-c2cnc3[nH]nc(-c4cc5c(-c6ccsc6)ccnc5[nH]4)c3c2)cn1] 307
TABLE 1-continued
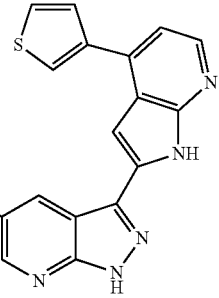 308
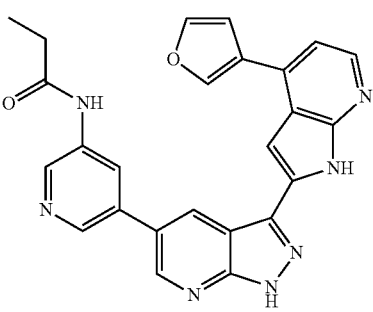 [SMILES: CCC(=O)Nc1cncc(-c2cnc3[nH]nc(-c4cc5c(-c6ccoc6)ccnc5[nH]4)c3c2)c1] 309
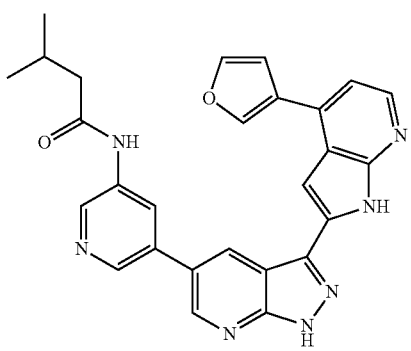 310
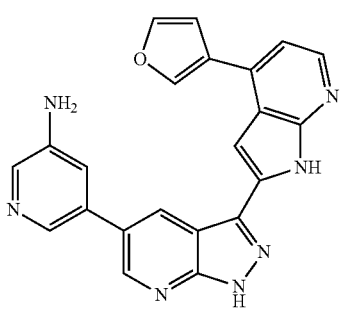 [SMILES: Nc1cncc(-c2cnc3[nH]nc(-c4cc5c(-c6ccoc6)ccnc5[nH]4)c3c2)c1] 311
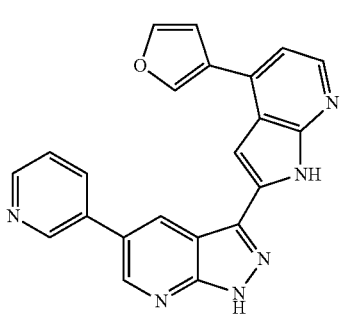 [SMILES: c1cncc(-c2cnc3[nH]nc(-c4cc5c(-c6ccoc6)ccnc5[nH]4)c3c2)c1] 312

TABLE 1-continued
313 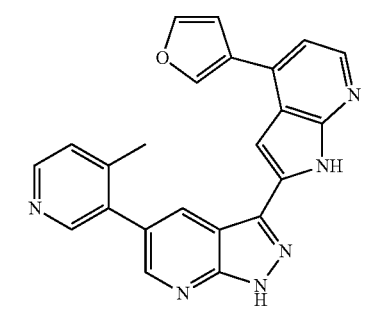 [SMILES: Cc1ccncc1-c1cnc2[nH]nc(-c3cc4c(-c5ccoc5)ccnc4[nH]3)c2c1]
314 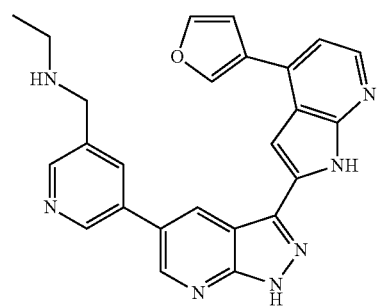 [SMILES: CCNCc1cncc(-c2cnc3[nH]nc(-c4cc5c(-c6ccoc6)ccnc5[nH]4)c3c2)c1]
315 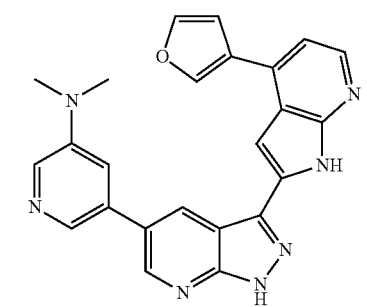
316 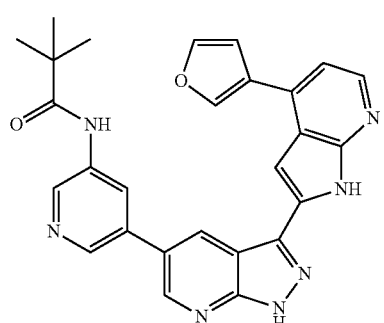
317 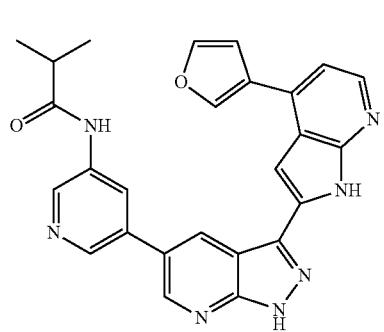 [SMILES: CC(C)C(=O)Nc1cncc(-c2cnc3[nH]nc(-c4cc5c(-c6ccoc6)ccnc5[nH]4)c3c2)c1]
TABLE 1-continued
318 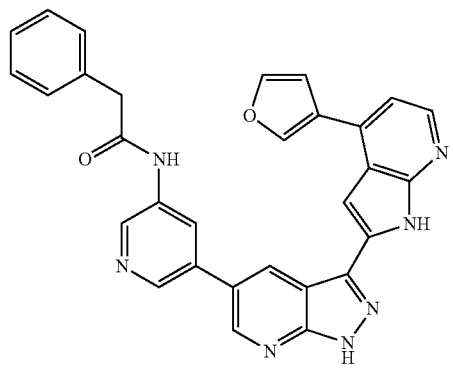
319 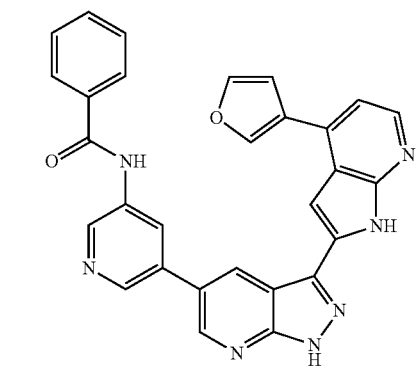 [SMILES: O=C(Nc1cncc(-c2cnc3[nH]nc(-c4cc5c(-c6ccoc6)ccnc5[nH]4)c3c2)c1)c1ccccc1]
320 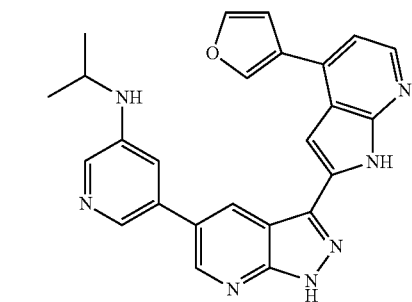 [SMILES: CC(C)Nc1cncc(-c2cnc3[nH]nc(-c4cc5c(-c6ccoc6)ccnc5[nH]4)c3c2)c1]
321 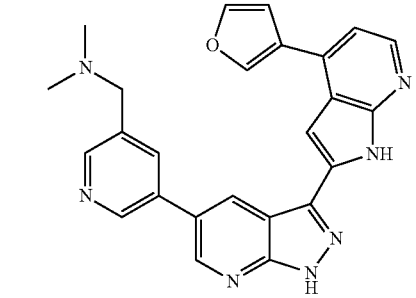
322 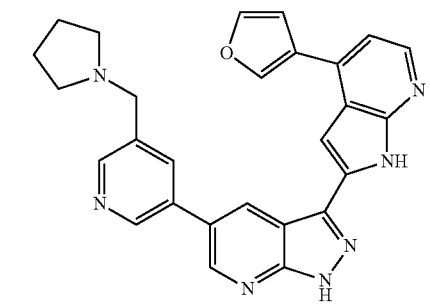

TABLE 1-continued
323
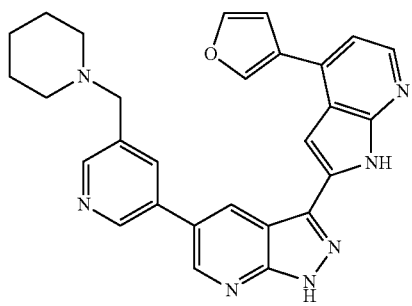 [SMILES: c1cc(-c2ccoc2)c2cc(-c3n[nH]c4ncc(-c5cncc(CN6CCCCC6)c5)cc34)[nH]c2n1]
324
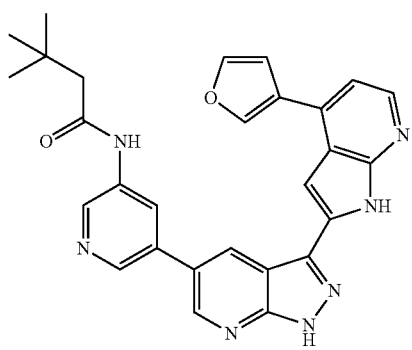
325
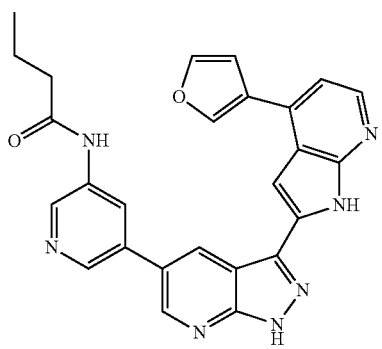 [SMILES: CCCC(=O)Nc1cncc(-c2cnc3[nH]nc(-c4cc5c(-c6ccoc6)ccnc5[nH]4)c3c2)c1]
326
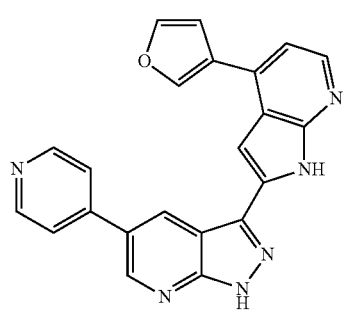 [SMILES: c1cc(-c2cnc3[nH]nc(-c4cc5c(-c6ccoc6)ccnc5[nH]4)c3c2)ccn1]
TABLE 1-continued
327
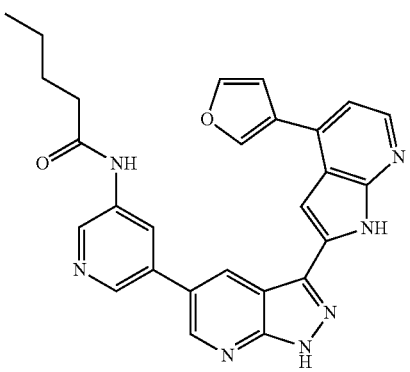
328
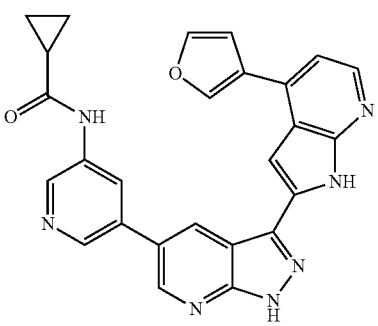 [SMILES: O=C(Nc1cncc(-c2cnc3[nH]nc(-c4cc5c(-c6ccoc6)ccnc5[nH]4)c3c2)c1)C1CC1]
329
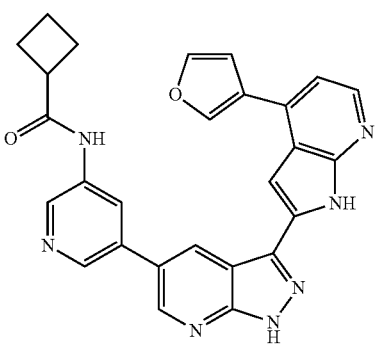 [SMILES: O=C(Nc1cncc(-c2cnc3[nH]nc(-c4cc5c(-c6ccoc6)ccnc5[nH]4)c3c2)c1)C1CCC1]
330
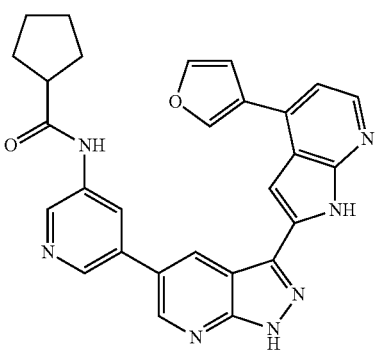 [SMILES: O=C(Nc1cncc(-c2cnc3[nH]nc(-c4cc5c(-c6ccoc6)ccnc5[nH]4)c3c2)c1)C1CCCC1]

TABLE 1-continued
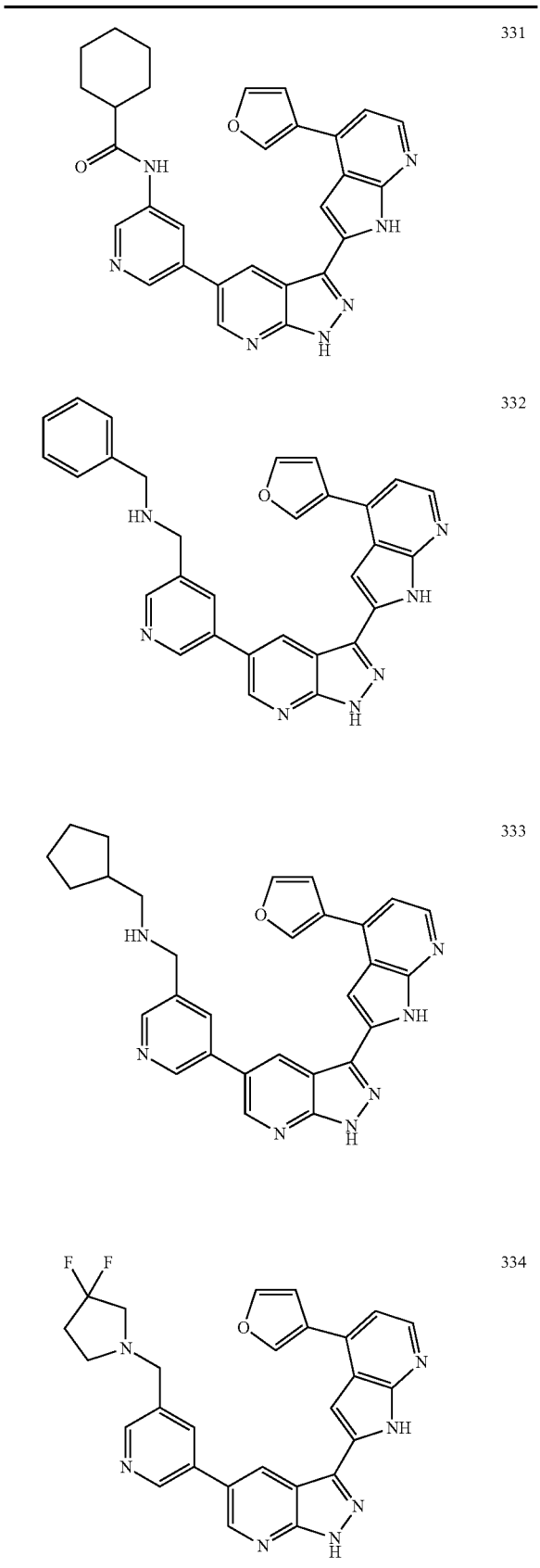
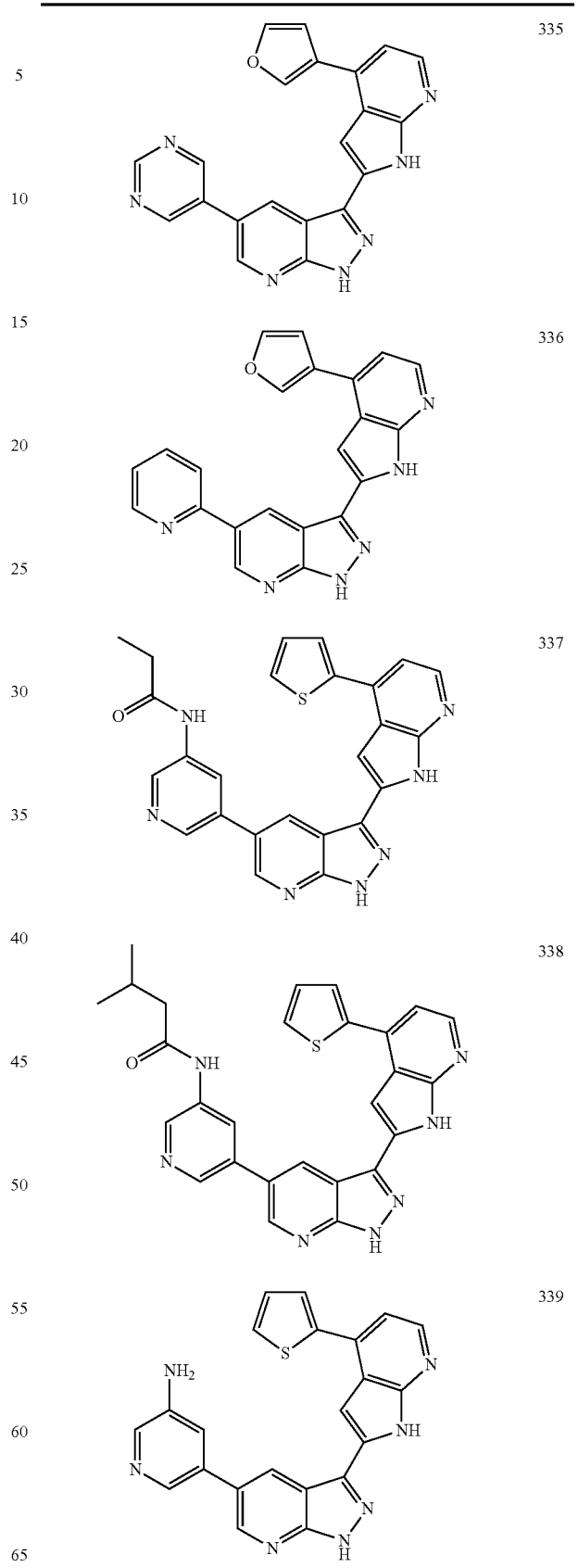

TABLE 1-continued
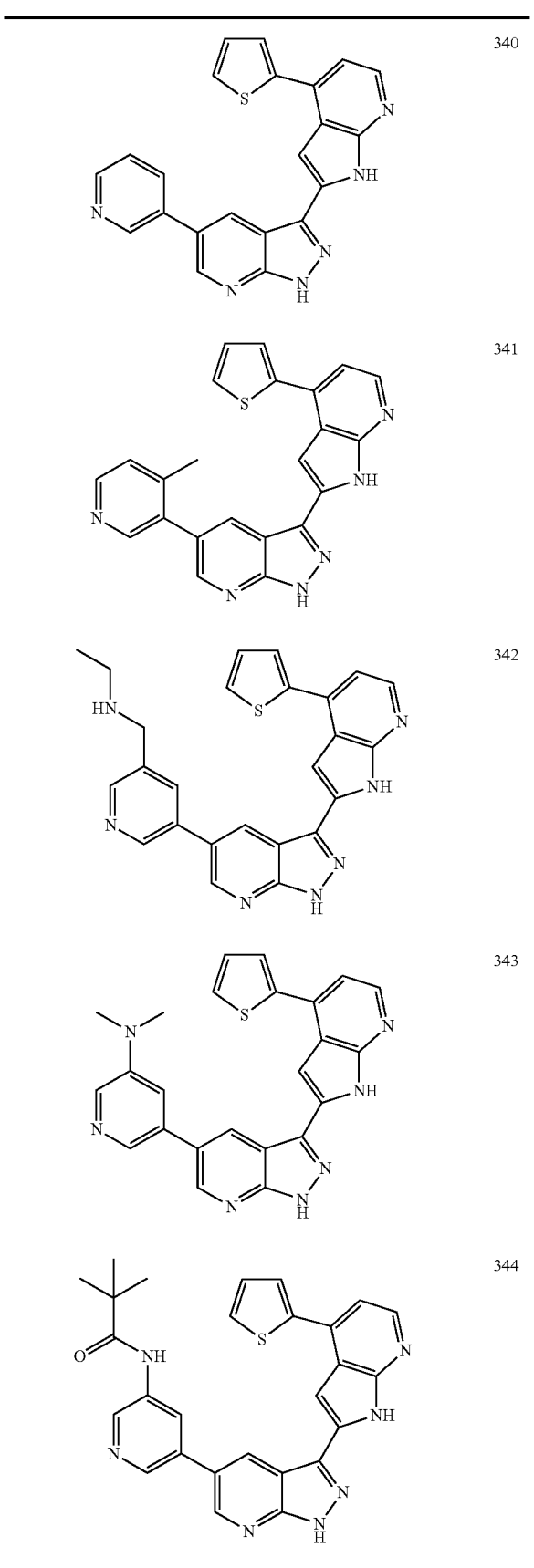
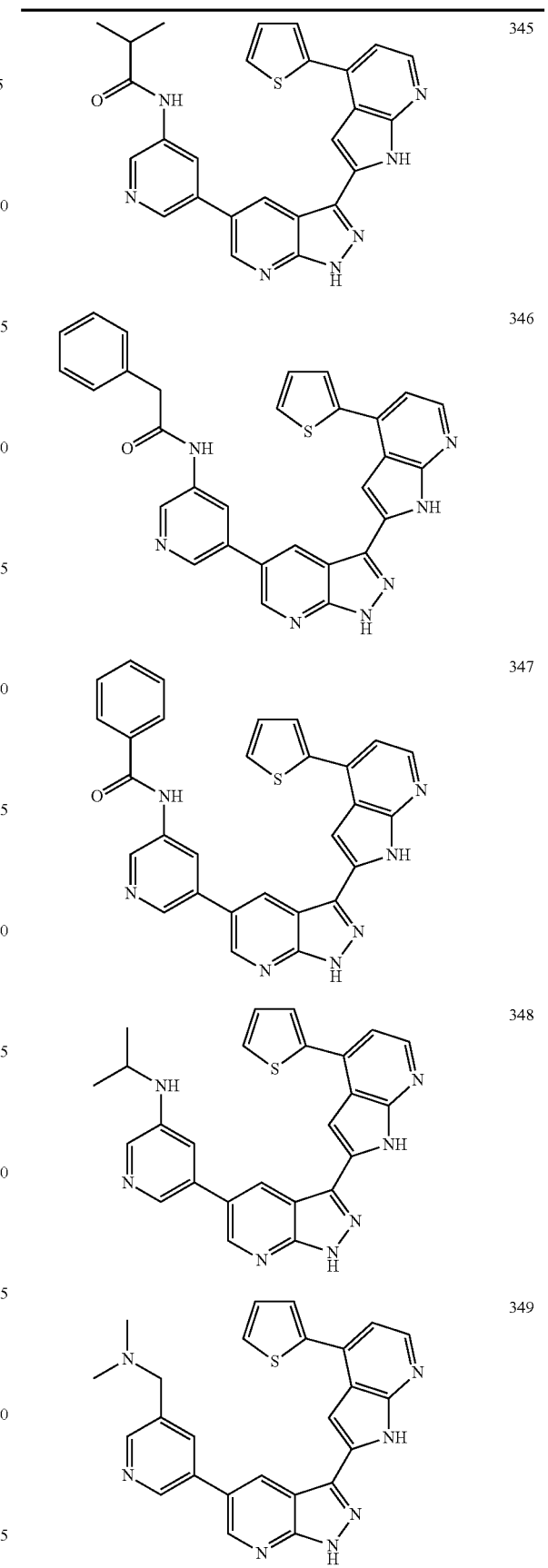

TABLE 1-continued
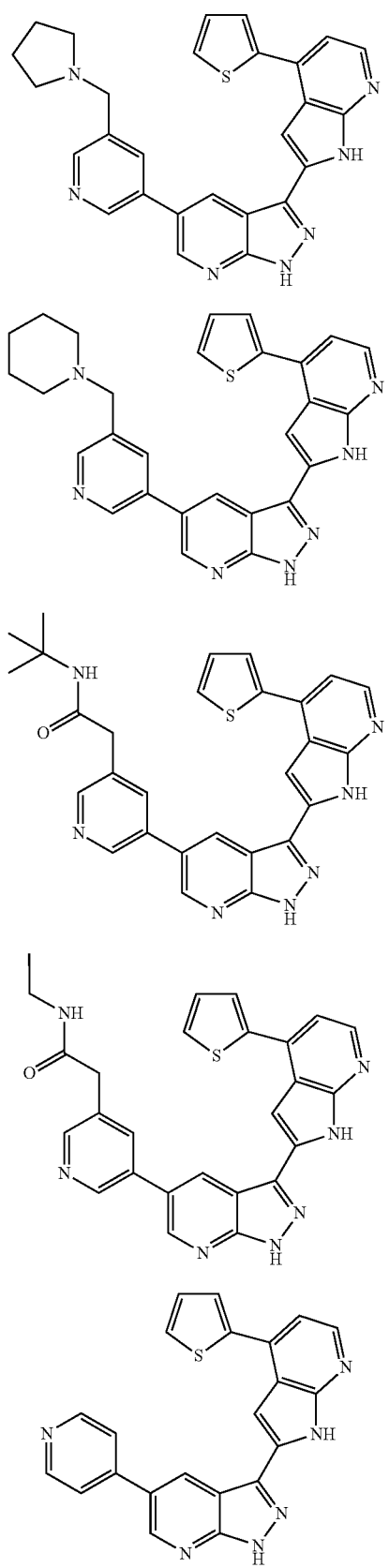
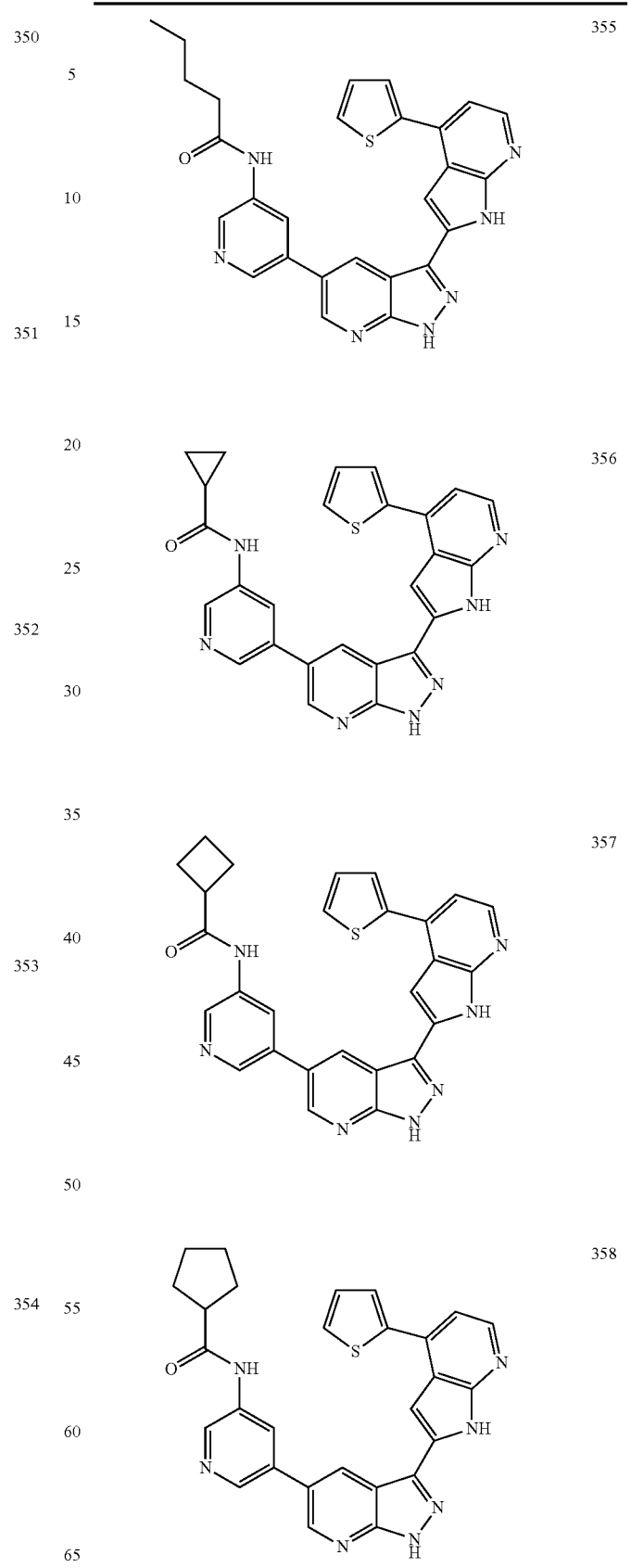

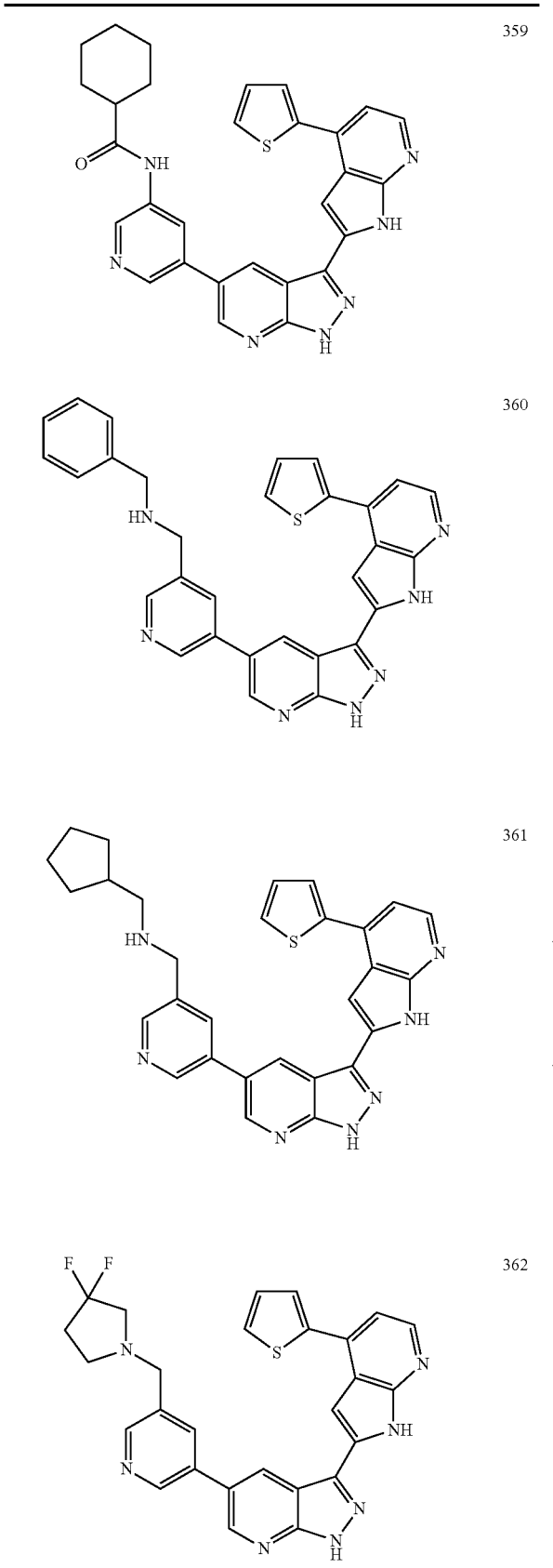

TABLE 1-continued
| | |
|---|---|
| 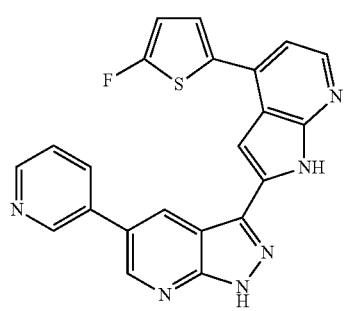 [SMILES: Cc1ccc(-c2ccnc3[nH]c(-c4n[nH]c5ncc(-c6cccnc6)cc45)cc23)s1] | 368 |
| 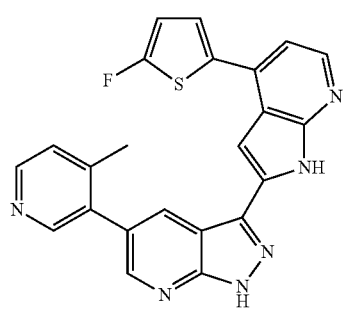 [SMILES: Cc1ccc(-c2ccnc3[nH]c(-c4n[nH]c5ncc(-c6cnccc6C)cc45)cc23)s1] | 369 |
| 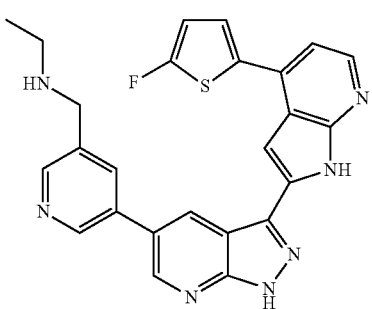 [SMILES: CCNCc1cncc(-c2cnc3[nH]nc(-c4cc5c(-c6ccc(C)s6)ccnc5[nH]4)c3c2)c1] | 370 |
| 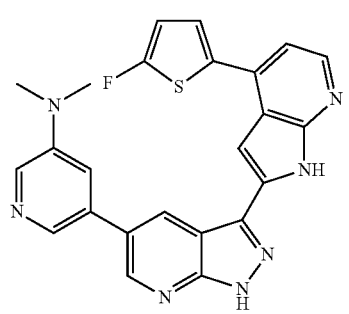 | 371 |
| 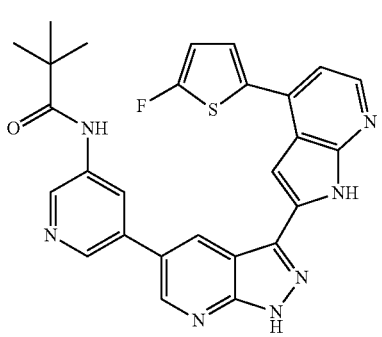 | 372 |
TABLE 1-continued
| | |
|---|---|
| 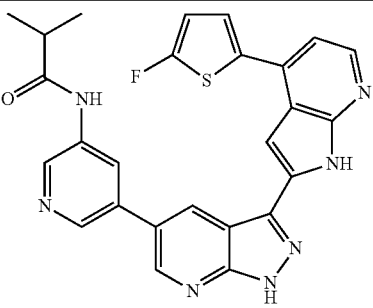 | 373 |
| 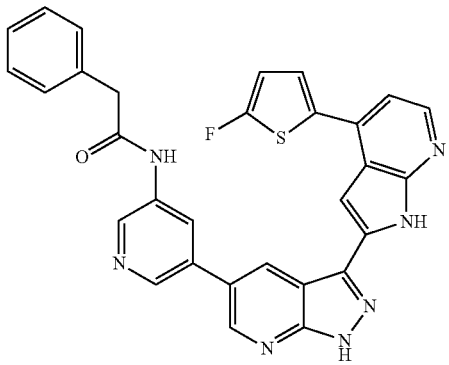 [SMILES: Cc1ccc(-c2ccnc3[nH]c(-c4n[nH]c5ncc(-c6cncc(NC(=O)Cc7ccccc7)c6)cc45)cc23)s1] | 374 |
| 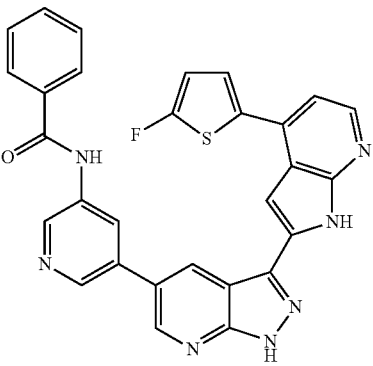 [SMILES: Cc1ccc(-c2ccnc3[nH]c(-c4n[nH]c5ncc(-c6cncc(NC(=O)c7ccccc7)c6)cc45)cc23)s1] | 375 |
| 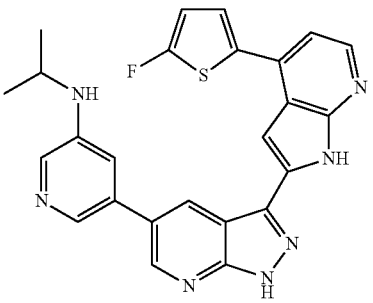 | 376 |
| 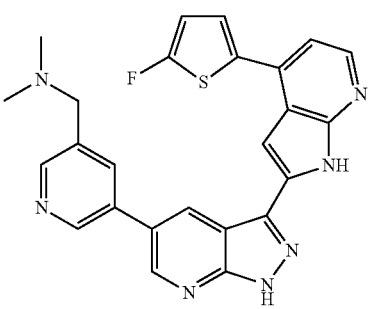 [SMILES: Cc1ccc(-c2ccnc3[nH]c(-c4n[nH]c5ncc(-c6cncc(CN(C)C)c6)cc45)cc23)s1] | 377 |

TABLE 1-continued
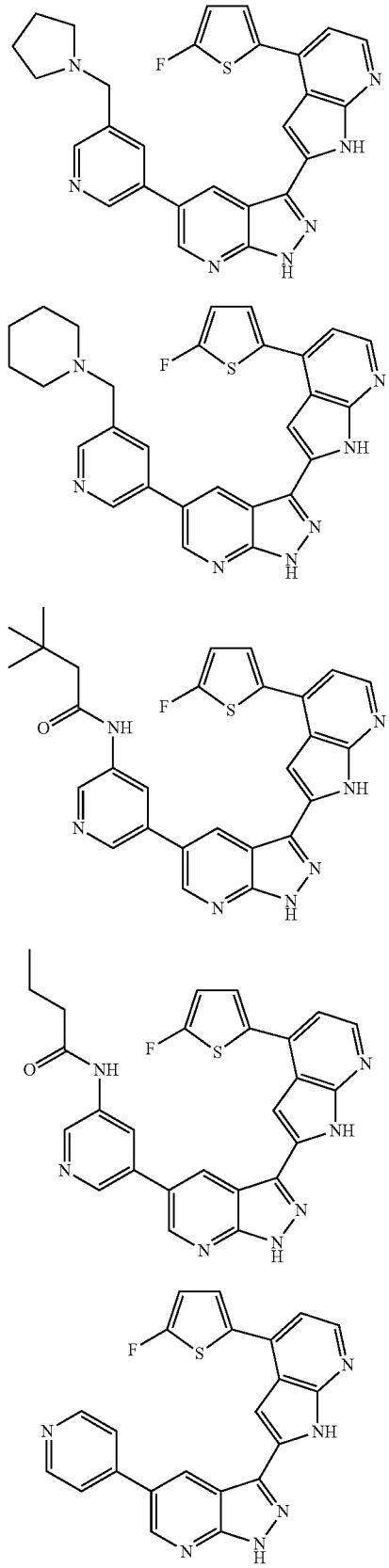
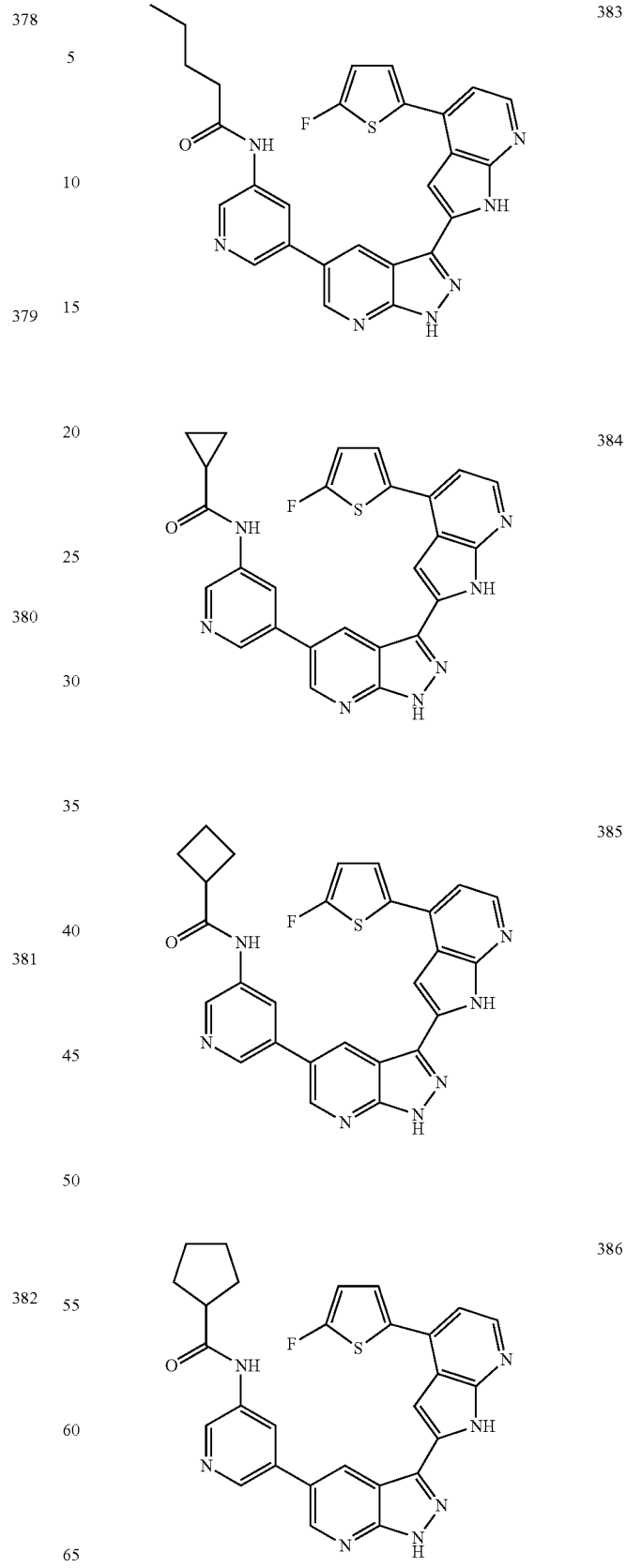

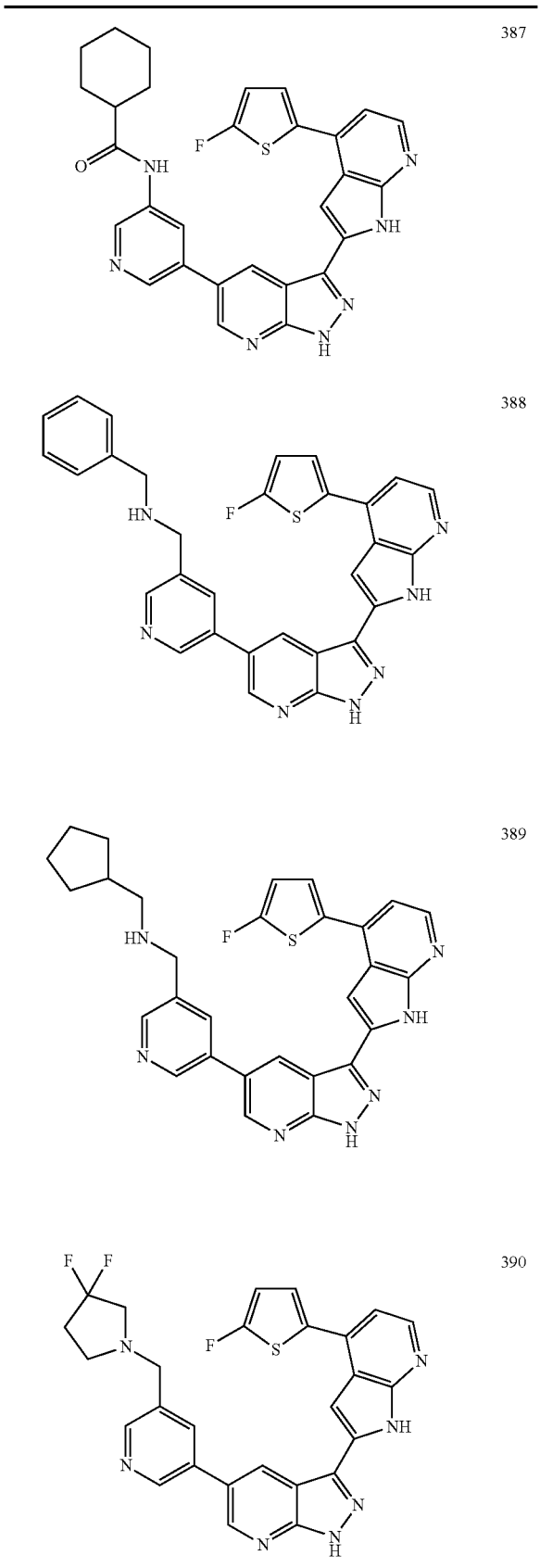

TABLE 1-continued
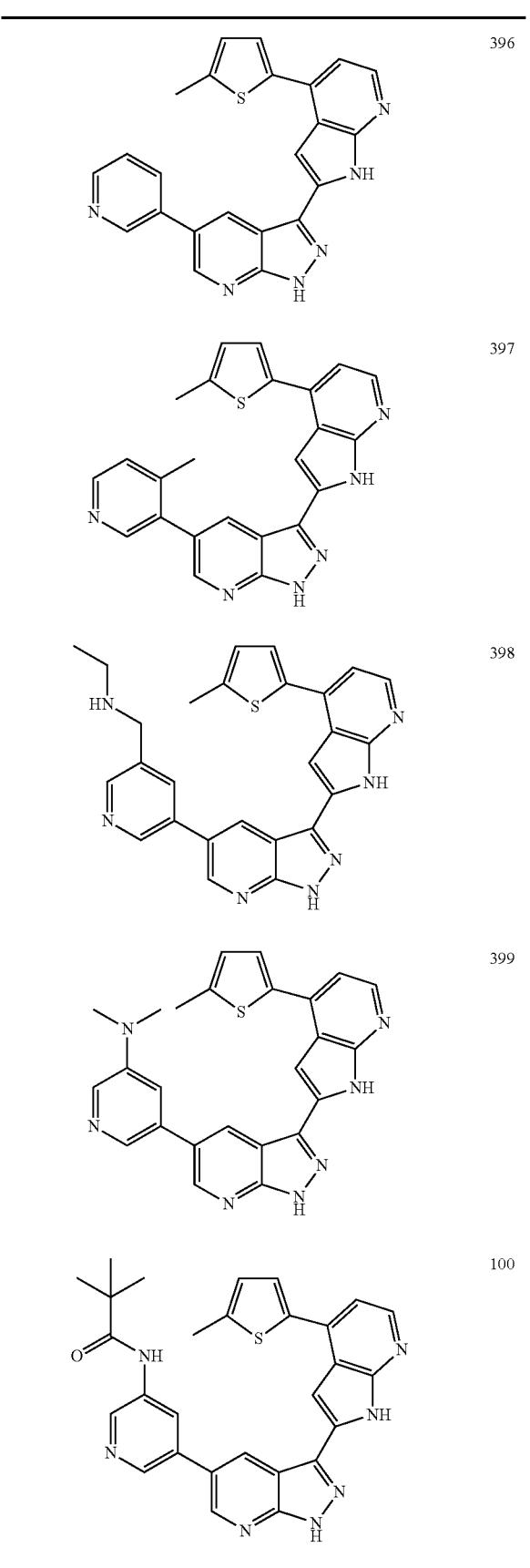
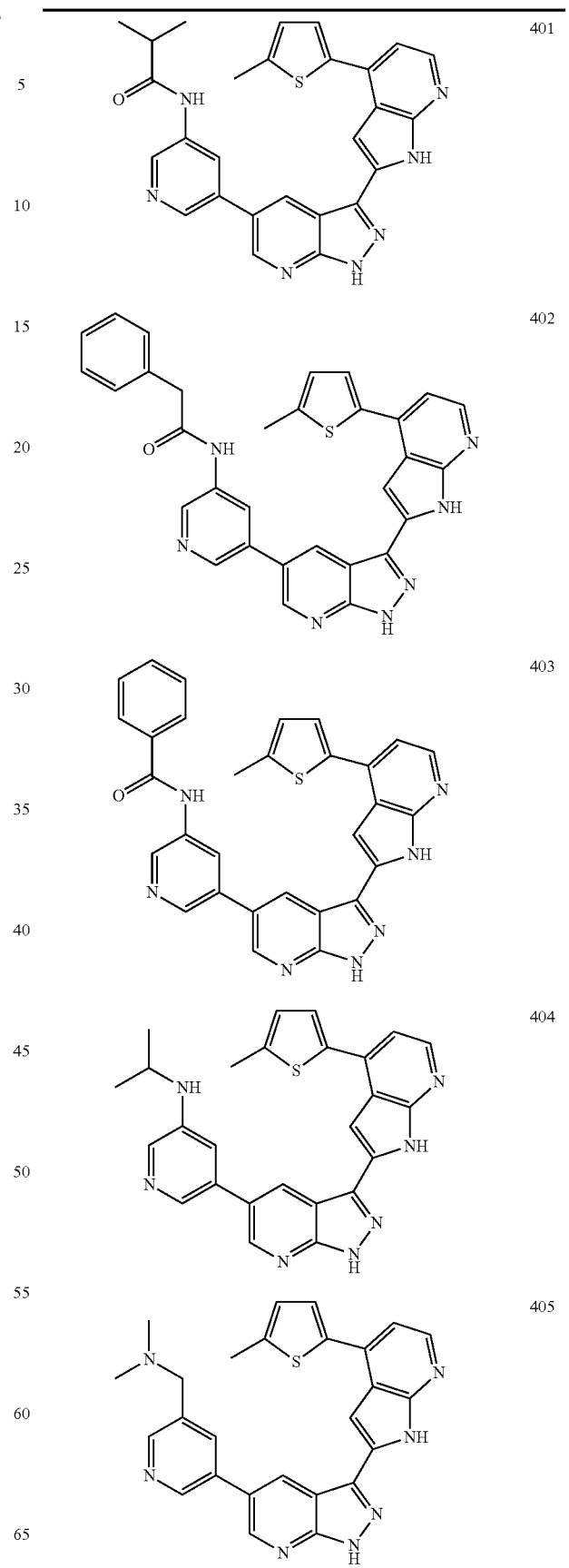

TABLE 1-continued
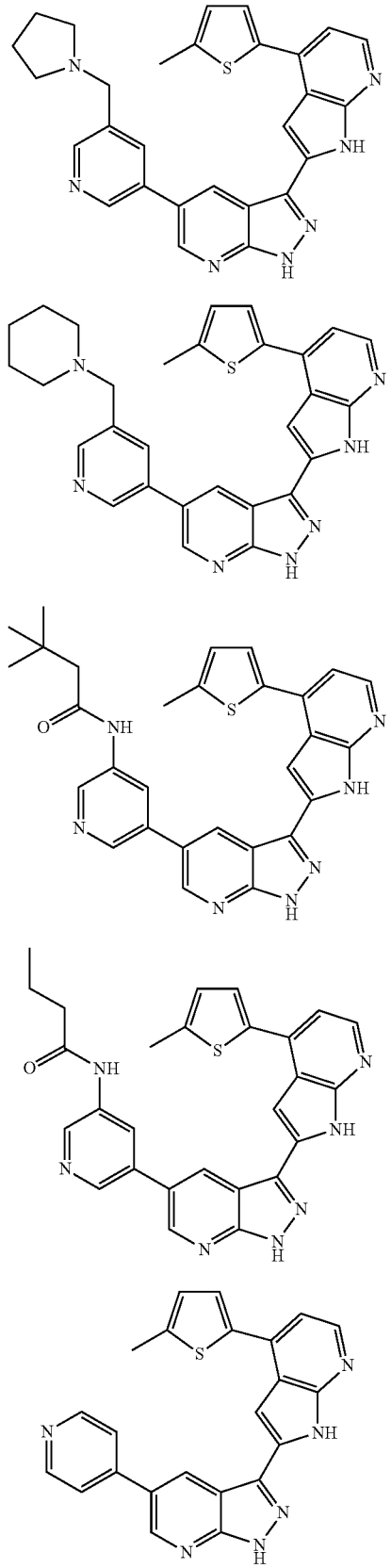
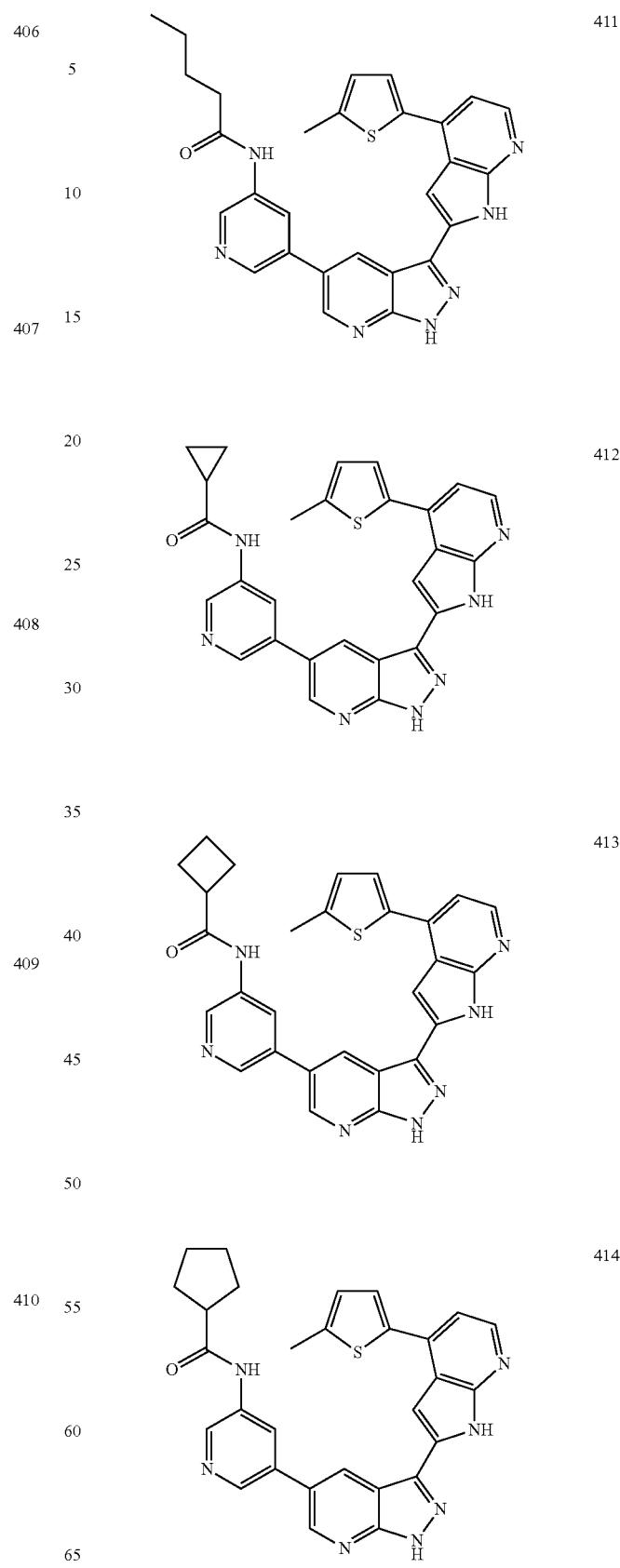

TABLE 1-continued
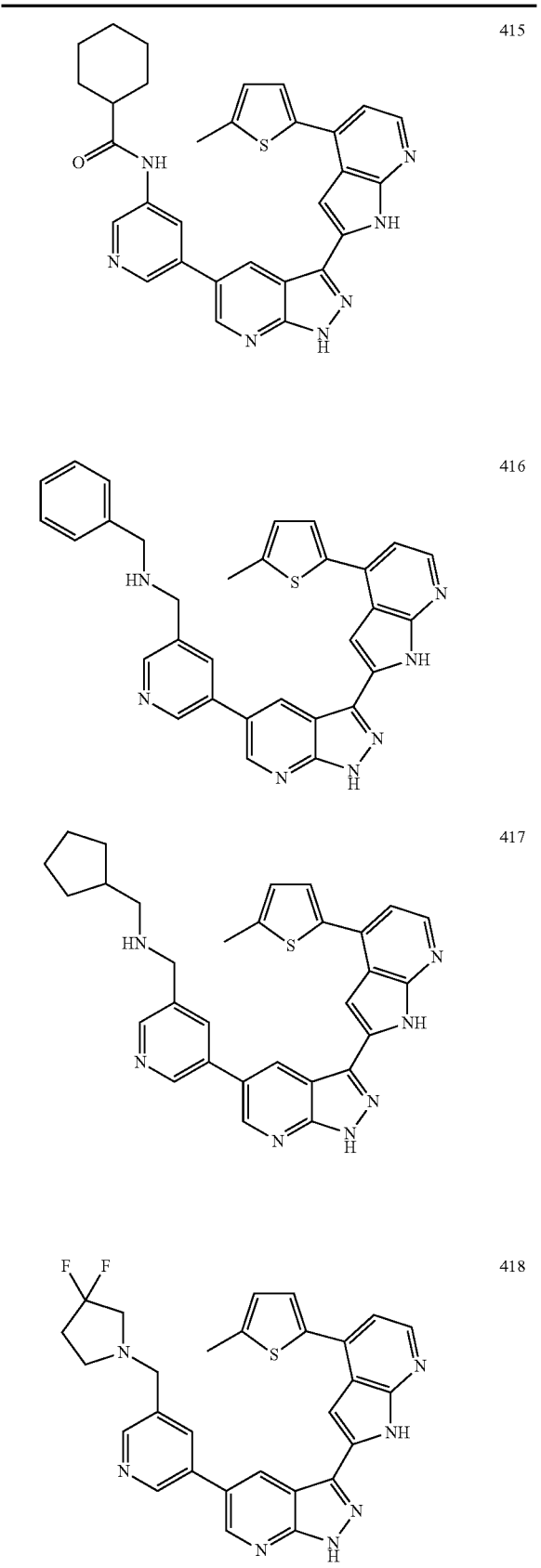
415
416
417
418
TABLE 1-continued
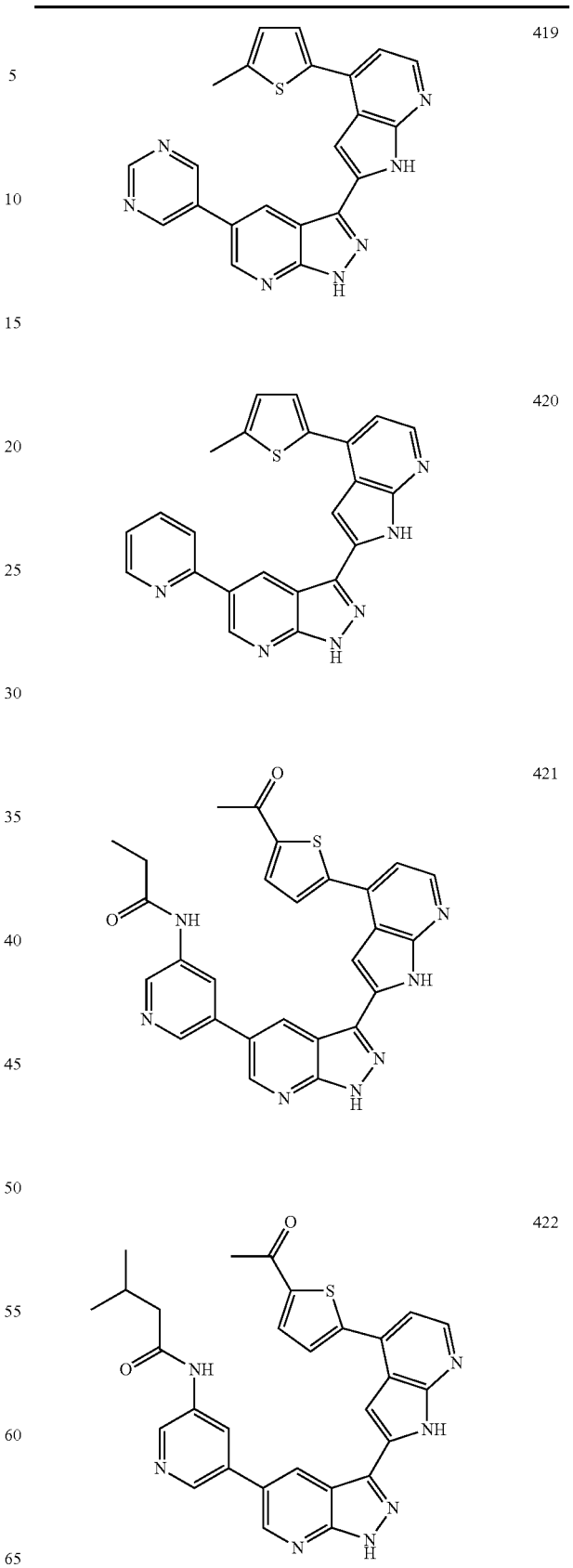
419
420
421
422

TABLE 1-continued
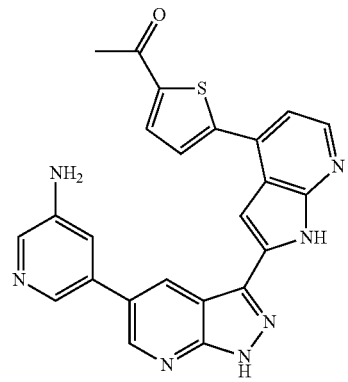 [SMILES: CC(=O)c1ccc(-c2ccnc3[nH]c(-c4n[nH]c5ncc(-c6cncc(N)c6)cc45)cc23)s1]
423
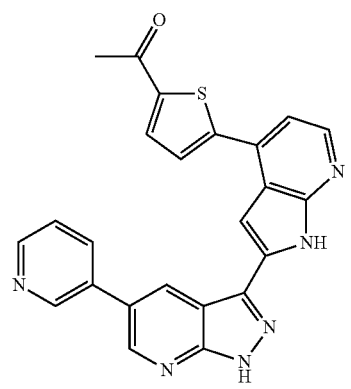
424
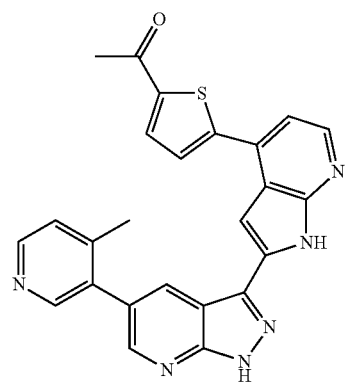 [SMILES: CC(=O)c1ccc(-c2ccnc3[nH]c(-c4n[nH]c5ncc(-c6cnccc6C)cc45)cc23)s1]
425
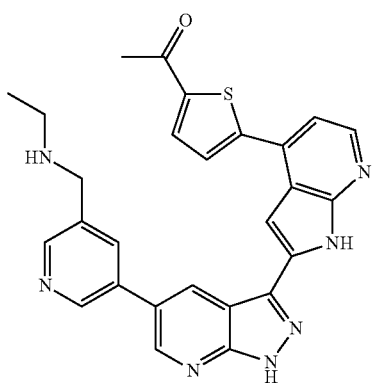 [SMILES: CCNCc1cncc(-c2cnc3[nH]nc(-c4cc5c(-c6ccc(C(C)=O)s6)ccnc5[nH]4)c3c2)c1]
426
TABLE 1-continued
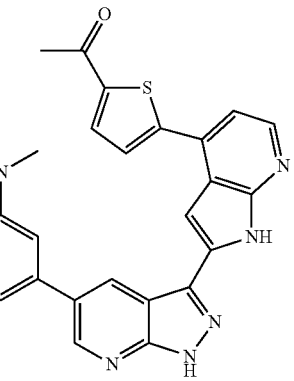
427
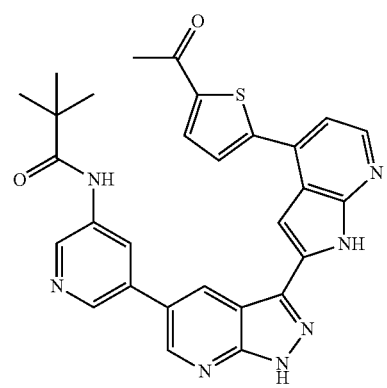 [SMILES: CC(=O)c1ccc(-c2ccnc3[nH]c(-c4n[nH]c5ncc(-c6cncc(NC(=O)C(C)(C)C)c6)cc45)cc23)s1]
428
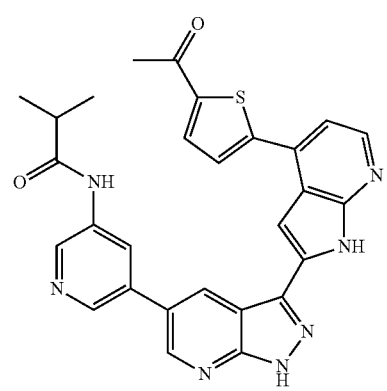 [SMILES: CC(=O)c1ccc(-c2ccnc3[nH]c(-c4n[nH]c5ncc(-c6cncc(NC(=O)C(C)C)c6)cc45)cc23)s1]
429
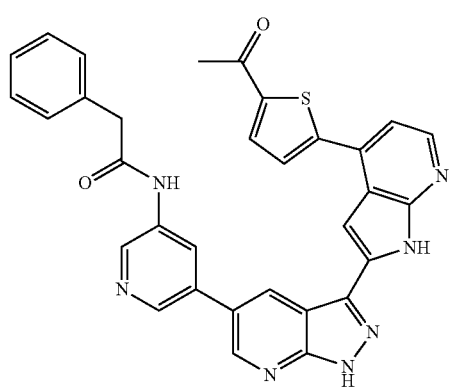 [SMILES: CC(=O)c1ccc(-c2ccnc3[nH]c(-c4n[nH]c5ncc(-c6cncc(NC(=O)Cc7ccccc7)c6)cc45)cc23)s1]
430

TABLE 1-continued
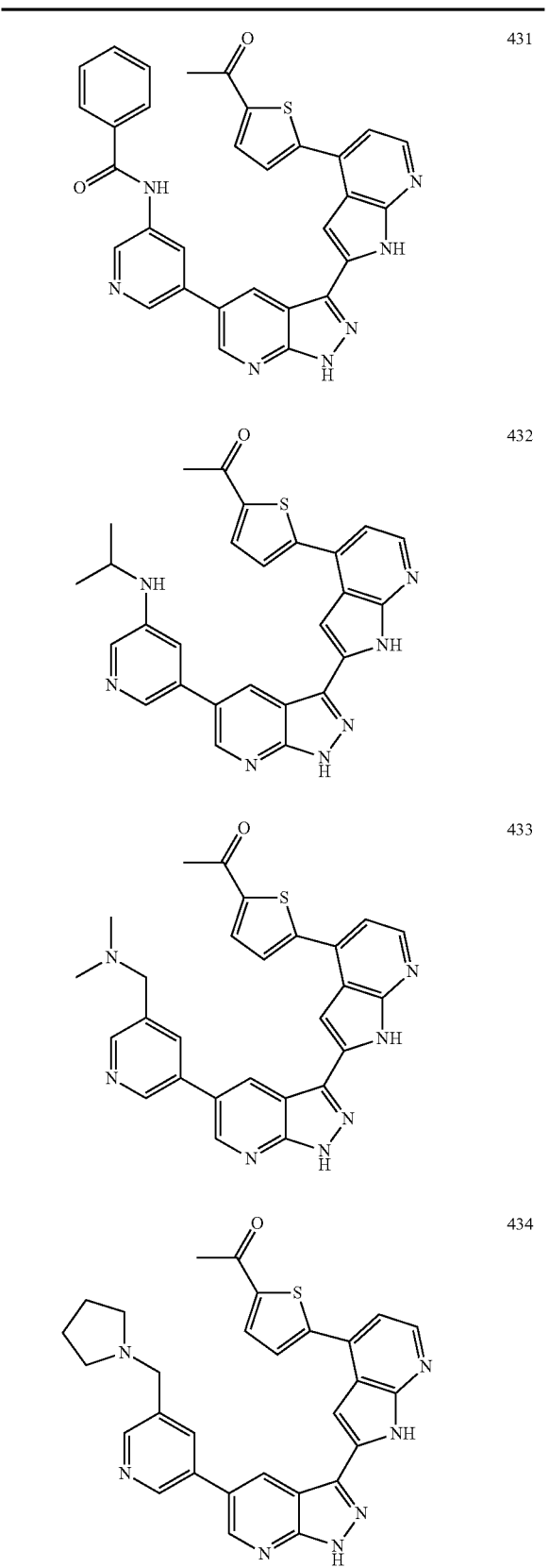
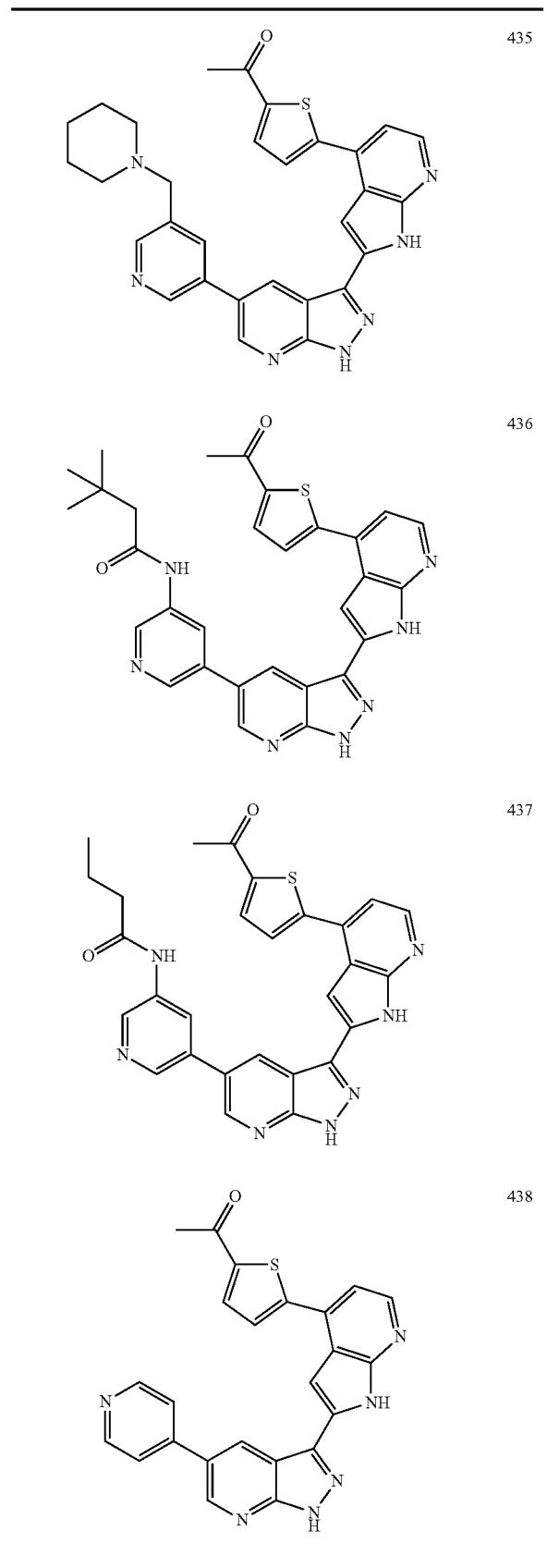

TABLE 1-continued
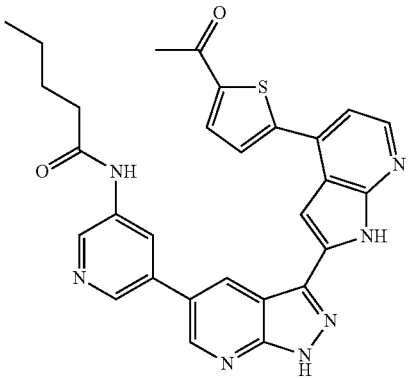 [SMILES: CCCCC(=O)Nc1cncc(-c2cnc3[nH]nc(-c4cc5c(-c6ccc(C(C)=O)s6)ccnc5[nH]4)c3c2)c1] 439
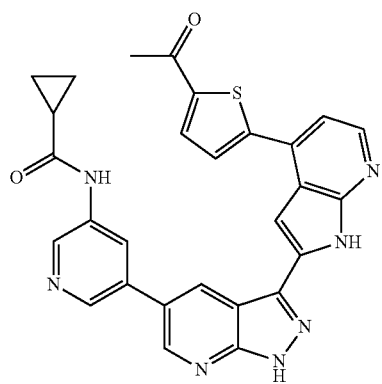 [SMILES: CC(=O)c1ccc(-c2ccnc3[nH]c(-c4n[nH]c5ncc(-c6cncc(NC(=O)C7CC7)c6)cc45)cc23)s1] 440
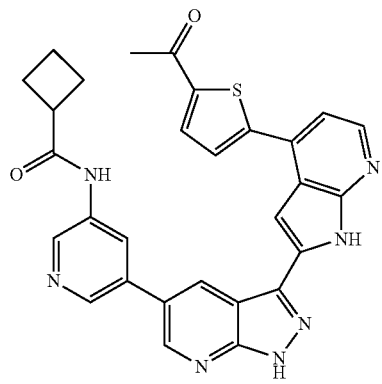 [SMILES: CC(=O)c1ccc(-c2ccnc3[nH]c(-c4n[nH]c5ncc(-c6cncc(NC(=O)C7CCC7)c6)cc45)cc23)s1] 441
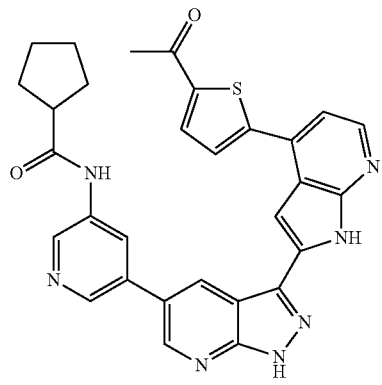 [SMILES: CC(=O)c1ccc(-c2ccnc3[nH]c(-c4n[nH]c5ncc(-c6cncc(NC(=O)C7CCCC7)c6)cc45)cc23)s1] 442
TABLE 1-continued
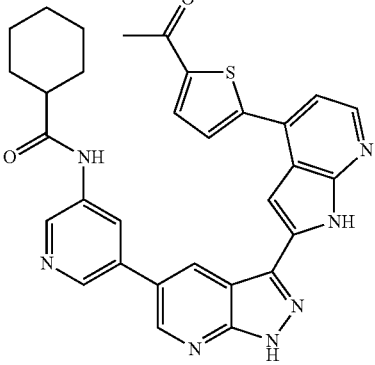 443
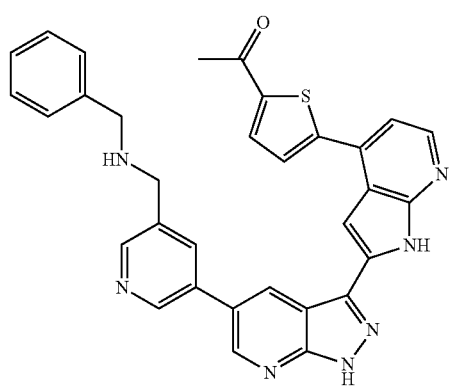 [SMILES: CC(=O)c1ccc(-c2ccnc3[nH]c(-c4n[nH]c5ncc(-c6cncc(CNCc7ccccc7)c6)cc45)cc23)s1] 444
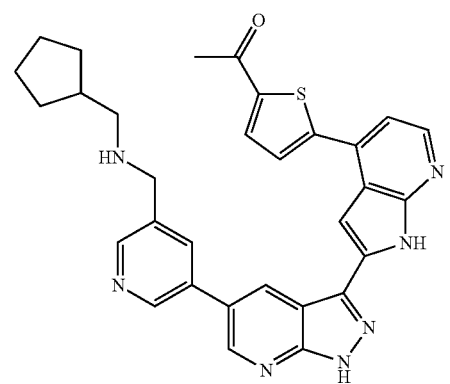 [SMILES: CC(=O)c1ccc(-c2ccnc3[nH]c(-c4n[nH]c5ncc(-c6cncc(CNCC7CCCC7)c6)cc45)cc23)s1] 445
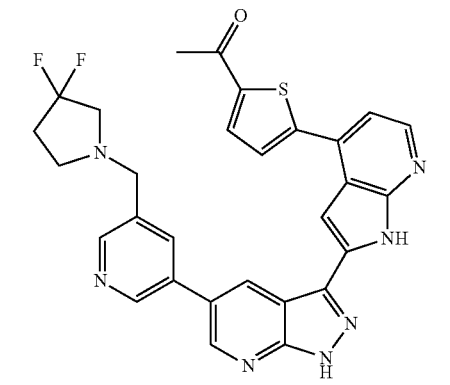 [SMILES: CC(=O)c1ccc(-c2ccnc3[nH]c(-c4n[nH]c5ncc(-c6cncc(CN7CCC(F)(F)C7)c6)cc45)cc23)s1] 446

TABLE 1-continued
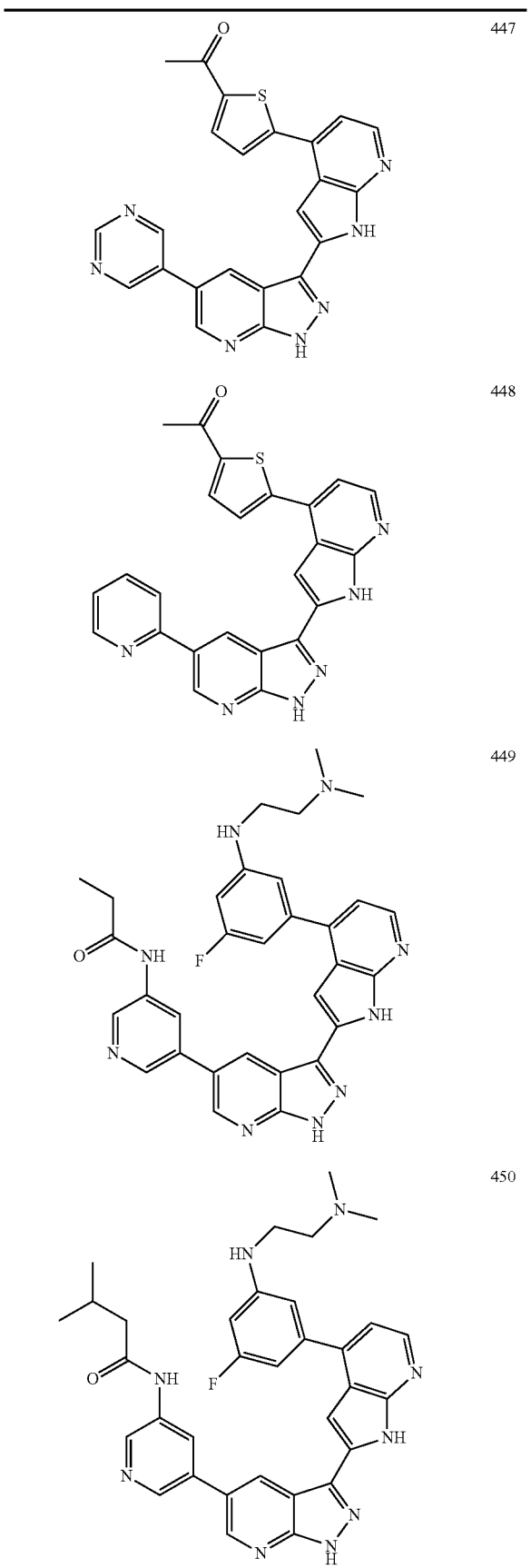

TABLE 1-continued
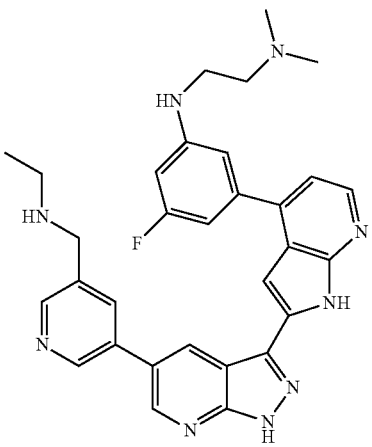
454
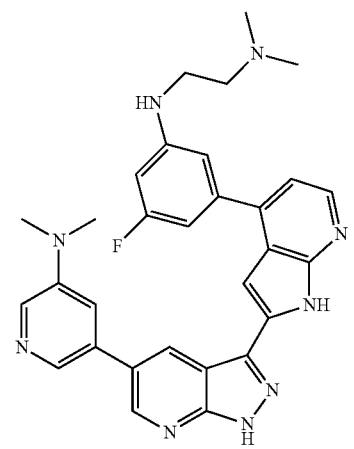 [SMILES: CN(C)CCNc1cc(F)cc(-c2ccnc3[nH]c(-c4n[nH]c5ncc(-c6cncc(N(C)C)c6)cc45)cc23)c1]
455
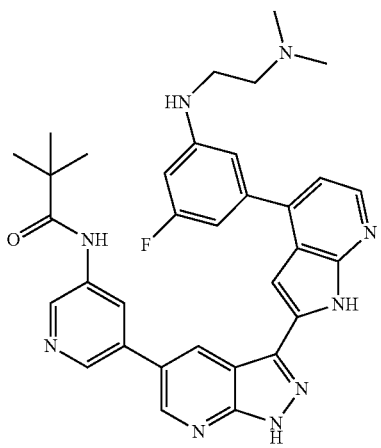 [SMILES: CN(C)CCNc1cc(F)cc(-c2ccnc3[nH]c(-c4n[nH]c5ncc(-c6cncc(NC(=O)C(C)(C)C)c6)cc45)cc23)c1]
456
TABLE 1-continued
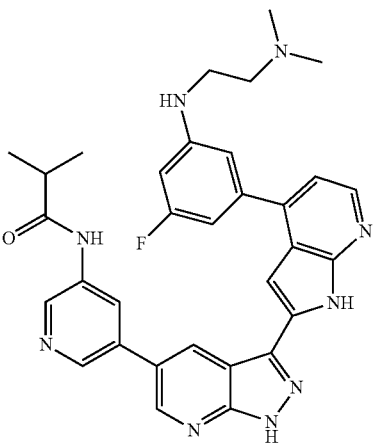 [SMILES: CC(C)C(=O)Nc1cncc(-c2cnc3[nH]nc(-c4cc5c(-c6cc(F)cc(NCCN(C)C)c6)ccnc5[nH]4)c3c2)c1]
457
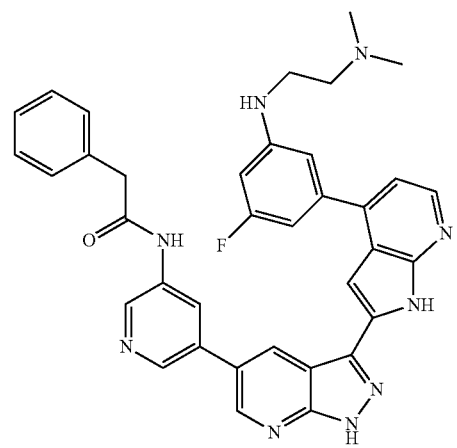 [SMILES: CN(C)CCNc1cc(F)cc(-c2ccnc3[nH]c(-c4n[nH]c5ncc(-c6cncc(NC(=O)Cc7ccccc7)c6)cc45)cc23)c1]
458
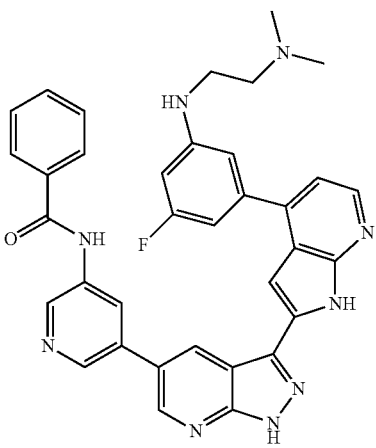 [SMILES: CN(C)CCNc1cc(F)cc(-c2ccnc3[nH]c(-c4n[nH]c5ncc(-c6cncc(NC(=O)c7ccccc7)c6)cc45)cc23)c1]
459

TABLE 1-continued
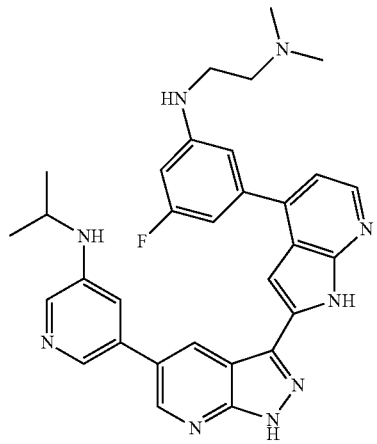
460
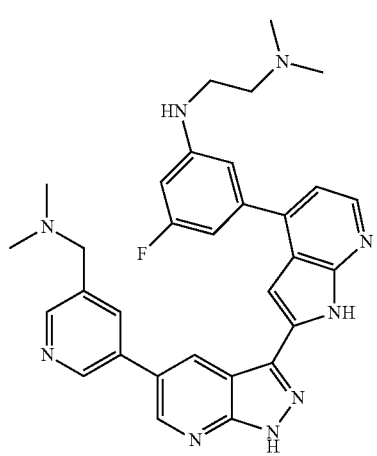 [SMILES: CN(C)CCNc1cc(F)cc(-c2ccnc3[nH]c(-c4n[nH]c5ncc(-c6cncc(CN(C)C)c6)cc45)cc23)c1]
461
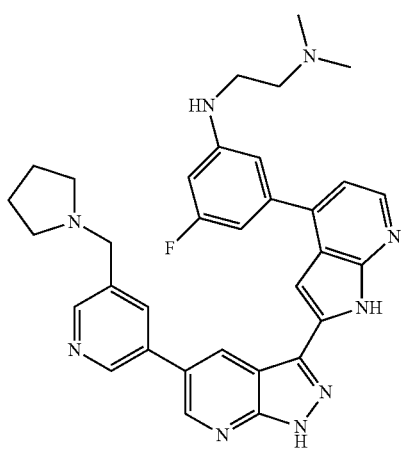 [SMILES: CN(C)CCNc1cc(F)cc(-c2ccnc3[nH]c(-c4n[nH]c5ncc(-c6cncc(CN7CCCC7)c6)cc45)cc23)c1]
462
TABLE 1-continued
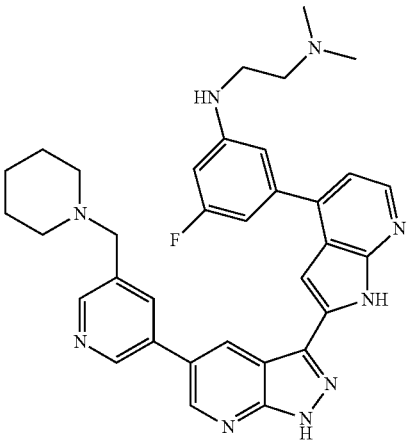 [SMILES: CN(C)CCNc1cc(F)cc(-c2ccnc3[nH]c(-c4n[nH]c5ncc(-c6cncc(CN7CCCCC7)c6)cc45)cc23)c1]
463
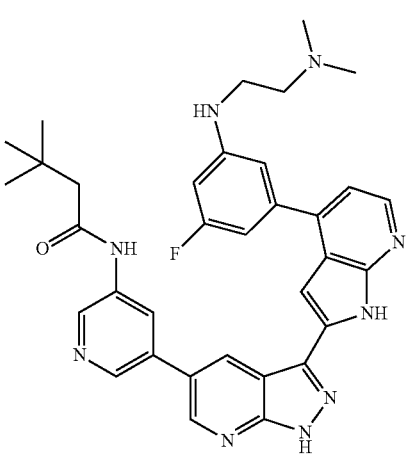 [SMILES: CN(C)CCNc1cc(F)cc(-c2ccnc3[nH]c(-c4n[nH]c5ncc(-c6cncc(NC(=O)CC(C)(C)C)c6)cc45)cc23)c1]
464
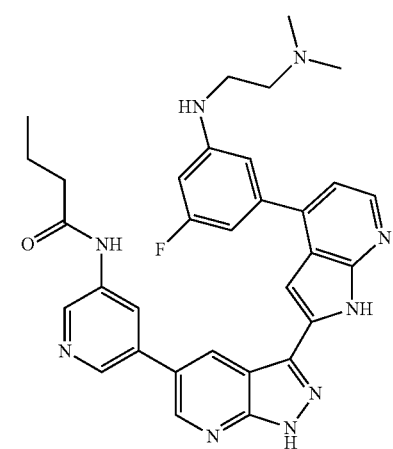 [SMILES: CCCC(=O)Nc1cncc(-c2cnc3[nH]nc(-c4cc5c(-c6cc(F)cc(NCCN(C)C)c6)ccnc5[nH]4)c3c2)c1]
465

TABLE 1-continued
466
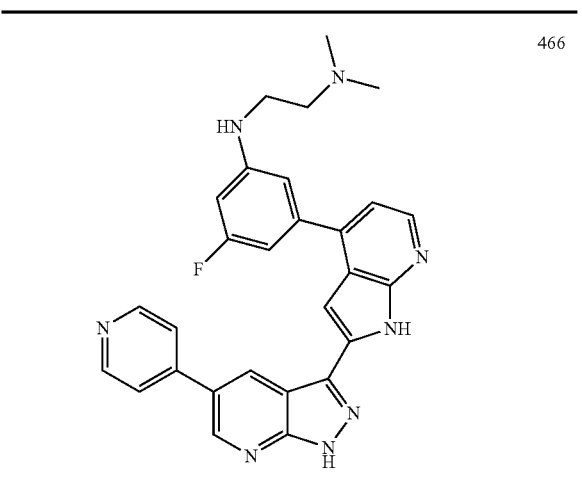
469
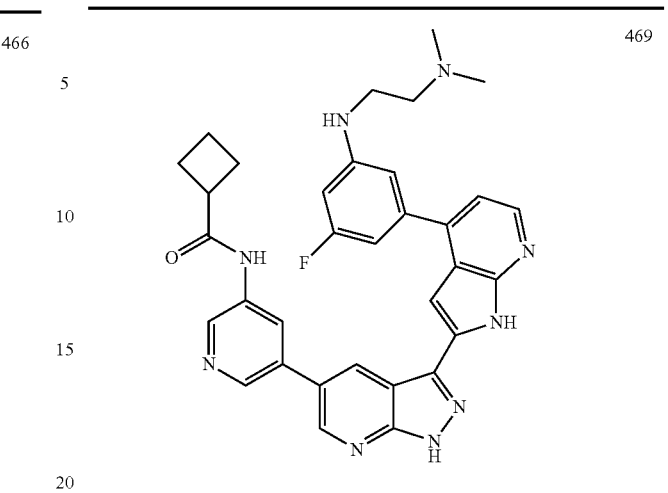
467
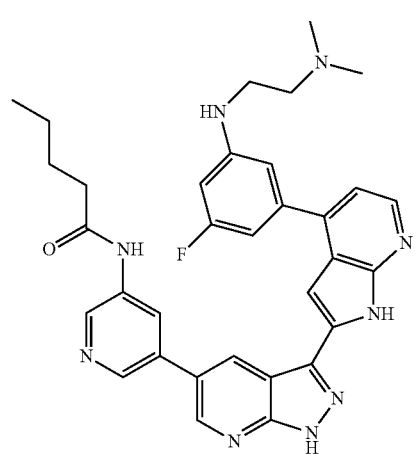 [SMILES: CCCCC(=O)Nc1cncc(-c2cnc3[nH]nc(-c4cc5c(-c6cc(F)cc(NCCN(C)C)c6)ccnc5[nH]4)c3c2)c1]
470
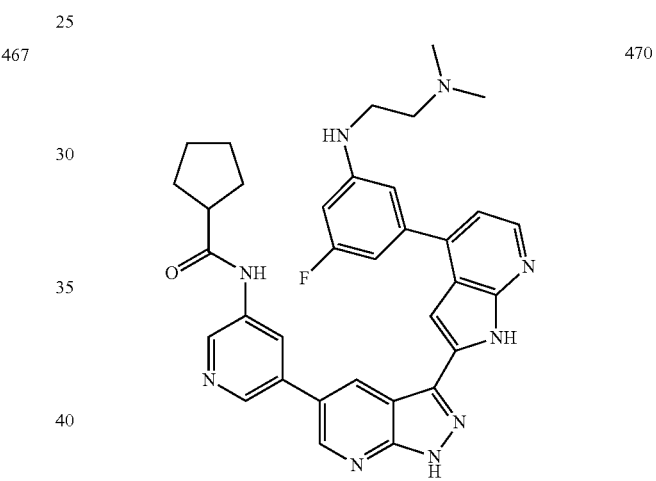
468
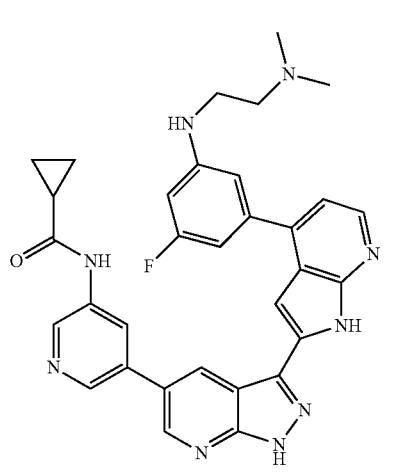
471
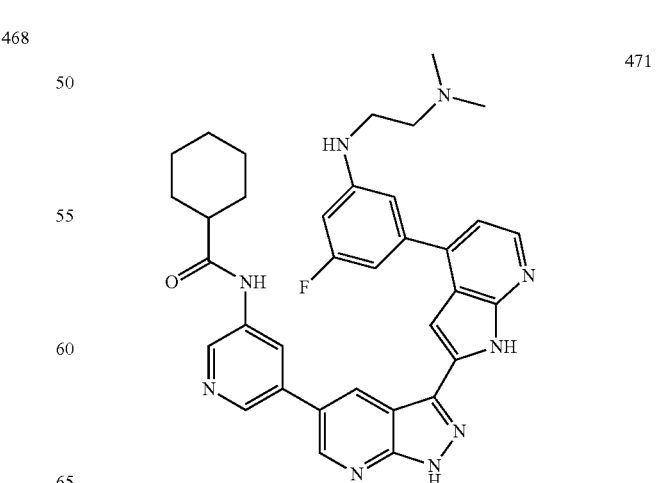

TABLE 1-continued
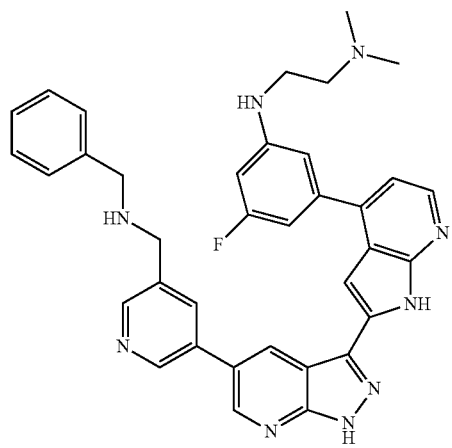
472
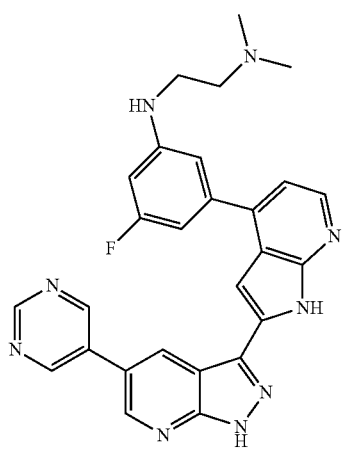
475
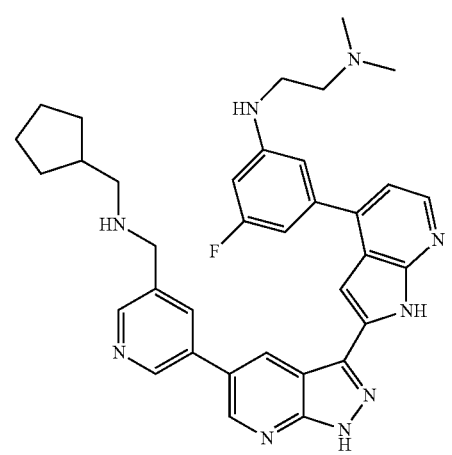 [SMILES: CN(C)CCNc1cc(F)cc(-c2ccnc3[nH]c(-c4n[nH]c5ncc(-c6cncc(CNCC7CCCC7)c6)cc45)cc23)c1]
473
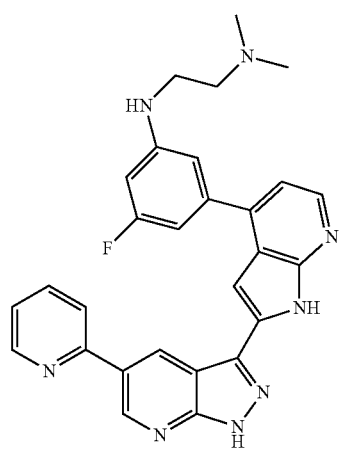
476
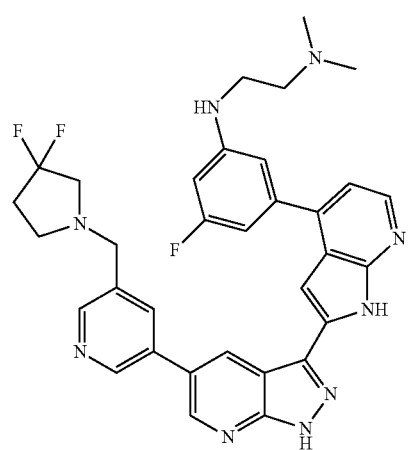 [SMILES: CN(C)CCNc1cc(F)cc(-c2ccnc3[nH]c(-c4n[nH]c5ncc(-c6cncc(CN7CCC(F)(F)C7)c6)cc45)cc23)c1]
474
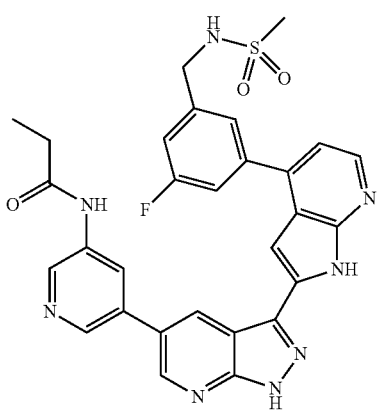 [SMILES: CCC(=O)Nc1cncc(-c2cnc3[nH]nc(-c4cc5c(-c6cc(F)cc(CNS(C)(=O)=O)c6)ccnc5[nH]4)c3c2)c1]
477

TABLE 1-continued
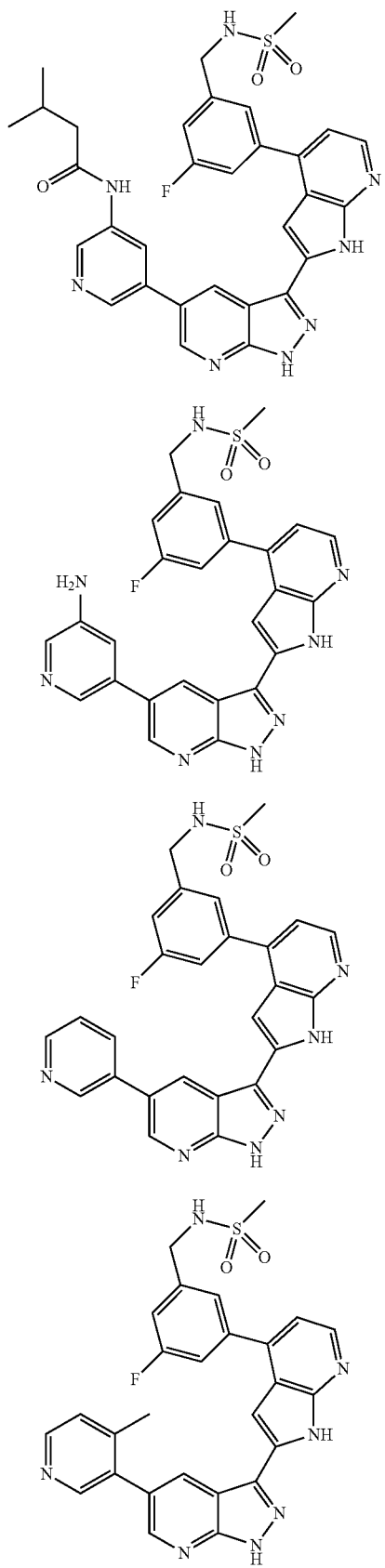
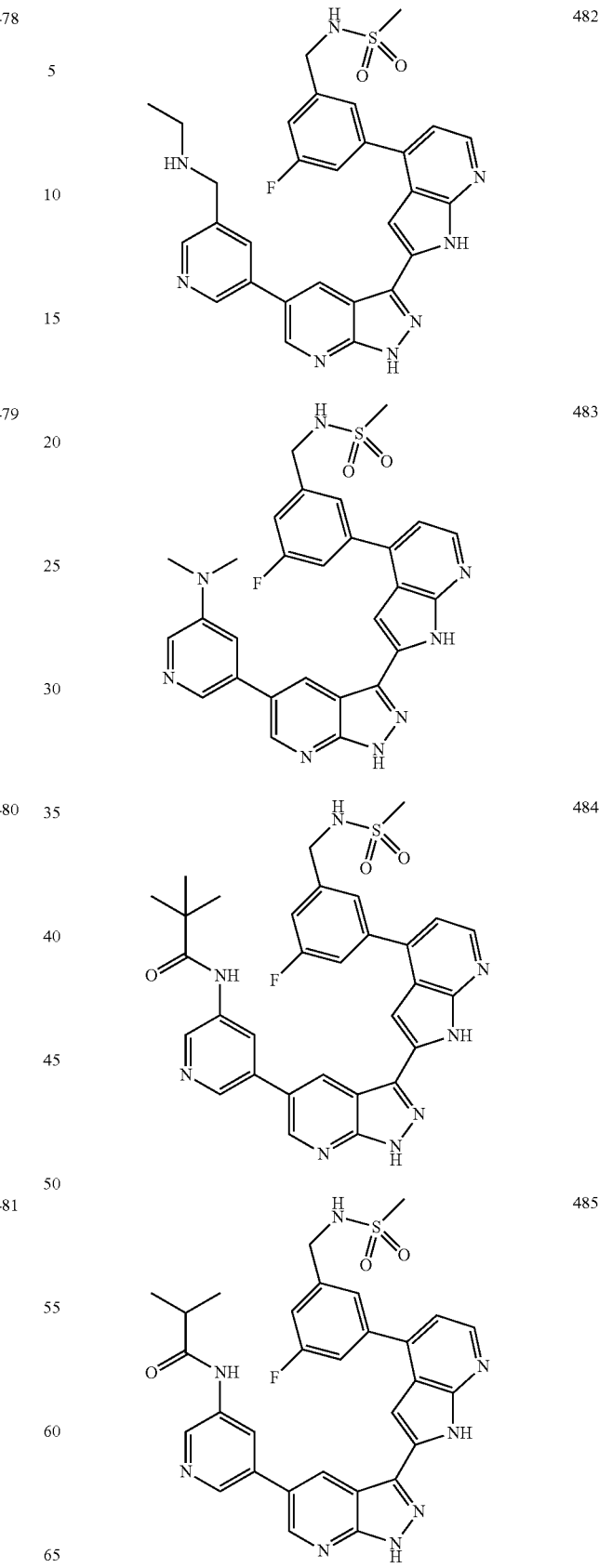

TABLE 1-continued
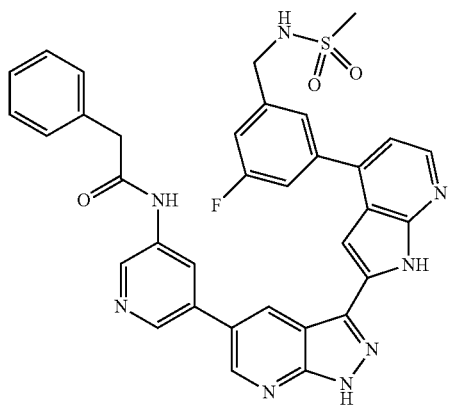 [SMILES: CS(=O)(=O)NCc1cc(F)cc(-c2ccnc3[nH]c(-c4n[nH]c5ncc(-c6cncc(NC(=O)Cc7ccccc7)c6)cc45)cc23)c1] 486
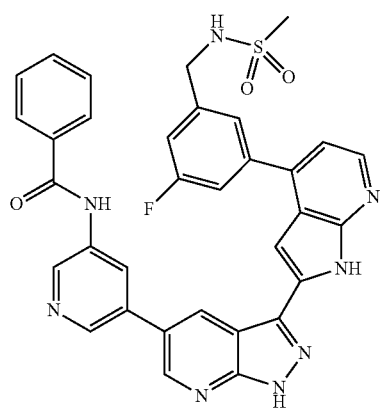 [SMILES: CS(=O)(=O)NCc1cc(F)cc(-c2ccnc3[nH]c(-c4n[nH]c5ncc(-c6cncc(NC(=O)c7ccccc7)c6)cc45)cc23)c1] 487
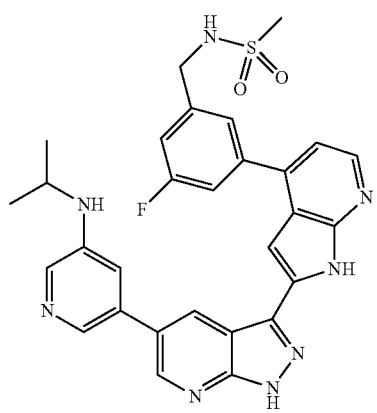 [SMILES: CC(C)Nc1cncc(-c2cnc3[nH]nc(-c4cc5c(-c6cc(F)cc(CNS(C)(=O)=O)c6)ccnc5[nH]4)c3c2)c1] 488
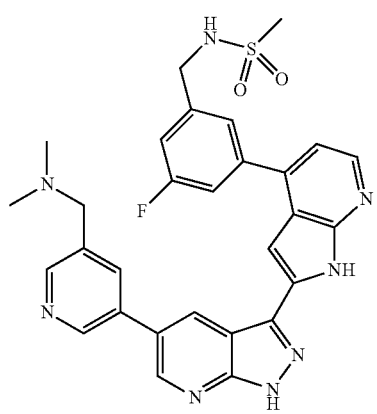 [SMILES: CN(C)Cc1cncc(-c2cnc3[nH]nc(-c4cc5c(-c6cc(F)cc(CNS(C)(=O)=O)c6)ccnc5[nH]4)c3c2)c1] 489
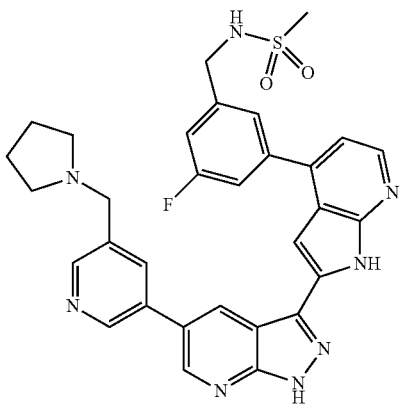 [SMILES: CS(=O)(=O)NCc1cc(F)cc(-c2ccnc3[nH]c(-c4n[nH]c5ncc(-c6cncc(CN7CCCC7)c6)cc45)cc23)c1] 490
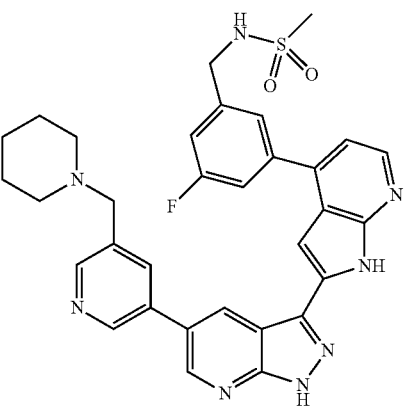 [SMILES: CS(=O)(=O)NCc1cc(F)cc(-c2ccnc3[nH]c(-c4n[nH]c5ncc(-c6cncc(CN7CCCCC7)c6)cc45)cc23)c1] 491
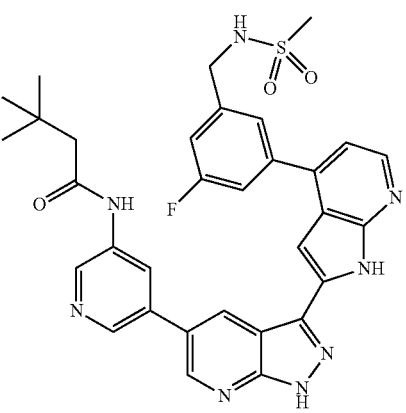 [SMILES: CC(C)(C)CC(=O)Nc1cncc(-c2cnc3[nH]nc(-c4cc5c(-c6cc(F)cc(CNS(C)(=O)=O)c6)ccnc5[nH]4)c3c2)c1] 492
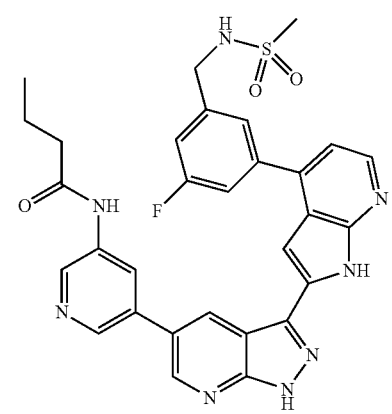 [SMILES: CCCC(=O)Nc1cncc(-c2cnc3[nH]nc(-c4cc5c(-c6cc(F)cc(CNS(C)(=O)=O)c6)ccnc5[nH]4)c3c2)c1] 493

TABLE 1-continued
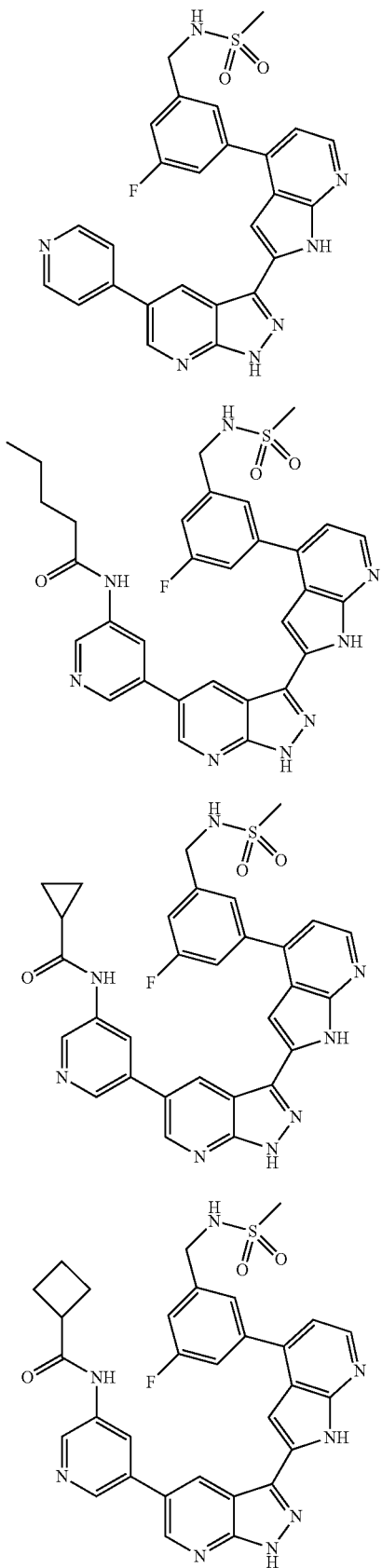
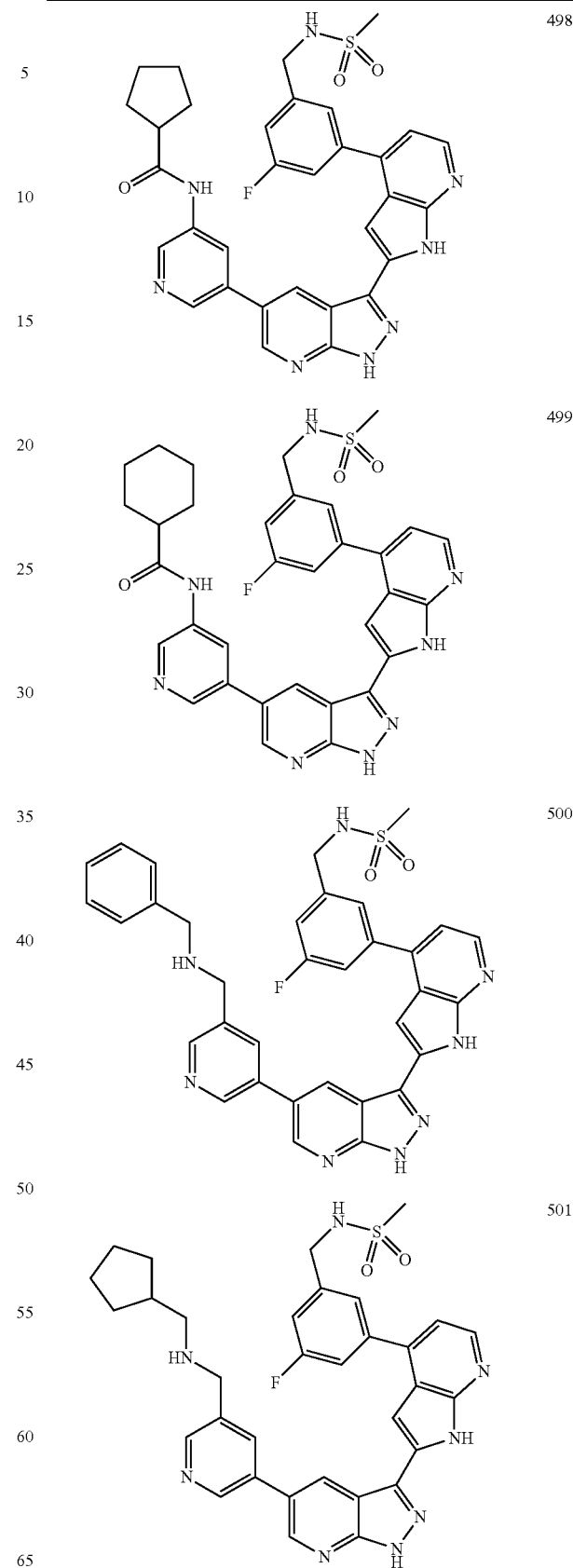

TABLE 1-continued
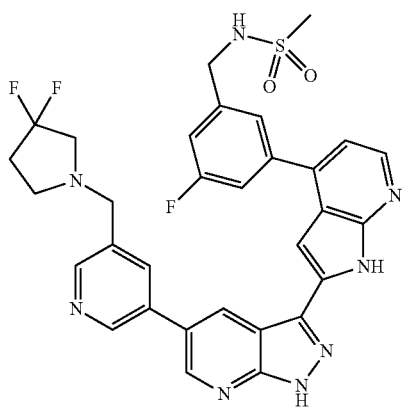 [SMILES: CS(=O)(=O)NCc1cc(F)cc(-c2ccnc3[nH]c(-c4n[nH]c5ncc(-c6cncc(CN7CCC(F)(F)C7)c6)cc45)cc23)c1] 502
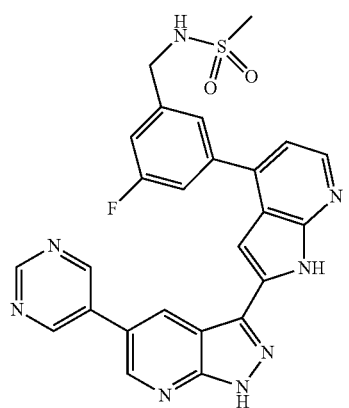 [SMILES: CS(=O)(=O)NCc1cc(F)cc(-c2ccnc3[nH]c(-c4n[nH]c5ncc(-c6cncnc6)cc45)cc23)c1] 503
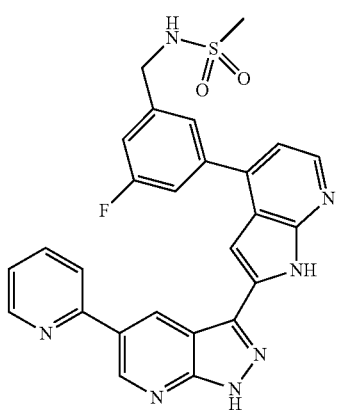 [SMILES: CS(=O)(=O)NCc1cc(F)cc(-c2ccnc3[nH]c(-c4n[nH]c5ncc(-c6ccccn6)cc45)cc23)c1] 504
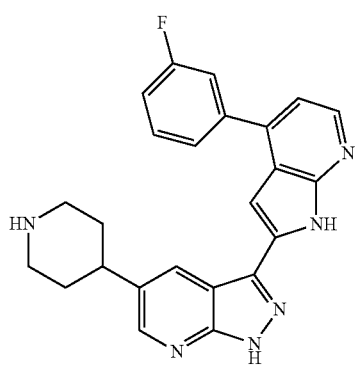 [SMILES: Fc1cccc(-c2ccnc3[nH]c(-c4n[nH]c5ncc(C6CCNCC6)cc45)cc23)c1] 505
TABLE 1-continued
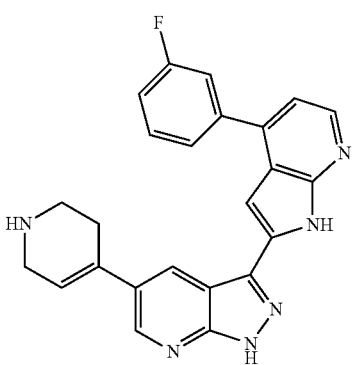 [SMILES: Fc1cccc(-c2ccnc3[nH]c(-c4n[nH]c5ncc(C6=CCNCC6)cc45)cc23)c1] 506
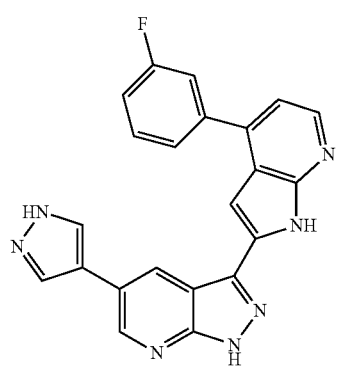 [SMILES: Fc1cccc(-c2ccnc3[nH]c(-c4n[nH]c5ncc(-c6cn[nH]c6)cc45)cc23)c1] 507
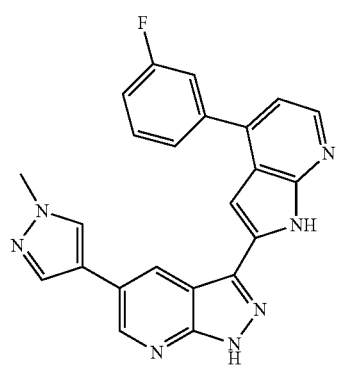 [SMILES: Cn1cc(-c2cnc3[nH]nc(-c4cc5c(-c6cccc(F)c6)ccnc5[nH]4)c3c2)cn1] 508
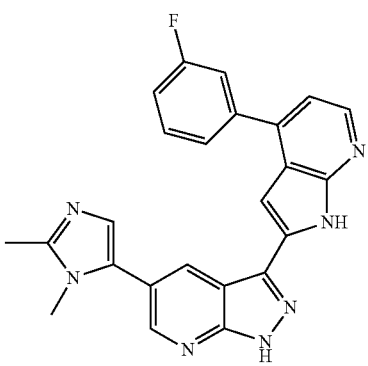 [SMILES: Cc1ncc(-c2cnc3[nH]nc(-c4cc5c(-c6cccc(F)c6)ccnc5[nH]4)c3c2)n1C] 509

TABLE 1-continued
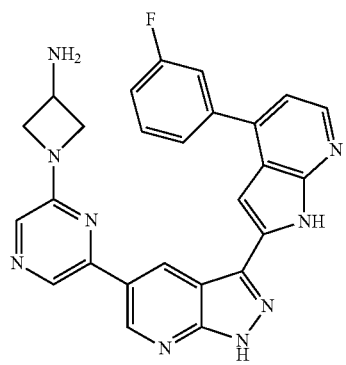 [SMILES: NC1CN(c2cncc(-c3cnc4[nH]nc(-c5cc6c(-c7cccc(F)c7)ccnc6[nH]5)c4c3)n2)C1] 510
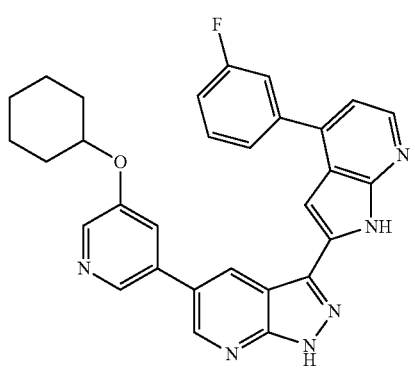 [SMILES: Fc1cccc(-c2ccnc3[nH]c(-c4n[nH]c5ncc(-c6cncc(OC7CCCCC7)c6)cc45)cc23)c1] 511
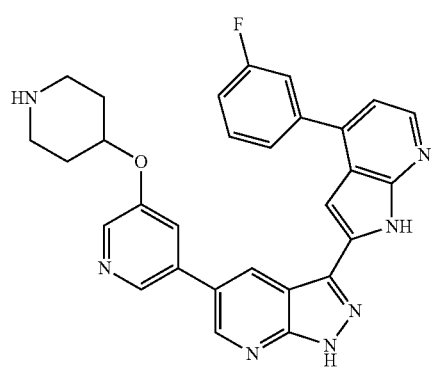 [SMILES: Fc1cccc(-c2ccnc3[nH]c(-c4n[nH]c5ncc(-c6cncc(OC7CCNCC7)c6)cc45)cc23)c1] 512
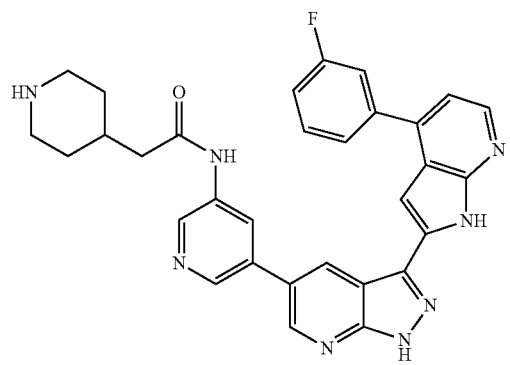 [SMILES: O=C(CC1CCNCC1)Nc1cncc(-c2cnc3[nH]nc(-c4cc5c(-c6cccc(F)c6)ccnc5[nH]4)c3c2)c1] 513
TABLE 1-continued
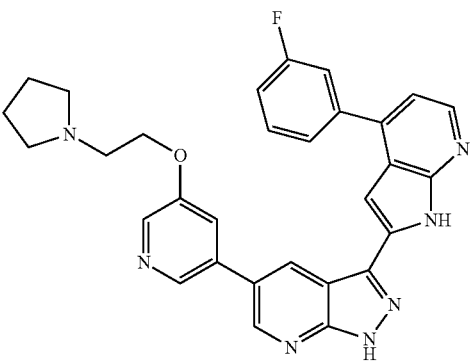 [SMILES: Fc1cccc(-c2ccnc3[nH]c(-c4n[nH]c5ncc(-c6cncc(OCCN7CCCC7)c6)cc45)cc23)c1] 514
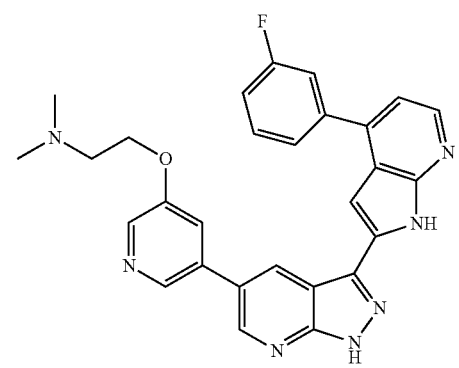 [SMILES: CN(C)CCOc1cncc(-c2cnc3[nH]nc(-c4cc5c(-c6cccc(F)c6)ccnc5[nH]4)c3c2)c1] 515
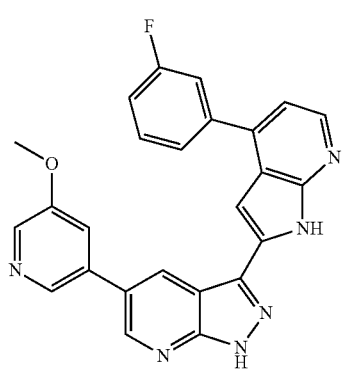 [SMILES: COc1cncc(-c2cnc3[nH]nc(-c4cc5c(-c6cccc(F)c6)ccnc5[nH]4)c3c2)c1] 516
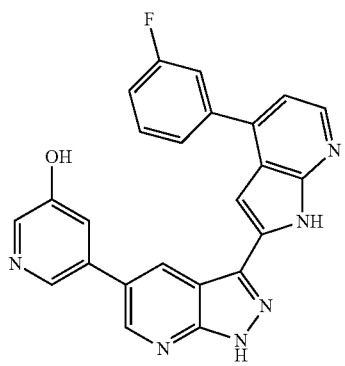 [SMILES: Oc1cncc(-c2cnc3[nH]nc(-c4cc5c(-c6cccc(F)c6)ccnc5[nH]4)c3c2)c1] 517

TABLE 1-continued
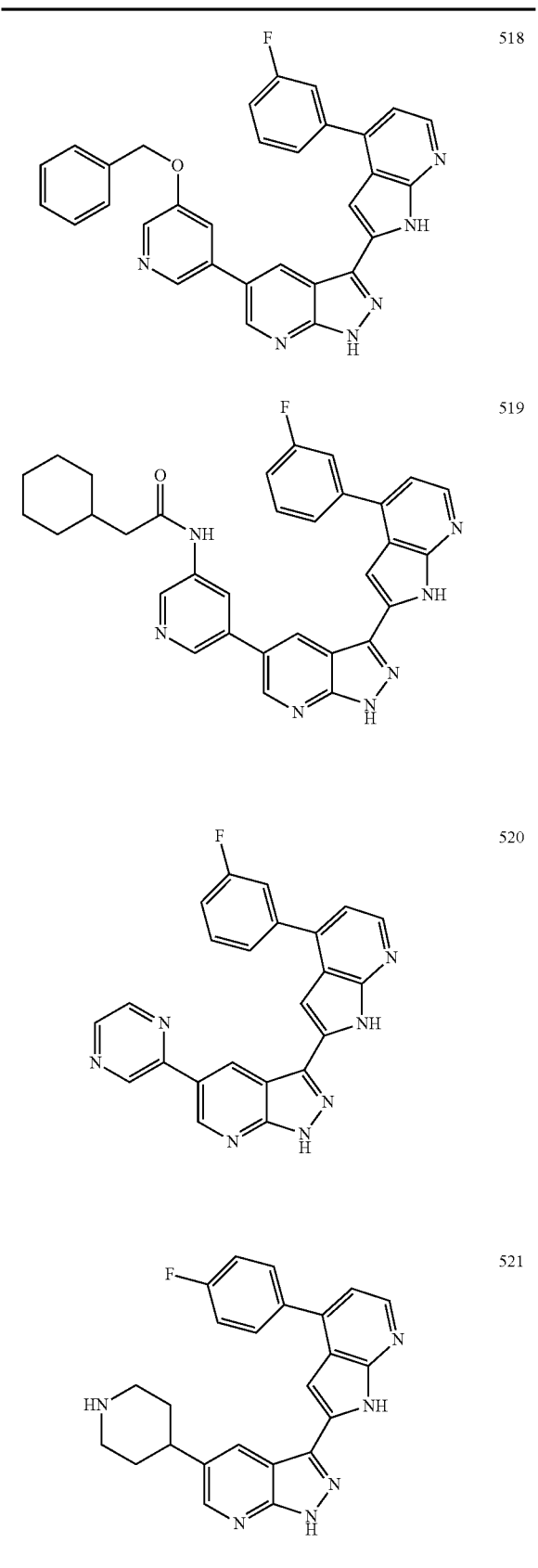
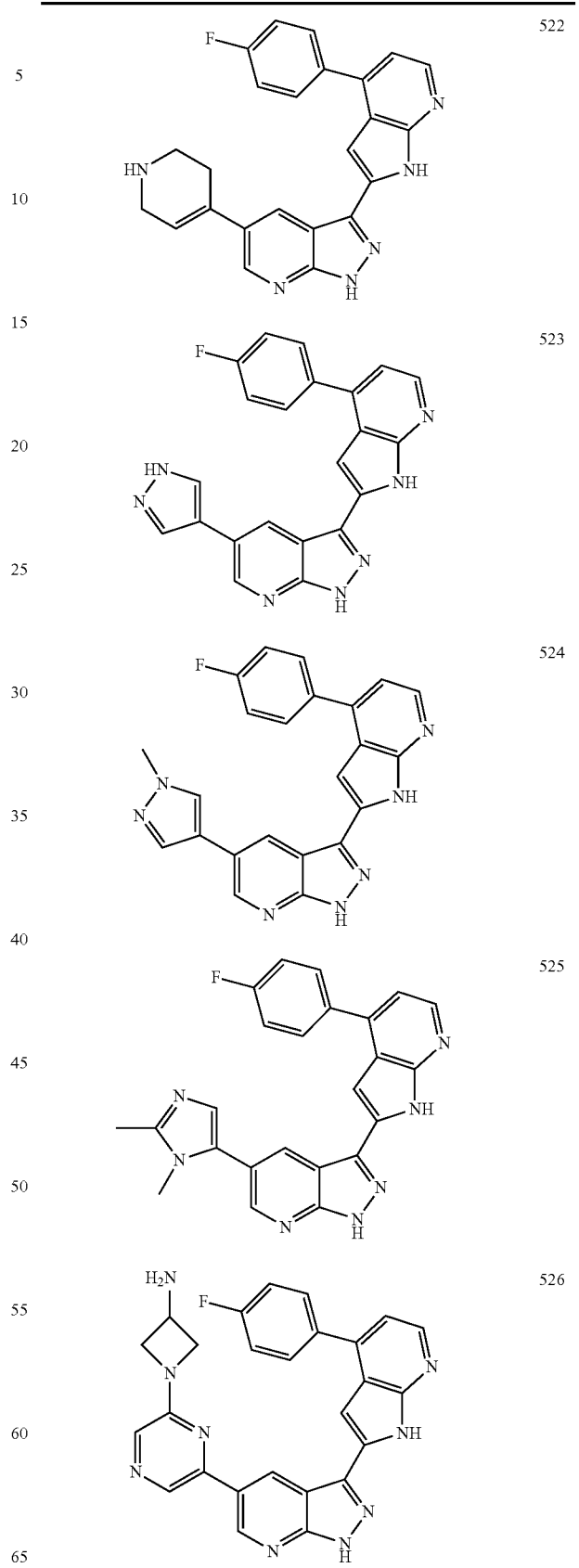

TABLE 1-continued
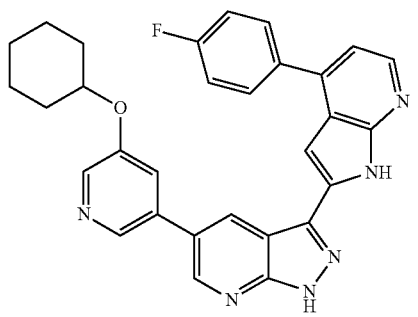 [SMILES: Fc1ccc(-c2ccnc3[nH]c(-c4n[nH]c5ncc(-c6cncc(OC7CCCCC7)c6)cc45)cc23)cc1]
527
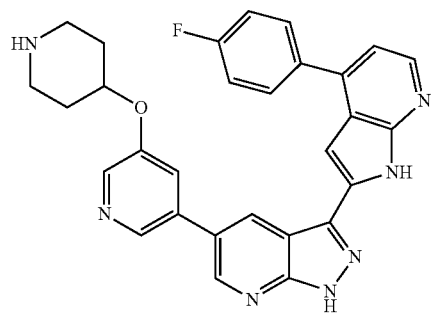 [SMILES: Fc1ccc(-c2ccnc3[nH]c(-c4n[nH]c5ncc(-c6cncc(OC7CCNCC7)c6)cc45)cc23)cc1]
528
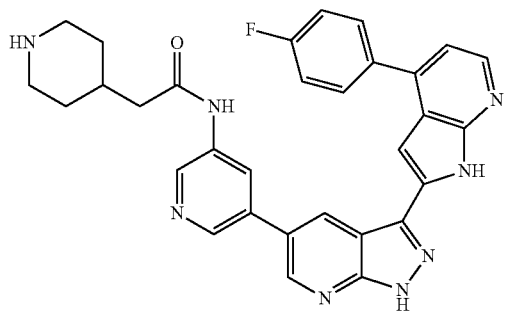 [SMILES: O=C(CC1CCNCC1)Nc1cncc(-c2cnc3[nH]nc(-c4cc5c(-c6ccc(F)cc6)ccnc5[nH]4)c3c2)c1]
529
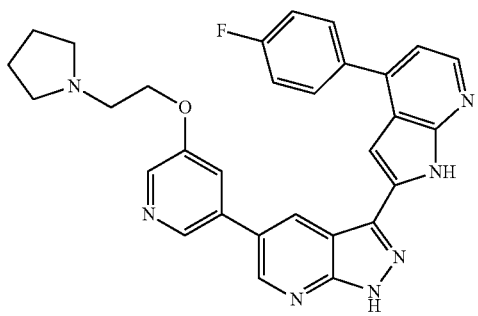 [SMILES: Fc1ccc(-c2ccnc3[nH]c(-c4n[nH]c5ncc(-c6cncc(OCCN7CCCC7)c6)cc45)cc23)cc1]
530
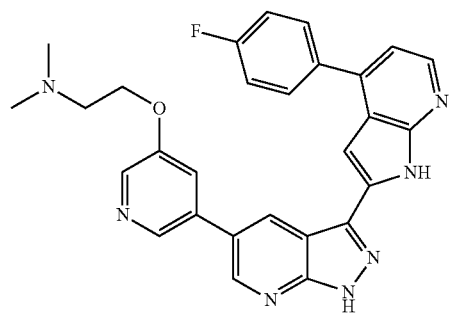 [SMILES: CN(C)CCOc1cncc(-c2cnc3[nH]nc(-c4cc5c(-c6ccc(F)cc6)ccnc5[nH]4)c3c2)c1]
531
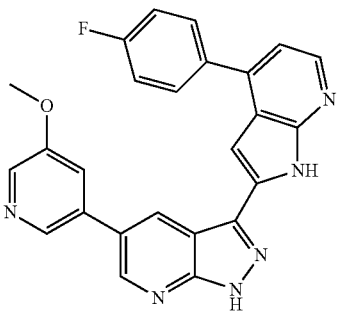 [SMILES: COc1cncc(-c2cnc3[nH]nc(-c4cc5c(-c6ccc(F)cc6)ccnc5[nH]4)c3c2)c1]
532
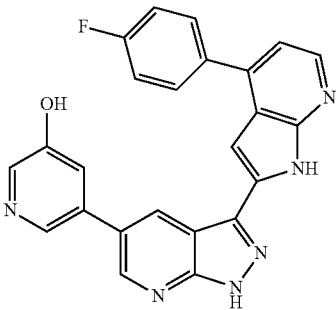 [SMILES: Oc1cncc(-c2cnc3[nH]nc(-c4cc5c(-c6ccc(F)cc6)ccnc5[nH]4)c3c2)c1]
533
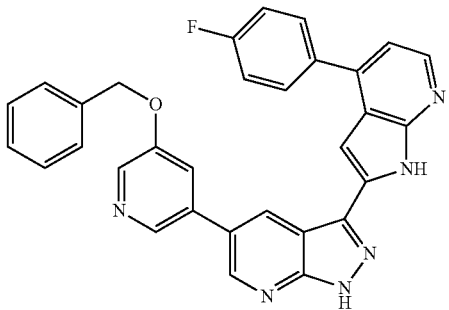 [SMILES: Fc1ccc(-c2ccnc3[nH]c(-c4n[nH]c5ncc(-c6cncc(OCc7ccccc7)c6)cc45)cc23)cc1]
534
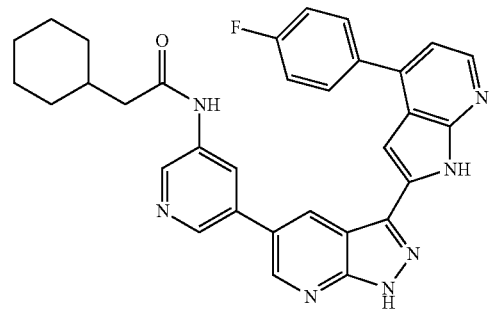 [SMILES: O=C(CC1CCCCC1)Nc1cncc(-c2cnc3[nH]nc(-c4cc5c(-c6ccc(F)cc6)ccnc5[nH]4)c3c2)c1]
535
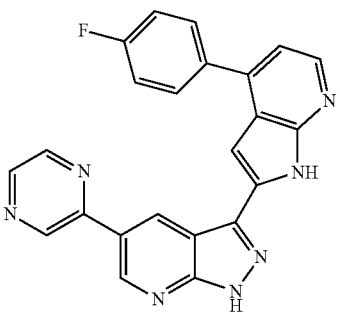 [SMILES: Fc1ccc(-c2ccnc3[nH]c(-c4n[nH]c5ncc(-c6cnccn6)cc45)cc23)cc1]
536

TABLE 1-continued
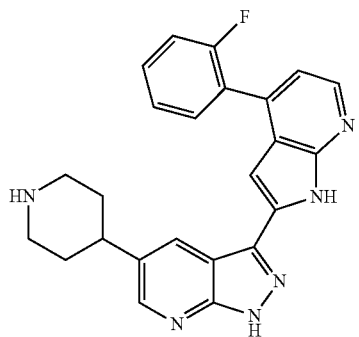 [SMILES: Fc1ccccc1-c1ccnc2[nH]c(-c3n[nH]c4ncc(C5CCNCC5)cc34)cc12] 537
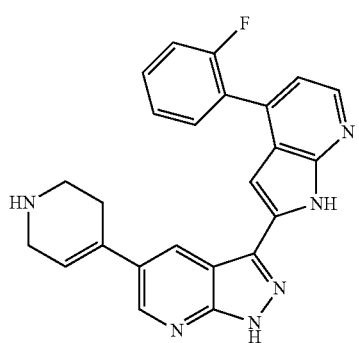 [SMILES: Fc1ccccc1-c1ccnc2[nH]c(-c3n[nH]c4ncc(C5=CCNCC5)cc34)cc12] 538
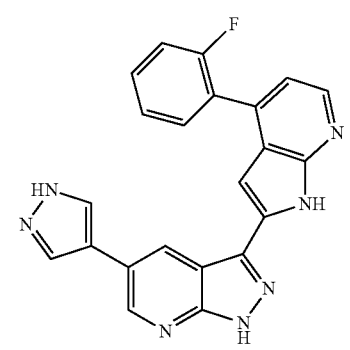 [SMILES: Fc1ccccc1-c1ccnc2[nH]c(-c3n[nH]c4ncc(-c5cn[nH]c5)cc34)cc12] 539
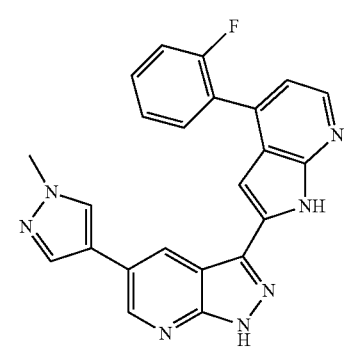 [SMILES: Cn1cc(-c2cnc3[nH]nc(-c4cc5c(-c6ccccc6F)ccnc5[nH]4)c3c2)cn1] 540
TABLE 1-continued
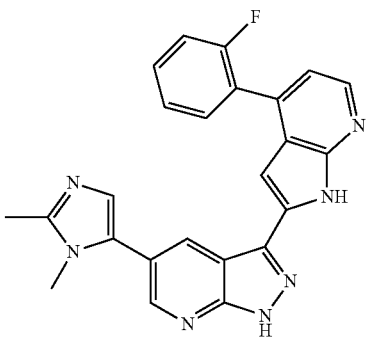 [SMILES: Cc1ncc(-c2cnc3[nH]nc(-c4cc5c(-c6ccccc6F)ccnc5[nH]4)c3c2)n1C] 541
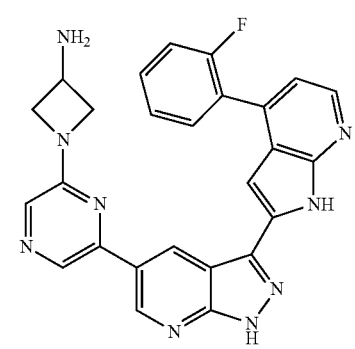 [SMILES: NC1CN(c2cncc(-c3cnc4[nH]nc(-c5cc6c(-c7ccccc7F)ccnc6[nH]5)c4c3)n2)C1] 542
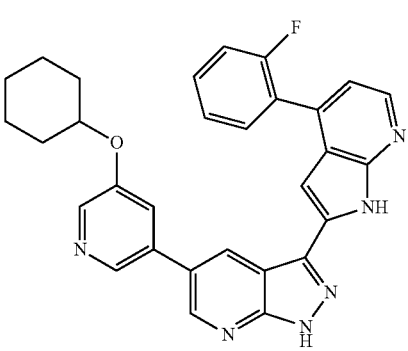 [SMILES: Fc1ccccc1-c1ccnc2[nH]c(-c3n[nH]c4ncc(-c5cncc(OC6CCCCC6)c5)cc34)cc12] 543
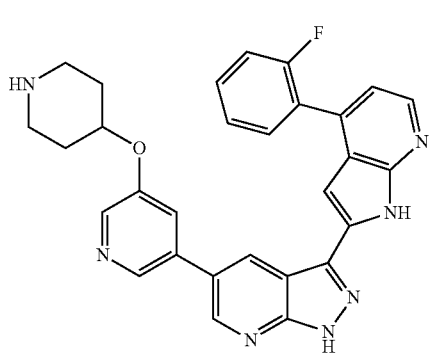 [SMILES: Fc1ccccc1-c1ccnc2[nH]c(-c3n[nH]c4ncc(-c5cncc(OC6CCNCC6)c5)cc34)cc12] 544

TABLE 1-continued
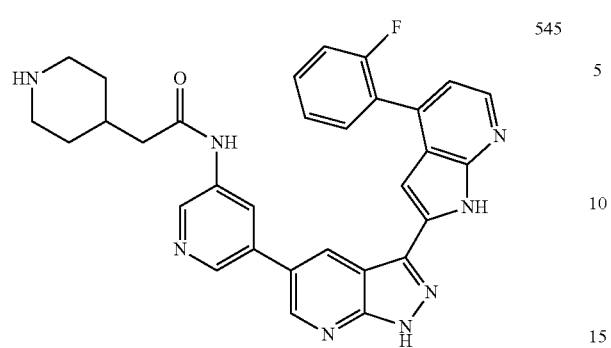
545
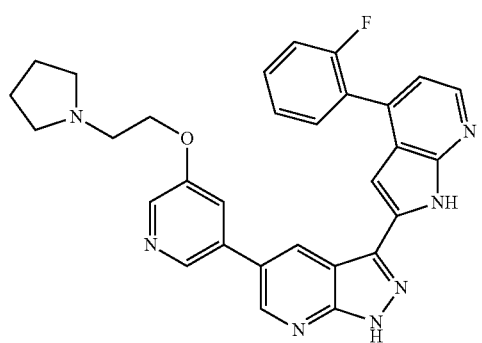 [SMILES: Fc1ccccc1-c1ccnc2[nH]c(-c3n[nH]c4ncc(-c5cncc(OCCN6CCCC6)c5)cc34)cc12]
546
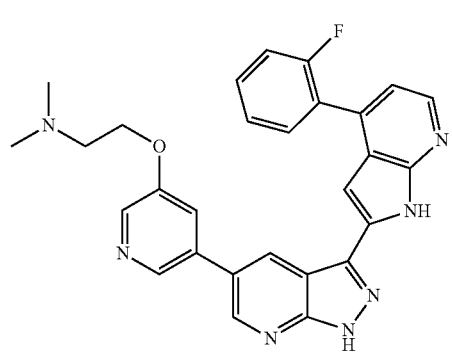 [SMILES: CN(C)CCOc1cncc(-c2cnc3[nH]nc(-c4cc5c(-c6ccccc6F)ccnc5[nH]4)c3c2)c1]
547
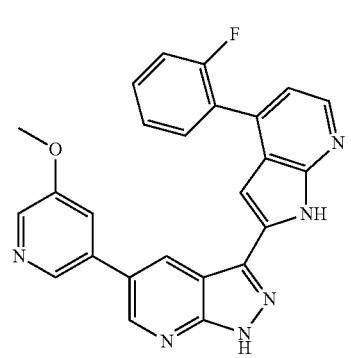 [SMILES: COc1cncc(-c2cnc3[nH]nc(-c4cc5c(-c6ccccc6F)ccnc5[nH]4)c3c2)c1]
548
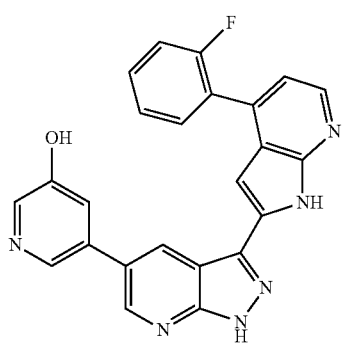
549
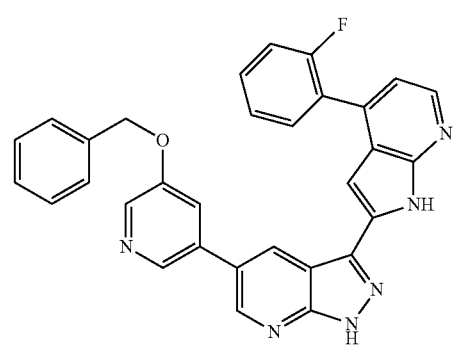 [SMILES: Fc1ccccc1-c1ccnc2[nH]c(-c3n[nH]c4ncc(-c5cncc(OCc6ccccc6)c5)cc34)cc12]
550
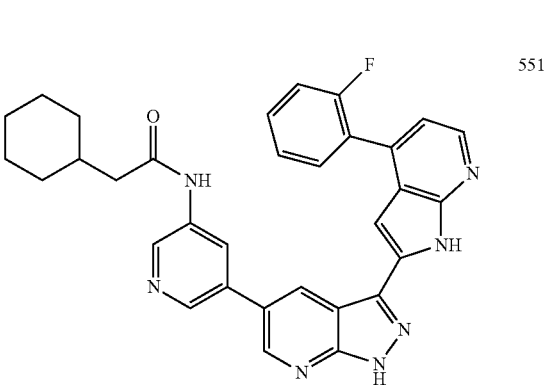
551
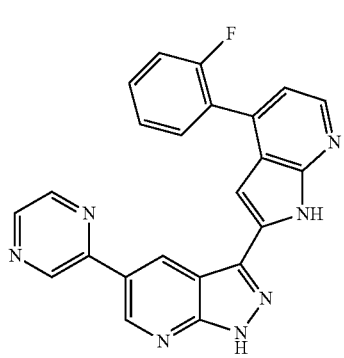 [SMILES: Fc1ccccc1-c1ccnc2[nH]c(-c3n[nH]c4ncc(-c5cnccn5)cc34)cc12]
552

TABLE 1-continued
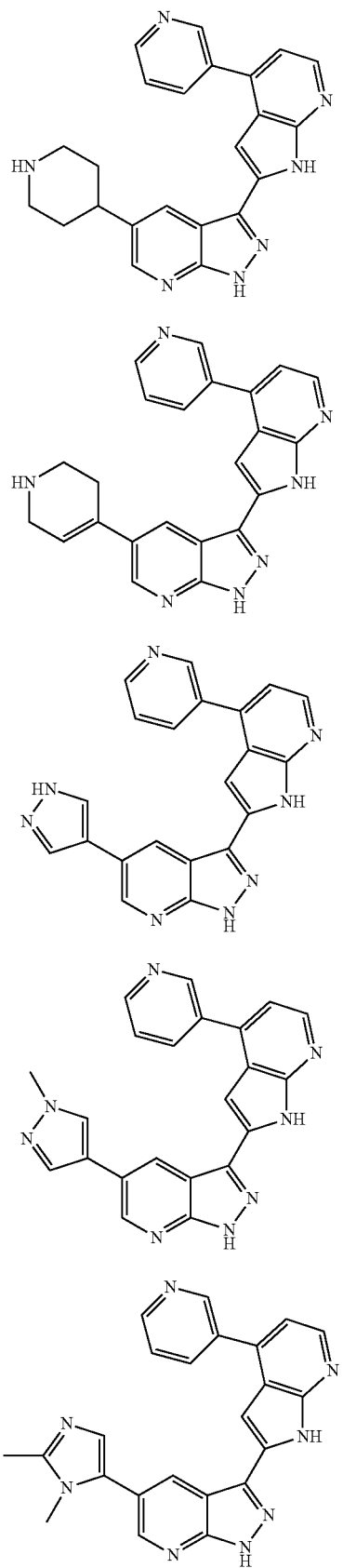
553
554
555
556
557
TABLE 1-continued
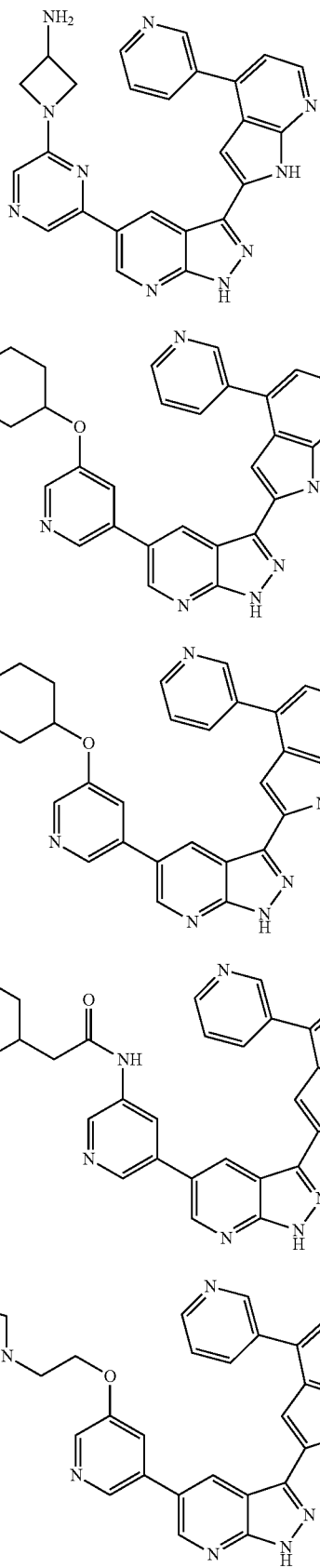
558
559
560
561
562

TABLE 1-continued
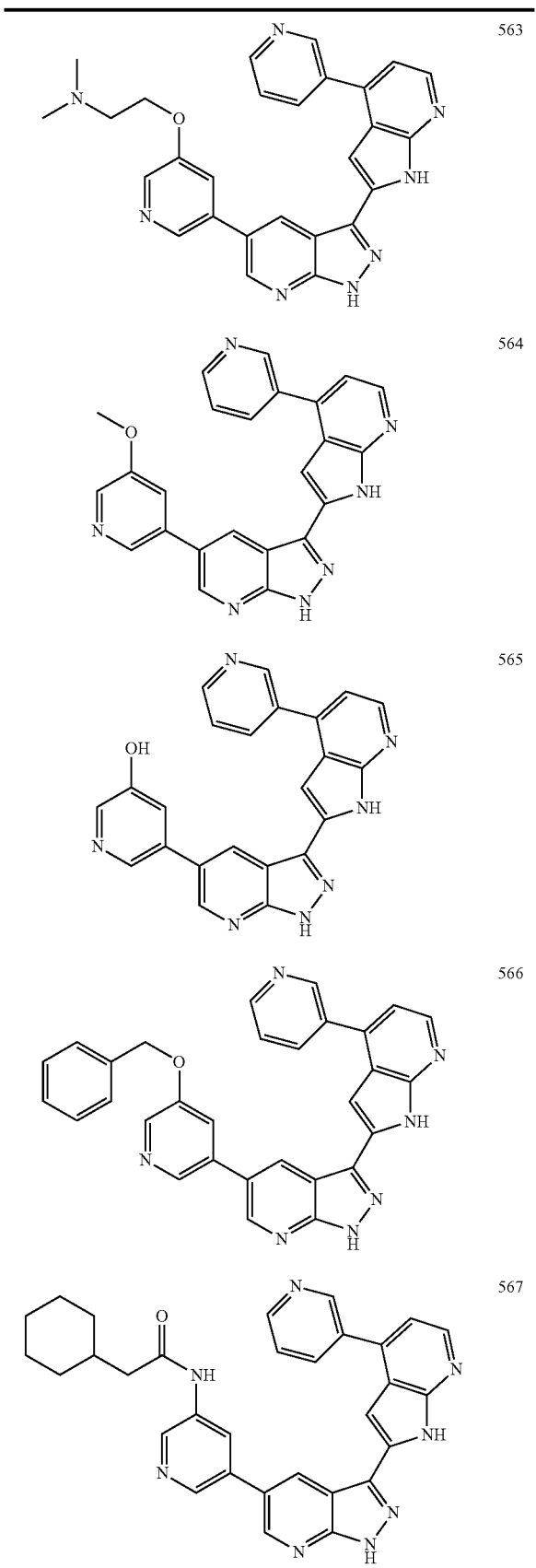
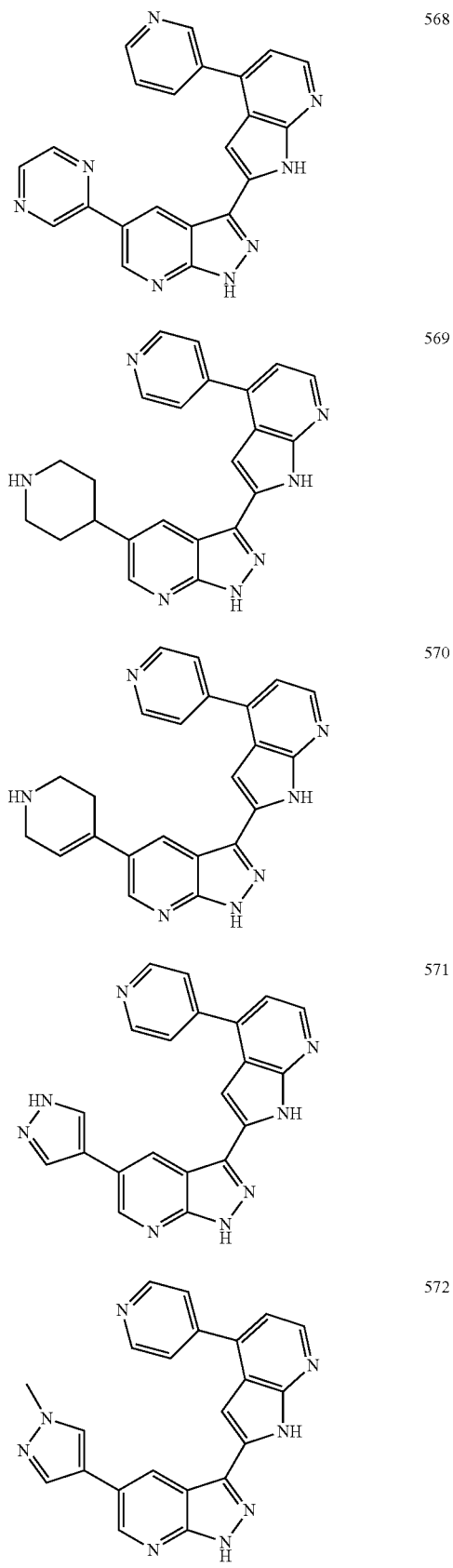

TABLE 1-continued
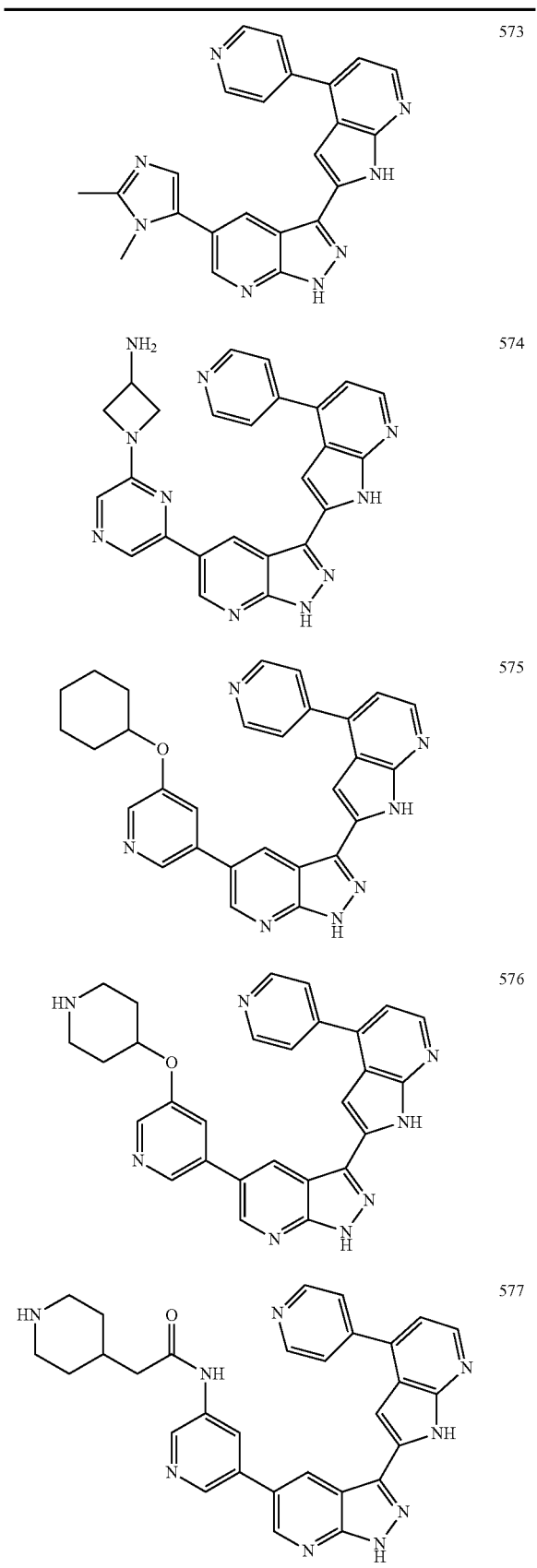
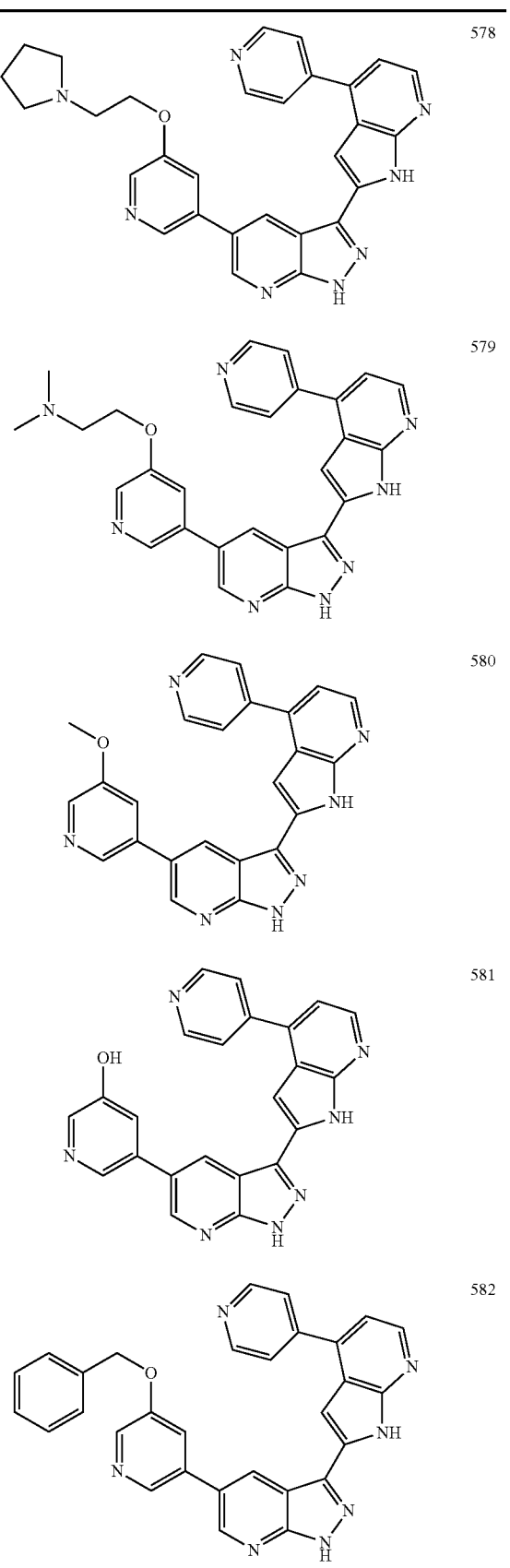

TABLE 1-continued
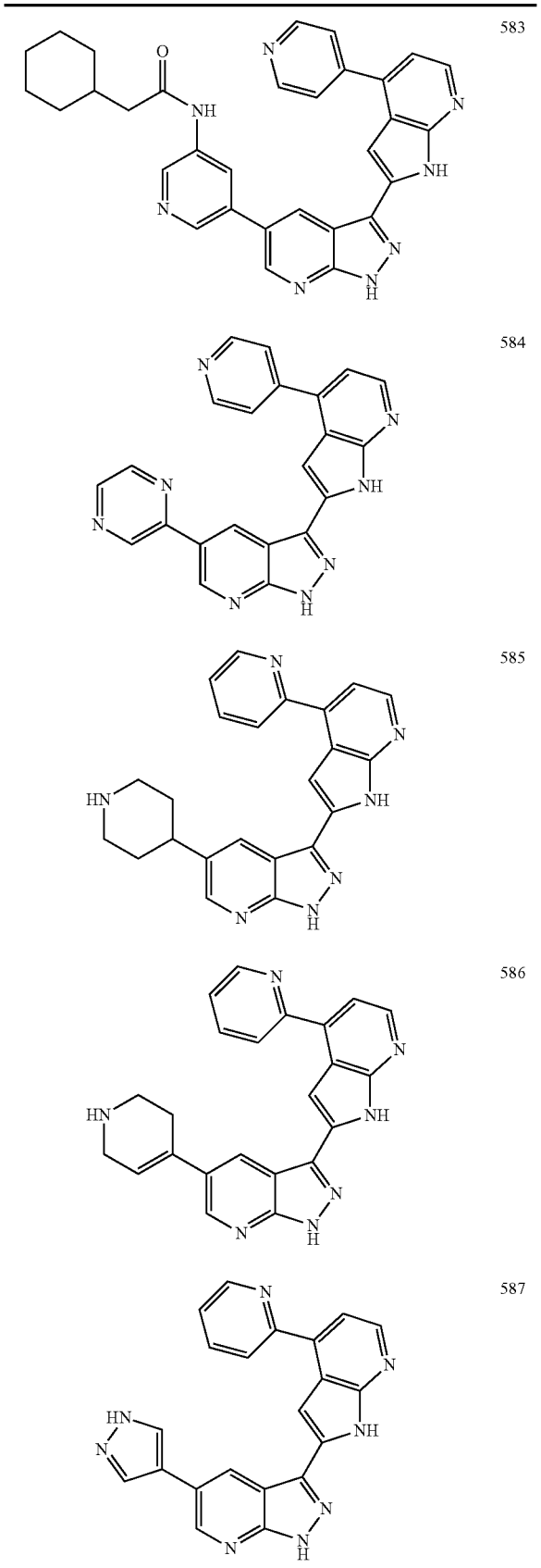
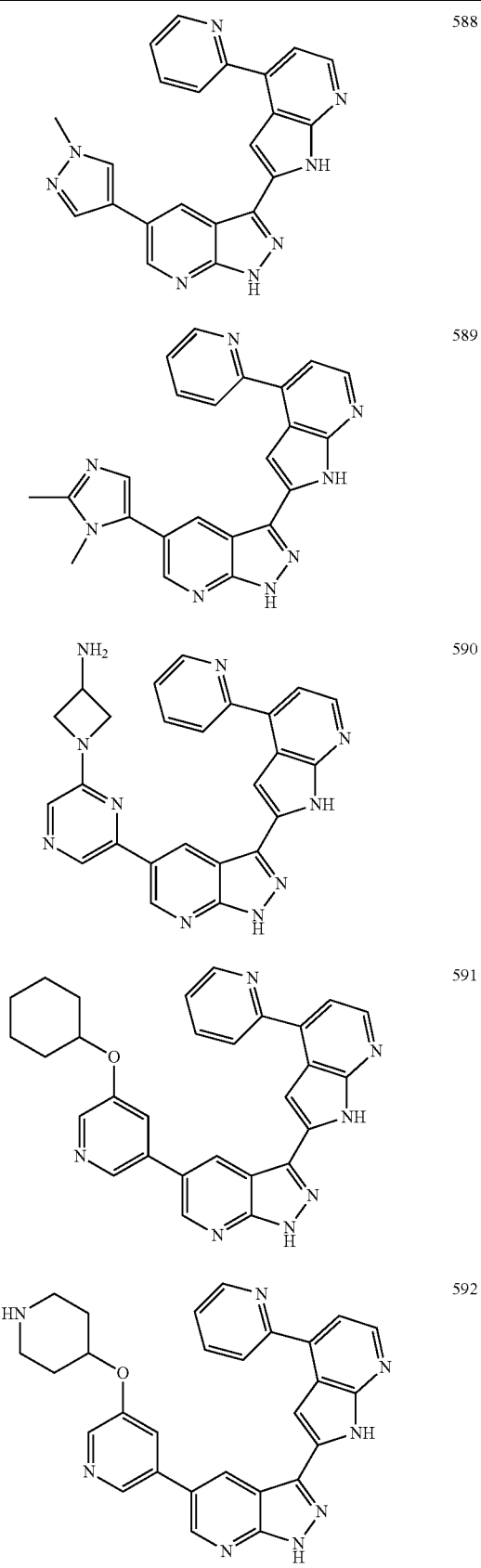

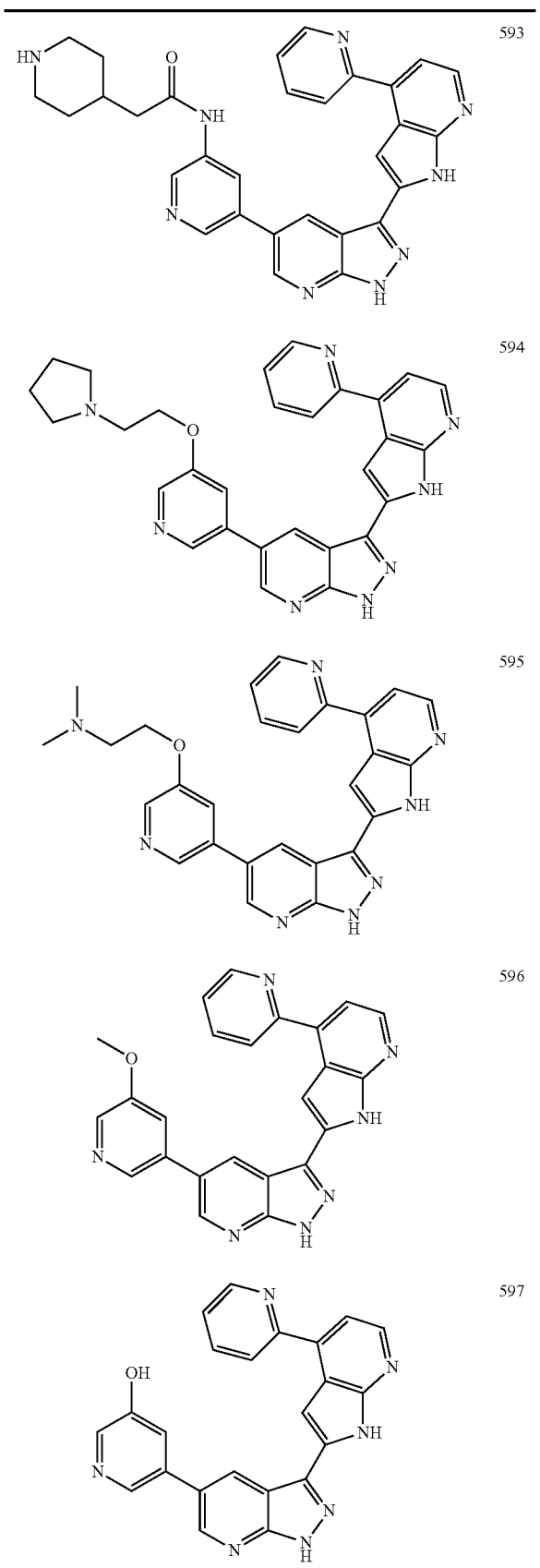

TABLE 1-continued
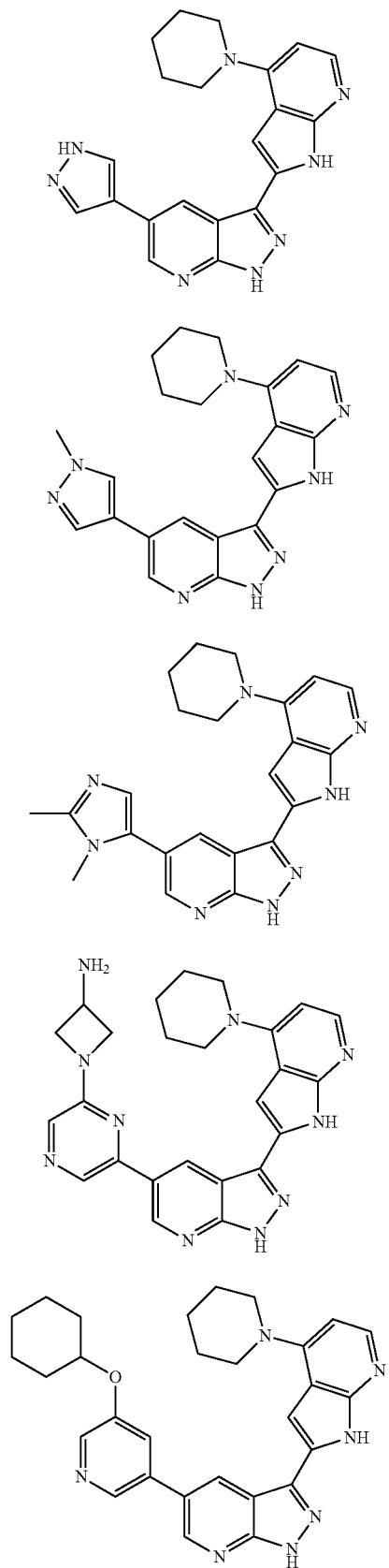
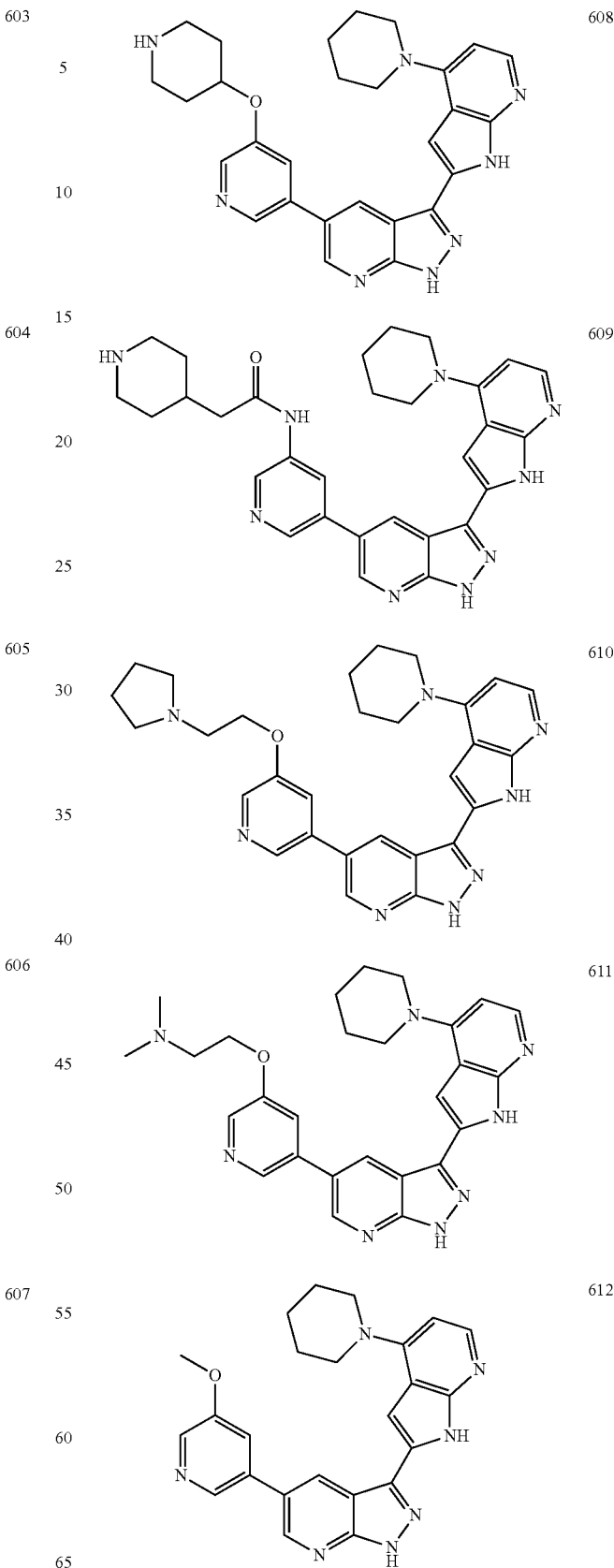

TABLE 1-continued
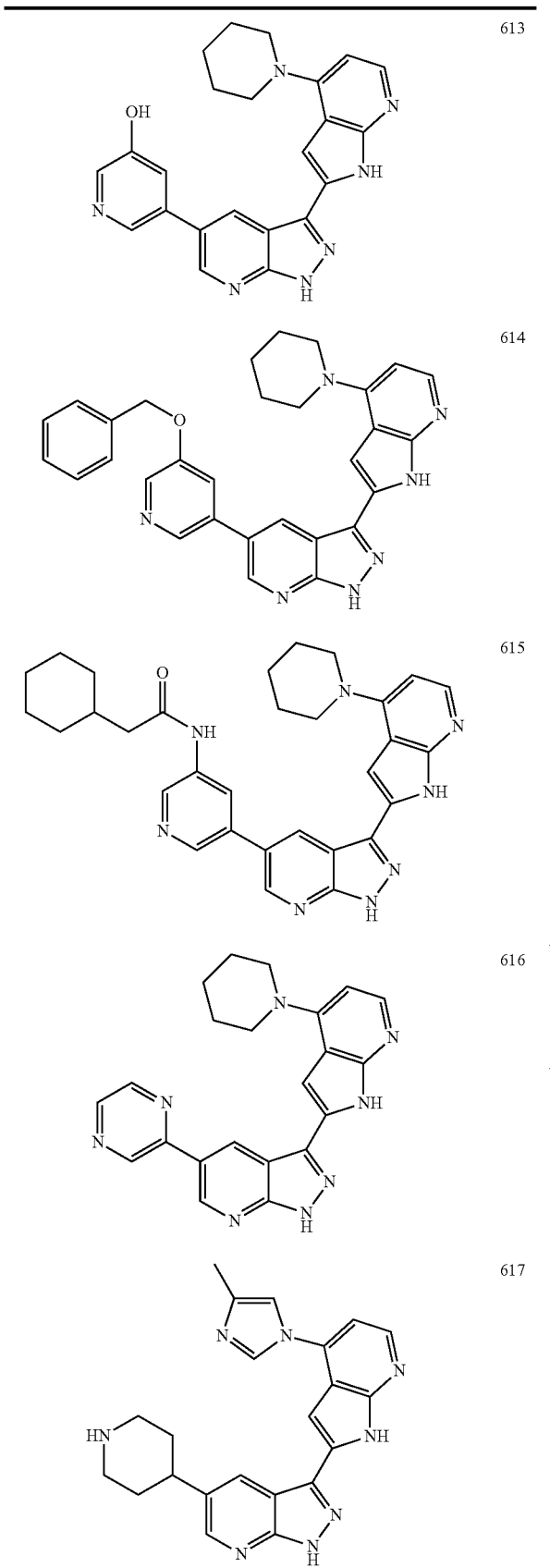
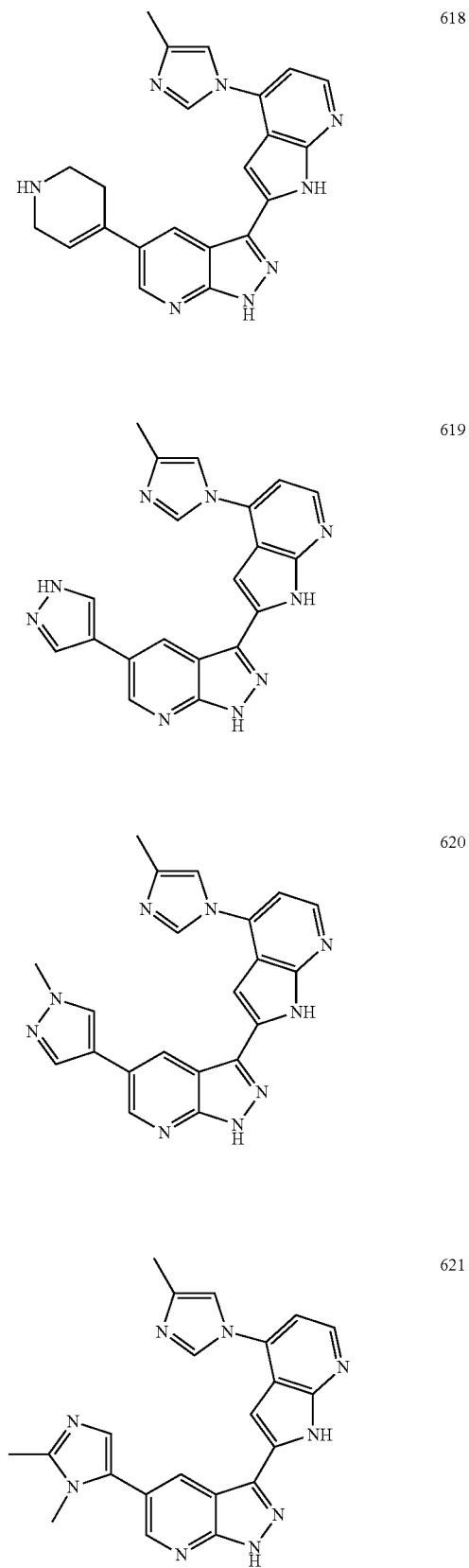

TABLE 1-continued
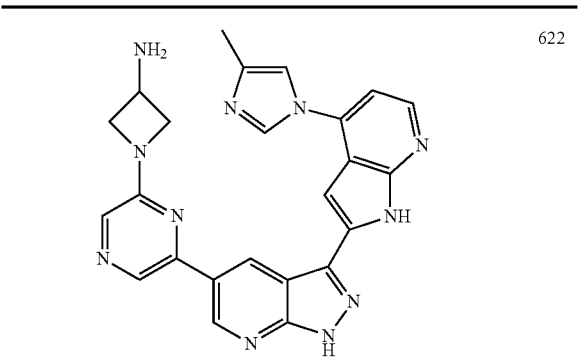
622
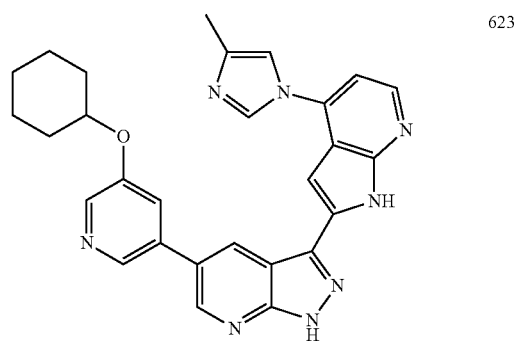
623
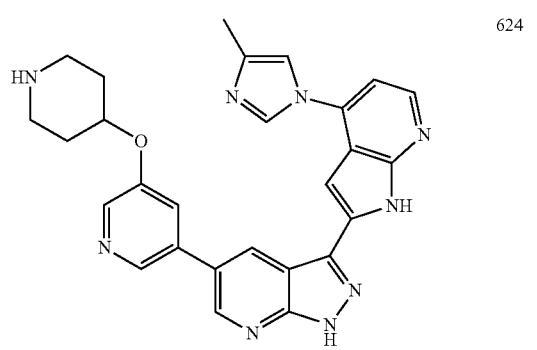
624
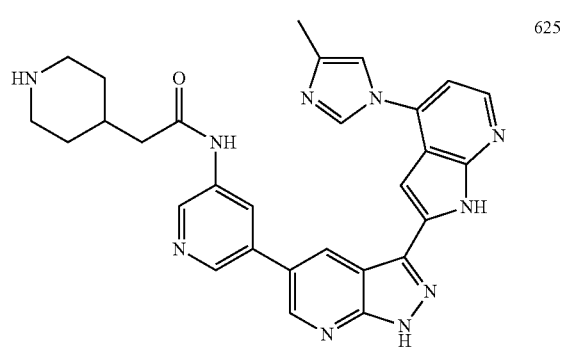
625
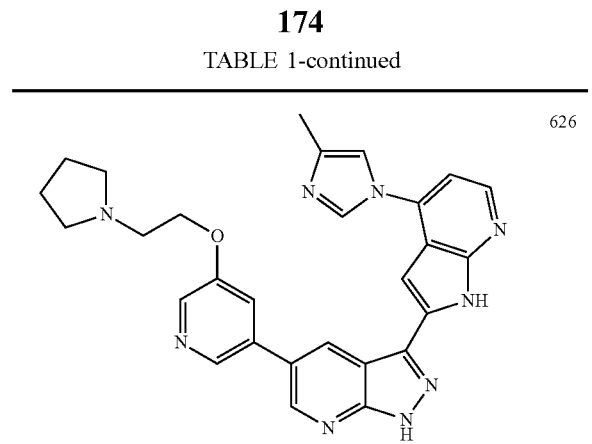
626
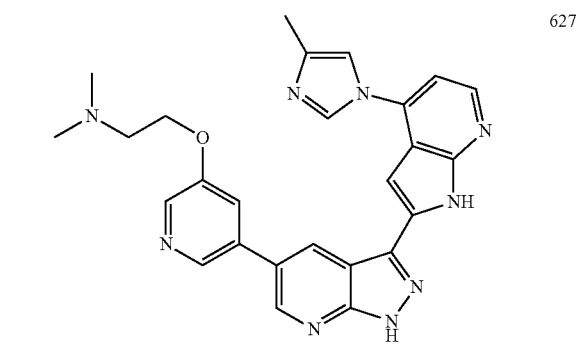
627
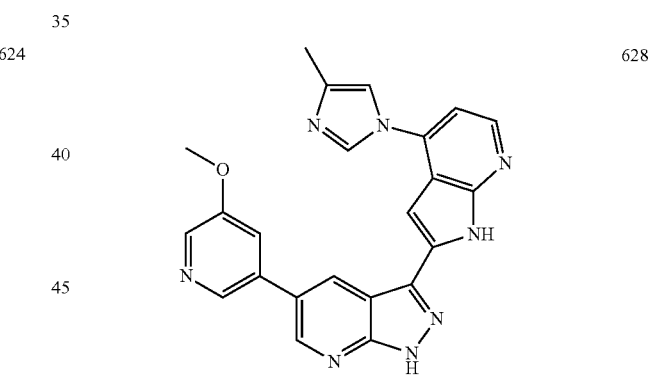
628
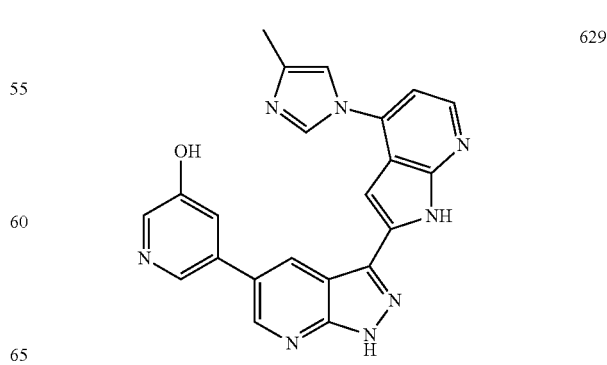
629

TABLE 1-continued
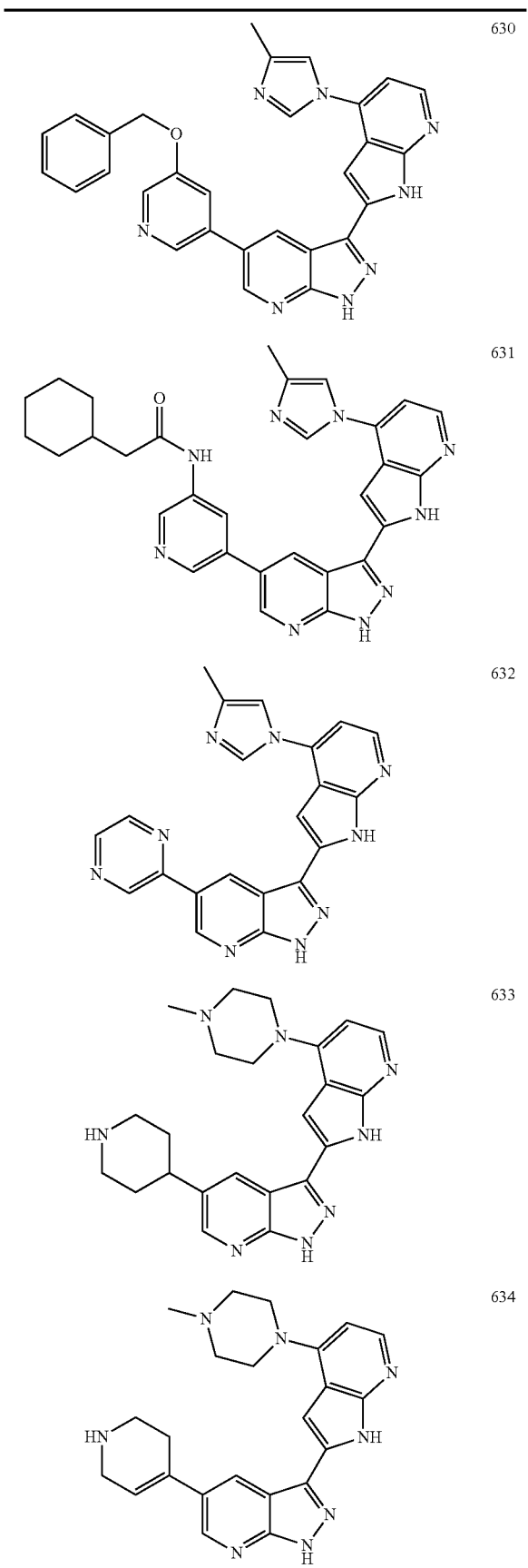
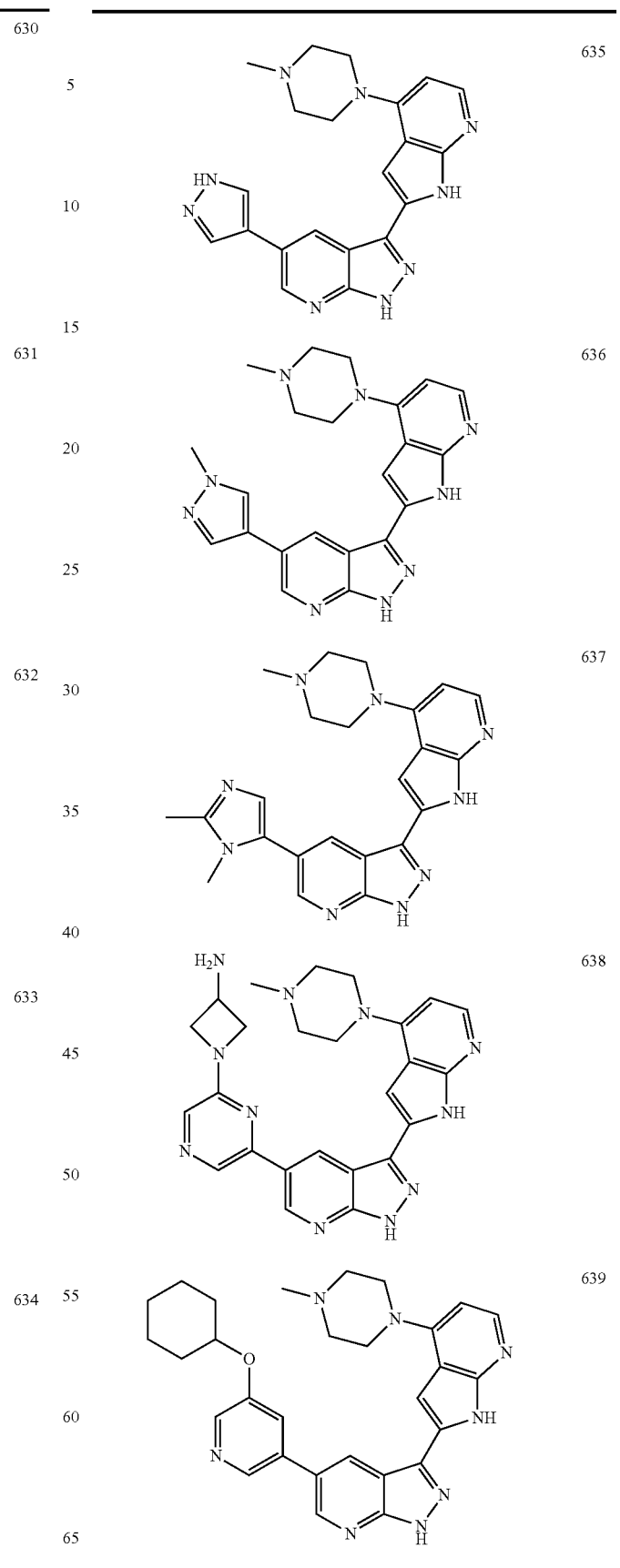

177
TABLE 1-continued
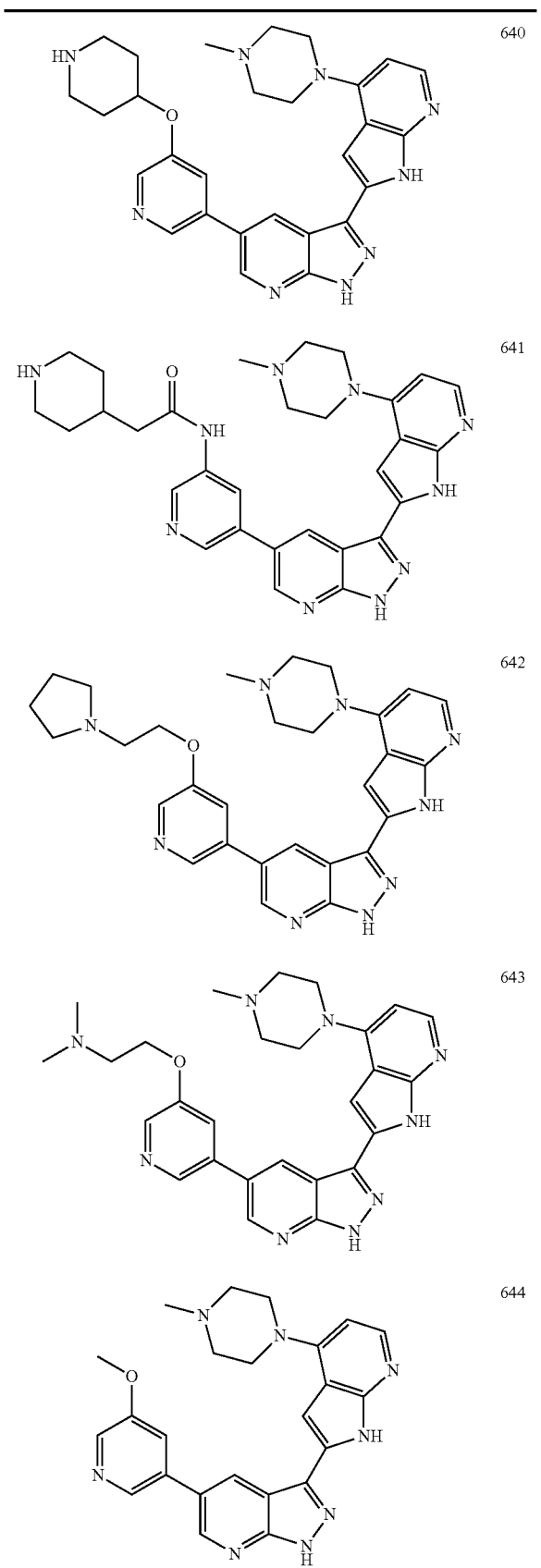
178
TABLE 1-continued
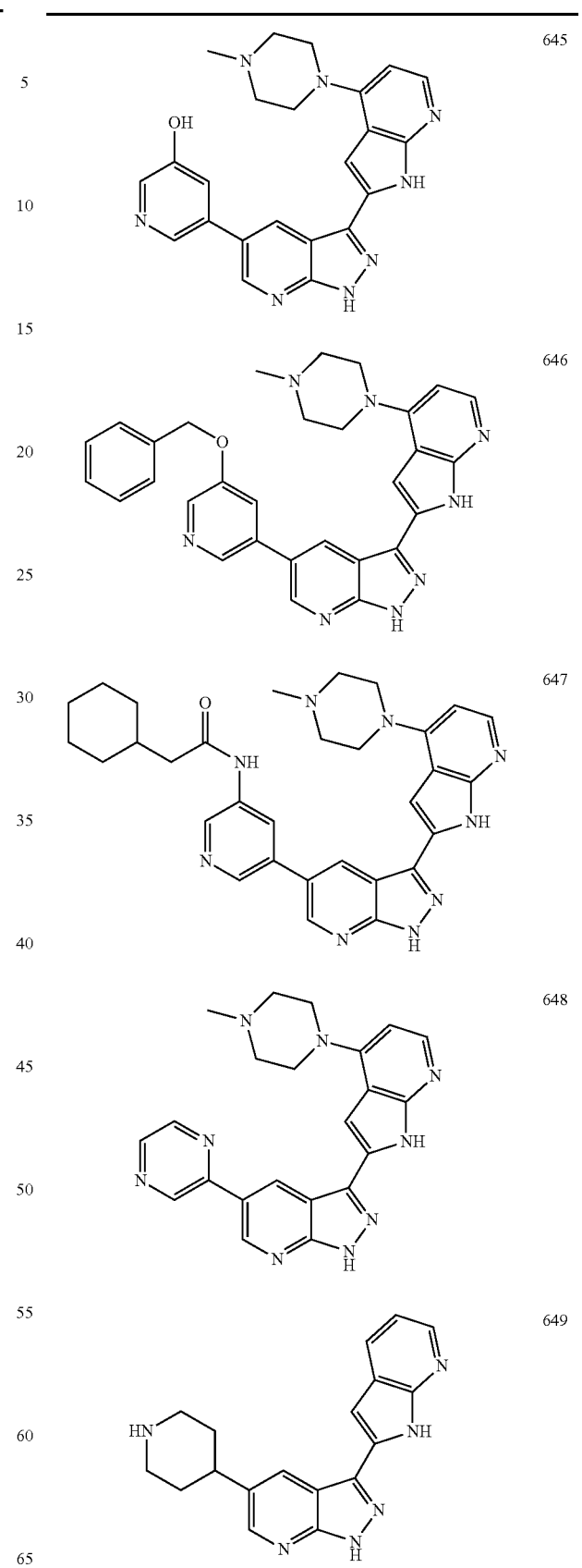

TABLE 1-continued
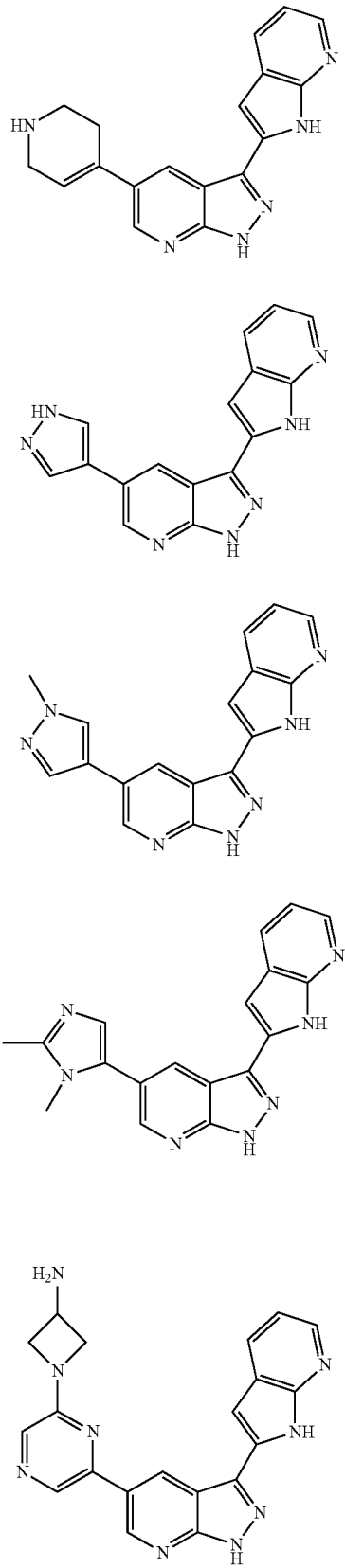
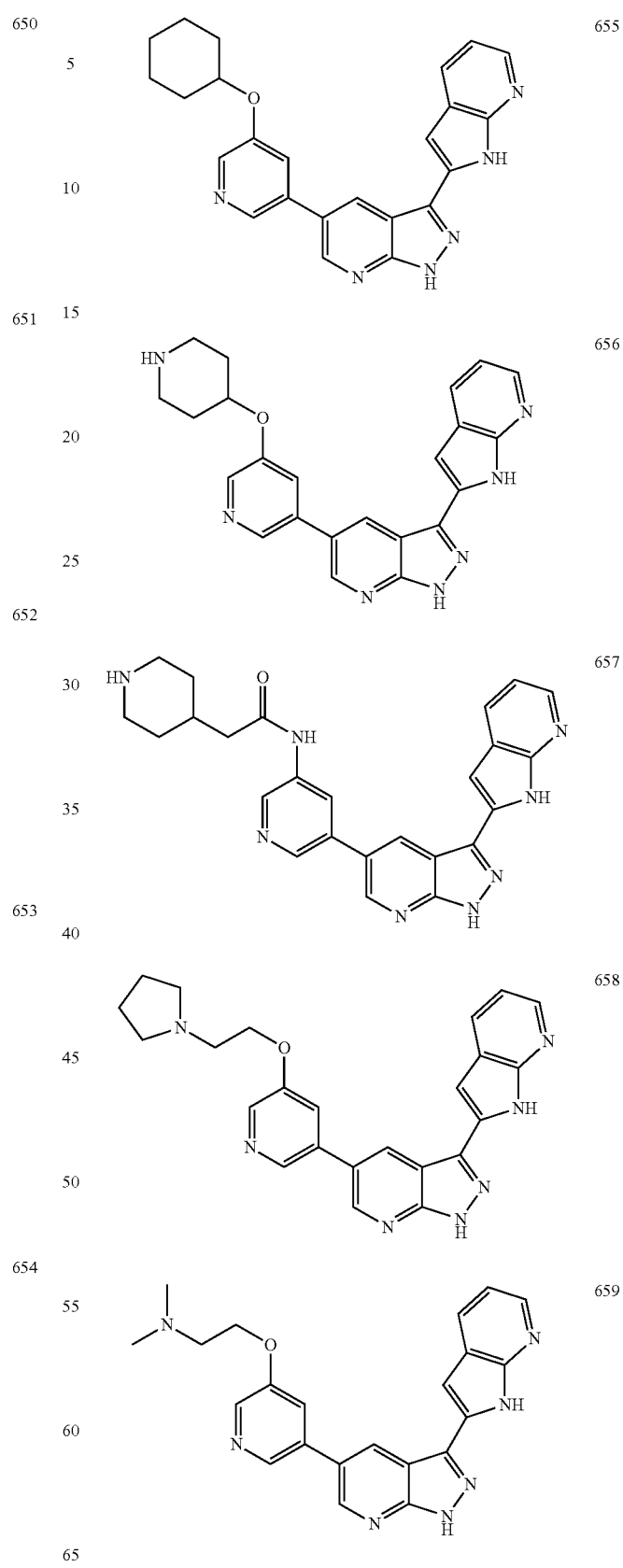

TABLE 1-continued
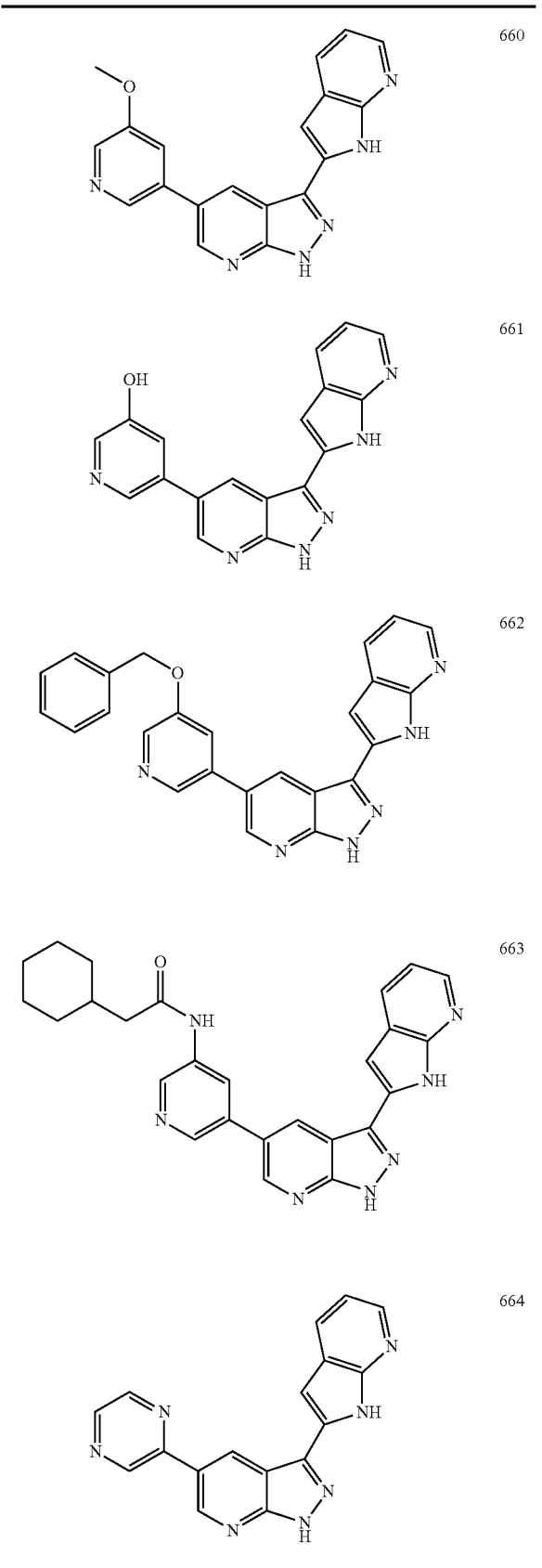
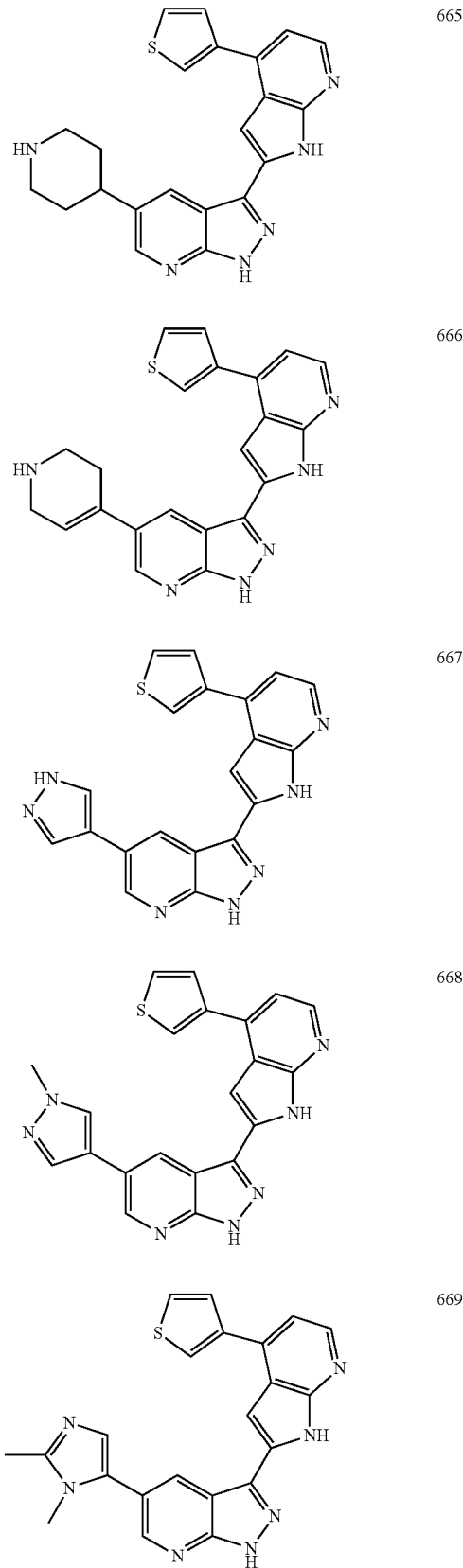

TABLE 1-continued
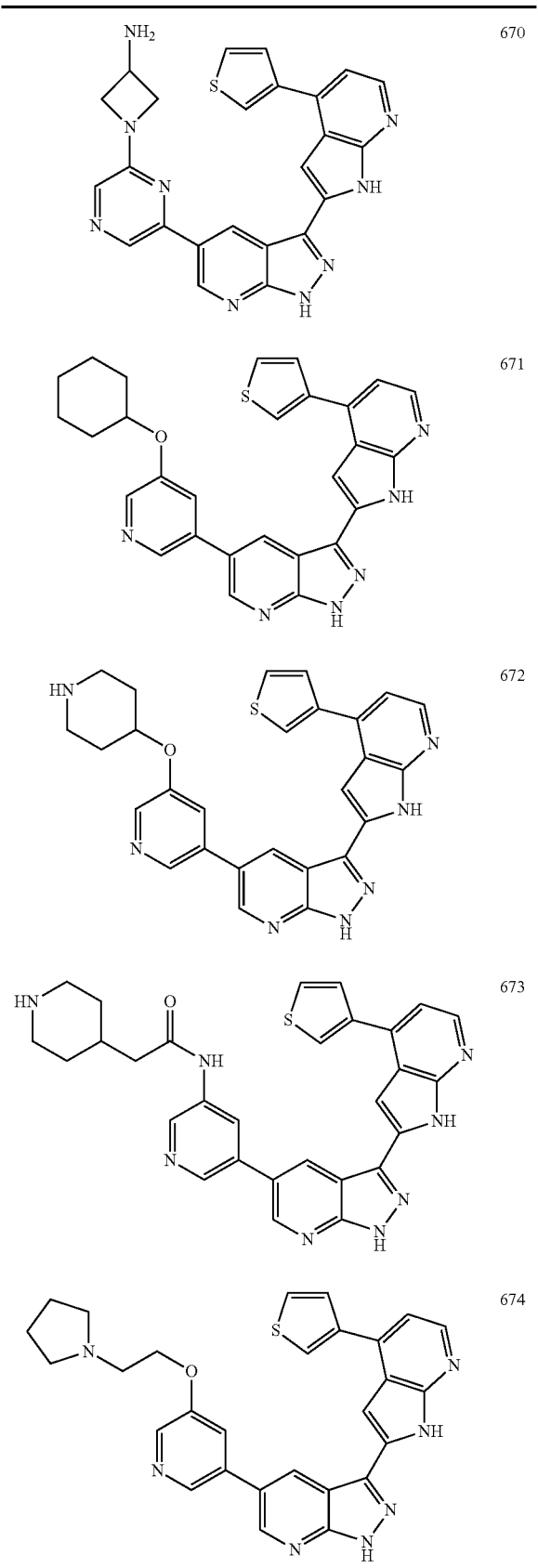
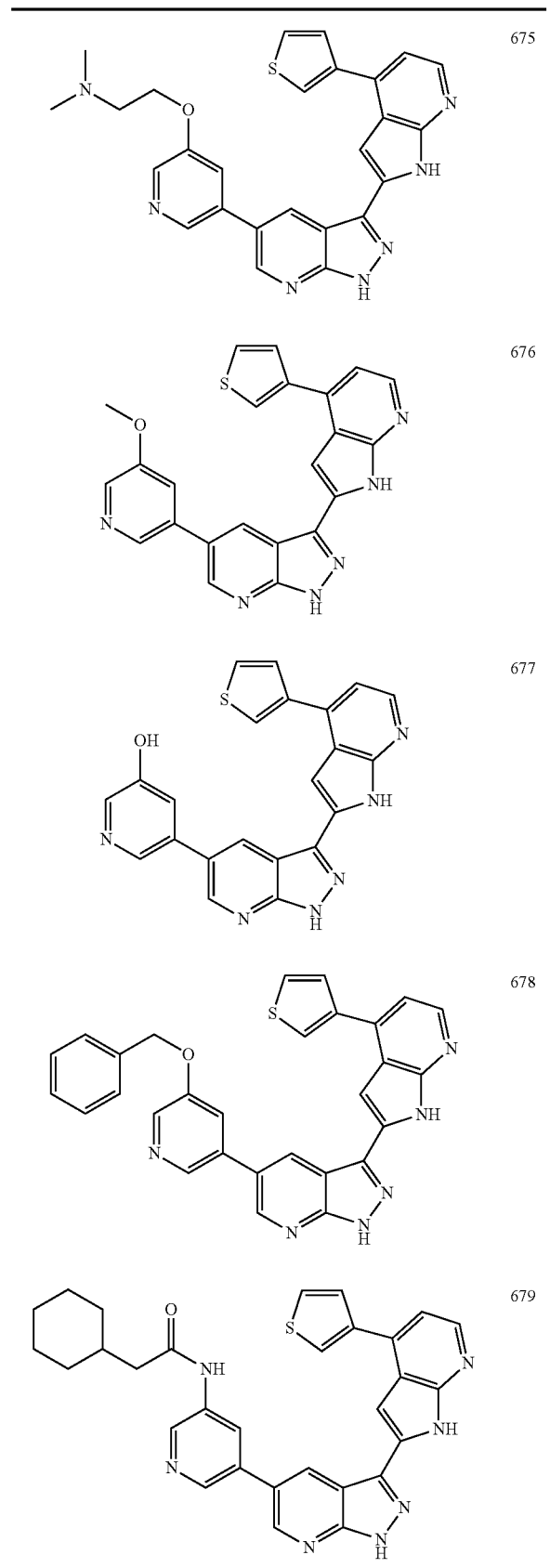

TABLE 1-continued
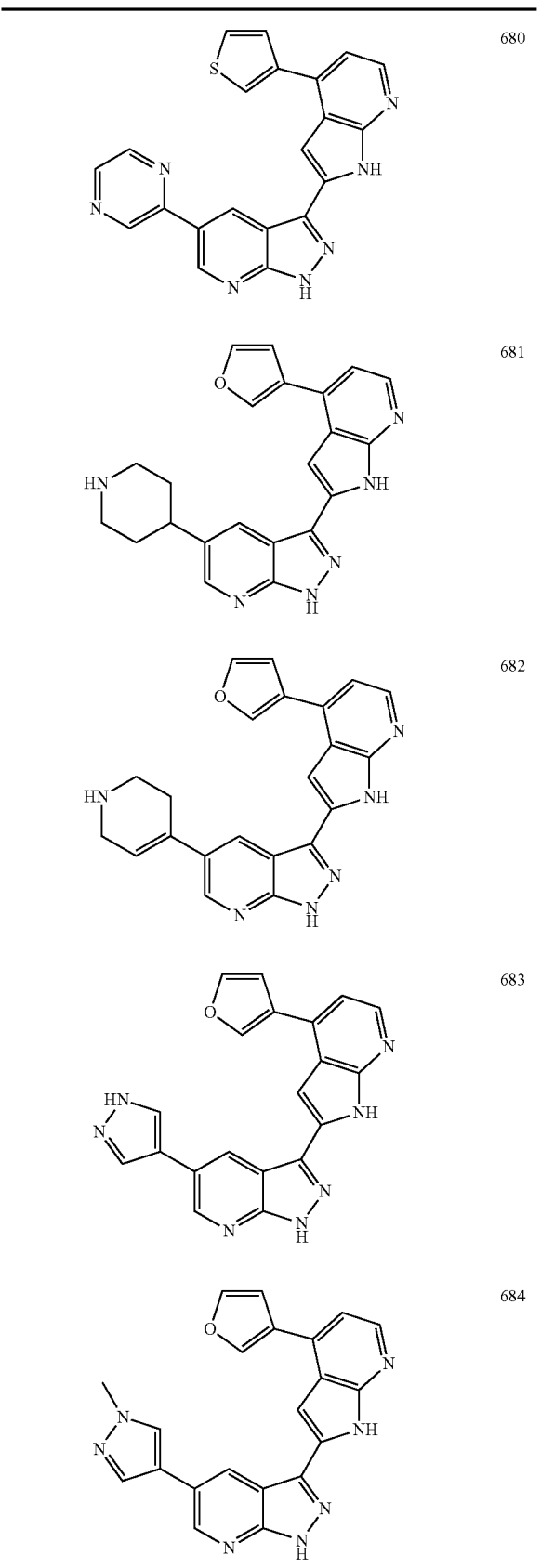
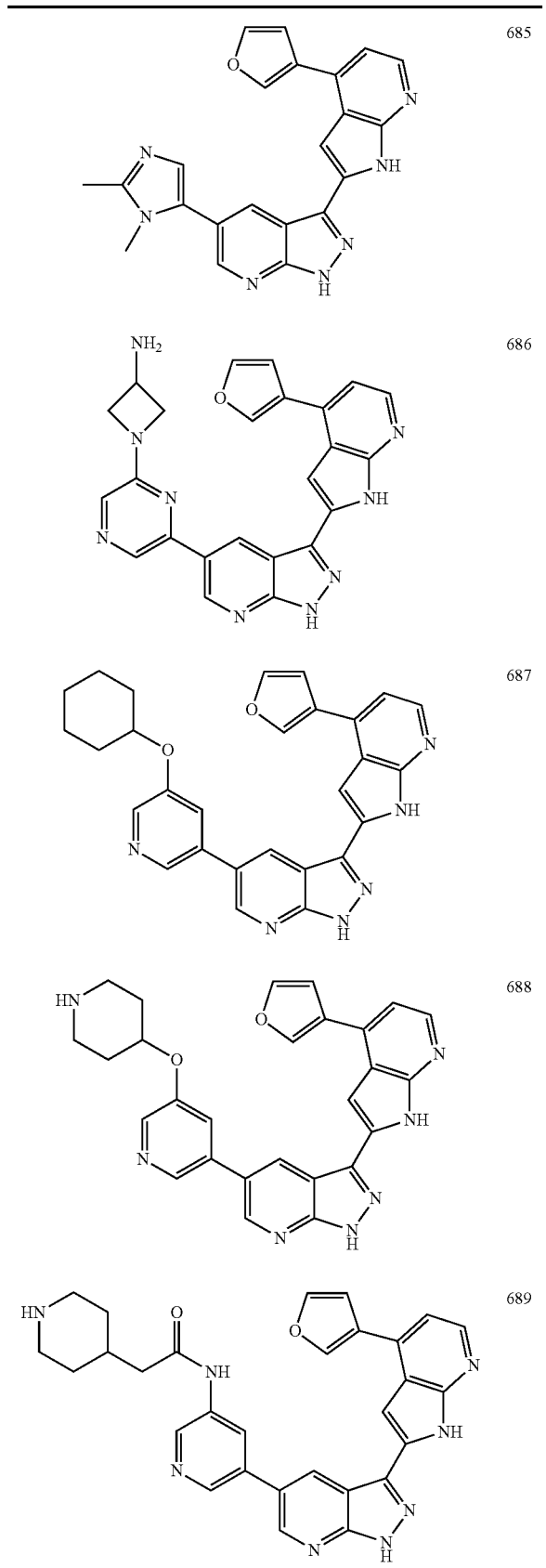

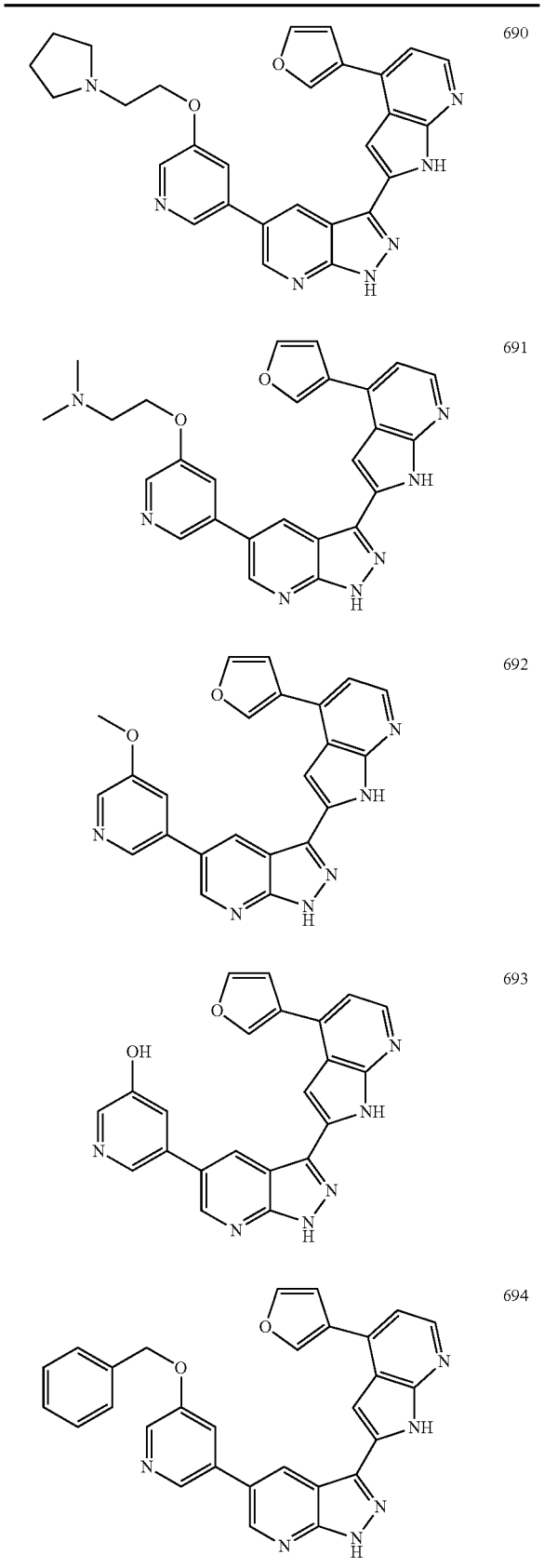

TABLE 1-continued
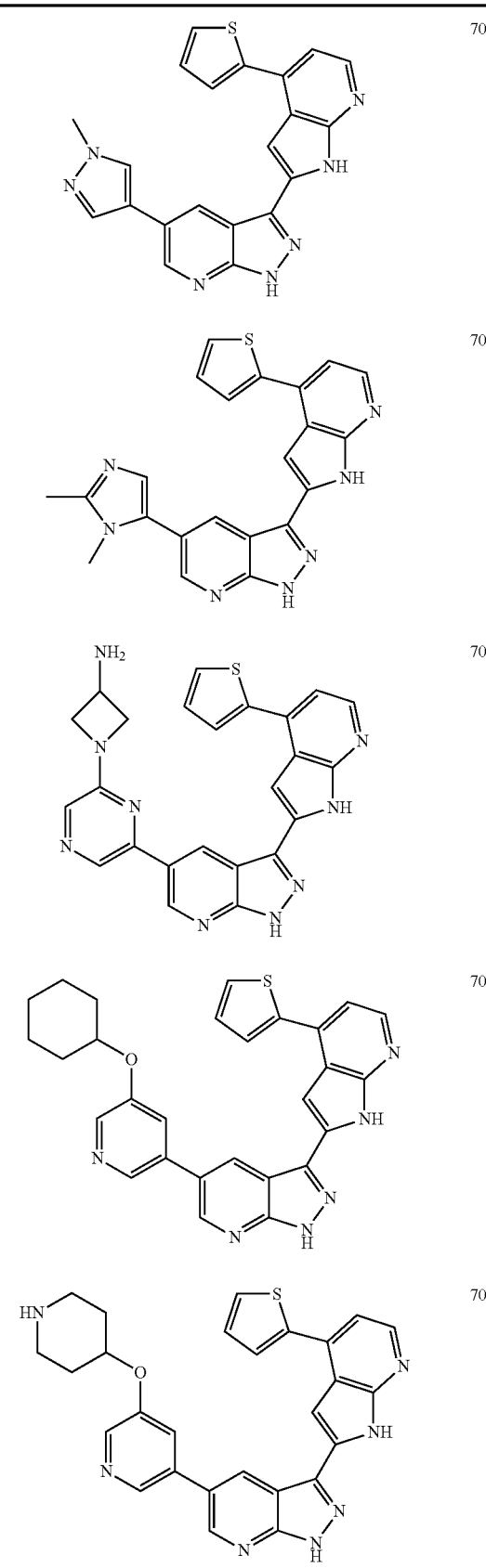
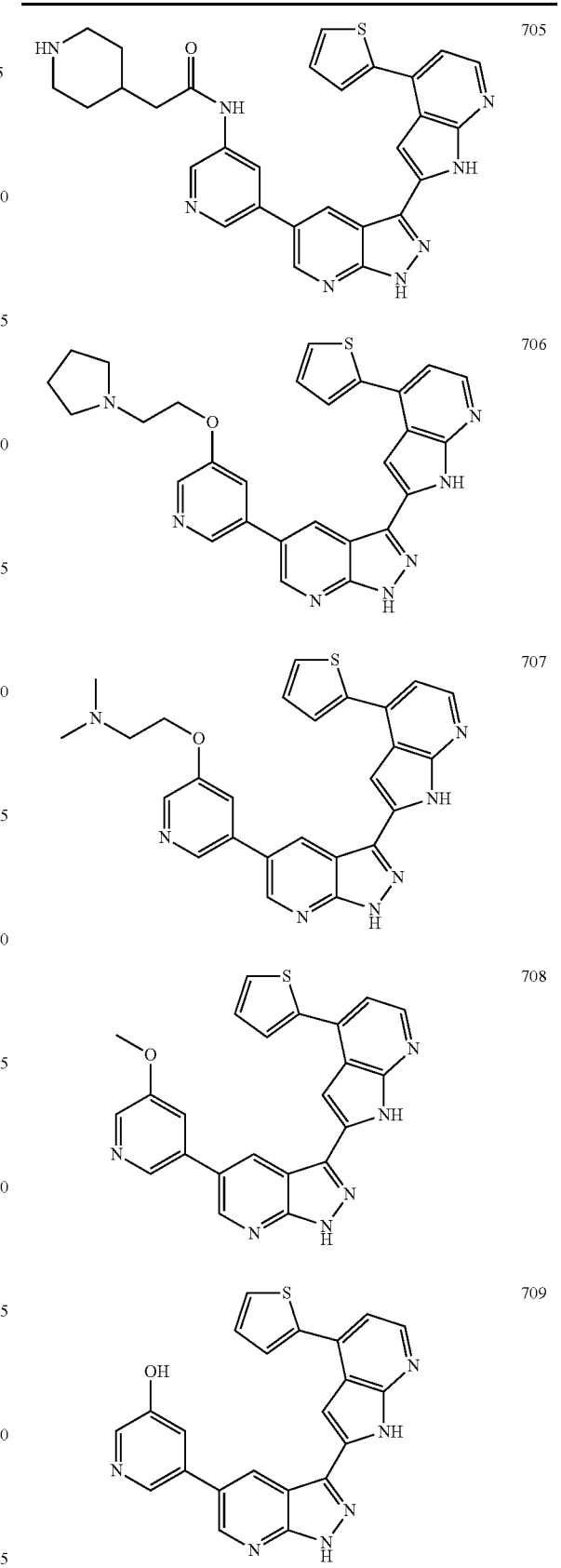

TABLE 1-continued
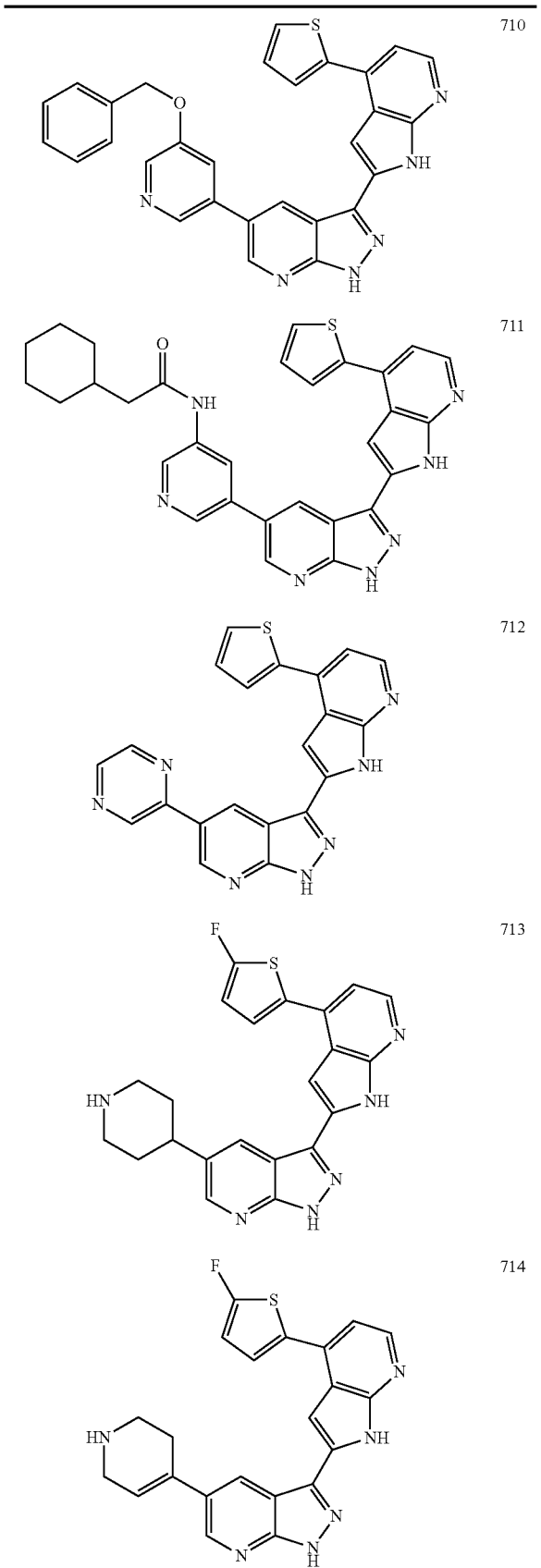
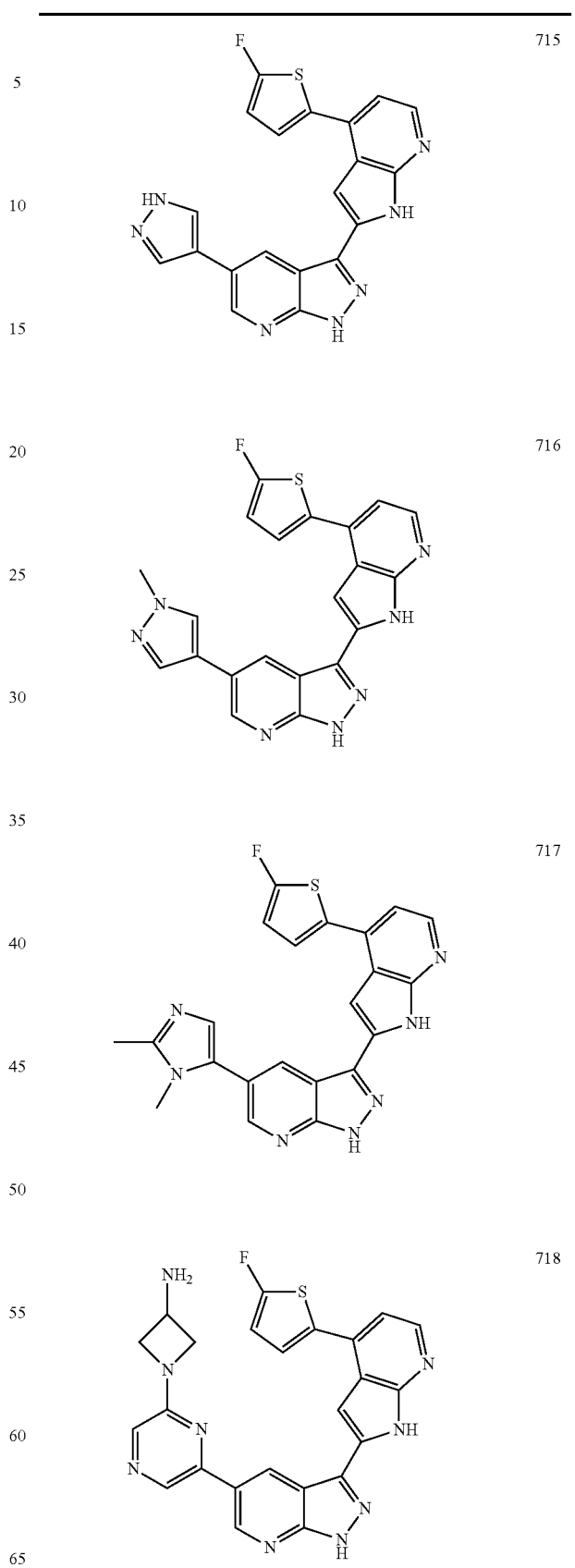

TABLE 1-continued
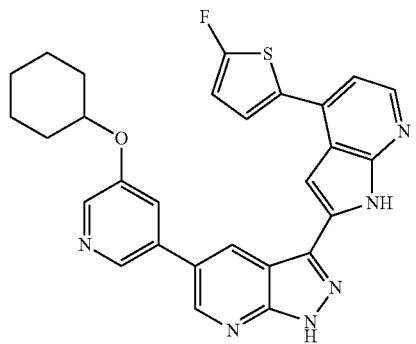 [SMILES: Fc1ccc(-c2ccnc3[nH]c(-c4n[nH]c5ncc(-c6cncc(OC7CCCCC7)c6)cc45)cc23)s1]
719
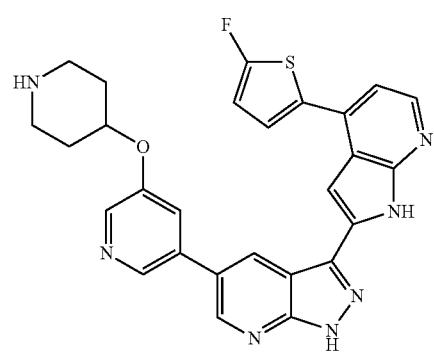 [SMILES: Fc1ccc(-c2ccnc3[nH]c(-c4n[nH]c5ncc(-c6cncc(OC7CCNCC7)c6)cc45)cc23)s1]
720
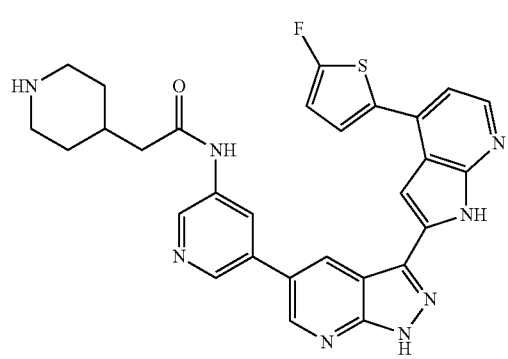 [SMILES: O=C(CC1CCNCC1)Nc1cncc(-c2cnc3[nH]nc(-c4cc5c(-c6ccc(F)s6)ccnc5[nH]4)c3c2)c1]
721
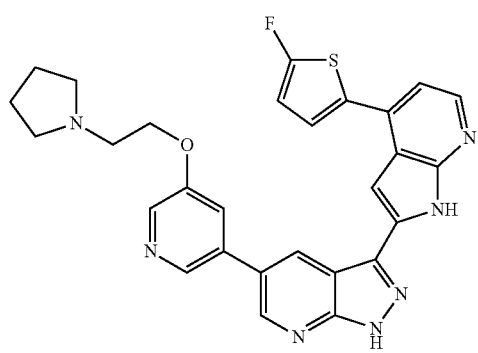 [SMILES: Fc1ccc(-c2ccnc3[nH]c(-c4n[nH]c5ncc(-c6cncc(OCCN7CCCC7)c6)cc45)cc23)s1]
722
TABLE 1-continued
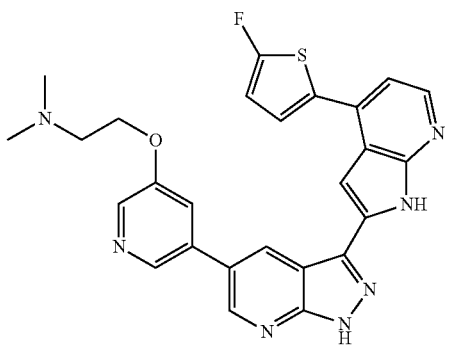 [SMILES: CN(C)CCOc1cncc(-c2cnc3[nH]nc(-c4cc5c(-c6ccc(F)s6)ccnc5[nH]4)c3c2)c1]
723
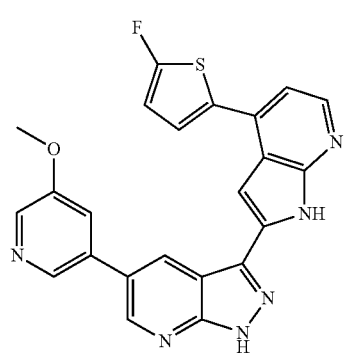 [SMILES: COc1cncc(-c2cnc3[nH]nc(-c4cc5c(-c6ccc(F)s6)ccnc5[nH]4)c3c2)c1]
724
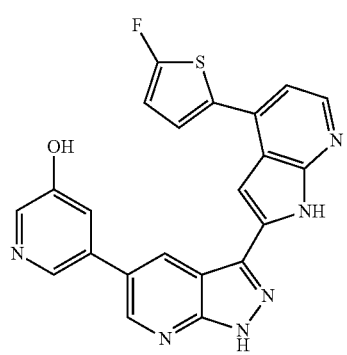 [SMILES: Oc1cncc(-c2cnc3[nH]nc(-c4cc5c(-c6ccc(F)s6)ccnc5[nH]4)c3c2)c1]
725
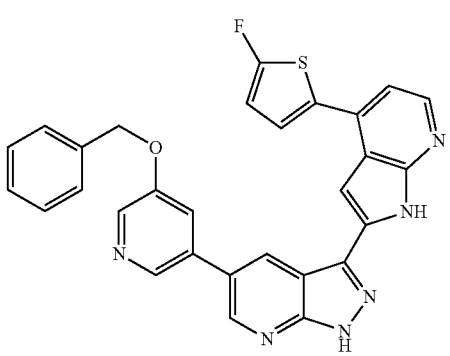 [SMILES: Fc1ccc(-c2ccnc3[nH]c(-c4n[nH]c5ncc(-c6cncc(OCc7ccccc7)c6)cc45)cc23)s1]
726

TABLE 1-continued
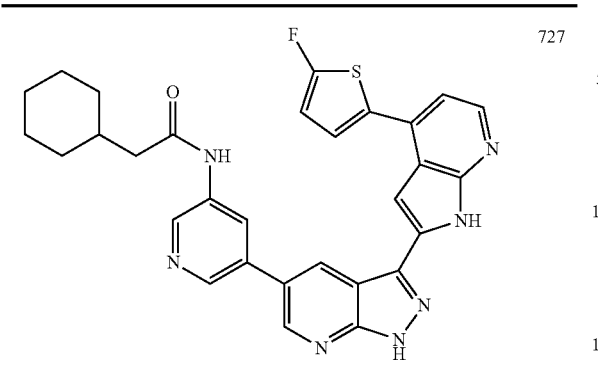 727
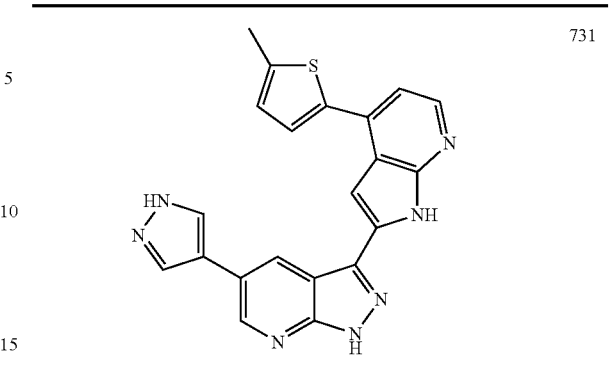 731
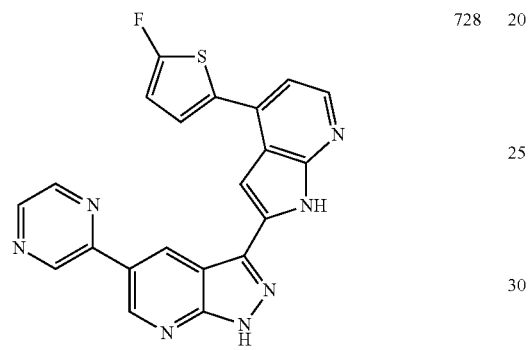 728
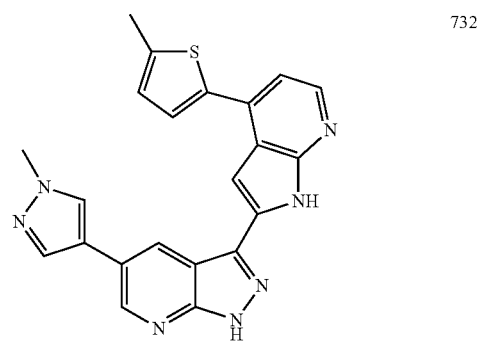 732
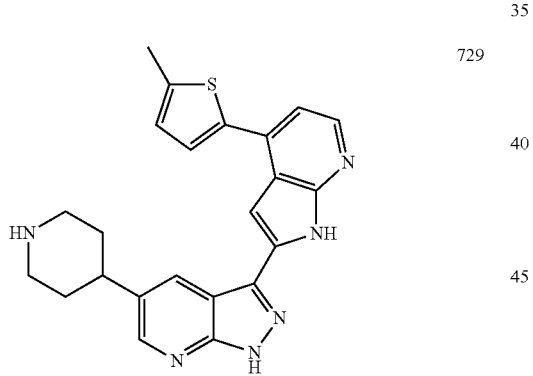 729
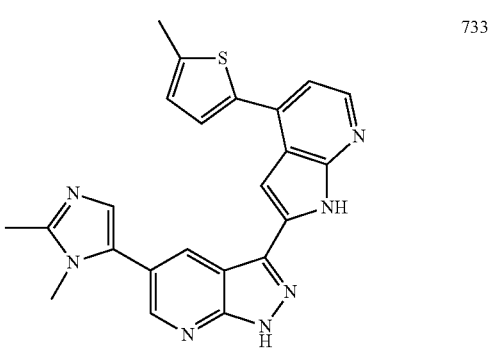 733
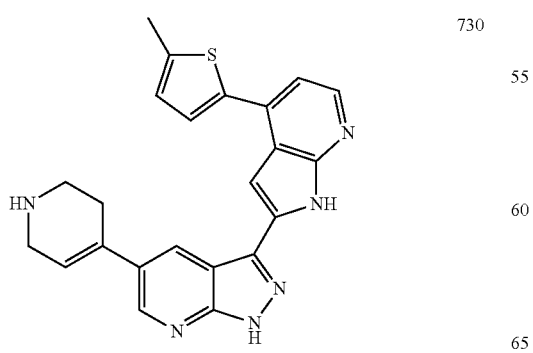 730
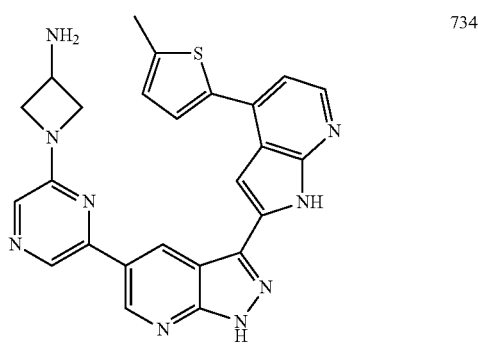 734

| 735 | 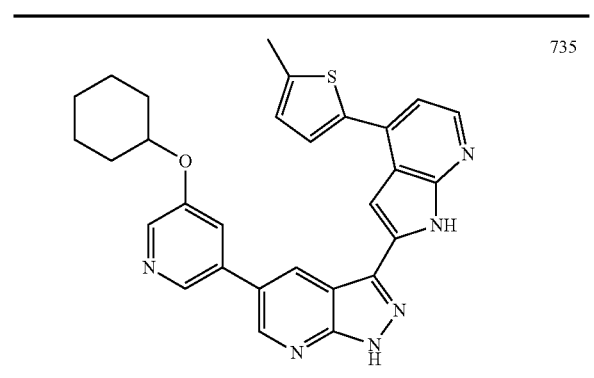 |
| 736 | 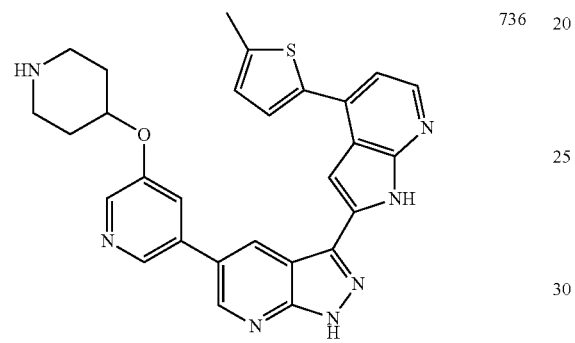 |
| 737 | 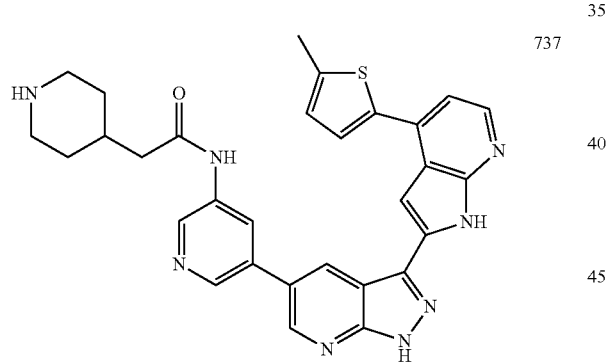 |
| 738 | 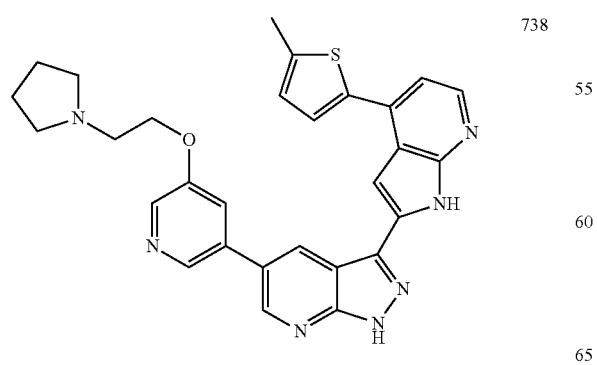 |
| 739 | 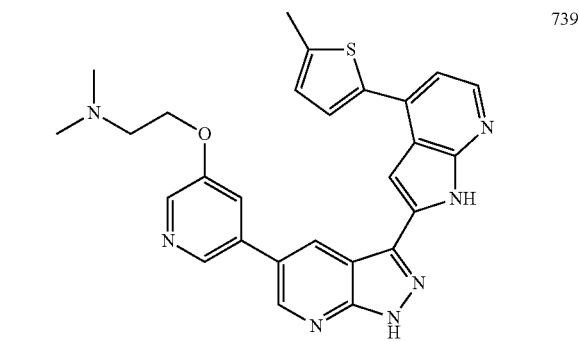 |
| 740 | 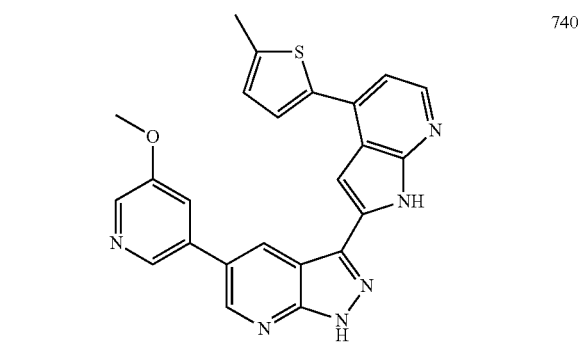 |
| 741 | 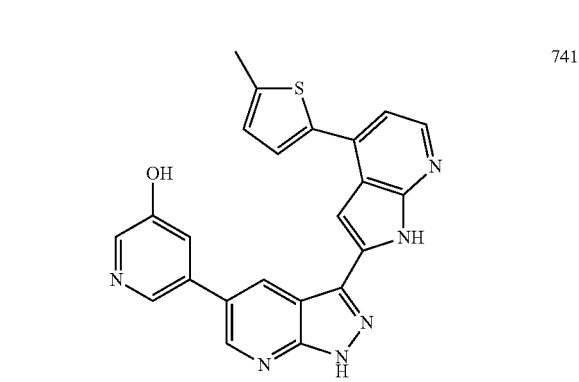 |
| 742 | 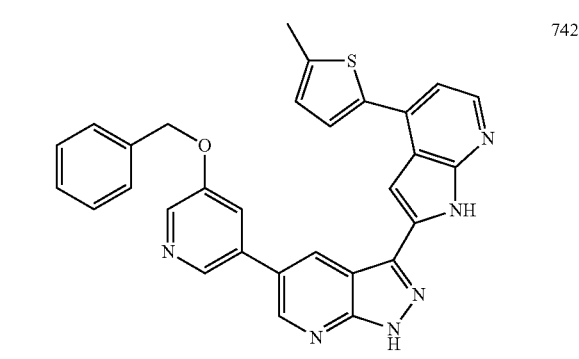 |

TABLE 1-continued
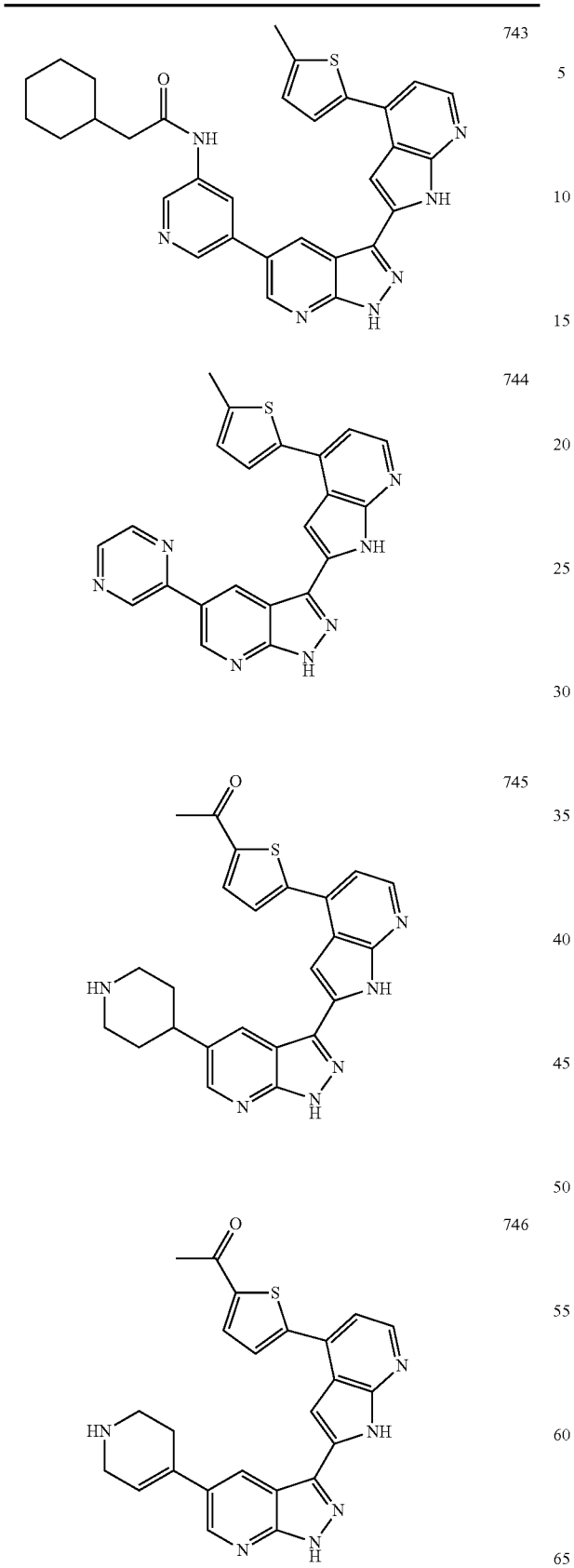
TABLE 1-continued
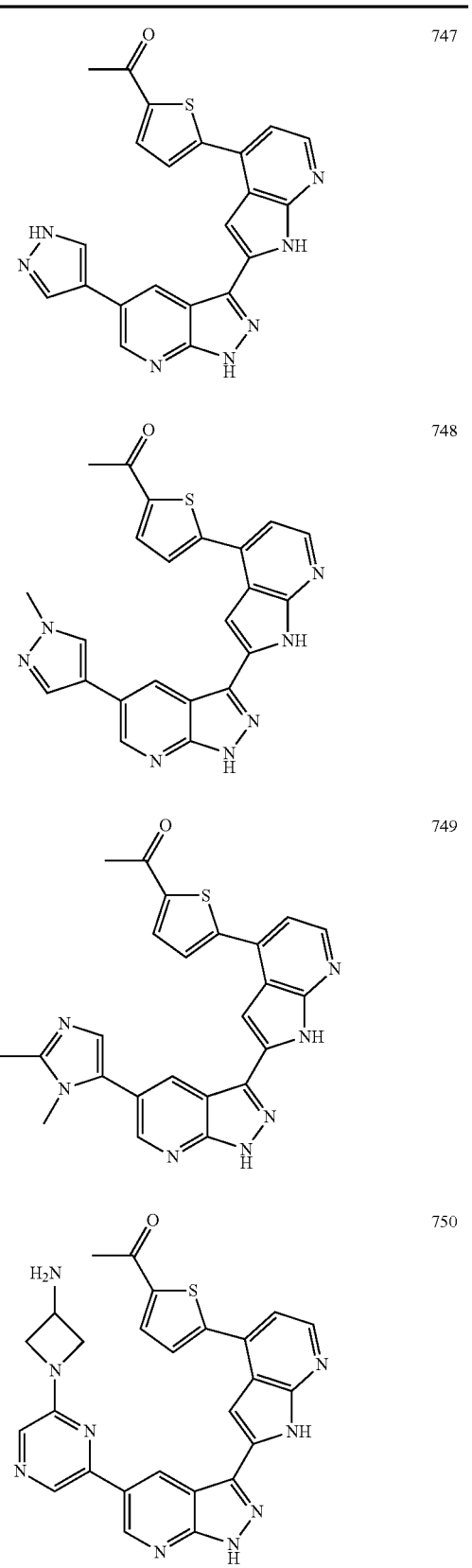

TABLE 1-continued
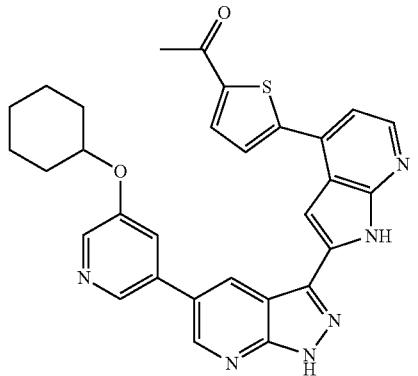 [SMILES: CC(=O)c1ccc(-c2ccnc3[nH]c(-c4n[nH]c5ncc(-c6cncc(OC7CCCCC7)c6)cc45)cc23)s1] 751
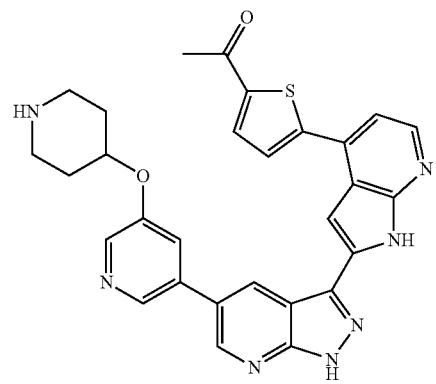 [SMILES: CC(=O)c1ccc(-c2ccnc3[nH]c(-c4n[nH]c5ncc(-c6cncc(OC7CCNCC7)c6)cc45)cc23)s1] 752
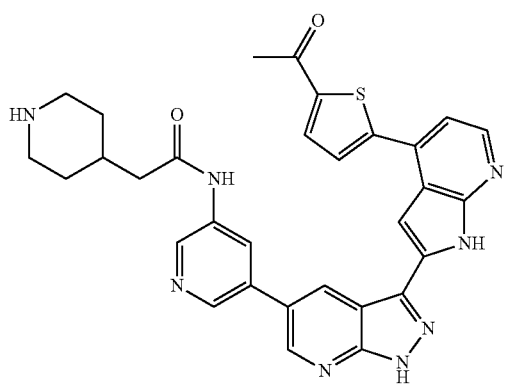 [SMILES: CC(=O)c1ccc(-c2ccnc3[nH]c(-c4n[nH]c5ncc(-c6cncc(NC(=O)CC7CCNCC7)c6)cc45)cc23)s1] 753
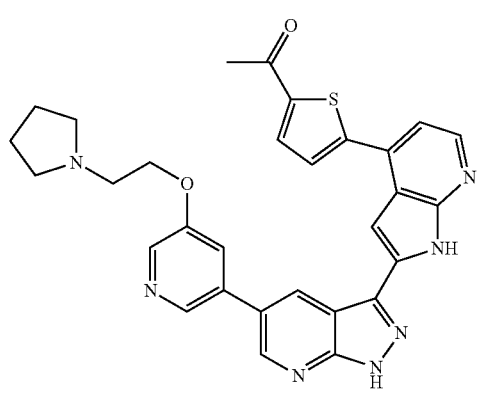 [SMILES: CC(=O)c1ccc(-c2ccnc3[nH]c(-c4n[nH]c5ncc(-c6cncc(OCCN7CCCC7)c6)cc45)cc23)s1] 754
TABLE 1-continued
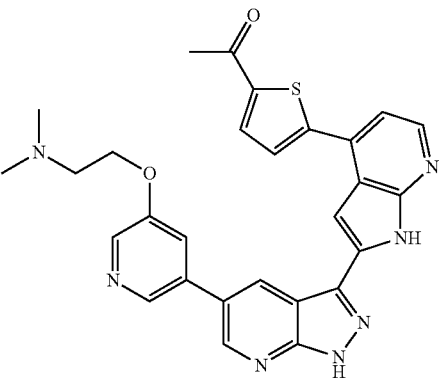 [SMILES: CC(=O)c1ccc(-c2ccnc3[nH]c(-c4n[nH]c5ncc(-c6cncc(OCCN(C)C)c6)cc45)cc23)s1] 755
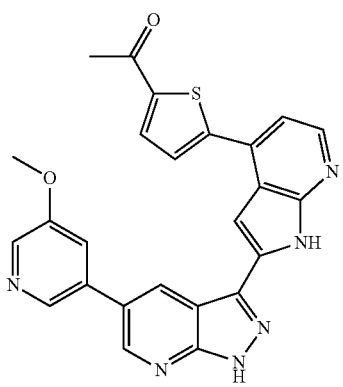 [SMILES: COc1cncc(-c2cnc3[nH]nc(-c4cc5c(-c6ccc(C(C)=O)s6)ccnc5[nH]4)c3c2)c1] 756
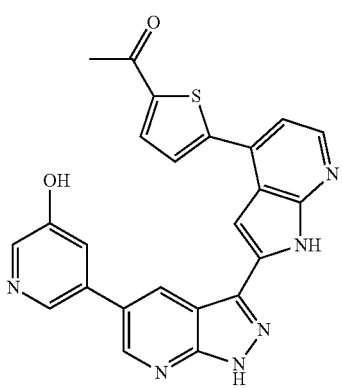 [SMILES: CC(=O)c1ccc(-c2ccnc3[nH]c(-c4n[nH]c5ncc(-c6cncc(O)c6)cc45)cc23)s1] 757
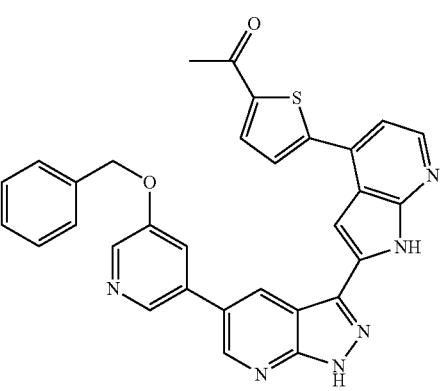 [SMILES: CC(=O)c1ccc(-c2ccnc3[nH]c(-c4n[nH]c5ncc(-c6cncc(OCc7ccccc7)c6)cc45)cc23)s1] 758

TABLE 1-continued
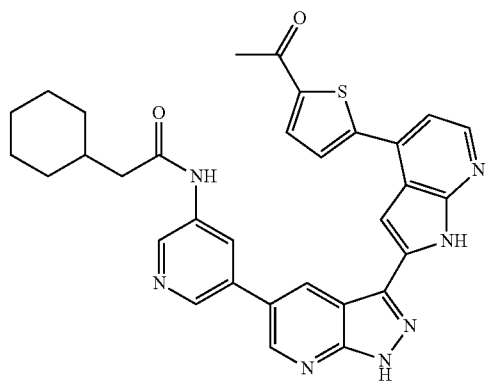 [SMILES: CC(=O)c1ccc(-c2ccnc3[nH]c(-c4n[nH]c5ncc(-c6cncc(NC(=O)CC7CCCCC7)c6)cc45)cc23)s1]
759
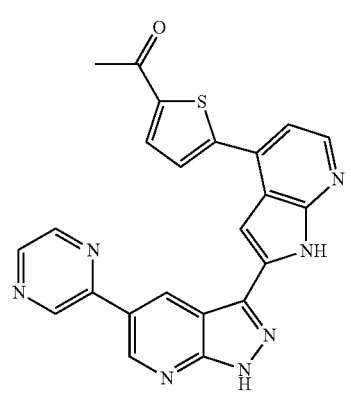 [SMILES: CC(=O)c1ccc(-c2ccnc3[nH]c(-c4n[nH]c5ncc(-c6cnccn6)cc45)cc23)s1]
760
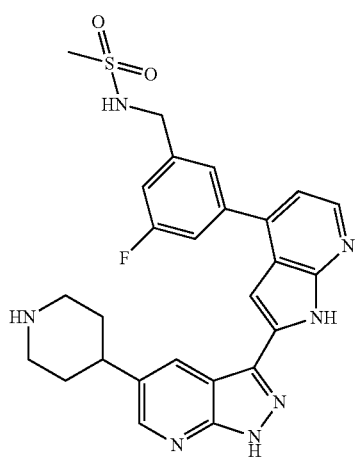 [SMILES: CS(=O)(=O)NCc1cc(F)cc(-c2ccnc3[nH]c(-c4n[nH]c5ncc(C6CCNCC6)cc45)cc23)c1]
761
TABLE 1-continued
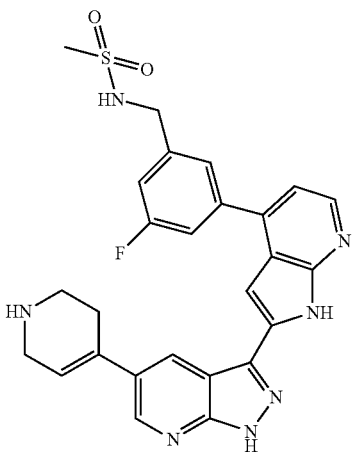 [SMILES: CS(=O)(=O)NCc1cc(F)cc(-c2ccnc3[nH]c(-c4n[nH]c5ncc(C6=CCNCC6)cc45)cc23)c1]
762
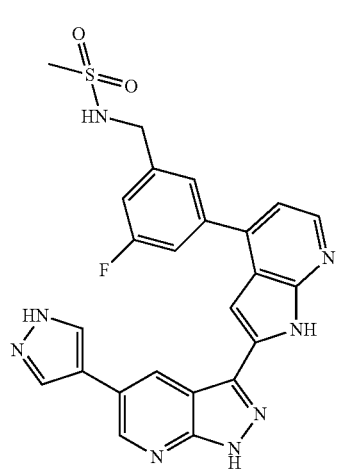 [SMILES: CS(=O)(=O)NCc1cc(F)cc(-c2ccnc3[nH]c(-c4n[nH]c5ncc(-c6cn[nH]c6)cc45)cc23)c1]
763
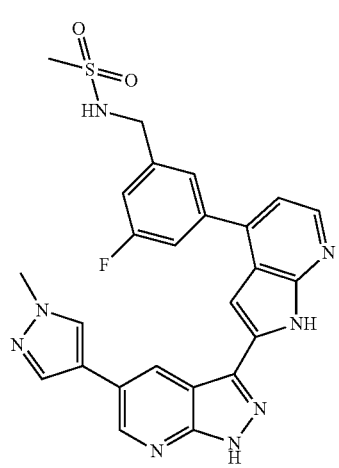 [SMILES: Cn1cc(-c2cnc3[nH]nc(-c4cc5c(-c6cc(F)cc(CNS(C)(=O)=O)c6)ccnc5[nH]4)c3c2)cn1]
764

TABLE 1-continued
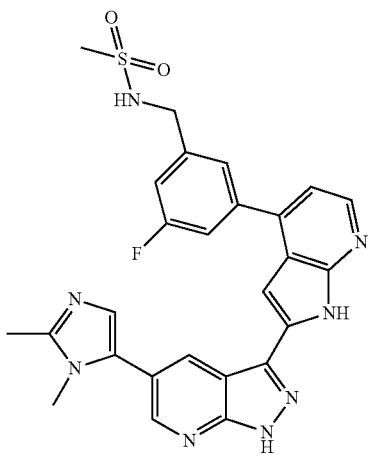 [SMILES: Cc1ncc(-c2cnc3[nH]nc(-c4cc5c(-c6cc(F)cc(CNS(C)(=O)=O)c6)ccnc5[nH]4)c3c2)n1C]
765
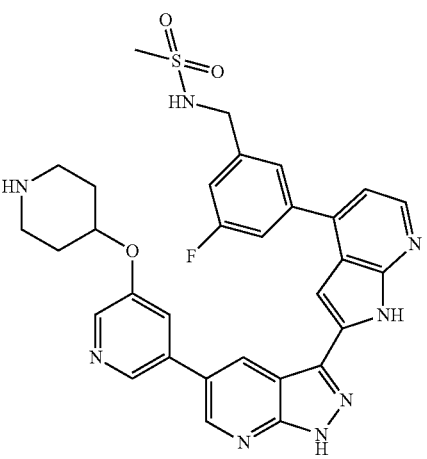 [SMILES: CS(=O)(=O)NCc1cc(F)cc(-c2ccnc3[nH]c(-c4n[nH]c5ncc(-c6cncc(OC7CCNCC7)c6)cc45)cc23)c1]
768
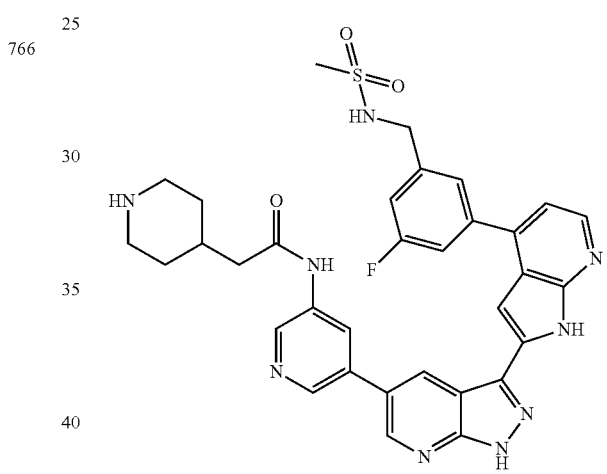
766
769
767
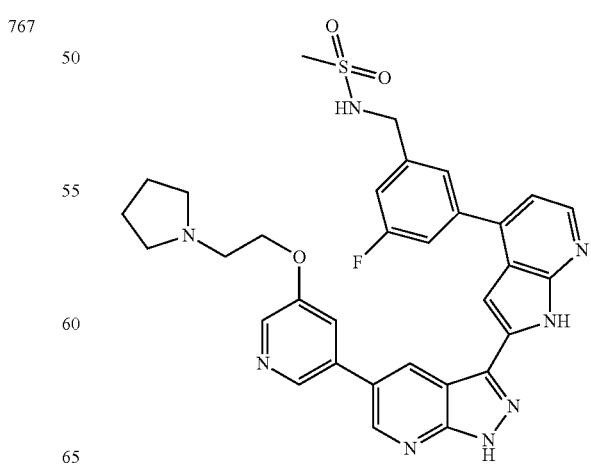
770

TABLE 1-continued
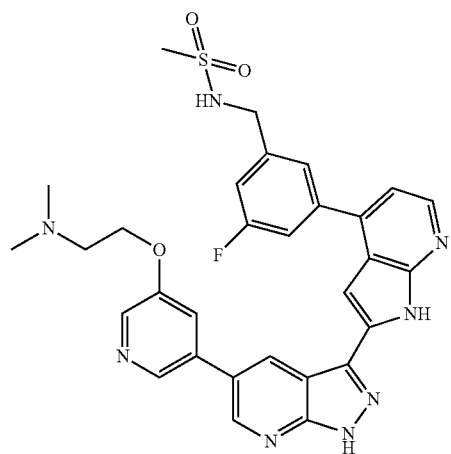 [SMILES: CN(C)CCOc1cncc(-c2cnc3[nH]nc(-c4cc5c(-c6cc(F)cc(CNS(C)(=O)=O)c6)ccnc5[nH]4)c3c2)c1]
771
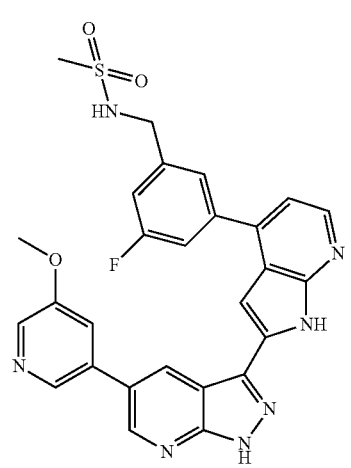 [SMILES: COc1cncc(-c2cnc3[nH]nc(-c4cc5c(-c6cc(F)cc(CNS(C)(=O)=O)c6)ccnc5[nH]4)c3c2)c1]
772
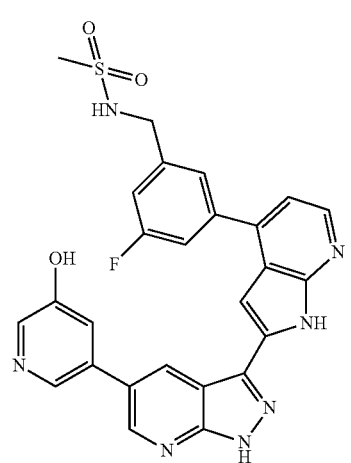 [SMILES: CS(=O)(=O)NCc1cc(F)cc(-c2ccnc3[nH]c(-c4n[nH]c5ncc(-c6cncc(O)c6)cc45)cc23)c1]
773
TABLE 1-continued
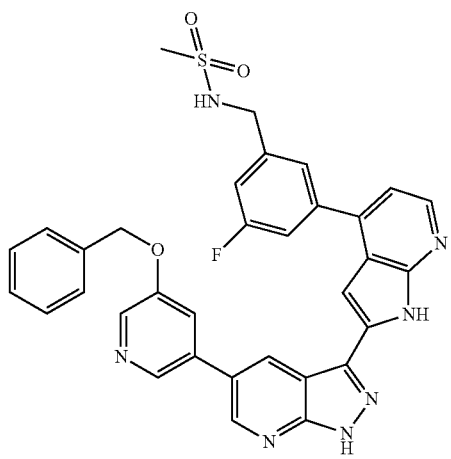 [SMILES: CS(=O)(=O)NCc1cc(F)cc(-c2ccnc3[nH]c(-c4n[nH]c5ncc(-c6cncc(OCc7ccccc7)c6)cc45)cc23)c1]
774
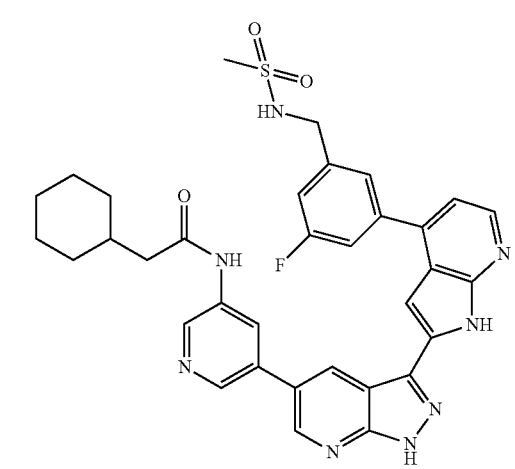 [SMILES: CS(=O)(=O)NCc1cc(F)cc(-c2ccnc3[nH]c(-c4n[nH]c5ncc(-c6cncc(NC(=O)CC7CCCCC7)c6)cc45)cc23)c1]
775
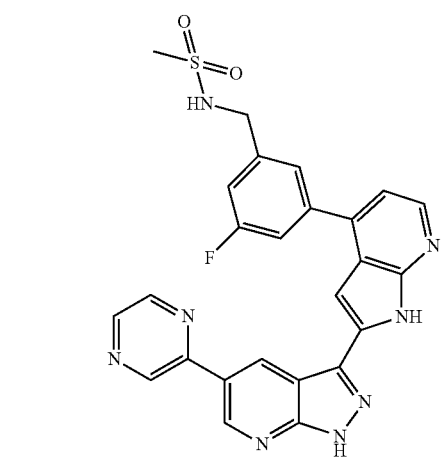 [SMILES: CS(=O)(=O)NCc1cc(F)cc(-c2ccnc3[nH]c(-c4n[nH]c5ncc(-c6cnccn6)cc45)cc23)c1]
776

TABLE 1-continued
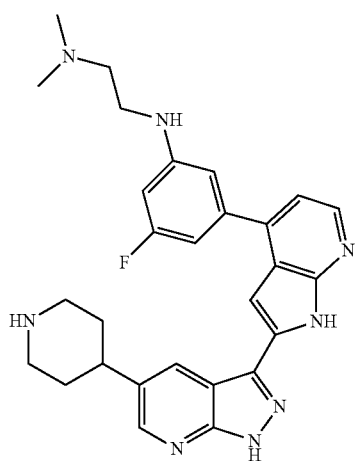 [SMILES: CN(C)CCNc1cc(F)cc(-c2ccnc3[nH]c(-c4n[nH]c5ncc(C6CCNCC6)cc45)cc23)c1]
777
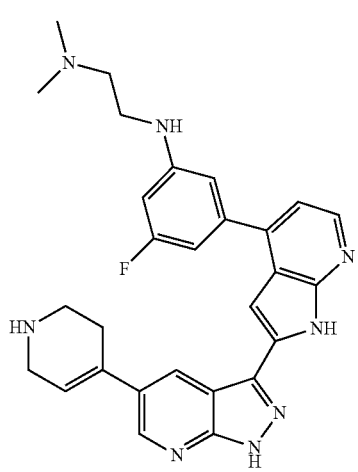 [SMILES: CN(C)CCNc1cc(F)cc(-c2ccnc3[nH]c(-c4n[nH]c5ncc(C6=CCNCC6)cc45)cc23)c1]
778
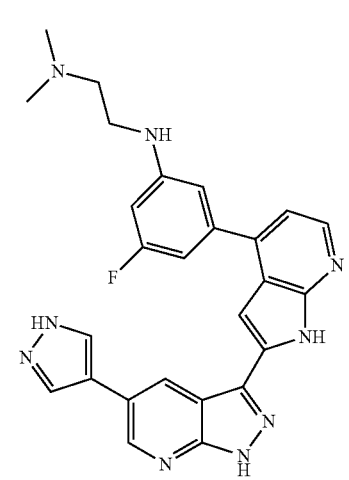 [SMILES: CN(C)CCNc1cc(F)cc(-c2ccnc3[nH]c(-c4n[nH]c5ncc(-c6cn[nH]c6)cc45)cc23)c1]
779
TABLE 1-continued
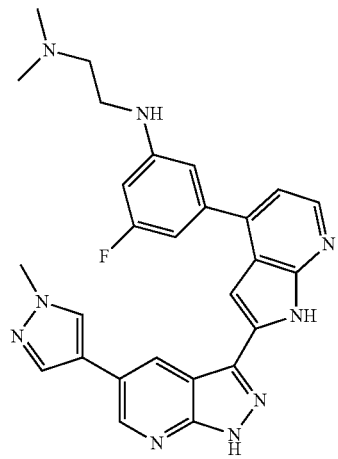 [SMILES: CN(C)CCNc1cc(F)cc(-c2ccnc3[nH]c(-c4n[nH]c5ncc(-c6cnn(C)c6)cc45)cc23)c1]
780
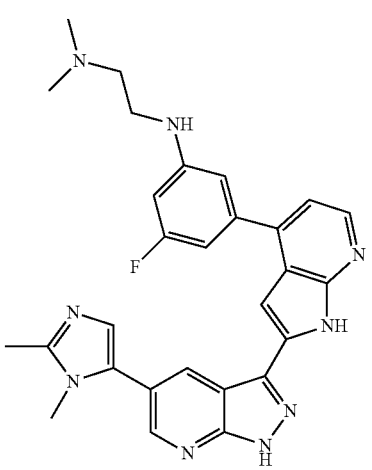 [SMILES: Cc1ncc(-c2cnc3[nH]nc(-c4cc5c(-c6cc(F)cc(NCCN(C)C)c6)ccnc5[nH]4)c3c2)n1C]
781
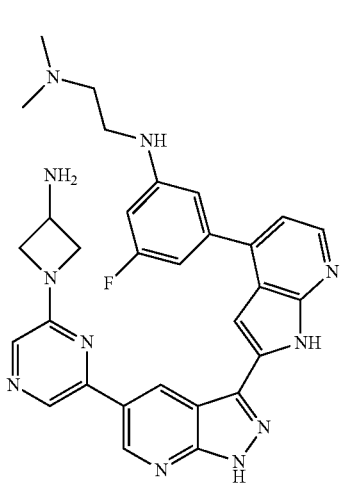 [SMILES: CN(C)CCNc1cc(F)cc(-c2ccnc3[nH]c(-c4n[nH]c5ncc(-c6cncc(N7CC(N)C7)n6)cc45)cc23)c1]
782

TABLE 1-continued
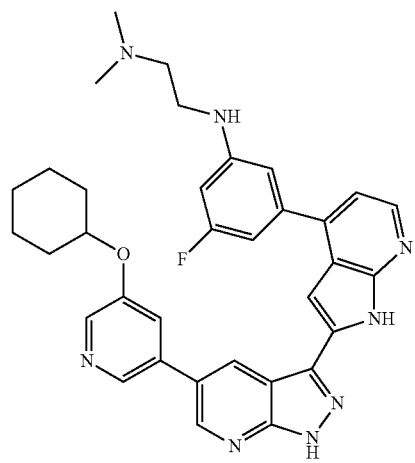 [SMILES: CN(C)CCNc1cc(F)cc(-c2ccnc3[nH]c(-c4n[nH]c5ncc(-c6cncc(OC7CCCCC7)c6)cc45)cc23)c1]
783
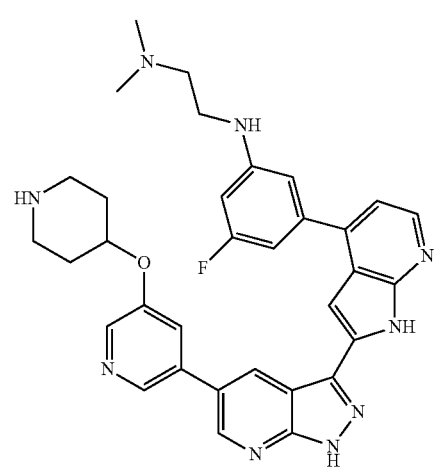 [SMILES: CN(C)CCNc1cc(F)cc(-c2ccnc3[nH]c(-c4n[nH]c5ncc(-c6cncc(OC7CCNCC7)c6)cc45)cc23)c1]
784
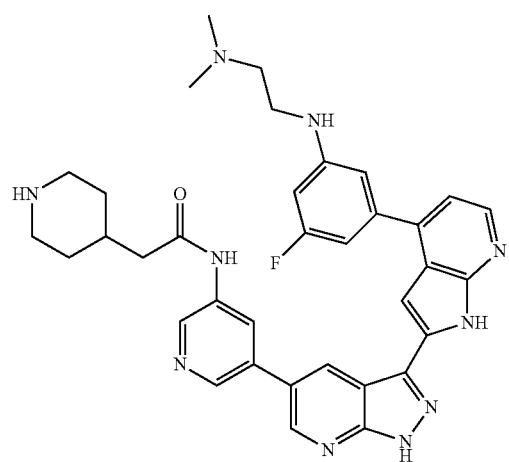 [SMILES: CN(C)CCNc1cc(F)cc(-c2ccnc3[nH]c(-c4n[nH]c5ncc(-c6cncc(NC(=O)CC7CCNCC7)c6)cc45)cc23)c1]
785
TABLE 1-continued
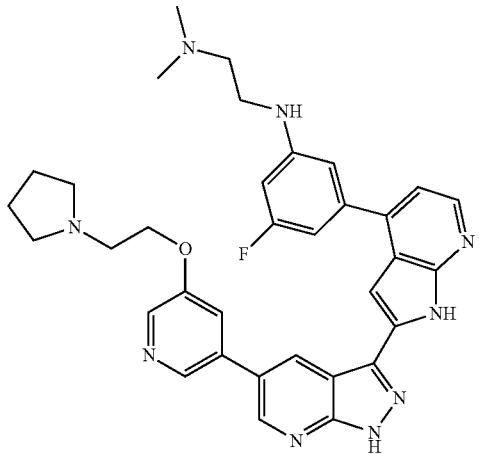 [SMILES: CN(C)CCNc1cc(F)cc(-c2ccnc3[nH]c(-c4n[nH]c5ncc(-c6cncc(OCCN7CCCC7)c6)cc45)cc23)c1]
786
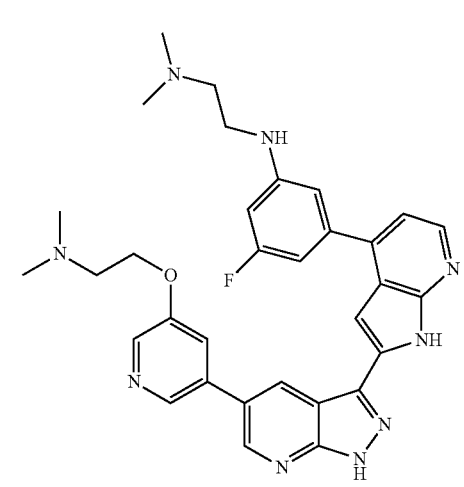 [SMILES: CN(C)CCNc1cc(F)cc(-c2ccnc3[nH]c(-c4n[nH]c5ncc(-c6cncc(OCCN(C)C)c6)cc45)cc23)c1]
787
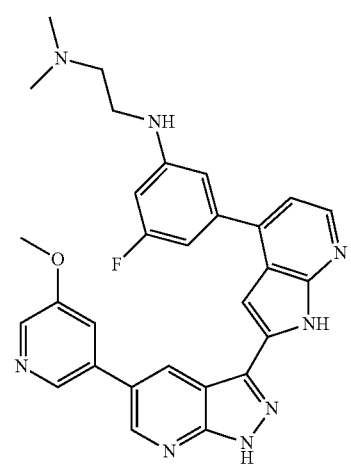 [SMILES: COc1cncc(-c2cnc3[nH]nc(-c4cc5c(-c6cc(F)cc(NCCN(C)C)c6)ccnc5[nH]4)c3c2)c1]
788

TABLE 1-continued
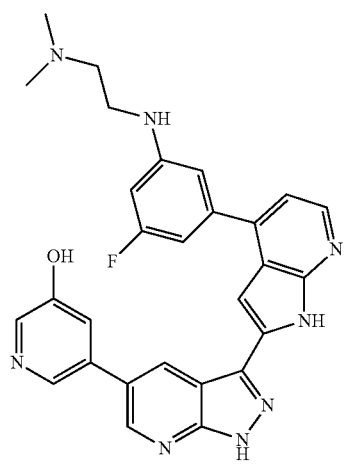 [SMILES: CN(C)CCNc1cc(F)cc(-c2ccnc3[nH]c(-c4n[nH]c5ncc(-c6cncc(O)c6)cc45)cc23)c1]
789
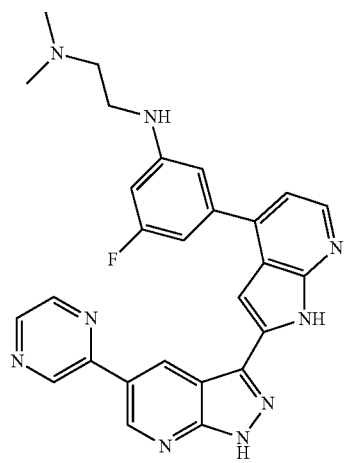 [SMILES: CN(C)CCNc1cc(F)cc(-c2ccnc3[nH]c(-c4n[nH]c5ncc(-c6cnccn6)cc45)cc23)c1]
792
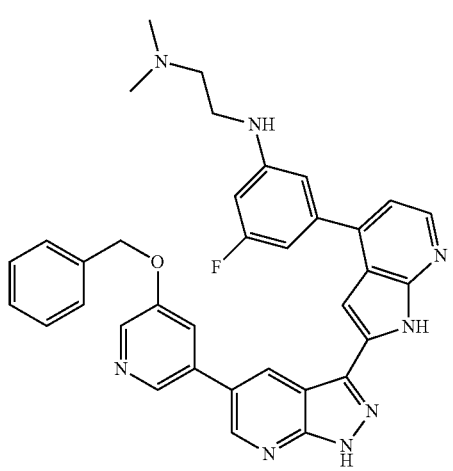
790
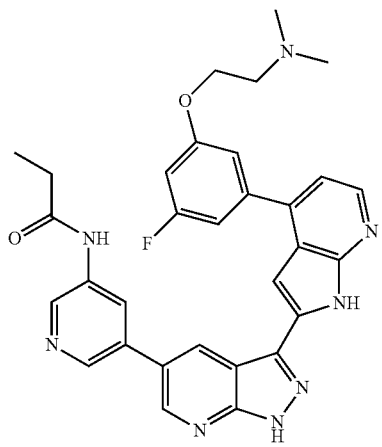 [SMILES: CCC(=O)Nc1cncc(-c2cnc3[nH]nc(-c4cc5c(-c6cc(F)cc(OCCN(C)C)c6)ccnc5[nH]4)c3c2)c1]
793
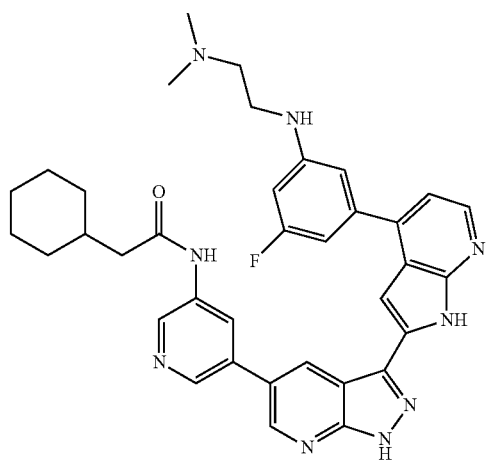
791
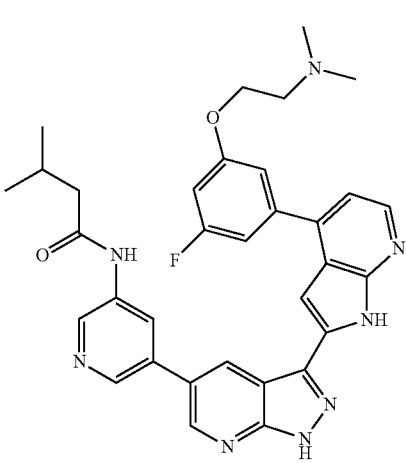
794

TABLE 1-continued
795
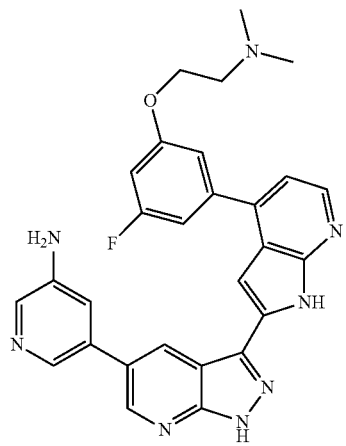 [SMILES: CN(C)CCOc1cc(F)cc(-c2ccnc3[nH]c(-c4n[nH]c5ncc(-c6cncc(N)c6)cc45)cc23)c1]
796
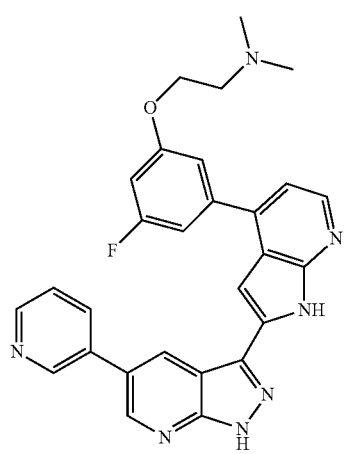 [SMILES: CN(C)CCOc1cc(F)cc(-c2ccnc3[nH]c(-c4n[nH]c5ncc(-c6cccnc6)cc45)cc23)c1]
797
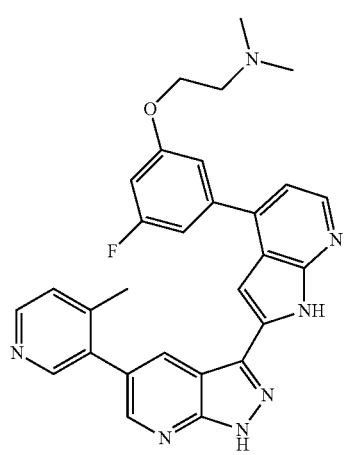 [SMILES: Cc1ccncc1-c1cnc2[nH]nc(-c3cc4c(-c5cc(F)cc(OCCN(C)C)c5)ccnc4[nH]3)c2c1]
TABLE 1-continued
798
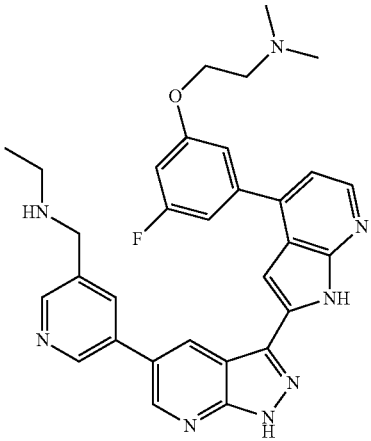 [SMILES: CCNCc1cncc(-c2cnc3[nH]nc(-c4cc5c(-c6cc(F)cc(OCCN(C)C)c6)ccnc5[nH]4)c3c2)c1]
799
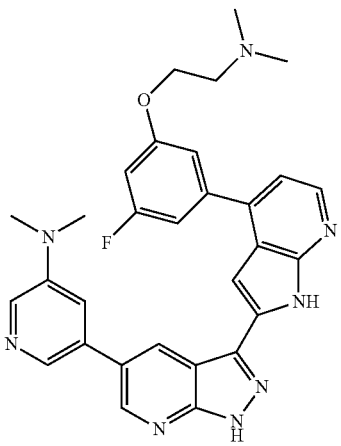 [SMILES: CN(C)CCOc1cc(F)cc(-c2ccnc3[nH]c(-c4n[nH]c5ncc(-c6cncc(N(C)C)c6)cc45)cc23)c1]
800
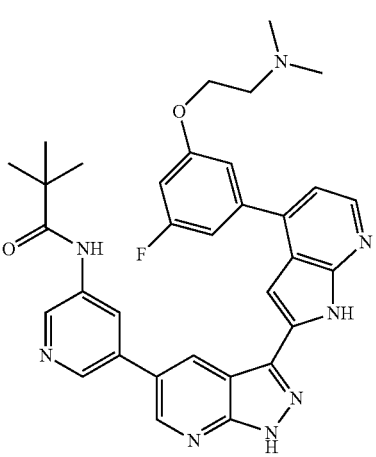 [SMILES: CN(C)CCOc1cc(F)cc(-c2ccnc3[nH]c(-c4n[nH]c5ncc(-c6cncc(NC(=O)C(C)(C)C)c6)cc45)cc23)c1]

TABLE 1-continued
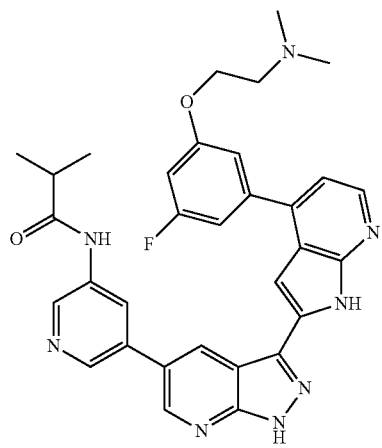 [SMILES: CC(C)C(=O)Nc1cncc(-c2cnc3[nH]nc(-c4cc5c(-c6cc(F)cc(OCCN(C)C)c6)ccnc5[nH]4)c3c2)c1]
801
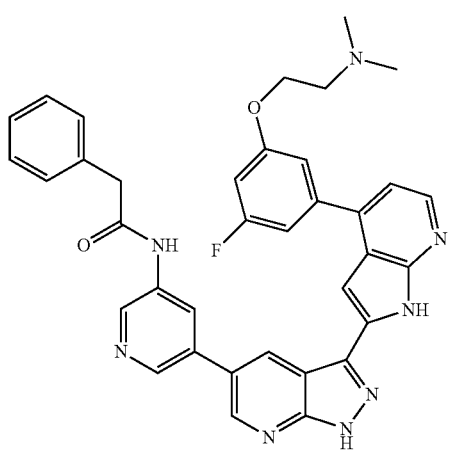 [SMILES: CN(C)CCOc1cc(F)cc(-c2ccnc3[nH]c(-c4n[nH]c5ncc(-c6cncc(NC(=O)Cc7ccccc7)c6)cc45)cc23)c1]
802
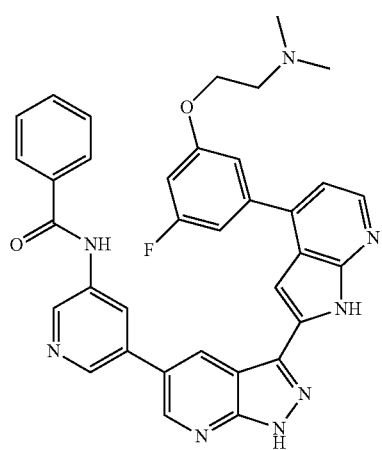 [SMILES: CN(C)CCOc1cc(F)cc(-c2ccnc3[nH]c(-c4n[nH]c5ncc(-c6cncc(NC(=O)c7ccccc7)c6)cc45)cc23)c1]
803
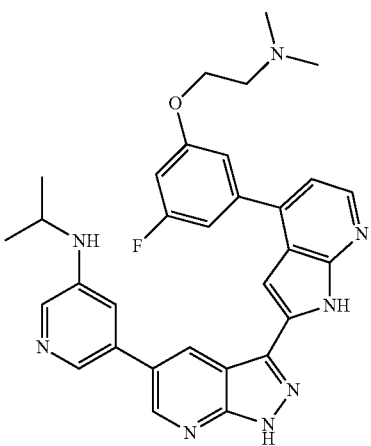 [SMILES: CC(C)Nc1cncc(-c2cnc3[nH]nc(-c4cc5c(-c6cc(F)cc(OCCN(C)C)c6)ccnc5[nH]4)c3c2)c1]
804
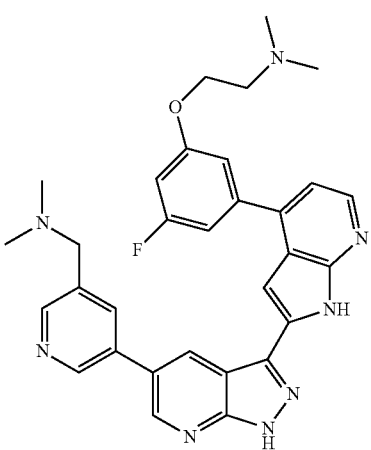 [SMILES: CN(C)CCOc1cc(F)cc(-c2ccnc3[nH]c(-c4n[nH]c5ncc(-c6cncc(CN(C)C)c6)cc45)cc23)c1]
805
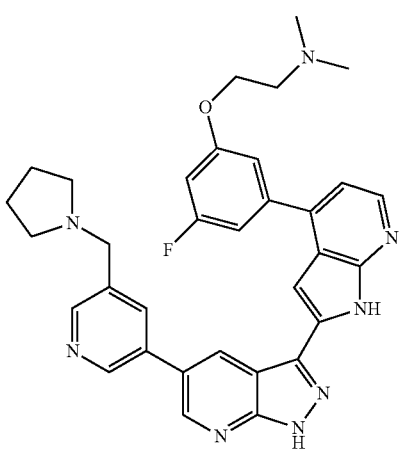
806

TABLE 1-continued
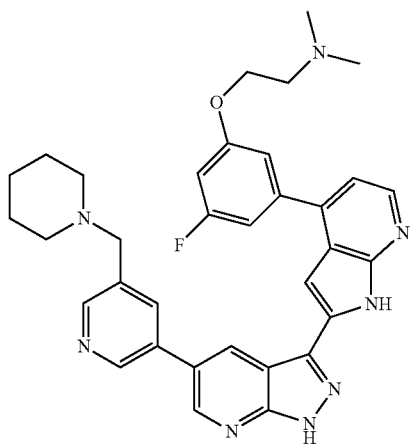 [SMILES: CN(C)CCOc1cc(F)cc(-c2ccnc3[nH]c(-c4n[nH]c5ncc(-c6cncc(CN7CCCCC7)c6)cc45)cc23)c1]
807
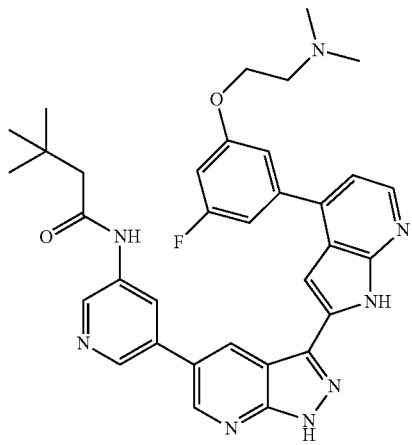 [SMILES: CN(C)CCOc1cc(F)cc(-c2ccnc3[nH]c(-c4n[nH]c5ncc(-c6cncc(NC(=O)CC(C)(C)C)c6)cc45)cc23)c1]
808
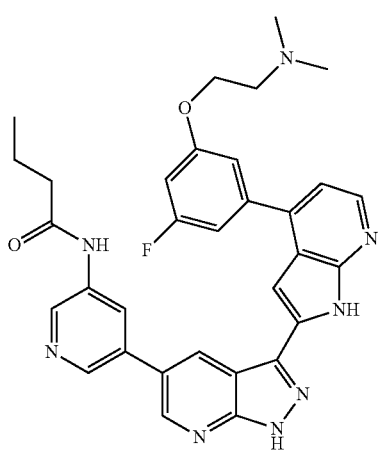 [SMILES: CCCC(=O)Nc1cncc(-c2cnc3[nH]nc(-c4cc5c(-c6cc(F)cc(OCCN(C)C)c6)ccnc5[nH]4)c3c2)c1]
809
TABLE 1-continued
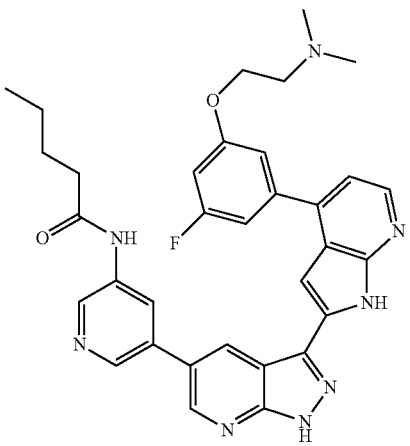 [SMILES: CCCCC(=O)Nc1cncc(-c2cnc3[nH]nc(-c4cc5c(-c6cc(F)cc(OCCN(C)C)c6)ccnc5[nH]4)c3c2)c1]
810
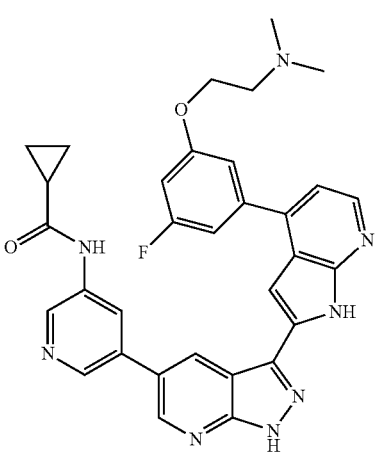 [SMILES: CN(C)CCOc1cc(F)cc(-c2ccnc3[nH]c(-c4n[nH]c5ncc(-c6cncc(NC(=O)C7CC7)c6)cc45)cc23)c1]
811
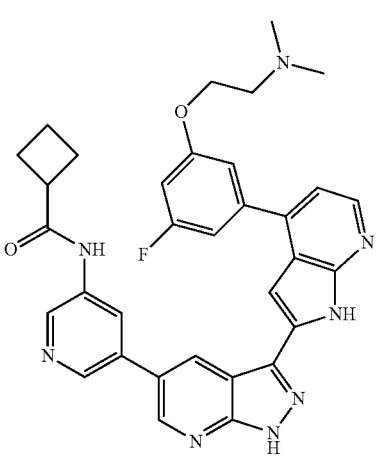 [SMILES: CN(C)CCOc1cc(F)cc(-c2ccnc3[nH]c(-c4n[nH]c5ncc(-c6cncc(NC(=O)C7CCC7)c6)cc45)cc23)c1]
812

TABLE 1-continued
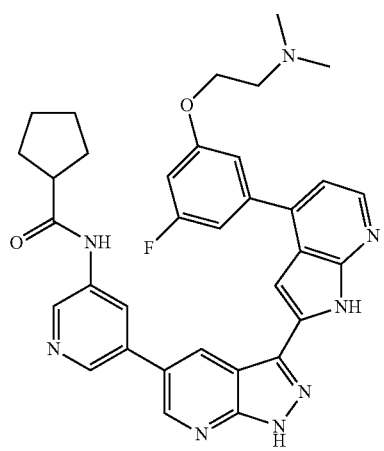 [SMILES: CN(C)CCOc1cc(F)cc(-c2ccnc3[nH]c(-c4n[nH]c5ncc(-c6cncc(NC(=O)C7CCCC7)c6)cc45)cc23)c1]
813
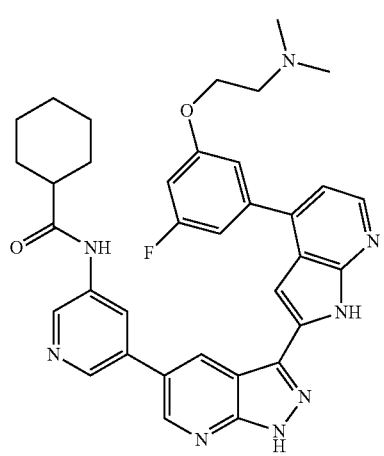 [SMILES: CN(C)CCOc1cc(F)cc(-c2ccnc3[nH]c(-c4n[nH]c5ncc(-c6cncc(NC(=O)C7CCCCC7)c6)cc45)cc23)c1]
814
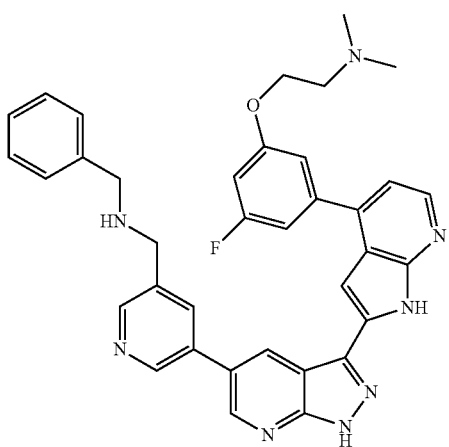 [SMILES: CN(C)CCOc1cc(F)cc(-c2ccnc3[nH]c(-c4n[nH]c5ncc(-c6cncc(CNCc7ccccc7)c6)cc45)cc23)c1]
815
TABLE 1-continued
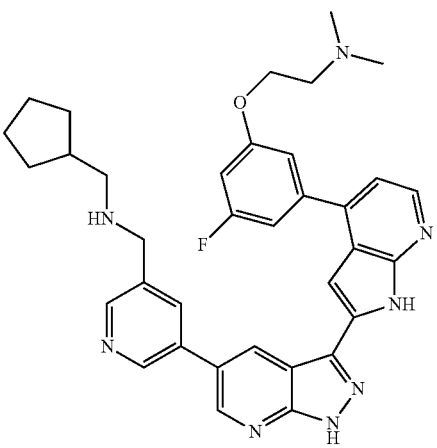 [SMILES: CN(C)CCOc1cc(F)cc(-c2ccnc3[nH]c(-c4n[nH]c5ncc(-c6cncc(CNCC7CCCC7)c6)cc45)cc23)c1]
816
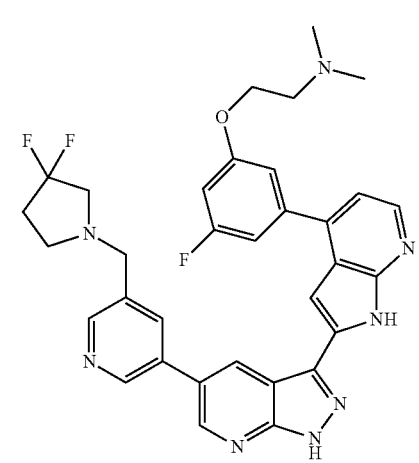 [SMILES: CN(C)CCOc1cc(F)cc(-c2ccnc3[nH]c(-c4n[nH]c5ncc(-c6cncc(CN7CCC(F)(F)C7)c6)cc45)cc23)c1]
817
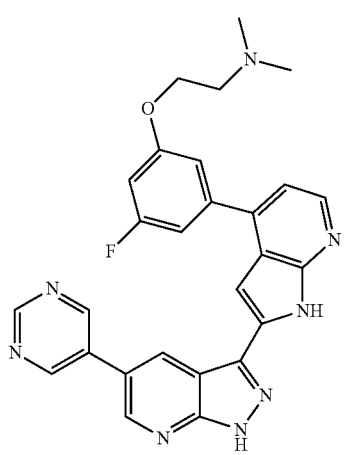 [SMILES: CN(C)CCOc1cc(F)cc(-c2ccnc3[nH]c(-c4n[nH]c5ncc(-c6cncnc6)cc45)cc23)c1]
818

TABLE 1-continued
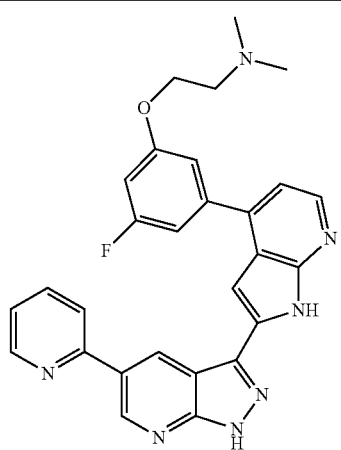
819
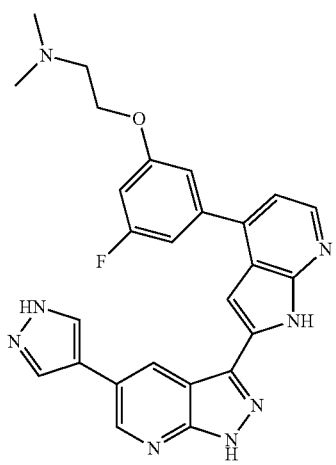
822
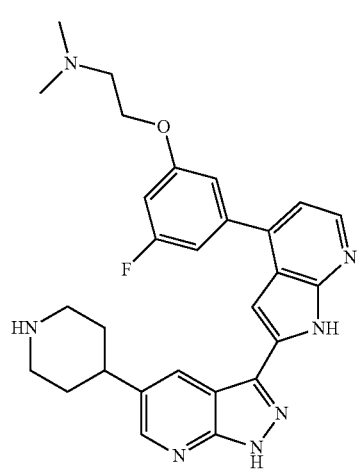 [SMILES: CN(C)CCOc1cc(F)cc(-c2ccnc3[nH]c(-c4n[nH]c5ncc(C6CCNCC6)cc45)cc23)c1]
820
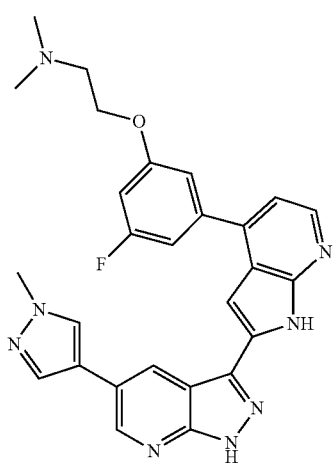
823
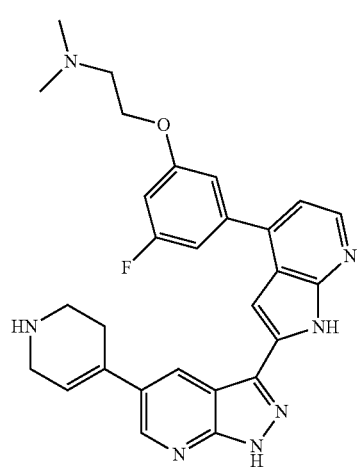 [SMILES: CN(C)CCOc1cc(F)cc(-c2ccnc3[nH]c(-c4n[nH]c5ncc(C6=CCNCC6)cc45)cc23)c1]
821
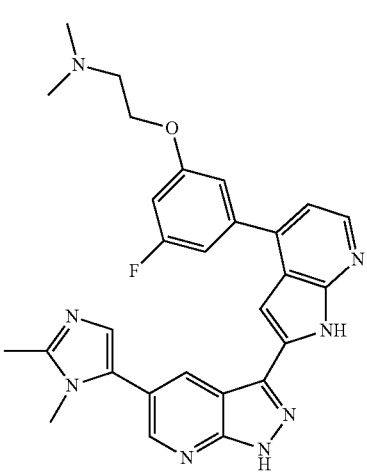 [SMILES: Cc1ncc(-c2cnc3[nH]nc(-c4cc5c(-c6cc(F)cc(OCCN(C)C)c6)ccnc5[nH]4)c3c2)n1C]
824

TABLE 1-continued
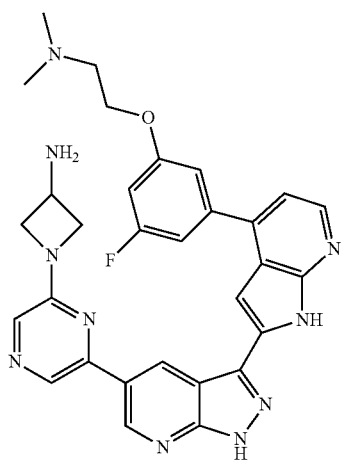 [SMILES: CN(C)CCOc1cc(F)cc(-c2ccnc3[nH]c(-c4n[nH]c5ncc(-c6cncc(N7CC(N)C7)n6)cc45)cc23)c1]
825
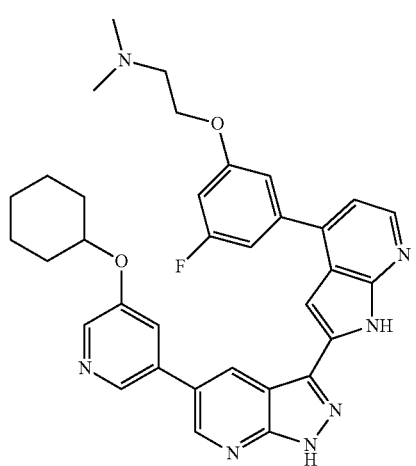 [SMILES: CN(C)CCOc1cc(F)cc(-c2ccnc3[nH]c(-c4n[nH]c5ncc(-c6cncc(OC7CCCCC7)c6)cc45)cc23)c1]
826
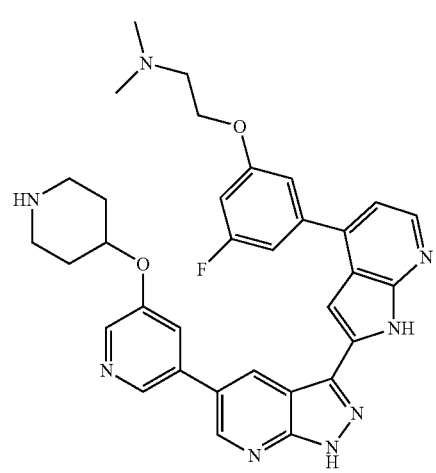 [SMILES: CN(C)CCOc1cc(F)cc(-c2ccnc3[nH]c(-c4n[nH]c5ncc(-c6cncc(OC7CCNCC7)c6)cc45)cc23)c1]
827
TABLE 1-continued
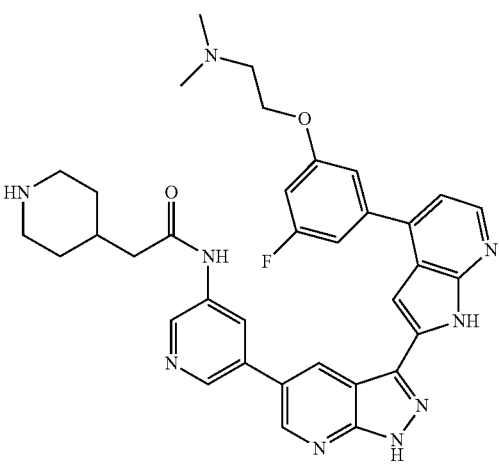 [SMILES: CN(C)CCOc1cc(F)cc(-c2ccnc3[nH]c(-c4n[nH]c5ncc(-c6cncc(NC(=O)CC7CCNCC7)c6)cc45)cc23)c1]
828
829
830

TABLE 1-continued
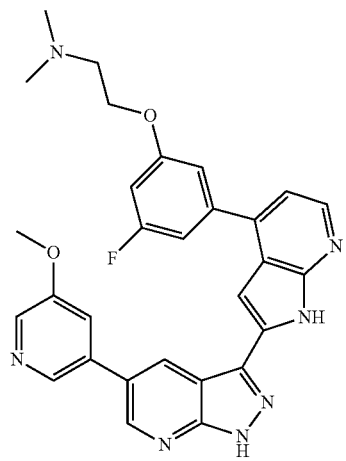 [SMILES: COc1cncc(-c2cnc3[nH]nc(-c4cc5c(-c6cc(F)cc(OCCN(C)C)c6)ccnc5[nH]4)c3c2)c1]
831
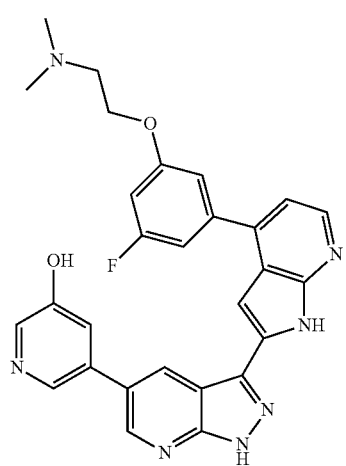 [SMILES: CN(C)CCOc1cc(F)cc(-c2ccnc3[nH]c(-c4n[nH]c5ncc(-c6cncc(O)c6)cc45)cc23)c1]
832
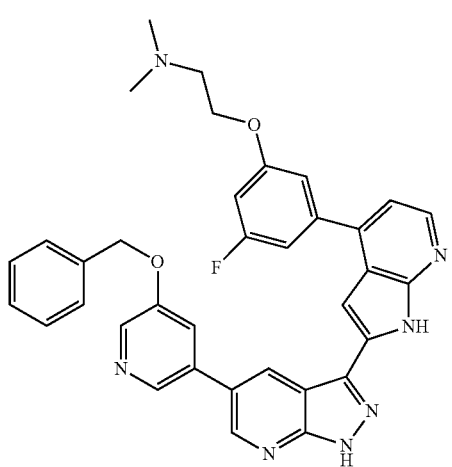 [SMILES: CN(C)CCOc1cc(F)cc(-c2ccnc3[nH]c(-c4n[nH]c5ncc(-c6cncc(OCc7ccccc7)c6)cc45)cc23)c1]
833
TABLE 1-continued
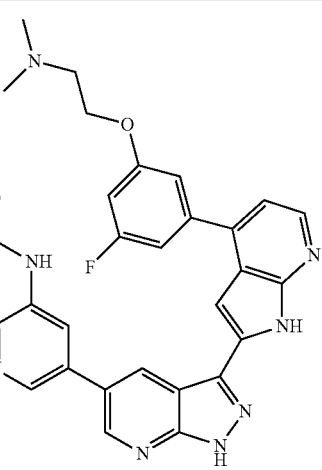
834
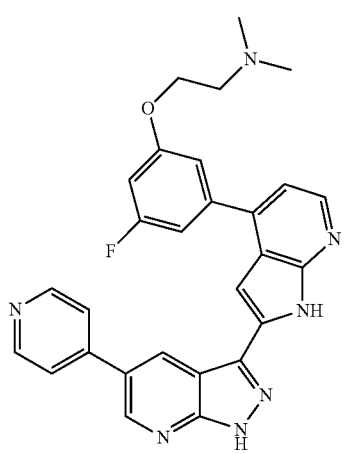 [SMILES: CN(C)CCOc1cc(F)cc(-c2ccnc3[nH]c(-c4n[nH]c5ncc(-c6ccncc6)cc45)cc23)c1]
835
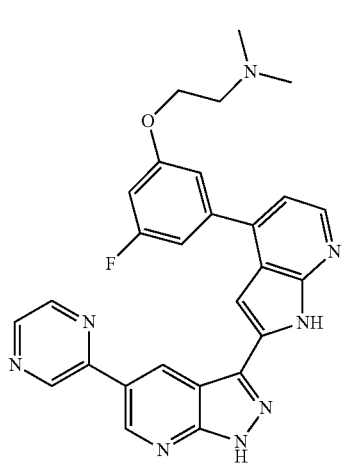 [SMILES: CN(C)CCOc1cc(F)cc(-c2ccnc3[nH]c(-c4n[nH]c5ncc(-c6cnccn6)cc45)cc23)c1]
836

TABLE 1-continued
837 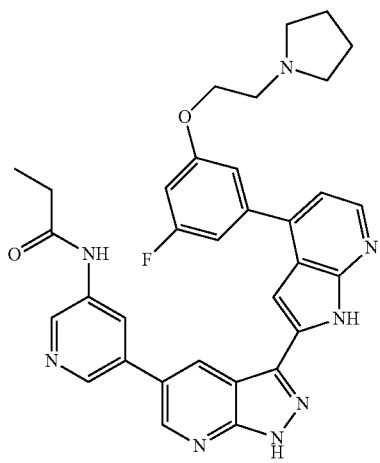 [SMILES: CCC(=O)Nc1cncc(-c2cnc3[nH]nc(-c4cc5c(-c6cc(F)cc(OCCN7CCCC7)c6)ccnc5[nH]4)c3c2)c1]
838 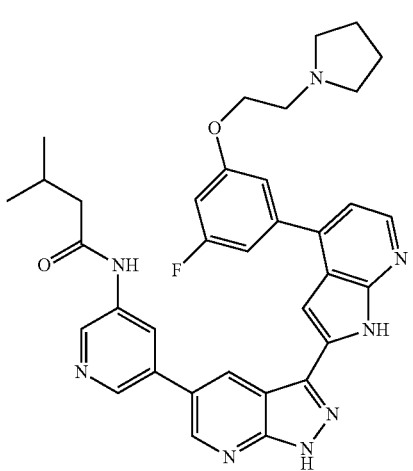 [SMILES: CC(C)CC(=O)Nc1cncc(-c2cnc3[nH]nc(-c4cc5c(-c6cc(F)cc(OCCN7CCCC7)c6)ccnc5[nH]4)c3c2)c1]
839 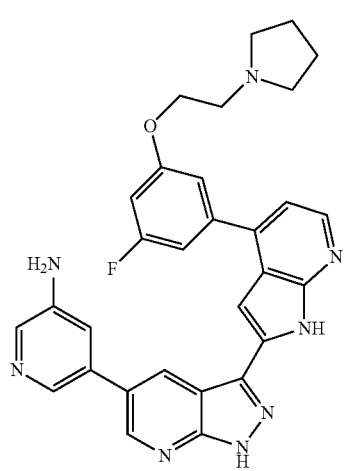 [SMILES: Nc1cncc(-c2cnc3[nH]nc(-c4cc5c(-c6cc(F)cc(OCCN7CCCC7)c6)ccnc5[nH]4)c3c2)c1]
TABLE 1-continued
840 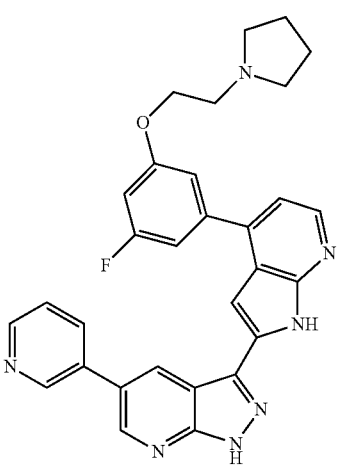
841 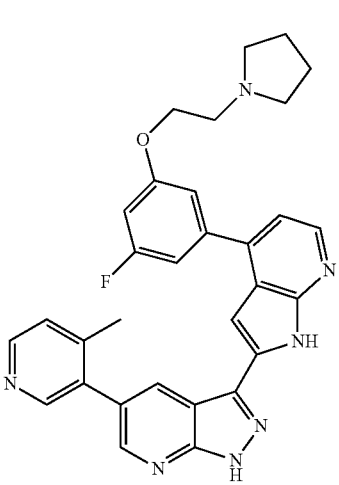 [SMILES: Cc1ccncc1-c1cnc2[nH]nc(-c3cc4c(-c5cc(F)cc(OCCN6CCCC6)c5)ccnc4[nH]3)c2c1]
842 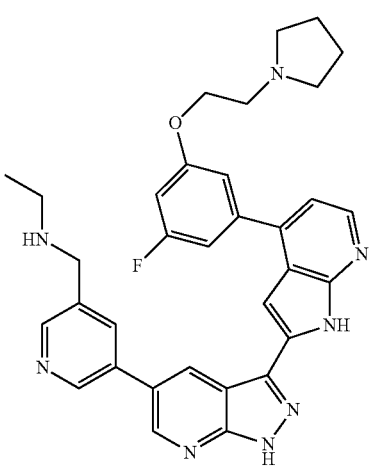 [SMILES: CCNCc1cncc(-c2cnc3[nH]nc(-c4cc5c(-c6cc(F)cc(OCCN7CCCC7)c6)ccnc5[nH]4)c3c2)c1]

TABLE 1-continued
| 843 | 846 |
|---|---|
| 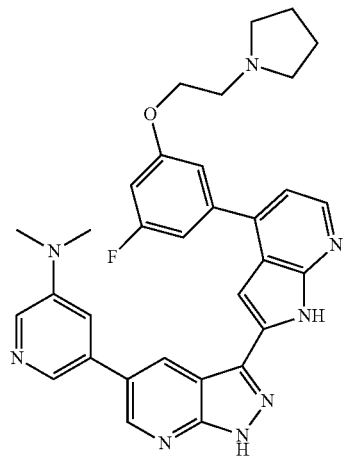 [SMILES: CN(C)c1cncc(-c2cnc3[nH]nc(-c4cc5c(-c6cc(F)cc(OCCN7CCCC7)c6)ccnc5[nH]4)c3c2)c1] | 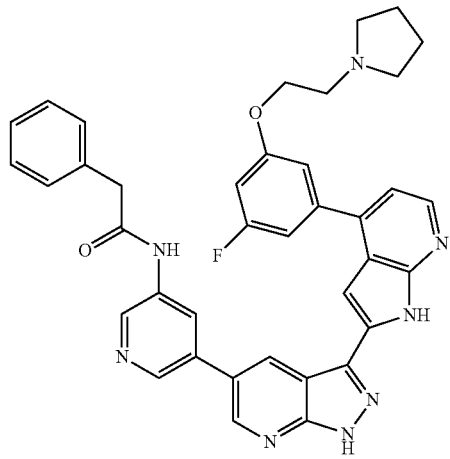 |
| 844 | 847 |
| 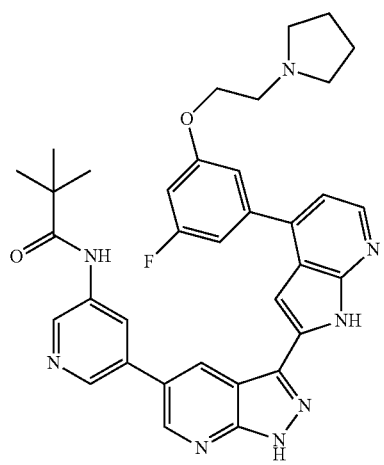 [SMILES: CC(C)(C)C(=O)Nc1cncc(-c2cnc3[nH]nc(-c4cc5c(-c6cc(F)cc(OCCN7CCCC7)c6)ccnc5[nH]4)c3c2)c1] | 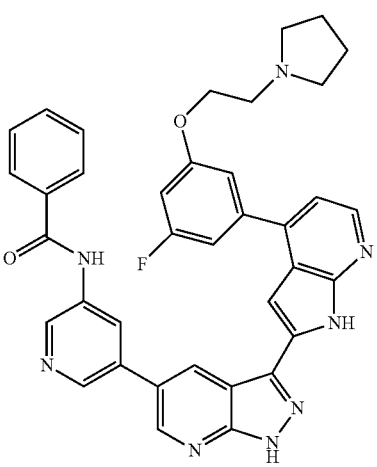 |
| 845 | 848 |
| 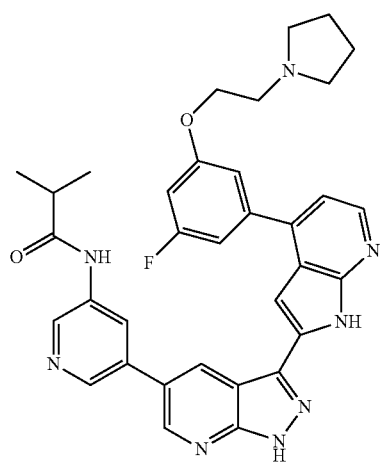 [SMILES: CC(C)C(=O)Nc1cncc(-c2cnc3[nH]nc(-c4cc5c(-c6cc(F)cc(OCCN7CCCC7)c6)ccnc5[nH]4)c3c2)c1] | 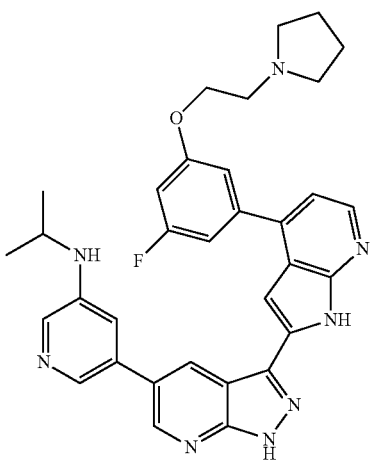 [SMILES: CC(C)Nc1cncc(-c2cnc3[nH]nc(-c4cc5c(-c6cc(F)cc(OCCN7CCCC7)c6)ccnc5[nH]4)c3c2)c1] |

TABLE 1-continued
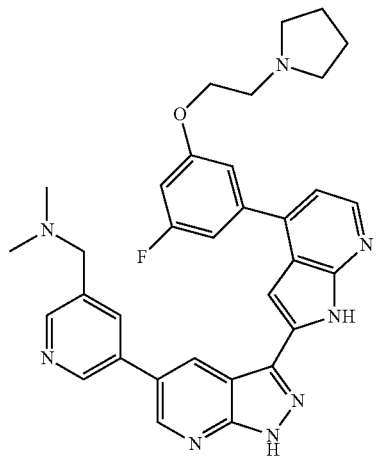 [SMILES: CN(C)Cc1cncc(-c2cnc3[nH]nc(-c4cc5c(-c6cc(F)cc(OCCN7CCCC7)c6)ccnc5[nH]4)c3c2)c1]
849
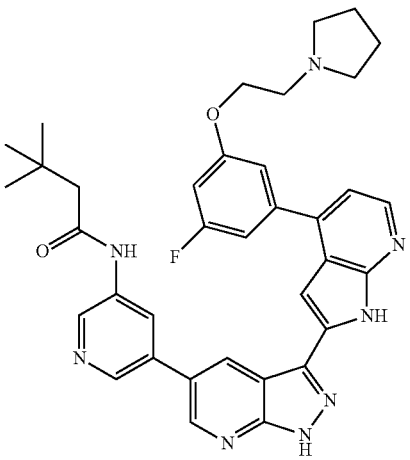
852
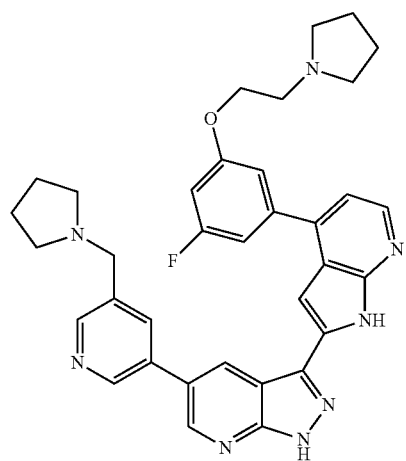 [SMILES: Fc1cc(OCCN2CCCC2)cc(-c2ccnc3[nH]c(-c4n[nH]c5ncc(-c6cncc(CN7CCCC7)c6)cc45)cc23)c1]
850
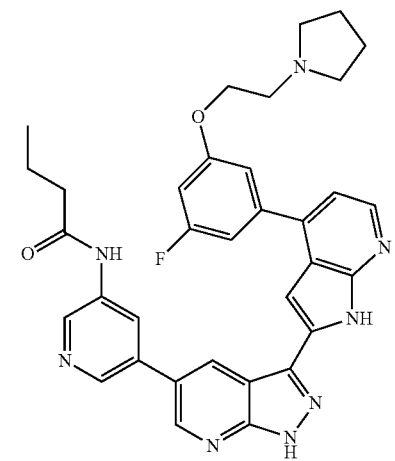
853
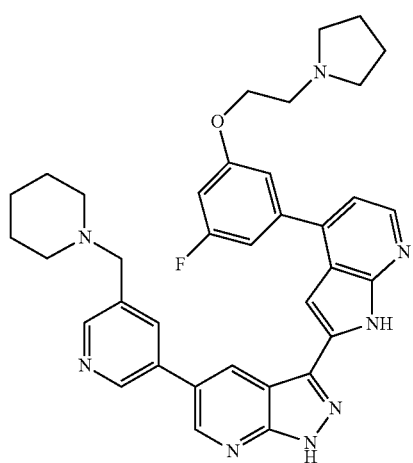 [SMILES: Fc1cc(OCCN2CCCC2)cc(-c2ccnc3[nH]c(-c4n[nH]c5ncc(-c6cncc(CN7CCCCC7)c6)cc45)cc23)c1]
851
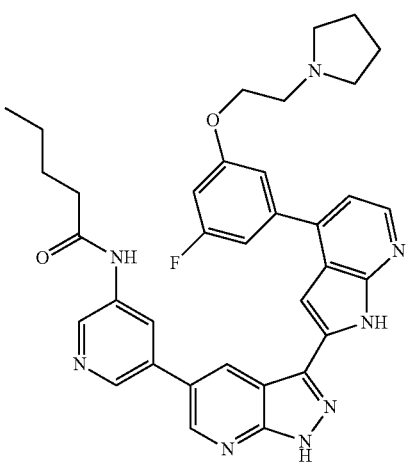 [SMILES: CCCCC(=O)Nc1cncc(-c2cnc3[nH]nc(-c4cc5c(-c6cc(F)cc(OCCN7CCCC7)c6)ccnc5[nH]4)c3c2)c1]
854

TABLE 1-continued
855
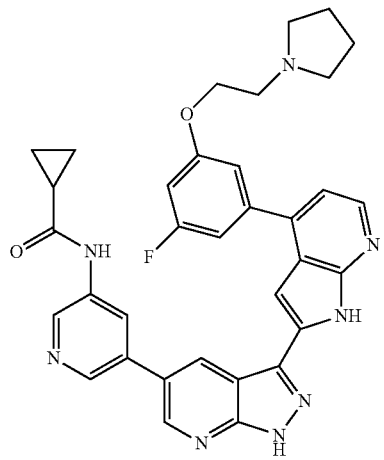 [SMILES: O=C(Nc1cncc(-c2cnc3[nH]nc(-c4cc5c(-c6cc(F)cc(OCCN7CCCC7)c6)ccnc5[nH]4)c3c2)c1)C1CC1]
856
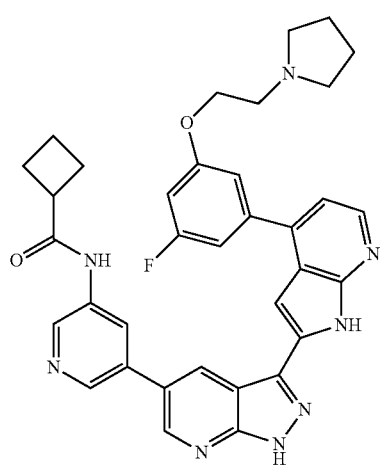 [SMILES: O=C(Nc1cncc(-c2cnc3[nH]nc(-c4cc5c(-c6cc(F)cc(OCCN7CCCC7)c6)ccnc5[nH]4)c3c2)c1)C1CCC1]
857
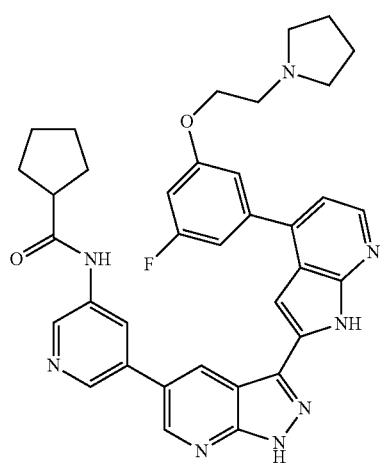 [SMILES: O=C(Nc1cncc(-c2cnc3[nH]nc(-c4cc5c(-c6cc(F)cc(OCCN7CCCC7)c6)ccnc5[nH]4)c3c2)c1)C1CCCC1]
TABLE 1-continued
858
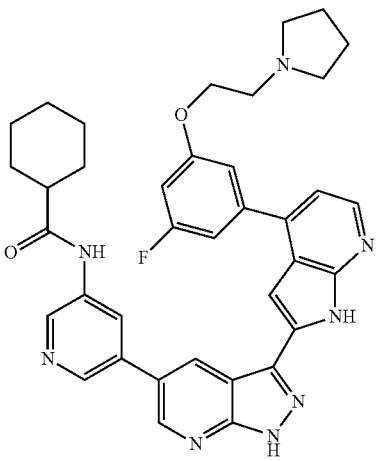 [SMILES: O=C(Nc1cncc(-c2cnc3[nH]nc(-c4cc5c(-c6cc(F)cc(OCCN7CCCC7)c6)ccnc5[nH]4)c3c2)c1)C1CCCCC1]
859
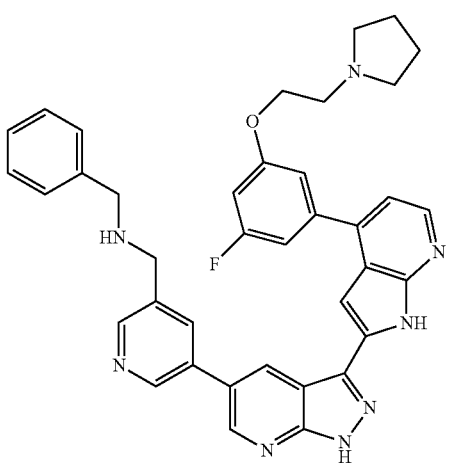 [SMILES: Fc1cc(OCCN2CCCC2)cc(-c2ccnc3[nH]c(-c4n[nH]c5ncc(-c6cncc(CNCc7ccccc7)c6)cc45)cc23)c1]
860
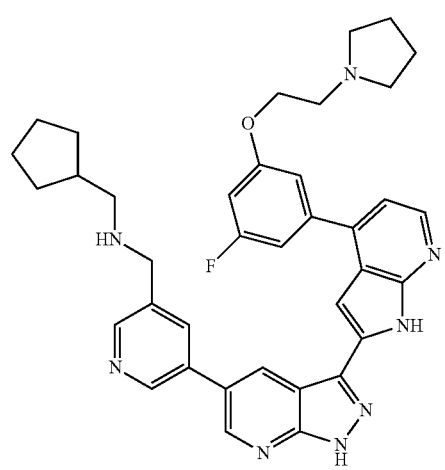 [SMILES: Fc1cc(OCCN2CCCC2)cc(-c2ccnc3[nH]c(-c4n[nH]c5ncc(-c6cncc(CNCC7CCCC7)c6)cc45)cc23)c1]

TABLE 1-continued
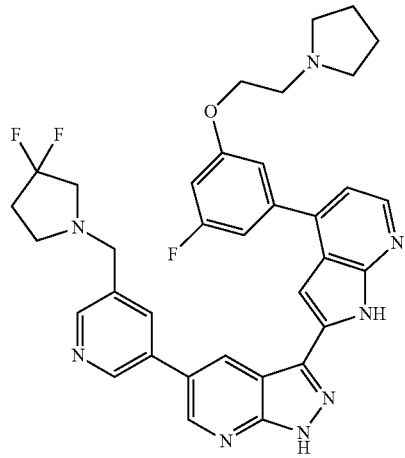 [SMILES: Fc1cc(OCCN2CCCC2)cc(-c2ccnc3[nH]c(-c4n[nH]c5ncc(-c6cncc(CN7CCC(F)(F)C7)c6)cc45)cc23)c1]
861
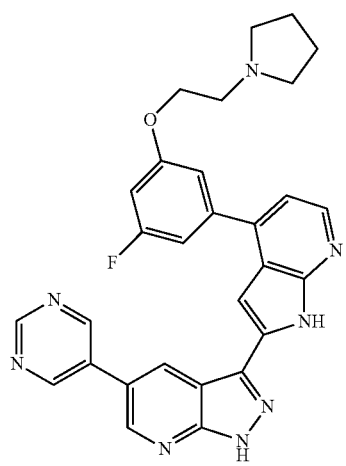 [SMILES: Fc1cc(OCCN2CCCC2)cc(-c2ccnc3[nH]c(-c4n[nH]c5ncc(-c6cncnc6)cc45)cc23)c1]
862
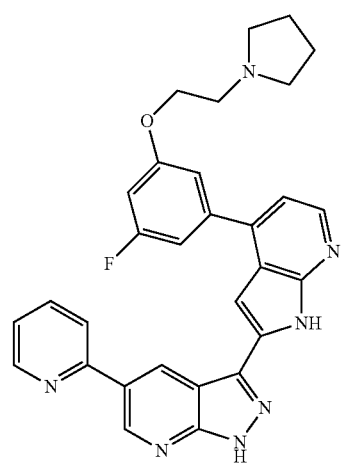 [SMILES: Fc1cc(OCCN2CCCC2)cc(-c2ccnc3[nH]c(-c4n[nH]c5ncc(-c6ccccn6)cc45)cc23)c1]
863
TABLE 1-continued
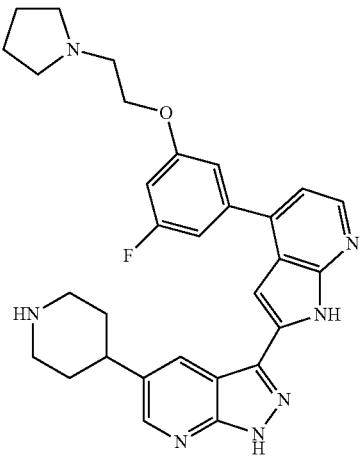 [SMILES: Fc1cc(OCCN2CCCC2)cc(-c2ccnc3[nH]c(-c4n[nH]c5ncc(C6CCNCC6)cc45)cc23)c1]
864
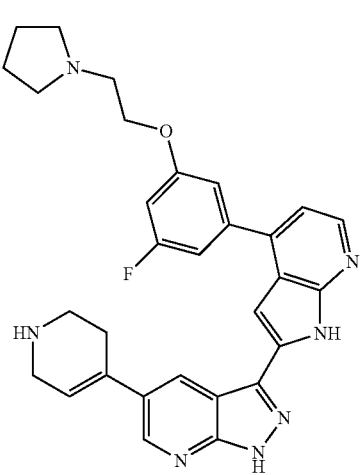
865
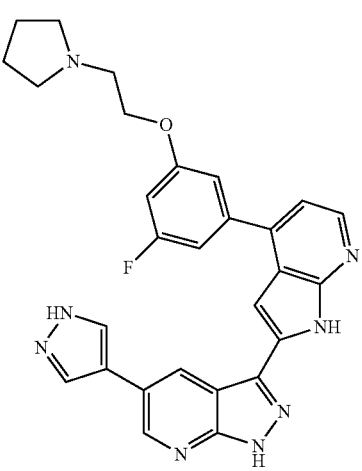 [SMILES: Fc1cc(OCCN2CCCC2)cc(-c2ccnc3[nH]c(-c4n[nH]c5ncc(-c6cn[nH]c6)cc45)cc23)c1]
866

TABLE 1-continued
867 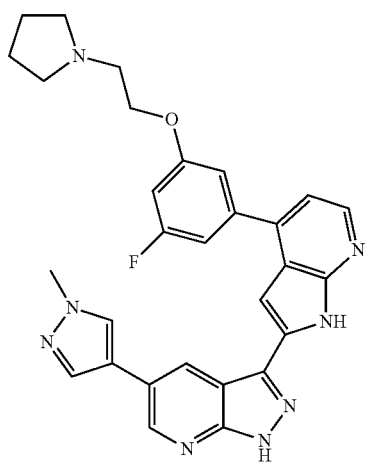 [SMILES: Cn1cc(-c2cnc3[nH]nc(-c4cc5c(-c6cc(F)cc(OCCN7CCCC7)c6)ccnc5[nH]4)c3c2)cn1]
868 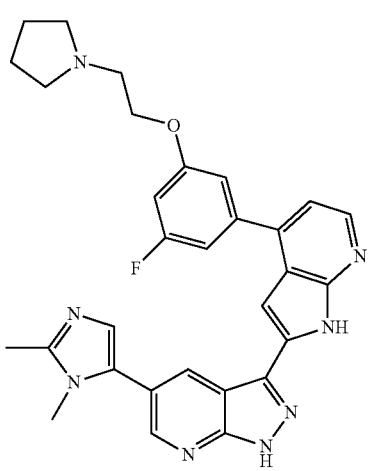 [SMILES: Cc1ncc(-c2cnc3[nH]nc(-c4cc5c(-c6cc(F)cc(OCCN7CCCC7)c6)ccnc5[nH]4)c3c2)n1C]
869 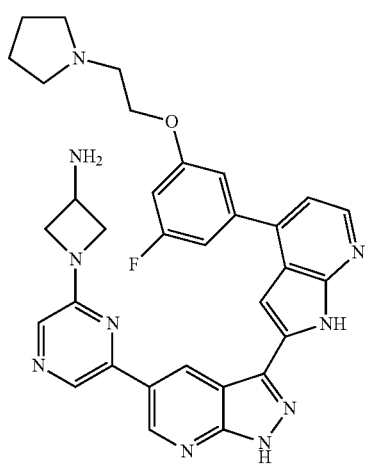 [SMILES: NC1CN(c2cncc(-c3cnc4[nH]nc(-c5cc6c(-c7cc(F)cc(OCCN8CCCC8)c7)ccnc6[nH]5)c4c3)n2)C1]
TABLE 1-continued
870 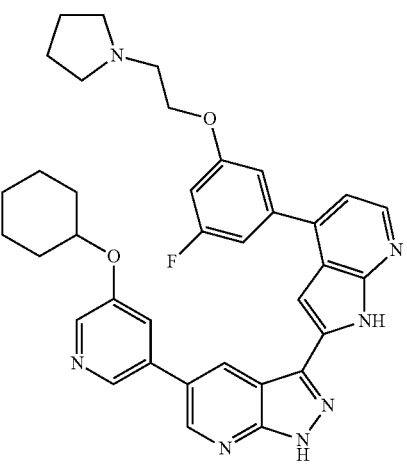 [SMILES: Fc1cc(OCCN2CCCC2)cc(-c2ccnc3[nH]c(-c4n[nH]c5ncc(-c6cncc(OC7CCCCC7)c6)cc45)cc23)c1]
871 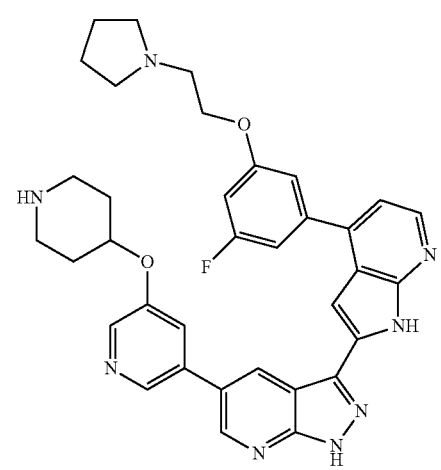 [SMILES: Fc1cc(OCCN2CCCC2)cc(-c2ccnc3[nH]c(-c4n[nH]c5ncc(-c6cncc(OC7CCNCC7)c6)cc45)cc23)c1]
872 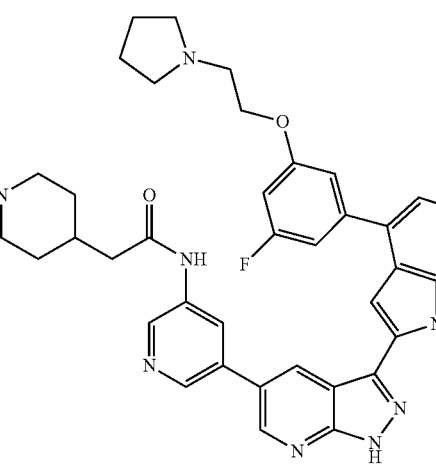

TABLE 1-continued
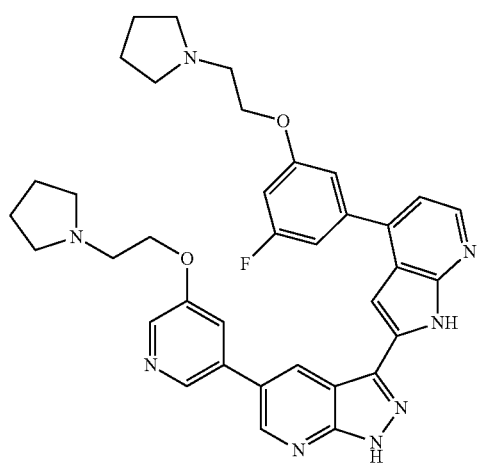 [SMILES: Fc1cc(OCCN2CCCC2)cc(-c2ccnc3[nH]c(-c4n[nH]c5ncc(-c6cncc(OCCN7CCCC7)c6)cc45)cc23)c1]
873
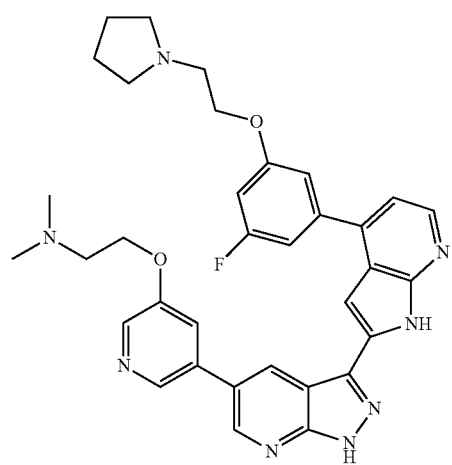 [SMILES: CN(C)CCOc1cncc(-c2cnc3[nH]nc(-c4cc5c(-c6cc(F)cc(OCCN7CCCC7)c6)ccnc5[nH]4)c3c2)c1]
874
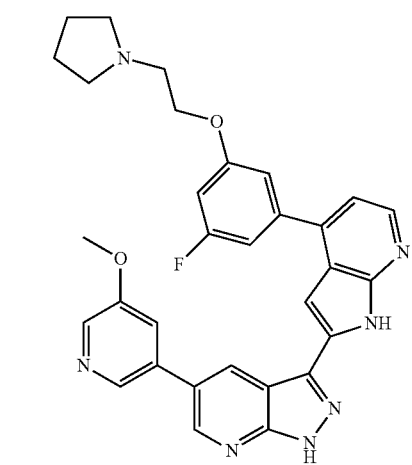 [SMILES: COc1cncc(-c2cnc3[nH]nc(-c4cc5c(-c6cc(F)cc(OCCN7CCCC7)c6)ccnc5[nH]4)c3c2)c1]
875
TABLE 1-continued
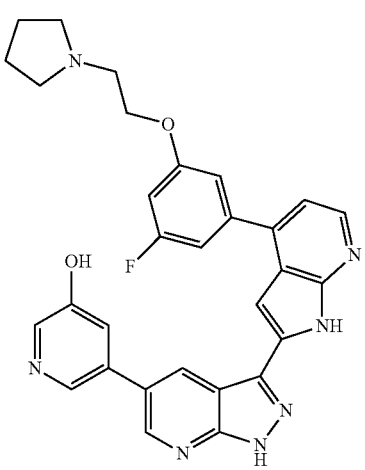
876
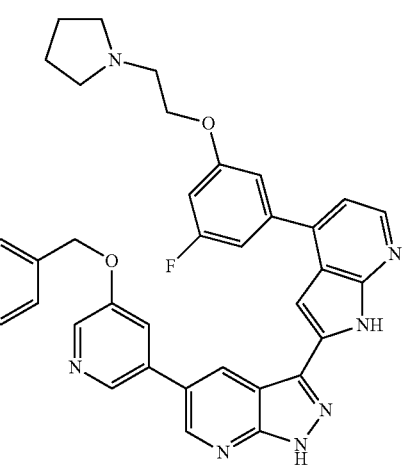
877
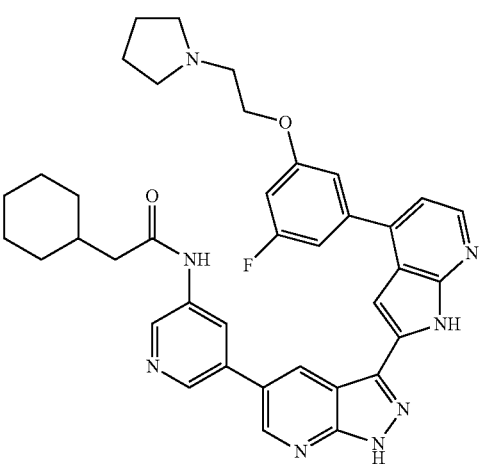 [SMILES: O=C(CC1CCCCC1)Nc1cncc(-c2cnc3[nH]nc(-c4cc5c(-c6cc(F)cc(OCCN7CCCC7)c6)ccnc5[nH]4)c3c2)c1]
878

TABLE 1-continued
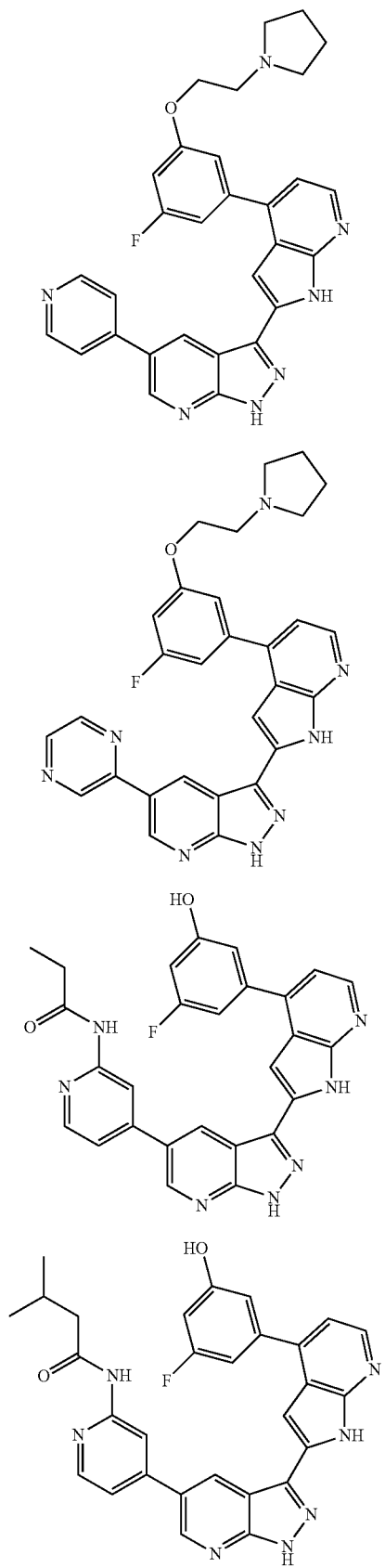
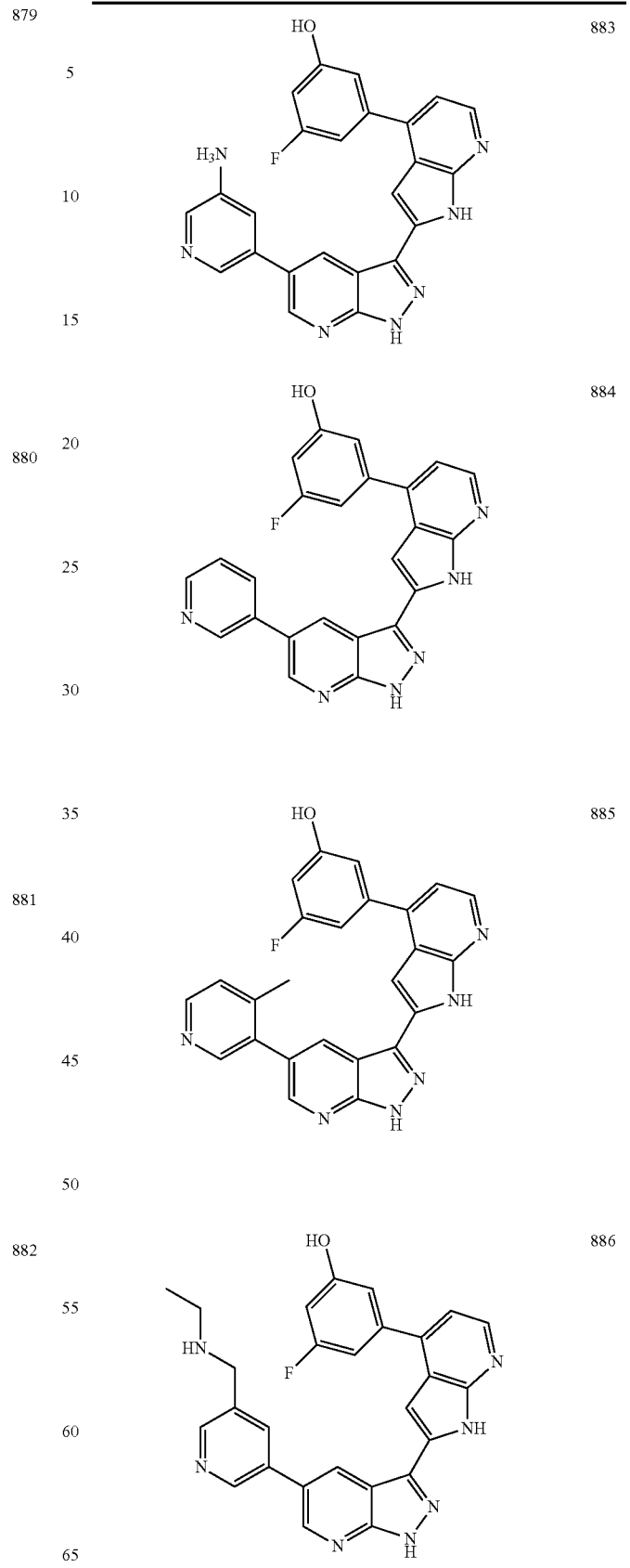

TABLE 1-continued
| | |
|---|---|
| 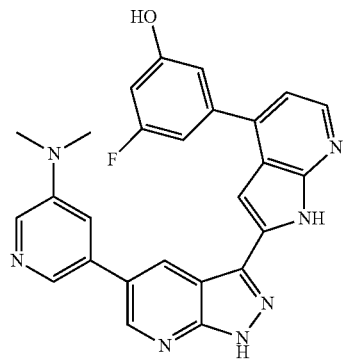 [SMILES: CN(C)c1cncc(-c2cnc3[nH]nc(-c4cc5c(-c6cc(O)cc(F)c6)ccnc5[nH]4)c3c2)c1] 887 | 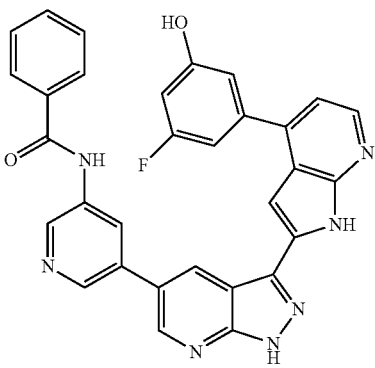 891 |
| 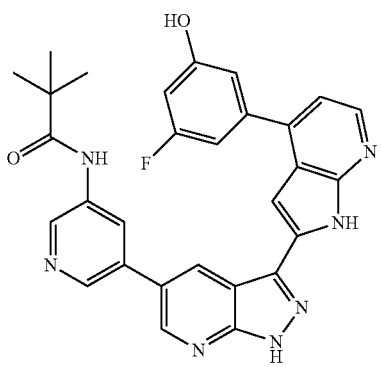 [SMILES: CC(C)(C)C(=O)Nc1cncc(-c2cnc3[nH]nc(-c4cc5c(-c6cc(O)cc(F)c6)ccnc5[nH]4)c3c2)c1] 888 | 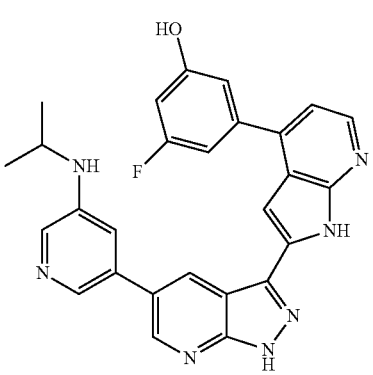 892 |
| 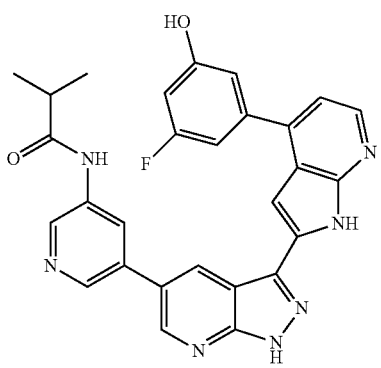 [SMILES: CC(C)C(=O)Nc1cncc(-c2cnc3[nH]nc(-c4cc5c(-c6cc(O)cc(F)c6)ccnc5[nH]4)c3c2)c1] 889 | 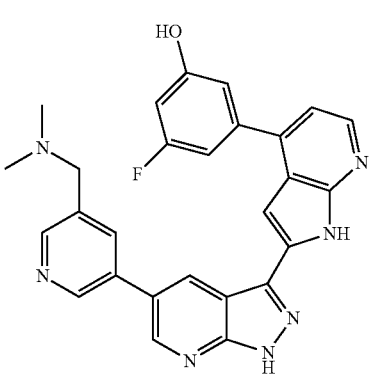 893 |
| 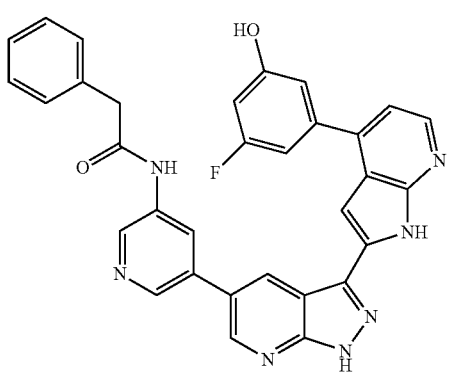 [SMILES: O=C(Cc1ccccc1)Nc1cncc(-c2cnc3[nH]nc(-c4cc5c(-c6cc(O)cc(F)c6)ccnc5[nH]4)c3c2)c1] 890 | 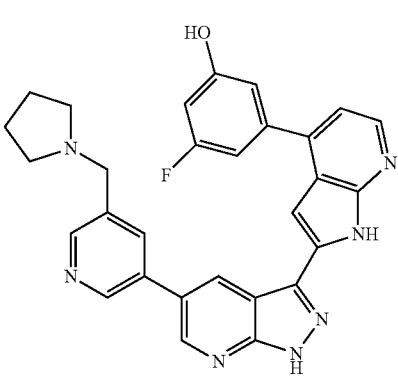 [SMILES: Oc1cc(F)cc(-c2ccnc3[nH]c(-c4n[nH]c5ncc(-c6cncc(CN7CCCC7)c6)cc45)cc23)c1] 894 |

TABLE 1-continued
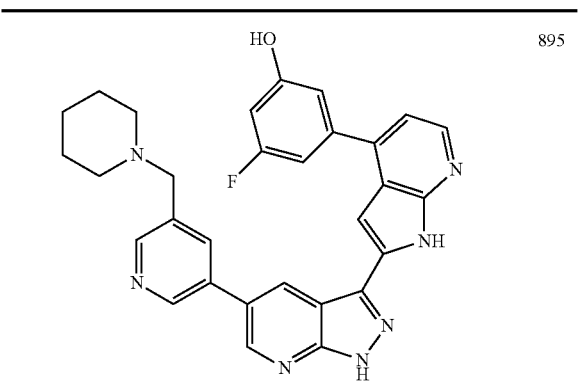 895
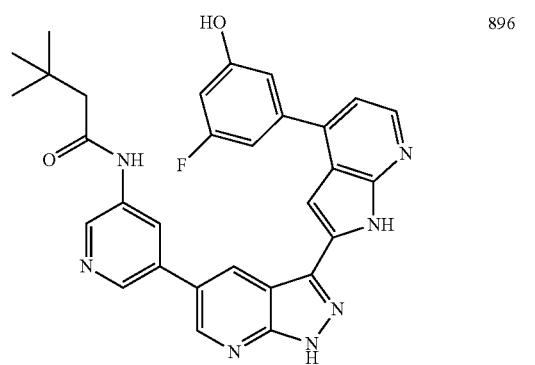 896
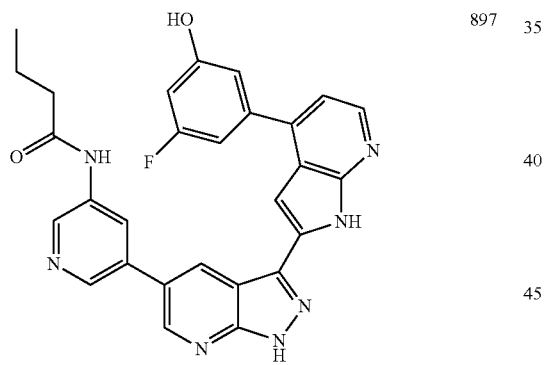 897
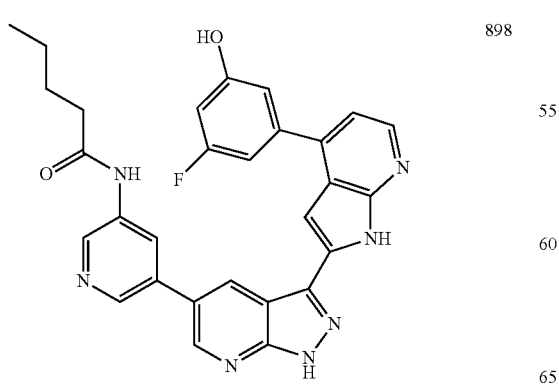 898
TABLE 1-continued
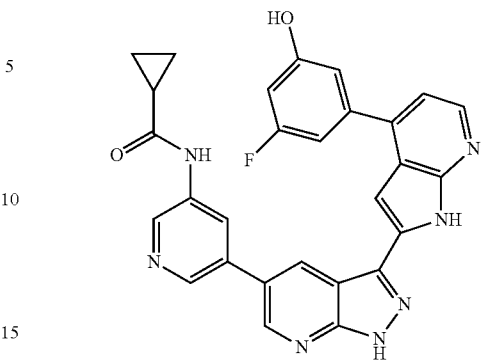 899
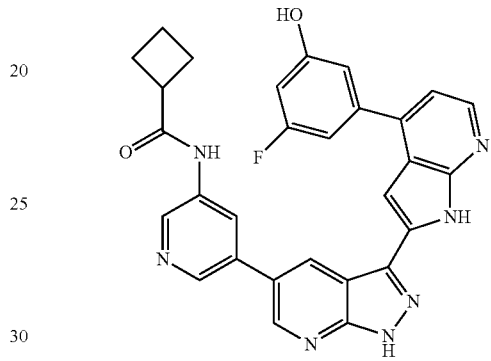 900
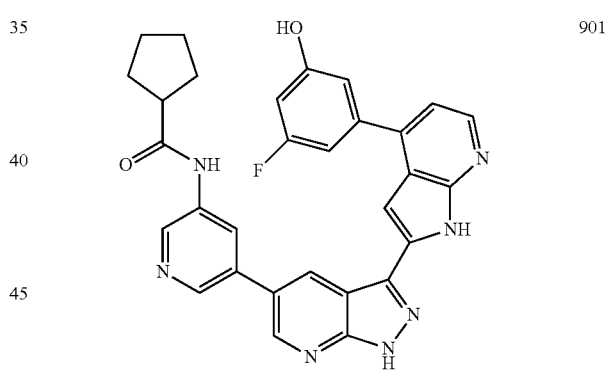 901
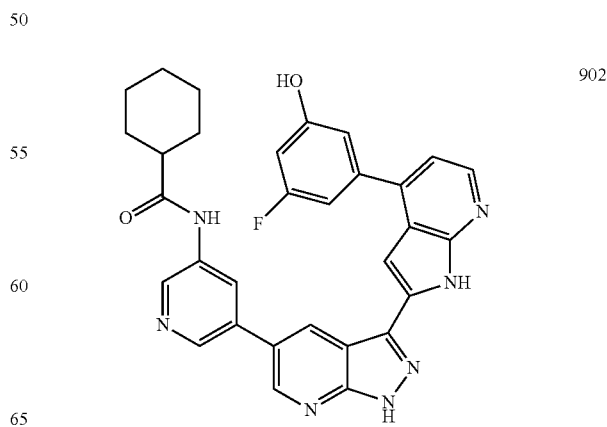 902

TABLE 1-continued
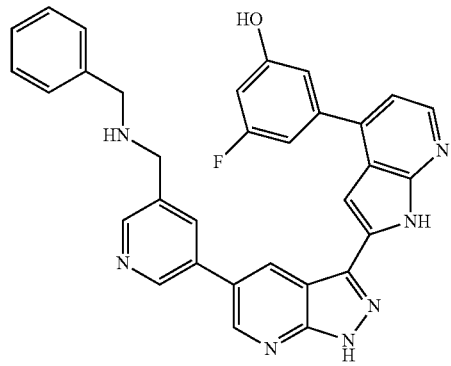 [SMILES: Oc1cc(F)cc(-c2ccnc3[nH]c(-c4n[nH]c5ncc(-c6cncc(CNCc7ccccc7)c6)cc45)cc23)c1] 903
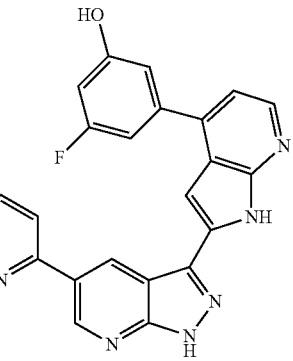 907
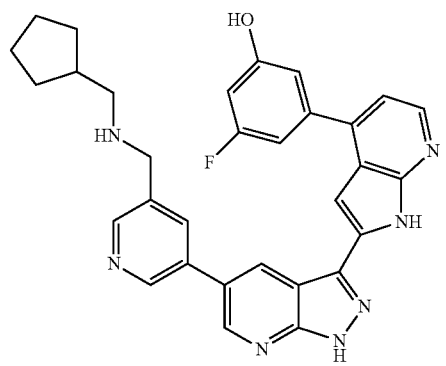 [SMILES: Oc1cc(F)cc(-c2ccnc3[nH]c(-c4n[nH]c5ncc(-c6cncc(CNCC7CCCC7)c6)cc45)cc23)c1] 904
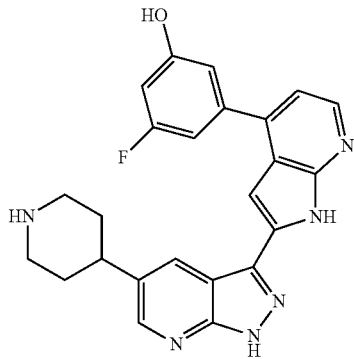 908
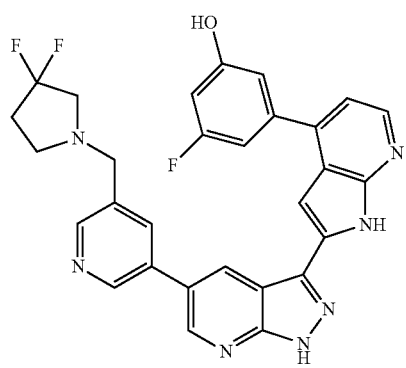 [SMILES: Oc1cc(F)cc(-c2ccnc3[nH]c(-c4n[nH]c5ncc(-c6cncc(CN7CCC(F)(F)C7)c6)cc45)cc23)c1] 905
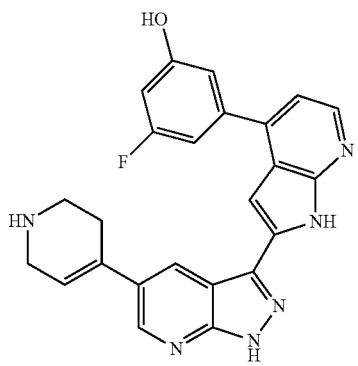 909
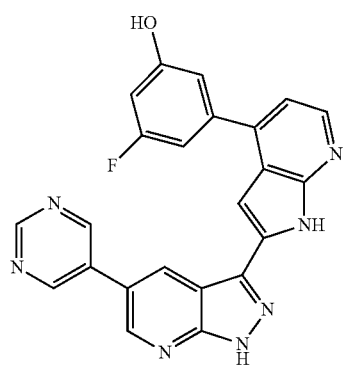 [SMILES: Oc1cc(F)cc(-c2ccnc3[nH]c(-c4n[nH]c5ncc(-c6cncnc6)cc45)cc23)c1] 906
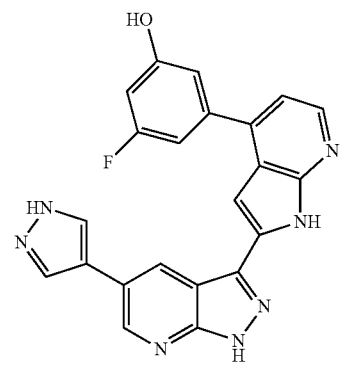 [SMILES: Oc1cc(F)cc(-c2ccnc3[nH]c(-c4n[nH]c5ncc(-c6cn[nH]c6)cc45)cc23)c1] 910

TABLE 1-continued
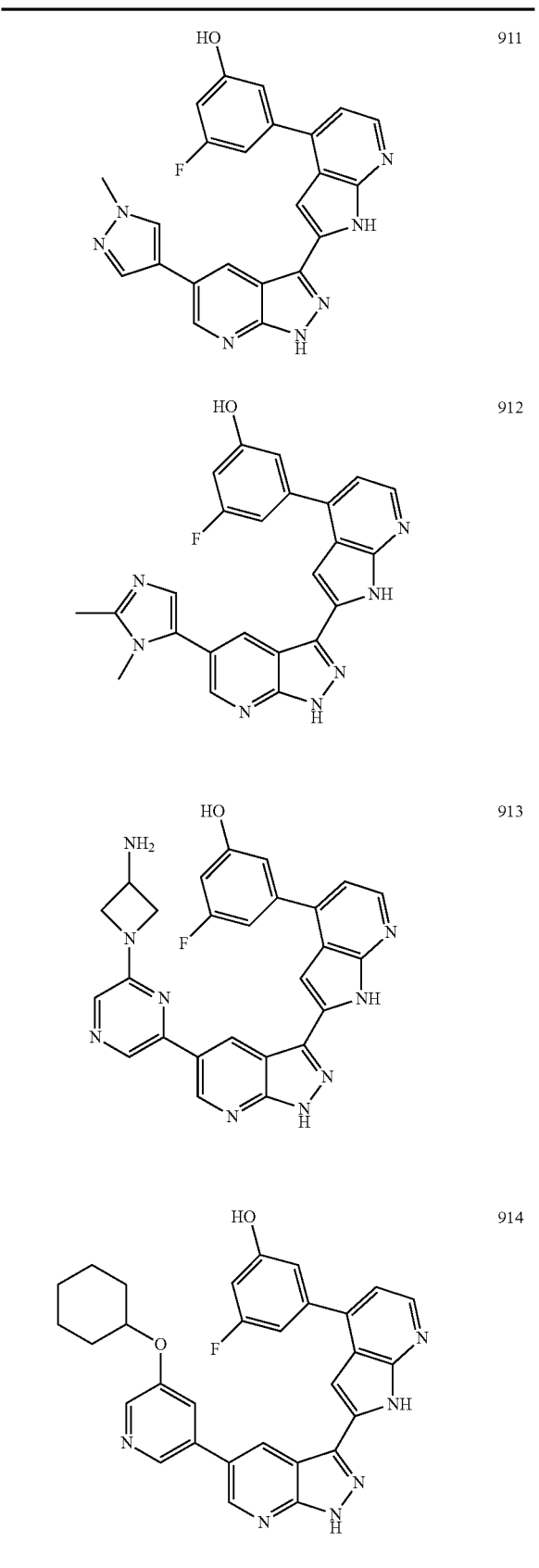
TABLE 1-continued
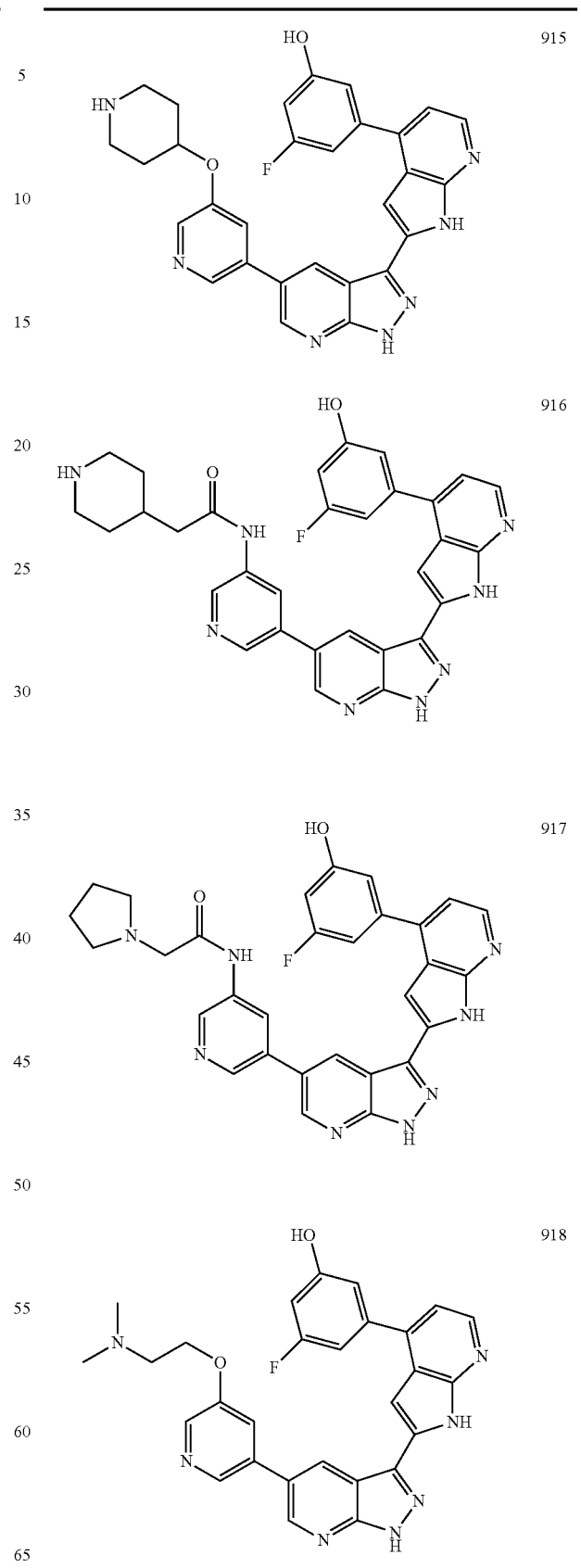

TABLE 1-continued
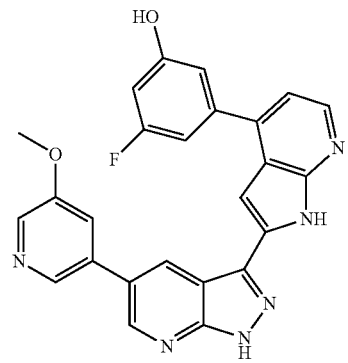 [SMILES: COc1cncc(-c2cnc3[nH]nc(-c4cc5c(-c6cc(O)cc(F)c6)ccnc5[nH]4)c3c2)c1] 919
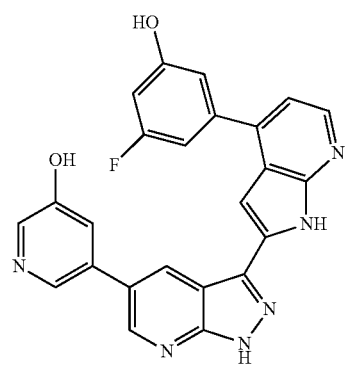 [SMILES: Oc1cncc(-c2cnc3[nH]nc(-c4cc5c(-c6cc(O)cc(F)c6)ccnc5[nH]4)c3c2)c1] 920
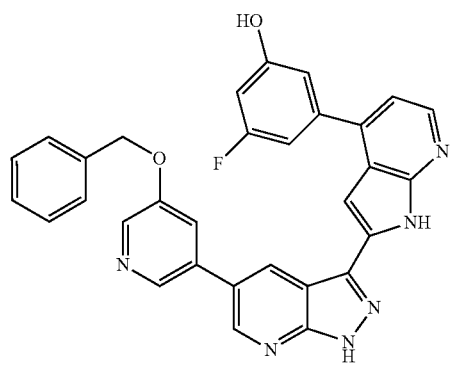 [SMILES: Oc1cc(F)cc(-c2ccnc3[nH]c(-c4n[nH]c5ncc(-c6cncc(OCc7ccccc7)c6)cc45)cc23)c1] 921
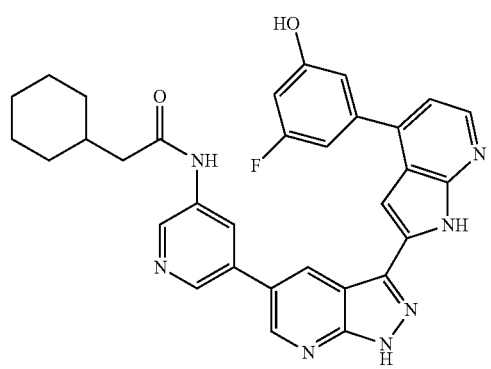 [SMILES: O=C(CC1CCCCC1)Nc1cncc(-c2cnc3[nH]nc(-c4cc5c(-c6cc(O)cc(F)c6)ccnc5[nH]4)c3c2)c1] 922
TABLE 1-continued
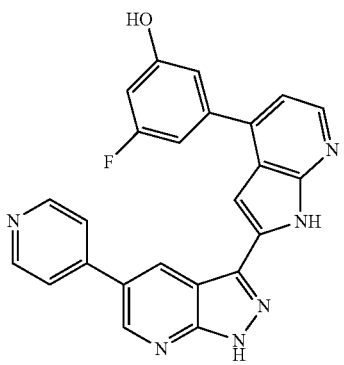 [SMILES: Oc1cc(F)cc(-c2ccnc3[nH]c(-c4n[nH]c5ncc(-c6ccncc6)cc45)cc23)c1] 923
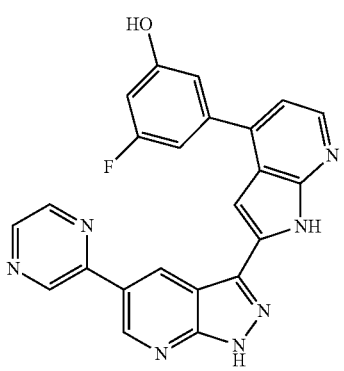 [SMILES: Oc1cc(F)cc(-c2ccnc3[nH]c(-c4n[nH]c5ncc(-c6cnccn6)cc45)cc23)c1] 924
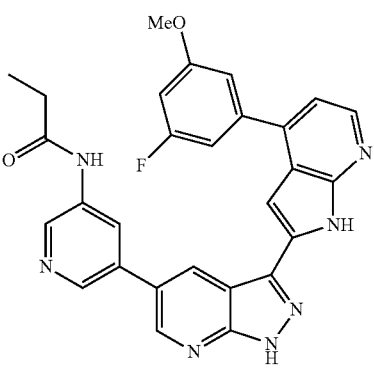 [SMILES: CCC(=O)Nc1cncc(-c2cnc3[nH]nc(-c4cc5c(-c6cc(F)cc(OC)c6)ccnc5[nH]4)c3c2)c1] 925
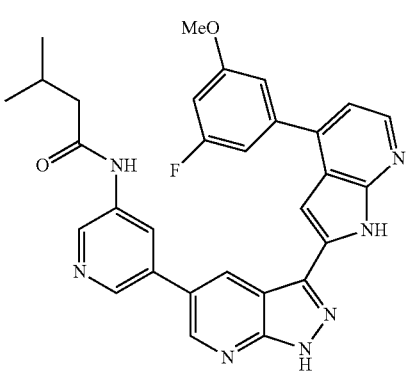 926

TABLE 1-continued
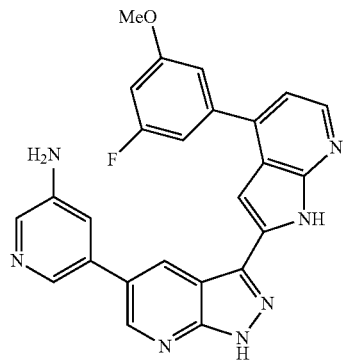 [SMILES: COc1cc(F)cc(-c2ccnc3[nH]c(-c4n[nH]c5ncc(-c6cncc(N)c6)cc45)cc23)c1] 927
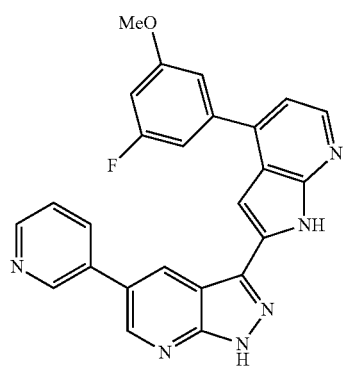 [SMILES: COc1cc(F)cc(-c2ccnc3[nH]c(-c4n[nH]c5ncc(-c6cccnc6)cc45)cc23)c1] 928
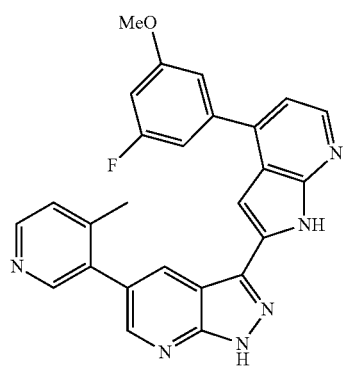 [SMILES: COc1cc(F)cc(-c2ccnc3[nH]c(-c4n[nH]c5ncc(-c6cnccc6C)cc45)cc23)c1] 929
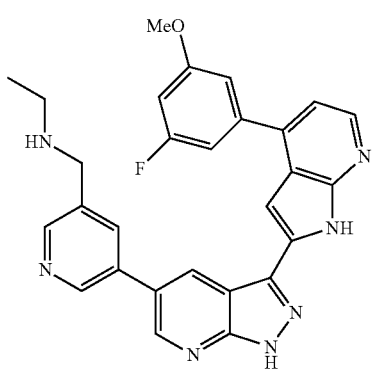 [SMILES: CCNCc1cncc(-c2cnc3[nH]nc(-c4cc5c(-c6cc(F)cc(OC)c6)ccnc5[nH]4)c3c2)c1] 930
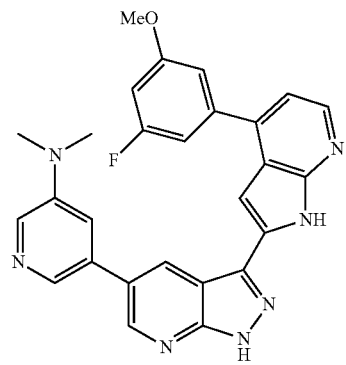 [SMILES: COc1cc(F)cc(-c2ccnc3[nH]c(-c4n[nH]c5ncc(-c6cncc(N(C)C)c6)cc45)cc23)c1] 931
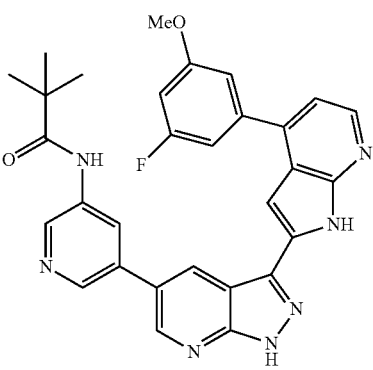 [SMILES: COc1cc(F)cc(-c2ccnc3[nH]c(-c4n[nH]c5ncc(-c6cncc(NC(=O)C(C)(C)C)c6)cc45)cc23)c1] 932
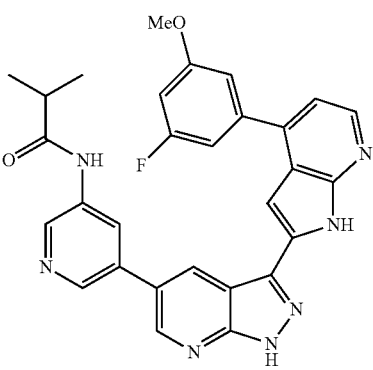 [SMILES: COc1cc(F)cc(-c2ccnc3[nH]c(-c4n[nH]c5ncc(-c6cncc(NC(=O)C(C)C)c6)cc45)cc23)c1] 933
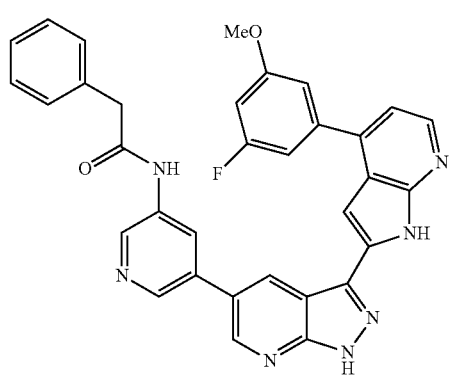 [SMILES: COc1cc(F)cc(-c2ccnc3[nH]c(-c4n[nH]c5ncc(-c6cncc(NC(=O)Cc7ccccc7)c6)cc45)cc23)c1] 934

TABLE 1-continued
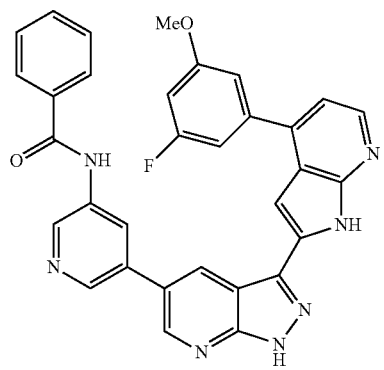 [SMILES: COc1cc(F)cc(-c2ccnc3[nH]c(-c4n[nH]c5ncc(-c6cncc(NC(=O)c7ccccc7)c6)cc45)cc23)c1]
935
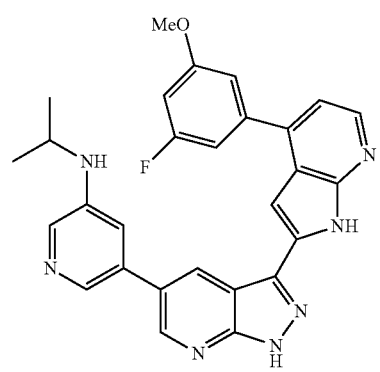 [SMILES: COc1cc(F)cc(-c2ccnc3[nH]c(-c4n[nH]c5ncc(-c6cncc(NC(C)C)c6)cc45)cc23)c1]
936
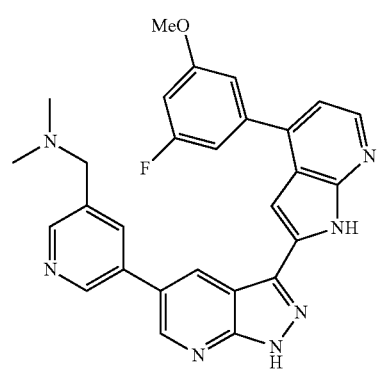 [SMILES: COc1cc(F)cc(-c2ccnc3[nH]c(-c4n[nH]c5ncc(-c6cncc(CN(C)C)c6)cc45)cc23)c1]
937
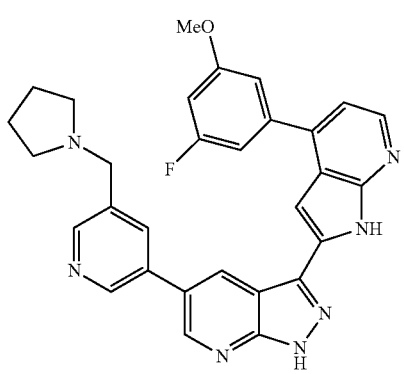 [SMILES: COc1cc(F)cc(-c2ccnc3[nH]c(-c4n[nH]c5ncc(-c6cncc(CN7CCCC7)c6)cc45)cc23)c1]
938
TABLE 1-continued
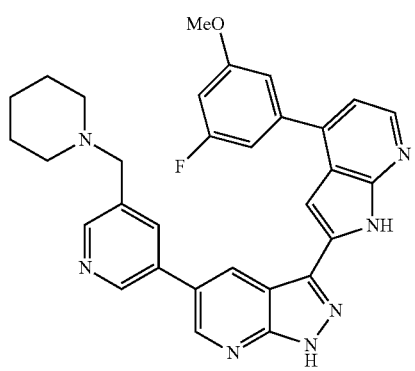 [SMILES: COc1cc(F)cc(-c2ccnc3[nH]c(-c4n[nH]c5ncc(-c6cncc(CN7CCCCC7)c6)cc45)cc23)c1]
939
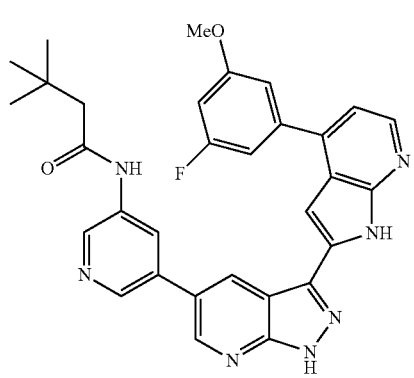 [SMILES: COc1cc(F)cc(-c2ccnc3[nH]c(-c4n[nH]c5ncc(-c6cncc(NC(=O)CC(C)(C)C)c6)cc45)cc23)c1]
940
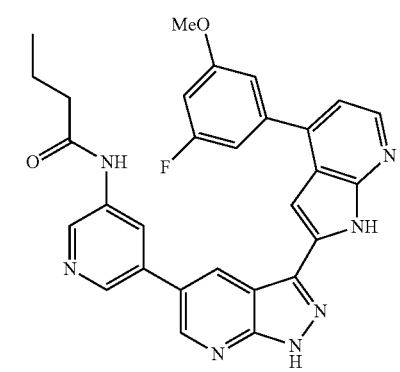 [SMILES: CCCC(=O)Nc1cncc(-c2cnc3[nH]nc(-c4cc5c(-c6cc(F)cc(OC)c6)ccnc5[nH]4)c3c2)c1]
941
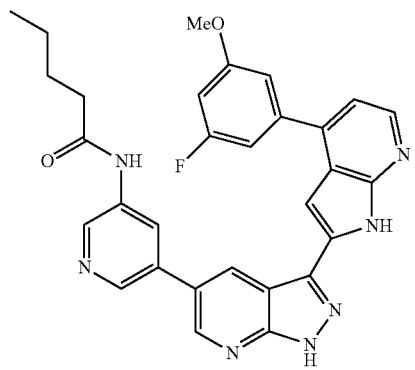 [SMILES: CCCCC(=O)Nc1cncc(-c2cnc3[nH]nc(-c4cc5c(-c6cc(F)cc(OC)c6)ccnc5[nH]4)c3c2)c1]
942

TABLE 1-continued
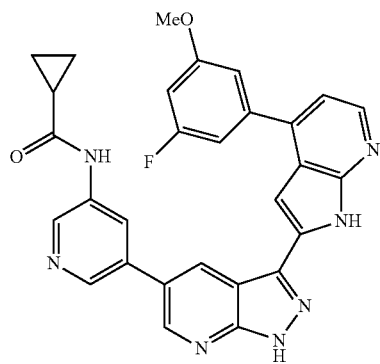 [SMILES: COc1cc(F)cc(-c2ccnc3[nH]c(-c4n[nH]c5ncc(-c6cncc(NC(=O)C7CC7)c6)cc45)cc23)c1] 943
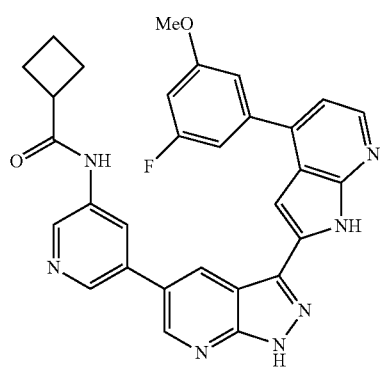 [SMILES: COc1cc(F)cc(-c2ccnc3[nH]c(-c4n[nH]c5ncc(-c6cncc(NC(=O)C7CCC7)c6)cc45)cc23)c1] 944
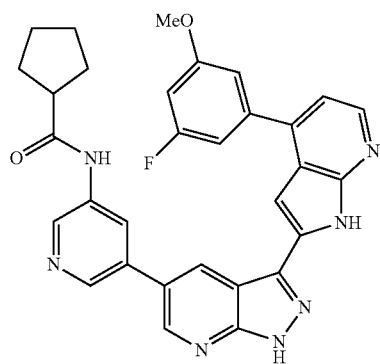 [SMILES: COc1cc(F)cc(-c2ccnc3[nH]c(-c4n[nH]c5ncc(-c6cncc(NC(=O)C7CCCC7)c6)cc45)cc23)c1] 945
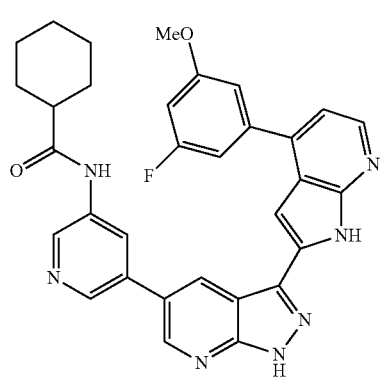 [SMILES: COc1cc(F)cc(-c2ccnc3[nH]c(-c4n[nH]c5ncc(-c6cncc(NC(=O)C7CCCCC7)c6)cc45)cc23)c1] 946
TABLE 1-continued
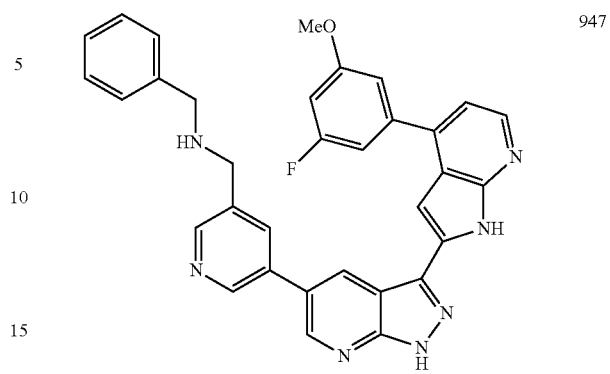 947
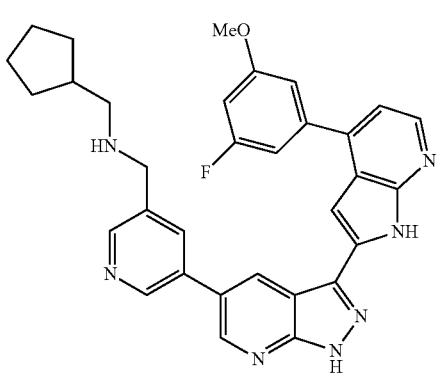 [SMILES: COc1cc(F)cc(-c2ccnc3[nH]c(-c4n[nH]c5ncc(-c6cncc(CNCC7CCCC7)c6)cc45)cc23)c1] 948
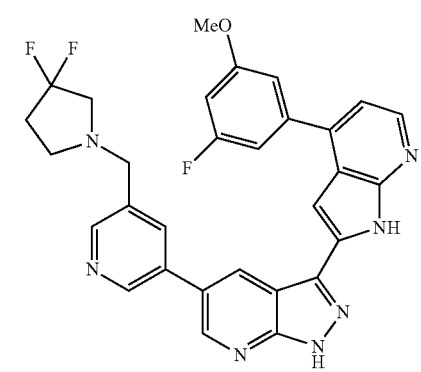 [SMILES: COc1cc(F)cc(-c2ccnc3[nH]c(-c4n[nH]c5ncc(-c6cncc(CN7CCC(F)(F)C7)c6)cc45)cc23)c1] 949
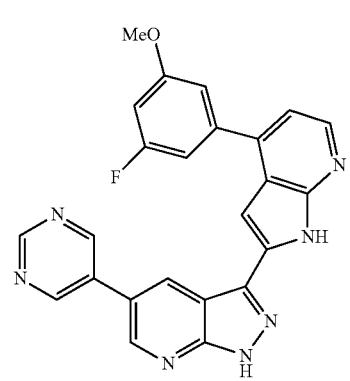 [SMILES: COc1cc(F)cc(-c2ccnc3[nH]c(-c4n[nH]c5ncc(-c6cncnc6)cc45)cc23)c1] 950

TABLE 1-continued
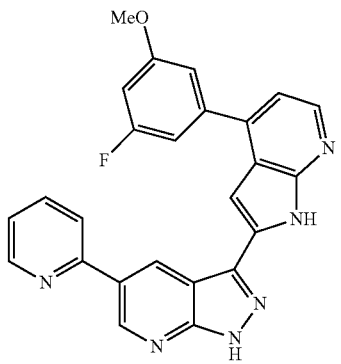 [SMILES: COc1cc(F)cc(-c2ccnc3[nH]c(-c4n[nH]c5ncc(-c6ccccn6)cc45)cc23)c1] 951
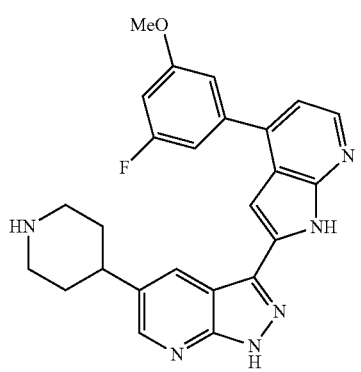 [SMILES: COc1cc(F)cc(-c2ccnc3[nH]c(-c4n[nH]c5ncc(C6CCNCC6)cc45)cc23)c1] 952
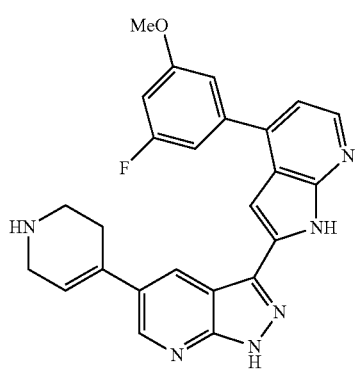 [SMILES: COc1cc(F)cc(-c2ccnc3[nH]c(-c4n[nH]c5ncc(C6=CCNCC6)cc45)cc23)c1] 953
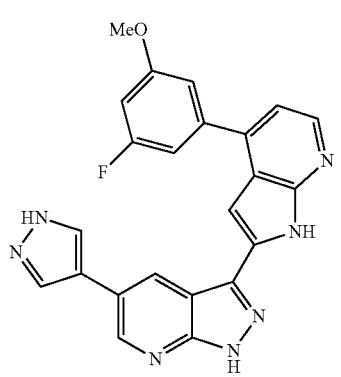 [SMILES: COc1cc(F)cc(-c2ccnc3[nH]c(-c4n[nH]c5ncc(-c6cn[nH]c6)cc45)cc23)c1] 954
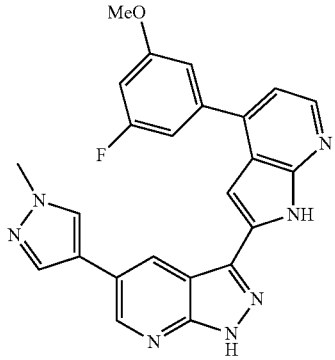 [SMILES: COc1cc(F)cc(-c2ccnc3[nH]c(-c4n[nH]c5ncc(-c6cnn(C)c6)cc45)cc23)c1] 955
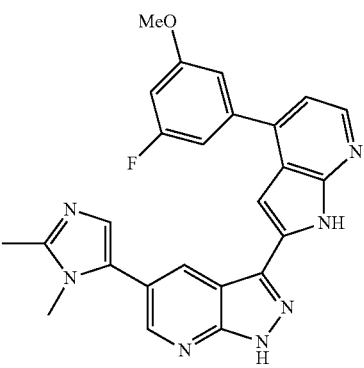 [SMILES: COc1cc(F)cc(-c2ccnc3[nH]c(-c4n[nH]c5ncc(-c6cnc(C)n6C)cc45)cc23)c1] 956
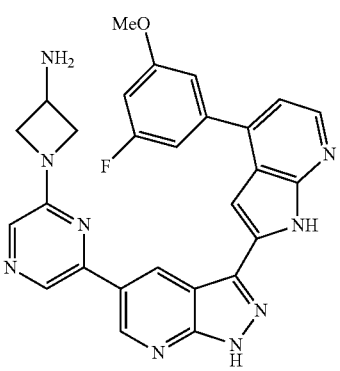 [SMILES: COc1cc(F)cc(-c2ccnc3[nH]c(-c4n[nH]c5ncc(-c6cncc(N7CC(N)C7)n6)cc45)cc23)c1] 957
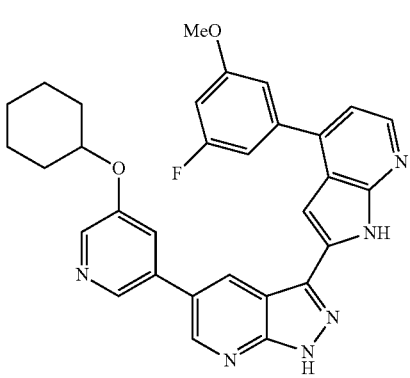 [SMILES: COc1cc(F)cc(-c2ccnc3[nH]c(-c4n[nH]c5ncc(-c6cncc(OC7CCCCC7)c6)cc45)cc23)c1] 958

TABLE 1-continued
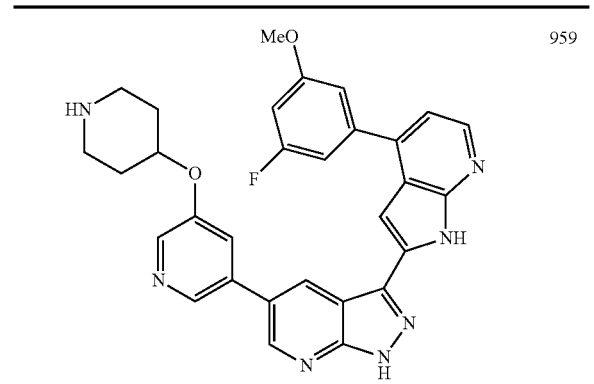 959
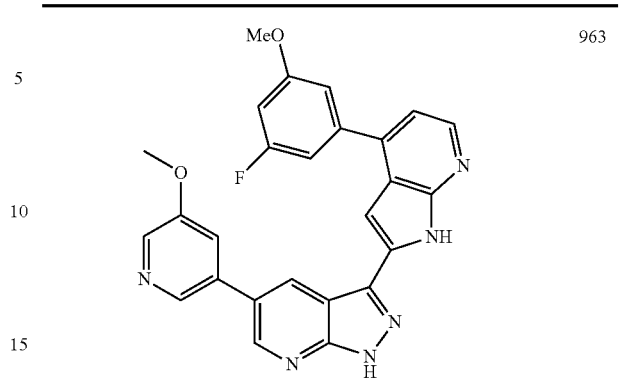 963
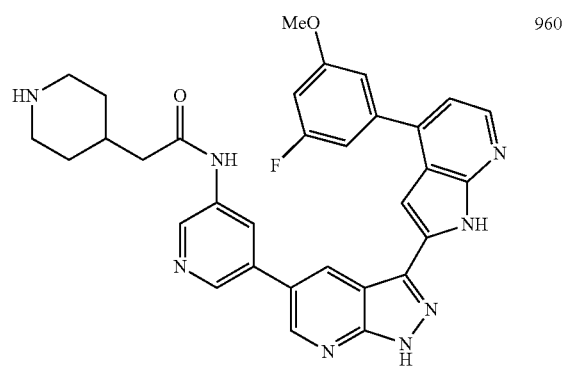 960
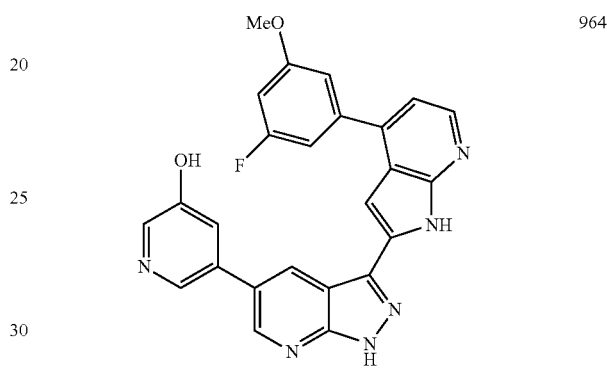 964
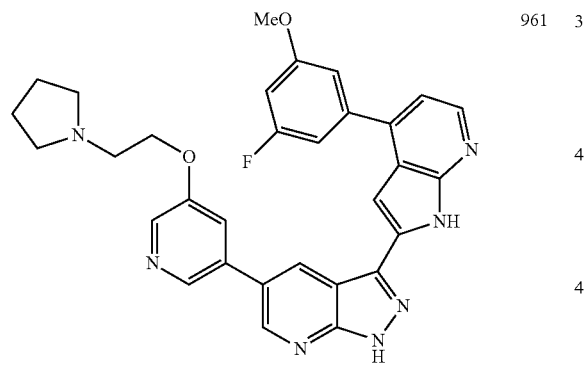 961
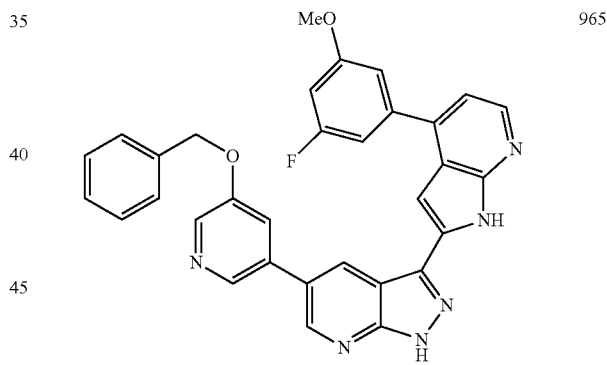 965
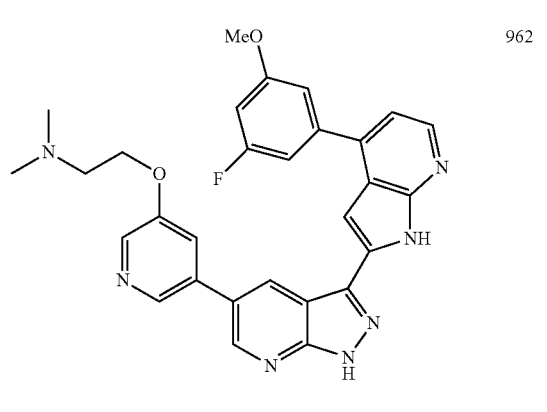 962
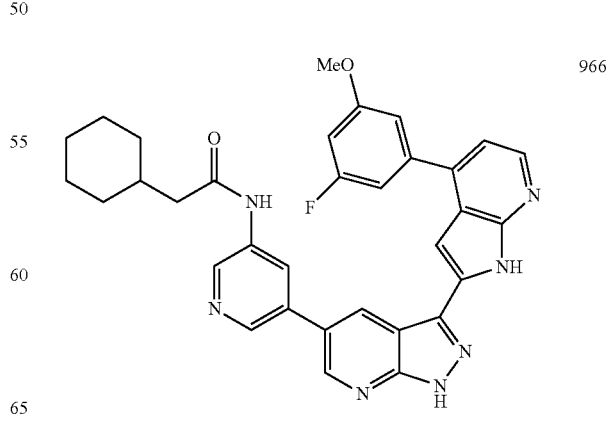 966

TABLE 1-continued
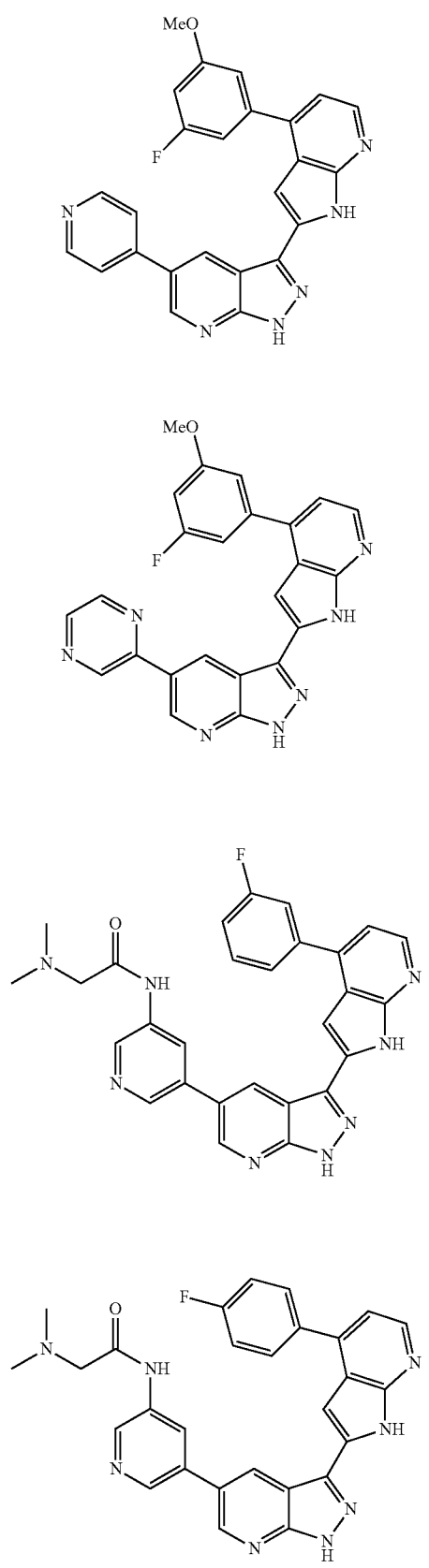
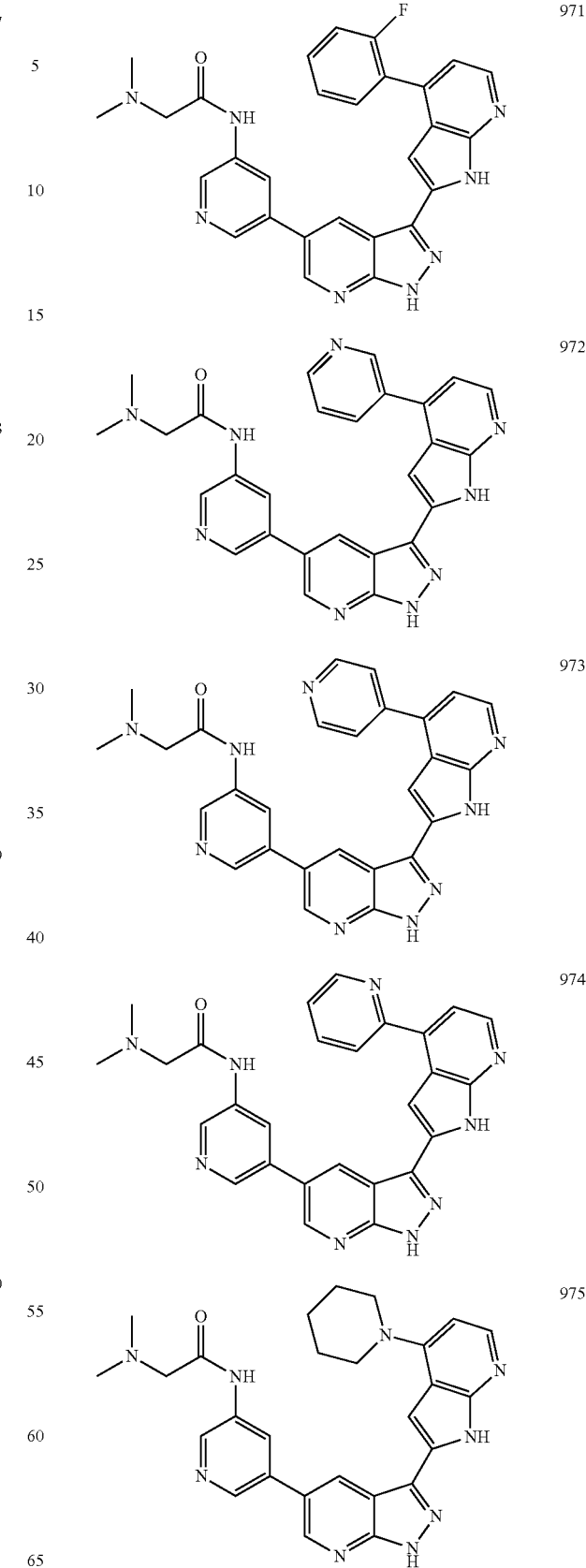

TABLE 1-continued
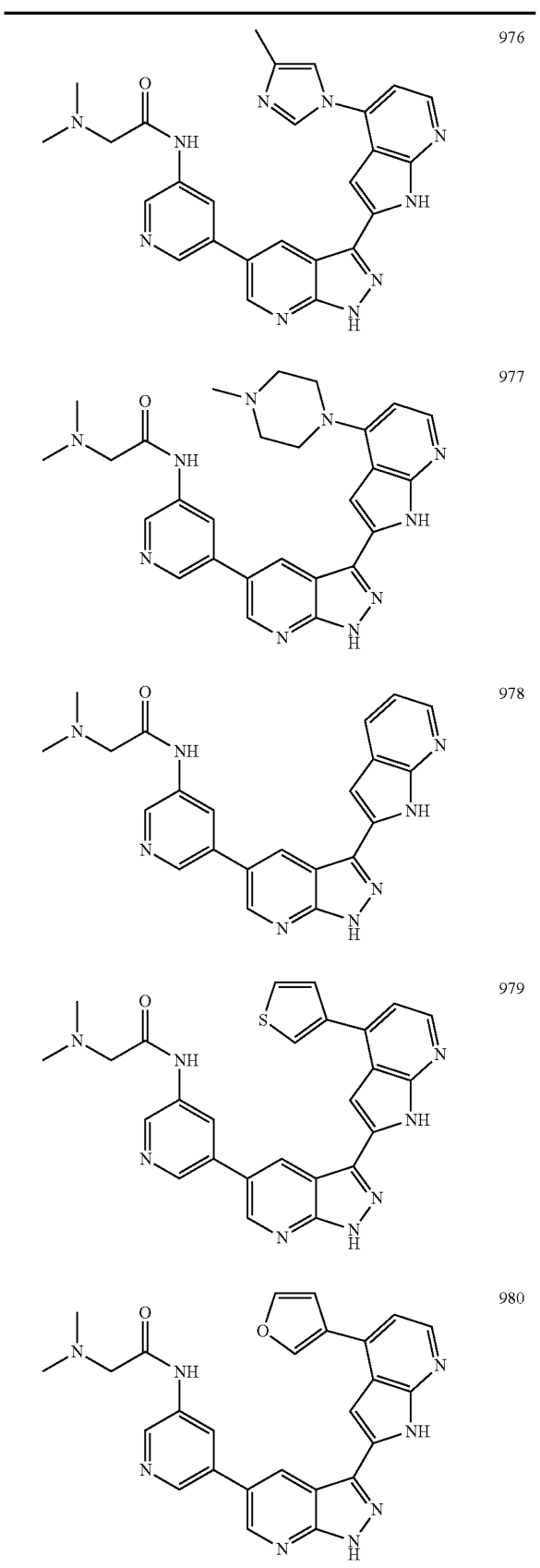
976
977
978
979
980
TABLE 1-continued
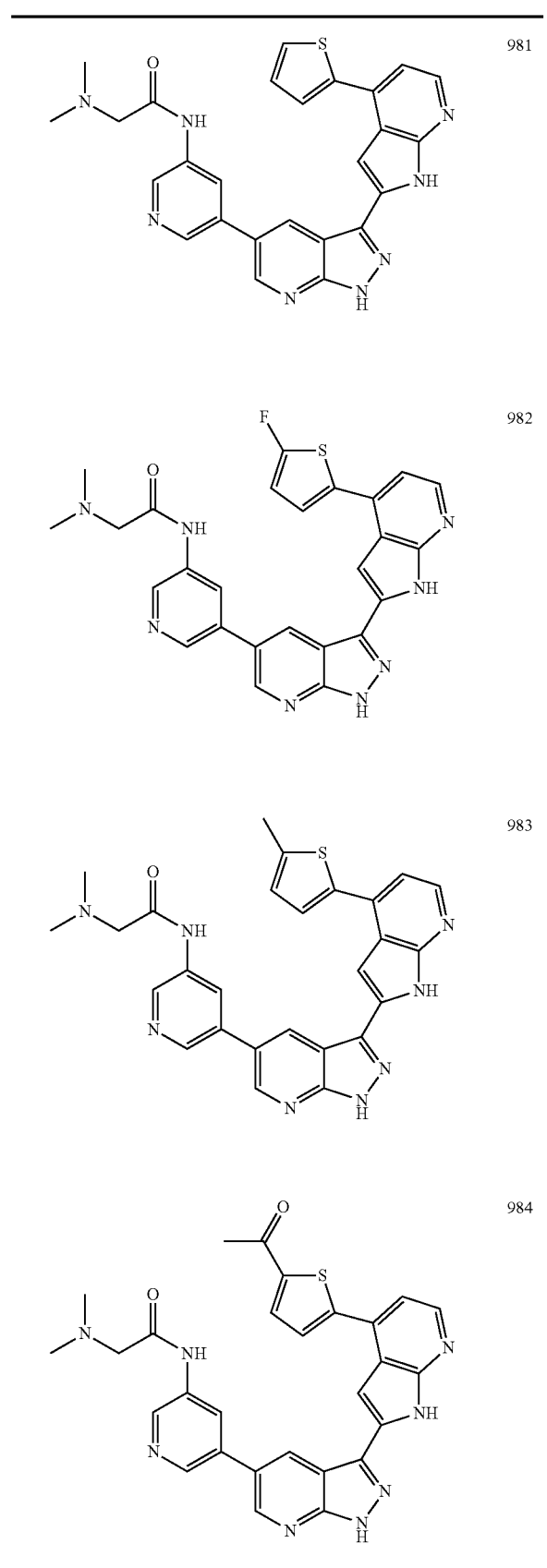
981
982
983
984

TABLE 1-continued

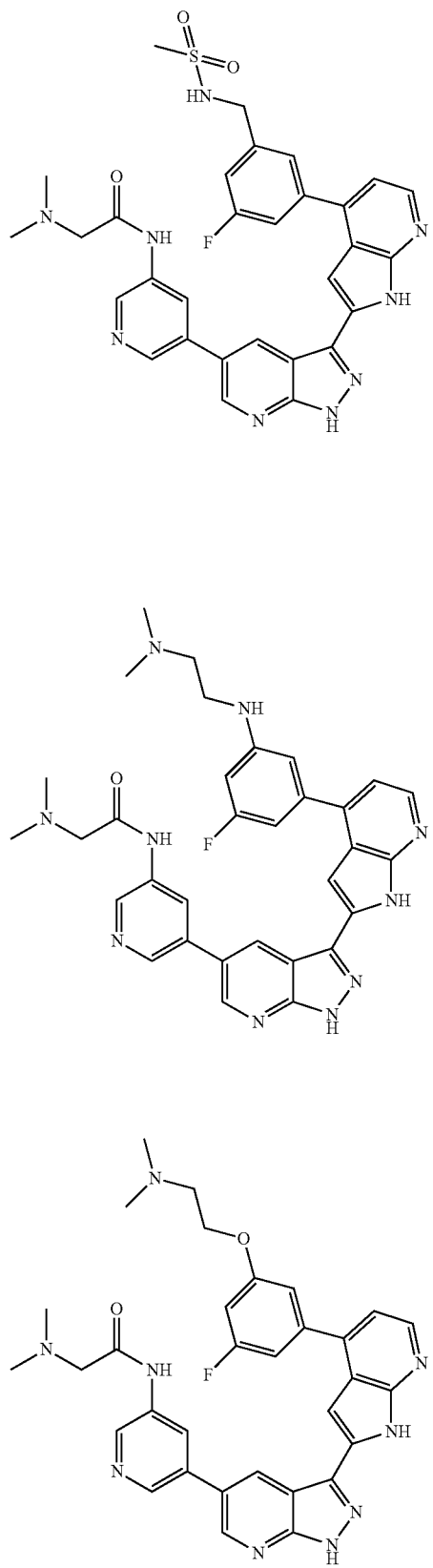

985

986

987

TABLE 1-continued

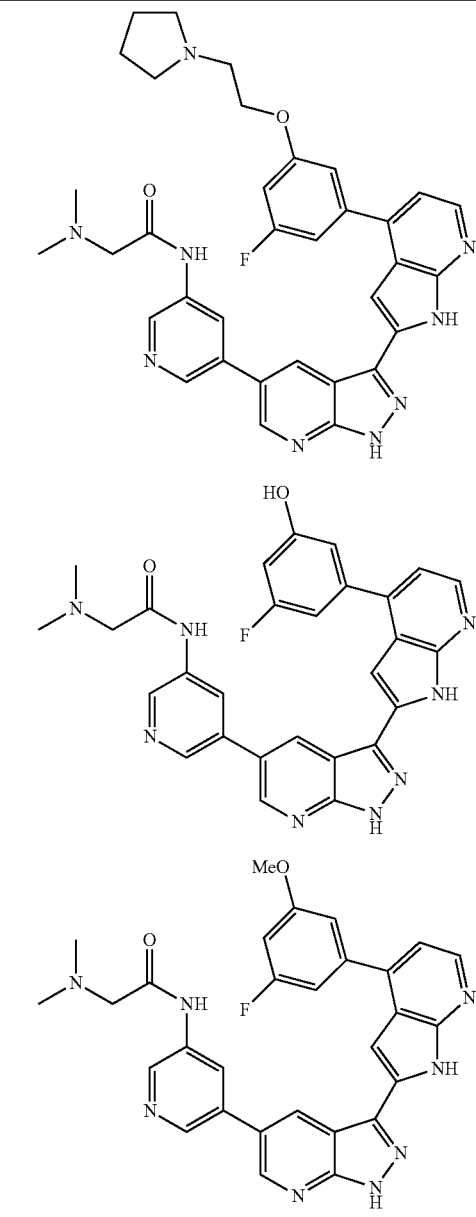

988

989

990

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other known agents are colorectal cancer, ovarian cancer, retinitis pigmentosa, macular degeneration, diabetic retinopathy, idiopathic pulmonary fibrosis/pulmonary fibrosis, and osteoarthritis.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions described herein can be used to treat tendinopathy includes all tendon pathologies (tendinitis, tendinosis and paratenonitis) localized in and around the tendons and is characterized by pain, swelling and impaired performance due to the degeneration of the tendon's collagen in response tendon overuse, often referred to as tendinosis. Tendinopathy may be categorized into two histopathologic entities—tendonitis, which results from acute injury to the tendon accompanied by intratendinous inflammation, and more commonly, tendinosis, which is a degenerative response to repetitive microtrauma resulting from overuse. Tendinosis may be accompanied by paratenonitis, an inflammatory condition of the lining of the tendon.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, de Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Fell syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina *bifida*, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease.

In some embodiments, the disorder or disease is tendinitis.

In some embodiments, the disorder or disease is tendinosis.

In some embodiments, the disorder or disease is paratenonitis.

In some embodiments, the disorder or disease is degeneration of the tendon's collagen.

In some embodiments, the disorder or disease is tendinopathy.

In some embodiments, the disorder or disease is a genetic disease caused by mutations in Wnt signaling components, wherein the genetic disease is selected from: polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay (Leyns, L. et al. *Cell* (1997), 88(6), 747-756).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations,* 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis,* 4th Ed., John Wiley & Sons (2007), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^{1}$H) nuclear magnetic resonance spectra (NMR) were measured in the indicated solvents on a Bruker NMR spectrometer (Avance™ DRX300, 300 MHz for $^{1}$H or Avance™ DRX500, 500 MHz for $^{1}$H) or Varian NMR spectrometer (Mercury 400BB, 400 MHz for $^{1}$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
$Ac_2O$=acetic anhydride
$BH_3$-$Me_2S$=borane dimethyl sulfide complex
B(i-PrO)$_3$=triisopropyl borate
(Boc)$_2$O=di-tert-butyl dicarbonate
brine=saturated aqueous sodium chloride
tBuOK=potassium tert-butoxide
$CDCl_3$=deuterated chloroform
$CD_3OD$=deuterated methanol
$Cy_3P$=tricyclohexylphosphine
DCAD=di-(4-chlorobenzyl)azodicarboxylate
DCE=dichloroethane
DCM=dichloromethane
DEAD=diethyl azodicarboxylate
DHP=dihydropyran
DIPEA—diisopropylethylamine
DMAP=4-dimethylaminopyridine
DMF=N,N-dimethylformamide
DMSO-d$_6$=deuterated dimethylsulfoxide
ESIMS=electron spray mass spectrometry
EtOAc=ethyl acetate
EtOH=ethanol
HCl=hydrochloric acid
HOAc=acetic acid
$K_2CO_3$=potassium carbonate
KOAc=potassium acetate
LC/MS=liquid chromatography-mass spectrometry
LDA=lithium diisopropylamide
MeOH=methanol
$MgSO_4$=magnesium sulfate
MPLC=Medium pressure liquid chromatography
MsCl=methanesulfonyl chloride or mesyl chloride
$NaBH_4$=sodium borohydride
$NaBH(OAc)_3$=sodium triacetoxyborohydride
$NaCNBH_3$=sodium cyanoborohydride
$NaHCO_3$=sodium bicarbonate
$NaH_2PO_4$=monosodium phosphate
$Na_2HPO_4$=disodium phosphate
$NaIO_4$=sodium periodate
NaOH=sodium hydroxide
$Na_2SO_4$=sodium sulfate
NMR=nuclear magnetic resonance
ON=overnight
$Pd_2(dba)_3$=tris(dibenzylideneacetone)dipalladium(0)
Pd(dppf)Cl$_2$=1,1'-bis(diphenylphosphino)ferrocene]palladium(II) chloride
Pd(PPh$_3$)$_4$=tetrakis(triphenylphosphine)palladium(0)
PE=petroleum ether
Pin$_2$B$_2$=bis(pinacolato)diboron
PPh$_3$=triphenylphosphine
prep-HPLC=preparative High-performance liquid chromatography
r.t=room temperature
SEM-Cl=2-(trimethylsilyl)ethoxymethyl chloride
TBAF=tetra-n-butylammonium fluoride
TEA=triethylamine
TFA=trifluoroacetic acid
THF=tetrahydrofuran
THP=tetrahydropyran
TLC=thin layer chromatography
p-TsOH=p-toluenesulfonic acid
XPhos=2-dicyclohexylphosphino-2',4',6'-triisopropylbiphenyl The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedure

Compounds of Formula (I) of the present disclosure can be prepared as depicted in Scheme 1a.

Scheme 1a

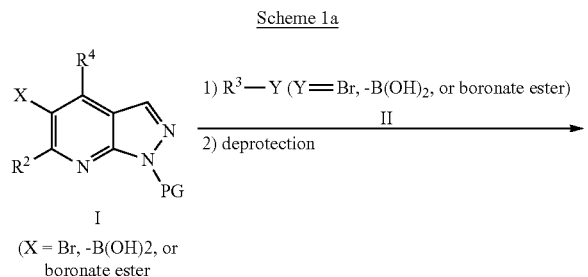

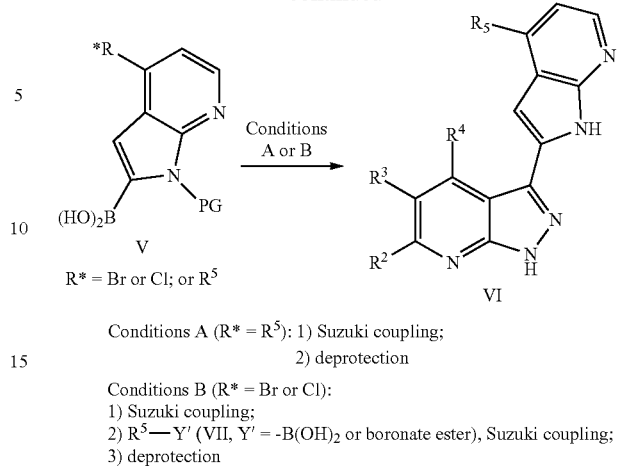

Conditions A (R* = $R^5$): 1) Suzuki coupling;
2) deprotection

Conditions B (R* = Br or Cl):
1) Suzuki coupling;
2) $R^5$—Y' (VII, Y' = -B(OH)$_2$ or boronate ester), Suzuki coupling;
3) deprotection Compound I, wherein PG is a protecting group such as THP, undergoes Suzuki coupling with Compound II to provide Compound III. In certain embodiments, Compound I (X=Br) undergoes Suzuki coupling with Compound II (Y=—B(OH)$_2$ or boronate ester) to provide Compound III after removal of the protecting group. In other embodiments, Compound I (X=Br) is first converted to the corresponding boronic acid or boronate ester (not shown), which in turn undergoes Suzuki coupling with Compound II (Y=Br) to provide Compound III after removal of the protecting group. Treatment of Compound III with KOH and I$_2$ followed by Boc$_2$O affords the protected iodide IV.

In certain embodiments, when R* is $R^5$ (e.g., a six-membered ring), Suzuki coupling between iodide (IV) and boronic acid (V) followed by removal of the protecting groups affords the desired bi-heteroaryl product VI (see, for example, conditions A above).

In other embodiments, when R* is Br or Cl, the resultant Suzuki product can further undergo a second Suzuki coupling to install the $R^5$ substituent. In some cases, this procedure is useful when the $R^5$ substituent is a five-membered ring. In these embodiments, removal of the protecting groups affords the desired bi-heteroaryl product VI. See, for example, conditions B above.

Compounds of Formula (I) of the present disclosure can be prepared as depicted in Scheme 1.

Scheme 1

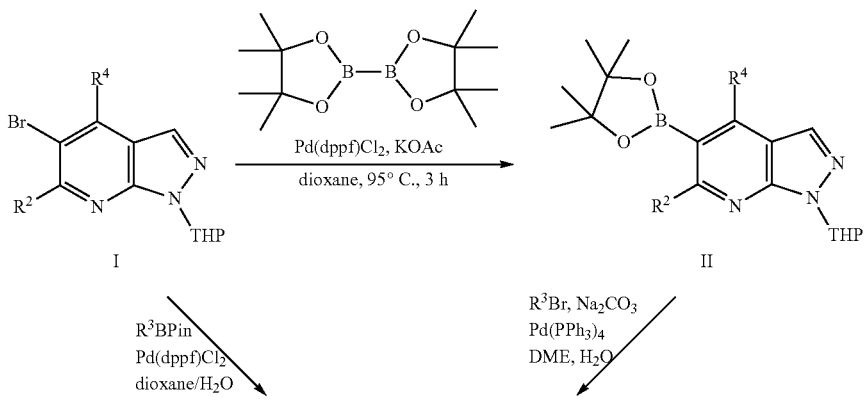

-continued

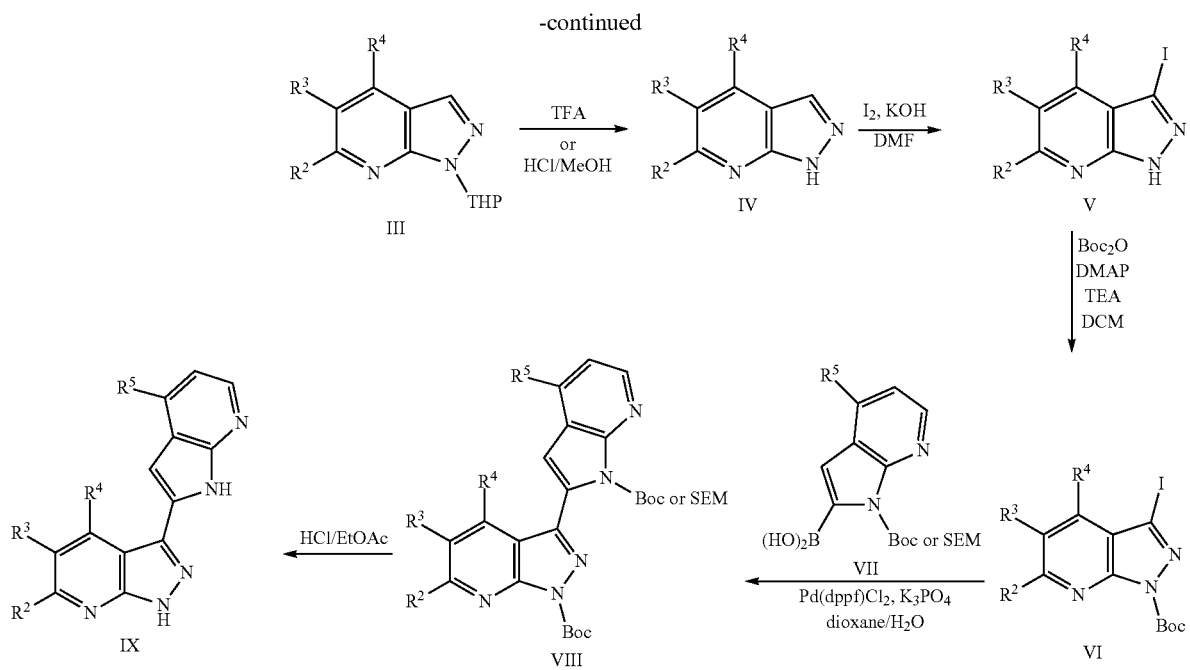

Scheme 1 describes a method for preparation of 3-(1H-pyrrolo[2,3-b]pyridin-2-yl)-1H-pyrazolo[3,4-b]pyridine compounds (IX) by either converting the 1H-pyrazolo[4,3-b]pyridine (I) to the boronate (II) followed by Suzuki coupling with various bromo compounds to form (III) analogs or by reacting (I) directly with various boronates using Suzuki coupling to produce compound (III) analogs. (III) is then deprotected before iodination of (IV) with iodine and potassium hydroxide to produce compound (V) analogs. The 3-iodo-1H-pyrazolo[4,3-b]pyridine (V) nitrogen is then protected with Boc followed by Suzuki coupling with the Boc/SEM protected (1H-pyrrolo[2,3-b]pyridin-2-yl)boronic acid (VII) to form the protected 3-(1H-pyrrolo[2,3-b]pyridin-2-yl)-1H-pyrazolo[3,4-b]pyridine compounds (VIII). Final deprotection of the pyrazole nitrogen yields the desired substituted 3-(1H-pyrrolo[2,3-b]pyridin-2-yl)-1H-pyrazolo[3,4-b]pyridine compounds (IX).

Alternatively, compounds of Formula (I) of the present disclosure can be prepared as depicted in Scheme 2.

-continued

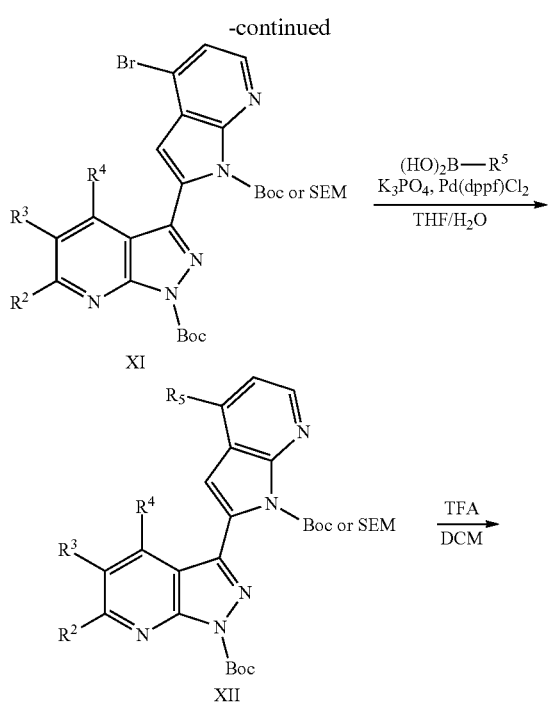

Scheme 2

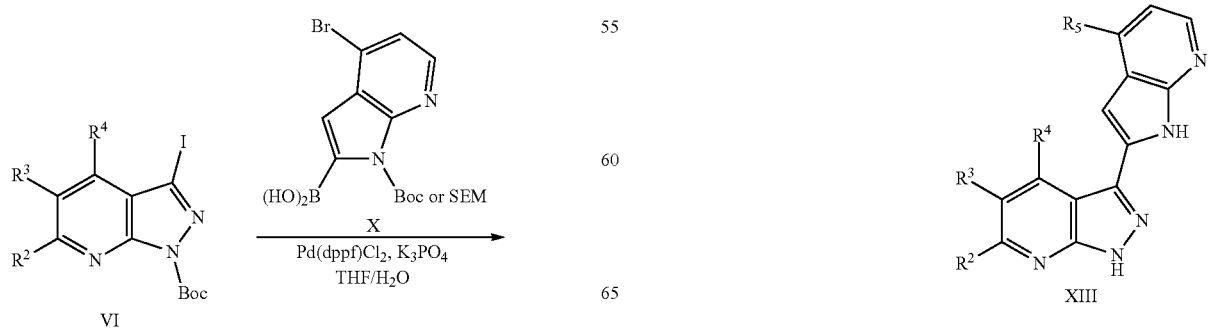

Scheme 2 describes an alternative method for preparation of 3-(1H-pyrrolo[2,3-b]pyridin-2-yl)-1H-pyrazolo[3,4-b]pyridine compounds (XIII) by reacting Boc protected 3-iodo-1H-pyrazolo[4,3-b]pyridine (VI) with the Boc protected (4-bromo-1H-pyrrolo[2,3-b]pyridin-2-yl)boronic acid (X) by Suzuki coupling. A second Suzuki coupling with various boronic acids yields the protected 3-(1H-pyrrolo[2,3-b]pyridin-2-yl)-1H-pyrazolo[3,4-b]pyridine (XII). Final deprotection of the pyrazole nitrogen yields the desired substituted 3-(1H-pyrrolo[2,3-b]pyridin-2-yl)-1H-pyrazolo[3,4-b]pyridine (XIII).

Illustrative Compound Examples

Preparation of intermediates (XVII) and (XVIII) are depicted below in Scheme 3.

reaction was then heated to 75~80° C. and stirred for 12 h. The solvent was removed under reduced pressure at 45° C. The residual crude solid was triturated in water (750 mL) and EtOH (250 mL). The resultant suspension was filtered and washed with ethanol to give 5-bromo-1H-pyrazolo[3,4-b]pyridine (XVI) (135 g, 0.68 mol, 55.4% yield) as yellowish solid which was used directly for the next step without further purification. ESIMS found for $C_6H_4BrN_3$ m/z 199.1 (M+H).

Step 3

To a stirred solution of 5-bromo-1H-pyrazolo[3,4-b]pyridine (XVI) (130 g, 656 mmol, 1.0 eq) in DCM (1300 mL) were added DHP (111 g, 1.31 mol, 2.0 eq) and p-TsOH (11.3 g, 65.6 mmol, 0.1 eq) at 25-30° C. The reaction suspension was stirred at 25-30° C. for 3 h. The reaction suspension changed to a brown solution. The reaction solution was

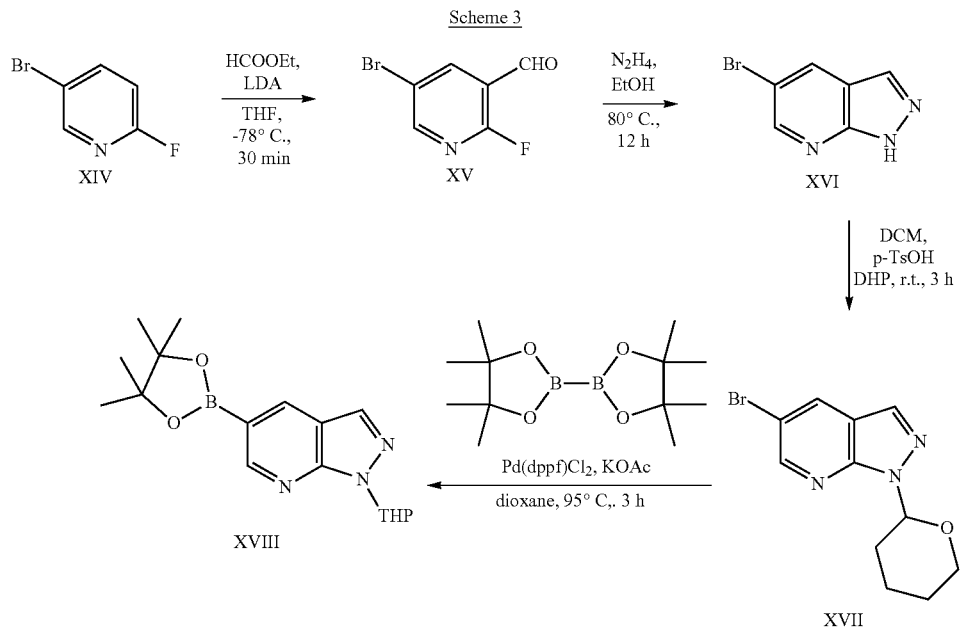

Scheme 3

Step 1

A 2000 mL three necked round bottom flask charged with a stirred solution of 5-bromo-2-fluoropyridine (XIV) (215 g, 1.22 mol, 1.00 eq) in anhydrous THF (2.58 L) was cooled to −85~−90° C. in an ethanol liquid nitrogen bath. LDA (2 M, 671.91 mL, 1.10 eq) was added dropwise keeping the inner temperature below −85° C. After addition, the reaction turned to be yellow suspension. The yellow suspension was stirred for 1 h below −85° C. before adding ethyl formate (135.75 g, 1.83 mol, 1.50 eq) dropwise. The yellow suspension turned into a yellow solution and was stirred for another 30 min below −80° C. The reaction solution was poured into saturated aqueous ammonium chloride (3.5 L) and extracted with EtOAc (500 mL×2). The combined organic layer was washed with brine (500 mL), dried over anhydrous sodium sulfate and concentrated to give 5-bromo-2-fluoronicotinaldehyde (XV) (251.50 g, crude) as yellow solid which was used for the next step without any purification. ESIMS found for $C_6H_3BrFNO$ m/z 205.0 (M+H).

Step 2

To a stirred solution of 5-bromo-2-fluoronicotinaldehyde (XV) (250 g, 1.23 mol, 1.0 eq) in EtOH (2.50 L) was added hydrazine hydrate (221 g, 4.41 mol, 3.6 eq) at 25° C. The poured into saturated sodium bicarbonate (2.5 L) and separated. The aqueous layer was then extracted with DCM (500 mL×2). The combined organic layer was washed with brine (500 mL), dried over anhydrous sodium sulfate and concentrated to give the crude product. The crude product was purified by column chromatography (100% PE→PE:EtOAc=10:1) to give 5-bromo-1-(tetrahydro-2H-pyran-2-yl)-1H-pyrazolo[3,4-b]pyridine (XVII) (112.5 g, 398.5 mmol, 60.7% yield) was obtained as a red oil. ESIMS found for $C_{11}H_{12}BrN_3O$ m/z 283.0 (M+H).

Step 4

A 2000 mL three-necked round bottom flask charged with 5-bromo-1-(tetrahydro-2H-pyran-2-yl)-1H-pyrazolo[3,4-b]pyridine (XVII) (88 g, 312 mmol, 1.0 eq), 4,4,5,5-tetramethyl-2-(4,4,5,5-tetramethyl-1,3,2-dioxaborolan-2-yl)-1,3,2-dioxaborolane (317 g, 1.25 mol, 4.0 eq) and Pd(dppf)Cl$_2$ (11.4 g, 15.6 mmol, 0.05 eq) in dioxane (880 mL) was degassed with nitrogen (×3). KOAc (91.8 g, 936 mmol, 3.0 eq) was added in one portion and degassed with nitrogen (×3). The reaction suspension was heated to 90-100° C. and stirred for 3 h. The reaction was filtered and the filtrate was concentrated under reduced pressure at 50° C. to give the crude product. The crude product was purified by column chromatography (PE:EtOAc=8:1→5:1) to give 1-(tetrahydro-2H-pyran-2-yl)-5-(4,4,5,5-tetramethyl-1,3,2-dioxaborolan-2-yl)-1H-pyrazolo[3,4-b]pyridine (XVIII) (82 g, 249 mmol, 79.9% yield) as a red solid. ESIMS found for C$_{17}$H$_{24}$BN$_3$O$_3$ m/z 330.1 (M+H).

Preparation of intermediate N-(5-bromopyridin-3-yl)pivalamide (XXI) is depicted below in Scheme 4.

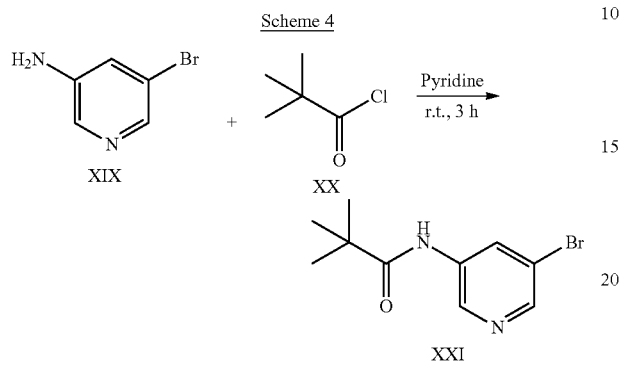

Step 1

To a solution of 3-amino-5-bromo pyridine (XIX) (1.0 g, 5.78 mmol) in dry pyridine (10 mL) was added pivaloyl chloride (XX) (769 mg, 6.38 mmol). The reaction mixture was stirred at room temperature for 3 h. The reaction was poured into an ice water/saturated aqueous NaHCO$_3$ mixture and stirred for 30 min. The precipitate was filtered, washed with cold water and dried at room temperature to yield N-(5-bromopyridin-3-yl)pivalamide (XXI) as an off-white solid (1.082 g, 4.22 mmol, 73.1% yield). $^1$H NMR (DMSO-d$_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found C$_{10}$H$_{13}$BrN$_2$O m/z 258.9 (Br$^{81}$M+H).

The following intermediates were prepared in accordance with the procedure described in the above Scheme 4.

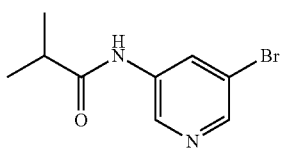

N-(5-Bromopyridin-3-yl)isobutyramide (XXII): Off-white solid, (71% yield). $^1$H NMR (CDCl$_3$) δ ppm 8.55-8.35 (m, 3H), 7.32 (s, 1H), 2.59-2.48 (m, 1H), 1.28-1.27 (d, 6 H); ESIMS found C$_9$H$_{11}$BrN$_2$O m/z 242.9 (Br$^{79}$M+H).

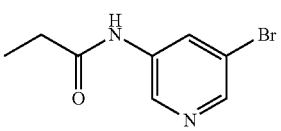

N-(5-Bromopyridin-3-yl)propionamide (XXIII): Off white solid (92% yield). $^1$H NMR (DMSO-d$_6$) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found C$_8$H$_9$BrN$_2$O m/z 231.1 (Br$^{81}$M+H).

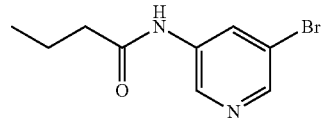

N-(5-Bromopyridin-3-yl)butyramide (XXIV): Yellow solid (2.1 g, 8.64 mmol, 88.8% yield). $^1$H NMR (CD$_3$OD, 400 MHz) δ ppm 1.02 (t, J=7.2 Hz, 3H), 1.74 (sxt, J=7.2 Hz, 2H), 2.40 (t, J=7.2 Hz, 2H), 8.35 (d, J=2 Hz, 1H), 8.46 (t, J=2 Hz, 1H), 8.63 (d, J=2 Hz, 1H); ESIMS found C$_9$H$_{11}$BrN$_2$O m/z 243.1 (Br$^{79}$M+H).

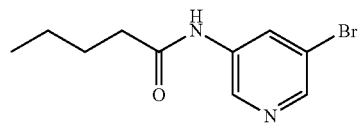

N-(5-Bromopyridin-3-yl)pentanamide (XXV): Yellow solid (2.0 g, 7.78 mmol, 85.3% yield). $^1$H NMR (CD$_3$OD, 400 MHz) δ ppm 0.98 (t, J=7.4 Hz, 3H), 1.43 (sxt, J=7.4 Hz, 2H), 1.70 (quin, J=7.4 Hz, 2H), 2.43 (t, J=7.6 Hz, 2H), 8.35 (s, 1H), 8.45 (d, J=2 Hz, 1H), 8.64 (d, J=2 Hz, 1H); ESIMS found C$_{10}$H$_{13}$BrN$_2$O m/z 256.9 (Br$^{79}$M+H).

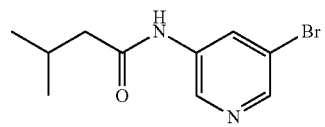

N-(5-Bromopyridin-3-yl)-3-methylbutanamide (XXVI): Off white solid, (67% yield), $^1$H NMR (CDCl$_3$, 500 MHz) δ ppm 8.55-8.42 (m, 3H), 7.62 (s, 1H), 2.31-2.18 (m, 3H), 1.02-1.01 (d, J=6 Hz, 6H); ESIMS found C$_{10}$H$_{13}$BrN$_2$O m/z 258.9 (Br$^{81}$M+H).

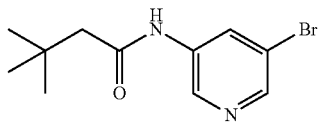

N-(5-Bromopyridin-3-yl)-3,3-dimethylbutanamide (XXVII): Yellow solid (1.7 g, 6.27 mmol, 78.6% yield). $^1$H NMR (CD$_3$OD, 400 MHz) δ ppm 1.10 (s, 9H), 2.29 (s, 2H), 8.36 (d, J=1.6 Hz, 1H), 8.46 (d, J=2.0 Hz, 1H), 8.64 (d, J=2.0 Hz, 1H); ESIMS found C$_{11}$H$_{15}$BrN$_2$O m/z 273.1 ((Br$^{81}$M+H).

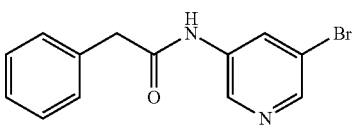

N-(5-Bromopyridin-3-yl)-2-phenylacetamide (XXVIII): White solid (2.5 g, 8.59 mmol, 77.9% yield). $^1$H NMR (CDCl$_3$, 400 MHz) δ ppm 3.76 (s, 2H), 7.26-7.45 (m, 5H), 7.57 (brs, 1H), 8.33 (s, 1H), 8.37 (s, 2H); ESIMS found C$_{13}$H$_{11}$BrN$_2$O m/z 292.8 (Br$^{81}$M+H).

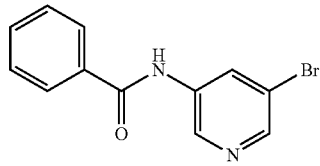

XXIX

N-(5-Bromopyridin-3-yl)benzamide (XXIX): White solid (2.7 g, 9.74 mmol, 60% yield). $^1$H NMR (CDCl$_3$, 400 MHz) δ ppm 7.40-7.52 (m, 2H), 7.52-7.62 (m, 1H), 7.86 (d, J=7.2 Hz, 2H), 8.39 (d, J=1.6 Hz, 1H), 8.46 (s, 1H), 8.55 (d, J=1.6 Hz, 1H), 8.57 (d, J=2.0 Hz, 1H); ESIMS found C$_{12}$H$_9$BrN$_2$O m/z 278.8 (Br$^{81}$M+H)

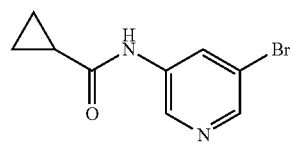

XXX

N-(5-Bromopyridin-3-yl)cyclopropanecarboxamide (XXX): Off-white solid, (83% yield), $^1$H NMR (CDCl$_3$, 500 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for C$_9$H$_9$BrN$_2$O m/z 240.9 (Br$^{79}$M+H).

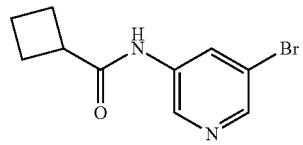

XXXI

N-(5-Bromopyridin-3-yl)cyclobutanecarboxamide (XXXI): Yellow solid (2.1 g, 6.27 mmol, 86.6% yield). $^1$H NMR (CD$_3$OD, 400 MHz) δ ppm 1.80-1.99 (m, 1H), 1.99-2.15 (m, 1H), 2.16-2.30 (m, 2H), 2.30-2.45 (m, 2H), 3.25-3.35 (m, 1H), 8.34 (d, J=2.0 Hz, 1H), 8.47 (s, 1H), 8.64 (d, J=2.0 Hz, 1H); ESIMS found C$_{10}$H$_{11}$BrN$_2$O m/z 257.1 (Br$^{81}$M+H).

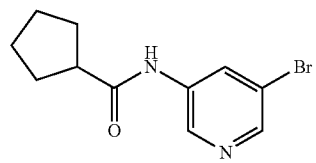

XXXII

N-(5-Bromopyridin-3-yl)cyclopentanecarboxamide (XXXII): Yellow solid (1.9 g, 7.06 mmol, 80.2% yield). $^1$H NMR (CD$_3$OD, 400 MHz) δ ppm 1.57-1.74 (m, 2H), 1.74-1.91 (m, 4 H), 1.91-2.07 (m, 2H), 2.77-2.92 (m, 1H), 8.34 (d, J=1.6 Hz, 1H), 8.45 (s, 1H), 8.65 (d, J=2.0 Hz, 1H); ESIMS found C$_{11}$H$_{13}$BrN$_2$O m/z 271.1 (Br$^{81}$M+H).

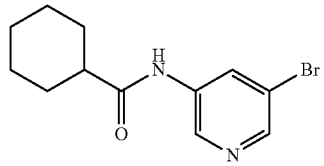

XXXIII

N-(5-bromopyridin-3-yl)cyclohexanecarboxamide (XXXIII): Yellow solid (2.0 g, 7.06 mmol, 84.3% yield). $^1$H NMR (CD$_3$OD, 400 MHz) δ ppm 1.19-1.46 (m, 3H), 1.46-1.63 (m, 2H), 1.74 (d, J=11.6 Hz, 1H), 1.88 (t, J=14.0 Hz, 4 H), 2.40 (tt, J=11.6 Hz, J=3.6 Hz, 1H), 8.34 (d, J=2.0 Hz, 1H), 8.44 (t, J=2.0 Hz, 1H), 8.64 (d, J=2.0 Hz, 1H); ESIMS found C$_{12}$H$_{15}$BrN$_2$O m/z 285.1 (Br$^{81}$M+H).

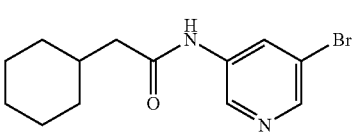

XXXIV

N-(5-bromopyridin-3-yl)-2-cyclohexylacetamide (XXXIV): Yellow solid (261 mg, 0.878 mmol, 84.4% yield). ESIMS found C$_{13}$H$_{17}$BrN$_2$O m/z 297.1 (Br$^{81}$M+H).

Preparation of intermediate 5-bromo-N,N-dimethylpyridin-3-amine (XXXVI) is depicted below in Scheme 5.

Scheme 5

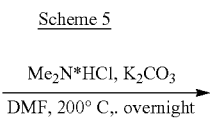

XXXV $\xrightarrow{\text{Me}_2\text{N*HCl, K}_2\text{CO}_3}{\text{DMF, 200° C,. overnight}}$

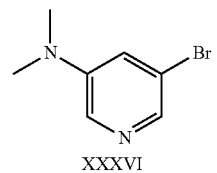

XXXVI

Step 1

To a solution of 3,5-dibromopyridine (XXXV) (2.37 g, 10.0 mmol) in dry DMF (20.0 mL) was added K$_2$CO$_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over MgSO$_4$, and concentrated to afford 5-bromo-N,N-dimethylpyridin-3-amine (XXXVI) as an off-white solid (1.78 g, 8.85 mmol, 88% yield). $^1$H NMR (DMSO-d$_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found C$_7$H$_9$BrN$_2$ m/z 201.1 (M+H).

Preparation of intermediate 5-bromo-N-isopropylpyridin-3-amine (XXXVII) is depicted below in Scheme 6.

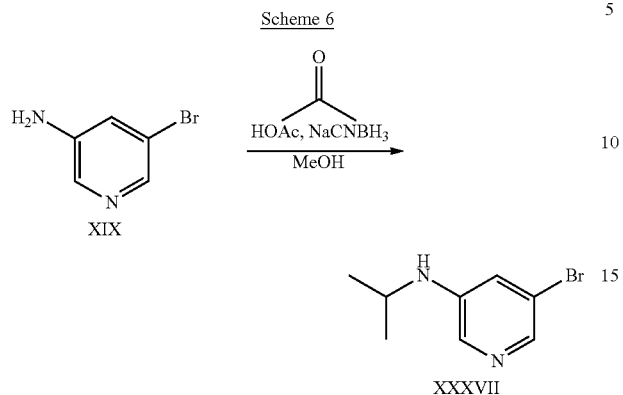

Steps 1

To a solution of 5-bromopyridin-3-amine (XIX) (535 mg, 3.09 mmol) in MeOH (62 mL) was added acetone (296 μL, 4.02 mL). The pH was adjusted to 4 using HOAc and stirred for 30 min. NaCNBH$_3$ (272 mg, 4.33 mmol) was added and stirred at room temperature overnight. The MeOH was removed under vacuum and the residue was partitioned between EtOAc and saturated aqueous NaHCO$_3$. The organic layer was dried over MgSO$_4$ and evaporated under vacuum. The crude product was purified on a silica gel column (100% hexane →90:10 hexane:EtOAc) to produce 5-bromo-N-isopropylpyridin-3-amine (XXXVII) as an oil which slowly solidified into an off-white solid (309 mg, 1.44 mmol, 47% yield). $^1$H NMR (DMSO-d$_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found C$_8$H$_{11}$BrN$_2$ m/z 215.1 (M+H).

Preparation of intermediate 1-(5-bromopyridin-3-yl)-N,N-dimethylmethanamine (XXXIX) is depicted below in Scheme 7.

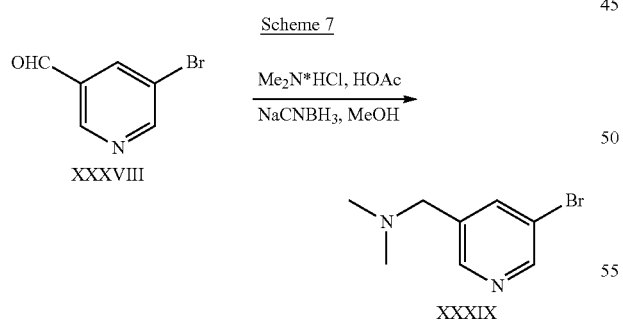

Steps 1

Preparation of 1-(5-bromopyridin-3-yl)-N,N-dimethylmethanamine (XXXIX) was performed following the procedure listed in Scheme 6, Step 1. Brown oil (1.20 g, 5.59 mmol, 45% yield). $^1$H NMR (DMSO-d$_6$, 500 MHz) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found C$_8$H$_{11}$BrN$_2$ m/z 215 (M$^{Br79}$+H) and 217 (M$^{Br81}$+H).

Preparation of intermediate 3-bromo-5-((3,3-difluoropyrrolidin-1-yl)methyl)pyridine (XL) is depicted below in Scheme 8.

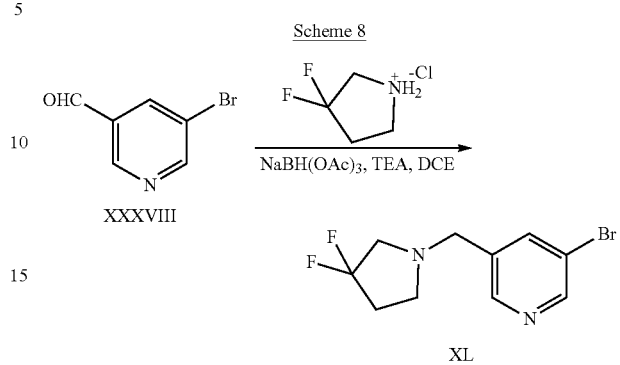

Steps 1

To a mixture of 5-bromopyridine-3-carbaldehyde (XXXVIII) (6.00 g, 32.26 mmol, 1.0 eq), 3,3-difluoropyrrolidine (5.56 g, 38.71 mmol, 1.20 eq) and TEA (5.39 mL, 38.71 mmol, 1.2 eq) in DCE (200 mL) was stirred at room temperature for 30 min, then added sodium triacetoxyborohydride (10.25 g, 48.38 mmol, 1.50 eq) in one portion at room temperature under N$_2$. The mixture was stirred at room temperature for 6 h. TLC showed the reaction was complete. The reaction was quenched with 1N NaOH (100 mL), extracted with DCE (100 mL×2). The combined organic layers were washed with brine (100 mL), dried and concentrated. The residue was purified by silica gel chromatography (column height: 50 mm, diameter: 50 mm, 300-400 mesh silica gel, DCM/MeOH=30/1→20/1) to give 3-bromo-5-((3,3-difluoropyrrolidin-1-yl)methyl) pyridine (XL): Yellow oil (8.00 g, 28.9 mmol, 89.5% yield). $^1$H NMR (CDCl$_3$, 400 MHz) δ ppm 2.30 (spt, J=7.2 Hz. 2H), 2.75 (t, J=6.8 Hz, 2H), 2.91 (t, J=13.2 Hz, 2H), 7.85 (s, 1H), 8.45 (s, 1H), 8.59 (d, J=2 Hz, 1H); ESIMS found for C$_{10}$H$_{11}$BrF$_2$N$_2$ m/z 277.0 (M+H).

The following intermediates were prepared in accordance with the procedure described in the above Schemes 6-8.

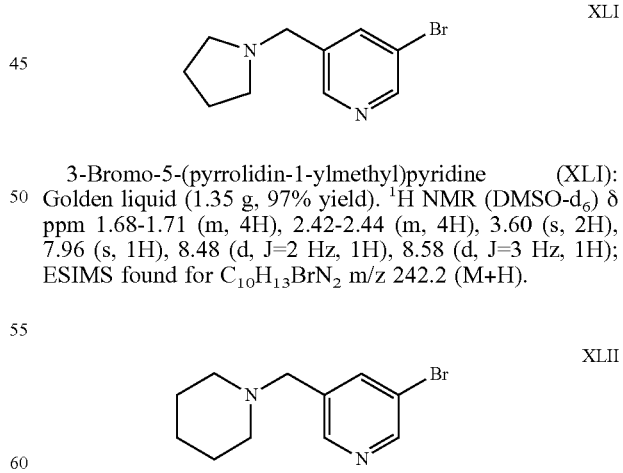

3-Bromo-5-(pyrrolidin-1-ylmethyl)pyridine (XLI): Golden liquid (1.35 g, 97% yield). $^1$H NMR (DMSO-d$_6$) δ ppm 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for C$_{10}$H$_{13}$BrN$_2$ m/z 242.2 (M+H).

3-Bromo-5-(piperidin-1-ylmethyl)pyridine (XLII): Brown liquid (13.1 g, 94% yield). $^1$H NMR (DMSO-d$_6$) δ ppm 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for C$_{11}$H$_{15}$BrN$_2$ m/z 257.0 (M+H).

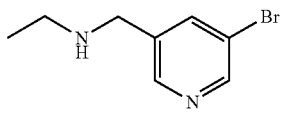

N-((5-Bromopyridin-3-yl)methyl)ethanamine (XLIII): Golden liquid (1.29 g, 6.00 mmol, 60% yield). $^1$H NMR (CDCl$_3$, 400 MHz) δ ppm 1.14 (t, J=7.2 Hz, 3H), 2.67 (q, J=7.2 Hz, 2H), 3.79 (s, 2H), 7.85 (t, J=2 Hz, 1H), 8.46 (d, J=1.6 Hz, 1H), 8.56 (d, J=2.4 Hz, 1H); ESIMS found for C$_8$H$_{11}$BrN$_2$ m/z 215.1 (M+H).

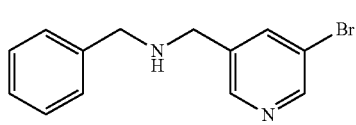

N-Benzyl-1-(5-bromopyridin-3-yl)methanamine (XLIV): Yellow oil (8.0 g, 28.9 mmol, 89.5% yield). $^1$H NMR (DMSO-d$_6$, 400 MHz) δ ppm 3.71 (s, 2H), 3.74 (s, 2H), 7.18-7.28 (m, 1H), 7.28-7.40 (m, 4H), 8.04 (s, 1H), 8.52 (s, 1H), 8.58 (s, 1H); ESIMS found for Cl$_3$H$_{13}$BrN$_2$ m/z 277.1 (M+H).

Preparation of intermediate tert-butyl (5-bromopyridin-3-yl)methyl (cyclopentylmethyl)carbamate (XLIX) is depicted below in Scheme 9.

2H), 7.90 (s, 1H), 8.47 (s, 1H), 8.57 (s, 1H). ESIMS found for C$_6$H$_6$BrNO m/z 188.0 (M+H).

Step 2

To a stirred solution of (5-bromopyridin-3-yl)methanol (XLV) (1.60 g, 8.5 mmol, 1 eq), phthalimide (1.24 g, 8.5 mmol, 1 eq) and PPh$_3$ (3.33 g, 12.75 mmol, 1.5 eq) in anhydrous THF (15 mL) was added DEAD (2.21 g, 12.75 mmol, 1.5 eq) dropwise at 0° C. under N$_2$. Then the reaction mixture was stirred at room temperature for 6 h. The mixture was washed with saturated NaHCO$_3$ solution (15 mL), water (15 mL) and brine (15 mL) subsequently. The organic layers were dried over MgSO$_4$, concentrated under reduced pressure, the resultant residue was purified by flash chromatography on silica gel (PE:EtOAc=4:1) to give 2-((5-bromopyridin-3-yl)methyl)isoindoline-1,3-dione (XLVI) (2.5 g, 7.88 mmol, 82.3% yield) as a white solid. ESIMS found for C$_{14}$H$_9$BrN$_2$O$_2$ m/z 317.1 (M+H).

Step 3

A solution of 2-((5-bromopyridin-3-yl)methyl)isoindoline-1,3-dione (XLVI) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite® pad and the filtrate was concentrated in vacuo, the crude product was dissolved in 1N HCl solution (15 mL) and concentrated to dryness, then it was washed with acetone (10 mL×3), the precipitate was collected by filtration, dried in vacuo to give (5-bromopyridin-3-yl)methanamine (XLVII) (1.3 g, 6.95 mmol, 97.7% yield) as a white solid. $^1$H NMR (D$_2$O, 500 MHz) δ ppm 4.34 (s, 2H), 8.56 (s, 1H), 8.75 (d, J=1.2 Hz, 1H), 8.91 (d, J=1.6 Hz, 1H). ESIMS found for C$_6$H$_7$BrN$_2$ m/z 187.0 (M+H).

Scheme 9

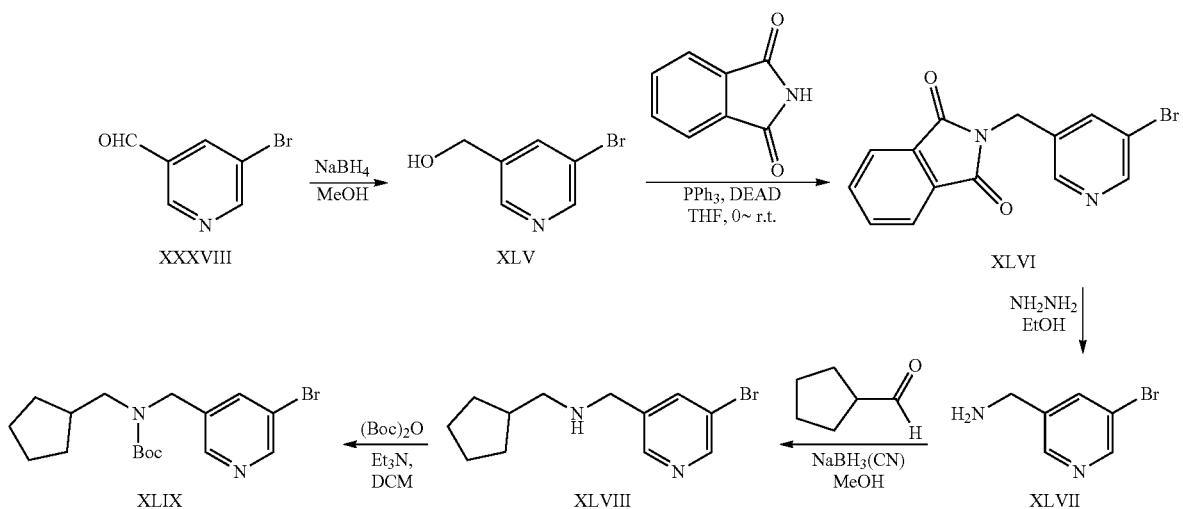

Step 1

To a solution of 5-bromonicotinaldehyde (XXXVIII) (2.0 g, 10.8 mmol, 1 eq) in MeOH (20 mL) was added NaBH$_4$ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over MgSO$_4$, filtered and concentrated in vacuo to afford (5-bromopyridin-3-yl)methanol (XLV) (1.8 g, 9.57 mmol, 90.0% yield) as a colorless oil. $^1$H NMR (CDCl$_3$, 500 MHz) δ ppm 4.73 (s, Step 4

A solution of (5-bromopyridin-3-yl)methanamine (XLVII) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then NaBH$_3$CN (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over MgSO$_4$ and concentrated in vacuo to give 1-(5-bromopyridin-3-yl)-N-(cyclopentylmethyl)methanamine (XLVIII) (1.23 g, 4.57 mmol, 79.3% yield) as a yellow oil. $^1$H NMR (CDCl$_3$, 400 MHz) δ ppm 1.07-1.23 (m, 2H), 1.47-1.67 (m, 4H), 1.70-1.84 (m, 2H), 2.02 (spt, J=7.6 Hz, 1H), 2.53 (d, J=7.2 Hz, 2H), 3.80 (s, 2H), 7.86 (s, 1H), 8.47 (s, 1H), 8.56 (d, J=2.0 Hz, 1H); ESIMS found for C$_{12}$H$_{17}$BrN$_2$ m/z 269.1 (M+H).

Step 5

To a solution of 1-(5-bromopyridin-3-yl)-N-(cyclopentylmethyl)methanamine (XLVIII) (1.00 g, 3.7 mmol, 1 eq) and TEA (0.93 g, 9.2 mmol, 2.5 eq) in DCM (20 mL) was added portion wise Boc$_2$O (0.85 g, 4.0 mmol, 1.1 eq) at 0° C., the reaction mixture was stirred at room temperature for 1 h. The mixture was washed with water (10 mL), brine (10 mL), the organic layer was separated, dried over MgSO$_4$ and concentrated in vacuo to give tert-butyl (5-bromopyridin-3-yl)methyl(cyclopentylmethyl) carbamate (XLIX) (1.25 g, 3.38 mmol, 91.9% yield) as a white solid. ESIMS found for C$_{17}$H$_{25}$BrN$_2$O$_2$ m/z 369.1 (M+H).

Preparation of intermediate 3-bromo-5-(cyclohexyloxy)pyridine (LII) is depicted below in Scheme 10.

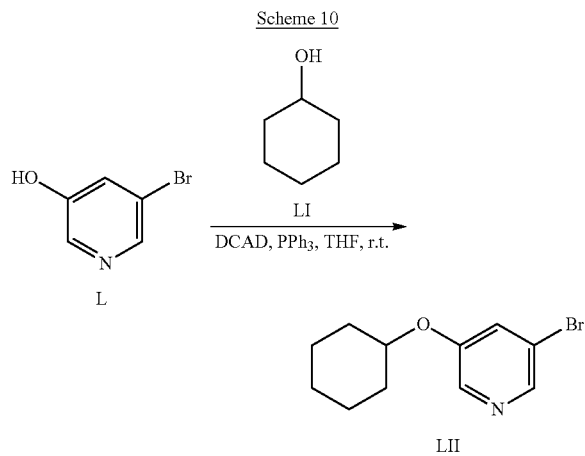

Step 1

To a solution of 5-bromopyridin-3-ol (L) (523 mg, 3.01 mmol) in THF (30 mL) cooled to 0° C. were added triphenylphosphine (867 mg, 3.31 mmol) and cyclohexanol (LI) (331 mg, 3.31 mmol) followed by (E)-bis(4-chlorobenzyl)diazene-1,2-dicarboxylate (1.21 g, 3.31 mmol), added portion wise. The reaction mixture was then stirred at 25° C. overnight. The reaction was worked-up with an EtOAc—NaHCO$_3$ extraction and the solid filtered off. The solvent was removed and the residue was purified by ISCO (20% EtOAc-hexanes) to give 3-bromo-5-(cyclohexyloxy)pyridine (LII) (209 mg, 0.82 mmol, 27.2% yield) as a yellow oil. $^1$H NMR (DMSO-d$_6$, 500 MHz) δ ppm 1.21-1.31 (m, 1 H) 1.34-1.48 (m, 4 H) 1.49-1.57 (m, 1 H) 1.70 (br dd, J=9.74, 4.25 Hz, 2 H) 1.88-1.96 (m, 2 H) 2.50 (dt, J=3.70, 1.72 Hz, 5 H) 4.46-4.54 (m, 1 H) 7.72 (t, J=2.20 Hz, 1 H) 8.24 (d, J=1.92 Hz, 1 H) 8.27 (d, J=2.47 Hz, 1 H).

The following intermediate was prepared in accordance with the procedure described in the above Scheme 10.

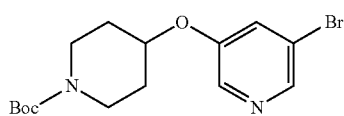

tert-Butyl 4-((5-bromopyridin-3-yl)oxy)piperidine-1-carboxylate (LIII): Yellow oil (244 mg, 0.683 mmol, 23.2% yield). ESIMS found for C$_{15}$H$_{21}$BrN$_2$O$_3$ m/z 358.3 (M+H).

Preparation of intermediate 3-(benzyloxy)-5-bromopyridine (LV) is depicted below in Scheme 11.

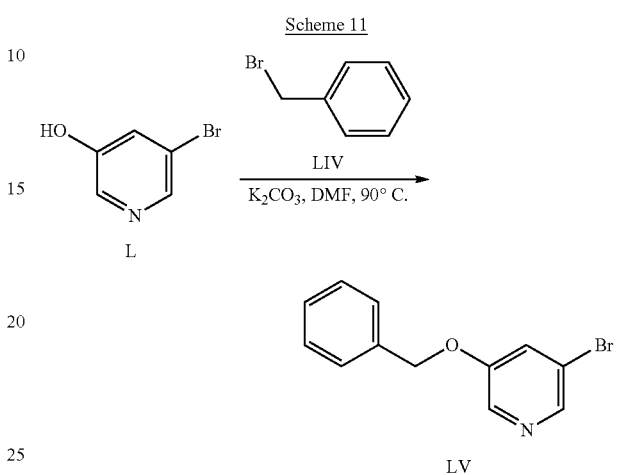

Step 1

To a solution of 5-bromopyridin-3-ol (L) (174 mg, 1.0 mmol) in DMF (3 mL) was added potassium carbonate (415 mg, 3.0 mmol). The slurry was heated at 90° C. for 1 h and then cooled to 25° C. The (bromomethyl)benzene (LIV) (171 mg, 1.0 mmol) was added and the mixture was stirred at 25° C. overnight. The reaction was worked-up using a saturated sodium bicarbonate and EtOAc extraction. The product was purified by ISCO column (40-100% EtOAc-hexanes). The 3-(benzyloxy)-5-bromopyridine (LV) (105 mg, 0.398 mmol, 39.8% yield) was obtained as yellow oil. ESIMS found for C$_{12}$H$_{10}$BrNO m/z 266.1 (M+H).

The following intermediates were prepared in accordance with the procedure described in the above Scheme 11.

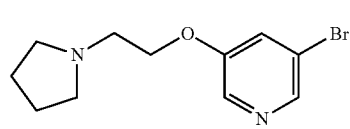

3-Bromo-5-(2-(pyrrolidin-1-yl)ethoxy)pyridine (LVI): Yellow oil (97 mg, 0.358 mmol, 15.56% yield). ESIMS found for C$_{11}$H$_{15}$BrN$_2$O m/z 272.2 (M+H).

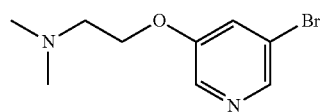

2-((5-Bromopyridin-3-yl)oxy)-N,N-dimethylethan-1-amine (LVII): Yellow oil (97 mg, 0.396 mmol, 28.9% yield). ESIMS found for C$_9$H$_{13}$BrN$_2$O m/z 245.1 (M+H).

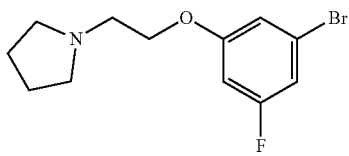

1-(2-(3-Bromo-5-fluorophenoxy)ethyl)pyrrolidine (LVIII): Yellow oil (370 mg, 1.284 mmol, 85.8% yield). ESIMS found for $C_{12}H_{15}BrFNO$ m/z 289.0 (M+H).

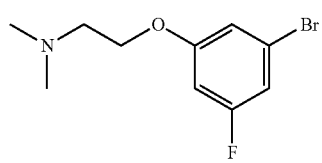

2-(3-Bromo-5-fluorophenoxy)-N,N-dimethylethan-1-amine (LIX): Yellow oil (364 mg, 1.389 mmol, 50.2% yield). ESIMS found for $C_{10}H_{13}BrFNO$ m/z 263.9 (M+H).

Preparation of intermediate tert-butyl 4-(2-((5-bromopyridin-3-yl)amino)-2-oxoethyl)piperidine-1-carboxylate (LXI) is depicted below in Scheme 12.

Scheme 12

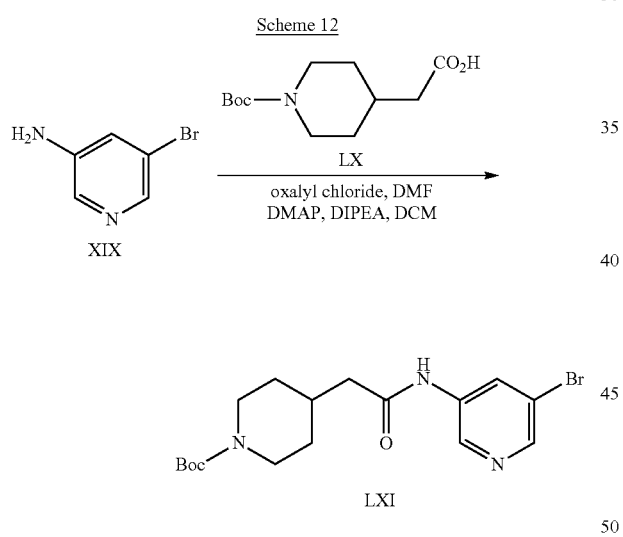

Step 1

To a solution of 2-(1-(tert-butoxycarbonyl)piperidin-4-yl)acetic acid (LX) (3.4 g, 13.97 mmol) in DCM (10 mL) was added DMF (1 mL). The solution was cooled in ice-water to 0° C. Oxalyl chloride (1.835 mL, 20.96 mmol) was then added dropwise. The mixture was stirred for 1 h at 25° C. The organic volatile was then removed under vacuum. The residue was dissolved in DCM (10 mL). DMAP (0.171 g, 1.397 mmol) and 5-bromopyridin-3-amine (XIX) (2.418 g, 13.97 mmol) were added to the solution and cooled to 0° C. DIPEA (4.88 ml, 27.9 mmol) was then added dropwise and the mixture was stirred for 2 h at 25° C. The reaction was worked-up with DCM and saturated NaHCO₃. The product was purified by ISCO (0-100% EtOAc-hexanes). The tert-butyl 4-(2-((5-bromopyridin-3-yl)amino)-2-oxoethyl)piperidine-1-carboxylate (LXI) (2.82 g, 7.08 mmol, 50.7% yield) was obtained as a yellow oil. ESIMS found for $C_{17}H_{24}BrN_3O_3$ m/z 343.1 (M-56).

The following intermediate was prepared in accordance with the procedure described in the above Scheme 12.

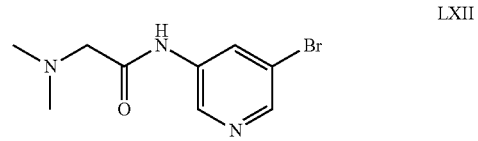

N-(5-Bromopyridin-3-yl)-2-(dimethylamino)acetamide (LXII): Yellow oil (528 mg, 2.05 mmol, 19.0% yield). ESIMS found for $C_9H_{12}BrN_3O$ m/z 259.3 (M+H).

Preparation of intermediate tert-butyl (1-(6-chloropyrazin-2-yl)azetidin-3-yl)carbamate (LXV) is depicted below in Scheme 13.

Scheme 13

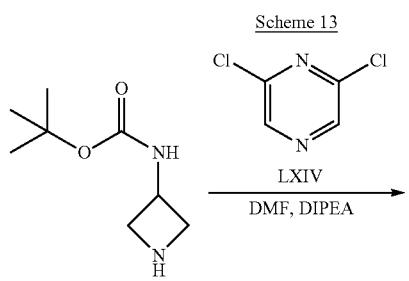

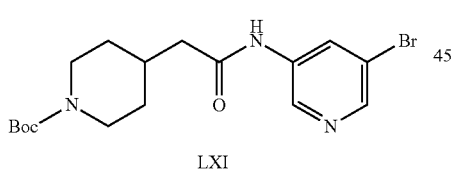

Step 1

To a solution of tert-butyl azetidin-3-ylcarbamate hydrochloride (LXIII) (2 g, 9.58 mmol) in dry DMF (19.2 mL) was added DIPEA (8.37 ml, 47.9 mmol). To this mixture was added 2,6-dichloropyrazine (LXIV) (1.428 g, 9.58 mmol) and the reaction was stirred at 95° C. for 3 h. The reaction was quenched with water (20 mL) and extracted with EtOAc. The organic layer was dried over anhydrous Na₂SO₄, filtered and concentrated. The residue was purified by silica gel column chromatography (40 g) (100% hexanes-hexanes:EtOAc 1:1) to yield tert-butyl (1-(6-chloropyrazin-2-yl)azetidin-3-yl)carbamate (LXV) (2.2882 g, 8.04 mmol, 84% yield) as a white solid. ESIMS found for $C_{12}H_{17}ClN_4O_2$ m/z 285.1 (M+H).

Preparation of intermediate N-(3-fluoro-5-(4,4,5,5-tetramethyl-1,3,2-dioxaborolan-2-yl)benzyl)methanesulfonamide (LXIX) is depicted below in Scheme 14.

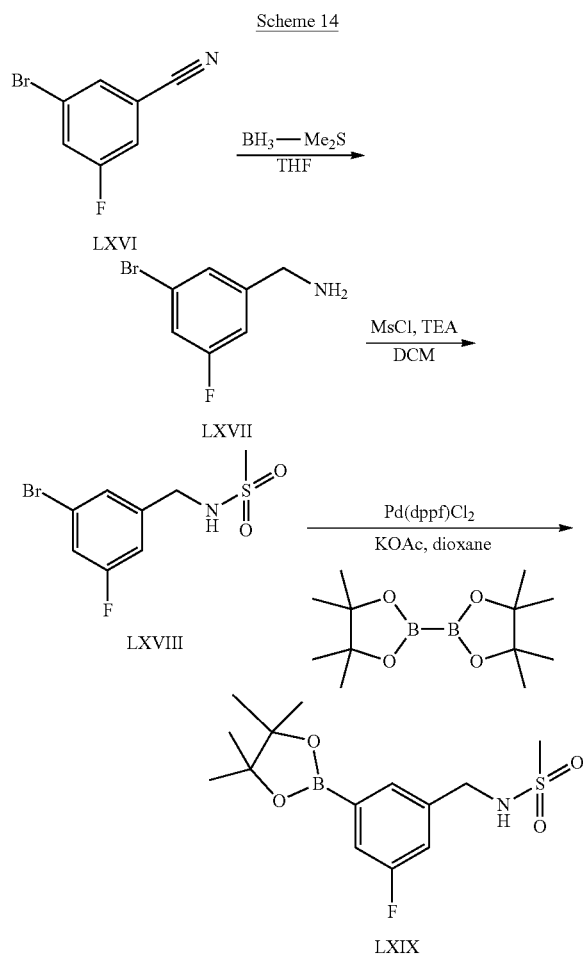

Step 1

A solution of 3-bromo-5-fluorobenzonitrile (LXVI) (44.0 g, 220.0 mmol, 1.0 eq) was dissolved in THF (30 mL). BH$_3$-Me$_2$S (33.43 g, 440.0 mmol, 2.0 eq) was added to the solution at 20° C. Then it was stirred at 80° C. for 2 h, HCl (6 N, 100 mL) was added to the mixture slowly at 20° C. The mixture was stirred at 80° C. for 1 h, then it was washed with EtOAc (300 mL). The water phase was basified with 50% aqueous NaOH and it was extracted with EtOAc (300 mL×3). The combined organic layers were dried over anhydrous Na$_2$SO$_4$ and concentrated in vacuo to produce (3-bromo-5-fluoro-phenyl)methanamine (LXVII) (24.0 g, 117.62 mmol, 53.5% yield). $^1$H NMR (CDCl$_3$, 300 MHz) ppm 3.86 (s, 2H), 7.01 (d, J=8 Hz, 1H), 7.12 (d, J=8 Hz, 1H), 7.28 (s, 1H); ESIMS found C$_7$H$_7$BrFN m/z 203.9 (Br$^{79}$M+H).

Step 2

A solution of (3-bromo-5-fluoro-phenyl)methanamine (LXVII) (23.0 g, 112.7 mmol, 1.0 eq) was dissolved in DCM (15 mL), TEA (34.22 g, 338.2 mmol, 3.0 eq) was added to the mixture. Then MsCl (13.44 g, 117.3 mmol, 1.04 eq) was added slowly to the solution at 0° C. It was stirred at 0-30° C. for 2 h. The reaction was washed with water and extracted with EtOAc. The combined organic layers were dried over anhydrous Na$_2$SO$_4$ and concentrated to give N-(3-bromo-5-fluorobenzyl)methanesulfonamide (LXVIII) (34.0 g, 102.44 mmol, 90.9% yield, 85% purity) as an oil. $^1$H NMR (CDCl$_3$, 300 MHz) ppm 2.88 (s, 3H), 4.24 (d, J=4.5 Hz, 2H), 6.99 (d, J=9 Hz, 1H), 7.13 (dt, J=8.1 Hz, J=2 Hz, 1H), 7.25 (s, 1H); ESIMS found C$_8$H$_9$BrFNO$_2$S m/z 282.0 (Br$^{79}$M+H).

Step 3

A solution of N-(3-bromo-5-fluorobenzyl)methanesulfonamide (LXVIII) (34.0 g, 102.4 mmol, 1.0 eq) and 4,4,5,5-tetramethyl-2-(4,4,5,5-tetramethyl-1,3,2-dioxaborolan-2-yl)-1,3,2-dioxaborolane (52.02 g, 204.9 mmol, 2.0 eq), KOAc (20.11 g, 204.9 mmol, 2.0 eq) was dissolved in dioxane (20 mL). Then Pd(dppf)Cl$_2$ (7.60 g, 10.2 mmol, 0.1 eq) was added to the mixture. It was stirred at 90° C. for 2 h. Then the solvent was removed to get the residue which was purified by silica gel column (PE:EtOAc=10:1→100% EtOAc) to get N-(3-fluoro-5-(4,4,5,5-tetramethyl-1,3,2-dioxaborolan-2-yl)benzyl)methanesulfonamide (LXIX) (30.0 g, crude). $^1$H NMR (CDCl$_3$, 400 MHz) δ ppm 1.37 (s, 12H), 2.92 (s, 3H), 4.34 (d, J=6.3 Hz, 2H), 7.19 (dt, J=9.3 Hz, J=2.1 Hz, 1H), 7.44 (dd, J=8.7 Hz, J=2.4 Hz, 1H), 7.54 (s, 1H); ESIMS found C$_{14}$H$_{21}$BFNO$_4$S m/z 330.1 (M+H).

Preparation of intermediate N-(3-fluoro-5-(4,4,5,5-tetramethyl-1,3,2-dioxaborolan-2-yl)benzyl) methanesulfonamide (LXXIII) is depicted below in Scheme 15.

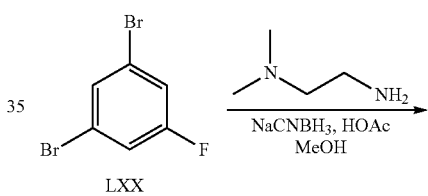

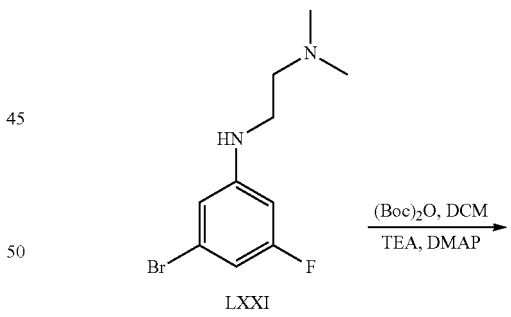

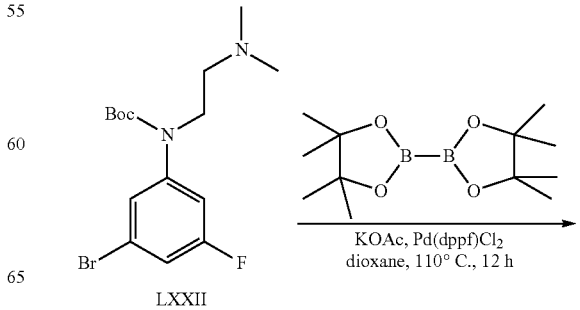

-continued

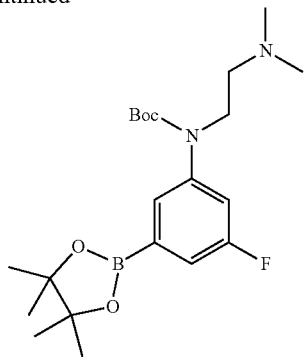

LXXIII

Step 1

To mixture of 1,3-dibromo-5-fluorobenzene (LXX) (100 g, 393 mmol) and N',N'-dimethylethane-1,2-diamine (173 g, 1.97 mol, 214 mL) was added t-BuOK (88 g, 787 mmol) in one portion at 25° C. under $N_2$. The mixture was stirred at 25° C. for 30 min, then heated to 110° C. and stirred for 11.5 h. The mixture was cooled to 25° C. and concentrated in reduced pressure at 45° C. The residue was purified by silica gel chromatography (column height: 250 mm, diameter: 100 mm, 100-200 mesh silica gel, PE/EtOAc=2:1, Rf=0.6) to give $N^1$-(3-bromo-5-fluorophenyl)-$N^2$,$N^2$-dimethylethane-1,2-diamine (LXXI) (30 g, 114.9 mmol, 29.2% yield) as a yellow oil. ESIMS found for $C_{10}H_{14}BrFN_2$ m/z 261.1 (M+H).

Step 2

To a mixture of N'-(3-bromo-5-fluorophenyl)-$N^2$,$N^2$-dimethylethane-1,2-diamine (LXXI) (30 g, 114 mmol) in DCM (200 mL) was added $(Boc)_2O$ (37.6 g, 172 mmol), TEA (34.8 g, 344 mmol) and DMAP (7 g, 57.4 mmol) in one portion at 25° C. under $N_2$. The mixture was stirred at 25° C. for 12 h. The mixture was concentrated in reduced pressure at 45° C. The residue was purified by silica gel chromatography (column height: 250 mm, diameter: 100 mm, 100-200 mesh silica gel, PE/EtOAc=2:1, $R_f$=0.43) to give tert-butyl (3-bromo-5-fluorophenyl)(2-(dimethylamino)ethyl)carbamate (LXXII) (20 g, 55.4 mmol, 48.2% yield) as yellow oil. $^1$H NMR ($CDCl_3$, 400 MHz) δ ppm 1.43 (s, 9H), 2.21 (s, 6H), 2.41 (t, J=7 Hz, 2H), 3.67 (t, J=7.2 Hz, 2H), 6.96 (d, J=9.6 Hz, 1H), 7.06 (d, J=6 Hz, 1H), 7.22 (s, 1H); ESIMS found for $C_{15}H_{22}BrFN_2O_2$ m/z 361.0 (M+H).

Step 3

To a mixture of tert-butyl (3-bromo-5-fluorophenyl)(2-(dimethylamino)ethyl) carbamate (LXXII) (19 g, 52.6 mmol) and bis(pinacolato)diboron (20 g, 78.9 mmol) in dioxane (60 mL) was added $Pd(dppf)Cl_2$ (3.8 g, 5.26 mmol) and KOAc (30.9 g, 315.6 mmol) in one portion at 25° C. under $N_2$. The mixture was stirred at 25° C. for 30 min, then heated to 110° C. and stirred for 11.5 h. The mixture was cooled to 25° C. and concentrated in reduced pressure at 45° C. The residue was purified by silica gel chromatography (column height: 250 mm, diameter: 100 mm, 100-200 mesh silica gel, PE/EtOAc=1:1, Rf=0.24) to give tert-butyl (2-(dimethylamino)ethyl)(3-fluoro-5-(4,4,5,5-tetramethyl-1,3,2-dioxaborolan-2-yl)phenyl)carbamate (LXXIII) (15 g, 36.7 mmol, 69.8% yield) as yellow oil. ESIMS found for $C_{21}H_{34}BFN_2O_4$ m/z 327.2 (M+H as the boronic acid).

Preparation of intermediate (1-(tert-butoxycarbonyl)-4-(3-fluorophenyl)-1H-pyrrolo[2,3-b]pyridin-2-yl)boronic acid (LXXVIII) is depicted below in Scheme 16

Scheme 16

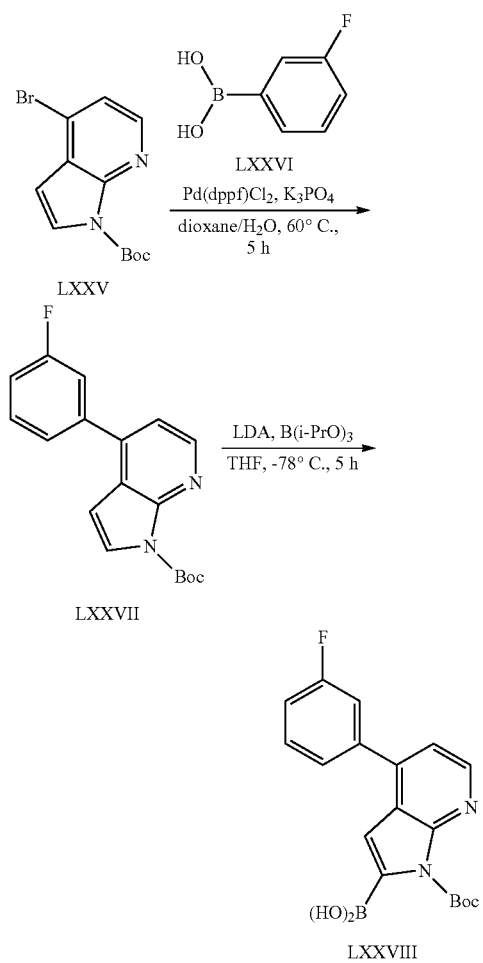

Step 1

To a solution of 4-bromo-1H-pyrrolo[2,3-b]pyridine (LXXIV) (5 g, 25.4 mmol, 1 eq.), DMAP (311 mg, 2.55 mmol, 0.1 eq.) and TEA (5.3 mL, 38 mmol, 3 eq.) in DCM (100 mL) was added $Boc_2O$ (7.2 mL, 31 mmol, 1.2 eq.) at 0° C. The reaction was warmed to room temperature and stirred for 2 h. Water (100 mL) was added and extracted with DCM (×2). Removal solvents gave tert-butyl 4-bromo-1H-pyrrolo[2,3-b]pyridine-1-carboxylate (LXXV) as a colorless oil (6.95 g, 23.4 mmol, 92.1% yield). $^1$H NMR ($CDCl_3$, 400 MHz) δ ppm 1.60 (s, 9H), 6.50 (d, J=4 Hz, 1H), 7.31 (d, J=5.2 Hz, 1H), 7.63 (d, J=4 Hz, 1H), 8.23 (d, J=5.2 Hz, 1H); ESIMS found for $C_{12}H_{13}BrN_2O_2$ m/z 297.1 (M+H).

Step 2

To a solution of tert-butyl 4-bromo-1H-pyrrolo[2,3-b]pyridine-1-carboxylate (LXXV) (1.5 g, 5.1 mmol, 1.0 eq)

and (3-fluorophenyl)boronic acid (LXXVI) (1.07 g, 7.65 mmol, 1.1 eq) in a mixture solvent of dioxane (18 mL) and water (6 mL) was added $K_3PO_4$ (2.11 g, 15.3 mmol, 2.5 eq). The suspension was purged with nitrogen (×3) followed by addition of Pd(dppf)Cl$_2$ (373 mg, 0.51 mmol, 0.1 eq). The reaction was stirred at 60° C. for 5 h. The suspension was poured into water (10 mL) and extracted with EtOAc (10 mL×3). The combined organic layer was washed with brine (5 mL), dried over Na$_2$SO$_4$ and concentrated under reduced pressure. Then the crude product was purified by column chromatography on silica gel to afford tert-butyl 4-(3-fluorophenyl)-1H-pyrrolo[2,3-b]pyridine-1-carboxylate (XLXXVII) as a white solid (1.37 g, 4.39 mmol, 86.0% yield). $^1$H NMR (CDCl$_3$, 400 MHz) δ ppm 1.69 (s, 9H), 6.68 (d, J=4 Hz, 1H), 7.17 (dt, J=2 Hz, J=8.4 Hz, 1H), 7.25 (d, J=4.8 Hz, 1H), 7.35 (d, J=12 Hz, 1H), 7.41-7.53 (m, 2H), 7.70 (d, J=4 Hz, 1H), 8.57 (d, J=4.8 Hz, 1H); ESIMS found for $C_{18}H_{17}FN_2O_2$ m/z 313.1 (M+H).

Step 3

To a solution of tert-butyl 4-(3-fluorophenyl)-1H-pyrrolo[2,3-b]pyridine-1-carboxylate (LXXVII) (1.37 g, 4.4 mmol, 1.0 eq) and triisopropyl borate (2.06 g, 10.9 mmol, 2.5 eq) in THF (10 mL), was added dropwise LDA (2 M, 5.45 mL, 10.9 mmol, 2.5 eq) at −78° C. under N$_2$. The reaction was stirred at this temperature for 5 h. The reaction was acidified with 1N HCl at −45° C. until pH<2. The aqueous phase was extracted with EtOAc (20 mL×3). The combined organic phase was washed with cooled 1N NaOH (50 ml×2). The aqueous was added ice and acidified with 1N HCl. The cloud solution was extracted with EtOAc (×2). The organic phase was separated and dried with Na$_2$SO$_4$. The solvent was removed under reduced pressure to give crude (1-(tert-butoxycarbonyl)-4-(3-fluorophenyl)-1H-pyrrolo[2,3-b]pyridin-2-yl)boronic acid (LXXVIII) as a brown solid (0.98 g, 2.75 mmol, 62.5% yield). ESIMS found for $C_{18}H_{18}BFN_2O_4$ m/z 357.0 (M+H).

The following intermediate was prepared in accordance with the procedure described in the above Scheme 16.

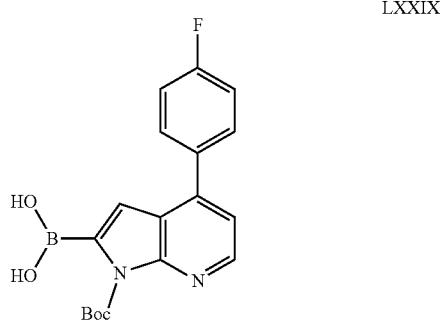 [SMILES: CC(C)(C)OC(=O)n1c(B(O)O)cc2c(-c3ccc(F)cc3)ccnc21]

LXXIX (1-(tert-Butoxycarbonyl)-4-(4-fluorophenyl)-1H-pyrrolo[2,3-b]pyridin-2-yl)boronic acid (LXXIX): White solid (580 mg, 1.63 mmol, 37.0% yield). $^1$H NMR (DMSO-d6, 400 MHz) δ ppm 1.60 (s, 9H), 7.36 (d, J=4.8 Hz, 1H), 7.41 (t, J=8.8 Hz, 2H), 7.78 (dd, J=5.6 Hz, J=9.2 Hz, 2H), 8.36 (s, 2H), 8.42 (d, J=5.2 Hz, 2H); ESIMS found for $C_{18}H_{18}BFN_2O_4$ m/z 357.0 (M+H).

Preparation of intermediate (1-(tert-butoxycarbonyl)-1H-pyrrolo[2,3-b]pyridin-2-yl)boronic acid (LXXXII) is depicted below in Scheme 17

Scheme 17

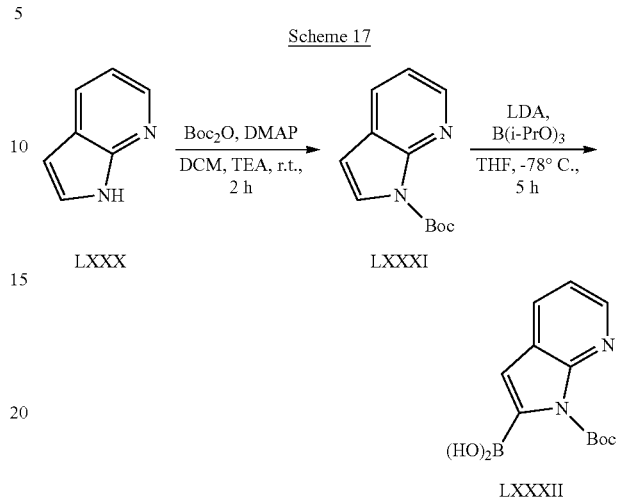

LXXX         LXXXI

LXXXII

Step 1

To a solution of 1H-pyrrolo[2,3-b]pyridine (LXXX) (2.0 g, 16.9 mmol, 1 eq.), DMAP (103 mg, 0.84 mmol, 0.05 eq.) and TEA (12.7 mL, 50.7 mmol, 3 eq.) in DCM (30 mL) was added Boc$_2$O (4.7 mL, 18.6 mmol, 1.1 eq.) at 0° C. The reaction was warmed to room temperature and stirred for 2 h. Water (50 mL) was added and extracted with DCM (×2). Removal solvents gave tert-butyl 1H-pyrrolo[2,3-b]pyridine-1-carboxylate (LXXXI) as a yellow oil (3.4 g, 15.6 mmol, 92.2% yield). ESIMS found for $C_{12}H_{14}N_2O_2$ m/z 219.1 (M+H).

Step 2

To a solution of tert-butyl 1H-pyrrolo[2,3-b]pyridine-1-carboxylate (LXXXI) (1.1 g, 5.0 mmol, 1.0 eq) and triisopropyl borate (2.0 g, 11.0 mmol, 2.2 eq) in THF (20 mL), was added dropwise LDA (2 M, 5.0 mL, 10.0 mmol, 2.0 eq) at −78° C. under N$_2$. The reaction was stirred at this temperature for 5 h. The reaction was acidified with 1N HCl at −45° C. until pH<2. The aqueous phase was extracted with EtOAc (20 mL×3). The combined organic phase was washed with cooled 1N NaOH (50 mL×2). The aqueous was added ice and acidified with 1N HCl. The cloud solution was extracted with EtOAc (×2). The organic phase was separated and dried with Na$_2$SO$_4$. The solvent was removed under reduced pressure to give crude (1-(tert-butoxycarbonyl)-1H-pyrrolo[2,3-b]pyridin-2-yl)boronic acid (LXXXII) as a white solid (0.89 g, 3.39 mmol, 67.9% yield). ESIMS found for $C_{12}H_{15}BN_2O_4$ m/z 263.1 (M+H).

Preparation of intermediate (1-(tert-butoxycarbonyl)-4-(pyridin-2-yl)-1H-pyrrolo[2,3-b]pyridin-2-yl)boronic acid (LXXXVI) is depicted below in Scheme 18

Scheme 18

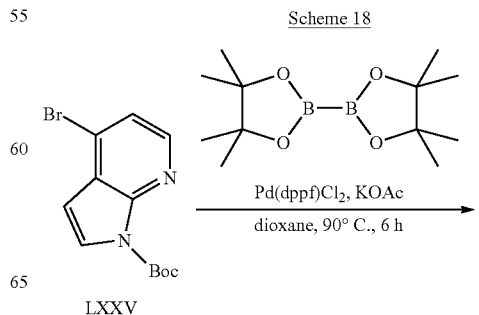

LXXV

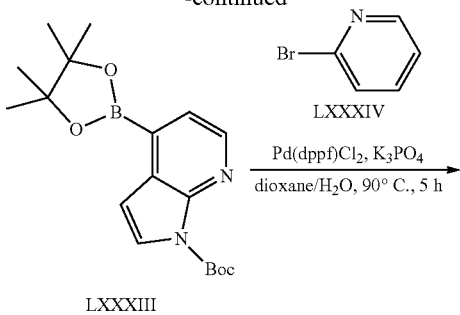

LXXXIII

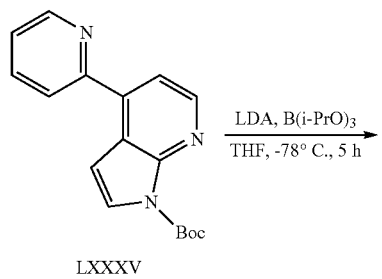

LXXXV

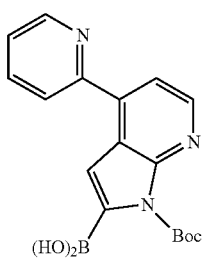

LXXXVI

Step 1

A solution of tert-butyl 4-bromo-1H-pyrrolo[2,3-b]pyridine-1-carboxylate (LXXV) (2 g, 6.8 mmol, 1.0 eq), 4,4,5,5-tetramethyl-2-(4,4,5,5-tetramethyl-1,3,2-dioxaborolan-2-yl)-1,3,2-dioxaborolane (2.07 g, 8.16 mmol, 1.02 eq), KOAc (1.99 g, 20.4 mmol, 3 eq) in dioxane (25 mL) was degassed (×3) with a water pump. Pd(dppf)Cl$_2$ (246 mg, 0.34 mmol, 0.05 eq) was then added quickly in one portion under nitrogen. The reaction was stirred at 90° C. for 6 h. Water (100 mL) was added and extracted with EtOAc (×3). Flash chromatography (PE:EtOAc 20:1) gave tert-butyl 4-(4,4,5,5-tetramethyl-1,3,2-dioxaborolan-2-yl)-1H-pyrrolo[2,3-b]pyridine-1-carboxylate (LXXXIII) as a green oil (2.0 g, 5.82 mmol, 86.4%). $^1$H NMR (CDCl$_3$, 400 MHz) δ ppm 1.39 (s, 12H), 1.67 (s, 9H), 6.93 (d, J=4 Hz, 1H), 7.54 (d, J=4.8 Hz, 1H), 7.65 (d, J=4 Hz, 1H), 8.51 (d, J=4.4 Hz, 1H); ESIMS found for C$_{18}$H$_{25}$BN$_2$O$_4$ m/z 345.1 (M+H).

Step 2

The solution of tert-butyl 4-(4,4,5,5-tetramethyl-1,3,2-dioxaborolan-2-yl)-1H-pyrrolo[2,3-b]pyridine-1-carboxylate (LXXXIII) (890 mg, 2.59 mmol, 1.0 eq), 2-bromopyridine (LXXXIV) (410 mg, 2.59 mmol, 1.0 eq), K$_2$CO$_3$ (1.07 g, 7.77 mmol, 3 eq) in dioxane/water (11 mL 10:1) was degassed (×3) with a water pump. Pd(dppf)Cl$_2$ (95 mg, 0.13 mmol, 0.05 eq) was added quickly in one portion under nitrogen. The reaction was stirred at 90° C. for 5 h. Water (10 mL) was added and extracted with EtOAc (×3). Flash chromatography gave tert-butyl 4-(pyridin-2-yl)-1H-pyrrolo[2,3-b]pyridine-1-carboxylate (LXXXV) as a yellow solid (420 mg, 1.42 mmol, 54.9%). $^1$H NMR (CDCl$_3$, 400 MHz) δ ppm 1.69 (s, 9H), 7.10 (d, J=4 Hz, 1H), 7.36 (t, J=6 Hz, 1H), 7.58 (d, J=5.2 Hz, 1H), 7.72 (d, J=4 Hz, 1H), 7.80-7.86 (m, 2H), 8.62 (d, J=4.8 Hz, 1H), 8.82 (d, J=4.4 Hz, 1H); ESIMS found for C$_{17}$H$_{17}$N$_3$O$_2$ m/z 318.2 (M+Na).

Step 3

To a solution of tert-butyl 4-(pyridin-2-yl)-1H-pyrrolo[2,3-b]pyridine-1-carboxylate (LXXXV) (1.91 g, 6.5 mmol, 1.0 eq) and triisopropyl borate (3.05 g, 16.2 mmol, 2.5 eq) in THF (30 mL), was added dropwise LDA (2 M, 8.1 mL, 16.2 mmol, 2.5 eq) at −78° C. under N$_2$. The reaction was stirred at this temperature for 5 h. The reaction was acidified with 1N HCl at −45° C. until pH<2. The aqueous phase was extracted with EtOAc (20 mL×3). The combined organic phase was washed with cooled 1N NaOH (50 ml×2). The aqueous was added ice and acidified with 1N HCl. The cloud solution was extracted with EtOAc (×2). The organic phase was separated and dried with Na$_2$SO$_4$. The solvent was removed under reduced pressure to give crude (1-(tert-butoxycarbonyl)-4-(pyridin-2-yl)-1H-pyrrolo[2,3-b]pyridin-2-yl)boronic acid (LXXXVI) as a white solid (1.31 g, 3.86 mmol, 59.4% yield). ESIMS found for C$_{17}$H$_{18}$BN$_3$O$_4$ m/z 362.1 (M+Na).

Preparation of intermediate (1-(tert-butoxycarbonyl)-4-(4-methylpiperazin-1-yl)-1H-pyrrolo[2,3-b]pyridin-2-yl)boronic acid (XCI) is depicted below in Scheme 19

Scheme 19

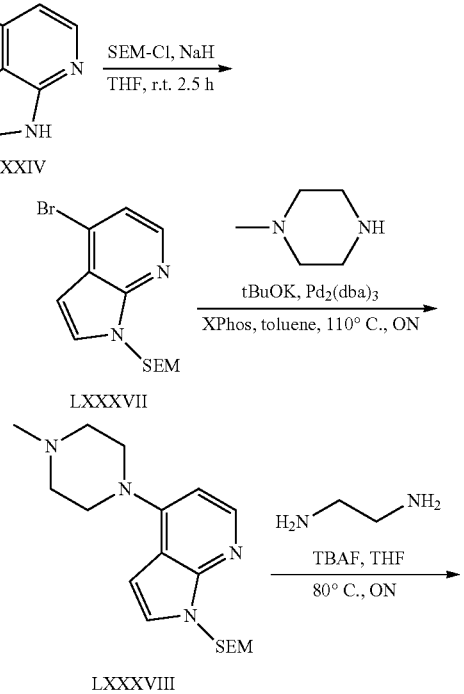

LXXIV

LXXXVII

LXXXVIII

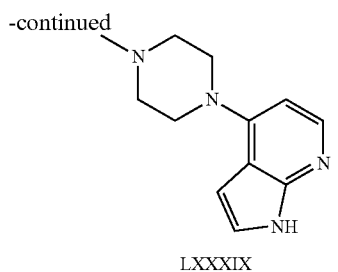

LXXXIX

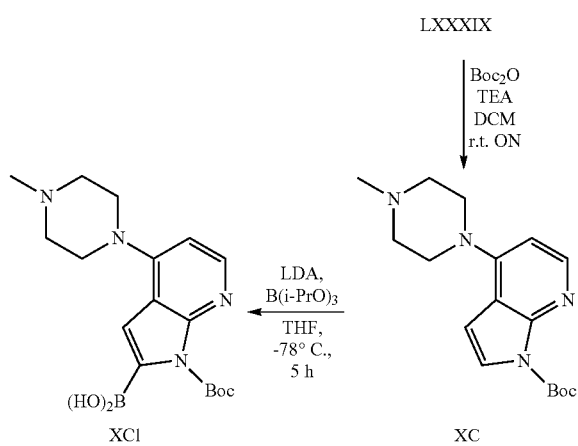

Step 1

A solution of 4-bromo-1H-pyrrolo[2,3-b]pyridine (LXXIV) (10 g, 50.8 mmol, 1.0 eq) in anhydrous THF (150 mL) was degassed (×3) with a water pump, then cooled to 0° C. under Ar. NaH (60% in mineral oil) (2.436 g, 60.9 mmol, 1.2 eq) was added portion wise slowly under Ar. The reaction was stirred at 0° C. for 30 min. (2-(chloromethoxy) ethyl)trimethylsilane (10.15 g, 60.9 mmol, 1.2 eq) was added dropwise slowly. The reaction was stirred at room temperature for 2.5 h. The reaction mixture was added water (2 mL) then was concentrated in vacuo and water (50 mL) was added and extracted with EtOAc (×3). The organic layer was washed with brine and dried over $Na_2SO_4$. Flash chromatography (PE:ETOAc=10:1) gave 4-bromo-1-((2-(trimethylsilyl)ethoxy)methyl)-1H-pyrrolo[2,3-b]pyridine (LXXXVII) as a yellow oil (14.38 g, 43.9 mmol, 86.6% yield). ESIMS found for $C_{13}H_{19}BrN_2OSi$ m/z 327.0 (M+H).

Step 2

A solution of 4-bromo-1-((2-(trimethylsilyl)ethoxy) methyl)-1H-pyrrolo[2,3-b]pyridine (LXXXVII) (3.27 g, 10 mmol, 1.0 eq), 1-methylpiperazine (2 g, 20 mmol, 2.0 eq), tBuOK (2.24 g, 20 mmol, 2.0 eq), $Pd_2(dba)_3$ (915 mg, 1.0 mmol, 0.1 eq), XPhos (953 mg, 2 mmol, 0.2 eq), and toluene (50 mL) was degassed (×3) with a water pump. The reaction was stirred at 110° C. for overnight. The reaction mixture was concentrated in vacuo and water (50 mL) was added and extracted with DCM (×3). The organic layer was washed with brine and dried over $Na_2SO_4$. Flash chromatography (DCM:MeOH=40:1) gave 4-(4-methylpiperazin-1-yl)-1-((2-(trimethylsilyl) ethoxy)methyl)-1H-pyrrolo[2,3-b]pyridine (LXXXVIII) as a yellow oil (2.81 g, 8.1 mmol, 81.1% yield). ESIMS found for $C_{18}H_{30}N_4OSi$ m/z 347.3 (M+H).

Step 3

A solution of 4-(4-methylpiperazin-1-yl)-1-((2-(trimethylsilyl)ethoxy) methyl)-1H-pyrrolo[2,3-b]pyridine (LXXXVIII) (2.4 g, 6.92 mmol, 1.0 eq), ethane-1,2-diamine (1.25 g, 20.76 mmol, 3.0 eq), TBAF (5.43 g, 20.76 mmol, 3.0 eq) and anhydrous THF (50 mL) was degassed (×3) with a water pump. Then the reaction was stirred at 80° C. for overnight. The reaction mixture was concentrated in vacuo and DCM (200 mL) was added. The organic layer was washed with brine and dried over $Na_2SO_4$. Flash chromatography (DCM:MeOH=30:1) gave 4-(4-methylpiperazin-1-yl)-1H-pyrrolo[2,3-b]pyridine (LXXXIX) as a yellow solid (1.2 g, 5.55 mmol, 80.2% yield). ESIMS found for $C_{12}H_{16}N_4$ m/z 217.1 (M+H).

Step 4

To a solution of 4-(4-methylpiperazin-1-yl)-1H-pyrrolo [2,3-b]pyridine (LXXXIX) (1.2 g, 5.55 mmol, 1 eq.), DMAP (68 mg, 0.56 mmol, 0.1 eq.) and DIPEA (1.9 mL, 11.1 mmol, 2 eq.) in DCM (50 mL) was added $Boc_2O$ (2.42 g, 11.1 mmol, 2.0 eq.) at 0° C. The reaction was warmed to room temperature and stirred overnight. The reaction mixture was concentrated in vacuo. Flash chromatography with (DCM:MeOH=30:1) gave tert-butyl 4-(4-methylpiperazin-1-yl)-1H-pyrrolo[2,3-b]pyridine-1-carboxylate (XC) as a yellow oil (980 mg, 3.10 mmol, 55.8% yield). $^1$H NMR ($CDCl_3$, 400 MHz) δ ppm 1.65 (s, 9H), 2.37 (s, 3H), 2.61 (t, J=4.8 Hz, 4H), 3.42 (t, J=4.8 Hz, 4H), 6.47 (d, J=4 Hz, 1H), 6.55 (d, J=5.2 Hz, 1H), 7.47 (d, J=4 Hz, 1H), 8.28 (d, J=5.6 Hz, 1H); ESIMS found for $C_{17}H_{24}N_4O_2$ m/z 317.2 (M+H).

Step 5

To a solution of tert-butyl 4-(4-methylpiperazin-1-yl)-1H-pyrrolo[2,3-b]pyridine-1-carboxylate (XC) (1.05 g, 3.3 mmol, 1.0 eq) and triisopropyl borate (1.57 g, 8.4 mmol, 2.5 eq) in THF (30 mL), was added dropwise LDA (2 M, 4.2 mL, 8.4 mmol, 2.5 eq) at −78° C. under $N_2$. The reaction was stirred at this temperature for 5 h. The reaction was acidified with 1N HCl at −45° C. until pH<2. The aqueous phase was extracted with EtOAc (50 mL×3). The combined organic phase was washed with cooled 1N NaOH (50 mL×2). The aqueous was added ice and acidified with 1N HCl. The cloud solution was extracted with EtOAc (×2). The organic phase was separated and dried with $Na_2SO_4$. The solvent was removed under reduced pressure to give crude (1-(tert-butoxycarbonyl)-4-(4-methylpiperazin-1-yl)-1H-pyrrolo[2, 3-b]pyridin-2-yl)boronic acid (XCI) as a white solid (732 mg, 2.03 mmol, 61.6% yield). ESIMS found for $C_{17}H_{25}BN_4O_4$ m/z 361.1 (M+H).

The following intermediate was prepared in accordance with the procedure described in the above Scheme 19.

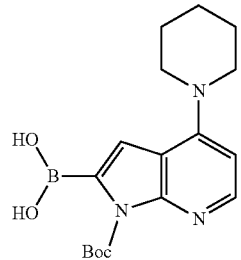

(1-(tert-Butoxycarbonyl)-4-(piperidin-1-yl)-1H-pyrrolo [2,3-b]pyridin-2-yl)boronic acid (XCII): White solid (580 mg, 1.68 mmol, 56.0% yield). ESIMS found $C_{17}H_{24}BN_3O_4$ m/z 346.1 (M+H).

Preparation of intermediate (4-(pyridin-3-yl)-1-((2-(trimethylsilyl)ethoxy) methyl)-1H-pyrrolo[2,3-b]pyridin-2-yl) boronic acid (XCV) is depicted below in Scheme 20.

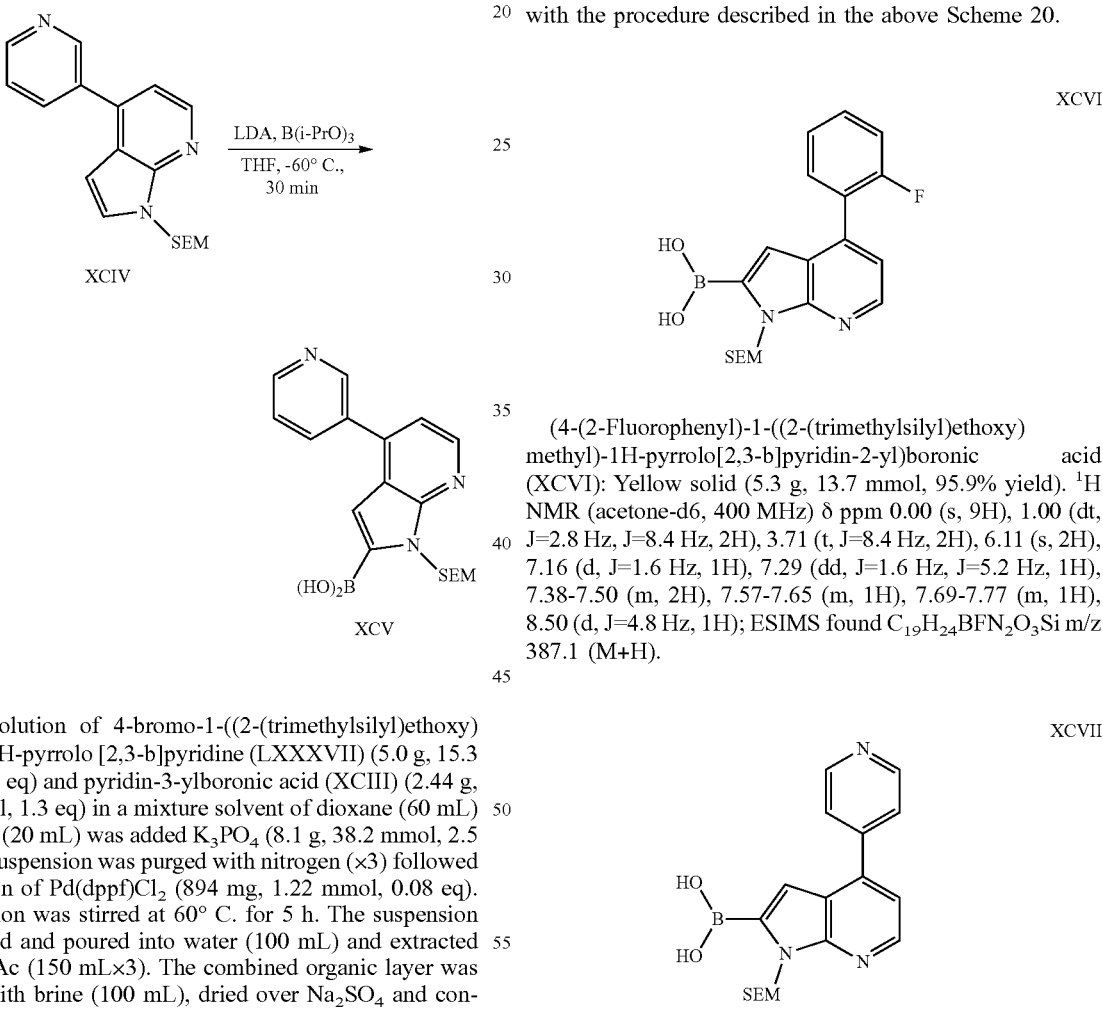

Step 1

To a solution of 4-bromo-1-((2-(trimethylsilyl)ethoxy) methyl)-1H-pyrrolo [2,3-b]pyridine (LXXXVII) (5.0 g, 15.3 mmol, 1.0 eq) and pyridin-3-ylboronic acid (XCIII) (2.44 g, 19.9 mmol, 1.3 eq) in a mixture solvent of dioxane (60 mL) and water (20 mL) was added $K_3PO_4$ (8.1 g, 38.2 mmol, 2.5 eq). The suspension was purged with nitrogen (×3) followed by addition of Pd(dppf)Cl$_2$ (894 mg, 1.22 mmol, 0.08 eq). The reaction was stirred at 60° C. for 5 h. The suspension was cooled and poured into water (100 mL) and extracted with EtOAc (150 mL×3). The combined organic layer was washed with brine (100 mL), dried over Na$_2$SO$_4$ and concentrated under reduced pressure. Then the residue was purified by silica gel chromatography (column height: 25 cm, diameter: 10 cm, 100-200 mesh silica gel) to afford 4-(pyridin-3-yl)-1-((2-(trimethylsilyl)ethoxy)methyl)-1H-pyrrolo[2,3-b]pyridine (XCIV) as a yellow oil (4.97 g, 15.3 mmol, 99.9% yield). ESIMS found for $C_{18}H_{23}N_3OSi$ m/z 326.0 (M+H).

Step 2

To a solution of 4-(pyridin-3-yl)-1-((2-(trimethylsilyl) ethoxy)methyl)-1H-pyrrolo[2,3-b]pyridine (XCIV) (3.8 g, 11.7 mmol, 1.0 eq) and triisopropyl borate (7.68 g, 40.6 mmol, 3.5 eq) in THF (65 mL), was added dropwise LDA (2 M, 23.3 mL, 46.7 mmol, 4.0 eq) at −78° C. under N$_2$. The reaction was stirred at this temperature for 30 min. The reaction was quench with buffer pH=7, then warmed to 25° C. and extracted with EtOAc (100 mL×3), washed with brine (50 mL), and dried with Na$_2$SO$_4$. The solvent was removed under reduced pressure to give crude (4-(pyridin-3-yl)-1-((2-(trimethylsilyl)ethoxy)methyl)-1H-pyrrolo[2,3-b]pyridin-2-yl) boronic acid (XCV) as a yellow solid (3.7 g, 10.0 mmol, 85.8% yield). $^1$H NMR (DMSO-d6, 400 MHz) δ ppm −0.12 (s, 9H), 0.79 (t, J=8 Hz, 2H), 3.49 (dt, J=4.8 Hz, J=8 Hz, 2H), 5.97 (s, 2H), 7.36 (dd, J=3.2 Hz, J=8 Hz, 2H), 7.75 (dd, J=4.8 Hz, J=8 Hz, 1H), 8.36 (d, J=8 Hz, 1H), 8.44 (d, J=4.8 Hz, 1H), 8.77 (dd, J=1.6 Hz, J=4.8 Hz, 1H), 9.08 (d, J=1.6 Hz, 1H); ESIMS found for $C_{18}H_{24}BN_3O_3Si$ m/z 370.1 (M+H).

The following intermediates were prepared in accordance with the procedure described in the above Scheme 20.

(4-(2-Fluorophenyl)-1-((2-(trimethylsilyl)ethoxy) methyl)-1H-pyrrolo[2,3-b]pyridin-2-yl)boronic acid (XCVI): Yellow solid (5.3 g, 13.7 mmol, 95.9% yield). $^1$H NMR (acetone-d6, 400 MHz) δ ppm 0.00 (s, 9H), 1.00 (dt, J=2.8 Hz, J=8.4 Hz, 2H), 3.71 (t, J=8.4 Hz, 2H), 6.11 (s, 2H), 7.16 (d, J=1.6 Hz, 1H), 7.29 (dd, J=1.6 Hz, J=5.2 Hz, 1H), 7.38-7.50 (m, 2H), 7.57-7.65 (m, 1H), 7.69-7.77 (m, 1H), 8.50 (d, J=4.8 Hz, 1H); ESIMS found $C_{19}H_{24}BFN_2O_3Si$ m/z 387.1 (M+H).

(4-(Pyridin-4-yl)-1-((2-(trimethylsilyl)ethoxy)methyl)-1H-pyrrolo[2,3-b]pyridin-2-yl)boronic acid (XCVII): Yellow solid (8.0 g, 21.7 mmol, 70.5% yield). $^1$H NMR (acetone-d6, 400 MHz) δ ppm 0.06 (s, 9H), 1.06 (dt, J=2.8 Hz, J=8.4 Hz, 2H), 3.76 (dt, J=2.8 Hz, J=8.4 Hz, 2H), 6.21 (s, 2H), 7.53 (s, 1H), 7.58 (d, J=5.2 Hz, 1H), 8.25 (d, J=6.4 Hz, 2H), 8.33 (brs, 2H), 8.65 (d, J=5.2 Hz, 1H), 9.10 (d, J=6 Hz, 1H); ESIMS found $C_{18}H_{24}BN_3O_3Si$ m/z 370.2 (M+H).

321

Preparation of intermediate (1-(tert-butoxycarbonyl)-4-(3-((tert-butoxycarbonyl)(2-(dimethylamino)ethyl)amino)-5-fluorophenyl)-1H-pyrrolo[2,3-b]pyridin-2-yl)boronic acid (CI) is depicted below in Scheme 21.

Scheme 21

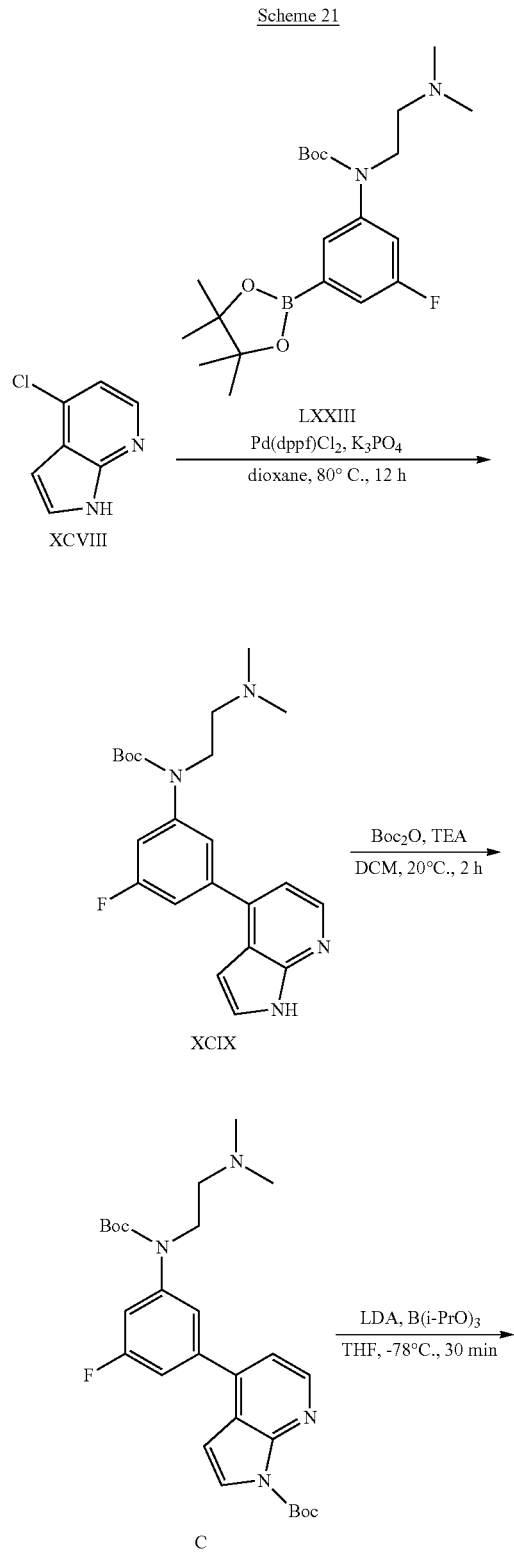

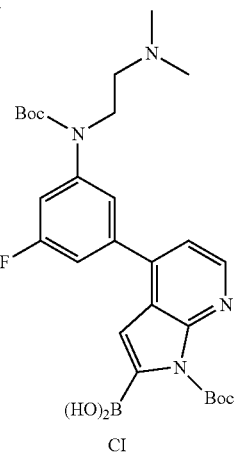

Step 1

To a solution of tert-butyl (2-(dimethylamino)ethyl)(3-fluoro-5-(4,4,5,5-tetramethyl-1,3,2-dioxaborolan-2-yl)phenyl)carbamate (LXXIII) (5.0 g, 12.2 mmol, 1.0 eq), 4-chloro-1H-pyrrolo[2,3-b]pyridine (XCVIII) (2.06 g, 13.5 mmol, 1.1 eq) and $K_2CO_3$ (3.4 g, 24.5 mmol, 2.0 eq), Pd(dppf)$Cl_2$ (896 mg, 1.22 mmol, 0.1 eq) in dioxane (100 mL) was de-gassed and then heated to 80° C. for 12 h under $N_2$. The suspension was poured into water (150 mL) and extracted with EtOAc (200 mL×2). The combined organic layers was washed with brine (100 mL), dried over $Na_2SO_4$ and concentrated under reduced pressure to give the crude product which was purified by silica gel (PE:EtOAc=30:1) to give tert-butyl (2-(dimethylamino)ethyl)(3-fluoro-5-(1H-pyrrolo[2,3-b]pyridin-4-yl)phenyl)carbamate (XCIX) (3.6 g, 9.06 mmol, 74.0% yield) as yellow oil. ESIMS found for $C_{22}H_{27}FN_4O_2$ m/z 399.1 (M+H).

Step 2

To a solution of tert-butyl (2-(dimethylamino)ethyl)(3-fluoro-5-(1H-pyrrolo[2,3-b]pyridin-4-yl)phenyl)carbamate (XCIX) (4.0 g, 10.0 mmol, 1.0 eq) and $Boc_2O$ (6.5 g, 30.0 mmol, 3.0 eq) in DCM (20 mL) was added $Et_3N$ (5.6 mL, 40.0 mmol, 4.0 eq) in one portion at 20° C. under $N_2$. The mixture was stirred at 20° C. for 12 h. The aqueous phase was extracted with DCM (50 mL×4). The combined organic phase was washed with brine (10 mL×2), dried with anhydrous $Na_2SO_4$, filtered and concentrated in vacuum to give tert-butyl 4-(3-((tert-butoxycarbonyl)(2-(dimethylamino)ethyl)amino)-5-fluorophenyl)-1H-pyrrolo[2,3-b]pyridine-1-carboxylate (C) as a yellow solid (2.0 g, 4.0 mmol, 40.0% yield). $^1$H NMR (CDCl$_3$, 400 MHz) δ ppm 1.49 (s, 9H), 1.70 (s, 9H), 2.27 (s, 6H), 2.52 (brs, 2H), 3.80 (t, J=6.4 Hz, 2H), 6.71 (d, J=4 Hz, 1H), 7.13 (d, J=10 Hz, 1H), 7.20 (d, J=8.8 Hz, 1H), 7.24 (d, J=5.2 Hz, 1H), 7.38 (s, 1H), 7.71 (d, J=4.4 Hz, 1H), 8.58 (d, J=4.8 Hz, 1H); ESIMS found for $C_{27}H_{35}FN_4O_4$ m/z 499.1 (M+H).

Step 3

To a solution of tert-butyl 4-(3-((tert-butoxycarbonyl)(2-(dimethylamino) ethyl)amino)-5-fluorophenyl)-1H-pyrrolo[2,3-b]pyridine-1-carboxylate (C) (1.5 g, 3.01 mmol, 1.0 eq) in THF (20 mL) was added triisopropyl borate (1.98 g, 10.5 mmol, 3.5 eq) at −30° C., then the solution was cooled to −78° C. LDA (2 M, 6 mL, 12.0 mmol, 4 eq) was added dropwise under $N_2$. The reaction was stirred at this temperature for 30 min. The reaction was quench with buffer solution (pH=7), then warmed to 25° C. and extracted with EtOAc (40 mL×3), washed with brine (10 mL), dried with Na$_2$SO$_4$, filtered and concentrated to afford the crude product (1-(tert-butoxycarbonyl)-4-(3-((tert-butoxycarbonyl)(2-(dimethylamino)ethyl)amino)-5-fluorophenyl)-1H-pyrrolo[2,3-b]pyridin-2-yl)boronic acid (CI) as a yellow solid (1.5 g, 2.77 mmol, 91.9% yield). $^1$H NMR (CDCl$_3$, 400 MHz) δ ppm 1.49 (s, 9H), 2.28 (s, 6H), 2.54 (t, J=6.4 Hz, 2H), 3.82 (t, J=6.4 Hz, 2H), 6.72 (s, 1H), 7.11 (d, J=9.6 Hz, 1H), 7.17 (d, J=3.6 Hz, 1H), 7.32 (d, J=8.8 Hz, 1H), 7.43 (s, 1H), 7.46 (s, 1H), 8.39 (d, J=3.2 Hz, 1H); ESIMS found for C$_{27}$H$_{36}$BFN$_4$O$_6$ m/z 543.2 (M+H).

The following intermediates were prepared in accordance with the procedure described in the above Scheme 21.

(1-(tert-Butoxycarbonyl)-4-(furan-3-yl)-1H-pyrrolo[2,3-b]pyridin-2-yl)boronic acid (CII): Yellow solid (2.0 g, 6.10 mmol, 57.5% yield). ESIMS found C$_{16}$H$_{17}$BN$_2$O$_5$ m/z 229.0 (M+H-Boc).

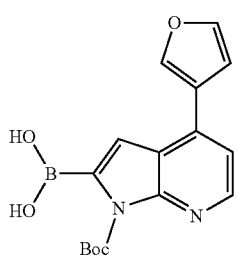

CII

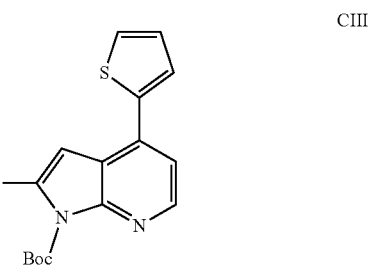

CIII (1-(tert-Butoxycarbonyl)-4-(thiophen-2-yl)-1H-pyrrolo[2,3-b]pyridin-2-yl)boronic acid (CIII): Yellow solid (2.0 g, 5.81 mmol, 58.2% yield). ESIMS found C$_{16}$H$_{17}$BN$_2$O$_4$S m/z 345.1 (M+H).

Example 1

Preparation of 5-(5-(cyclohexyloxy)pyridin-3-yl)-3-(4-(thiophen-2-yl)-1H-pyrrolo[2,3-b]pyridin-2-yl)-1H-pyrazolo[3,4-b]pyridine (703) is depicted below in Scheme 22.

Scheme 22

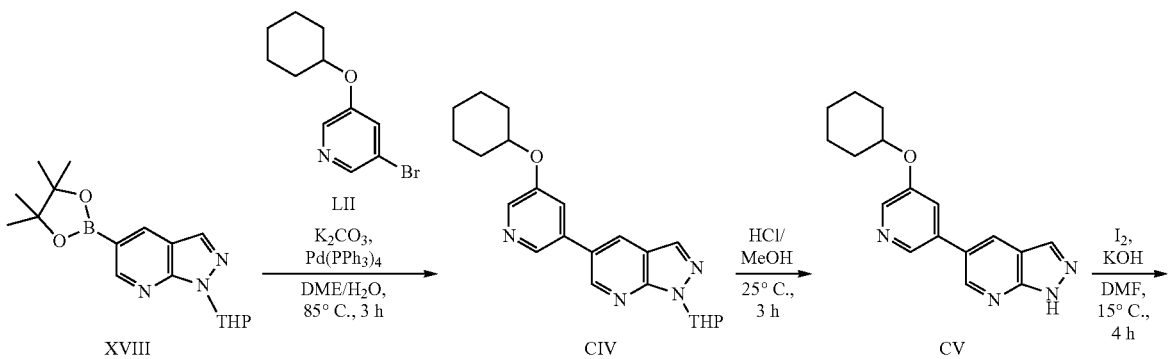

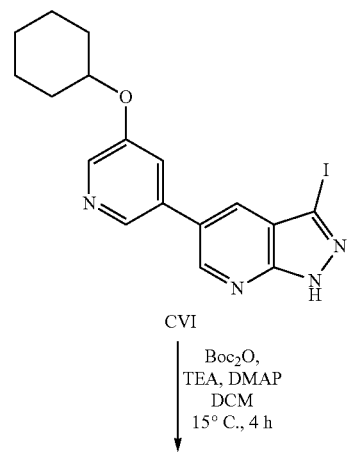

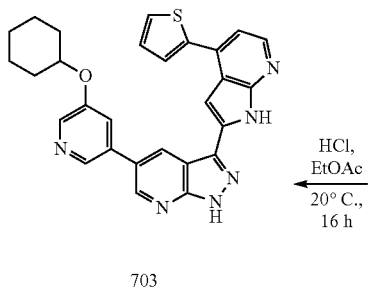 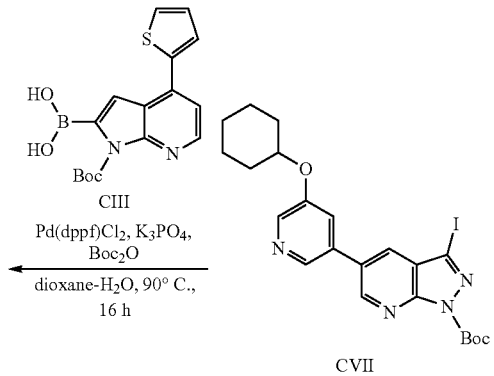

Steps 1

To a stirred solution of 1-(tetrahydro-2H-pyran-2-yl)-5-(tributylstannyl)-1H-pyrazolo[4,3-b]pyridine (XVIII) (5.0 g, 15.2 mmol, 1.0 eq) in DME (105 mL) and $H_2O$ (17.5 mL) was added 3-bromo-5-(cyclohexyloxy)pyridine (LII) (3.89 g, 15.2 mmol, 1.0 eq) and $Na_2CO_3$ (3.2 g, 30.4 mmol, 2.0 eq). The reaction suspension was degassed with nitrogen (×3) before $Pd(PPh_3)_4$ (526.5 mg, 0.46 mmol, 0.03 eq) was added. The reaction was degassed with nitrogen (×3) again and then heated to 80-90° C. and stirred for 3 h. The reaction was poured into water (150 mL) and extracted with EtOAc (100 mL×3). The combined organic layer was washed with brine, dried over anhydrous sodium sulfate and concentrated to give crude 5-(5-(cyclohexyloxy)pyridin-3-yl)-1-(tetrahydro-2H-pyran-2-yl)-1H-pyrazolo[3,4-b]pyridine (CIV) as a yellow solid (4.70 g, 12.42 mmol, 81.8% yield) which was used directly for the next step without further purification. $^1H$ NMR ($CDCl_3$, 400 MHz) δ ppm 1.25 (d, J=6.8 Hz, 1H), 1.30-1.50 (m, 3H), 1.52-1.73 (m, 3H), 1.74-1.92 (m, 4H), 1.97-2.22 (m, 3H), 2.28 (br s, 1H), 2.63-2.77 (m, 1H), 3.85 (t, J=10 Hz, 1H), 4.05-4.20 (m, 1H), 4.33-4.46 (m, 1H), 6.16 (d, J=9.6 Hz, 1H), 7.37 (s, 1H), 8.15 (s, 1H), 8.21 (s, 1H), 8.33 (s, 1H), 8.43 (s, 1H), 8.77 (s, 1H); ESIMS found for $C_{22}H_{26}N_4O_2$ m/z 379.1 (M+H).

Step 2

To a stirred solution of 5-(5-(cyclohexyloxy)pyridin-3-yl)-1-(tetrahydro-2H-pyran-2-yl)-1H-pyrazolo[3,4-b]pyridine (CIV) (6.0 g, 15.9 mmol, 1.0 eq) in MeOH (18 mL) was added HCl/MeOH (4 M, 60 mL) at 20-25° C. The reaction suspension was stirred at this temperature for 3 h. The reaction suspension was concentrated under reduced pressure and triturated in EtOAc (18 mL). The resulted slurry was filtered and dried in vacuum to give 5-(5-(cyclohexyloxy)pyridin-3-yl)-1H-pyrazolo[3,4-b]pyridine (CV) (6.8 g, crude) which was used directly for the next step without further purification. $^1H$ NMR ($CDCl_3$, 400 MHz) δ ppm 0.75-0.88 (m, 1H), 1.20-1.35 (m, 2H), 1.35-1.60 (m, 5H), 1.67-1.79 (m, 2H), 4.75-4.87 (m, 1H), 8.28 (s, 1H), 8.48 (s, 1H), 8.65 (d, J=1.6 Hz, 1H), 8.76 (d, J=2 Hz, 1H), 8.89 (s, 1H); ESIMS found for $C_{17}H_{18}N_4O$ m/z 295.1 (M+H).

Steps 3

To a solution of 5-(5-(cyclohexyloxy)pyridin-3-yl)-1H-pyrazolo[3,4-b]pyridine (CV) (6.8 g, 23.1 mmol, 1.0 eq) and KOH (6.48 g, 115.5 mmol, 5.0 eq) in DMF (50 mL) was added $I_2$ (4.4 g, 34.7 mmol, 1.5 eq) and the mixture was stirred at 15° C. for 4 h. The reaction mixture was quenched by addition saturated aqueous $Na_2S_2O_3$ (50 mL), and acidified with 1 N HCl to pH=6. The suspension was filtered and the filtrate cake was dried under reduced pressure to give 5-(5-(cyclohexyloxy)pyridin-3-yl)-3-iodo-1H-pyrazolo[3,4-b]pyridine (CVI) as a brown solid (7.0 g, 16.7 mmol, 72.1% yield) which was used for next step without further purification. $^1H$ NMR (DMSO-d6, 400 MHz) δ ppm 1.27 (br s, 1H), 1.33-1.60 (m, 5H), 1.71 (br s, 2H), 1.95 (br s, 2H), 4.61 (br s, 1H), 7.79 (s, 1H), 8.18 (s, 1H), 8.28 (s, 1H), 8.53 (s, 1H), 8.91 (s, 1H); ESIMS found for $C_{17}H_{17}IN_4O$ m/z 421.0 (M+H).

Steps 4

To a solution of 5-(5-(cyclohexyloxy)pyridin-3-yl)-3-iodo-1H-pyrazolo[3,4-b]pyridine (CVI) (7.0 g, 16.7 mmol, 1.0 eq), $Boc_2O$ (4.0 g, 18.3 mmol, 1.1 eq) and TEA (4.6 mL, 33.3 mmol, 2.0 eq) in DCM (100 mL) was added DMAP (203 mg, 1.67 mmol, 0.1 eq) and the mixture was stirred at 15° C. for 4 h. The reaction was concentrated and the residue was purified by column chromatography ($SiO_2$, PE/EtOAc) to give tert-butyl 5-(5-(cyclohexyloxy)pyridin-3-yl)-3-iodo-1H-pyrazolo[3,4-b]pyridine-1-carboxylate (CVII) as a white solid (7.0 g, 13.5 mmol, 80.8% yield). $^1H$ NMR (DMSO-d6, 400 MHz) δ ppm 1.35-1.58 (m, 6H), 1.63 (s, 9H), 1.67-1.76 (m, 2H), 1.95 (br s, 2H), 4.63 (br s, 1H), 7.86 (s, 1H), 8.32 (d, J=3.2 Hz, 2H), 8.59 (s, 1H), 9.09 (s, 1H); ESIMS found for $C_{22}H_{25}IN_4O_3$ m/z 521.2 (M+H).

Steps 5

A mixture of tert-butyl 5-(5-(cyclohexyloxy)pyridin-3-yl)-3-iodo-1H-pyrazolo[3,4-b]pyridine-1-carboxylate (CVII) (91 mg, 0.175 mmol, 1.0 eq), (1-(tert-butoxycarbonyl)-4-(thiophen-2-yl)-1H-pyrrolo[2,3-b]pyridin-2-yl)boronic acid (CIII) (66.2 mg, 0.192 mmol, 1.1 eq), $Pd(dppf)Cl_2$ (12.8 mg, 0.017 mmol, 0.1 eq), $Boc_2O$ (76.3 mg, 0.35 mmol, 2.0 eq), and $K_3PO_4$ (74.2 mg, 0.35 mmol, 2.0 eq) in dioxane (10 mL) and water (1 mL) was stirred at 90° C. for 16 h. The mixture was filtered and the filtrate was concentrated to give the tert-butyl 3-(1-(tert-butoxycarbonyl)-4-(thiophen-2-yl)-1H-pyrrolo[2,3-b]pyridin-2-yl)-5-(5-(cyclohexyloxy) pyridin-3-yl)-1H-pyrazolo[3,4-b]pyridine-1-carboxylate (CVIII) as a yellow solid (121 mg, 0.175 mmol, 99.8% yield) which was used in the next step directly. ESIMS found for $C_{38}H_{40}N_6O_5S$ m/z 693.3 (M+1).

Step 6

A mixture of tert-butyl 3-(1-(tert-butoxycarbonyl)-4-(thiophen-2-yl)-1H-pyrrolo[2,3-b]pyridin-2-yl)-5-(5-(cyclohexyloxy)pyridin-3-yl)-1H-pyrazolo[3,4-b]pyridine-1-carboxylate (CVIII) (121 mg, 0.175 mmol, 1.0 eq) in HCl/EtOAc (4 M, 50 mL) was stirred at 20° C. for 16 h. The mixture was filtered and the filtrate was concentrated. The residue was purified by acid prep-HPLC to give 5-(5-(cyclohexyloxy)pyridin-3-yl)-3-(4-(thiophen-2-yl)-1H-pyrrolo[2,3-b]pyridin-2-yl)-1H-pyrazolo[3,4-b]pyridine (703)

as an off-white solid (54.0 mg, 0.110 mmol, 62.7% yield). $^{1}$H NMR (400 MHz, DMSO-$d_6$) δ ppm 1.24-1.37 (m, 1 H), 1.39-1.64 (m, 5 H), 1.71-1.83 (m, 2 H), 1.97-2.09 (m, 2 H), 4.76-4.86 (m, 1 H), 7.04-7.13 (m, 1 H), 7.68 (d, J=5.51 Hz, 1 H), 7.71-7.79 (m, 1 H), 8.10 (d, J=3.97 Hz, 1 H), 8.26 (d, J=3.97 Hz, 1 H), 8.38 (d, J=5.51 Hz, 1 H), 8.49 (s, 1 H), 8.64 (br d, J=1.98 Hz, 1 H), 8.98 (s, 1 H), 9.08 (d, J=1.98 Hz, 1 H), 9.10 (d, J=1.98 Hz, 1 H), 12.45 (br s, 1 H), 14.24 (br s, 1 H); ESIMS found for $C_{28}H_{24}N_6OS$ m/z 493.1 (M+1).

The following compounds were prepared in accordance with the procedures described herein. See, for example, Schemes 1a and 1-22.

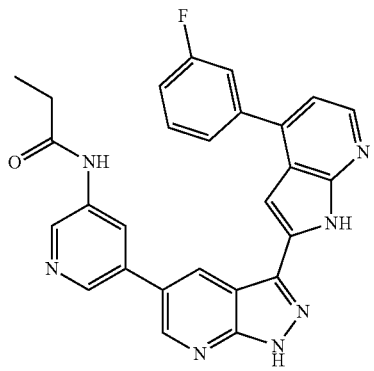

N-(5-(3-(4-(3-Fluorophenyl)-1H-pyrrolo[2,3-b]pyridin-2-yl)-1H-pyrazolo [3,4-b]pyridin-5-yl)pyridin-3-yl)propionamide 1

$^{1}$H NMR (400 MHz, DMSO-$d_6$) δ ppm 1.13 (t, J=7.61 Hz, 3 H), 2.41 (q, J=7.50 Hz, 2 H), 7.28 (d, J=4.85 Hz, 1 H), 7.30-7.40 (m, 2 H), 7.61-7.72 (m, 2 H), 7.76 (br d, J=7.72 Hz, 1 H), 8.36 (d, J=4.85 Hz, 1 H), 8.43 (t, J=1.98 Hz, 1 H), 8.76 (d, J=1.98 Hz, 1 H), 8.79 (d, J=2.20 Hz, 1 H), 8.88 (d, J=1.98 Hz, 1 H), 8.94 (d, J=1.98 Hz, 1 H), 10.23 (s, 1 H), 12.54 (br s, 1 H), 14.17 (br s, 1 H); ESIMS found for $C_{27}H_{20}FN_7O$ m/z 478.1 (M+1).

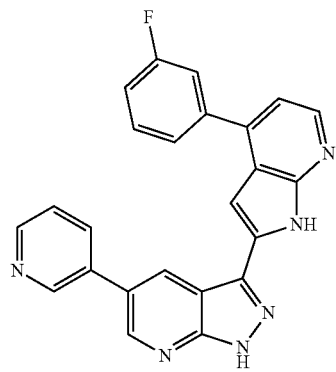

3-(4-(3-Fluorophenyl)-1H-pyrrolo[2,3-b]pyridin-2-yl)-5-(pyridin-3-yl)-1H-pyrazolo[3,4-b]pyridine 4

$^{1}$H NMR (400 MHz, DMSO-$d_6$) δ ppm 7.28 (d, J=4.85 Hz, 1 H), 7.31-7.38 (m, 1 H), 7.41 (d, J=2.20 Hz, 1 H), 7.54-7.60 (m, 1 H), 7.60-7.73 (m, 2 H), 7.76 (d, J=7.72 Hz, 1 H), 8.30 (dt, J=8.27, 1.82 Hz, 1 H), 8.36 (d, J=5.07 Hz, 1 H), 8.64 (dd, J=4.63, 1.54 Hz, 1 H), 8.97 (d, J=2.20 Hz, 1 H), 9.01 (d, J=1.98 Hz, 1 H), 9.11 (d, J=2.65 Hz, 1 H), 12.52 (s, 1 H), 14.18 (s, 1 H); ESIMS found for $C_{24}H_{15}FN_6$ m/z 407.0 (M+1).

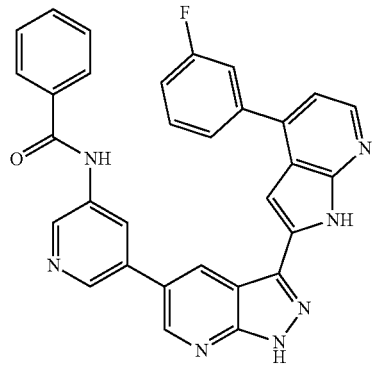

N-(5-(3-(4-(3-Fluorophenyl)-1H-pyrrolo[2,3-b]pyridin-2-yl)-1H-pyrazolo [3,4-b]pyridin-5-yl)pyridin-3-yl)benzamide 11

$^{1}$H NMR (400 MHz, DMSO-$d_6$) δ ppm 7.26-7.36 (m, 2 H), 7.39 (d, J=1.76 Hz, 1 H), 7.53-7.71 (m, 5 H), 7.76 (d, J=8.16 Hz, 1 H), 8.03 (d, J=7.06 Hz, 2 H), 8.36 (d, J=4.85 Hz, 1 H), 8.60 (s, 1 H), 8.85 (d, J=1.98 Hz, 1 H), 8.94 (d, J=1.98 Hz, 1 H), 8.99 (d, J=1.54 Hz, 1 H), 9.02 (d, J=1.98 Hz, 1 H), 10.61 (s, 1 H), 12.57 (s, 1 H), 14.21 (s, 1 H); ESIMS found for $C_{31}H_{20}FN_7O$ m/z 526.1 (M+1).

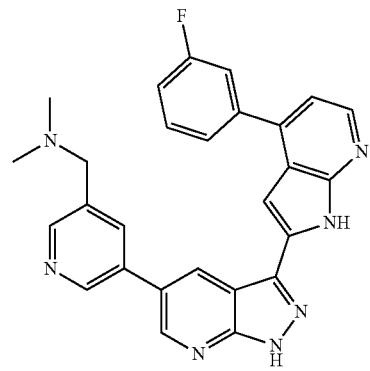

1-(5-(3-(4-(3-Fluorophenyl)-1H-pyrrolo[2,3-b]pyridin-2-yl)-1H-pyrazolo [3,4-b]pyridin-5-yl)pyridin-3-yl)-N,N-dimethylmethanamine 13

$^{1}$H NMR (400 MHz, DMSO-$d_6$) δ ppm 2.21 (s, 6 H), 3.54 (s, 2 H), 7.29 (d, J=5.09 Hz, 1 H), 7.35 (td, J=8.51, 2.15 Hz, 1 H), 7.39 (s, 1 H), 7.59-7.67 (m, 1 H), 7.69 (br d, J=9.78 Hz, 1 H), 7.76 (d, J=8.22 Hz, 1 H), 8.18 (s, 1 H), 8.36 (d, J=4.70 Hz, 1 H), 8.54 (d, J=1.57 Hz, 1 H), 8.96 (d, J=1.57 Hz, 1 H), 8.97-9.03 (m, 2 H), 12.57 (br s, 1 H); ESIMS found for $C_{27}H_{22}FN_7$ m/z 464.2 (M+1).

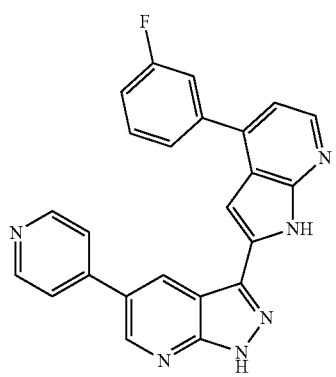

3-(4-(3-Fluorophenyl)-1H-pyrrolo[2,3-b]pyridin-2-yl)-5-(pyridin-4-yl)-1H-pyrazolo[3,4-b]pyridine 18

¹H NMR (400 MHz, DMSO-d₆) δ ppm 7.33 (d, J=5.07 Hz, 1 H), 7.37 (td, J=8.65, 2.32 Hz, 1 H), 7.49 (d, J=1.76 Hz, 1 H), 7.61-7.74 (m, 2 H), 7.77 (d, J=7.94 Hz, 1 H), 8.40 (d, J=5.07 Hz, 1 H), 8.61 (br d, J=5.51 Hz, 2 H), 9.01 (d, J=6.17 Hz, 2 H), 9.24 (d, J=1.99 Hz, 1 H), 9.29 (d, J=1.98 Hz, 1 H), 12.67 (br s, 1 H), 14.44 (br s, 1 H); ESIMS found for C₂₄H₁₅FN₆ m/z 407.1 (M+1).

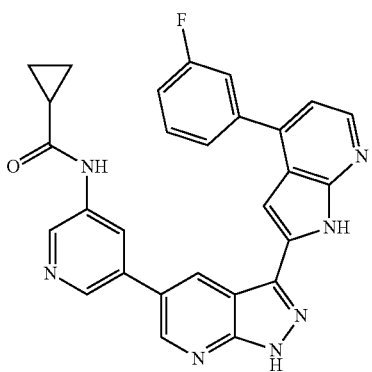

N-(5-(3-(4-(3-Fluorophenyl)-1H-pyrrolo[2,3-b]pyridin-2-yl)-1H-pyrazolo[3,4-b]pyridin-5-yl)pyridin-3-yl)cyclopropanecarboxamide 20

¹H NMR (400 MHz, DMSO-d₆) δ ppm 0.87 (br d, J=5.07 Hz, 4 H), 1.79-1.91 (m, 1 H), 7.28 (br d, J=4.63 Hz, 1 H), 7.30-7.42 (m, 2 H), 7.59-7.71 (m, 2 H), 7.75 (br d, J=7.28 Hz, 1 H), 8.36 (br d, J=4.85 Hz, 1 H), 8.43 (br s, 1 H), 8.76 (br s, 1 H), 8.78 (br s, 1 H), 8.88 (br s, 1 H), 8.93 (br s, 1 H), 10.57 (br s, 1 H), 12.53 (br s, 1 H), 14.16 (br s, 1 H); ESIMS found for C₂₈H₂₀FN₇O m/z 490.1 (M+1).

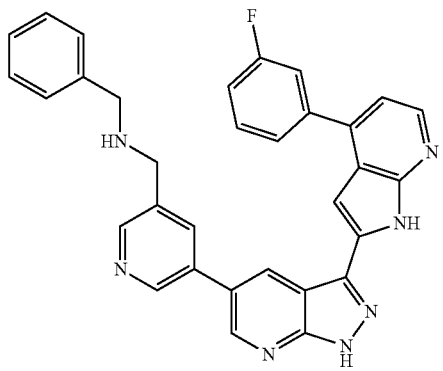

N-Benzyl-1-(5-(3-(4-(3-fluorophenyl)-1H-pyrrolo[2,3-b]pyridin-2-yl)-1H-pyrazolo[3,4-b]pyridin-5-yl)pyridin-3-yl)methanamine 24

¹H NMR (400 MHz, DMSO-d₆) δ ppm 4.43 (br dd, J=7.39, 1.43 Hz, 2 H), 5.43-5.55 (m, 2 H), 7.14-7.21 (m, 1 H), 7.24-7.35 (m, 3 H), 7.35-7.48 (m, 3 H), 7.57-7.70 (m, 3 H), 7.70-7.81 (m, 2 H), 8.30-8.41 (m, 2 H), 8.48 (br dd, J=6.73, 2.54 Hz, 1 H), 8.71-8.83 (m, 2 H), 12.47 (br s, 1 H), 14.16 (br s, 1H); ESIMS found for C₃₂H₂₄FN₇ m/z 526.1 (M+1).

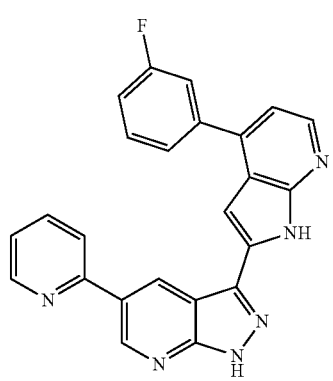

3-(4-(3-Fluorophenyl)-1H-pyrrolo[2,3-b]pyridin-2-yl)-5-(pyridin-2-yl)-1H-pyrazolo[3,4-b]pyridine 28

¹H NMR (400 MHz, DMSO-d₆) δ ppm 7.33-7.42 (m, 2 H), 7.46 (s, 1 H), 7.59 (br s, 1 H), 7.64-7.75 (m, 2 H), 7.80 (br d, J=7.72 Hz, 1 H), 8.11-8.23 (m, 1 H), 8.35 (br d, J=7.94 Hz, 1 H), 8.40 (d, J=5.07 Hz, 1 H), 8.81 (br d, J=4.63 Hz, 1 H), 9.27 (s, 1 H), 9.32 (d, J=1.98 Hz, 1 H), 12.83 (br s, 1 H), 14.34 (s, 1 H); ESIMS found for C₂₄H₁₅FN₆ m/z 407.1 (M+1).

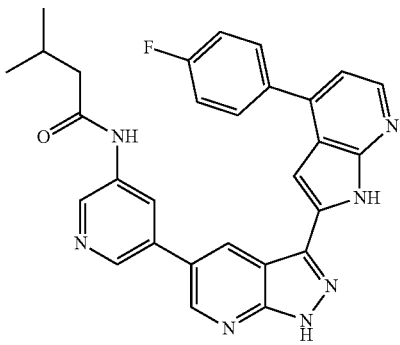

N-(5-(3-(4-(4-Fluorophenyl)-1H-pyrrolo[2,3-b]pyridin-2-yl)-1H-pyrazolo [3,4-b]pyridin-5-yl)pyridin-3-yl)-3-methylbutanamide 30

¹H NMR (400 MHz, DMSO-d₆) δ ppm 0.98 (br d, J=6.62 Hz, 5 H), 2.15 (tt, J=13.26, 6.48 Hz, 1 H), 2.28 (br d, J=7.06 Hz, 2 H), 7.23 (br d, J=4.85 Hz, 1 H), 7.33 (s, 1 H), 7.42 (br t, J=8.60 Hz, 2 H), 7.95 (br dd, J=8.05, 5.84 Hz, 2 H), 8.33 (br d, J=4.85 Hz, 1 H), 8.48 (br s, 1 H), 8.76 (br s, 1 H), 8.78 (br s, 1 H), 8.89 (br s, 1 H), 8.91 (br s, 1 H), 10.28 (s, 1 H), 12.49 (br s, 1 H); ESIMS found for C₂₉H₂₄FN₇O m/z 506.1 (M+1).

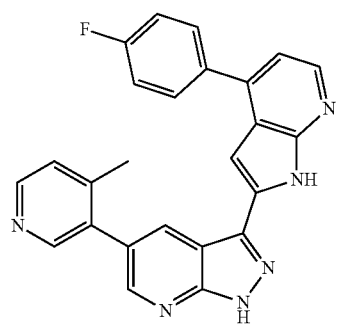

3-(4-(4-Fluorophenyl)-1H-pyrrolo[2,3-b]pyridin-2-yl)-5-(4-methylpyridin-3-yl)-1H-pyrazolo[3,4-b]pyridine 33

¹H NMR (400 MHz, DMSO-d₆) δ ppm 2.33 (br s, 3 H), 7.21 (br d, J=3.53 Hz, 1 H), 7.31 (br s, 1 H), 7.34-7.48 (m, 3 H), 7.91 (br s, 2 H), 8.33 (br d, J=3.75 Hz, 1 H), 8.50 (br s, 1 H), 8.55 (br s, 1 H), 8.63 (br s, 1 H), 8.77 (br s, 1 H), 12.45 (br s, 1 H), 14.16 (br s, 1 H); ESIMS found for C₂₅H₁₇FN₆ m/z 421.0 (M+1).

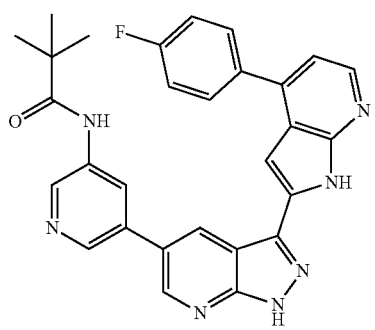

N-(5-(3-(4-(4-Fluorophenyl)-1H-pyrrolo[2,3-b]pyridin-2-yl)-1H-pyrazolo [3,4-b]pyridin-5-yl)pyridin-3-yl)pivalamide 36

¹H NMR (400 MHz, DMSO-d₆) δ ppm 1.29 (s, 9 H), 7.25 (d, J=5.07 Hz, 1 H), 7.36 (d, J=1.98 Hz, 1 H), 7.43 (br t, J=8.93 Hz, 2 H), 7.91-7.99 (m, 2 H), 8.34 (d, J=4.85 Hz, 1 H), 8.49 (t, J=2.09 Hz, 1 H), 8.78 (br d, J=1.54 Hz, 1 H), 8.89 (br d, J=1.76 Hz, 1 H), 8.93 (br d, J=2.21 Hz, 2 H), 9.58 (s, 1 H), 12.53 (s, 1 H), 14.18 (s, 1 H); ESIMS found for C₂₉H₂₄FN₇O m/z 506.2 (M+1).

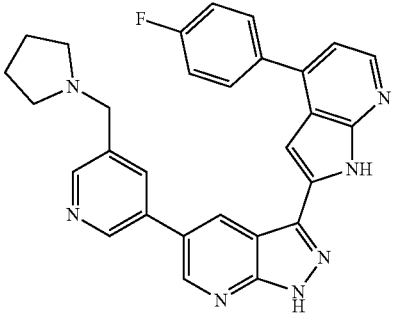

3-(4-(4-Fluorophenyl)-1H-pyrrolo[2,3-b]pyridin-2-yl)-5-(5-(pyrrolidin-1-ylmethyl)pyridin-3-yl)-1H-pyrazolo[3,4-b]pyridine 42

¹H NMR (400 MHz, DMSO-d₆) δ ppm 1.90-2.01 (m, 2 H), 2.01-2.13 (m, 2 H), 3.11-3.23 (m, 2 H), 3.41-3.53 (m, 2 H), 4.55 (br d, J=5.48 Hz, 2 H), 7.36 (d, J=5.09 Hz, 1 H), 7.45 (t, J=8.80 Hz, 2 H), 7.53 (d, J=1.96 Hz, 1 H), 8.03 (dd, J=8.61, 5.48 Hz, 2 H), 8.39 (d, J=5.09 Hz, 1 H), 8.88 (d, J=1.57 Hz, 1 H), 8.90 (br s, 1 H), 9.09 (d, J=1.96 Hz, 1 H), 9.17 (d, J=1.96 Hz, 1 H), 9.29 (d, J=1.96 Hz, 1 H), 12.85 (br s, 1 H); ESIMS found for C₂₉H₂₄FN₇ m/z 490.2 (M+1).

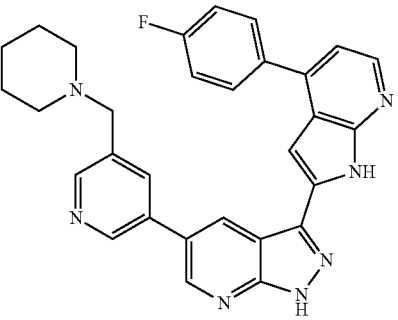

3-(4-(4-Fluorophenyl)-1H-pyrrolo[2,3-b]pyridin-2-yl)-5-(5-(piperidin-1-ylmethyl)pyridin-3-yl)-1H-pyrazolo[3,4-b]pyridine 43

¹H NMR (400 MHz, DMSO-d₆) δ ppm 1.40 (br d, J=3.09 Hz, 2 H), 1.50 (br d, J=4.85 Hz, 4 H), 2.39 (br s, 4 H), 3.57 (s, 2 H), 7.24 (d, J=4.85 Hz, 1 H), 7.33-7.46 (m, 3 H), 7.95 (br dd, J=8.27, 5.62 Hz, 2 H), 8.15 (br s, 1 H), 8.34 (d, J=4.85 Hz, 1 H), 8.54 (s, 1 H), 8.95 (s, 2 H), 8.97 (br s, 1

H), 12.48 (s, 1 H), 14.15 (br s, 1 H); ESIMS found for C$_{30}$H$_{26}$FN$_7$ m/z 504.1 (M+1).

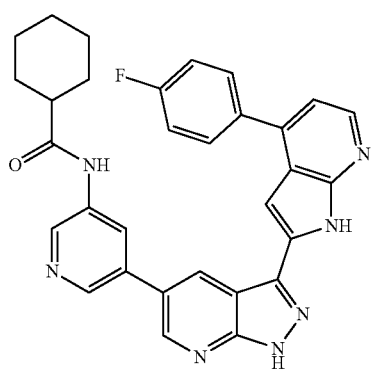

N-(5-(3-(4-(4-Fluorophenyl)-1H-pyrrolo[2,3-b]pyridin-2-yl)-1H-pyrazolo [3,4-b]pyridin-5-yl)pyridin-3-yl)cyclohexanecarboxamide 51

$^1$H NMR (400 MHz, DMSO-d$_6$) δ ppm 1.18-1.39 (m, 3 H), 1.41-1.56 (m, 2 H), 1.63-1.72 (m, 1 H), 1.74-1.83 (m, 2 H), 1.88 (br dd, J=11.58, 0.99 Hz, 2 H), 2.35-2.46 (m, 1 H), 7.25 (br d, J=5.07 Hz, 1 H), 7.35 (s, 1 H), 7.44 (br t, J=8.71 Hz, 2 H), 7.95 (br dd, J=8.38, 5.51 Hz, 2 H), 8.34 (br d, J=4.85 Hz, 1 H), 8.52 (br s, 1 H), 8.76 (s, 2 H), 8.91 (s, 2 H), 10.18 (s, 1 H), 12.50 (br s, 1 H), 14.08 (br s, 1 H); ESIMS found for C$_{31}$H$_{26}$FN$_7$O m/z 532.2 (M+1).

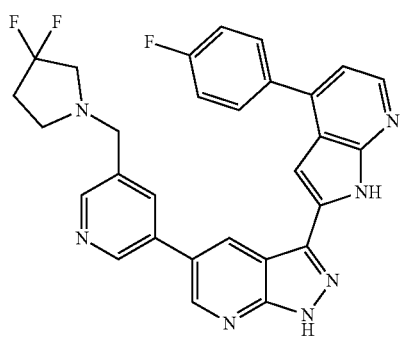

5-(5-((3,3-Difluoropyrrolidin-1-yl)methyl)pyridin-3-yl)-3-(4-(4-fluorophenyl)-1H-pyrrolo[2,3-b]pyridin-2-yl)-1H-pyrazolo[3,4-b]pyridine 54

$^1$H NMR (400 MHz, DMSO-d$_6$) δ ppm 2.51-2.55 (m, 2 H), 2.73-2.83 (m, 2 H), 2.96 (br t, J=13.23 Hz, 2 H), 3.78 (s, 2 H), 7.24 (br d, J=5.07 Hz, 1 H), 7.35-7.45 (m, 2 H), 7.65-7.72 (m, 1 H), 7.95 (br dd, J=8.82, 5.73 Hz, 2 H), 8.19 (br d, J=1.98 Hz, 1 H), 8.34 (br d, J=5.07 Hz, 1 H), 8.58 (br d, J=2.43 Hz, 1 H), 8.96 (br d, J=2.20 Hz, 1 H), 8.98 (br d, J=1.98 Hz, 1 H), 9.01 (br d, J=2.43 Hz, 1 H), 12.47 (br s, 1 H), 14.15 (br s, 1 H); ESIMS found for C$_{29}$H$_{22}$F$_3$N$_7$ m/z 526.1 (M+1).

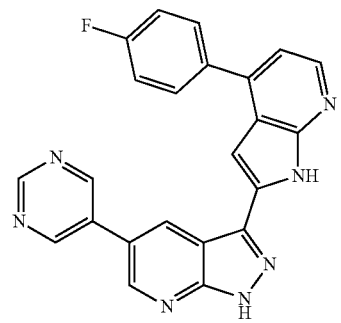

3-(4-(4-Fluorophenyl)-1H-pyrrolo[2,3-b]pyridin-2-yl)-5-(pyrimidin-5-yl)-1H-pyrazolo[3,4-b]pyridine 55

$^1$H NMR (400 MHz, DMSO-d$_6$) δ ppm 7.23 (d, J=4.85 Hz, 1 H), 7.38-7.46 (m, 3 H), 7.94 (dd, J=8.60, 5.51 Hz, 2 H), 8.34 (d, J=4.85 Hz, 1 H), 9.03 (d, J=1.98 Hz, 1 H), 9.11 (d, J=1.76 Hz, 1 H), 9.25 (s, 1 H), 9.35 (s, 2 H), 12.46 (s, 1 H), 14.22 (s, 1 H); ESIMS found for C$_{23}$H$_{14}$FN$_7$ m/z 408.1 (M+1).

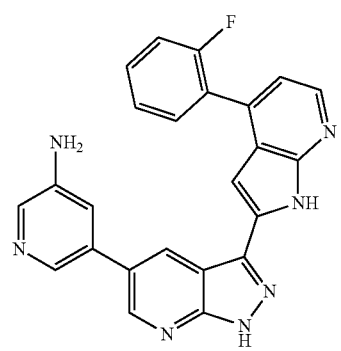

5-(3-(4-(2-Fluorophenyl)-1H-pyrrolo[2,3-b]pyridin-2-yl)-1H-pyrazolo[3,4-b]pyridin-5-yl)pyridin-3-amine 59

$^1$H NMR (400 MHz, DMSO-d$_6$) δ ppm 5.49 (s, 2 H), 7.10 (s, 1 H), 7.18 (br d, J=4.82 Hz, 1 H), 7.27 (s, 1 H), 7.37-7.50 (m, 2 H), 7.53-7.63 (m, 1 H), 7.75 (td, J=7.62, 0.99 Hz, 1 H), 7.98 (d, J=2.41 Hz, 1 H), 8.19 (d, J=1.75 Hz, 1 H), 8.35 (d, J=5.04 Hz, 1 H), 8.80 (br s, 1 H), 8.81 (br s, 1 H), 12.50 (br d, J=0.66 Hz, 1 H), 14.14 (s, 1 H); ESIMS found for C$_{24}$H$_{16}$FN$_7$ m/z 422.1 (M+1).

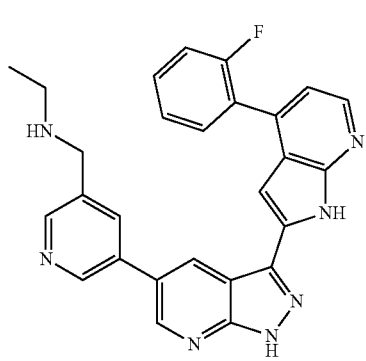

62

N-((5-(3-(4-(2-Fluorophenyl)-1H-pyrrolo[2,3-b]pyridin-2-yl)-1H-pyrazolo [3,4-b]pyridin-5-yl)pyridin-3-yl)methyl)ethanamine 62

$^1$H NMR (400 MHz, DMSO-d$_6$) δ ppm 1.10 (t, J=7.23 Hz, 3 H), 2.95-3.08 (m, 2 H), 3.93 (s, 2 H), 7.13 (d, J=1.32 Hz, 1 H), 7.19 (d, J=5.04 Hz, 1 H), 7.38-7.48 (m, 2 H), 7.51-7.61 (m, 1 H), 7.72-7.81 (m, 1 H), 8.25 (s, 1 H), 8.36 (d, J=4.82 Hz, 1 H), 8.60 (d, J=0.88 Hz, 1 H), 8.93 (d, J=1.97 Hz, 1 H), 8.95 (d, J=1.97 Hz, 1 H), 9.00 (s, 1 H), 12.51 (br s, 1 H), 14.16 (br s, 1 H); ESIMS found for C$_{27}$H$_{22}$FN$_7$ m/z 464.1 (M+1).

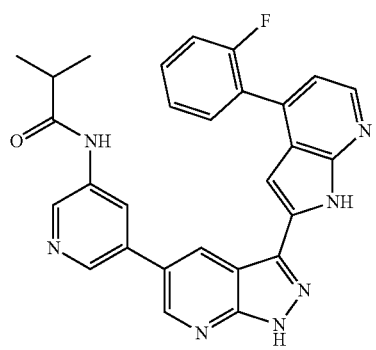

65

N-(5-(3-(4-(2-Fluorophenyl)-1H-pyrrolo[2,3-b]pyridin-2-yl)-1H-pyrazolo [3,4-b]pyridin-5-yl)pyridin-3-yl)isobutyramide 65

$^1$H NMR (400 MHz, DMSO-d$_6$) δ ppm 1.15 (d, J=7.04 Hz, 6 H), 2.63-2.74 (m, 1 H), 7.07 (d, J=1.96 Hz, 1 H), 7.15-7.20 (m, 1 H), 7.40-7.47 (m, 2 H), 7.50-7.60 (m, 1 H), 7.72-7.81 (m, 1 H), 8.34 (d, J=4.70 Hz, 1 H), 8.46 (t, J=1.96 Hz, 1 H), 8.74 (d, J=1.96 Hz, 1 H), 8.81 (d, J=1.96 Hz, 1 H), 8.85 (s, 1 H), 8.86 (s, 1 H), 10.31 (s, 1 H), 12.52 (br s, 1 H); ESIMS found for C$_{28}$H$_{22}$FN$_7$O m/z 492.2 (M+1).

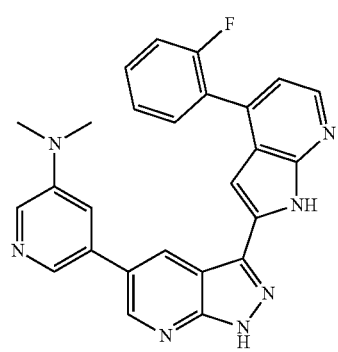

63

5-(3-(4-(2-Fluorophenyl)-1H-pyrrolo[2,3-b]pyridin-2-yl)-1H-pyrazolo[3,4-b]pyridin-5-yl)-N,N-dimethylpyridin-3-amine 63

$^1$H NMR (400 MHz, DMSO-d$_6$) δ ppm 3.04 (s, 6 H), 7.13 (s, 1 H), 7.19 (dd, J=4.85, 1.10 Hz, 1 H), 7.36-7.48 (m, 3 H), 7.52-7.61 (m, 1 H), 7.77 (td, J=7.66, 1.43 Hz, 1 H), 8.16 (d, J=2.87 Hz, 1 H), 8.34 (d, J=1.54 Hz, 1 H), 8.36 (d, J=5.07 Hz, 1 H), 8.86 (d, J=1.76 Hz, 1 H), 8.94 (d, J=1.76 Hz, 1 H), 12.46 (s, 1 H), 14.11 (s, 1 H); ESIMS found for C$_{26}$H$_{20}$FN$_7$ m/z 450.1 (M+1).

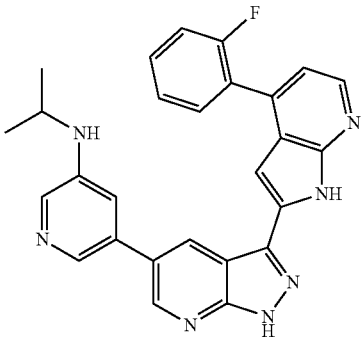

68

5-(3-(4-(2-Fluorophenyl)-1H-pyrrolo[2,3-b]pyridin-2-yl)-1H-pyrazolo[3,4-b]pyridin-5-yl)-N-isopropylpyridin-3-amine 68

$^1$H NMR (400 MHz, DMSO-d$_6$) δ ppm 1.18 (br d, J=6.17 Hz, 6 H), 3.68-3.81 (m, 1 H), 5.85 (br d, J=8.82 Hz, 1 H), 7.12 (s, 1 H), 7.15-7.21 (m, 1 H), 7.24 (br s, 1 H), 7.37-7.47 (m, 2 H), 7.51-7.60 (m, 1 H), 7.72-7.81 (m, 1 H), 7.99 (br d, J=1.98 Hz, 1 H), 8.16 (br d, J=0.88 Hz, 1 H), 8.35 (br d, J=4.85 Hz, 1 H), 8.79 (s, 1 H), 8.86 (s, 1 H), 12.49 (br s, 1 H), 14.12 (s, 1 H); ESIMS found for C$_{27}$H$_{22}$FN$_7$ m/z 464.1 (M+1).

337

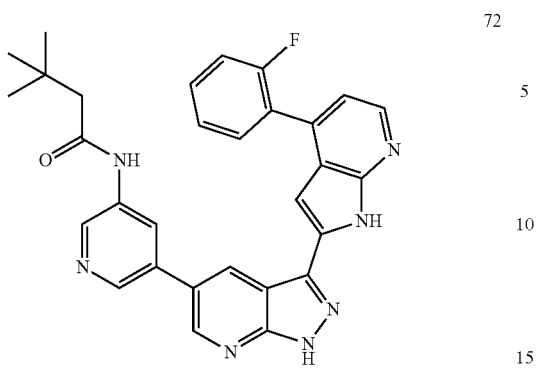

72

N-(5-(3-(4-(2-Fluorophenyl)-1H-pyrrolo[2,3-b]pyridin-2-yl)-1H-pyrazolo [3,4-b]pyridin-5-yl)pyridin-3-yl)-3,3-dimethylbutanamide 72

$^1$H NMR (400 MHz, DMSO-d$_6$) δ ppm 1.07 (s, 9 H), 2.35 (s, 2 H), 7.21 (s, 1 H), 7.27 (dd, J=4.96, 1.21 Hz, 1 H), 7.40-7.50 (m, 2 H), 7.54-7.62 (m, 1 H), 7.77 (td, J=7.66, 1.65 Hz, 1 H), 8.40 (d, J=5.07 Hz, 1 H), 8.79 (s, 1 H), 8.95 (d, J=2.21 Hz, 1 H), 9.02 (d, J=2.21 Hz, 1 H), 9.06 (br d, J=1.54 Hz, 1 H), 9.18 (br d, J=1.54 Hz, 1 H), 11.03 (s, 1 H), 12.78 (br s, 1 H), 14.36 (s, 1 H); ESIMS found for C$_{30}$H$_{26}$FN$_7$O m/z 520.2 (M+1).

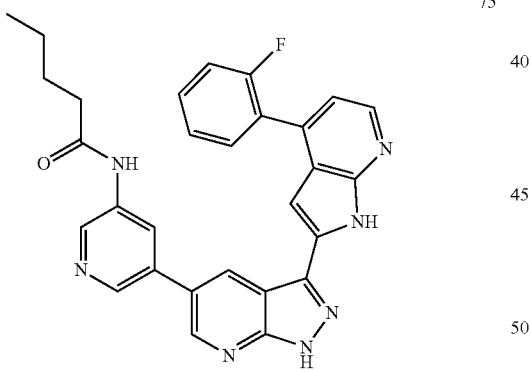

75

N-(5-(3-(4-(2-Fluorophenyl)-1H-pyrrolo[2,3-b]pyridin-2-yl)-1H-pyrazolo [3,4-b]pyridin-5-yl)pyridin-3-yl)pentanamide 75

$^1$H NMR (400 MHz, DMSO-d$_6$) δ ppm 0.92 (br t, J=7.28 Hz, 3 H), 1.36 (dq, J=14.66, 7.09 Hz, 2 H), 1.62 (dt, J=14.55, 7.28 Hz, 2 H), 2.39 (br t, J=7.28 Hz, 2 H), 7.10 (s, 1 H), 7.19 (br d, J=4.19 Hz, 1 H), 7.35-7.47 (m, 2 H), 7.50-7.60 (m, 1 H), 7.75 (br t, J=7.17 Hz, 1 H), 8.36 (br d, J=4.85 Hz, 1 H), 8.42 (br s, 1 H), 8.73 (s, 1 H), 8.79 (br s, 1 H), 8.87 (br s, 2 H), 10.28 (br s, 1 H), 12.50 (br s, 1 H); ESIMS found for C$_{29}$H$_{24}$FN$_7$O m/z 506.1 (M+1).

338

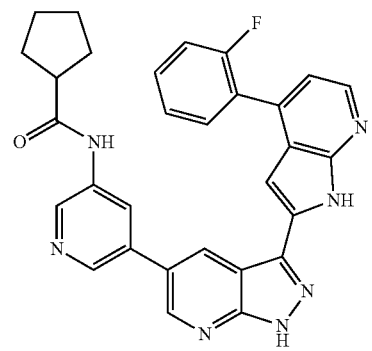

78

N-(5-(3-(4-(2-Fluorophenyl)-1H-pyrrolo[2,3-b]pyridin-2-yl)-1H-pyrazolo [3,4-b]pyridin-5-yl)pyridin-3-yl)cyclopentanecarboxamide 78

$^1$H NMR (400 MHz, DMSO-d$_6$) δ ppm 1.52-1.64 (m, 2 H), 1.65-1.84 (m, 4 H), 1.85-1.96 (m, 2 H), 2.81-2.92 (m, 1 H), 7.12 (br d, J=1.76 Hz, 1 H), 7.17-7.23 (m, 1 H), 7.39-7.48 (m, 2 H), 7.51-7.60 (m, 1 H), 7.76 (td, J=7.66, 1.43 Hz, 1 H), 8.36 (br d, J=4.63 Hz, 1 H), 8.48 (br d, J=1.98 Hz, 1 H), 8.77 (s, 1 H), 8.82 (br d, J=1.32 Hz, 1 H), 8.89 (br d, J=1.76 Hz, 2 H), 10.30 (s, 1 H), 12.53 (br s, 1 H), 14.20 (br s, 1 H); ESIMS found for C$_{30}$H$_{24}$FN$_7$O m/z 518.2 (M+1).

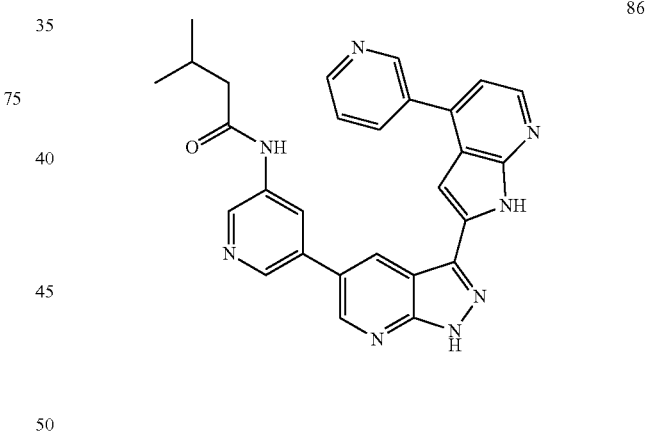

86

3-Methyl-N-(5-(3-(4-(pyridin-3-yl)-1H-pyrrolo[2,3-b]pyridin-2-yl)-1H-pyrazolo[3,4-b]pyridin-5-yl)pyridin-3-yl)butanamide 86

$^1$H NMR (400 MHz, DMSO-d$_6$) δ ppm 0.97 (d, J=6.62 Hz, 6 H), 2.07-2.18 (m, 1 H), 2.27 (d, J=7.28 Hz, 2 H), 7.32 (d, J=4.85 Hz, 1 H), 7.41 (d, J=1.76 Hz, 1 H), 7.62 (dd, J=8.16, 4.63 Hz, 1 H), 8.31 (dd, J=7.72, 1.76 Hz, 1 H), 8.38 (d, J=4.85 Hz, 1 H), 8.40 (br t, J=2.00 Hz, 1 H), 8.70 (dd, J=4.85, 1.10 Hz, 1 H), 8.76 (d, J=1.98 Hz, 1 H), 8.82 (d, J=1.98 Hz, 1H), 8.87 (d, J=1.98 Hz, 1 H), 8.97 (d, J=1.54 Hz, 1 H), 9.08 (d, J=1.54 Hz, 1 H), 10.25 (s, 1 H), 12.58 (s, 1 H), 14.20 (br s, 1 H); ESIMS found for C$_{28}$H$_{24}$N$_8$O m/z 489.1 (M+1).

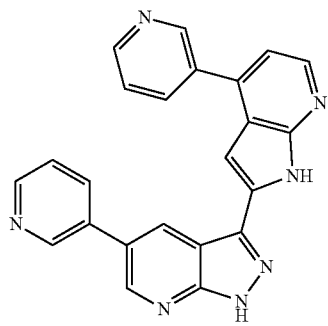

5-(Pyridin-3-yl)-3-(4-(pyridin-3-yl)-1H-pyrrolo[2,3-b]pyridin-2-yl)-1H-pyrazolo[3,4-b]pyridine 88

¹H NMR (400 MHz, DMSO-d₆) δ ppm 7.32 (d, J=4.85 Hz, 1 H), 7.45 (d, J=1.98 Hz, 1 H), 7.52-7.60 (m, 1 H), 7.60-7.67 (m, 1 H), 8.30 (ddt, J=7.88, 5.90, 2.15, 2.15 Hz, 2 H), 8.38 (d, J=4.85 Hz, 1 H), 8.64 (dd, J=4.63, 1.54 Hz, 1 H), 8.71 (dd, J=4.85, 1.54 Hz, 1 H), 8.96 (d, J=2.20 Hz, 1 H), 9.03 (d, J=1.98 Hz, 1 H), 9.10 (dt, J=4.69, 1.19 Hz, 2 H), 12.54 (br d, J=1.32 Hz, 1 H), 14.18 (s, 1 H); ESIMS found for $C_{23}H_{15}N_7$ m/z 390.1 (M+1).

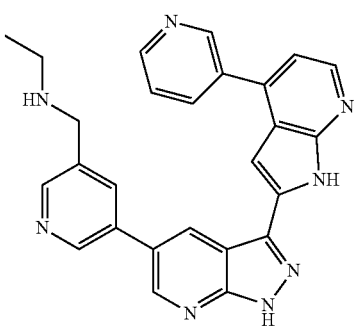

N-((5-(3-(4-(Pyridin-3-yl)-1H-pyrrolo[2,3-b]pyridin-2-yl)-1H-pyrazolo[3,4-b]pyridin-5-yl)pyridin-3-yl)methyl)ethanamine 90

¹H NMR (400 MHz, DMSO-d₆) δ ppm 1.09 (t, J=7.17 Hz, 3H), 2.67 (dt, J=3.14, 1.63 Hz, 2 H), 3.91 (br t, J=3.75 Hz, 2 H), 7.32 (d, J=5.07 Hz, 1 H), 7.43 (d, J=1.76 Hz, 1 H), 7.59-7.66 (m, 1 H), 8.20-8.26 (m, 1 H), 8.29-8.35 (m, 1 H), 8.38 (d, J=5.07 Hz, 1 H), 8.60 (s, 1 H), 8.70 (dd, J=4.63, 1.76 Hz, 1 H), 8.96 (d, J=2.43 Hz, 1 H), 9.00 (d, J=1.76 Hz, 2 H), 9.09 (d, J=2.43 Hz, 1 H), 12.57 (s, 1 H), 14.20 (br s, 1 H); ESIMS found for $C_{26}H_{22}N_8$ m/z 447.0 (M+1).

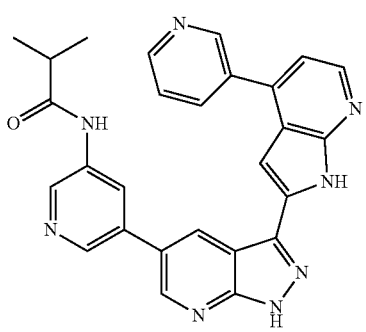

N-(5-(3-(4-(Pyridin-3-yl)-1H-pyrrolo[2,3-b]pyridin-2-yl)-1H-pyrazolo[3,4-b]pyridin-5-yl)pyridin-3-yl)isobutyramide 93

¹H NMR (400 MHz, DMSO-d₆) δ ppm 1.16 (d, J=6.84 Hz, 6 H), 2.67 (dt, J=13.67, 6.84 Hz, 1 H), 7.32 (d, J=4.85 Hz, 1 H), 7.40 (s, 1 H), 7.63 (dd, J=7.61, 4.96 Hz, 1 H), 8.31 (dt, J=7.94, 1.76 Hz, 1 H), 8.38 (d, J=4.85 Hz, 1 H), 8.43 (t, J=2.09 Hz, 1 H), 8.70 (dd, J=4.63, 1.54 Hz, 1 H), 8.76 (d, J=1.99 Hz, 1 H), 8.83 (d, J=2.20 Hz, 1 H), 8.87 (d, J=1.98 Hz, 1 H), 8.97 (d, J=1.99 Hz, 1 H), 9.08 (d, J=1.76 Hz, 1 H), 10.20 (s, 1 H), 12.56 (br s, 1 H), 14.16 (br s, 1 H); ESIMS found for $C_{27}H_{22}N_8O$ m/z 475.1 (M+1).

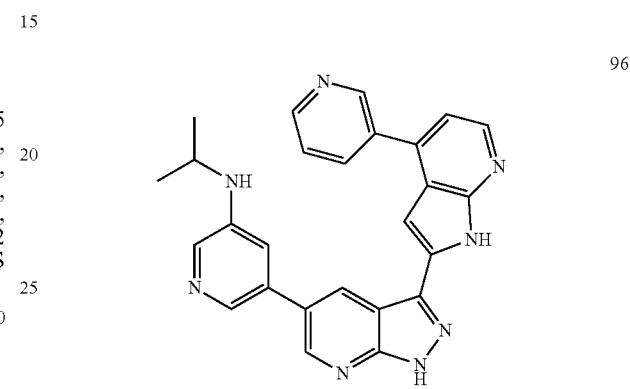

N-Isopropyl-5-(3-(4-(pyridin-3-yl)-1H-pyrrolo[2,3-b]pyridin-2-yl)-1H-pyrazolo[3,4-b]pyridin-5-yl)pyridin-3-amine 96

¹H NMR (400 MHz, DMSO-d₆) δ ppm 1.23 (d, J=6.26 Hz, 6 H), 3.84-3.95 (m, 1 H), 7.18 (br s, 1 H), 7.43 (d, J=4.70 Hz, 1 H), 7.53 (d, J=1.96 Hz, 1 H), 7.90 (dd, J=7.63, 5.28 Hz, 1 H), 8.04 (s, 1 H), 8.10 (d, J=2.35 Hz, 1 H), 8.44 (d, J=5.09 Hz, 1 H), 8.56 (s, 1 H), 8.69 (br d, J=7.04 Hz, 1 H), 8.87 (dd, J=5.28, 1.37 Hz, 1 H), 9.00 (d, J=1.96 Hz, 1 H), 9.08 (d, J=1.96 Hz, 1 H), 9.26 (d, J=1.96 Hz, 1 H), 12.75 (br s, 1 H); ESIMS found for $C_{26}H_{22}N_8$ m/z 447.1 (M+1).

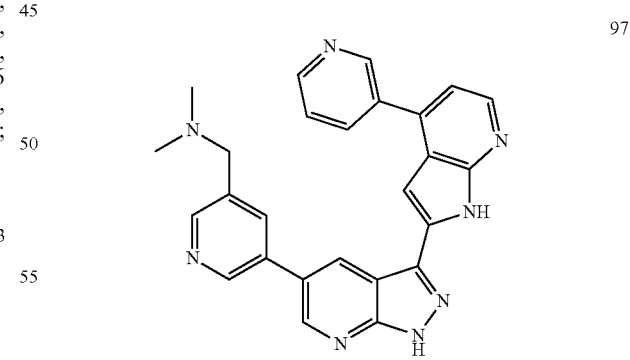

N,N-Dimethyl-1-(5-(3-(4-(pyridin-3-yl)-1H-pyrrolo[2,3-b]pyridin-2-yl)-1H-pyrazolo[3,4-b]pyridin-5-yl)pyridin-3-yl)methanamine 97

¹H NMR (400 MHz, DMSO-d₆) δ ppm 2.21 (s, 6 H), 3.54 (s, 2 H), 7.32 (d, J=5.07 Hz, 1 H), 7.42 (br d, J=1.32 Hz, 1 H), 7.59-7.66 (m, 1 H), 8.13-8.20 (m, 1 H), 8.28-8.35 (m, 1

H), 8.38 (d, J=4.85 Hz, 1 H), 8.54 (br d, J=1.54 Hz, 1 H), 8.71 (br dd, J=4.74, 1.43 Hz, 1 H), 8.95 (br d, J=1.98 Hz, 1 H), 8.99 (br d, J=2.20 Hz, 1 H), 9.00 (d, J=1.98 Hz, 1 H), 9.06-9.14 (m, 1 H), 12.57 (s, 1 H), 14.16 (br s, 1 H); ESIMS found for $C_{26}H_{22}N_8$ m/z 447.0 (M+1).

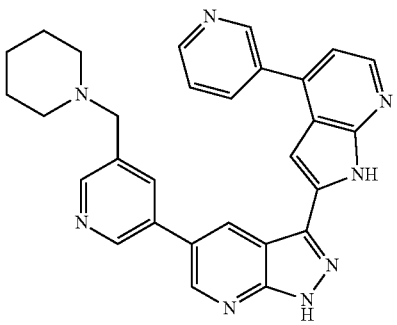

5-(5-(Piperidin-1-ylmethyl)pyridin-3-yl)-3-(4-(pyridin-3-yl)-1H-pyrrolo[2,3-b]pyridin-2-yl)-1H-pyrazolo[3,4-b]pyridine 99

$^1$H NMR (400 MHz, DMSO-d$_6$) δ ppm 1.31-1.43 (m, 2 H), 1.50 (br s, 4 H), 2.34-2.43 (m, 4 H), 3.57 (s, 2 H), 7.32 (br d, J=4.85 Hz, 1 H), 7.43 (br d, J=2.65 Hz, 1 H), 7.56-7.67 (m, 1 H), 8.13 (br s, 1 H), 8.27-8.35 (m, 1 H), 8.35-8.44 (m, 1 H), 8.54 (br s, 1 H), 8.66-8.77 (m, 1 H), 8.94 (br d, J=1.76 Hz, 1 H), 8.96-9.04 (m, 2 H), 9.09 (br d, J=1.98 Hz, 1 H), 12.56 (br d, J=0.66 Hz, 1 H), 14.18 (br d, J=1.32 Hz, 1 H); ESIMS found for $C_{29}H_{26}N_8$ m/z 487.2 (M+1).

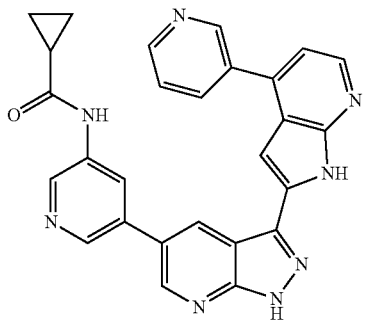

N-(5-(3-(4-(Pyridin-3-yl)-1H-pyrrolo[2,3-b]pyridin-2-yl)-1H-pyrazolo[3,4-b]pyridin-5-yl)pyridin-3-yl)cyclopropanecarboxamide 104

$^1$H NMR (400 MHz, DMSO-d$_6$) δ ppm 0.87 (br d, J=0.88 Hz, 4 H), 1.79-1.90 (m, 1 H), 7.26-7.36 (m, 1 H), 7.41 (br s, 1 H), 7.63 (br d, J=2.19 Hz, 1 H), 8.27-8.34 (m, 1 H), 8.39 (br s, 2 H), 8.71 (br s, 1 H), 8.76 (br s, 1 H), 8.78-8.84 (m, 1 H), 8.84-8.92 (m, 1 H), 8.97 (br s, 1 H), 9.09 (br s, 1 H), 10.58 (br s, 1 H), 12.57 (br s, 1 H), 14.20 (br s, 1 H); ESIMS found for $C_{27}H_{20}N_8O$ m/z 473.1 (M+1).

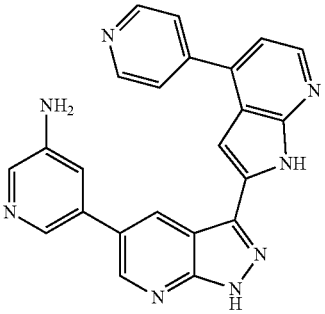

5-(3-(4-(Pyridin-4-yl)-1H-pyrrolo[2,3-b]pyridin-2-yl)-1H-pyrazolo[3,4-b]pyridin-5-yl)pyridin-3-amine 115

$^1$H NMR (400 MHz, DMSO-d$_6$) δ ppm 6.64 (br s, 2 H), 7.47 (br d, J=5.07 Hz, 1 H), 7.52 (br d, J=1.98 Hz, 1 H), 8.03 (s, 1 H), 8.07 (br d, J=2.43 Hz, 1 H), 8.20-8.29 (m, 2H), 8.47 (d, J=4.85 Hz, 1 H), 8.59 (br d, J=1.10 Hz, 1 H), 8.93 (br d, J=6.17 Hz, 2 H), 8.96 (d, J=2.21 Hz, 1 H), 9.06 (d, J=1.98 Hz, 1 H), 12.78 (br s, 1 H), 14.38 (br s, 1 H); ESIMS found for $C_{23}H_{16}N_8$ m/z 405.1 (M+1).

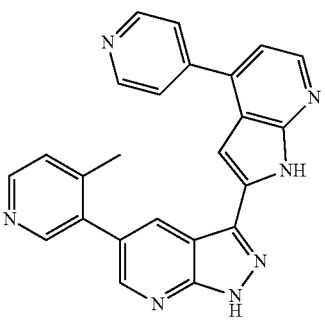

5-(4-Methylpyridin-3-yl)-3-(4-(pyridin-4-yl)-1H-pyrrolo[2,3-b]pyridin-2-yl)-1H-pyrazolo[3,4-b]pyridine 117

$^1$H NMR (400 MHz, DMSO-d$_6$) δ ppm 2.34 (br s, 3 H), 7.29-7.37 (m, 1 H), 7.40 (br s, 2 H), 7.87 (br d, J=2.43 Hz, 2 H), 8.39 (br d, J=1.32 Hz, 1 H), 8.51 (br s, 1 H), 8.55 (br s, 1 H), 8.64 (br s, 1 H), 8.74 (br d, J=1.76 Hz, 2 H), 8.81 (br d, J=4.19 Hz, 1 H), 12.56 (br s, 1 H), 14.20 (br s, 1 H); ESIMS found for $C_{24}H_{17}N_7$ m/z 404.1 (M+1).

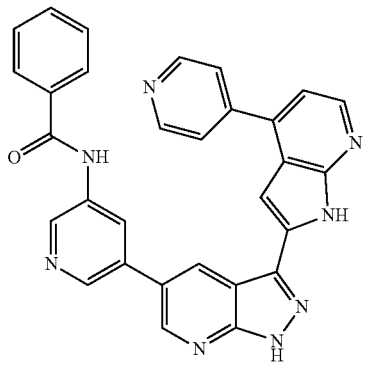

N-(5-(3-(4-(Pyridin-4-yl)-1H-pyrrolo[2,3-b]pyridin-2-yl)-1H-pyrazolo[3,4-b]pyridin-5-yl)pyridin-3-yl) benzamide 123

¹H NMR (400 MHz, DMSO-d₆) δ ppm 7.35 (br d, J=4.85 Hz, 1 H), 7.45 (s, 1 H), 7.54-7.70 (m, 3 H), 7.90 (br s, 2 H), 8.04 (br d, J=7.28 Hz, 2 H), 8.40 (br d, J=4.63 Hz, 1 H), 8.61 (br s, 1 H), 8.78 (br s, 2 H), 8.85 (br s, 1 H), 8.94 (s, 1 H), 8.97-9.06 (m, 2 H), 10.61 (s, 1 H), 12.63 (br s, 1 H), 14.23 (br s, 1 H); ESIMS found for $C_{30}H_{20}N_8O$ m/z 509.0 (M+1).

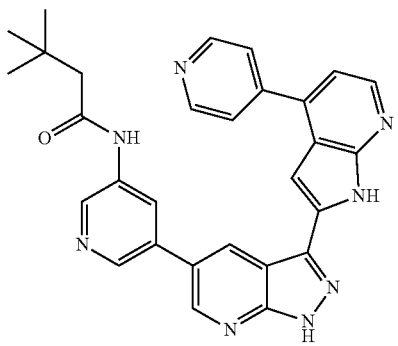

3,3-Dimethyl-N-(5-(3-(4-(pyridin-4-yl)-1H-pyrrolo[2,3-b]pyridin-2-yl)-1H-pyrazolo[3,4-b]pyridin-5-yl)pyridin-3-yl)butanamide 128

¹H NMR (400 MHz, DMSO-d₆) δ ppm 1.06 (s, 9 H), 2.27 (s, 2 H), 7.36 (d, J=5.07 Hz, 1 H), 7.43 (s, 1 H), 7.86-7.94 (m, 2 H), 8.40 (d, J=5.07 Hz, 1 H), 8.43 (t, J=2.09 Hz, 1 H), 8.76 (d, J=1.98 Hz, 1 H), 8.77 (d, J=1.10 Hz, 1 H), 8.78 (s, 1 H), 8.80 (d, J=2.20 Hz, 1 H), 8.88 (d, J=1.98 Hz, 1 H), 8.95 (d, J=1.98 Hz, 1 H), 10.19 (s, 1 H), 12.61 (br s, 1 H), 14.15 (br s, 1 H); ESIMS found for $C_{29}H_{26}N_8O$ m/z 503.1 (M+1).

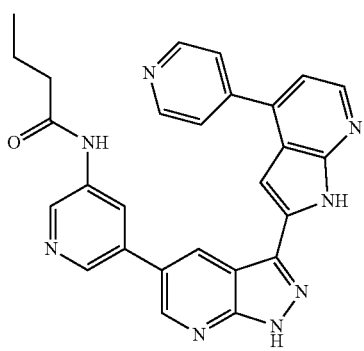

N-(5-(3-(4-(Pyridin-4-yl)-1H-pyrrolo[2,3-b]pyridin-2-yl)-1H-pyrazolo[3,4-b]pyridin-5-yl)pyridin-3-yl) butyramide 129

¹H NMR (400 MHz, DMSO-d₆) δ ppm 0.95 (br t, J=7.39 Hz, 3 H), 1.60-1.74 (m, 2 H), 2.37 (br t, J=7.17 Hz, 2 H), 7.33-7.40 (m, 1 H), 7.45 (br d, J=0.66 Hz, 1 H), 7.85-7.97 (m, 2 H), 8.40 (br d, J=4.85 Hz, 1 H), 8.45 (br s, 1 H), 8.79 (br s, 4 H), 8.90 (s, 1 H), 8.97 (br s, 1 H), 10.26 (br s, 1 H), 12.64 (br s, 1 H), 14.22 (br s, 1 H); ESIMS found for $C_{27}H_{22}N_8O$ m/z 475.1 (M+1).

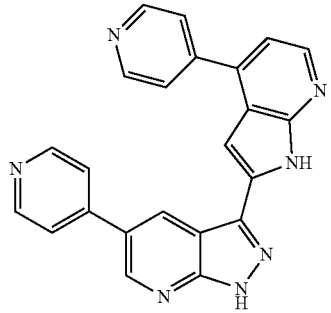

5-(Pyridin-4-yl)-3-(4-(pyridin-4-yl)-1H-pyrrolo[2,3-b]pyridin-2-yl)-1H-pyrazolo[3,4-b]pyridine 130

¹H NMR (400 MHz, DMSO-d₆) δ ppm 7.45 (br d, J=4.85 Hz, 1 H), 7.55 (br d, J=1.76 Hz, 1 H), 8.12-8.20 (m, 2 H), 8.39 (br dd, J=4.30, 2.09 Hz, 2 H), 8.46 (br d, J=4.85 Hz, 1 H), 8.85-8.96 (m, 4 H), 9.19 (br d, J=1.98 Hz, 1 H), 9.23 (br d, J=2.20 Hz, 1 H), 12.76 (br s, 1 H), 14.43 (br s, 1 H); ESIMS found for $C_{23}H_{15}N_7$ m/z 390.0 (M+1).

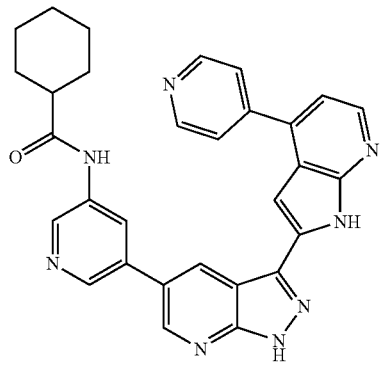

N-(5-(3-(4-(Pyridin-4-yl)-1H-pyrrolo[2,3-b]pyridin-2-yl)-1H-pyrazolo[3,4-b]pyridin-5-yl)pyridin-3-yl) cyclohexanecarboxamide 135

¹H NMR (400 MHz, DMSO-d₆) δ ppm 1.15-1.37 (m, 3 H), 1.39-1.54 (m, 2 H), 1.62-1.71 (m, 1 H), 1.74-1.83 (m, 2 H), 1.83-1.93 (m, 2 H), 2.35-2.44 (m, 1 H), 7.36 (d, J=4.85 Hz, 1 H), 7.44 (s, 1 H), 7.90 (d, J=6.17 Hz, 2 H), 8.40 (d, J=4.85 Hz, 1 H), 8.46-8.51 (m, 1 H), 8.76 (d, J=2.21 Hz, 1 H), 8.77-8.83 (m, 3H), 8.90 (d, J=1.98 Hz, 1 H), 8.96 (d, J=1.54 Hz, 1 H), 10.19 (s, 1 H), 12.63 (br s, 1 H), 14.22 (br s, 1 H); ESIMS found for $C_{30}H_{26}N_8O$ m/z 515.2 (M+1).

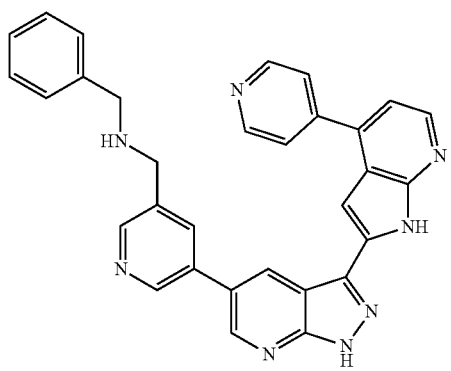

N-Benzyl-1-(5-(3-(4-(pyridin-4-yl)-1H-pyrrolo[2,3-b]pyridin-2-yl)-1H-pyrazolo[3,4-b]pyridin-5-yl)pyridin-3-yl)methanamine 136

$^1$H NMR (400 MHz, DMSO-d$_6$) δ ppm 4.29 (br dd, J=5.70, 4.38 Hz, 2 H), 4.39 (br s, 2 H), 7.39-7.50 (m, 3 H), 7.55 (d, J=4.82 Hz, 1 H), 7.60-7.68 (m, 3 H), 8.50 (d, J=4.82 Hz, 1 H), 8.55 (br d, J=6.58 Hz, 2 H), 8.80 (s, 1 H), 8.92 (br d, J=1.32 Hz, 1 H), 9.04 (br d, J=6.58 Hz, 2 H), 9.09 (s, 1 H), 9.21 (s, 1 H), 9.26 (d, J=1.75 Hz, 1 H), 10.08 (br s, 2 H), 12.87 (s, 1 H), 14.40 (s, 1 H); ESIMS found for C$_{31}$H$_{24}$N$_8$ m/z 509.1 (M+1).

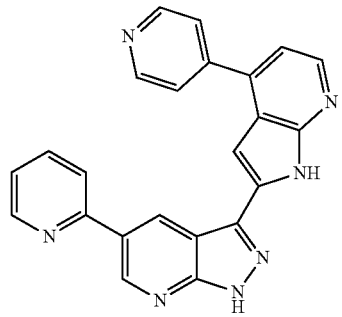

5-(Pyridin-2-yl)-3-(4-(pyridin-4-yl)-1H-pyrrolo[2,3-b]pyridin-2-yl)-1H-pyrazolo[3,4-b]pyridine 140

$^1$H NMR (400 MHz, DMSO-d$_6$) δ ppm 7.36 (d, J=5.29 Hz, 1 H), 7.38-7.47 (m, 2 H), 7.87-7.94 (m, 2 H), 7.94-8.03 (m, 1 H), 8.25 (br d, J=8.38 Hz, 1 H), 8.41 (br d, J=5.29 Hz, 1 H), 8.70-8.77 (m, 1 H), 8.79 (br d, J=5.95 Hz, 2 H), 9.21 (br d, J=1.32 Hz, 1 H), 9.35 (s, 1 H), 12.65 (br s, 1 H), 14.20 (br s, 1 H); ESIMS found for C$_{23}$H$_{15}$N$_7$ m/z 390.1 (M+1).

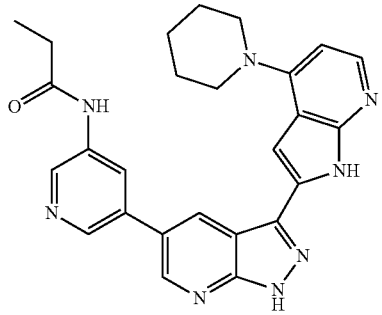

N-(5-(3-(4-(Piperidin-1-yl)-1H-pyrrolo[2,3-b]pyridin-2-yl)-1H-pyrazolo[3,4-b]pyridin-5-yl)pyridin-3-yl)propionamide 169

$^1$H NMR (400 MHz, DMSO-d$_6$) δ ppm 1.12 (t, J=7.45 Hz, 3 H), 1.61-1.69 (m, 2 H), 1.69-1.79 (m, 4 H), 2.41 (q, J=7.60 Hz, 2 H), 3.42-3.54 (m, 4 H), 6.46 (d, J=5.70 Hz, 1 H), 7.11 (s, 1 H), 7.99 (d, J=5.48 Hz, 1 H), 8.49 (d, J=1.97 Hz, 1 H), 8.76 (d, J=1.53 Hz, 1 H), 8.78 (d, J=1.10 Hz, 1 H), 8.89 (br d, J=2.19 Hz, 2 H), 10.26 (s, 1 H), 12.07 (br s, 1 H), 14.03 (s, 1 H); ESIMS found for C$_{26}$H$_{26}$N$_8$O m/z 467.1 (M+1).

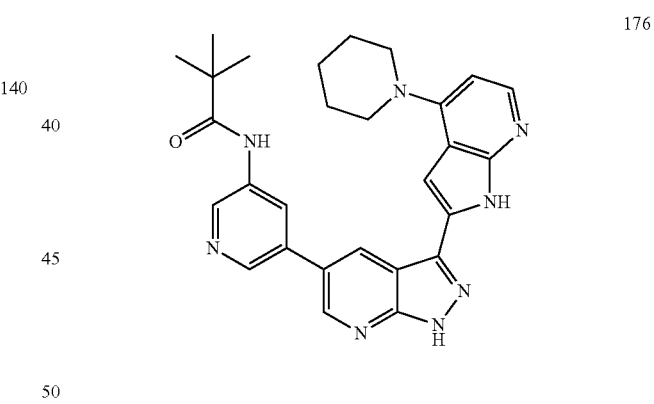

N-(5-(3-(4-(Piperidin-1-yl)-1H-pyrrolo[2,3-b]pyridin-2-yl)-1H-pyrazolo[3,4-b]pyridin-5-yl)pyridin-3-yl)pivalamide 176

$^1$H NMR (400 MHz, DMSO-d$_6$) δ ppm 1.28 (s, 9 H), 1.60-1.69 (m, 2 H), 1.69-1.79 (m, 4 H), 3.47 (br d, J=5.04 Hz, 4 H), 6.46 (d, J=5.48 Hz, 1 H), 7.12 (s, 1 H), 7.99 (d, J=5.70 Hz, 1 H), 8.52 (s, 1 H), 8.80 (d, J=1.53 Hz, 1 H), 8.87 (d, J=1.75 Hz, 1 H), 8.90 (br s, 1 H), 8.91 (br s, 1 H), 9.58 (s, 1 H), 12.08 (br s, 1 H), 14.02 (s, 1 H); ESIMS found for C$_{28}$H$_{30}$N$_8$O m/z 495.1 (M+1).

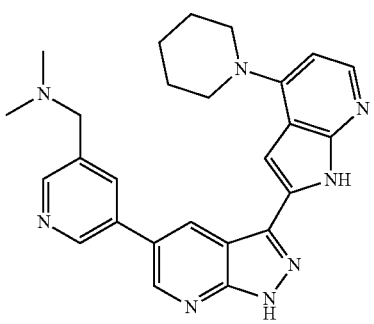

N,N-Dimethyl-1-(5-(3-(4-(piperidin-1-yl)-1H-pyr-rolo[2,3-b]pyridin-2-yl)-1H-pyrazolo[3,4-b]pyridin-5-yl)pyridin-3-yl)methanamine 181

$^1$H NMR (400 MHz, DMSO-d$_6$) δ ppm 1.58-1.68 (m, 2 H), 1.68-1.80 (m, 4 H), 2.22 (s, 6 H), 3.42-3.51 (m, 4 H), 3.55 (br s, 2 H), 6.46 (br d, J=5.73 Hz, 1 H), 7.14 (br d, J=0.66 Hz, 1 H), 7.99 (br d, J=5.95 Hz, 1 H), 8.19 (br d, J=1.98 Hz, 1 H), 8.54 (br d, J=1.10 Hz, 1 H), 8.93 (br d, J=1.76 Hz, 1 H), 8.95 (br s, 1 H), 9.00 (br d, J=1.98 Hz, 1 H), 12.05 (br s, 1 H), 14.00 (br s, 1 H); ESIMS found for C$_{26}$H$_{28}$N$_8$ m/z 453.2 (M+1).

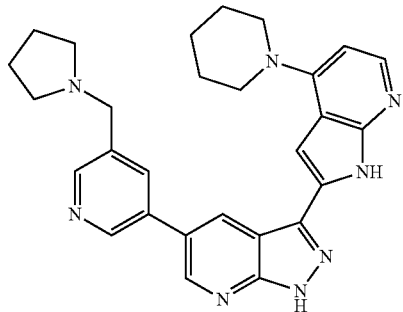

3-(4-(Piperidin-1-yl)-1H-pyrrolo[2,3-b]pyridin-2-yl)-5-(5-(pyrrolidin-1-ylmethyl)pyridin-3-yl)-1H-pyrazolo[3,4-b]pyridine 182

$^1$H NMR (400 MHz, DMSO-d$_6$) δ ppm 1.61-1.69 (m, 2 H), 1.72 (br s, 4 H), 3.48 (br s, 4 H), 3.73 (br s, 4 H), 3.82 (br s, 2 H), 6.46 (br d, J=5.95 Hz, 1 H), 7.14 (br s, 1 H), 7.99 (br d, J=5.51 Hz, 1 H), 8.19 (s, 1 H), 8.55 (br s, 1 H), 8.92 (br s, 1 H), 8.94 (br s, 1 H), 8.98 (br s, 1 H), 12.01 (br s, 1 H), 13.99 (br s, 1 H); ESIMS found for C$_{28}$H$_{30}$N$_8$ m/z 479.1 (M+1).

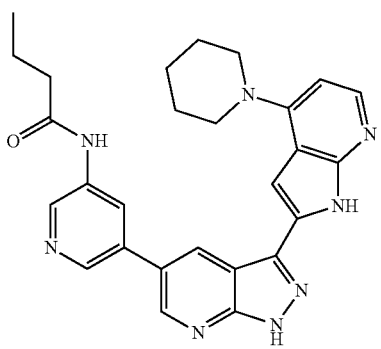

N-(5-(3-(4-(Piperidin-1-yl)-1H-pyrrolo[2,3-b]pyridin-2-yl)-1H-pyrazolo[3,4-b]pyridin-5-yl)pyridin-3-yl)butyramide 185

$^1$H NMR (400 MHz, DMSO-d$_6$) δ ppm 0.94 (t, J=7.34 Hz, 3 H), 1.60-1.69 (m, 2 H), 1.71 (br s, 6 H), 2.37 (br t, J=7.45 Hz, 2 H), 3.73 (br d, J=0.88 Hz, 4 H), 6.62-6.72 (m, 1 H), 7.33 (s, 1 H), 7.95 (d, J=6.58 Hz, 1 H), 8.50 (br d, J=1.53 Hz, 1 H), 8.76 (d, J=0.88 Hz, 2H), 8.90 (s, 2 H), 10.34 (s, 1 H), 12.68 (s, 1 H), 14.18 (br d, J=0.66 Hz, 1 H); ESIMS found for C$_{27}$H$_{28}$N$_8$O m/z 481.2 (M+1).

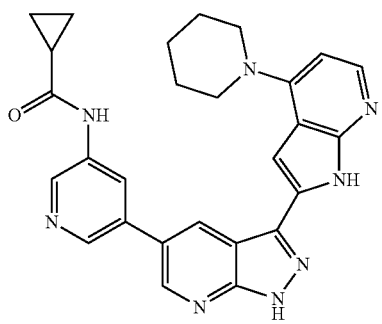

N-(5-(3-(4-(Piperidin-1-yl)-1H-pyrrolo[2,3-b]pyridin-2-yl)-1H-pyrazolo[3,4-b]pyridin-5-yl)pyridin-3-yl)cyclopropanecarboxamide 188

$^1$H NMR (400 MHz, DMSO-d$_6$) δ ppm 0.77-0.92 (m, 4 H), 1.60-1.69 (m, 2 H), 1.69-1.79 (m, 4 H), 1.80-1.92 (m, 1 H), 3.47 (br d, J=4.85 Hz, 4 H), 6.46 (d, J=5.51 Hz, 1 H), 7.07-7.15 (m, 1 H), 7.99 (d, J=5.51 Hz, 1 H), 8.50 (t, J=2.09 Hz, 1 H), 8.75 (d, J=2.43 Hz, 1 H), 8.78 (d, J=1.98 Hz, 1 H), 8.88 (d, J=1.76 Hz, 2 H), 10.59 (s, 1 H), 12.04 (s, 1 H), 14.01 (br s, 1 H); ESIMS found for C$_{27}$H$_{26}$N$_8$O m/z 479.3 (M+1).

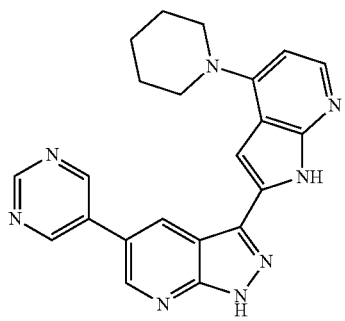

3-(4-(Piperidin-1-yl)-1H-pyrrolo[2,3-b]pyridin-2-yl)-5-(pyrimidin-5-yl)-1H-pyrazolo[3,4-b]pyridine 195

$^1$H NMR (400 MHz, DMSO-d$_6$) δ ppm 1.60-1.69 (m, 2 H), 1.69-1.78 (m, 4 H), 3.41 (s, 6 H), 6.46 (br d, J=5.51 Hz, 1 H), 7.18 (br d, J=1.10 Hz, 1 H), 7.99 (br d, J=5.51 Hz, 1 H), 9.02 (br d, J=1.98 Hz, 1 H), 9.08 (br d, J=1.98 Hz, 1 H), 9.25 (s, 1 H), 9.37 (s, 2 H), 11.99 (br s, 1 H), 14.07 (br s, 1 H); ESIMS found for C$_{22}$H$_{20}$N$_8$ m/z 397.1 (M+1).

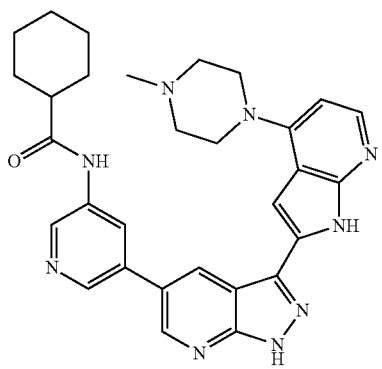

247

N-(5-(3-(4-(4-Methylpiperazin-1-yl)-1H-pyrrolo[2,3-b]pyridin-2-yl)-1H-pyrazolo[3,4-b]pyridin-5-yl)pyridin-3-yl)cyclohexanecarboxamide 247

¹H NMR (400 MHz, DMSO-d₆) δ ppm 1.16-1.37 (m, 3 H), 1.40-1.56 (m, 2 H), 1.61-1.71 (m, 1 H), 1.72-1.83 (m, 2 H), 1.89 (br d, J=12.13 Hz, 2 H), 2.44-2.48 (m, 1 H), 2.85 (br s, 3 H), 3.24-3.40 (m, 2 H), 3.55-3.67 (m, 2 H), 3.90 (br t, J=13.01 Hz, 2 H), 4.61-4.72 (m, 2 H), 6.98 (d, J=7.06 Hz, 1 H), 7.65 (br d, J=1.54 Hz, 1 H), 8.11 (d, J=7.28 Hz, 1 H), 8.86 (br s, 1 H), 8.97 (d, J=1.76 Hz, 1 H), 9.06 (br s, 1 H), 9.08 (br d, J=0.66 Hz, 1 H), 9.11 (br d, J=1.76 Hz, 1 H), 10.94 (br s, 1 H), 11.66 (br s, 1 H), 13.46 (s, 1 H), 14.43 (br s, 1 H); ESIMS found for C₃₀H₃₃N₉O m/z 536.2 (M+1).

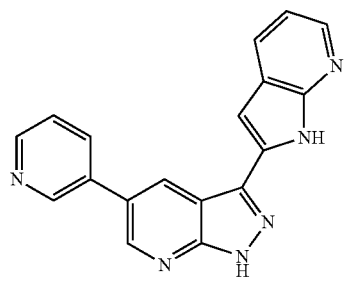

256

5-(Pyridin-3-yl)-3-(1H-pyrrolo[2,3-b]pyridin-2-yl)-1H-pyrazolo[3,4-b]pyridine 256

¹H NMR (400 MHz, DMSO-d₆) δ ppm 7.23 (br dd, J=7.83, 4.96 Hz, 1 H), 7.54 (d, J=1.54 Hz, 1 H), 8.02-8.13 (m, 1 H), 8.17 (br d, J=7.94 Hz, 1 H), 8.32 (br dd, J=4.96, 1.43 Hz, 1 H), 8.89 (d, J=5.51 Hz, 1 H), 8.92-9.00 (m, 1 H), 9.10 (d, J=1.98 Hz, 1 H), 9.17 (d, J=2.20 Hz, 1 H), 9.44 (br d, J=1.32 Hz, 1 H), 12.70 (br s, 1 H), 14.32 (br s, 1 H); ESIMS found for C₁₈H₁₂N₆ m/z 313.1 (M+1).

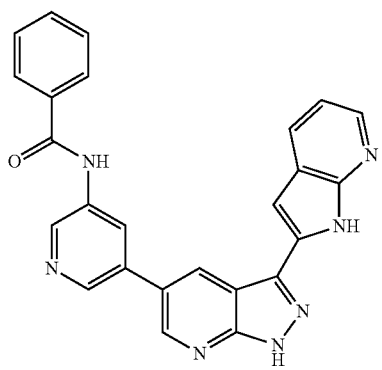

263

N-(5-(3-(1H-Pyrrolo[2,3-b]pyridin-2-yl)-1H-pyrazolo[3,4-b]pyridin-5-yl) pyridin-3-yl)benzamide 263

¹H NMR (400 MHz, DMSO-d₆) δ ppm 7.29 (dd, J=7.94, 5.07 Hz, 1 H), 7.57-7.64 (m, 3H), 7.65-7.73 (m, 1 H), 8.09-8.18 (m, 2 H), 8.23-8.31 (m, 1 H), 8.35 (br d, J=4.85 Hz, 1 H), 9.04 (d, J=2.21 Hz, 1 H), 9.13 (br s, 1 H), 9.15 (d, J=1.98 Hz, 1 H), 9.18 (s, 1 H), 9.34 (br d, J=1.54 Hz, 1 H), 11.24 (s, 1 H), 12.92 (br s, 1 H), 14.39 (br s, 1 H); ESIMS found for C₂₅H₁₇N₇O m/z 432.1 (M+1).

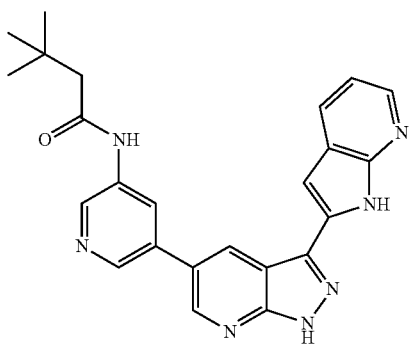

268

N-(5-(3-(1H-Pyrrolo[2,3-b]pyridin-2-yl)-1H-pyrazolo[3,4-b]pyridin-5-yl) pyridin-3-yl)-3,3-dimethylbutanamide 268

¹H NMR (400 MHz, DMSO-d₆) δ ppm 1.07 (s, 9H), 2.32 (s, 2 H), 7.22 (br dd, J=7.83, 5.18 Hz, 1 H), 7.48 (br d, J=1.54 Hz, 1 H), 8.10-8.19 (m, 1 H), 8.28-8.36 (m, 1 H), 8.65 (br s, 1 H), 8.96 (br d, J=2.21 Hz, 1 H), 9.00 (br s, 1 H), 9.05 (br d, J=1.76 Hz, 1 H), 9.10 (br s, 1 H), 10.69 (br s, 1 H), 12.65 (br s, 1 H), 14.28 (br s, 1 H); ESIMS found for C₂₄H₂₃N₇O m/z 426.2 (M+1).

270

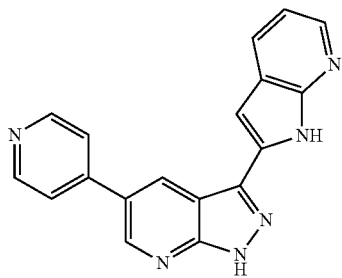

5-(Pyridin-4-yl)-3-(1H-pyrrolo[2,3-b]pyridin-2-yl)-1H-pyrazolo[3,4-b]pyridine 270

¹H NMR (400 MHz, DMSO-d₆) δ ppm 7.34 (br dd, J=7.72, 5.51 Hz, 1 H), 7.68 (s, 1 H), 8.34 (br d, J=7.72 Hz, 1 H), 8.39 (d, J=5.07 Hz, 1 H), 8.74 (d, J=6.39 Hz, 2 H), 9.05 (d, J=6.39 Hz, 2 H), 9.27 (d, J=1.76 Hz, 1 H), 9.35 (d, J=1.76 Hz, 1 H), 13.10 (br s, 1 H), 14.60 (br s, 1 H); ESIMS found for $C_{18}H_{12}N_6$ m/z 313.0 (M+1).

271

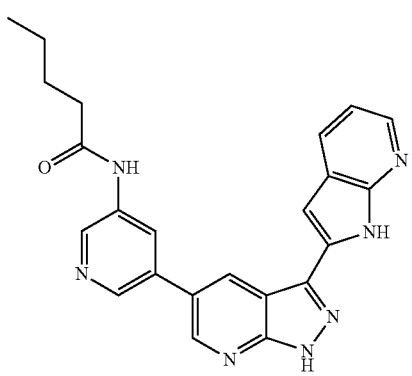

N-(5-(3-(1H-Pyrrolo[2,3-b]pyridin-2-yl)-1H-pyrazolo[3,4-b]pyridin-5-yl) pyridin-3-yl)pentanamide 271

¹H NMR (400 MHz, DMSO-d₆) δ ppm 0.92 (t, J=7.39 Hz, 3H), 1.36 (dq, J=14.86, 7.40 Hz, 2 H), 1.63 (quin, J=7.50 Hz, 2 H), 2.41 (t, J=7.39 Hz, 2 H), 7.14 (dd, J=7.83, 4.74 Hz, 1 H), 7.39 (d, J=1.76 Hz, 1 H), 8.01-8.09 (m, 1 H), 8.28 (dd, J=4.74, 1.43 Hz, 1 H), 8.51 (s, 1 H), 8.85 (d, J=1.76 Hz, 1 H), 8.91 (t, J=2.76 Hz, 2 H), 8.97 (d, J=1.98 Hz, 1 H), 10.46 (s, 1 H), 12.38 (br s, 1 H), 14.17 (br s, 1 H); ESIMS found for $C_{23}H_{21}N_7O$ m/z 412.1 (M+1).

274

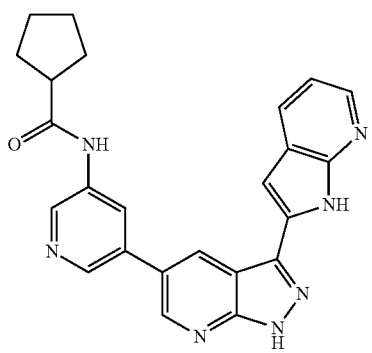

N-(5-(3-(1H-Pyrrolo[2,3-b]pyridin-2-yl)-1H-pyrazolo[3,4-b]pyridin-5-yl) pyridin-3-yl)cyclopentanecarboxamide 274

¹H NMR (400 MHz, DMSO-d₆) δ ppm 1.53-1.65 (m, 2 H), 1.65-1.73 (m, 2H), 1.73-1.85 (m, 2 H), 1.88-1.99 (m, 2 H), 2.98 (dt, J=15.88, 7.94 Hz, 1 H), 7.35 (dd, J=7.94, 5.29 Hz, 1 H), 7.63 (s, 1 H), 8.35 (d, J=7.72 Hz, 1 H), 8.38 (d, J=5.29 Hz, 1 H), 8.98 (s, 1 H), 9.00 (d, J=1.98 Hz, 1 H), 9.14 (d, J=2.21 Hz, 1 H), 9.17 (d, J=1.54 Hz, 1 H), 9.25 (d, J=1.76 Hz, 1 H), 11.31 (s, 1 H), 13.12 (br s, 1 H), 14.45 (br s, 1 H); ESIMS found for $C_{24}H_{21}N_7O$ m/z 424.1 (M+1).

275

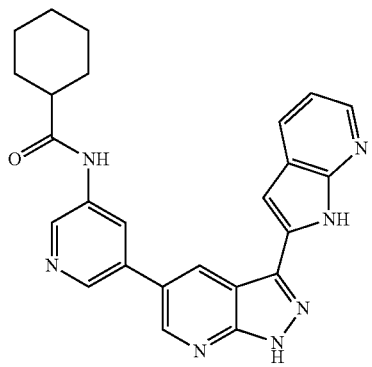

N-(5-(3-(1H-Pyrrolo[2,3-b]pyridin-2-yl)-1H-pyrazolo[3,4-b]pyridin-5-yl) pyridin-3-yl)cyclohexanecarboxamide 275

¹H NMR (400 MHz, DMSO-d₆) δ ppm 1.16-1.37 (m, 3H), 1.39-1.53 (m, 2H), 1.63-1.72 (m, 1 H), 1.73-1.83 (m, 2 H), 1.83-1.94 (m, 2 H), 2.40-2.47 (m, 1 H), 7.23 (br dd, J=7.83, 4.74 Hz, 1 H), 7.50 (s, 1 H), 8.17 (br d, J=7.94 Hz, 1 H), 8.32 (dd, J=5.07, 1.54 Hz, 1H), 8.72 (br s, 1 H), 8.96 (d, J=1.98 Hz, 1 H), 9.03 (s, 1 H), 9.07 (d, J=1.76 Hz, 1 H), 9.11 (s, 1H), 10.75 (br s, 1 H), 12.71 (br s, 1 H), 14.31 (br s, 1 H); ESIMS found for $C_{25}H_{23}N_7O$ m/z 438.2 (M+1).

324

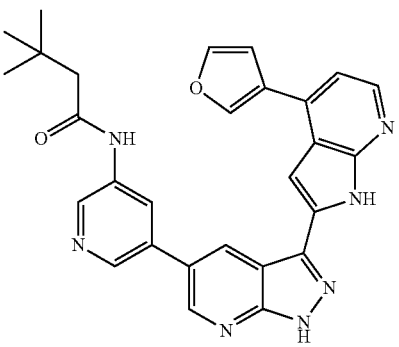

N-(5-(3-(4-(Furan-3-yl)-1H-pyrrolo[2,3-b]pyridin-2-yl)-1H-pyrazolo[3,4-b]pyridin-5-yl)pyridin-3-yl)-3,3-dimethylbutanamide 324

¹H NMR (400 MHz, DMSO-d₆) δ ppm 1.06 (s, 9H), 2.27 (s, 2 H), 7.25 (br s, 1 H), 7.36 (br d, J=4.85 Hz, 1 H), 7.48

(br s, 1 H), 7.89 (br s, 1 H), 8.28 (br d, J=5.07 Hz, 1 H), 8.42 (br s, 1 H), 8.75 (br s, 1 H), 8.80 (br s, 1 H), 8.88 (br dd, J=6.62, 1.76 Hz, 2 H), 9.05 (br d, J=1.54 Hz, 1 H), 10.25 (br s, 1 H), 12.44 (s, 1 H), 14.19 (s, 1 H); ESIMS found for C$_{28}$H$_{25}$N$_7$O$_2$ m/z 492.1 (M+1).

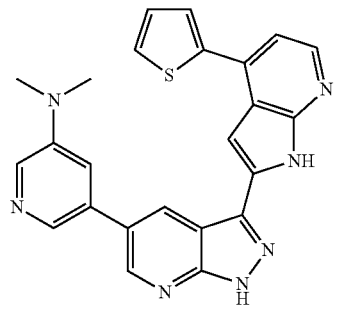

N,N-Dimethyl-5-(3-(4-(thiophen-2-yl)-1H-pyrrolo[2,3-b]pyridin-2-yl)-1H-pyrazolo[3,4-b]pyridin-5-yl)pyridin-3-amine 343

$^1$H NMR (400 MHz, DMSO-d$_6$) δ ppm 3.18 (s, 6 H), 6.96 (br d, J=1.76 Hz, 1H), 7.51 (br d, J=5.29 Hz, 1 H), 7.63-7.71 (m, 1 H), 7.98 (br d, J=3.97 Hz, 1 H), 8.11 (br s, 1 H), 8.19 (br d, J=3.97 Hz, 1 H), 8.22 (br d, J=2.65 Hz, 1 H), 8.30 (br d, J=5.29 Hz, 1 H), 8.65 (br s, 1H), 9.08 (s, 2 H), 12.05 (br s, 1 H), 14.20 (s, 1 H); ESIMS found for C$_{24}$H$_{19}$N$_7$S m/z 438.0 (M+1).

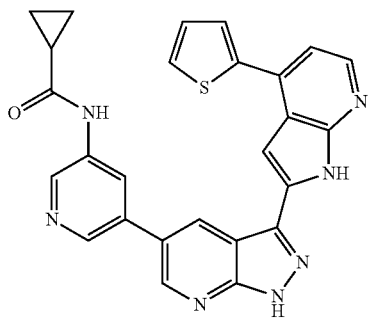

N-(5-(3-(4-(Thiophen-2-yl)-1H-pyrrolo[2,3-b]pyridin-2-yl)-1H-pyrazolo[3,4-b]pyridin-5-yl)pyridin-3-yl)cyclopropanecarboxamide 356

$^1$H NMR (400 MHz, DMSO-d$_6$) δ ppm 0.79-1.01 (m, 4 H), 1.87-1.98 (m, 1H), 7.01 (br d, J=1.54 Hz, 1 H), 7.58 (br d, J=5.29 Hz, 1 H), 7.66-7.74 (m, 1 H), 8.01 (br d, J=3.75 Hz, 1 H), 8.18 (d, J=3.97 Hz, 1 H), 8.33 (br d, J=5.51 Hz, 1 H), 8.63 (br s, 1H), 8.88-8.99 (m, 2 H), 9.01 (br d, J=1.98 Hz, 2 H), 11.04 (br s, 1 H), 12.18 (br s, 1 H), 14.18 (br s, 1 H); ESIMS found for C$_{26}$H$_{19}$N$_7$OS m/z 478.1 (M+1).

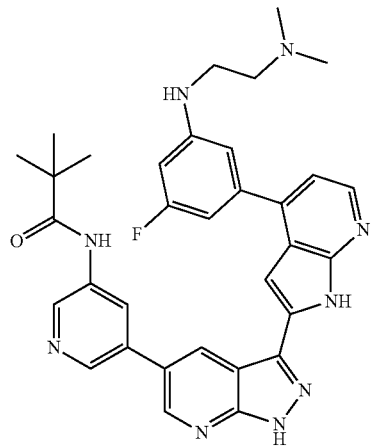

N-(5-(3-(4-(3-((2-(Dimethylamino)ethyl)amino)-5-fluorophenyl)-1H-pyrrolo [2,3-b]pyridin-2-yl)-1H-pyrazolo[3,4-b]pyridin-5-yl)pyridin-3-yl)pivalamide 456

$^1$H NMR (400 MHz, DMSO-d$_6$) δ ppm 1.27 (s, 9H), 2.17 (s, 6 H), 3.12-3.23 (m, 4 H), 6.09 (br t, J=4.85 Hz, 1 H), 6.43-6.56 (m, 1 H), 6.74 (br d, J=9.70 Hz, 1 H), 6.96 (s, 1 H), 7.22 (br d, J=4.85 Hz, 1 H), 7.34 (br d, J=1.76 Hz, 1 H), 8.32 (br d, J=4.85 Hz, 1 H), 8.44 (br t, J=2.09 Hz, 1 H), 8.78 (br d, J=1.98 Hz, 1 H), 8.89 (br d, J=1.98 Hz, 1 H), 8.92 (d, J=2.21 Hz, 1 H), 9.56 (s, 1 H), 12.49 (br s, 1 H), 14.17 (s, 1 H); ESIMS found for C$_{33}$H$_{34}$FN$_9$O m/z 592.2 (M+1).

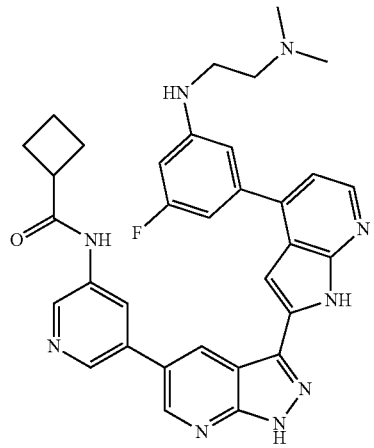

N-(5-(3-(4-(3-((2-(Dimethylamino)ethyl)amino)-5-fluorophenyl)-1H-pyrrolo [2,3-b]pyridin-2-yl)-1H-pyrazolo[3,4-b]pyridin-5-yl)pyridin-3-yl)cyclobutanecarboxamide 469

$^1$H NMR (400 MHz, DMSO-d$_6$) δ ppm 1.74-1.87 (m, 2 H), 1.92-2.03 (m, 2H), 2.13 (s, 6 H), 2.21-2.30 (m, 2 H), 2.40-2.46 (m, 1 H), 3.11-3.22 (m, 4 H), 6.05-6.13 (m, 1 H), 6.48 (d, J=11.40 Hz, 1 H), 6.70-6.78 (m, 1 H), 6.97 (s, 1 H), 7.22 (d, J=4.82 Hz, 1 H), 7.34 (s, 1 H), 8.42 (d, J=0.88 Hz, 1 H), 8.76 (d, J=2.19 Hz, 1 H), 8.83 (d, J=2.19 Hz, 1 H), 8.88

(d, J=2.19 Hz, 1 H), 8.91 (s, 1 H), 10.10 (d, J=1.75 Hz, 1 H), 12.49 (br s, 1 H), 14.18 (br s, 1 H); ESIMS found for C₃₃H₃₂FN₉O m/z 590.2 (M+1).

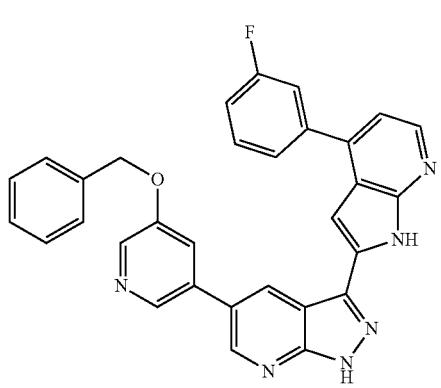

518

5-(5-(Benzyloxy)pyridin-3-yl)-3-(4-(3-fluorophenyl)-1H-pyrrolo[2,3-b]pyridin-2-yl)-1H-pyrazolo[3,4-b]pyridine 518

¹H NMR (400 MHz, DMSO-d₆) δ ppm 5.33 (s, 2 H), 7.29 (br d, J=4.82 Hz, 2H), 7.36 (br d, J=7.45 Hz, 1 H), 7.39-7.46 (m, 3H), 7.53 (br d, J=7.45 Hz, 2 H), 7.58-7.66 (m, 1 H), 7.71 (br d, J=10.52 Hz, 1 H), 7.77 (br d, J=7.02 Hz, 1 H), 8.02 (br s, 1 H), 8.36 (d, J=5.26 Hz, 1 H), 8.41 (br s, 1 H), 8.71 (s, 1 H), 8.99 (s, 2 H), 12.51 (s, 1 H), 14.18 (s, 1 H); ESIMS found for C₃₁H₂₁FN₆O m/z 513.0 (M+1).

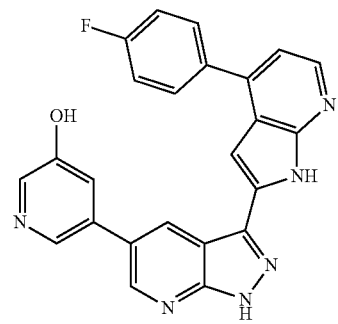

533

5-(3-(4-(4-Fluorophenyl)-1H-pyrrolo[2,3-b]pyridin-2-yl)-1H-pyrazolo[3,4-b]pyridin-5-yl)pyridin-3-ol 533

¹H NMR (400 MHz, METHANOL-d₄) δ ppm 7.41-7.50 (m, 2 H), 7.71 (br d, J=6.17 Hz, 1 H), 7.74 (br s, 1 H), 8.04-8.13 (m, 2 H), 8.40 (br d, J=7.28 Hz, 2 H), 8.46 (br d, J=5.95 Hz, 1 H), 8.86 (br s, 1 H), 8.99 (s, 1 H), 9.06-9.12 (m, 1 H); ESIMS found for C₂₄H₁₅FN₆O m/z 423.1 (M+1).

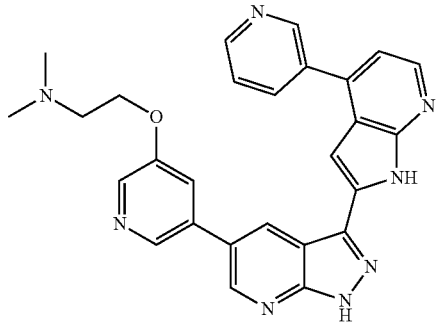

563

N,N-dimethyl-2-((5-(3-(4-(pyridin-3-yl)-1H-pyrrolo[2,3-b]pyridin-2-yl)-1H-pyrazolo[3,4-b]pyridin-5-yl)pyridin-3-yl)oxy)ethan-1-amine 563

¹H NMR (400 MHz, DMSO-d₆) δ ppm 2.90 (br s, 6 H), 3.60 (br s, 2 H), 4.51-4.64 (m, 2 H), 7.03-7.08 (m, 1 H), 7.31-7.41 (m, 2 H), 7.49 (br s, 1 H), 7.69-7.78 (m, 1 H), 8.02 (br s, 1 H), 8.37-8.43 (m, 1 H), 8.43-8.51 (m, 1 H), 8.74-8.79 (m, 1 H), 8.80 (br s, 1 H), 9.03 (br d, J=6.61 Hz, 1 H), 9.18 (br s, 1 H), 12.61 (br s, 1 H), 14.23 (br d, J=4.63 Hz, 1 H); ESIMS found for C₂₇H₂₄N₈O m/z 477.1 (M+1).

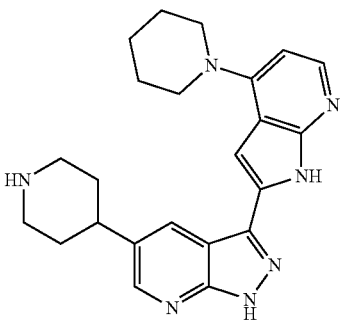

601

3-(4-(Piperidin-1-yl)-1H-pyrrolo[2,3-b]pyridin-2-yl)-5-(piperidin-4-yl)-1H-pyrazolo[3,4-b]pyridine 601

¹H NMR (400 MHz, DMSO-d₆) δ ppm 1.76 (br s, 6 H), 1.98-2.09 (m, 2 H), 2.09-2.25 (m, 2 H), 2.95-3.09 (m, 2 H), 3.09-3.20 (m, 1 H), 3.40 (br d, J=11.91 Hz, 2 H), 3.95 (br s, 4 H), 6.83 (d, J=7.28 Hz, 1 H), 7.34 (d, J=0.88 Hz, 1 H), 7.94 (d, J=7.28 Hz, 1 H), 8.45 (d, J=1.54 Hz, 1 H), 8.56 (d, J=1.98 Hz, 1 H), 9.10-9.22 (m, 1 H), 9.27-9.40 (m, 1 H), 13.22 (s, 1H), 14.12 (br s, 1 H); ESIMS found for C₂₃H₂₇N₇ m/z 402.2 (M+1).

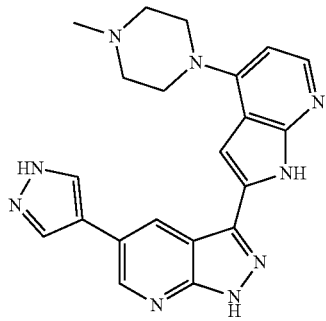

3-(4-(4-Methylpiperazin-1-yl)-1H-pyrrolo[2,3-b]pyridin-2-yl)-5-(1H-pyrazol-4-yl)-1H-pyrazolo[3,4-b]pyridine 635

$^1$H NMR (400 MHz, DMSO-d$_6$) δ ppm 2.88 (s, 3H), 3.54-3.65 (m, 2 H), 3.65-3.79 (m, 2 H), 4.39-4.58 (m, 2 H), 6.84 (br d, J=5.73 Hz, 1 H), 7.47 (br s, 1 H), 8.09 (br d, J=6.39 Hz, 1 H), 8.32 (br s, 2 H), 8.84 (br d, J=1.54 Hz, 1 H), 8.97 (br d, J=1.76 Hz, 1 H), 11.20 (br s, 1 H), 12.92 (br s, 1 H), 14.06 (br s, 1 H); ESIMS found for C$_{21}$H$_{21}$N$_9$ m/z 400.2 (M+1).

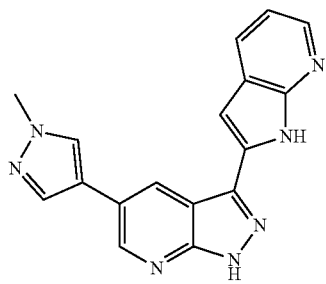

5-(1-Methyl-1H-pyrazol-4-yl)-3-(1H-pyrrolo[2,3-b]pyridin-2-yl)-1H-pyrazolo[3,4-b]pyridine 652

$^1$H NMR (400 MHz, DMSO-d$_6$) δ ppm 3.92 (s, 3H), 7.41 (dd, J=7.83, 5.40 Hz, 1 H), 7.63 (s, 1 H), 8.16 (d, J=0.66 Hz, 1 H), 8.39 (dd, J=5.40, 1.21 Hz, 1 H), 8.41-8.47 (m, 2 H), 8.82 (d, J=2.21 Hz, 1 H), 8.93 (d, J=2.21 Hz, 1 H), 13.23 (br s, 1 H), 14.22 (br s, 1 H); ESIMS found for C$_{17}$H$_{13}$N$_7$ m/z 316.0 (M+1).

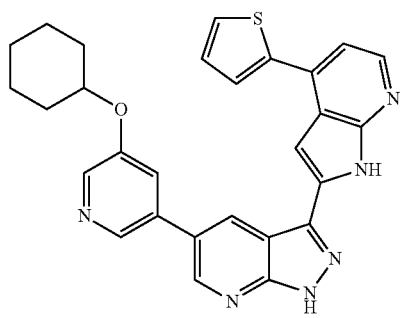

5-(5-(Cyclohexyloxy)pyridin-3-yl)-3-(4-(thiophen-2-yl)-1H-pyrrolo[2,3-b]pyridin-2-yl)-1H-pyrazolo[3,4-b]pyridine 703

$^1$H NMR (400 MHz, DMSO-d$_6$) δ ppm 1.24-1.37 (m, 1 H), 1.39-1.64 (m, 5H), 1.71-1.83 (m, 2 H), 1.97-2.09 (m, 2 H), 4.76-4.86 (m, 1 H), 7.04-7.13 (m, 1 H), 7.68 (d, J=5.51 Hz, 1 H), 7.71-7.79 (m, 1 H), 8.10 (d, J=3.97 Hz, 1 H), 8.26 (d, J=3.97 Hz, 1 H), 8.38 (d, J=5.51 Hz, 1 H), 8.49 (s, 1 H), 8.64 (br d, J=1.98 Hz, 1 H), 8.98 (s, 1 H), 9.08 (d, J=1.98 Hz, 1H), 9.10 (d, J=1.98 Hz, 1 H), 12.45 (br s, 1 H), 14.24 (br s, 1 H); ESIMS found for C$_{28}$H$_{24}$N$_6$OS m/z 493.1 (M+1).

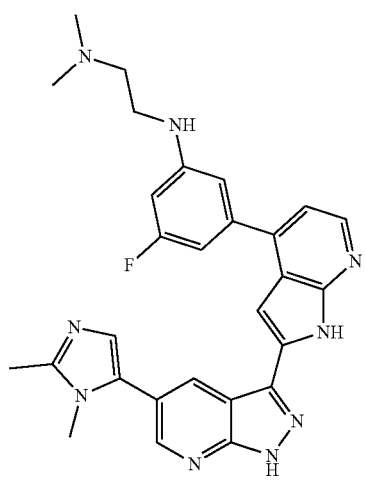

N$^1$-(3-(2-(5-(1,2-Dimethyl-1H-imidazol-5-yl)-1H-pyrazolo[3,4-b]pyridin-3-yl)-1H-pyrrolo[2,3-b]pyridin-4-yl)-5-fluorophenyl)-N$^2$,N$^2$-dimethylethane-1,2-diamine 781

$^1$H NMR (400 MHz, DMSO-d$_6$) δ ppm 2.17 (s, 6 H), 2.39 (s, 3H), 3.03-3.27 (m, 4 H), 3.59 (s, 3H), 6.02-6.14 (m, 1 H), 6.42-6.56 (m, 1 H), 6.73 (br d, J=9.92 Hz, 1H), 6.98 (s, 1 H), 7.04 (s, 1 H), 7.20 (d, J=5.07 Hz, 1 H), 7.29 (br d, J=1.76 Hz, 1 H), 8.30 (d, J=4.85 Hz, 1 H), 8.66 (s, 2 H), 12.43 (br s, 1 H), 14.14 (br s, 1 H); ESIMS found for C$_{28}$H$_{28}$FN$_9$ m/z 510.1 (M+1).

Example 2

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities.

Each compound was dissolved in DMSO as a 10 mM stock and used to prepare compound source plates. Serial dilution (1:3, 10-point dose-response curves starting from 10 μM)

and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with medium containing 1% fetal bovine serum and incubated overnight at 37° C. and 5% $CO_2$. Following incubation, 20 µl of BrightGlo luminescence reagent (Promega) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for $EC_{50}$ calculations using the dose-response log (inhibitor) vs. response—variable slope (four parameters) nonlinear regression feature available in GraphPad Prism 5.0 (or Dotmatics). For $EC_{50}$ of >10 µM, the percent inhibition at 10 µM is provided.

Table 2 shows the measured activity for representative compounds of Formula I as described herein.

TABLE 2

| Compound | $EC_{50}$ (µM) |
| --- | --- |
| 1 | >10 (46.1%) |
| 4 | >10 (7.6%) |
| 11 | >10 (10.0%) |
| 13 | >10 (22.6%) |
| 18 | >10 (11.7%) |
| 20 | >10 (57.3%) |
| 24 | >10 (25.8%) |
| 28 | >10 (15.0%) |
| 30 | >10 (11.9%) |
| 33 | >10 (2.7%) |
| 36 | >10 (12.7%) |
| 42 | >10 (26.0%) |
| 43 | >10 (2.8%) |
| 51 | >10 (14.2%) |
| 54 | >10 (8.7%) |
| 55 | >10 (13.6%) |
| 59 | >10 (48.3%) |
| 62 | >10 (0%) |
| 63 | >10 (4.0%) |
| 65 | >10 (30.8%) |
| 68 | >10 (4.6%) |
| 72 | >10 (16.0%) |
| 75 | >10 (2.1%) |
| 78 | >10 (17.0%) |
| 86 | >10 (2.7%) |
| 88 | >10 (17.0%) |
| 90 | >10 (8.2%) |
| 93 | >10 (15.4%) |
| 96 | >10 (30.1%) |
| 97 | >10 (0%) |
| 99 | >10 (26.0%) |
| 104 | >10 (0%) |
| 115 | >10 (5.6%) |
| 117 | >10 (13.0%) |
| 123 | >10 (5.2%) |
| 128 | >10 (0%) |
| 129 | >10 (35.0%) |
| 130 | >10 (6.3%) |
| 135 | >10 (16.4%) |
| 136 | >10 (0%) |
| 140 | >10 (12.3%) |
| 169 | 0.861 |
| 176 | >10 (5.0%) |
| 181 | >10 (38.8%) |
| 182 | >10 (7.1%) |
| 185 | >10 (10.9%) |
| 188 | 3.310 |
| 195 | >10 (6.9%) |
| 247 | >10 (6.4%) |
| 256 | 1.065 |
| 263 | >10 (29.7%) |
| 268 | 0.860 |
| 270 | >10 (0%) |
| 271 | >10 (6.5%) |
| 274 | >10 (40.3%) |
| 275 | 1.260 |
| 324 | >10 (4.2%) |
| 343 | >10 (18.3%) |
| 356 | 6.369 |
| 456 | >10 (42.4%) |
| 469 | >10 (47.5%) |
| 518 | >10 (0%) |
| 533 | >10 (3.4%) |
| 563 | >10 (20.6%) |
| 577 | >10 (12.5%) |
| 601 | >10 (36.6%) |
| 635 | >10 (5.8%) |
| 652 | >10 (23.4%) |
| 703 | >10 (38.6%) |
| 781 | 4.464 |

Example 3

Representative compounds were screened using the following assay procedure to assess the effect on cell viability as described below.

Each compound was dissolved in DMSO as a 10 mM stock and used to prepare compound source plates. Serial dilution (1:3, 8-point dose-response curves from 10 µM to 0.0045 µM) and compound transfer was performed using the ECHO 550 (Labcyte, Sunnyvale, Calif.) into 96-well clear bottom, black-walled plates (Corning-Costar).

Approximately 2×103 SW480 colon cancer cells were seeded into each well and allowed to incubate in the presence or absence of compound for four days at 37° C./5% $CO_2$. Eight replicates of DMSO-treated cells served as controls and cells treated with compound were performed in duplicate.

After incubation, 20 µL of CellTiter-Blue (Promega) was added to each well allowed to incubate for approximately 3 hours. This reagent was a buffered solution which contains resazurin, metabolically active cells were able to reduce rezarurin (blue) into resorufin (pink) which was highly fluorescent. This measured fluorescence was used as a readout for cell viability.

After incubation, the plates were read at Ex 560 nm Em 590 nm (Cytation 3, BioTek). Dose-response curves were generated and $EC_{50}$ concentration values were calculated using non-linear regression curve fit in the GraphPad Prism (San Diego, Calif.) or Dotmatics' Studies Software (Bishops Stortford, UK). For $EC_{50}$ of >10 µM, the percent inhibition at 10 µM is provided.

Table 3 shows the activity of representative compounds of Formula I as provided herein.

TABLE 3

| Compound | $EC_{50}$ (µM) |
| --- | --- |
| 1 | >10 (9.8%) |
| 4 | >10 (17.5%) |
| 11 | 0.643 |
| 13 | >10 (11.6%) |
| 18 | >10 (23.2%) |
| 20 | >10 (51.4%) |
| 24 | 2.449 |
| 28 | >10 (16.3%) |
| 30 | >10 (18.5%) |
| 33 | >10 (25.0%) |

TABLE 3-continued

| Compound | EC$_{50}$ (µM) |
| --- | --- |
| 36 | >10 (11.9%) |
| 42 | >10 (24.8%) |
| 43 | >10 (6.9%) |
| 51 | >10 (17.7%) |
| 54 | >10 (6.9%) |
| 55 | >10 (3.5%) |
| 59 | >10 (20.1%) |
| 62 | >10 (38.2%) |
| 63 | >10 (16.1%) |
| 65 | >10 (32.1%) |
| 68 | >10 (1.0%) |
| 72 | >10 (14.7%) |
| 75 | >10 (23.6%) |
| 78 | >10 (11.3%) |
| 86 | >10 (24.1%) |
| 88 | >10 (10.8%) |
| 90 | >10 (17.0%) |
| 93 | >10 (10.1%) |
| 96 | >10 (14.3%) |
| 97 | >10 (19.6%) |
| 99 | >10 (9.6%) |
| 104 | >10 (10.4%) |
| 115 | >10 (0%) |
| 117 | >10 (10.1%) |
| 123 | >10 (12.0%) |
| 128 | >10 (10.7%) |
| 129 | >10 (3.8%) |
| 130 | >10 (5.7%) |
| 135 | >10 (13.9%) |
| 136 | >10 (14.9%) |
| 140 | >10 (20.2%) |
| 169 | >10 (36.1%) |
| 176 | >10 (2.9%) |
| 181 | >10 (40.9%) |
| 182 | >10 (26.0%) |
| 185 | >10 (4.9%) |
| 188 | >10 (40.8%) |
| 195 | >10 (13.9%) |
| 247 | >10 (11.7%) |
| 256 | >10 (5.8%) |
| 263 | >10 (21.1%) |
| 268 | 1.987 |
| 270 | >10 (23.9%) |
| 271 | >10 (11.4%) |
| 274 | >10 (54.2%) |
| 275 | 2.427 |
| 324 | >10 (5.3%) |
| 343 | >10 (36.8%) |
| 356 | >10 (14.5%) |
| 456 | >10 (0%) |
| 469 | >10 (0%) |
| 518 | >10 (16.3%) |
| 533 | >10 (19.0%) |
| 563 | >10 (5.3%) |
| 577 | >10 (8.7%) |
| 601 | 5.383 |
| 635 | >10 (3.6%) |
| 652 | >10 (9.2%) |
| 703 | >10 (23.3%) |
| 781 | >10 (0%) |

Example 4

Representative compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and Penicillin/Streptomycin.

Compound Screening:

Each compound was dissolved in DMSO as a 10 mM stock and used to prepare compound source plates. Serial dilution (1:2, 11-point dose-response curves from 10 M to 1.87 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells are plated at 1,500 cells/well in 80 µL/well F12 medium supplemented with 1% Fetal Bovine Serum. One hour after addition of the cells, TGF-β1 (Peprotech; 20 ng/mL) was added to the plates to induce fibrosis (ref. 1 and 2 above). Wells treated with TGF-β1 and containing DMSO were used as controls. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 µM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and EC$_{50}$ values were calculated using non-linear regression curve fit in the Dotmatics' Studies Software. For EC$_{50}$ of >10 µM, the percent inhibition at 10 µM is provided.

Table 4 shows the activity of representative compounds of Formula I as provided herein.

TABLE 4

| Compound | EC$_{50}$ (µM) |
| --- | --- |
| 1 | >10 (0%) |
| 4 | 2.720 |
| 11 | 0.320 |
| 13 | >10 (5.2%) |
| 18 | 1.446 |
| 20 | 2.632 |
| 24 | 1.054 |
| 28 | >10 (52.0%) |
| 30 | >10 (12.8%) |
| 33 | 4.513 |

TABLE 4-continued

| Compound | EC$_{50}$ (μM) |
| --- | --- |
| 36 | >10 (33.9%) |
| 42 | 4.977 |
| 43 | >10 (0%) |
| 51 | >10 (1.3%) |
| 54 | 4.876 |
| 55 | >10 (1.8%) |
| 59 | >10 (0%) |
| 62 | >10 (0%) |
| 63 | >10 (0%) |
| 65 | 0.812 |
| 68 | 8.540 |
| 72 | 0.759 |
| 75 | >10 (0%) |
| 78 | 7.090 |
| 86 | >10 (0%) |
| 88 | >10 (0%) |
| 90 | >10 (5.1%) |
| 93 | >10 (42.1%) |
| 96 | 1.559 |
| 97 | >10 (0%) |
| 99 | >10 (73.8%) |
| 104 | >10 (19.6%) |
| 115 | 5.901 |
| 117 | >10 (52.9%) |
| 123 | >10 (0%) |
| 128 | >10 (0%) |
| 129 | 0.621 |
| 130 | >10 (20.5%) |
| 135 | >10 (19.8%) |
| 136 | 3.040 |
| 140 | >10 (24.5%) |
| 169 | 2.979 |
| 176 | >10 (22.4%) |
| 181 | 0.007 |
| 182 | >10 (21.9%) |
| 185 | >10 (0%) |
| 188 | 1.791 |
| 195 | 4.377 |
| 247 | 5.032 |
| 256 | 0.529 |
| 263 | 0.363 |
| 268 | 0.420 |
| 270 | >10 (55.6%) |
| 271 | 5.350 |
| 274 | 0.760 |
| 275 | 1.557 |
| 324 | >10 (0%) |
| 343 | 1.754 |
| 356 | >10 (0%) |
| 456 | >10 (0%) |
| 469 | >10 (0%) |
| 518 | >10 (0%) |
| 533 | 6.757 |
| 563 | 2.440 |
| 577 | 1.411 |
| 601 | 9.658 |
| 635 | >10 (26.0%) |
| 652 | 0.230 |
| 703 | 2.506 |
| 781 | 0.938 |

Example 5

Representative compounds were screened using primary human mesenchymal stem cells (hMSCs) to determine their ability to induce chondrogenesis (process by which cartilage is developed).

Human Mesenchymal Stem Cell Culture:

Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening:

Each compound was dissolved in DMSO as a 10 mM stock and used to prepare compound source plates. Serial dilution (1:3, 6-point dose-response curves from 2700 nM to 10 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 μL/well Incomplete Chondrogenic Induction Medium (Lonza; DMEM, dexamethasone, ascorbate, insulin-transferrin-selenium [ITS supplement], gentamycin-amphotericin [GA-1000], sodium pyruvate, proline and L-glutamine). TGF-β3 (10 ng/mL) was used as a positive control for differentiation while negative control wells were treated with 75 nL DMSO for normalization and calculating EC$_{50}$ values. Cells were incubated at 37° C. and 5% $CO_2$ for 6 days. To image chondrogenic nodules, the cells were fixed using 4% formaldehyde (Electron Microscopy Sciences), and stained with 2 μg/mL Rhodamine B (Sigma-Aldrich) and 20 μM Nile Red (Sigma-Aldrich) [Johnson K., et. al, A Stem Cell-Based Approach to Cartilage Repair, Science, (2012), 336(6082), 717-721]. The nodules imaged (4 images per well at 4× magnification) by excitation at 531 nm and emission at 625 nm and quantified using the CellInsight CX5 (Thermo Scientific). Number of nodules in each well was normalized to the average of 3 DMSO treated wells on the same plate using Excel (Microsoft Inc.). The normalized averages (fold change over DMSO) of 3 replicate wells for each compound concentration were calculated. Due to solubility limitations of some of the compounds, curve fitting was incomplete leading to inaccurate EC$_{50}$ determinations.

Using TGF-β3 as a positive control, the concentration of representative compounds required to induce 50% levels of chondrogenesis is reported. In addition, the maximum activity of each compound and the respective dose that each compound reached maximum chondrogenesis activity is reported. Table 5 shows the activity of representative compounds as provided herein.

TABLE 5

| Compound | Conc (nM) of Max. activity | Max. Activity as % TGF-β3 activity | Conc (nM) of 50% TGF-β3 activity |
| --- | --- | --- | --- |
| 13 | 100 | 102 | 100 |
| 33 | 900 | 108 | 900 |
| 42 | 300 | 25 | NA |
| 59 | 100 | 28 | NA |
| 62 | 100 | 55 | 100 |
| 63 | 900 | 35 | NA |
| 68 | 10 | 82 | 10 |
| 75 | 30 | 82 | 30 |
| 86 | 10 | 44 | NA |
| 90 | 10 | 92 | 10 |
| 97 | 2700 | 49 | NA |
| 99 | 300 | 44 | NA |
| 115 | 100 | 12 | NA |
| 128 | 900 | 79 | 300 |
| 129 | 30 | 50 | 30 |
| 136 | 2700 | 93 | 2,700 |
| 169 | 2700 | 183 | 900 |
| 181 | 2700 | 46 | NA |
| 256 | 10 | 11 | NA |
| 263 | 10 | 22 | NA |
| 268 | 2700 | 23 | NA |
| 271 | 2700 | 260 | 900 |

TABLE 5-continued

| Compound | Conc (nM) of Max. activity | Max. Activity as % TGF-β3 activity | Conc (nM) of 50% TGF-β3 activity |
|---|---|---|---|
| 275 | 100 | 28 | NA |
| 577 | 30 | 27 | NA |
| 635 | 300 | 20 | NA |
| 652 | 300 | 52 | 300 |

Example 6

Representative compounds were screened using the following assay procedure to determine their ability to inhibit IL-6 and therefore demonstrate their anti-inflammatory properties.

Human Monocyte Cell Culture:

Human monocyte cell line (THP-1 cells; Catalog # TIB-202, ATCC, Manassas, Va.) were cultured in Roswell Park Memorial Institute (RPMI) 1640 Medium (Catalog #21870-100, Buffalo, N.Y.) with 1% L-glutamine, 1% HEPES, 1% Sodium Pyruvate, 2% Sodium Bicarbonate supplemented with 100 units/mL penicillin, 50 µg/mL streptomycin, 2-mercaptoethanol (0.05 mM) [basal medium] and 10% fetal bovine serum (Catalog #16140089, Life Technologies, Carlsbad, Calif.) at 37° C. and 5% $CO_2$.

Compound Screening:

THP-1 cells were cultured in basal media with 1% FBS for 24 hours before the start of the assay. Each compound was dissolved in DMSO as a 10 mM stock and used to prepare compound source plates. Serial dilution (1:3, 10-point dose-response curves starting from 10 M) and compound transfer was performed using the ECHO 550 (Labcyte, Sunnyvale, Calif.) into 384-well white low volume assay plates (Greiner Bio-One) with appropriate DMSO backfill for a final DMSO concentration of 0.1%. THP-1 cells were plated at 5000 cells/well in the 384-well plates and incubated at 37° C. for 2 h. 500 ng/mL of LPS was added after 2 hours and cells were incubated for another 22 hours at 37° C. Plates were spun in a centrifuge for 1 minute at 10,000 rpm and a mixture of anti-IL6 XL665, and anti-IL6 Cryptate diluted in reconstitution buffer (Cisbio Inc.) was added to each well. Following incubation for 3 hrs at room temperature, Homogeneous Time-Resolved Fluorescence (HTRF) was measured using the Envision (Perkin Elmer) at 665 nm and 620 nM. The ratio of fluorescence at 665 nm to 620 nm was used as a readout for IL6 quantification. All samples were processed in duplicate. Readings were normalized to DMSO treated cells and normalized activities were utilized for $EC_{50}$ calculations using the dose-response log (inhibitor) vs. response—variable slope (four parameters) nonlinear regression feature available in GraphPad Prism 5.0 (or Dotmatics). For $EC_{50}$ of >10 µM, the percent inhibition at 10 µM is provided.

Table 6 shows the activity of representative compounds of Formula I as provided herein.

TABLE 6

| Compound | $EC_{50}$ (µM) |
|---|---|
| 1 | >10 (23.8%) |
| 4 | >10 (22.6%) |
| 11 | >10 (14.1%) |
| 13 | >10 (27.5%) |
| 18 | >10 (37.2%) |
| 20 | 2.126 |
| 24 | 4.159 |
| 28 | >10 (49.5%) |
| 30 | >10 (0%) |
| 33 | >10 (27.7%) |
| 42 | >10 (36.8%) |
| 43 | >10 (36.7%) |
| 51 | >10 (19.4%) |
| 54 | >10 (32.3%) |
| 55 | >10 (32.2%) |
| 59 | >10 (34.8%) |
| 62 | >10 (13.3%) |
| 63 | >10 (11.3%) |
| 65 | >10 (25.6%) |
| 68 | >10 (42.9%) |
| 72 | >10 (38.1%) |
| 75 | >10 (33.8%) |
| 78 | 0.627 |
| 86 | >10 (34.3%) |
| 88 | >10 (22.6%) |
| 90 | 5.355 |
| 93 | >10 (26.2%) |
| 96 | 0.094 |
| 97 | >10 (38.5%) |
| 99 | >10 (37.0%) |
| 104 | >10 (35.8%) |
| 115 | >10 (40.6%) |
| 117 | >10 (17.1%) |
| 123 | >10 (15.1%) |
| 128 | >10 (45.8%) |
| 129 | 0.6212 |
| 130 | >10 (45.9%) |
| 135 | >10 (37.7%) |
| 136 | >10 (23.5%) |
| 140 | >10 (24.5%) |
| 169 | 4.812 |
| 176 | 1.197 |
| 181 | 0.007 |
| 182 | 0.463 |
| 185 | >10 (41.2%) |
| 188 | 0.348 |
| 195 | >10 (49.8%) |
| 247 | 0.496 |
| 256 | 0.121 |
| 263 | 0.310 |
| 268 | 0.359 |
| 270 | 4.653 |
| 271 | 0.041 |
| 274 | 0.415 |
| 275 | 0.063 |
| 324 | >10 (28.6%) |
| 343 | 0.032 |
| 356 | 0.280 |
| 456 | 1.519 |
| 469 | 0.222 |
| 518 | >10 (6.3%) |
| 533 | >10 (20.7%) |
| 563 | >10 (18.7%) |
| 577 | >10 (0%) |
| 601 | 3.892 |
| 635 | >10 (21.4%) |
| 652 | 0.772 |
| 703 | >10 (11.0%) |
| 781 | >10 (44.5%) |

What is claimed is:

1. A compound, or a pharmaceutically acceptable salt thereof, of Formula I:

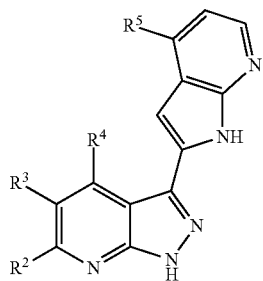

I wherein:
R$^2$ and R$^4$ are independently selected from the group consisting of H and halide;
R$^3$ is selected from the group consisting of -heteroaryl optionally substituted with 1-4 R$^6$ and -heterocyclyl optionally substituted with 1-10 R$^7$;
R$^5$ is selected from the group consisting of H, -heteroaryl optionally substituted with 1-4 R$^8$, -heterocyclyl optionally substituted with 1-10 R$^9$, and -aryl optionally substituted with 1-5 R$^{10}$;
each R$^6$ is independently selected from the group consisting of halide, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 R$^{11}$, —(C$_{2-4}$ alkenylene)$_p$heterocyclyl optionally substituted with 1-10 R$^{11}$, —(C$_{2-4}$ alkynylene)$_p$heterocyclyl optionally substituted with 1-10 R$^{11}$, —C$_{1-4}$ alkylene)$_p$carbocyclyl optionally substituted with 1-12 R$^{12}$, —(C$_{2-4}$ alkenylene)$_p$carbocyclyl optionally substituted with 1-12 R$^{12}$, —(C$_{2-4}$ alkynylene)$_p$carbocyclyl optionally substituted with 1-12 R$^{12}$, —(C$_{1-4}$ alkylene)$_p$aryl optionally substituted with 1-5 R$^{13}$, —(C$_{2-4}$ alkenylene)$_p$aryl optionally substituted with 1-5 R$^{13}$, —(C$_{2-4}$ alkynylene)$_p$aryl optionally substituted with 1-5 R$^{13}$, —NHC(=O)R$^{14}$, —NR$^{15}$R$^{16}$, —(C$_{1-6}$ alkylene)NR$^{17}$R$^{18}$, —(C$_{2-6}$ alkenylene)NR$^{17}$R$^{18}$, —(C$_{2-6}$ alkynylene)NR$^{17}$R$^{18}$, and —(C$_{1-4}$ alkylene)$_p$OR$^{24}$;
each R$^7$ is independently selected from the group consisting of —(C$_{1-4}$ alkyl), —(C$_{2-4}$ alkenyl), —(C$_{2-4}$ alkynyl), halide, —CF$_3$, and —CN;
each R$^8$ is independently selected from the group consisting of —(C$_{1-6}$ alkyl), —(C$_{2-6}$ alkenyl), —(C$_{2-6}$ alkynyl), halide, —CF$_3$, —OCH$_3$, —CN, and —C(=O)R$^{19}$;
each R$^9$ is independently selected from the group consisting of —(C$_{1-6}$ alkyl), —(C$_{2-6}$ alkenyl), —(C$_{2-6}$ alkynyl), halide, —CF$_3$, —CN, and —OCH$_3$;
each R$^{10}$ is independently selected from the group consisting of —(C$_{1-6}$ alkyl), —(C$_{2-6}$ alkenyl), —(C$_{2-6}$ alkynyl), halide, —CF$_3$, —CN, —(C$_{1-6}$ alkylene)$_p$NHSO$_2$R$^{19}$, —(C$_{2-6}$ alkenylene)$_p$NHSO$_2$R$^{19}$, —(C$_{2-6}$ alkynylene)$_p$NHSO$_2$R$^{19}$, —NR$^{15}$(C$_{1-6}$ alkylene)NR$^{15}$R$^{16}$, —NR$^{15}$(C$_{2-6}$ alkenylene)NR$^{15}$R$^{16}$, —NR$^{15}$(C$_{2-6}$ alkynylene)NR$^{15}$R$^{16}$, —(C$_{1-6}$ alkylene)$_p$NR$^{15}$R$^{16}$, —(C$_{2-6}$ alkenylene)$_p$NR$^{15}$R$^{16}$, —(C$_{2-6}$ alkynylene)$_p$NR$^{15}$R$^{16}$, and —OR$^{27}$;
each R$^{11}$ is independently selected from the group consisting of amino, —(C$_{1-4}$ alkyl), —(C$_{2-4}$ alkenyl), —(C$_{2-4}$ alkynyl), halide, —CF$_3$, and —CN;
each R$^{12}$ is independently selected from the group consisting of —(C$_{1-4}$ alkyl), —(C$_{2-4}$ alkenyl), (C$_{2-4}$ alkynyl), halide, —CF$_3$, and —CN;
each R$^{13}$ is independently selected from the group consisting of —(C$_{1-4}$ alkyl), —(C$_{2-4}$ alkenyl), —(C$_{2-4}$ alkynyl), halide, —CF$_3$, and —CN;
each R$^{14}$ is independently selected from the group consisting of —(C$_{1-9}$ alkyl), —(C$_{1-4}$ haloalkyl), —(C$_{2-9}$ alkenyl), —(C$_{2-9}$ alkynyl), -heteroaryl optionally substituted with 1-4 R$^{20}$, -aryl optionally substituted with 1-5 R$^{21}$, —CH$_2$aryl optionally substituted with 1-5 R$^{21}$, -carbocyclyl optionally substituted with 1-12 R$^{22}$, —CH$_2$carbocyclyl optionally substituted with 1-12 R$^{22}$, —(C$_{1-4}$ alkylene)$_p$NR$^{25}$R$^{26}$, —(C$_{2-4}$ alkenylene)$_p$NR$^{25}$R$^{26}$, —(C$_{2-4}$ alkynylene)$_p$NR$^{25}$R$^{26}$, -heterocyclyl optionally substituted with 1-10 R$^{23}$, and —CH$_2$heterocyclyl optionally substituted with 1-10 R$^{23}$;
each R$^{15}$ is independently selected from the group consisting of H, —(C$_{1-6}$ alkyl), —(C$_{2-6}$ alkenyl), and —(C$_{2-6}$ alkynyl);
each R$^{16}$ is independently selected from the group consisting of H, —(C$_{1-6}$ alkyl), —(C$_{2-6}$ alkenyl), —(C$_{2-6}$ alkynyl), —CH$_2$aryl optionally substituted with 1-5 R$^{21}$, and —CH$_2$carbocyclyl optionally substituted with 1-12 R$^{22}$;
each R$^{17}$ is independently selected from the group consisting of H, —(C$_{1-6}$ alkyl), —(C$_{2-6}$ alkenyl), and —(C$_{2-6}$ alkynyl);
each R$^{18}$ is independently selected from the group consisting of H, —(C$_{1-6}$ alkyl), —(C$_{2-6}$ alkenyl), —(C$_{2-6}$ alkynyl), —CH$_2$aryl optionally substituted with 1-5 R$^{21}$, and —CH$_2$carbocyclyl optionally substituted with 1-12 R$^{22}$;
each R$^{19}$ is independently selected from the group consisting of —(C$_{1-6}$ alkyl), —(C$_{2-6}$ alkenyl), and —(C$_{2-6}$ alkynyl);
each R$^{20}$ is independently selected from the group consisting of —(C$_{1-4}$ alkyl), —(C$_{2-4}$ alkenyl), —(C$_{2-4}$ alkynyl), halide, —CF$_3$, and —CN;
each R$^{21}$ is independently selected from the group consisting of —(C$_{1-4}$ alkyl), —(C$_{2-4}$ alkenyl), (C$_{2-4}$ alkynyl), halide, —CF$_3$, and —CN;
each R$^{22}$ is independently selected from the group consisting of —(C$_{1-4}$ alkyl), —(C$_{2-4}$ alkenyl), —(C$_{2-4}$ alkynyl), halide, —CF$_3$, and —CN;
each R$^{23}$ is independently selected from the group consisting of —(C$_{1-4}$ alkyl), —(C$_{2-4}$ alkenyl), —(C$_{2-4}$ alkynyl), halide, —CF$_3$, and —CN;
R$^{24}$ is selected from the group consisting of H, —(C$_{1-6}$ alkyl), —(C$_{2-6}$ alkenyl), —(C$_{2-6}$ alkynyl), —(C$_{1-4}$ alkylene)$_p$heterocyclyl optionally substituted with 1-10 R$^{23}$, —(C$_{2-4}$ alkenylene)$_p$heterocyclyl optionally substituted with 1-10 R$^{23}$, —(C$_{2-4}$ alkynylene)$_p$heterocyclyl optionally substituted with 1-10 R$^{23}$, —(C$_{1-4}$ alkylene)$_p$carbocyclyl optionally substituted with 1-12 R$^{22}$, —(C$_{2-4}$ alkenylene)$_p$carbocyclyl optionally substituted with 1-12 R$^{22}$, —(C$_{2-4}$ alkynylene)$_p$carbocyclyl optionally substituted with 1-12 R$^{22}$, —(C$_{1-4}$ alkylene)$_p$aryl optionally substituted with 1-5 R$^{21}$, —(C$_{2-4}$ alkenylene)$_p$aryl optionally substituted with 1-5 R$^{21}$, —(C$_{2-4}$ alkynylene)$_p$aryl optionally substituted with 1-5 R$^{21}$, —(C$_{1-6}$ alkylene)$_p$NR$^{25}$R$^{26}$, —(C$_{2-4}$ alkenylene)$_p$NR$^{25}$R$^{26}$, and —(C$_{2-4}$ alkynylene)$_p$NR$^{25}$R$^{26}$;
each R$^{25}$ is independently selected from the group consisting of H, —(C$_{1-6}$ alkyl), —(C$_{2-6}$ alkenyl), and —(C$_{2-6}$ alkynyl);

each $R^{26}$ is independently selected from the group consisting of H, —($C_{1-6}$ alkyl), —($C_{2-6}$ alkenyl), and —($C_{2-6}$ alkynyl);

$R^{27}$ is selected from the group consisting of H, —($C_{1-6}$ alkyl), —($C_{2-6}$ alkenyl), —($C_{2-6}$ alkynyl), —($C_{1-4}$ alkylene)$_p$heterocyclyl optionally substituted with 1-10 $R^{23}$, —($C_{2-4}$ alkenylene)$_p$heterocyclyl optionally substituted with 1-10 $R^{23}$, —($C_{2-4}$ alkynylene)$_p$heterocyclyl optionally substituted with 1-10 $R^{23}$, —($C_{1-6}$ alkylene)$_p$NR$^{25}$R$^{26}$, —($C_{2-6}$ alkenylene)$_p$NR$^{25}$R$^{26}$, and —($C_{2-6}$ alkynylene)$_p$NR$^{25}$R$^{26}$; and each p is independently an integer of 0 or 1.

2. The compound of claim 1, wherein $R^2$ and $R^4$ are H.

3. The compound of claim 2, wherein $R^3$ is -pyridin-3-yl optionally substituted with 1 $R^6$.

4. The compound of claim 2, wherein $R^3$ is -pyrimidin-5-yl optionally substituted with 1 $R^6$.

5. The compound of claim 2, wherein $R^3$ is -pyrazolyl optionally substituted with 1 $R^6$.

6. The compound of claim 2, wherein $R^3$ is -imidazolyl substituted with 1-2 $R^6$.

7. The compound of claim 3, wherein $R^6$ is selected from the group consisting of —($C_{1-3}$ alkyl), —CH$_2$heterocyclyl optionally substituted with 1-2 $R^{11}$, —NHC(=O)R$^{14}$, —NR$^{15}$R$^{16}$, —CH$_2$NR$^{17}$R$^{18}$, and —OR$^{24}$.

8. The compound of claim 5, wherein $R^6$ is —($C_{1-3}$ alkyl).

9. The compound of claim 6, wherein $R^6$ is —($C_{1-3}$ alkyl).

10. The compound of claim 7, wherein $R^{14}$ is selected from the group consisting of —($C_{1-5}$ alkyl), -phenyl optionally substituted with 1-2 $R^{21}$, —CH$_2$phenyl optionally substituted with 1-2 $R^{21}$, and -carbocyclyl optionally substituted with 1-2 $R^{22}$.

11. The compound of claim 7, wherein $R^{15}$ and $R^{16}$ are independently selected from H and —($C_{1-3}$ alkyl).

12. The compound of claim 7, wherein $R^{17}$ and $R^{18}$ are independently selected from H and —($C_{1-3}$ alkyl).

13. The compound of claim 7, wherein $R^{24}$ is selected from the group consisting of H, —($C_{1-3}$ alkyl), -heterocyclyl optionally substituted with 1-2 $R^{23}$, —(CH$_2$)heterocyclyl optionally substituted with 1-2 $R^{23}$, —(CH$_2$CH$_2$)heterocyclyl optionally substituted with 1-2 $R^{23}$, -carbocyclyl optionally substituted with 1-2 $R^{22}$, —(CH$_2$)aryl optionally substituted with 1-2 $R^{21}$, and —(CH$_2$CH$_2$)N(C$_{1-2}$ alkyl)$_2$.

14. The compound of claim 2, wherein $R^5$ is -phenyl optionally substituted with 1-2 $R^{10}$.

15. The compound of claim 14, wherein $R^{10}$ is one halide.

16. The compound of claim 14, wherein one $R^{10}$ is halide and one $R^{10}$ is —CH$_2$NHSO$_2$R$^{19}$.

17. The compound of claim 14, wherein one $R^{10}$ is halide and one $R^{10}$ is —NHCH$_2$CH$_2$NR$^{15}$R$^{16}$.

18. The compound of claim 2, wherein $R^5$ is selected from the group consisting of -pyridinyl optionally substituted with 1-2 $R^8$, -imidazolyl optionally substituted with 1-2 $R^8$, -furanyl optionally substituted with 1-2 $R^8$, and -thiophenyl optionally substituted with 1-2 $R^8$.

19. The compound of claim 18, wherein $R^8$ is selected from the group consisting of halide, —($C_{1-3}$ alkyl), and —C(=O)R$^{19}$, and $R^{19}$ is —(C$_{1-2}$ alkyl).

20. The compound of claim 2, wherein $R^5$ is selected from the group consisting of -piperidinyl optionally substituted with 1-2 $R^9$ and -piperazinyl optionally substituted with 1-2 $R^9$.

21. The compound of claim 1, wherein the compound of Formula I is selected from the group consisting of:

N-(5-(3-(4-(3-fluorophenyl)-1H-pyrrolo[2,3-b]pyridin-2-yl)-1H-pyrazolo[3,4-b]pyridin-5-yl)pyridin-3-yl)propionamide [1];

N-(5-(3-(4-(3-fluorophenyl)-1H-pyrrolo[2,3-b]pyridin-2-yl)-1H-pyrazolo[3,4-b]pyridin-5-yl)pyridin-3-yl)-3-methylbutanamide [2];

5-(3-(4-(3-fluorophenyl)-1H-pyrrolo[2,3-b]pyridin-2-yl)-1H-pyrazolo[3,4-b]pyridin-5-yl)pyridin-3-amine [3];

3-(4-(3-fluorophenyl)-1H-pyrrolo[2,3-b]pyridin-2-yl)-5-(pyridin-3-yl)-1H-pyrazolo[3,4-b]pyridine [4];

3-(4-(3-fluorophenyl)-1H-pyrrolo[2,3-b]pyridin-2-yl)-5-(4-methylpyridin-3-yl)-1H-pyrazolo[3,4-b]pyridine [5];

N-((5-(3-(4-(3-fluorophenyl)-1H-pyrrolo[2,3-b]pyridin-2-yl)-1H-pyrazolo[3,4-b]pyridin-5-yl)pyridin-3-yl)methyl)ethanamine [6];

5-(3-(4-(3-fluorophenyl)-1H-pyrrolo[2,3-b]pyridin-2-yl)-1H-pyrazolo[3,4-b]pyridin-5-yl)-N,N-dimethylpyridin-3-amine [7];

N-(5-(3-(4-(3-fluorophenyl)-1H-pyrrolo[2,3-b]pyridin-2-yl)-1H-pyrazolo[3,4-b]pyridin-5-yl)pyridin-3-yl)pivalamide [8];

N-(5-(3-(4-(3-fluorophenyl)-1H-pyrrolo[2,3-b]pyridin-2-yl)-1H-pyrazolo[3,4-b]pyridin-5-yl)pyridin-3-yl)isobutyramide [9];

N-(5-(3-(4-(3-fluorophenyl)-1H-pyrrolo[2,3-b]pyridin-2-yl)-1H-pyrazolo[3,4-b]pyridin-5-yl)pyridin-3-yl)-2-phenylacetamide [10];

N-(5-(3-(4-(3-fluorophenyl)-1H-pyrrolo[2,3-b]pyridin-2-yl)-1H-pyrazolo[3,4-b]pyridin-5-yl)pyridin-3-yl)benzamide [11];

5-(3-(4-(3-fluorophenyl)-1H-pyrrolo[2,3-b]pyridin-2-yl)-1H-pyrazolo[3,4-b]pyridin-5-yl)-N-isopropylpyridin-3-amine [12];

1-(5-(3-(4-(3-fluorophenyl)-1H-pyrrolo[2,3-b]pyridin-2-yl)-1H-pyrazolo[3,4-b]pyridin-5-yl)pyridin-3-yl)-N,N-dimethylmethanamine [13];

3-(4-(3-fluorophenyl)-1H-pyrrolo[2,3-b]pyridin-2-yl)-5-(5-(pyrrolidin-1-ylmethyl)pyridin-3-yl)-1H-pyrazolo[3,4-b]pyridine [14];

3-(4-(3-fluorophenyl)-1H-pyrrolo[2,3-b]pyridin-2-yl)-5-(5-(piperidin-1-ylmethyl)pyridin-3-yl)-1H-pyrazolo[3,4-b]pyridine [15];

N-(5-(3-(4-(3-fluorophenyl)-1H-pyrrolo[2,3-b]pyridin-2-yl)-1H-pyrazolo[3,4-b]pyridin-5-yl)pyridin-3-yl)-3,3-dimethylbutanamide [16];

N-(5-(3-(4-(3-fluorophenyl)-1H-pyrrolo[2,3-b]pyridin-2-yl)-1H-pyrazolo[3,4-b]pyridin-5-yl)pyridin-3-yl)butyramide [17];

3-(4-(3-fluorophenyl)-1H-pyrrolo[2,3-b]pyridin-2-yl)-5-(pyridin-4-yl)-1H-pyrazolo[3,4-b]pyridine [18];

N-(5-(3-(4-(3-fluorophenyl)-1H-pyrrolo[2,3-b]pyridin-2-yl)-1H-pyrazolo[3,4-b]pyridin-5-yl)pyridin-3-yl)pentanamide [19];

N-(5-(3-(4-(3-fluorophenyl)-1H-pyrrolo[2,3-b]pyridin-2-yl)-1H-pyrazolo[3,4-b]pyridin-5-yl)pyridin-3-yl)cyclopropanecarboxamide [20];

N-(5-(3-(4-(3-fluorophenyl)-1H-pyrrolo[2,3-b]pyridin-2-yl)-1H-pyrazolo[3,4-b]pyridin-5-yl)pyridin-3-yl)cyclobutanecarboxamide [21];

N-(5-(3-(4-(3-fluorophenyl)-1H-pyrrolo[2,3-b]pyridin-2-yl)-1H-pyrazolo[3,4-b]pyridin-5-yl)pyridin-3-yl)cyclopentanecarboxamide [22];

N-(5-(3-(4-(3-fluorophenyl)-1H-pyrrolo[2,3-b]pyridin-2-yl)-1H-pyrazolo[3,4-b]pyridin-5-yl)pyridin-3-yl)cyclohexanecarboxamide [23];

N-benzyl-1-(5-(3-(4-(3-fluorophenyl)-1H-pyrrolo[2,3-b]pyridin-2-yl)-1H-pyrazolo[3,4-b]pyridin-5-yl)pyridin-3-yl)methanamine [24];

1-cyclopentyl-N-((5-(3-(4-(3-fluorophenyl)-1H-pyrrolo[2,3-b]pyridin-2-yl)-1H-pyrazolo[3,4-b]pyridin-5-yl)pyridin-3-yl)methyl)methanamine [25];

5-(5-((3,3-difluoropyrrolidin-1-yl)methyl)pyridin-3-yl)-3-(4-(3-fluorophenyl)-1H-pyrrolo[2,3-b]pyridin-2-yl)-1H-pyrazolo[3,4-b]pyridine [26];

3-(4-(3-fluorophenyl)-1H-pyrrolo[2,3-b]pyridin-2-yl)-5-(pyrimidin-5-yl)-1H-pyrazolo[3,4-b]pyridine [27];

3-(4-(3-fluorophenyl)-1H-pyrrolo[2,3-b]pyridin-2-yl)-5-(pyridin-2-yl)-1H-pyrazolo[3,4-b]pyridine [28];

N-(5-(3-(4-(4-fluorophenyl)-1H-pyrrolo[2,3-b]pyridin-2-yl)-1H-pyrazolo[3,4-b]pyridin-5-yl)pyridin-3-yl)propionamide [29];

N-(5-(3-(4-(4-fluorophenyl)-1H-pyrrolo[2,3-b]pyridin-2-yl)-1H-pyrazolo[3,4-b]pyridin-5-yl)pyridin-3-yl)-3-methylbutanamide [30];

5-(3-(4-(4-fluorophenyl)-1H-pyrrolo[2,3-b]pyridin-2-yl)-1H-pyrazolo[3,4-b]pyridin-5-yl)pyridin-3-amine [31];

3-(4-(4-fluorophenyl)-1H-pyrrolo[2,3-b]pyridin-2-yl)-5-(pyridin-3-yl)-1H-pyrazolo[3,4-b]pyridine [32];

3-(4-(4-fluorophenyl)-1H-pyrrolo[2,3-b]pyridin-2-yl)-5-(4-methylpyridin-3-yl)-1H-pyrazolo[3,4-b]pyridine [33];

N-((5-(3-(4-(4-fluorophenyl)-1H-pyrrolo[2,3-b]pyridin-2-yl)-1H-pyrazolo[3,4-b]pyridin-5-yl)pyridin-3-yl)methyl)ethanamine [34];

5-(3-(4-(4-fluorophenyl)-1H-pyrrolo[2,3-b]pyridin-2-yl)-1H-pyrazolo[3,4-b]pyridin-5-yl)-N,N-dimethylpyridin-3-amine [35];

N-(5-(3-(4-(4-fluorophenyl)-1H-pyrrolo[2,3-b]pyridin-2-yl)-1H-pyrazolo[3,4-b]pyridin-5-yl)pyridin-3-yl)pivalamide [36];

N-(5-(3-(4-(4-fluorophenyl)-1H-pyrrolo[2,3-b]pyridin-2-yl)-1H-pyrazolo[3,4-b]pyridin-5-yl)pyridin-3-yl)isobutyramide [37];

N-(5-(3-(4-(4-fluorophenyl)-1H-pyrrolo[2,3-b]pyridin-2-yl)-1H-pyrazolo[3,4-b]pyridin-5-yl)pyridin-3-yl)-2-phenylacetamide [38];

N-(5-(3-(4-(4-fluorophenyl)-1H-pyrrolo[2,3-b]pyridin-2-yl)-1H-pyrazolo[3,4-b]pyridin-5-yl)pyridin-3-yl)benzamide [39];

5-(3-(4-(4-fluorophenyl)-1H-pyrrolo[2,3-b]pyridin-2-yl)-1H-pyrazolo[3,4-b]pyridin-5-yl)-N-isopropylpyridin-3-amine [40];

1-(5-(3-(4-(4-fluorophenyl)-1H-pyrrolo[2,3-b]pyridin-2-yl)-1H-pyrazolo[3,4-b]pyridin-5-yl)pyridin-3-yl)-N,N-dimethylmethanamine [41];

3-(4-(4-fluorophenyl)-1H-pyrrolo[2,3-b]pyridin-2-yl)-5-(5-(pyrrolidin-1-ylmethyl)pyridin-3-yl)-1H-pyrazolo[3,4-b]pyridine [42];

3-(4-(4-fluorophenyl)-1H-pyrrolo[2,3-b]pyridin-2-yl)-5-(5-(piperidin-1-ylmethyl)pyridin-3-yl)-1H-pyrazolo[3,4-b]pyridine [43];

N-(5-(3-(4-(4-fluorophenyl)-1H-pyrrolo[2,3-b]pyridin-2-yl)-1H-pyrazolo[3,4-b]pyridin-5-yl)pyridin-3-yl)-3,3-dimethylbutanamide [44];

N-(5-(3-(4-(4-fluorophenyl)-1H-pyrrolo[2,3-b]pyridin-2-yl)-1H-pyrazolo[3,4-b]pyridin-5-yl)pyridin-3-yl)butyramide [45];

3-(4-(4-fluorophenyl)-1H-pyrrolo[2,3-b]pyridin-2-yl)-5-(pyridin-4-yl)-1H-pyrazolo[3,4-b]pyridine [46];

N-(5-(3-(4-(4-fluorophenyl)-1H-pyrrolo[2,3-b]pyridin-2-yl)-1H-pyrazolo[3,4-b]pyridin-5-yl)pyridin-3-yl)pentanamide [47];

N-(5-(3-(4-(4-fluorophenyl)-1H-pyrrolo[2,3-b]pyridin-2-yl)-1H-pyrazolo[3,4-b]pyridin-5-yl)pyridin-3-yl)cyclopropanecarboxamide [48];

N-(5-(3-(4-(4-fluorophenyl)-1H-pyrrolo[2,3-b]pyridin-2-yl)-1H-pyrazolo[3,4-b]pyridin-5-yl)pyridin-3-yl)cyclobutanecarboxamide [49];

N-(5-(3-(4-(4-fluorophenyl)-1H-pyrrolo[2,3-b]pyridin-2-yl)-1H-pyrazolo[3,4-b]pyridin-5-yl)pyridin-3-yl)cyclopentanecarboxamide [50];

N-(5-(3-(4-(4-fluorophenyl)-1H-pyrrolo[2,3-b]pyridin-2-yl)-1H-pyrazolo[3,4-b]pyridin-5-yl)pyridin-3-yl)cyclohexanecarboxamide [51];

N-benzyl-1-(5-(3-(4-(4-fluorophenyl)-1H-pyrrolo[2,3-b]pyridin-2-yl)-1H-pyrazolo[3,4-b]pyridin-5-yl)pyridin-3-yl)methanamine [52];

1-cyclopentyl-N-((5-(3-(4-(4-fluorophenyl)-1H-pyrrolo[2,3-b]pyridin-2-yl)-1H-pyrazolo[3,4-b]pyridin-5-yl)pyridin-3-yl)methyl)methanamine [53];

5-(5-((3,3-difluoropyrrolidin-1-yl)methyl)pyridin-3-yl)-3-(4-(4-fluorophenyl)-1H-pyrrolo[2,3-b]pyridin-2-yl)-1H-pyrazolo[3,4-b]pyridine [54];

3-(4-(4-fluorophenyl)-1H-pyrrolo[2,3-b]pyridin-2-yl)-5-(pyrimidin-5-yl)-1H-pyrazolo[3,4-b]pyridine [55];

3-(4-(4-fluorophenyl)-1H-pyrrolo[2,3-b]pyridin-2-yl)-5-(pyridin-2-yl)-1H-pyrazolo[3,4-b]pyridine [56];

N-(5-(3-(4-(2-fluorophenyl)-1H-pyrrolo[2,3-b]pyridin-2-yl)-1H-pyrazolo[3,4-b]pyridin-5-yl)pyridin-3-yl)propionamide [57];

N-(5-(3-(4-(2-fluorophenyl)-1H-pyrrolo[2,3-b]pyridin-2-yl)-1H-pyrazolo[3,4-b]pyridin-5-yl)pyridin-3-yl)-3-methylbutanamide [58];

5-(3-(4-(2-fluorophenyl)-1H-pyrrolo[2,3-b]pyridin-2-yl)-1H-pyrazolo[3,4-b]pyridin-5-yl)pyridin-3-amine [59];

3-(4-(2-fluorophenyl)-1H-pyrrolo[2,3-b]pyridin-2-yl)-5-(pyridin-3-yl)-1H-pyrazolo[3,4-b]pyridine [60];

3-(4-(2-fluorophenyl)-1H-pyrrolo[2,3-b]pyridin-2-yl)-5-(4-methylpyridin-3-yl)-1H-pyrazolo[3,4-b]pyridine [61];

N-((5-(3-(4-(2-fluorophenyl)-1H-pyrrolo[2,3-b]pyridin-2-yl)-1H-pyrazolo[3,4-b]pyridin-5-yl)pyridin-3-yl)methyl)ethanamine [62];

5-(3-(4-(2-fluorophenyl)-1H-pyrrolo[2,3-b]pyridin-2-yl)-1H-pyrazolo[3,4-b]pyridin-5-yl)-N,N-dimethylpyridin-3-amine [63];

N-(5-(3-(4-(2-fluorophenyl)-1H-pyrrolo[2,3-b]pyridin-2-yl)-1H-pyrazolo[3,4-b]pyridin-5-yl)pyridin-3-yl)pivalamide [64];

N-(5-(3-(4-(2-fluorophenyl)-1H-pyrrolo[2,3-b]pyridin-2-yl)-1H-pyrazolo[3,4-b]pyridin-5-yl)pyridin-3-yl)isobutyramide [65];

N-(5-(3-(4-(2-fluorophenyl)-1H-pyrrolo[2,3-b]pyridin-2-yl)-1H-pyrazolo[3,4-b]pyridin-5-yl)pyridin-3-yl)-2-phenylacetamide [66];

N-(5-(3-(4-(2-fluorophenyl)-1H-pyrrolo[2,3-b]pyridin-2-yl)-1H-pyrazolo[3,4-b]pyridin-5-yl)pyridin-3-yl)benzamide [67];

5-(3-(4-(2-fluorophenyl)-1H-pyrrolo[2,3-b]pyridin-2-yl)-1H-pyrazolo[3,4-b]pyridin-5-yl)-N-isopropylpyridin-3-amine [68];

1-(5-(344-(2-fluorophenyl)-1H-pyrrolo[2,3-b]pyridin-2-yl)-1H-pyrazolo[3,4-b]pyridin-5-yl)pyridin-3-yl)-N,N-dimethylmethanamine [69];

3-(4-(2-fluorophenyl)-1H-pyrrolo[2,3-b]pyridin-2-yl)-5-(5-(pyrrolidin-1-ylmethyl)pyridin-3-yl)-1H-pyrazolo[3,4-b]pyridine [70];

3-(4-(2-fluorophenyl)-1H-pyrrolo[2,3-b]pyridin-2-yl)-5-(5-(piperidin-1-ylmethyl)pyridin-3-yl)-1H-pyrazolo[3,4-b]pyridine [71];

N-(5-(3-(4-(2-fluorophenyl)-1H-pyrrolo[2,3-b]pyridin-2-yl)-1H-pyrazolo[3,4-b]pyridin-5-yl)pyridin-3-yl)-3,3-dimethylbutanamide [72];

N-(5-(3-(4-(2-fluorophenyl)-1H-pyrrolo[2,3-b]pyridin-2-yl)-1H-pyrazolo[3,4-b]pyridin-5-yl)pyridin-3-yl)butyramide [73];

3-(4-(2-fluorophenyl)-1H-pyrrolo[2,3-b]pyridin-2-yl)-5-(pyridin-4-yl)-1H-pyrazolo[3,4-b]pyridine [74];

N-(5-(3-(4-(2-fluorophenyl)-1H-pyrrolo[2,3-b]pyridin-2-yl)-1H-pyrazolo[3,4-b]pyridin-5-yl)pyridin-3-yl)pentanamide [75];

N-(5-(3-(4-(2-fluorophenyl)-1H-pyrrolo[2,3-b]pyridin-2-yl)-1H-pyrazolo[3,4-b]pyridin-5-yl)pyridin-3-yl)cyclopropanecarboxamide [76];

N-(5-(3-(4-(2-fluorophenyl)-1H-pyrrolo[2,3-b]pyridin-2-yl)-1H-pyrazolo[3,4-b]pyridin-5-yl)pyridin-3-yl)cyclobutanecarboxamide [77];

N-(5-(3-(4-(2-fluorophenyl)-1H-pyrrolo[2,3-b]pyridin-2-yl)-1H-pyrazolo[3,4-b]pyridin-5-yl)pyridin-3-yl)cyclopentanecarboxamide [78];

N-(5-(3-(4-(2-fluorophenyl)-1H-pyrrolo[2,3-b]pyridin-2-yl)-1H-pyrazolo[3,4-b]pyridin-5-yl)pyridin-3-yl)cyclohexanecarboxamide [79];

N-benzyl-1-(5-(344-(2-fluorophenyl)-1H-pyrrolo[2,3-b]pyridin-2-yl)-1H-pyrazolo[3,4-b]pyridin-5-yl)pyridin-3-yl)methanamine [80];

1-cyclopentyl-N-((5-(3-(4-(2-fluorophenyl)-1H-pyrrolo[2,3-b]pyridin-2-yl)-1H-pyrazolo[3,4-b]pyridin-5-yl)pyridin-3-yl)methyl)methanamine [81];

5-(5-((3,3-difluoropyrrolidin-1-yl)methyl)pyridin-3-yl)-3-(4-(2-fluorophenyl)-1H-pyrrolo[2,3-b]pyridin-2-yl)-1H-pyrazolo[3,4-b]pyridine [82];

3-(4-(2-fluorophenyl)-1H-pyrrolo[2,3-b]pyridin-2-yl)-5-(pyrimidin-5-yl)-1H-pyrazolo[3,4-b]pyridine [83];

3-(4-(2-fluorophenyl)-1H-pyrrolo[2,3-b]pyridin-2-yl)-5-(pyridin-2-yl)-1H-pyrazolo[3,4-b]pyridine [84];

N-(5-(3-(4-(pyridin-3-yl)-1H-pyrrolo[2,3-b]pyridin-2-yl)-1H-pyrazolo[3,4-b]pyridin-5-yl)pyridin-3-yl)propionamide [85];

3-methyl-N-(5-(3-(4-(pyridin-3-yl)-1H-pyrrolo[2,3-b]pyridin-2-yl)-1H-pyrazolo[3,4-b]pyridin-5-yl)pyridin-3-yl)butanamide [86];

5-(3-(4-(pyridin-3-yl)-1H-pyrrolo[2,3-b]pyridin-2-yl)-1H-pyrazolo[3,4-b]pyridin-5-yl)pyridin-3-amine [87];

5-(pyridin-3-yl)-3-(4-(pyridin-3-yl)-1H-pyrrolo[2,3-b]pyridin-2-yl)-1H-pyrazolo[3,4-b]pyridine [88];

5-(4-methylpyridin-3-yl)-3-(4-(pyridin-3-yl)-1H-pyrrolo[2,3-b]pyridin-2-yl)-1H-pyrazolo[3,4-b]pyridine [89];

N-((5-(3-(4-(pyridin-3-yl)-1H-pyrrolo[2,3-b]pyridin-2-yl)-1H-pyrazolo[3,4-b]pyridin-5-yl)pyridin-3-yl)methyl)ethanamine [90];

N,N-dimethyl-5-(3-(4-(pyridin-3-yl)-1H-pyrrolo[2,3-b]pyridin-2-yl)-1H-pyrazolo[3,4-b]pyridin-5-yl)pyridin-3-amine [91];

N-(5-(3-(4-(pyridin-3-yl)-1H-pyrrolo[2,3-b]pyridin-2-yl)-1H-pyrazolo[3,4-b]pyridin-5-yl)pyridin-3-yl)pivalamide [92];

N-(5-(3-(4-(pyridin-3-yl)-1H-pyrrolo[2,3-b]pyridin-2-yl)-1H-pyrazolo[3,4-b]pyridin-5-yl)pyridin-3-yl)isobutyramide [93];

2-phenyl-N-(5-(3-(4-(pyridin-3-yl)-1H-pyrrolo[2,3-b]pyridin-2-yl)-1H-pyrazolo[3,4-b]pyridin-5-yl)pyridin-3-yl)acetamide [94];

N-(5-(3-(4-(pyridin-3-yl)-1H-pyrrolo[2,3-b]pyridin-2-yl)-1H-pyrazolo[3,4-b]pyridin-5-yl)pyridin-3-yl)benzamide [95];

N-isopropyl-5-(3-(4-(pyridin-3-yl)-1H-pyrrolo[2,3-b]pyridin-2-yl)-1H-pyrazolo[3,4-b]pyridin-5-yl)pyridin-3-amine [96];

N,N-dimethyl -1-(5-(3-(4-(pyridin-3-yl)-1H-pyrrolo[2,3-b]pyridin-2-yl)-1H-pyrazolo[3,4-b]pyridin-5-yl)pyridin-3-yl)methanamine [97];

3-(4-(pyridin-3-yl)-1H-pyrrolo[2,3-b]pyridin-2-yl)-5-(5-(pyrrolidin-1-ylmethyl)pyridin-3-yl)-1H-pyrazolo[3,4-b]pyridine [98];

5-(5-(piperidin-1-ylmethyl)pyridin-3-yl)-3-(4-(pyridin-3-yl)-1H-pyrrolo[2,3-b]pyridin-2-yl)-1H-pyrazolo[3,4-b]pyridine [99];

3,3-dimethyl-N-(5-(3-(4-(pyridin-3-yl)-1H-pyrrolo[2,3-b]pyridin-2-yl)-1H-pyrazolo[3,4-b]pyridin-5-yl)pyridin-3-yl)butanamide [100];

N-(5-(3-(4-(pyridin-3-yl)-1H-pyrrolo[2,3-b]pyridin-2-yl)-1H-pyrazolo[3,4-b]pyridin-5-yl)pyridin-3-yl)butyramide [101];

3-(4-(pyridin-3-yl)-1H-pyrrolo[2,3-b]pyridin-2-yl)-5-(pyridin-4-yl)-1H-pyrazolo[3,4-b]pyridine [102];

N-(5-(3-(4-(pyridin-3-yl)-1H-pyrrolo[2,3-b]pyridin-2-yl)-1H-pyrazolo[3,4-b]pyridin-5-yl)pyridin-3-yl)pentanamide [103];

N-(5-(3-(4-(pyridin-3-yl)-1H-pyrrolo[2,3-b]pyridin-2-yl)-1H-pyrazolo[3,4-b]pyridin-5-yl)pyridin-3-yl)cyclopropanecarboxamide [104];

N-(5-(3-(4-(pyridin-3-yl)-1H-pyrrolo[2,3-b]pyridin-2-yl)-1H-pyrazolo[3,4-b]pyridin-5-yl)pyridin-3-yl)cyclobutanecarboxamide [105];

N-(5-(3-(4-(pyridin-3-yl)-1H-pyrrolo[2,3-b]pyridin-2-yl)-1H-pyrazolo[3,4-b]pyridin-5-yl)pyridin-3-yl)cyclopentanecarboxamide [106];

N-(5-(3-(4-(pyridin-3-yl)-1H-pyrrolo[2,3-b]pyridin-2-yl)-1H-pyrazolo[3,4-b]pyridin-5-yl)pyridin-3-yl)cyclohexanecarboxamide [107];

N-benzyl-1-(5-(3-(4-(pyridin-3-yl)-1H-pyrrolo[2,3-b]pyridin-2-yl)-1H-pyrazolo[3,4-b]pyridin-5-yl)pyridin-3-yl)methanamine [108];

1-cyclopentyl-N-((5-(3-(4-(pyridin-3-yl)-1H-pyrrolo[2,3-b]pyridin-2-yl)-1H-pyrazolo[3,4-b]pyridin-5-yl)pyridin-3-yl)methyl)methanamine [109];

5-(5-((3,3-difluoropyrrolidin-1-yl)methyl)pyridin-3-yl)-3-(4-(pyridin-3-yl)-1H-pyrrolo[2,3-b]pyridin-2-yl)-1H-pyrazolo[3,4-b]pyridine [110];

3-(4-(pyridin-3-yl)-1H-pyrrolo[2,3-b]pyridin-2-yl)-5-(pyrimidin-5-yl)-1H-pyrazolo[3,4-b]pyridine [111];

5-(pyridin-2-yl)-3-(4-(pyridin-3-yl)-1H-pyrrolo[2,3-b]pyridin-2-yl)-1H-pyrazolo[3,4-b]pyridine [112];

N-(5-(3-(4-(pyridin-4-yl)-1H-pyrrolo[2,3-b]pyridin-2-yl)-1H-pyrazolo[3,4-b]pyridin-5-yl)pyridin-3-yl)propionamide [113];

3-methyl-N-(5-(3-(4-(pyridin-4-yl)-1H-pyrrolo[2,3-b]pyridin-2-yl)-1H-pyrazolo[3,4-b]pyridin-5-yl)pyridin-3-yl)butanamide [114];

5-(3-(4-(pyridin-4-yl)-1H-pyrrolo[2,3-b]pyridin-2-yl)-1H-pyrazolo[3,4-b]pyridin-5-yl)pyridin-3-amine [115];

5-(pyridin-3-yl)-3-(4-(pyridin-4-yl)-1H-pyrrolo[2,3-b]pyridin-2-yl)-1H-pyrazolo[3,4-b]pyridine [116];

5-(4-methylpyridin-3-yl)-3-(4-(pyridin-4-yl)-1H-pyrrolo[2,3-b]pyridin-2-yl)-1H-pyrazolo[3,4-b]pyridine [117];

N-((5-(3-(4-(pyridin-4-yl)-1H-pyrrolo[2,3-b]pyridin-2-yl)-1H-pyrazolo[3,4-b]pyridin-5-yl)pyridin-3-yl)methyl)ethanamine [118];

N,N-dimethyl-5-(3-(4-(pyridin-4-yl)-1H-pyrrolo[2,3-b]pyridin-2-yl)-1H-pyrazolo[3,4-b]pyridin-5-yl)pyridin-3-amine [119];

N-(5-(3-(4-(pyridin-4-yl)-1H-pyrrolo[2,3-b]pyridin-2-yl)-1H-pyrazolo[3,4-b]pyridin-5-yl)pyridin-3-yl)pivalamide [120];

N-(5-(3-(4-(pyridin-4-yl)-1H-pyrrolo[2,3-b]pyridin-2-yl)-1H-pyrazolo[3,4-b]pyridin-5-yl)pyridin-3-yl)isobutyramide [121];

2-phenyl-N-(5-(3-(4-(pyridin-4-yl)-1H-pyrrolo[2,3-b]pyridin-2-yl)-1H-pyrazolo[3,4-b]pyridin-5-yl)pyridin-3-yl)acetamide [122];

N-(5-(3-(4-(pyridin-4-yl)-1H-pyrrolo[2,3-b]pyridin-2-yl)-1H-pyrazolo[3,4-b]pyridin-5-yl)pyridin-3-yl)benzamide [123];

N-isopropyl-5-(3-(4-(pyridin-4-yl)-1H-pyrrolo[2,3-b]pyridin-2-yl)-1H-pyrazolo[3,4-b]pyridin-5-yl)pyridin-3-amine [124];

N,N-dimethyl -1-(5-(3-(4-(pyridin-4-yl)-1H-pyrrolo[2,3-b]pyridin-2-yl)-1H-pyrazolo[3,4-b]pyridin-5-yl)pyridin-3-yl)methanamine [125];

3-(4-(pyridin-4-yl)-1H-pyrrolo[2,3-b]pyridin-2-yl)-5-(5-(pyrrolidin-1-ylmethyl)pyridin-3-yl)-1H-pyrazolo[3,4-b]pyridine [126];

5-(5-(piperidin-1-ylmethyl)pyridin-3-yl)-3-(4-(pyridin-4-yl)-1H-pyrrolo[2,3-b]pyridin-2-yl)-1H-pyrazolo[3,4-b]pyridine [127];

3,3-dimethyl-N-(5-(3-(4-(pyridin-4-yl)-1H-pyrrolo[2,3-b]pyridin-2-yl)-1H-pyrazolo[3,4-b]pyridin-5-yl)pyridin-3-yl)butanamide [128];

N-(5-(3-(4-(pyridin-4-yl)-1H-pyrrolo[2,3-b]pyridin-2-yl)-1H-pyrazolo[3,4-b]pyridin-5-yl)pyridin-3-yl)butyramide [129];

5-(pyridin-4-yl)-3-(4-(pyridin-4-yl)-1H-pyrrolo[2,3-b]pyridin-2-yl)-1H-pyrazolo[3,4-b]pyridine [130];

N-(5-(3-(4-(pyridin-4-yl)-1H-pyrrolo[2,3-b]pyridin-2-yl)-1H-pyrazolo[3,4-b]pyridin-5-yl)pyridin-3-yl)pentanamide [131];

N-(5-(3-(4-(pyridin-4-yl)-1H-pyrrolo[2,3-b]pyridin-2-yl)-1H-pyrazolo[3,4-b]pyridin-5-yl)pyridin-3-yl)cyclopropanecarboxamide [132];

N-(5-(3-(4-(pyridin-4-yl)-1H-pyrrolo[2,3-b]pyridin-2-yl)-1H-pyrazolo[3,4-b]pyridin-5-yl)pyridin-3-yl)cyclobutanecarboxamide [133];

N-(5-(3-(4-(pyridin-4-yl)-1H-pyrrolo[2,3-b]pyridin-2-yl)-1H-pyrazolo[3,4-b]pyridin-5-yl)pyridin-3-yl)cyclopentanecarboxamide [134];

N-(5-(3-(4-(pyridin-4-yl)-1H-pyrrolo[2,3-b]pyridin-2-yl)-1H-pyrazolo[3,4-b]pyridin-5-yl)pyridin-3-yl)cyclohexanecarboxamide [135];

N-benzyl-1-(5-(3-(4-(pyridin-4-yl)-1H-pyrrolo[2,3-b]pyridin-2-yl)-1H-pyrazolo[3,4-b]pyridin-5-yl)pyridin-3-yl)methanamine [136];

1-cyclopentyl-N-((5-(3-(4-(pyridin-4-yl)-1H-pyrrolo[2,3-b]pyridin-2-yl)-1H-pyrazolo[3,4-b]pyridin-5-yl)pyridin-3-yl)methyl)methanamine [137];

5-(5-((3,3-difluoropyrrolidin-1-yl)methyl)pyridin-3-yl)-3-(4-(pyridin-4-yl)-1H-pyrrolo[2,3-b]pyridin-2-yl)-1H-pyrazolo[3,4-b]pyridine [138];

3-(4-(pyridin-4-yl)-1H-pyrrolo[2,3-b]pyridin-2-yl)-5-(pyrimidin-5-yl)-1H-pyrazolo[3,4-b]pyridine [139];

5-(pyridin-2-yl)-3-(4-(pyridin-4-yl)-1H-pyrrolo[2,3-b]pyridin-2-yl)-1H-pyrazolo[3,4-b]pyridine [140];

N-(5-(3-(4-(pyridin-2-yl)-1H-pyrrolo[2,3-b]pyridin-2-yl)-1H-pyrazolo[3,4-b]pyridin-5-yl)pyridin-3-yl)propionamide [141];

3-methyl-N-(5-(3-(4-(pyridin-2-yl)-1H-pyrrolo[2,3-b]pyridin-2-yl)-1H-pyrazolo[3,4-b]pyridin-5-yl)pyridin-3-yl)butanamide [142];

5-(3-(4-(pyridin-2-yl)-1H-pyrrolo[2,3-b]pyridin-2-yl)-1H-pyrazolo[3,4-b]pyridin-5-yl)pyridin-3-amine [143];

3-(4-(pyridin-2-yl)-1H-pyrrolo[2,3-b]pyridin-2-yl)-5-(pyridin-3-yl)-1H-pyrazolo[3,4-b]pyridine [144];

5-(4-methylpyridin-3-yl)-3-(4-(pyridin-2-yl)-1H-pyrrolo[2,3-b]pyridin-2-yl)-1H-pyrazolo[3,4-b]pyridine [145];

N-((5-(3-(4-(pyridin-2-yl)-1H-pyrrolo[2,3-b]pyridin-2-yl)-1H-pyrazolo[3,4-b]pyridin-5-yl)pyridin-3-yl)methyl)ethanamine [146];

N,N-dimethyl-5-(3-(4-(pyridin-2-yl)-1H-pyrrolo[2,3-b]pyridin-2-yl)-1H-pyrazolo[3,4-b]pyridin-5-yl)pyridin-3-amine [147];

N-(5-(3-(4-(pyridin-2-yl)-1H-pyrrolo[2,3-b]pyridin-2-yl)-1H-pyrazolo[3,4-b]pyridin-5-yl)pyridin-3-yl)pivalamide [148];

N-(5-(3-(4-(pyridin-2-yl)-1H-pyrrolo[2,3-b]pyridin-2-yl)-1H-pyrazolo[3,4-b]pyridin-5-yl)pyridin-3-yl)isobutyramide [149];

2-phenyl-N-(5-(3-(4-(pyridin-2-yl)-1H-pyrrolo[2,3-b]pyridin-2-yl)-1H-pyrazolo[3,4-b]pyridin-5-yl)pyridin-3-yl)acetamide [150];

N-(5-(3-(4-(pyridin-2-yl)-1H-pyrrolo[2,3-b]pyridin-2-yl)-1H-pyrazolo[3,4-b]pyridin-5-yl)pyridin-3-yl)benzamide [151];

N-isopropyl-5-(3-(4-(pyridin-2-yl)-1H-pyrrolo[2,3-b]pyridin-2-yl)-1H-pyrazolo[3,4-b]pyridin-5-yl)pyridin-3-amine [152];

N,N-dimethyl -1-(5-(3-(4-(pyridin-2-yl)-1H-pyrrolo[2,3-b]pyridin-2-yl)-1H-pyrazolo[3,4-b]pyridin-5-yl)pyridin-3-yl)methanamine [153];

3-(4-(pyridin-2-yl)-1H-pyrrolo[2,3-b]pyridin-2-yl)-5-(5-(pyrrolidin-1-ylmethyl)pyridin-3-yl)-1H-pyrazolo[3,4-b]pyridine [154];

5-(5-(piperidin-1-ylmethyl)pyridin-3-yl)-3-(4-(pyridin-2-yl)-1H-pyrrolo[2,3-b]pyridin-2-yl)-1H-pyrazolo[3,4-b]pyridine [155];

3,3-dimethyl-N-(5-(3-(4-(pyridin-2-yl)-1H-pyrrolo[2,3-b]pyridin-2-yl)-1H-pyrazolo[3,4-b]pyridin-5-yl)pyridin-3-yl)butanamide [156];

N-(5-(3-(4-(pyridin-2-yl)-1H-pyrrolo[2,3-b]pyridin-2-yl)-1H-pyrazolo[3,4-b]pyridin-5-yl)pyridin-3-yl)butyramide [157];

3-(4-(pyridin-2-yl)-1H-pyrrolo[2,3-b]pyridin-2-yl)-5-(pyridin-4-yl)-1H-pyrazolo[3,4-b]pyridine [158];

N-(5-(3-(4-(pyridin-2-yl)-1H-pyrrolo[2,3-b]pyridin-2-yl)-1H-pyrazolo[3,4-b]pyridin-5-yl)pyridin-3-yl)pentanamide [159];

N-(5-(3-(4-(pyridin-2-yl)-1H-pyrrolo[2,3-b]pyridin-2-yl)-1H-pyrazolo[3,4-b]pyridin-5-yl)pyridin-3-yl)cyclopropanecarboxamide [160];

N-(5-(3-(4-(pyridin-2-yl)-1H-pyrrolo[2,3-b]pyridin-2-yl)-1H-pyrazolo[3,4-b]pyridin-5-yl)pyridin-3-yl)cyclobutanecarboxamide [161];

N-(5-(3-(4-(pyridin-2-yl)-1H-pyrrolo[2,3-b]pyridin-2-yl)-1H-pyrazolo[3,4-b]pyridin-5-yl)pyridin-3-yl)cyclopentanecarboxamide [162];

N-(5-(3-(4-(pyridin-2-yl)-1H-pyrrolo[2,3-b]pyridin-2-yl)-1H-pyrazolo[3,4-b]pyridin-5-yl)pyridin-3-yl)cyclohexanecarboxamide [163];

N-benzyl-1-(5-(3-(4-(pyridin-2-yl)-1H-pyrrolo[2,3-b]pyridin-2-yl)-1H-pyrazolo[3,4-b]pyridin-5-yl)pyridin-3-yl)methanamine [164];

1-cyclopentyl-N-((5-(3-(4-(pyridin-2-yl)-1H-pyrrolo[2,3-b]pyridin-2-yl)-1H-pyrazolo[3,4-b]pyridin-5-yl)pyridin-3-yl)methyl)methanamine [165];

5-(5-((3,3-difluoropyrrolidin-1-yl)methyl)pyridin-3-yl)-3-(4-(pyridin-2-yl)-1H-pyrrolo[2,3-b]pyridin-2-yl)-1H-pyrazolo[3,4-b]pyridine [166];

3-(4-(pyridin-2-yl)-1H-pyrrolo[2,3-b]pyridin-2-yl)-5-(pyrimidin-5-yl)-1H-pyrazolo[3,4-b]pyridine [167];

5-(pyridin-2-yl)-3-(4-(pyridin-2-yl)-1H-pyrrolo[2,3-b]pyridin-2-yl)-1H-pyrazolo[3,4-b]pyridine [168];

N-(5-(3-(4-(piperidin-1-yl)-1H-pyrrolo[2,3-b]pyridin-2-yl)-1H-pyrazolo[3,4-b]pyridin-5-yl)pyridin-3-yl)propionamide [169];

3-methyl-N-(5-(3-(4-(piperidin-1-yl)-1H-pyrrolo[2,3-b]pyridin-2-yl)-1H-pyrazolo[3,4-b]pyridin-5-yl)pyridin-3-yl)butanamide [170];

5-(3-(4-(piperidin-1-yl)-1H-pyrrolo[2,3-b]pyridin-2-yl)-1H-pyrazolo[3,4-b]pyridin-5-yl)pyridin-3-amine [171];

3-(4-(piperidin-1-yl)-1H-pyrrolo[2,3-b]pyridin-2-yl)-5-(pyridin-3-yl)-1H-pyrazolo[3,4-b]pyridine [172];

5-(4-methylpyridin-3-yl)-3-(4-(piperidin-1-yl)-1H-pyrrolo[2,3-b]pyridin-2-yl)-1H-pyrazolo[3,4-b]pyridine [173];

N-((5-(3-(4-(piperidin-1-yl)-1H-pyrrolo[2,3-b]pyridin-2-yl)-1H-pyrazolo[3,4-b]pyridin-5-yl)pyridin-3-yl)methyl)ethanamine [174];

N,N-dimethyl-5-(3-(4-(piperidin-1-yl)-1H-pyrrolo[2,3-b]pyridin-2-yl)-1H-pyrazolo[3,4-b]pyridin-5-yl)pyridin-3-amine [175];

N-(5-(3-(4-(piperidin-1-yl)-1H-pyrrolo[2,3-b]pyridin-2-yl)-1H-pyrazolo[3,4-b]pyridin-5-yl)pyridin-3-yl)pivalamide [176];

N-(5-(3-(4-(piperidin-1-yl)-1H-pyrrolo[2,3-b]pyridin-2-yl)-1H-pyrazolo[3,4-b]pyridin-5-yl)pyridin-3-yl)isobutyramide [177];

2-phenyl-N-(5-(3-(4-(piperidin-1-yl)-1H-pyrrolo[2,3-b]pyridin-2-yl)-1H-pyrazolo[3,4-b]pyridin-5-yl)pyridin-3-yl)acetamide [178];

N-(5-(3-(4-(piperidin-1-yl)-1H-pyrrolo[2,3-b]pyridin-2-yl)-1H-pyrazolo[3,4-b]pyridin-5-yl)pyridin-3-yl)benzamide [179];

N-isopropyl-5-(3-(4-(piperidin-1-yl)-1H-pyrrolo[2,3-b]pyridin-2-yl)-1H-pyrazolo[3,4-b]pyridin-5-yl)pyridin-3-amine [180];

N,N-dimethyl-1-(5-(3-(4-(piperidin-1-yl)-1H-pyrrolo[2,3-b]pyridin-2-yl)-1H-pyrazolo[3,4-b]pyridin-5-yl)pyridin-3-yl)methanamine [181];

3-(4-(piperidin-1-yl)-1H-pyrrolo[2,3-b]pyridin-2-yl)-5-(5-(pyrrolidin-1-ylmethyl)pyridin-3-yl)-1H-pyrazolo[3,4-b]pyridine [182];

3-(4-(piperidin-1-yl)-1H-pyrrolo[2,3-b]pyridin-2-yl)-5-(5-(piperidin-1-ylmethyl)pyridin-3-yl)-1H-pyrazolo[3,4-b]pyridine [183];

3,3-dimethyl-N-(5-(3-(4-(piperidin-1-yl)-1H-pyrrolo[2,3-b]pyridin-2-yl)-1H-pyrazolo[3,4-b]pyridin-5-yl)pyridin-3-yl)butanamide [184];

N-(5-(3-(4-(piperidin-1-yl)-1H-pyrrolo[2,3-b]pyridin-2-yl)-1H-pyrazolo[3,4-b]pyridin-5-yl)pyridin-3-yl)butyramide [185];

3-(4-(piperidin-1-yl)-1H-pyrrolo[2,3-b]pyridin-2-yl)-5-(pyridin-4-yl)-1H-pyrazolo[3,4-b]pyridine [186];

N-(5-(3-(4-(piperidin-1-yl)-1H-pyrrolo[2,3-b]pyridin-2-yl)-1H-pyrazolo[3,4-b]pyridin-5-yl)pyridin-3-yl)pentanamide [187];

N-(5-(3-(4-(piperidin-1-yl)-1H-pyrrolo[2,3-b]pyridin-2-yl)-1H-pyrazolo[3,4-b]pyridin-5-yl)pyridin-3-yl)cyclopropanecarboxamide [188];

N-(5-(3-(4-(piperidin-1-yl)-1H-pyrrolo[2,3-b]pyridin-2-yl)-1H-pyrazolo[3,4-b]pyridin-5-yl)pyridin-3-yl)cyclobutanecarboxamide [189];

N-(5-(3-(4-(piperidin-1-yl)-1H-pyrrolo[2,3-b]pyridin-2-yl)-1H-pyrazolo[3,4-b]pyridin-5-yl)pyridin-3-yl)cyclopentanecarboxamide [190];

N-(5-(3-(4-(piperidin-1-yl)-1H-pyrrolo[2,3-b]pyridin-2-yl)-1H-pyrazolo[3,4-b]pyridin-5-yl)pyridin-3-yl)cyclohexanecarboxamide [191];

N-benzyl-1-(5-(3-(4-(piperidin-1-yl)-1H-pyrrolo[2,3-b]pyridin-2-yl)-1H-pyrazolo[3 pyridin-5-yl)pyridin-3-yl)methanamine [192];

1-cyclopentyl-N-((5-(3-(4-(piperidin-1-yl)-1H-pyrrolo[2,3-b]pyridin-2-yl)-1H-pyrazolo[3 pyridin-5-yl)pyridin-3-yl)methyl)methanamine [193];

5-(5-((3,3-difluoropyrrolidin-1-yl)methyl)pyridin-3-yl)-3-(4-(piperidin-1-yl)-1H-pyrrolo[2,3-b]pyridin-2-yl)-1H-pyrazolo[3,4-b]pyridine [194];

3-(4-(piperidin-1-yl)-1H-pyrrolo[2,3-b]pyridin-2-yl)-5-(pyrimidin-5-yl)-1H-pyrazolo[3,4-b]pyridine [195];

3-(4-(piperidin-1-yl)-1H-pyrrolo[2,3-b]pyridin-2-yl)-5-(pyridin-2-yl)-1H-pyrazolo[3,4-b]pyridine [196];

N-(5-(3-(4-(4-methyl-1H-imidazol-1-yl)-1H-pyrrolo[2,3-b]pyridin-2-yl)-1H-pyrazolo[3 pyridin-5-yl)pyridin-3-yl)propionamide [197];

3-methyl-N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)butanamide [198];

5-(3-(4-(4-methyl-1H-imidazol-1-yl)-1H-pyrrolo[2,3-b]pyridin-2-yl)-1H-pyrazolo[3 pyridin-5-yl)pyridin-3-amine [199];

3-(4-(4-methyl-1H-imidazol-1-yl)-1H-pyrrolo[2,3-b]pyridin-2-yl)-5-(pyridin-3-yl)-1H-pyrazolo[3,4-b]pyridine [200];

3-(4-(4-methyl-1H-imidazol-1-yl)-1H-pyrrolo[2,3-b]pyridin-2-yl)-5-(4-methylpyridin-3-yl)-1H-pyrazolo[3,4-b]pyridine [201];

N-((5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)methyl)ethanamine [202];

N,N-dimethyl-5-(3-(4-(4-methyl-1H-imidazol-1-yl)-1H-pyrrolo[2,3-b]pyridin-2-yl)-1H-pyrazolo[3,4-b]pyridin-5-yl)pyridin-3-amine [203];

N-(5-(3-(4-(4-methyl-1H-imidazol-1-yl)-1H-pyrrolo[2,3-b]pyridin-2-yl)-1H-pyrazolo[3 pyridin-5-yl)pyridin-3-yl)pivalamide [204];

N-(5-(3-(4-(4-methyl-1H-imidazol-1-yl)-1H-pyrrolo[2,3-b]pyridin-2-yl)-1H-pyrazolo[3 pyridin-5-yl)pyridin-3-yl)isobutyramide [205];

N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)-2-phenylacetamide [206];

N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)benzamide [207];

N-isopropyl-5-(3-(4-(4-methyl-1H-imidazol-1-yl)-1H-pyrrolo[2,3-b]pyridin-2-yl)-1H-pyrazolo[3,4-b]pyridin-5-yl)pyridin-3-amine [208];

N,N-dimethyl-1-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)methanamine [209];

3-(4-(4-methyl-1H-imidazol-1-yl)-1H-pyrrolo[2,3-b]pyridin-2-yl)-5-(5-(pyrrolidin-1-ylmethyl)pyridin-3-yl)-1H-pyrazolo[3,4-b]pyridine [210];

3-(4-(4-methyl-1H-imidazol-1-yl)-1H-pyrrolo[2,3-b]pyridin-2-yl)-5-(5-(piperidin-1-ylmethyl)pyridin-3-yl)-1H-pyrazolo[3,4-b]pyridine [211];

3,3-dimethyl-N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)butanamide [212];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)butyramide [213];

3-(4-(4-methyl -1H-imidazol -1-yl)-1H-pyrrolo[2,3-b]pyridin-2-yl)-5-(pyridin-4-yl)-1H-pyrazolo[3,4-b]pyridine [214];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)pentanamide [215];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)cyclopropanecarboxamide [216];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)cyclobutanecarboxamide [217];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)cyclopentanecarboxamide [218];

N-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)cyclohexanecarboxamide [219];

N-benzyl-1-(5-(3-(4-(4-methyl -1H-imidazol -1-yl)-1H-pyrrolo[2,3-b]pyridin-2-yl)-1H-pyrazolo[3,4-b]pyridin-5-yl)pyridin-3-yl)methanamine [220];

1-cyclopentyl-N-((5-(3-(4-(4-methyl -1H-imidazol-1-yl)-1H-pyrrolo[2,3-b]pyridin-2-yl)-1H-pyrazolo[3,4-b]pyridin-5-yl)pyridin-3-yl)methyl)methanamine [221];

5-(5-((3,3-difluoropyrrolidin-1-yl)methyl)pyridin-3-yl)-3-(4-(4-methyl -1H-imidazol-1-yl)-1H-pyrrolo[2,3-b]pyridin-2-yl)-1H-pyrazolo[3,4-b]pyridine [222];

3-(4-(4-methyl -1H-imidazol -1-yl)-1H-pyrrolo[2,3-b]pyridin-2-yl)-5-(pyrimidin-5-yl)-1H-pyrazolo[3,4-b]pyridine [223];

3-(4-(4-methyl -1H-imidazol -1-yl)-1H-pyrrolo[2,3-b]pyridin-2-yl)-5-(pyridin-2-yl)-1H-pyrazolo[3,4-b]pyridine [224];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)propionamide [225];

3-methyl-N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)butanamide [226];

5-(3-(4-(4-methylpipe razin-1-yl)-1H-pyrrolo[2,3-b]pyridin-2-yl)-1H-pyrazolo[3,4-b]pyridin-5-yl)pyridin-3-amine [227];

3-(4-(4-methylpiperazin-1-yl)-1H-pyrrolo[2,3-b]pyridin-2-yl)-5-(pyridin-3-yl)-1H-pyrazolo[3,4-b]pyridine [228];

3-(4-(4-methylpiperazin-1-yl)-1H-pyrrolo[2,3-b]pyridin-2-yl)-5-(4-methylpyridin-3-yl)-1H-pyrazolo[3,4-b]pyridine [229];

N-((5-(3-(4-(4-methylpip erazin-1-yl)-1H-pyrrolo[2,3-b]pyridin-2-yl)-1H-pyrazolo[3,4-b]pyridin-5-yl)pyridin-3-yl)methyl)ethanamine [230];

N,N-dimethyl-5-(3-(4-(4-methylpiperazin-1-yl)-1H-pyrrolo[2,3-b]pyridin-2-yl)-1H-pyrazolo[3,4-b]pyridin-5-yl)pyridin-3-amine [231];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)pivalamide [232];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)isobutyramide [233];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)-2-phenylacetamide [234];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)benzamide [235];

N-isopropyl-5-(3-(4-(4-methylpipe razin-1-yl)-1H-pyrrolo[2,3-b]pyridin-2-yl)-1H-pyrazolo[3,4-b]pyridin-5-yl)pyridin-3-amine [236];

N,N-dimethyl -1-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)methanamine [237];

3-(4-(4-methylpiperazin-1-yl)-1H-pyrrolo[2,3-b]pyridin-2-yl)-5-(5-(pyrrolidin-1-ylmethyl)pyridin-3-yl)-1H-pyrazolo[3,4-b]pyridine [238];

3-(4-(4-methylpiperazin-1-yl)-1H-pyrrolo[2,3-b]pyridin-2-yl)-5-(5-(piperidin-1-ylmethyl)pyridin-3-yl)-1H-pyrazolo[3,4-b]pyridine [239];

3,3-dimethyl-N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)butanamide [240];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)butyramide [241];

3-(4-(4-methylpiperazin-1-yl)-1H-pyrrolo[2,3-b]pyridin-2-yl)-5-(pyridin-4-yl)-1H-pyrazolo[3,4-b]pyridine [242];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)pentanamide [243];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)cyclopropanecarboxamide [244];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)cyclobutanecarboxamide [245];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)cyclopentanecarboxamide [246];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)cyclohexanecarboxamide [247];

N-benzyl-1-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)methanamine [248];

1-cyclopentyl-N-((5-(3-(4-(4-methylpiperazin-1-yl)-1H-pyrrolo[2,3-b]pyridin-2-yl)-1H-pyrazolo[3,4-b]pyridin-5-yl)pyridin-3-yl)methyl)methanamine [249];

5-(5-((3,3-difluoropyrrolidin-1-yl)methyl)pyridin-3-yl)-3-(4-(4-methylpipe razin-1-yl)-1H-pyrrolo[2,3-b]pyridin-2-yl)-1H-pyrazolo[3,4-b]pyridine [250];

3-(4-(4-methylpiperazin-1-yl)-1H-pyrrolo[2,3-b]pyridin-2-yl)-5-(pyrimidin-5-yl)-1H-pyrazolo[3,4-b]pyridine [251];

3-(4-(4-methylpiperazin-1-yl)-1H-pyrrolo[2,3-b]pyridin-2-yl)-5-(pyridin-2-yl)-1H-pyrazolo[3,4-b]pyridine [252];

N-(5-(3-(1H-pyrrolo[2,3-b]pyridin-2-yl)-1H-pyrazolo[3,4-b]pyridin-5-yl)pyridin-3-yl)propionamide [253];

N-(5-(3-(1H-pyrrolo[2,3-b]pyridin-2-yl)-1H-pyrazolo[3,4-b]pyridin-5-yl)pyridin-3-yl)-3-methylbutanamide [254];

5-(3-(1H-pyrrolo[2,3-b]pyridin-2-yl)-1H-pyrazolo[3,4-b]pyridin-5-yl)pyridin-3-amine [255];

5-(pyridin-3-yl)-3-(1H-pyrrolo[2,3-b]pyridin-2-yl)-1H-pyrazolo[3,4-b]pyridine [256];

5-(4-methylpyridin-3-yl)-3-(1H-pyrrolo[2,3-b]pyridin-2-yl)-1H-pyrazolo[3,4-b]pyridine [257];

N-((5-(3-(1H-pyrrolo[2,3-b]pyridin-2-yl)-1H-pyrazolo[3,4-b]pyridin-5-yl)pyridin-3-yl)methyl)ethanamine [258];

5-(3-(1H-pyrrolo[2,3-b]pyridin-2-yl)-1H-pyrazolo[3,4-b]pyridin-5-yl)-N,N-dimethylpyridin-3-amine [259];

N-(5-(3-(1H-pyrrolo[2,3-b]pyridin-2-yl)-1H-pyrazolo[3,4-b]pyridin-5-yl)pyridin-3-yl)pivalamide [260];

N-(5-(3-(1H-pyrrolo[2,3-b]pyridin-2-yl)-1H-pyrazolo[3,4-b]pyridin-5-yl)pyridin-3-yl)isobutyramide [261];

N-(5-(3-(1H-pyrrolo[2,3-b]pyridin-2-yl)-1H-pyrazolo[3,4-b]pyridin-5-yl)pyridin-3-yl)-2-phenylacetamide [262];

N-(5-(3-(1H-pyrrolo[2,3-b]pyridin-2-yl)-1H-pyrazolo[3,4-b]pyridin-5-yl)pyridin-3-yl)benzamide [263];

5-(3-(1H-pyrrolo[2,3-b]pyridin-2-yl)-1H-pyrazolo[3,4-b]pyridin-5-yl)-N-i sopropylpyridin-3-amine [264];

145-(3-(1H-pyrrolo[2,3-b]pyridin-2-yl)-1H-pyrazolo[3,4-b]pyridin-5-yl)pyridin-3-yl)-N,N-dimethylmethanamine [265];

5-(5-(pyrrolidin-1-ylmethyl)pyridin-3-yl)-3-(1H-pyrrolo[2,3-b]pyridin-2-yl)-1H-pyrazolo[3,4-b]pyridine [266];

5-(5-(piperidin-1-ylmethyl)pyridin-3-yl)-3-(1H-pyrrolo[2,3-b]pyridin-2-yl)-1H-pyrazolo[3,4-b]pyridine [267];

N-(5-(3-(1H-pyrrolo[2,3-b]pyridin-2-yl)-1H-pyrazolo[3,4-b]pyridin-5-yl)pyridin-3-yl)-3,3-dimethylbutanamide [268];

N-(5-(3-(1H-pyrrolo[2,3-b]pyridin-2-yl)-1H-pyrazolo[3,4-b]pyridin-5-yl)pyridin-3-yl)butyramide [269];

5-(pyridin-4-yl)-3-(1H-pyrrolo[2,3-b]pyridin-2-yl)-1H-pyrazolo[3,4-b]pyridine [270];

N-(5-(3-(1H-pyrrolo[2,3-b]pyridin-2-yl)-1H-pyrazolo[3,4-b]pyridin-5-yl)pyridin-3-yl)pentanamide [271];

N-(5-(3-(1H-pyrrolo[2,3-b]pyridin-2-yl)-1H-pyrazolo[3,4-b]pyridin-5-yl)pyridin-3-yl)cyclopropanecarboxamide [272];

N-(5-(3-(1H-pyrrolo[2,3-b]pyridin-2-yl)-1H-pyrazolo[3,4-b]pyridin-5-yl)pyridin-3-yl)cyclobutanecarboxamide [273];

N-(5-(3-(1H-pyrrolo[2,3-b]pyridin-2-yl)-1H-pyrazolo[3,4-b]pyridin-5-yl)pyridin-3-yl)cyclopentanecarboxamide [274];

N-(5-(3-(1H-pyrrolo[2,3-b]pyridin-2-yl)-1H-pyrazolo[3,4-b]pyridin-5-yl)pyridin-3-yl)cyclohexanecarboxamide [275];

145-(3-(1H-pyrrolo[2,3-b]pyridin-2-yl)-1H-pyrazolo[3,4-b]pyridin-5-yl)pyridin-3-yl)-N-benzylmethanamine [276];

145-(3-(1H-pyrrolo[2,3-b]pyridin-2-yl)-1H-pyrazolo[3,4-b]pyridin-5-yl)pyridin-3-yl)-N-(cyclopentylmethyl)methanamine [277];

5-(5-((3,3-difluoropyrrolidin-1-yl)methyl)pyridin-3-yl)-3-(1H-pyrrolo[2,3-b]pyridin-2-yl)-1H-pyrazolo[3,4-b]pyridine [278];

5-(pyrimidin-5-yl)-3-(1H-pyrrolo[2,3-b]pyridin-2-yl)-1H-pyrazolo[3,4-b]pyridine [279];

5-(pyridin-2-yl)-3-(1H-pyrrolo[2,3-b]pyridin-2-yl)-1H-pyrazolo[3,4-b]pyridine [280];

N-(5-(3-(4-(thiophen-3-yl)-1H-pyrrolo[2,3-b]pyridin-2-yl)-1H-pyrazolo[3,4-b]pyridin-5-yl)pyridin-3-yl)propionamide [281];

3-methyl-N-(5-(3-(4-(thiophen-3-yl)-1H-pyrrolo[2,3-b]pyridin-2-yl)-1H-pyrazolo[3,4-b]pyridin-5-yl)pyridin-3-yl)butanamide [282];

5-(3-(4-(thiophen-3-yl)-1H-pyrrolo[2,3-b]pyridin-2-yl)-1H-pyrazolo[3,4-b]pyridin-5-yl)pyridin-3-amine [283];

5-(pyridin-3-yl)-3-(4-(thiophen-3-yl)-1H-pyrrolo[2,3-b]pyridin-2-yl)-1H-pyrazolo[3,4-b]pyridine [284];

5-(4-methylpyridin-3-yl)-3-(4-(thiophen-3-yl)-1H-pyrrolo[2,3-b]pyridin-2-yl)-1H-pyrazolo[3,4-b]pyridine [285];

N-((5-(3-(4-(thiophen-3-yl)-1H-pyrrolo[2,3-b]pyridin-2-yl)-1H-pyrazolo[3,4-b]pyridin-5-yl)pyridin-3-yl)methyl)ethanamine [286];

N,N-dimethyl-5-(3-(4-(thiophen-3-yl)-1H-pyrrolo[2,3-b]pyridin-2-yl)-1H-pyrazolo[3,4-b]pyridin-5-yl)pyridin-3-amine [287];

N-(5-(3-(4-(thiophen-3-yl)-1H-pyrrolo[2,3-b]pyridin-2-yl)-1H-pyrazolo[3,4-b]pyridin-5-yl)pyridin-3-yl)pivalamide [288];

N-(5-(3-(4-(thiophen-3-yl)-1H-pyrrolo[2,3-b]pyridin-2-yl)-1H-pyrazolo[3,4-b]pyridin-5-yl)pyridin-3-yl)isobutyramide [289];

2-phenyl-N-(5-(3-(4-(thiophen-3-yl)-1H-pyrrolo[2,3-b]pyridin-2-yl)-1H-pyrazolo[3,4-b]pyridin-5-yl)pyridin-3-yl)acetamide [290];

N-(5-(3-(4-(thiophen-3-yl)-1H-pyrrolo[2,3-b]pyridin-2-yl)-1H-pyrazolo[3,4-b]pyridin-5-yl)pyridin-3-yl)benzamide [291];

N-isopropyl-5-(3-(4-(thiophen-3-yl)-1H-pyrrolo[2,3-b]pyridin-2-yl)-1H-pyrazolo[3,4-b]pyridin-5-yl)pyridin-3-amine [292];

N,N-dimethyl 1-(5-(3-(4-(thiophen-3-yl)-1H-pyrrolo[2,3-b]pyridin-2-yl)-1H-pyrazolo[3,4-b]pyridin-5-yl)pyridin-3-yl)methanamine [293];

5-(5-(pyrrolidin-1-ylmethyl)pyridin-3-yl)-3-(4-(thiophen-3-yl)-1H-pyrrolo[2,3-b]pyridin-2-yl)-1H-pyrazolo[3,4-b]pyridine [294];

5-(5-(piperidin-1-ylmethyl)pyridin-3-yl)-3-(4-(thiophen-3-yl)-1H-pyrrolo[2,3-b]pyridin-2-yl)-1H-pyrazolo[3,4-b]pyridine [295];

3,3-dimethyl-N-(5-(3-(4-(thiophen-3-yl)-1H-pyrrolo[2,3-b]pyridin-2-yl)-1H-pyrazolo[3,4-b]pyridin-5-yl)pyridin-3-yl)butanamide [296];

N-(5-(3-(4-(thiophen-3-yl)-1H-pyrrolo[2,3-b]pyridin-2-yl)-1H-pyrazolo[3,4-b]pyridin-5-yl)pyridin-3-yl)butyramide [297];

5-(pyridin-4-yl)-3-(4-(thiophen-3-yl)-1H-pyrrolo[2,3-b]pyridin-2-yl)-1H-pyrazolo[3,4-b]pyridine [298];

N-(5-(3-(4-(thiophen-3-yl)-1H-pyrrolo[2,3-b]pyridin-2-yl)-1H-pyrazolo[3,4-b]pyridin-5-yl)pyridin-3-yl)pentanamide [299];

N-(5-(3-(4-(thiophen-3-yl)-1H-pyrrolo[2,3-b]pyridin-2-yl)-1H-pyrazolo[3,4-b]pyridin-5-yl)pyridin-3-yl)cyclopropanecarboxamide [300];

N-(5-(3-(4-(thiophen-3-yl)-1H-pyrrolo[2,3-b]pyridin-2-yl)-1H-pyrazolo[3,4-b]pyridin-5-yl)pyridin-3-yl)cyclobutanecarboxamide [301];

N-(5-(3-(4-(thiophen-3-yl)-1H-pyrrolo[2,3-b]pyridin-2-yl)-1H-pyrazolo[3,4-b]pyridin-5-yl)pyridin-3-yl)cyclopentanecarboxamide [302];

N-(5-(3-(4-(thiophen-3-yl)-1H-pyrrolo[2,3-b]pyridin-2-yl)-1H-pyrazolo[3,4-b]pyridin-5-yl)pyridin-3-yl)cyclohexanecarboxamide [303];

N-benzyl-1-(5-(3-(4-(thiophen-3-yl)-1H-pyrrolo[2,3-b]pyridin-2-yl)-1H-pyrazolo[3,4-b]pyridin-5-yl)pyridin-3-yl)methanamine [304];

1-cyclopentyl-N-((5-(3-(4-(thiophen-3-yl)-1H-pyrrolo[2,3-b]pyridin-2-yl)-1H-pyrazolo[3,4-b]pyridin-5-yl)pyridin-3-yl)methyl)methanamine [305];

5-(5-((3,3-difluoropyrrolidin-1-yl)methyl)pyridin-3-yl)-3-(4-(thiophen-3-yl)-1H-pyrrolo[2,3-b]pyridin-2-yl)-1H-pyrazolo[3,4-b]pyridine [306];
5-(pyrimidin-5-yl)-3-(4-(thiophen-3-yl)-1H-pyrrolo[2,3-b]pyridin-2-yl)-1H-pyrazolo[3,4-b]pyridine [307];
5-(pyridin-2-yl)-3-(4-(thiophen-3-yl)-1H-pyrrolo[2,3-b]pyridin-2-yl)-1H-pyrazolo[3,4-b]pyridine [308];
N-(5-(3-(4-(furan-3-yl)-1H-pyrrolo[2,3-b]pyridin-2-yl)-1H-pyrazolo[3,4-b]pyridin-5-yl)pyridin-3-yl)propionamide [309];
N-(5-(3-(4-(furan-3-yl)-1H-pyrrolo[2,3-b]pyridin-2-yl)-1H-pyrazolo[3,4-b]pyridin-5-yl)pyridin-3-yl)-3-methylbutanamide [310];
5-(3-(4-(furan-3-yl)-1H-pyrrolo[2,3-b]pyridin-2-yl)-1H-pyrazolo[3,4-b]pyridin-5-yl)pyridin-3-amine [311];
3-(4-(furan-3-yl)-1H-pyrrolo[2,3-b]pyridin-2-yl)-5-(pyridin-3-yl)-1H-pyrazolo[3,4-b]pyridine [312];
3-(4-(furan-3-yl)-1H-pyrrolo[2,3-b]pyridin-2-yl)-5-(4-methylpyridin-3-yl)-1H-pyrazolo[3,4-b]pyridine [313];
N-((5-(3-(4-(furan-3-yl)-1H-pyrrolo[2,3-b]pyridin-2-yl)-1H-pyrazolo[3,4-b]pyridin-5-yl)pyridin-3-yl)methyl)ethanamine [314];
5-(3-(4-(furan-3-yl)-1H-pyrrolo[2,3-b]pyridin-2-yl)-1H-pyrazolo[3,4-b]pyridin-5-yl)-N,N-dimethylpyridin-3-amine [315];
N-(5-(3-(4-(furan-3-yl)-1H-pyrrolo[2,3-b]pyridin-2-yl)-1H-pyrazolo[3,4-b]pyridin-5-yl)pyridin-3-yl)pivalamide [316];
N-(5-(3-(4-(furan-3-yl)-1H-pyrrolo[2,3-b]pyridin-2-yl)-1H-pyrazolo[3,4-b]pyridin-5-yl)pyridin-3-yl)isobutyramide [317];
N-(5-(3-(4-(furan-3-yl)-1H-pyrrolo[2,3-b]pyridin-2-yl)-1H-pyrazolo[3,4-b]pyridin-5-yl)pyridin-3-yl)-2-phenylacetamide [318];
N-(5-(3-(4-(furan-3-yl)-1H-pyrrolo[2,3-b]pyridin-2-yl)-1H-pyrazolo[3,4-b]pyridin-5-yl)pyridin-3-yl)benzamide [319];
5-(3-(4-(furan-3-yl)-1H-pyrrolo[2,3-b]pyridin-2-yl)-1H-pyrazolo[3,4-b]pyridin-5-yl)-N-isopropylpyridin-3-amine [320];
1-(5-(3-(4-(furan-3-yl)-1H-pyrrolo[2,3-b]pyridin-2-yl)-1H-pyrazolo[3,4-b]pyridin-5-yl)pyridin-3-yl)-N,N-dimethylmethanamine [321];
3-(4-(furan-3-yl)-1H-pyrrolo[2,3-b]pyridin-2-yl)-5-(5-(pyrrolidin-1-ylmethyl)pyridin-3-yl)-1H-pyrazolo[3,4-b]pyridine [322];
3-(4-(furan-3-yl)-1H-pyrrolo[2,3-b]pyridin-2-yl)-5-(5-(piperidin-1-ylmethyl)pyridin-3-yl)-1H-pyrazolo[3,4-b]pyridine [323];
N-(5-(3-(4-(furan-3-yl)-1H-pyrrolo[2,3-b]pyridin-2-yl)-1H-pyrazolo[3,4-b]pyridin-5-yl)pyridin-3-yl)-3,3-dimethylbutanamide [324];
N-(5-(3-(4-(furan-3-yl)-1H-pyrrolo[2,3-b]pyridin-2-yl)-1H-pyrazolo[3,4-b]pyridin-5-yl)pyridin-3-yl)butyramide [325];
3-(4-(furan-3-yl)-1H-pyrrolo[2,3-b]pyridin-2-yl)-5-(pyridin-4-yl)-1H-pyrazolo[3,4-b]pyridine [326];
N-(5-(3-(4-(furan-3-yl)-1H-pyrrolo[2,3-b]pyridin-2-yl)-1H-pyrazolo[3,4-b]pyridin-5-yl)pyridin-3-yl)pentanamide [327];
N-(5-(3-(4-(furan-3-yl)-1H-pyrrolo[2,3-b]pyridin-2-yl)-1H-pyrazolo[3,4-b]pyridin-5-yl)pyridin-3-yl)cyclopropanecarboxamide [328];
N-(5-(3-(4-(furan-3-yl)-1H-pyrrolo[2,3-b]pyridin-2-yl)-1H-pyrazolo[3,4-b]pyridin-5-yl)pyridin-3-yl)cyclobutanecarboxamide [329];
N-(5-(3-(4-(furan-3-yl)-1H-pyrrolo[2,3-b]pyridin-2-yl)-1H-pyrazolo[3,4-b]pyridin-5-yl)pyridin-3-yl)cyclopentanecarboxamide [330];
N-(5-(3-(4-(furan-3-yl)-1H-pyrrolo[2,3-b]pyridin-2-yl)-1H-pyrazolo[3,4-b]pyridin-5-yl)pyridin-3-yl)cyclohexanecarboxamide [331];
N-benzyl-1-(5-(3-(4-(furan-3-yl)-1H-pyrrolo[2,3-b]pyridin-2-yl)-1H-pyrazolo[3,4-b]pyridin-5-yl)pyridin-3-yl)methanamine [332];
1-cyclopentyl-N-((5-(3-(4-(furan-3-yl)-1H-pyrrolo[2,3-b]pyridin-2-yl)-1H-pyrazolo[3,4-b]pyridin-5-yl)pyridin-3-yl)methyl)methanamine [333];
5-(5-((3,3-difluoropyrrolidin-1-yl)methyl)pyridin-3-yl)-3-(4-(furan-3-yl)-1H-pyrrolo[2,3-b]pyridin-2-yl)-1H-pyrazolo[3,4-b]pyridine [334];
3-(4-(furan-3-yl)-1H-pyrrolo[2,3-b]pyridin-2-yl)-5-(pyrimidin-5-yl)-1H-pyrazolo[3,4-b]pyridine [335];
3-(4-(furan-3-yl)-1H-pyrrolo[2,3-b]pyridin-2-yl)-5-(pyridin-2-yl)-1H-pyrazolo[3,4-b]pyridine [336];
N-(5-(3-(4-(thiophen-2-yl)-1H-pyrrolo[2,3-b]pyridin-2-yl)-1H-pyrazolo[3,4-b]pyridin-5-yl)pyridin-3-yl)propionamide [337];
3-methyl-N-(5-(3-(4-(thiophen-2-yl)-1H-pyrrolo[2,3-b]pyridin-2-yl)-1H-pyrazolo[3,4-b]pyridin-5-yl)pyridin-3-yl)butanamide [338];
5-(3-(4-(thiophen-2-yl)-1H-pyrrolo[2,3-b]pyridin-2-yl)-1H-pyrazolo[3,4-b]pyridin-5-yl)pyridin-3-amine [339];
5-(pyridin-3-yl)-3-(4-(thiophen-2-yl)-1H-pyrrolo[2,3-b]pyridin-2-yl)-1H-pyrazolo[3,4-b]pyridine [340];
5-(4-methylpyridin-3-yl)-3-(4-(thiophen-2-yl)-1H-pyrrolo[2,3-b]pyridin-2-yl)-1H-pyrazolo[3,4-b]pyridine [341];
N-((5-(3-(4-(thiophen-2-yl)-1H-pyrrolo[2,3-b]pyridin-2-yl)-1H-pyrazolo[3,4-b]pyridin-5-yl)pyridin-3-yl)methyl)ethanamine [342];
N,N-dimethyl-5-(3-(4-(thiophen-2-yl)-1H-pyrrolo[2,3-b]pyridin-2-yl)-1H-pyrazolo[3,4-b]pyridin-5-yl)pyridin-3-amine [343];
N-(5-(3-(4-(thiophen-2-yl)-1H-pyrrolo[2,3-b]pyridin-2-yl)-1H-pyrazolo[3,4-b]pyridin-5-yl)pyridin-3-yl)pivalamide [344];
N-(5-(3-(4-(thiophen-2-yl)-1H-pyrrolo[2,3-b]pyridin-2-yl)-1H-pyrazolo[3,4-b]pyridin-5-yl)pyridin-3-yl)isobutyramide [345];
2-phenyl-N-(5-(3-(4-(thiophen-2-yl)-1H-pyrrolo[2,3-b]pyridin-2-yl)-1H-pyrazolo[3,4-b]pyridin-5-yl)pyridin-3-yl)acetamide [346];
N-(5-(3-(4-(thiophen-2-yl)-1H-pyrrolo[2,3-b]pyridin-2-yl)-1H-pyrazolo[3,4-b]pyridin-5-yl)pyridin-3-yl)benzamide [347];
N-isopropyl-5-(3-(4-(thiophen-2-yl)-1H-pyrrolo[2,3-b]pyridin-2-yl)-1H-pyrazolo[3,4-b]pyridin-5-yl)pyridin-3-amine [348];
N,N-dimethyl-1-(5-(3-(4-(thiophen-2-yl)-1H-pyrrolo[2,3-b]pyridin-2-yl)-1H-pyrazolo[3,4-b]pyridin-5-yl)pyridin-3-yl)methanamine [349];
5-(5-(pyrrolidin-1-ylmethyl)pyridin-3-yl)-3-(4-(thiophen-2-yl)-1H-pyrrolo[2,3-b]pyridin-2-yl)-1H-pyrazolo[3,4-b]pyridine [350];
5-(5-(piperidin-1-ylmethyl)pyridin-3-yl)-3-(4-(thiophen-2-yl)-1H-pyrrolo[2,3-b]pyridin-2-yl)-1H-pyrazolo[3,4-b]pyridine [351];
3,3-dimethyl-N-(5-(3-(4-(thiophen-2-yl)-1H-pyrrolo[2,3-b]pyridin-2-yl)-1H-pyrazolo[3,4-b]pyridin-5-yl)pyridin-3-yl)butanamide [352];

N-(5-(3-(4-(thiophen-2-yl)-1H-pyrrolo[2,3-b]pyridin-2-yl)-1H-pyrazolo[3,4-b]pyridin-5-yl)pyridin-3-yl)butyramide [353];

5-(pyridin-4-yl)-3-(4-(thiophen-2-yl)-1H-pyrrolo[2,3-b]pyridin-2-yl)-1H-pyrazolo[3,4-b]pyridine [354];

N-(5-(3-(4-(thiophen-2-yl)-1H-pyrrolo[2,3-b]pyridin-2-yl)-1H-pyrazolo[3,4-b]pyridin-5-yl)pyridin-3-yl)pentanamide [355];

N-(5-(3-(4-(thiophen-2-yl)-1H-pyrrolo[2,3-b]pyridin-2-yl)-1H-pyrazolo[3,4-b]pyridin-5-yl)pyridin-3-yl)cyclopropanecarboxamide [356];

N-(5-(3-(4-(thiophen-2-yl)-1H-pyrrolo[2,3-b]pyridin-2-yl)-1H-pyrazolo[3,4-b]pyridin-5-yl)pyridin-3-yl)cyclobutanecarboxamide [357];

N-(5-(3-(4-(thiophen-2-yl)-1H-pyrrolo[2,3-b]pyridin-2-yl)-1H-pyrazolo[3,4-b]pyridin-5-yl)pyridin-3-yl)cyclopentanecarboxamide [358];

N-(5-(3-(4-(thiophen-2-yl)-1H-pyrrolo[2,3-b]pyridin-2-yl)-1H-pyrazolo[3,4-b]pyridin-5-yl)pyridin-3-yl)cyclohexanecarboxamide [359];

N-benzyl-1-(5-(3-(4-(thiophen-2-yl)-1H-pyrrolo[2,3-b]pyridin-2-yl)-1H-pyrazolo[3,4-b]pyridin-5-yl)pyridin-3-yl)methanamine [360];

1-cyclopentyl-N-((5-(3-(4-(thiophen-2-yl)-1H-pyrrolo[2,3-b]pyridin-2-yl)-1H-pyrazolo[3,4-b]pyridin-5-yl)pyridin-3-yl)methyl)methanamine [361];

5-(5-((3,3-difluoropyrrolidin-1-yl)methyl)pyridin-3-yl)-3-(4-(thiophen-2-yl)-1H-pyrrolo[2,3-b]pyridin-2-yl)-1H-pyrazolo[3,4-b]pyridine [362];

5-(pyrimidin-5-yl)-3-(4-(thiophen-2-yl)-1H-pyrrolo[2,3-b]pyridin-2-yl)-1H-pyrazolo[3,4-b]pyridine [363];

5-(pyridin-2-yl)-3-(4-(thiophen-2-yl)-1H-pyrrolo[2,3-b]pyridin-2-yl)-1H-pyrazolo[3,4-b]pyridine [364];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)propionamide [365];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)-3-methylbutanamide [366];

5-(3-(4-(5-fluorothiophen-2-yl)-1H-pyrrolo[2,3-b]pyridin-2-yl)-1H-pyrazolo[3,4-b]pyridin-5-yl)pyridin-3-amine [367];

3-(4-(5-fluorothiophen-2-yl)-1H-pyrrolo[2,3-b]pyridin-2-yl)-5-(pyridin-3-yl)-1H-pyrazolo[3,4-b]pyridine [368];

3-(4-(5-fluorothiophen-2-yl)-1H-pyrrolo[2,3-b]pyridin-2-yl)-5-(4-methylpyridin-3-yl)-1H-pyrazolo[3,4-b]pyridine [369];

N-((5-(3-(4-(5-fluorothiophen-2-yl)-1H-pyrrolo[2,3-b]pyridin-2-yl)-1H-pyrazolo[3,4-b]pyridin-5-yl)pyridin-3-yl)methyl)ethanamine [370];

5-(3-(4-(5-fluorothiophen-2-yl)-1H-pyrrolo[2,3-b]pyridin-2-yl)-1H-pyrazolo[3,4-b]pyridin-5-yl)-N,N-dimethylpyridin-3-amine [371];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)pivalamide [372];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)isobutyramide [373];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)-2-phenylacetamide [374];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)benzamide [375];

5-(3-(4-(5-fluorothiophen-2-yl)-1H-pyrrolo[2,3-b]pyridin-2-yl)-1H-pyrazolo[3,4-b]pyridin-5-yl)-N-isopropylpyridin-3-amine [376];

1-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)-N,N-dimethylmethanamine [377];

3-(4-(5-fluorothiophen-2-yl)-1H-pyrrolo[2,3-b]pyridin-2-yl)-5-(5-(pyrrolidin-1-ylmethyl)pyridin-3-yl)-1H-pyrazolo[3,4-b]pyridine [378];

3-(4-(5-fluorothiophen-2-yl)-1H-pyrrolo[2,3-b]pyridin-2-yl)-5-(5-(piperidin-1-ylmethyl)pyridin-3-yl)-1H-pyrazolo[3,4-b]pyridine [379];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)-3,3-dimethylbutanamide [380];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)butyramide [381];

3-(4-(5-fluorothiophen-2-yl)-1H-pyrrolo[2,3-b]pyridin-2-yl)-5-(pyridin-4-yl)-1H-pyrazolo[3,4-b]pyridine [382];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)pentanamide [383];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)cyclopropanecarboxamide [384];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)cyclobutanecarboxamide [385];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)cyclopentanecarboxamide [386];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)cyclohexanecarboxamide [387];

N-benzyl-1-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)methanamine [388];

1-cyclopentyl-N-((5-(3-(4-(5-fluorothiophen-2-yl)-1H-pyrrolo[2,3-b]pyridin-2-yl)-1H-pyrazolo[3,4-b]pyridin-5-yl)pyridin-3-yl)methyl)methanamine [389];

5-(5-((3,3-difluoropyrrolidin-1-yl)methyl)pyridin-3-yl)-3-(4-(5-fluorothiophen-2-yl)-1H-pyrrolo[2,3-b]pyridin-2-yl)-1H-pyrazolo[3,4-b]pyridine [390];

3-(4-(5-fluorothiophen-2-yl)-1H-pyrrolo[2,3-b]pyridin-2-yl)-5-(pyrimidin-5-yl)-1H-pyrazolo[3,4-b]pyridine [391];

3-(4-(5-fluorothiophen-2-yl)-1H-pyrrolo[2,3-b]pyridin-2-yl)-5-(pyridin-2-yl)-1H-pyrazolo[3,4-b]pyridine [392];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)propionamide [393];

3-methyl-N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)butanamide [394];

5-(3-(4-(5-methylthiophen-2-yl)-1H-pyrrolo[2,3-b]pyridin-2-yl)-1H-pyrazolo[3,4-b]pyridin-5-yl)pyridin-3-amine [395];

3-(4-(5-methylthiophen-2-yl)-1H-pyrrolo[2,3-b]pyridin-2-yl)-5-(pyridin-3-yl)-1H-pyrazolo[3,4-b]pyridine [396];

5-(4-methylpyridin-3-yl)-3-(4-(5-methylthiophen-2-yl)-1H-pyrrolo[2,3-b]pyridin-2-yl)-1H-pyrazolo[3,4-b]pyridine [397];

N-((5-(3-(4-(5-methylthiophen-2-yl)-1H-pyrrolo[2,3-b]pyridin-2-yl)-1H-pyrazolo[3,4-b]pyridin-5-yl)pyridin-3-yl)methyl)ethanamine [398];

N,N-dimethyl-5-(3-(4-(5-methylthiophen-2-yl)-1H-pyrrolo[2,3-b]pyridin-2-yl)-1H-pyrazolo[3,4-b]pyridin-5-yl)pyridin-3-amine [399];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)pivalamide [400];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)isobutyramide [401];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)-2-phenylacetamide [402];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)benzamide [403];

N-isopropyl-5-(3-(4-(5-methylthiophen-2-yl)-1H-pyrrolo[2,3-b]pyridin-2-yl)-1H-pyrazolo[3,4-b]pyridin-5-yl)pyridin-3-amine [404];

N,N-dimethyl -1-(5-(3-(4-(5-methylthiophen-2-yl)-1H-pyrrolo[2,3-b]pyridin-2-yl)-1H-pyrazolo[3,4-1)]pyridin-5-yl)pyridin-3-yl)methanamine [405];

3-(4-(5-methylthiophen-2-yl)-1H-pyrrolo[2,3-b]pyridin-2-yl)-5-(5-(pyrrolidin-1-ylmethyl)pyridin-3-yl)-1H-pyrazolo[3,4-b]pyridine [406];

3-(4-(5-methylthiophen-2-yl)-1H-pyrrolo[2,3-b]pyridin-2-yl)-5-(5-(piperidin-1-ylmethyl)pyridin-3-yl)-1H-pyrazolo[3,4-b]pyridine [407];

3,3-dimethyl-N-(5-(3-(4-(5-methylthiophen-2-yl)-1H-pyrrolo[2,3-b]pyridin-2-yl)-1H-pyrazolo[3,4-1)]pyridin-5-yl)pyridin-3-yl)butanamide [408];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)butyramide [409];

3-(4-(5-methylthiophen-2-yl)-1H-pyrrolo[2,3-b]pyridin-2-yl)-5-(pyridin-4-yl)-1H-pyrazolo[3,4-b]pyridine [410];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)pentanamide [411];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)cyclopropanecarboxamide [412];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)cyclobutanecarboxamide [413];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)cyclopentanecarboxamide [414];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)cyclohexanecarboxamide [415];

N-benzyl-1-(5-(3-(4-(5-methylthiophen-2-yl)-1H-pyrrolo[2,3-b]pyridin-2-yl)-1H-pyrazolo[3,4-b]pyridin-5-yl)pyridin-3-yl)methanamine [416];

1-cyclopentyl-N-((5-(3-(4-(5-methylthiophen-2-yl)-1H-pyrrolo[2,3-b]pyridin-2-yl)-1H-pyrazolo[3,4-b]pyridin-5-yl)pyridin-3-yl)methyl)methanamine [417];

5-(5-(((3,3-difluoropyrrolidin-1-yl)methyl)pyridin-3-yl)-3-(4-(5-methylthiophen-2-yl)-1H-pyrrolo[2,3-b]pyridin-2-yl)-1H-pyrazolo[3,4-b]pyridine [418];

3-(4-(5-methylthiophen-2-yl)-1H-pyrrolo[2,3-b]pyridin-2-yl)-5-(pyrimidin-5-yl)-1H-pyrazolo[3,4-b]pyridine [419];

3-(4-(5-methylthiophen-2-yl)-1H-pyrrolo[2,3-b]pyridin-2-yl)-5-(pyridin-2-yl)-1H-pyrazolo[3,4-b]pyridine [420];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)propionamide [421];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-3-methylbutanamide [422];

1-(5-(2-(5-(5-aminopyridin-3-yl)-1H-pyrazolo[3,4-b]pyridin-3-yl)-1H-pyrrolo[2,3-b]pyridin-4-yl)thiophen-2-yl)ethan-1-one [423];

1-(5-(2-(5-(pyridin-3-yl)-1H-pyrazolo[3,4-b]pyridin-3-yl)-1H-pyrrolo[2,3-b]pyridin-4-yl)thiophen-2-yl)ethan-1-one [424];

1-(5-(2-(5-(4-methylpyridin-3-yl)-1H-pyrazolo[3,4-b]pyridin-3-yl)-1H-pyrrolo[2,3-b]pyridin-4-yl)thiophen-2-yl)ethan-1-one [425];

1-(5-(2-(5-(5-((ethylamino)methyl)pyridin-3-yl)-1H-pyrazolo[3,4-b]pyridin-3-yl)-1H-pyrrolo[2,3-b]pyridin-4-yl)thiophen-2-yl)ethan-1-one [426];

1-(5-(2-(5-(5-(dimethylamino)pyridin-3-yl)-1H-pyrazolo[3,4-b]pyridin-3-yl)-1H-pyrrolo[2,3-b]pyridin-4-yl)thiophen-2-yl)ethan-1-one [427];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)pivalamide [428];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)isobutyramide [429];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-2-phenylacetamide [430];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)benzamide [431];

1-(5-(2-(5-(5-(isopropylamino)pyridin-3-yl)-1H-pyrazolo[3,4-b]pyridin-3-yl)-1H-pyrrolo[2,3-b]pyridin-4-yl)thiophen-2-yl)ethan-1-one [432];

1-(5-(2-(5-(5-((dimethylamino)methyl)pyridin-3-yl)-1H-pyrazolo[3 pyridin-3-yl)-1H-pyrrolo[2,3-b]pyridin-4-yl)thiophen-2-yl)ethan-1-one [433];

1-(5-(2-(5-(5-(pyrrolidin-1-ylmethyl)pyridin-3-yl)-1H-pyrazolo[3,4-b]pyridin-3-yl)-1H-pyrrolo[2,3-b]pyridin-4-yl)thiophen-2-yl)ethan-1-one [434];

1-(5-(2-(5-(5-(piperidin-1-ylmethyl)pyridin-3-yl)-1H-pyrazolo[3,4-b]pyridin-3-yl)-1H-pyrrolo[2,3-b]pyridin-4-yl)thiophen-2-yl)ethan-1-one [435];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-3,3-dimethylbutanamide [436];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)butyramide [437];

1-(5-(2-(5-(pyridin-4-yl)-1H-pyrazolo[3,4-b]pyridin-3-yl)-1H-pyrrolo[2,3-b]pyridin-4-yl)thiophen-2-yl)ethan-1-one [438];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)pentanamide [439];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)cyclopropanecarboxamide [440];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)cyclobutanecarboxamide [441];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)cyclopentanecarboxamide [442];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)cyclohexanecarboxamide [443];

1-(5-(2-(5-(5-((benzylamino)methyl)pyridin-3-yl)-1H-pyrazolo[3,4-b]pyridin-3-yl)-1H-pyrrolo[2,3-b]pyridin-4-yl)thiophen-2-yl)ethan-1-one [444];

1-(5-(2-(5-(5-(((cyclopentylmethyl)amino)methyl)pyridin-3-yl)-1H-pyrazolo[3 pyridin-3-yl)-1H-pyrrolo[2,3-b]pyridin-4-yl)thiophen-2-yl)ethan-1-one [445];

1-(5-(2-(5-(5-((3,3-difluoropyrrolidin-1-yl)methyl)pyridin-3-yl)-1H-pyrazolo[3 pyridin-3-yl)-1H-pyrrolo[2,3-b]pyridin-4-yl)thiophen-2-yl)ethan-1-one [446];

1-(5-(2-(5-(pyrimidin-5-yl)-1H-pyrazolo[3,4-b]pyridin-3-yl)-1H-pyrrolo[2,3-b]pyridin-4-yl)thiophen-2-yl)ethan-1-one [447];

1-(5-(2-(5-(pyridin-2-yl)-1H-pyrazolo[3,4-b]pyridin-3-yl)-1H-pyrrolo[2,3-b]pyridin-4-yl)thiophen-2-yl)ethan-1-one [448];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)propionamide [449];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)-3-methylbutanamide [450];

$N^1$-(3-(2-(5-(5-aminopyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [451];

$N^1$-(3-fluoro-5-(2-(5-(pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [452];

$N^1$-(3-fluoro-5-(2-(5-(4-methylpyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [453];

$N^1$-(3-(2-(5-(5-((ethylamino)methyl)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [454];

$N^1$-(3-(2-(5-(5-(dimethylamino)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [455];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)pivalamide [456];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)isobutyramide [457];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)-2-phenylacetamide [458];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)benzamide [459];

$N^1$-(3-fluoro-5-(2-(5-(5-(isopropylamino)pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [460];

$N^1$-(3-(2-(5-(5-((dimethylamino)methyl)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [461];

$N^1$-(3-fluoro-5-(2-(5-(5-(pyrrolidin-1-ylmethyl)pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [462];

$N^1$-(3-fluoro-5-(2-(5-(5-(piperidin-1-ylmethyl)pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [463];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)-3,3-dimethylbutanamide [464];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)butyramide [465];

$N^1$-(3-fluoro-5-(2-(5-(pyridin-4-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [466];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)pentanamide [467];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)cyclopropanecarboxamide [468];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)cyclobutanecarboxamide [469];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)cyclopentanecarboxamide [470];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)cyclohexanecarboxamide [471];

$N^1$-(3-(2-(5-(5-((benzylamino)methyl)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [472];

$N^1$-(3-(2-(5-(5-(((cyclopentylmethyl)amino)methyl)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [473];

$N^1$-(3-(2-(5-(5-((3,3-difluoropyrrolidin-1-yl)methyl)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [474];

$N^1$-(3-fluoro-5-(2-(5-(pyrimidin-5-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [475];

$N^1$-(3-fluoro-5-(2-(5-(pyridin-2-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [476];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)propionamide [477];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)-3-methylbutanamide [478];

N-(3-(2-(5-(5-aminopyridin-3-yl)-1H-pyrazolo[3,4-b]pyridin-3-yl)-1H-pyrrolo[2,3-b]pyridin-4-yl)-5-fluorobenzyl)methanesulfonamide [479];

N-(3-fluoro-5-(2-(5-(pyridin-3-yl)-1H-pyrazolo[3,4-b]pyridin-3-yl)-1H-pyrrolo[2,3-b]pyridin-4-yl)benzyl)methanesulfonamide [480];

N-(3-fluoro-5-(2-(5-(4-methylpyridin-3-yl)-1H-pyrazolo[3,4-b]pyridin-3-yl)-1H-pyrrolo[2,3-b]pyridin-4-yl)benzyl)methanesulfonamide [481];

N-(3-(2-(5-(5-((ethylamino)methyl)pyridin-3-yl)-1H-pyrazolo[3,4-b]pyridin-3-yl)-1H-pyrrolo[2,3-b]pyridin-4-yl)-5-fluorobenzyl)methanesulfonamide [482];

N-(3-(2-(5-(5-(dimethylamino)pyridin-3-yl)-1H-pyrazolo[3,4-b]pyridin-3-yl)-1H-pyrrolo[2,3-b]pyridin-4-yl)-5-fluorobenzyl)methanesulfonamide [483];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)pivalamide [484];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)isobutyramide [485];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)-2-phenylacetamide [486];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)benzamide [487];

N-(3-fluoro-5-(2-(5-(5-(isopropylamino)pyridin-3-yl)-1H-pyrazolo[3,4-b]pyridin-3-yl)-1H-pyrrolo[2,3-b]pyridin-4-yl)benzyl)methanesulfonamide [488];

N-(3-(2-(5-(5-((dimethylamino)methyl)pyridin-3-yl)-1H-pyrazolo[3,4-b]pyridin-3-yl)-1H-pyrrolo[2,3-b]pyridin-4-yl)-5-fluorobenzyl)methanesulfonamide [489];

N-(3-fluoro-5-(2-(5-(5-(pyrrolidin-1-ylmethyl)pyridin-3-yl)-1H-pyrazolo[3,4-b]pyridin-3-yl)-1H-pyrrolo[2,3-b]pyridin-4-yl)benzyl)methanesulfonamide [490];

N-(3-fluoro-5-(2-(5-(5-(piperidin-1-ylmethyl)pyridin-3-yl)-1H-pyrazolo[3,4-b]pyridin-3-yl)-1H-pyrrolo[2,3-b]pyridin-4-yl)benzyl)methanesulfonamide [491];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)-3,3-dimethylbutanamide [492];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)butyramide [493];

N-(3-fluoro-5-(2-(5-(pyridin-4-yl)-1H-pyrazolo[3,4-b]pyridin-3-yl)-1H-pyrrolo[2,3-b]pyridin-4-yl)benzyl)methanesulfonamide [494];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)pentanamide [495];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)cyclopropanecarboxamide [496];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)cyclobutanecarboxamide [497];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)cyclopentanecarboxamide [498];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)cyclohexanecarboxamide [499];

N-(3-(2-(5-(5-((benzylamino)methyl)pyridin-3-yl)-1H-pyrazolo[3,4-b]pyridin-3-yl)-1H-pyrrolo[2,3-b]pyridin-4-yl)-5-fluorobenzyl)methanesulfonamide [500];

N-(3-(2-(5-(5-((((cyclopentylmethyl)amino)methyl)pyridin-3-yl)-1H-pyrazolo[3,4-b]pyridin-3-yl)-1H-pyrrolo[2,3-b]pyridin-4-yl)-5-fluorobenzyl)methanesulfonamide [501];

N-(3-(2-(5-(5-((3,3-difluoropyrrolidin-1-yl)methyl)pyridin-3-yl)-1H-pyrazolo[3,4-b]pyridin-3-yl)-1H-pyrrolo[2,3-b]pyridin-4-yl)-5-fluorobenzyl)methanesulfonamide [502];

N-(3-fluoro-5-(2-(5-(pyrimidin-5-yl)-1H-pyrazolo[3,4-b]pyridin-3-yl)-1H-pyrrolo[2,3-b]pyridin-4-yl)benzyl)methanesulfonamide [503];

N-(3-fluoro-5-(2-(5-(pyridin-2-yl)-1H-pyrazolo[3,4-b]pyridin-3-yl)-1H-pyrrolo[2,3-b]pyridin-4-yl)benzyl)methanesulfonamide [504];

3-(4-(3-fluorophenyl)-1H-pyrrolo[2,3-b]pyridin-2-yl)-5-(piperidin-4-yl)-1H-pyrazolo[3,4-b]pyridine [505];

3-(4-(3-fluorophenyl)-1H-pyrrolo[2,3-b]pyridin-2-yl)-5-(1,2,3,6-tetrahydropyridin-4-yl)-1H-pyrazolo[3,4-b]pyridine [506];

3-(4-(3-fluorophenyl)-1H-pyrrolo[2,3-b]pyridin-2-yl)-5-(1H-pyrazol-4-yl)-1H-pyrazolo[3,4-b]pyridine [507];

3-(4-(3-fluorophenyl)-1H-pyrrolo[2,3-b]pyridin-2-yl)-5-(1-methyl-1H-pyrazol-4-yl)-1H-pyrazolo[3,4-b]pyridine [508];

5-(1,2-dimethyl-1H-imidazol-5-yl)-3-(4-(3-fluorophenyl)-1H-pyrrolo[2,3-b]pyridin-2-yl)-1H-pyrazolo[3,4-b]pyridine [509];

1-(6-(3-(4-(3-fluorophenyl)-1H-pyrrolo[2,3-b]pyridin-2-yl)-1H-pyrazolo[3,4-b]pyridin-5-yl)pyrazin-2-yl)azetidin-3-amine [510];

5-(5-(cyclohexyloxy)pyridin-3-yl)-3-(4-(3-fluorophenyl)-1H-pyrrolo[2,3-b]pyridin-2-yl)-1H-pyrazolo[3,4-b]pyridine [511];

3-(4-(3-fluorophenyl)-1H-pyrrolo[2,3-b]pyridin-2-yl)-5-(5-(piperidin-4-yloxy)pyridin-3-yl)-1H-pyrazolo[3,4-b]pyridine [512];

N-(5-(3-(4-(3-fluorophenyl)-1H-pyrrolo[2,3-b]pyridin-2-yl)-1H-pyrazolo[3,4-b]pyridin-5-yl)pyridin-3-yl)-2-(piperidin-4-yl)acetamide [513];

3-(4-(3-fluorophenyl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [514];

2-((5-(3-(4-(3-fluorophenyl)-1H-pyrrolo[2,3-b]pyridin-2-yl)-1H-pyrazolo[3,4-b]pyridin-5-yl)pyridin-3-yl)oxy)-N,N-dimethylethan-1-amine [515];

3-(4-(3-fluorophenyl)-1H-pyrrolo[2,3-b]pyridin-2-yl)-5-(5-methoxypyridin-3-yl)-1H-pyrazolo[3,4-b]pyridine [516];

5-(3-(4-(3-fluorophenyl)-1H-pyrrolo[2,3-b]pyridin-2-yl)-1H-pyrazolo[3,4-b]pyridin-5-yl)pyridin-3-ol [517];

5-(5-(benzyloxy)pyridin-3-yl)-3-(4-(3-fluorophenyl)-1H-pyrrolo[2,3-b]pyridin-2-yl)-1H-pyrazolo[3,4-b]pyridine [518];

2-cyclohexyl-N-(5-(3-(4-(3-fluorophenyl)-1H-pyrrolo[2,3-b]pyridin-2-yl)-1H-pyrazolo[3,4-b]pyridin-5-yl)pyridin-3-yl)acetamide [519];

3-(4-(3-fluorophenyl)-1H-pyrrolo[2,3-b]pyridin-2-yl)-5-(pyrazin-2-yl)-1H-pyrazolo[3,4-b]pyridine [520];

3-(4-(4-fluorophenyl)-1H-pyrrolo[2,3-b]pyridin-2-yl)-5-(piperidin-4-yl)-1H-pyrazolo[3,4-b]pyridine [521];

3-(4-(4-fluorophenyl)-1H-pyrrolo[2,3-b]pyridin-2-yl)-5-(1,2,3,6-tetrahydropyridin-4-yl)-1H-pyrazolo[3,4-b]pyridine [522];

3-(4-(4-fluorophenyl)-1H-pyrrolo[2,3-b]pyridin-2-yl)-5-(1H-pyrazol-4-yl)-1H-pyrazolo[3,4-b]pyridine [523];

3-(4-(4-fluorophenyl)-1H-pyrrolo[2,3-b]pyridin-2-yl)-5-(1-methyl-1H-pyrazol-4-yl)-1H-pyrazolo[3,4-b]pyridine [524];

5-(1,2-dimethyl-1H-imidazol-5-yl)-3-(4-(4-fluorophenyl)-1H-pyrrolo[2,3-b]pyridin-2-yl)-1H-pyrazolo[3,4-b]pyridine [525];

1-(6-(3-(4-(4-fluorophenyl)-1H-pyrrolo[2,3-b]pyridin-2-yl)-1H-pyrazolo[3,4-b]pyridin-5-yl)pyrazin-2-yl)azetidin-3-amine [526];

5-(5-(cyclohexyloxy)pyridin-3-yl)-3-(4-(4-fluorophenyl)-1H-pyrrolo[2,3-b]pyridin-2-yl)-1H-pyrazolo[3,4-b]pyridine [527];

3-(4-(4-fluorophenyl)-1H-pyrrolo[2,3-b]pyridin-2-yl)-5-(5-(piperidin-4-yloxy)pyridin-3-yl)-1H-pyrazolo[3,4-b]pyridine [528];

N-(5-(3-(4-(4-fluorophenyl)-1H-pyrrolo[2,3-b]pyridin-2-yl)-1H-pyrazolo[3,4-b]pyridin-5-yl)pyridin-3-yl)-2-(piperidin-4-yl)acetamide [529];

3-(4-(4-fluorophenyl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [530];

2-((5-(3-(4-(4-fluorophenyl)-1H-pyrrolo[2,3-b]pyridin-2-yl)-1H-pyrazolo[3,4-b]pyridin-5-yl)pyridin-3-yl)oxy)-N,N-dimethylethan-1-amine [531];

3-(4-(4-fluorophenyl)-1H-pyrrolo[2,3-b]pyridin-2-yl)-5-(5-methoxypyridin-3-yl)-1H-pyrazolo[3,4-b]pyridine [532];

5-(3-(4-(4-fluorophenyl)-1H-pyrrolo[2,3-b]pyridin-2-yl)-1H-pyrazolo[3,4-b]pyridin-5-yl)pyridin-3-ol [533];

5-(5-(benzyloxy)pyridin-3-yl)-3-(4-(4-fluorophenyl)-1H-pyrrolo[2,3-b]pyridin-2-yl)-1H-pyrazolo[3,4-b]pyridine [534];

2-cyclohexyl-N-(5-(3-(4-(4-fluorophenyl)-1H-pyrrolo[2,3-b]pyridin-2-yl)-1H-pyrazolo[3,4-b]pyridin-5-yl)pyridin-3-yl)acetamide [535];

3-(4-(4-fluorophenyl)-1H-pyrrolo[2,3-b]pyridin-2-yl)-5-(pyrazin-2-yl)-1H-pyrazolo[3,4-b]pyridine [536];

3-(4-(2-fluorophenyl)-1H-pyrrolo[2,3-b]pyridin-2-yl)-5-(piperidin-4-yl)-1H-pyrazolo[3,4-b]pyridine [537];

3-(4-(2-fluorophenyl)-1H-pyrrolo[2,3-b]pyridin-2-yl)-5-(1,2,3,6-tetrahydropyridin-4-yl)-1H-pyrazolo[3,4-b]pyridine [538];

3-(4-(2-fluorophenyl)-1H-pyrrolo[2,3-b]pyridin-2-yl)-5-(1H-pyrazol-4-yl)-1H-pyrazolo[3,4-b]pyridine [539];

3-(4-(2-fluorophenyl)-1H-pyrrolo[2,3-b]pyridin-2-yl)-5-(1-methyl-1H-pyrazol-4-yl)-1H-pyrazolo[3,4-b]pyridine [540];

5-(1,2-dimethyl-1H-imidazol-5-yl)-3-(4-(2-fluorophenyl)-1H-pyrrolo[2,3-b]pyridin-2-yl)-1H-pyrazolo[3,4-b]pyridine [541];

1-(6-(3-(4-(2-fluorophenyl)-1H-pyrrolo[2,3-b]pyridin-2-yl)-1H-pyrazolo[3,4-b]pyridin-5-yl)pyrazin-2-yl)azetidin-3-amine [542];

5-(5-(cyclohexyloxy)pyridin-3-yl)-3-(4-(2-fluorophenyl)-1H-pyrrolo[2,3-b]pyridin-2-yl)-1H-pyrazolo[3,4-b]pyridine [543];

3-(4-(2-fluorophenyl)-1H-pyrrolo[2,3-b]pyridin-2-yl)-5-(5-(piperidin-4-yloxy)pyridin-3-yl)-1H-pyrazolo[3,4-b]pyridine [544];

N-(5-(3-(4-(2-fluorophenyl)-1H-pyrrolo[2,3-b]pyridin-2-yl)-1H-pyrazolo[3,4-b]pyridin-5-yl)pyridin-3-yl)-2-(piperidin-4-yl)acetamide [545];

3-(4-(2-fluorophenyl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [546];

2-((5-(3-(4-(2-fluorophenyl)-1H-pyrrolo[2,3-b]pyridin-2-yl)-1H-pyrazolo[3,4-b]pyridin-5-yl)pyridin-3-yl)oxy)-N,N-dimethylethan-1-amine [547];

3-(4-(2-fluorophenyl)-1H-pyrrolo[2,3-b]pyridin-2-yl)-5-(5-methoxypyridin-3-yl)-1H-pyrazolo[3,4-b]pyridine [548];

5-(3-(4-(2-fluorophenyl)-1H-pyrrolo[2,3-b]pyridin-2-yl)-1H-pyrazolo[3,4-b]pyridin-5-yl)pyridin-3-ol [549];

5-(5-(benzyloxy)pyridin-3-yl)-3-(4-(2-fluorophenyl)-1H-pyrrolo[2,3-b]pyridin-2-yl)-1H-pyrazolo[3,4-b]pyridine [550];

2-cyclohexyl-N-(5-(3-(4-(2-fluorophenyl)-1H-pyrrolo[2,3-b]pyridin-2-yl)-1H-pyrazolo[3,4-b]pyridin-5-yl)pyridin-3-yl)acetamide [551];

3-(4-(2-fluorophenyl)-1H-pyrrolo[2,3-b]pyridin-2-yl)-5-(pyrazin-2-yl)-1H-pyrazolo[3,4-b]pyridine [552];

5-(piperidin-4-yl)-3-(4-(pyridin-3-yl)-1H-pyrrolo[2,3-b]pyridin-2-yl)-1H-pyrazolo[3,4-b]pyridine [553];

3-(4-(pyridin-3-yl)-1H-pyrrolo[2,3-b]pyridin-2-yl)-5-(1,2,3,6-tetrahydropyridin-4-yl)-1H-pyrazolo[3,4-b]pyridine [554];

5-(1H-pyrazol-4-yl)-3-(4-(pyridin-3-yl)-1H-pyrrolo[2,3-b]pyridin-2-yl)-1H-pyrazolo[3,4-b]pyridine [555];

5-(1-methyl-1H-pyrazol-4-yl)-3-(4-(pyridin-3-yl)-1H-pyrrolo[2,3-b]pyridin-2-yl)-1H-pyrazolo[3,4-b]pyridine [556];

5-(1,2-dimethyl-1H-imidazol-5-yl)-3-(4-(pyridin-3-yl)-1H-pyrrolo[2,3-b]pyridin-2-yl)-1H-pyrazolo[3,4-b]pyridine [557];

1-(6-(3-(4-(pyridin-3-yl)-1H-pyrrolo[2,3-b]pyridin-2-yl)-1H-pyrazolo[3,4-b]pyridin-5-yl)pyrazin-2-yl)azetidin-3-amine [558];

5-(5-(cyclohexyloxy)pyridin-3-yl)-3-(4-(pyridin-3-yl)-1H-pyrrolo[2,3-b]pyridin-2-yl)-1H-pyrazolo[3,4-b]pyridine [559];

5-(5-(piperidin-4-yloxy)pyridin-3-yl)-3-(4-(pyridin-3-yl)-1H-pyrrolo[2,3-b]pyridin-2-yl)-1H-pyrazolo[3,4-b]pyridine [560];

2-(piperidin-4-yl)-N-(5-(3-(4-(pyridin-3-yl)-1H-pyrrolo[2,3-b]pyridin-2-yl)-1H-pyrazolo[3,4-b]pyridin-5-yl)pyridin-3-yl)acetamide [561];

3-(4-(pyridin-3-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [562];

N,N-dimethyl-2-((5-(3-(4-(pyridin-3-yl)-1H-pyrrolo[2,3-b]pyridin-2-yl)-1H-pyrazolo[3,4-b]pyridin-5-yl)pyridin-3-yl)oxy)ethan-1-amine [563];

5-(5-methoxypyridin-3-yl)-3-(4-(pyridin-3-yl)-1H-pyrrolo[2,3-b]pyridin-2-yl)-1H-pyrazolo[3,4-b]pyridine [564];

5-(3-(4-(pyridin-3-yl)-1H-pyrrolo[2,3-b]pyridin-2-yl)-1H-pyrazolo[3,4-b]pyridin-5-yl)pyridin-3-ol [565];

5-(pyrazin-2-yl)-3-(4-(pyridin-3-yl)-1H-pyrrolo[2,3-b]pyridin-2-yl)-1H-pyrazolo[3,4-b]pyridine [566];

2-cyclohexyl-N-(5-(3-(4-(pyridin-3-yl)-1H-pyrrolo[2,3-b]pyridin-2-yl)-1H-pyrazolo[3,4-b]pyridin-5-yl)pyridin-3-yl)acetamide [567];

5-(pyrazin-2-yl)-3-(4-(pyridin-3-yl)-1H-pyrrolo[2,3-b]pyridin-2-yl)-1H-pyrazolo[3,4-b]pyridine [568];

5-(piperidin-4-yl)-3-(4-(pyridin-4-yl)-1H-pyrrolo[2,3-b]pyridin-2-yl)-1H-pyrazolo[3,4-b]pyridine [569];

3-(4-(pyridin-4-yl)-1H-pyrrolo[2,3-b]pyridin-2-yl)-5-(1,2,3,6-tetrahydropyridin-4-yl)-1H-pyrazolo[3,4-b]pyridine [570];

5-(1H-pyrazol-4-yl)-3-(4-(pyridin-4-yl)-1H-pyrrolo[2,3-b]pyridin-2-yl)-1H-pyrazolo[3,4-b]pyridine [571];
5-(1-methyl-1H-pyrazol-4-yl)-3-(4-(pyridin-4-yl)-1H-pyrrolo[2,3-b]pyridin-2-yl)-1H-pyrazolo[3,4-b]pyridine [572];
5-(1,2-dimethyl-1H-imidazol-5-yl)-3-(4-(pyridin-4-yl)-1H-pyrrolo[2,3-b]pyridin-2-yl)-1H-pyrazolo[3,4-b]pyridine [573];
1-(6-(3-(4-(pyridin-4-yl)-1H-pyrrolo[2,3-b]pyridin-2-yl)-1H-pyrazolo[3,4-b]pyridin-5-yl)pyrazin-2-yl)azetidin-3-amine [574];
5-(5-(cyclohexyloxy)pyridin-3-yl)-3-(4-(pyridin-4-yl)-1H-pyrrolo[2,3-b]pyridin-2-yl)-1H-pyrazolo[3,4-b]pyridine [575];
5-(5-(piperidin-4-yloxy)pyridin-3-yl)-3-(4-(pyridin-4-yl)-1H-pyrrolo[2,3-b]pyridin-2-yl)-1H-pyrazolo[3,4-b]pyridine [576];
2-(piperidin-4-yl)-N-(5-(3-(4-(pyridin-4-yl)-1H-pyrrolo[2,3-b]pyridin-2-yl)-1H-pyrazolo[3,4-b]pyridin-5-yl)pyridin-3-yl)acetamide [577];
3-(4-(pyridin-4-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [578];
N,N-dimethyl-2-((5-(3-(4-(pyridin-4-yl)-1H-pyrrolo[2,3-b]pyridin-2-yl)-1H-pyrazolo[3,4-b]pyridin-5-yl)pyridin-3-yl)oxy)ethan-1-amine [579];
5-(5-methoxypyridin-3-yl)-3-(4-(pyridin-4-yl)-1H-pyrrolo[2,3-b]pyridin-2-yl)-1H-pyrazolo[3,4-b]pyridine [580];
5-(3-(4-(pyridin-4-yl)-1H-pyrrolo[2,3-b]pyridin-2-yl)-1H-pyrazolo[3,4-b]pyridin-5-yl)pyridin-3-ol [581];
5-(5-(benzyloxy)pyridin-3-yl)-3-(4-(pyridin-4-yl)-1H-pyrrolo[2,3-b]pyridin-2-yl)-1H-pyrazolo[3,4-b]pyridine [582];
2-cyclohexyl-N-(5-(3-(4-(pyridin-4-yl)-1H-pyrrolo[2,3-b]pyridin-2-yl)-1H-pyrazolo[3,4-b]pyridin-5-yl)pyridin-3-yl)acetamide [583];
5-(pyrazin-2-yl)-3-(4-(pyridin-4-yl)-1H-pyrrolo[2,3-b]pyridin-2-yl)-1H-pyrazolo[3,4-b]pyridine [584];
5-(piperidin-4-yl)-3-(4-(pyridin-2-yl)-1H-pyrrolo[2,3-b]pyridin-2-yl)-1H-pyrazolo[3,4-b]pyridine [585];
3-(4-(pyridin-2-yl)-1H-pyrrolo[2,3-b]pyridin-2-yl)-5-(1,2,3,6-tetrahydropyridin-4-yl)-1H-pyrazolo[3,4-b]pyridine [586];
5-(1H-pyrazol-4-yl)-3-(4-(pyridin-2-yl)-1H-pyrrolo[2,3-b]pyridin-2-yl)-1H-pyrazolo[3,4-b]pyridine [587];
5-(1-methyl-1H-pyrazol-4-yl)-3-(4-(pyridin-2-yl)-1H-pyrrolo[2,3-b]pyridin-2-yl)-1H-pyrazolo[3,4-b]pyridine [588];
5-(1,2-dimethyl-1H-imidazol-5-yl)-3-(4-(pyridin-2-yl)-1H-pyrrolo[2,3-b]pyridin-2-yl)-1H-pyrazolo[3,4-b]pyridine [589];
1-(6-(3-(4-(pyridin-2-yl)-1H-pyrrolo[2,3-b]pyridin-2-yl)-1H-pyrazolo[3,4-b]pyridin-5-yl)pyrazin-2-yl)azetidin-3-amine [590];
5-(5-(cyclohexyloxy)pyridin-3-yl)-3-(4-(pyridin-2-yl)-1H-pyrrolo[2,3-b]pyridin-2-yl)-1H-pyrazolo[3,4-b]pyridine [591];
5-(5-(piperidin-4-yloxy)pyridin-3-yl)-3-(4-(pyridin-2-yl)-1H-pyrrolo[2,3-b]pyridin-2-yl)-1H-pyrazolo[3,4-b]pyridine [592];
2-(piperidin-4-yl)-N-(5-(3-(4-(pyridin-2-yl)-1H-pyrrolo[2,3-b]pyridin-2-yl)-1H-pyrazolo[3,4-b]pyridin-5-yl)pyridin-3-yl)acetamide [593];
3-(4-(pyridin-2-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [594];
N,N-dimethyl-2-((5-(3-(4-(pyridin-2-yl)-1H-pyrrolo[2,3-b]pyridin-2-yl)-1H-pyrazolo[3,4-b]pyridin-5-yl)pyridin-3-yl)oxy)ethan-1-amine [595];
5-(5-methoxypyridin-3-yl)-3-(4-(pyridin-2-yl)-1H-pyrrolo[2,3-b]pyridin-2-yl)-1H-pyrazolo[3,4-b]pyridine [596];
5-(3-(4-(pyridin-2-yl)-1H-pyrrolo[2,3-b]pyridin-2-yl)-1H-pyrazolo[3,4-b]pyridin-5-yl)pyridin-3-ol [597];
5-(5-(benzyloxy)pyridin-3-yl)-3-(4-(pyridin-2-yl)-1H-pyrrolo[2,3-b]pyridin-2-yl)-1H-pyrazolo[3,4-b]pyridine [598];
2-cyclohexyl-N-(5-(3-(4-(pyridin-2-yl)-1H-pyrrolo[2,3-b]pyridin-2-yl)-1H-pyrazolo[3,4-b]pyridin-5-yl)pyridin-3-yl)acetamide [599];
5-(pyrazin-2-yl)-3-(4-(pyridin-2-yl)-1H-pyrrolo[2,3-b]pyridin-2-yl)-1H-pyrazolo[3,4-b]pyridine [600];
3-(4-(piperidin-1-yl)-1H-pyrrolo[2,3-b]pyridin-2-yl)-5-(piperidin-4-yl)-1H-pyrazolo[3,4-b]pyridine [601];
3-(4-(piperidin-1-yl)-1H-pyrrolo[2,3-b]pyridin-2-yl)-5-(1,2,3,6-tetrahydropyridin-4-yl)-1H-pyrazolo[3,4-b]pyridine [602];
3-(4-(piperidin-1-yl)-1H-pyrrolo[2,3-b]pyridin-2-yl)-5-(1H-pyrazol-4-yl)-1H-pyrazolo[3,4-b]pyridine [603];
5-(1-methyl-1H-pyrazol-4-yl)-3-(4-(piperidin-1-yl)-1H-pyrrolo[2,3-b]pyridin-2-yl)-1H-pyrazolo[3,4-b]pyridine [604];
5-(1,2-dimethyl-1H-imidazol-5-yl)-3-(4-(piperidin-1-yl)-1H-pyrrolo[2,3-b]pyridin-2-yl)-1H-pyrazolo[3,4-b]pyridine [605];
1-(6-(3-(4-(piperidin-1-yl)-1H-pyrrolo[2,3-b]pyridin-2-yl)-1H-pyrazolo[3,4-b]pyridin-5-yl)pyrazin-2-yl)azetidin-3-amine [606];
5-(5-(cyclohexyloxy)pyridin-3-yl)-3-(4-(piperidin-1-yl)-1H-pyrrolo[2,3-b]pyridin-2-yl)-1H-pyrazolo[3,4-b]pyridine [607];
3-(4-(piperidin-1-yl)-1H-pyrrolo[2,3-b]pyridin-2-yl)-5-(5-(piperidin-4-yloxy)pyridin-3-yl)-1H-pyrazolo[3,4-b]pyridine [608];
N-(5-(3-(4-(piperidin-1-yl)-1H-pyrrolo[2,3-b]pyridin-2-yl)-1H-pyrazolo[3,4-b]pyridin-5-yl)pyridin-3-yl)-2-(piperidin-4-yl)acetamide [609];
3-(4-(piperidin-1-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [610];
N,N-dimethyl-2-((5-(3-(4-(piperidin-1-yl)-1H-pyrrolo[2,3-b]pyridin-2-yl)-1H-pyrazolo[3,4-b]pyridin-5-yl)pyridin-3-yl)oxy)ethan-1-amine [611];
5-(5-methoxypyridin-3-yl)-3-(4-(piperidin-1-yl)-1H-pyrrolo[2,3-b]pyridin-2-yl)-1H-pyrazolo[3,4-b]pyridine [612];
5-(3-(4-(piperidin-1-yl)-1H-pyrrolo[2,3-b]pyridin-2-yl)-1H-pyrazolo[3,4-b]pyridin-5-yl)pyridin-3-ol [613];
5-(5-(benzyloxy)pyridin-3-yl)-3-(4-(piperidin-1-yl)-1H-pyrrolo[2,3-b]pyridin-2-yl)-1H-pyrazolo[3,4-b]pyridine [614];
2-cyclohexyl-N-(5-(3-(4-(piperidin-1-yl)-1H-pyrrolo[2,3-b]pyridin-2-yl)-1H-pyrazolo[3,4-b]pyridin-5-yl)pyridin-3-yl)acetamide [615];
3-(4-(piperidin-1-yl)-1H-pyrrolo[2,3-b]pyridin-2-yl)-5-(pyrazin-2-yl)-1H-pyrazolo[3,4-b]pyridine [616];
3-(4-(4-methyl-1H-imidazol-1-yl)-1H-pyrrolo[2,3-b]pyridin-2-yl)-5-(piperidin-4-yl)-1H-pyrazolo[3,4-b]pyridine [617];
3-(4-(4-methyl-1H-imidazol-1-yl)-1H-pyrrolo[2,3-b]pyridin-2-yl)-5-(1,2,3,6-tetrahydropyridin-4-yl)-1H-pyrazolo[3,4-b]pyridine [618];

3-(4-(4-methyl-1H-imidazol-1-yl)-1H-pyrrolo[2,3-b]pyridin-2-yl)-5-(1H-pyrazol-4-yl)-1H-pyrazolo[3,4-b]pyridine [619];

3-(4-(4-methyl-1H-imidazol-1-yl)-1H-pyrrolo[2,3-b]pyridin-2-yl)-5-(1-methyl-1H-pyrazol-4-yl)-1H-pyrazolo[3,4-b]pyridine [620];

5-(1,2-dimethyl-1H-imidazol-5-yl)-3-(4-(4-methyl-1H-imidazol-1-yl)-1H-pyrrolo[2,3-b]pyridin-2-yl)-1H-pyrazolo[3,4-b]pyridine [621];

14643-(4-(4-methyl-1H-imidazol-1-yl)-1H-pyrrolo[2,3-b]pyridin-2-yl)-1H-pyrazolo[3,4-b]pyridin-5-yl)pyrazin-2-yl)azetidin-3-amine [622];

5-(5-(cyclohexyloxy)pyridin-3-yl)-3-(4-(4-methyl-1H-imidazol-1-yl)-1H-pyrrolo[2,3-b]pyridin-2-yl)-1H-pyrazolo[3,4-b]pyridine [623];

3-(4-(4-methyl-1H-imidazol-1-yl)-1H-pyrrolo[2,3-b]pyridin-2-yl)-5-(5-(piperidin-4-yloxy)pyridin-3-yl)-1H-pyrazolo[3,4-b]pyridine [624];

N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)-2-(piperidin-4-yl)acetamide [625];

3-(4-(4-methyl-1H-imidazol-1-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [626];

N,N-dimethyl-2-((5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)oxy)ethan-1-amine [627];

5-(5-methoxypyridin-3-yl)-3-(4-(4-methyl-1H-imidazol-1-yl)-1H-pyrrolo[2,3-b]pyridin-2-yl)-1H-pyrazolo[3,4-b]pyridine [628];

5-(3-(4-(4-methyl-1H-imidazol-1-yl)-1H-pyrrolo[2,3-b]pyridin-2-yl)-1H-pyrazolo[3,4-b]pyridin-5-yl)pyridin-3-ol [629];

5-(5-(benzyloxy)pyridin-3-yl)-3-(4-(4-methyl-1H-imidazol-1-yl)-1H-pyrrolo[2,3-b]pyridin-2-yl)-1H-pyrazolo[3,4-b]pyridine [630];

2-cyclohexyl-N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)acetamide [631];

3-(4-(4-methyl-1H-imidazol-1-yl)-1H-pyrrolo[2,3-b]pyridin-2-yl)-5-(pyrazin-2-yl)-1H-pyrazolo[3,4-b]pyridine [632];

3-(4-(4-methylpiperazin-1-yl)-1H-pyrrolo[2,3-b]pyridin-2-yl)-5-(piperidin-4-yl)-1H-pyrazolo[3,4-b]pyridine [633];

3-(4-(4-methylpiperazin-1-yl)-1H-pyrrolo[2,3-b]pyridin-2-yl)-5-(1,2,3,6-tetrahydropyridin-4-yl)-1H-pyrazolo[3,4-b]pyridine [634];

3-(4-(4-methylpiperazin-1-yl)-1H-pyrrolo[2,3-b]pyridin-2-yl)-5-(1H-pyrazol-4-yl)-1H-pyrazolo[3,4-b]pyridine [635];

5-(1-methyl-1H-pyrazol-4-yl)-3-(4-(4-methylpiperazin-1-yl)-1H-pyrrolo[2,3-b]pyridin-2-yl)-1H-pyrazolo[3,4-b]pyridine [636];

5-(1,2-dimethyl-1H-imidazol-5-yl)-3-(4-(4-methylpiperazin-1-yl)-1H-pyrrolo[2,3-b]pyridin-2-yl)-1H-pyrazolo[3,4-b]pyridine [637];

1-(6-(3-(4-(4-methylpiperazin-1-yl)-1H-pyrrolo[2,3-b]pyridin-2-yl)-1H-pyrazolo[3,4-b]pyridin-5-yl)pyrazin-2-yl)azetidin-3-amine [638];

5-(5-(cyclohexyloxy)pyridin-3-yl)-3-(4-(4-methylpiperazin-1-yl)-1H-pyrrolo[2,3-b]pyridin-2-yl)-1H-pyrazolo[3,4-b]pyridine [639];

3-(4-(4-methylpiperazin-1-yl)-1H-pyrrolo[2,3-b]pyridin-2-yl)-5-(5-(piperidin-4-yloxy)pyridin-3-yl)-1H-pyrazolo[3,4-b]pyridine [640];

N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)-2-(piperidin-4-yl)acetamide [641];

3-(4-(4-methylpiperazin-1-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [642];

N,N-dimethyl-2-((5-(3-(4-(4-methylpiperazin-1-yl)-1H-pyrrolo[2,3-b]pyridin-2-yl)-1H-pyrazolo[3,4-b]pyridin-5-yl)pyridin-3-yl)oxy)ethan-1-amine [643];

5-(5-methoxypyridin-3-yl)-3-(4-(4-methylpiperazin-1-yl)-1H-pyrrolo[2,3-b]pyridin-2-yl)-1H-pyrazolo[3,4-b]pyridine [644];

5-(3-(4-(4-methylpipe razin-1-yl)-1H-pyrrolo[2,3-b]pyridin-2-yl)-1H-pyrazolo[3,4-b]pyridin-5-yl)pyridin-3-ol [645];

5-(5-(benzyloxy)pyridin-3-yl)-3-(4-(4-methylpiperazin-1-yl)-1H-pyrrolo[2,3-b]pyridin-2-yl)-1H-pyrazolo[3,4-b]pyridine [646];

2-cyclohexyl-N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)acetamide [647];

3-(4-(4-methylpiperazin-1-yl)-1H-pyrrolo[2,3-b]pyridin-2-yl)-5-(pyrazin-2-yl)-1H-pyrazolo[3,4-b]pyridine [648];

5-(piperidin-4-yl)-3-(1H-pyrrolo[2,3-b]pyridin-2-yl)-1H-pyrazolo[3,4-b]pyridine [649];

3-(1H-pyrrolo[2,3-b]pyridin-2-yl)-5-(1,2,3,6-tetrahydropyridin-4-yl)-1H-pyrazolo[3,4-b]pyridine [650];

5-(1H-pyrazol-4-yl)-3-(1H-pyrrolo[2,3-b]pyridin-2-yl)-1H-pyrazolo[3,4-b]pyridine [651];

5-(1-methyl-1H-pyrazol-4-yl)-3-(1H-pyrrolo[2,3-b]pyridin-2-yl)-1H-pyrazolo[3,4-b]pyridine [652];

5-(1,2-dimethyl-1H-imidazol-5-yl)-3-(1H-pyrrolo[2,3-b]pyridin-2-yl)-1H-pyrazolo[3,4-b]pyridine [653];

1-(6-(3-(1H-pyrrolo[2,3-b]pyridin-2-yl)-1H-pyrazolo[3,4-b]pyridin-5-yl)pyrazin-2-yl)azetidin-3-amine [654];

5-(5-(cyclohexyloxy)pyridin-3-yl)-3-(1H-pyrrolo[2,3-b]pyridin-2-yl)-1H-pyrazolo[3,4-b]pyridine [655];

5-(5-(piperidin-4-yloxy)pyridin-3-yl)-3-(1H-pyrrolo[2,3-b]pyridin-2-yl)-1H-pyrazolo[3,4-b]pyridine [656];

N-(5-(3-(1H-pyrrolo[2,3-b]pyridin-2-yl)-1H-pyrazolo[3,4-b]pyridin-5-yl)pyridin-3-yl)-2-(piperidin-4-yl)acetamide [657];

5-(5-(2-(pyrrolidin-1-yl)ethoxy)pyridin-3-yl)-3-(1H-pyrrolo[2,3-b]pyridin-2-yl)-1H-pyrazolo[3,4-b]pyridine [658];

2-((5-(3-(1H-pyrrolo[2,3-b]pyridin-2-yl)-1H-pyrazolo[3,4-b]pyridin-5-yl)pyridin-3-yl)oxy)-N,N-dimethylethan-1-amine [659];

5-(5-methoxypyridin-3-yl)-3-(1H-pyrrolo[2,3-b]pyridin-2-yl)-1H-pyrazolo[3,4-b]pyridine [660];

5-(3-(1H-pyrrolo[2,3-b]pyridin-2-yl)-1H-pyrazolo[3,4-b]pyridin-5-yl)pyridin-3-ol [661];

5-(5-(benzyloxy)pyridin-3-yl)-3-(1H-pyrrolo[2,3-b]pyridin-2-yl)-1H-pyrazolo[3,4-b]pyridine [662];

N-(5-(3-(1H-pyrrolo[2,3-b]pyridin-2-yl)-1H-pyrazolo[3,4-b]pyridin-5-yl)pyridin-3-yl)-2-cyclohexylacetamide [663];

5-(pyrazin-2-yl)-3-(1H-pyrrolo[2,3-b]pyridin-2-yl)-1H-pyrazolo[3,4-b]pyridine [664];

5-(piperidin-4-yl)-3-(4-(thiophen-3-yl)-1H-pyrrolo[2,3-b]pyridin-2-yl)-1H-pyrazolo[3,4-b]pyridine [665];

5-(1,2,3,6-tetrahydropyridin-4-yl)-3-(4-(thiophen-3-yl)-1H-pyrrolo[2,3-b]pyridin-2-yl)-1H-pyrazolo[3,4-b]pyridine [666];

5-(1H-pyrazol-4-yl)-3-(4-(thiophen-3-yl)-1H-pyrrolo[2,3-b]pyridin-2-yl)-1H-pyrazolo[3,4-b]pyridine [667];

5-(1-methyl-1H-pyrazol-4-yl)-3-(4-(thiophen-3-yl)-1H-pyrrolo[2,3-b]pyridin-2-yl)-1H-pyrazolo[3,4-b]pyridine [668];

5-(1,2-dimethyl-1H-imidazol-5-yl)-3-(4-(thiophen-3-yl)-1H-pyrrolo[2,3-b]pyridin-2-yl)-1H-pyrazolo[3,4-b]pyridine [669];

1-(6-(3-(4-(thiophen-3-yl)-1H-pyrrolo[2,3-b]pyridin-2-yl)-1H-pyrazolo[3,4-b]pyridin-5-yl)pyrazin-2-yl)azetidin-3-amine [670];

5-(5-(cyclohexyloxy)pyridin-3-yl)-3-(4-(thiophen-3-yl)-1H-pyrrolo[2,3-b]pyridin-2-yl)-1H-pyrazolo[3,4-b]pyridine [671];

5-(5-(piperidin-4-yloxy)pyridin-3-yl)-3-(4-(thiophen-3-yl)-1H-pyrrolo[2,3-b]pyridin-2-yl)-1H-pyrazolo[3,4-b]pyridine [672];

2-(piperidin-4-yl)-N-(5-(3-(4-(thiophen-3-yl)-1H-pyrrolo[2,3-b]pyridin-2-yl)-1H-pyrazolo[3,4-b]pyridin-5-yl)pyridin-3-yl)acetamide [673];

5-(5-(2-(pyrrolidin-1-yl)ethoxy)pyridin-3-yl)-3-(4-(thiophen-3-yl)-1H-pyrrolo[2,3-b]pyridin-2-yl)-1H-pyrazolo[3,4-b]pyridine [674];

N,N-dimethyl-2-((5-(3-(4-(thiophen-3-yl)-1H-pyrrolo[2,3-b]pyridin-2-yl)-1H-pyrazolo[3,4-b]pyridin-5-yl)pyridin-3-yl)oxy)ethan-1-amine [675];

5-(5-methoxypyridin-3-yl)-3-(4-(thiophen-3-yl)-1H-pyrrolo[2,3-b]pyridin-2-yl)-1H-pyrazolo[3,4-b]pyridine [676];

5-(3-(4-(thiophen-3-yl)-1H-pyrrolo[2,3-b]pyridin-2-yl)-1H-pyrazolo[3,4-b]pyridin-5-yl)pyridin-3-ol [677];

5-(5-(benzyloxy)pyridin-3-yl)-3-(4-(thiophen-3-yl)-1H-pyrrolo[2,3-b]pyridin-2-yl)-1H-pyrazolo[3,4-b]pyridine [678];

2-cyclohexyl-N-(5-(3-(4-(thiophen-3-yl)-1H-pyrrolo[2,3-b]pyridin-2-yl)-1H-pyrazolo[3,4-b]pyridin-5-yl)pyridin-3-yl)acetamide [679];

5-(pyrazin-2-yl)-3-(4-(thiophen-3-yl)-1H-pyrrolo[2,3-b]pyridin-2-yl)-1H-pyrazolo[3,4-b]pyridine [680];

3-(4-(furan-3-yl)-1H-pyrrolo[2,3-b]pyridin-2-yl)-5-(piperidin-4-yl)-1H-pyrazolo[3,4-b]pyridine [681];

3-(4-(furan-3-yl)-1H-pyrrolo[2,3-b]pyridin-2-yl)-5-(1,2,3,6-tetrahydropyridin-4-yl)-1H-pyrazolo[3,4-b]pyridine [682];

3-(4-(furan-3-yl)-1H-pyrrolo[2,3-b]pyridin-2-yl)-5-(1H-pyrazol-4-yl)-1H-pyrazolo[3,4-b]pyridine [683];

3-(4-(furan-3-yl)-1H-pyrrolo[2,3-b]pyridin-2-yl)-5-(1-methyl-1H-pyrazol-4-yl)-1H-pyrazolo[3,4-b]pyridine [684];

5-(1,2-dimethyl-1H-imidazol-5-yl)-3-(4-(furan-3-yl)-1H-pyrrolo[2,3-b]pyridin-2-yl)-1H-pyrazolo[3,4-b]pyridine [685];

1-(6-(3-(4-(furan-3-yl)-1H-pyrrolo[2,3-b]pyridin-2-yl)-1H-pyrazolo[3,4-b]pyridin-5-yl)pyrazin-2-yl)azetidin-3-amine [686];

5-(5-(cyclohexyloxy)pyridin-3-yl)-3-(4-(furan-3-yl)-1H-pyrrolo[2,3-b]pyridin-2-yl)-1H-pyrazolo[3,4-b]pyridine [687];

3-(4-(furan-3-yl)-1H-pyrrolo[2,3-b]pyridin-2-yl)-5-(5-(piperidin-4-yloxy)pyridin-3-yl)-1H-pyrazolo[3,4-b]pyridine [688];

N-(5-(3-(4-(furan-3-yl)-1H-pyrrolo[2,3-b]pyridin-2-yl)-1H-pyrazolo[3,4-b]pyridin-5-yl)pyridin-3-yl)-2-(piperidin-4-yl)acetamide [689];

3-(4-(furan-3-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [690];

2-((5-(3-(4-(furan-3-yl)-1H-pyrrolo[2,3-b]pyridin-2-yl)-1H-pyrazolo[3,4-b]pyridin-5-yl)pyridin-3-yl)oxy)-N,N-dimethylethan-1-amine [691];

3-(4-(furan-3-yl)-1H-pyrrolo[2,3-b]pyridin-2-yl)-5-(5-methoxypyridin-3-yl)-1H-pyrazolo[3,4-b]pyridine [692];

5-(3-(4-(furan-3-yl)-1H-pyrrolo[2,3-b]pyridin-2-yl)-1H-pyrazolo[3,4-b]pyridin-5-yl)pyridin-3-ol [693];

5-(5-(benzyloxy)pyridin-3-yl)-3-(4-(furan-3-yl)-1H-pyrrolo[2,3-b]pyridin-2-yl)-1H-pyrazolo[3,4-b]pyridine [694];

2-cyclohexyl-N-(5-(3-(4-(furan-3-yl)-1H-pyrrolo[2,3-b]pyridin-2-yl)-1H-pyrazolo[3,4-b]pyridin-5-yl)pyridin-3-yl)acetamide [695];

3-(4-(furan-3-yl)-1H-pyrrolo[2,3-b]pyridin-2-yl)-5-(pyrazin-2-yl)-1H-pyrazolo[3,4-b]pyridine [696];

5-(piperidin-4-yl)-3-(4-(thiophen-2-yl)-1H-pyrrolo[2,3-b]pyridin-2-yl)-1H-pyrazolo[3,4-b]pyridine [697];

5-(1,2,3,6-tetrahydropyridin-4-yl)-3-(4-(thiophen-2-yl)-1H-pyrrolo[2,3-b]pyridin-2-yl)-1H-pyrazolo[3,4-b]pyridine [698];

5-(1H-pyrazol-4-yl)-3-(4-(thiophen-2-yl)-1H-pyrrolo[2,3-b]pyridin-2-yl)-1H-pyrazolo[3,4-b]pyridine [699];

5-(1-methyl-1H-pyrazol-4-yl)-3-(4-(thiophen-2-yl)-1H-pyrrolo[2,3-b]pyridin-2-yl)-1H-pyrazolo[3,4-b]pyridine [700];

5-(1,2-dimethyl-1H-imidazol-5-yl)-3-(4-(thiophen-2-yl)-1H-pyrrolo[2,3-b]pyridin-2-yl)-1H-pyrazolo[3,4-b]pyridine [701];

1-(6-(3-(4-(thiophen-2-yl)-1H-pyrrolo[2,3-b]pyridin-2-yl)-1H-pyrazolo[3,4-b]pyridin-5-yl)pyrazin-2-yl)azetidin-3-amine [702];

5-(5-(cyclohexyloxy)pyridin-3-yl)-3-(4-(thiophen-2-yl)-1H-pyrrolo[2,3-b]pyridin-2-yl)-1H-pyrazolo[3,4-b]pyridine [703];

5-(5-(piperidin-4-yloxy)pyridin-3-yl)-3-(4-(thiophen-2-yl)-1H-pyrrolo[2,3-b]pyridin-2-yl)-1H-pyrazolo[3,4-b]pyridine [704];

2-(piperidin-4-yl)-N-(5-(3-(4-(thiophen-2-yl)-1H-pyrrolo[2,3-b]pyridin-2-yl)-1H-pyrazolo[3,4-b]pyridin-5-yl)pyridin-3-yl)acetamide [705];

5-(5-(2-(pyrrolidin-1-yl)ethoxy)pyridin-3-yl)-3-(4-(thiophen-2-yl)-1H-pyrrolo[2,3-b]pyridin-2-yl)-1H-pyrazolo[3,4-b]pyridine [706];

N,N-dimethyl-2-((5-(3-(4-(thiophen-2-yl)-1H-pyrrolo[2,3-b]pyridin-2-yl)-1H-pyrazolo[3,4-b]pyridin-5-yl)pyridin-3-yl)oxy)ethan-1-amine [707];

5-(5-methoxypyridin-3-yl)-3-(4-(thiophen-2-yl)-1H-pyrrolo[2,3-b]pyridin-2-yl)-1H-pyrazolo[3,4-b]pyridine [708];

5-(3-(4-(thiophen-2-yl)-1H-pyrrolo[2,3-b]pyridin-2-yl)-1H-pyrazolo[3,4-b]pyridin-5-yl)pyridin-3-ol [709];

5-(5-(benzyloxy)pyridin-3-yl)-3-(4-(thiophen-2-yl)-1H-pyrrolo[2,3-b]pyridin-2-yl)-1H-pyrazolo[3,4-b]pyridine [710];

2-cyclohexyl-N-(5-(3-(4-(thiophen-2-yl)-1H-pyrrolo[2,3-b]pyridin-2-yl)-1H-pyrazolo[3,4-b]pyridin-5-yl)pyridin-3-yl)acetamide [711];

5-(pyrazin-2-yl)-3-(4-(thiophen-2-yl)-1H-pyrrolo[2,3-b]pyridin-2-yl)-1H-pyrazolo[3,4-b]pyridine [712];

3-(4-(5-fluorothiophen-2-yl)-1H-pyrrolo[2,3-b]pyridin-2-yl)-5-(piperidin-4-yl)-1H-pyrazolo[3,4-b]pyridine [713];

3-(4-(5-fluorothiophen-2-yl)-1H-pyrrolo[2,3-b]pyridin-2-yl)-5-(1,2,3,6-tetrahydropyridin-4-yl)-1H-pyrazolo[3,4-b]pyridine [714];

3-(4-(5-fluorothiophen-2-yl)-1H-pyrrolo[2,3-b]pyridin-2-yl)-5-(1H-pyrazol-4-yl)-1H-pyrazolo[3,4-b]pyridine [715];

3-(4-(5-fluorothiophen-2-yl)-1H-pyrrolo[2,3-b]pyridin-2-yl)-5-(1-methyl-1H-pyrazol-4-yl)-1H-pyrazolo[3,4-b]pyridine [716];

5-(1,2-dimethyl-1H-imidazol-5-yl)-3-(4-(5-fluorothiophen-2-yl)-1H-pyrrolo[2,3-b]pyridin-2-yl)-1H-pyrazolo[3,4-b]pyridine [717];

1-(6-(3-(4-(5-fluorothiophen-2-yl)-1H-pyrrolo[2,3-b]pyridin-2-yl)-1H-pyrazolo[3,4-b]pyridin-5-yl)pyrazin-2-yl)azetidin-3-amine [718];

5-(5-(cyclohexyloxy)pyridin-3-yl)-3-(4-(5-fluorothiophen-2-yl)-1H-pyrrolo[2,3-b]pyridin-2-yl)-1H-pyrazolo[3,4-b]pyridine [719];

3-(4-(5-fluorothiophen-2-yl)-1H-pyrrolo[2,3-b]pyridin-2-yl)-5-(5-(piperidin-4-yloxy)pyridin-3-yl)-1H-pyrazolo[3,4-b]pyridine [720];

N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)-2-(piperidin-4-yl)acetamide [721];

3-(4-(5-fluorothiophen-2-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [722];

2-((5-(3-(4-(5-fluorothiophen-2-yl)-1H-pyrrolo[2,3-b]pyridin-2-yl)-1H-pyrazolo[3,4-b]pyridin-5-yl)pyridin-3-yl)oxy)-N,N-dimethylethan-1-amine [723];

3-(4-(5-fluorothiophen-2-yl)-1H-pyrrolo[2,3-b]pyridin-2-yl)-5-(5-methoxypyridin-3-yl)-1H-pyrazolo[3,4-b]pyridine [724];

5-(3-(4-(5-fluorothiophen-2-yl)-1H-pyrrolo[2,3-b]pyridin-2-yl)-1H-pyrazolo[3,4-b]pyridin-5-yl)pyridin-3-ol [725];

5-(5-(benzyloxy)pyridin-3-yl)-3-(4-(5-fluorothiophen-2-yl)-1H-pyrrolo[2,3-b]pyridin-2-yl)-1H-pyrazolo[3,4-b]pyridine [726];

2-cyclohexyl-N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)acetamide [727];

3-(4-(5-fluorothiophen-2-yl)-1H-pyrrolo[2,3-b]pyridin-2-yl)-5-(pyrazin-2-yl)-1H-pyrazolo[3,4-b]pyridine [728];

3-(4-(5-methylthiophen-2-yl)-1H-pyrrolo[2,3-b]pyridin-2-yl)-5-(piperidin-4-yl)-1H-pyrazolo[3,4-b]pyridine [729];

3-(4-(5-methylthiophen-2-yl)-1H-pyrrolo[2,3-b]pyridin-2-yl)-5-(1,2,3,6-tetrahydropyridin-4-yl)-1H-pyrazolo[3,4-b]pyridine [730];

3-(4-(5-methylthiophen-2-yl)-1H-pyrrolo[2,3-b]pyridin-2-yl)-5-(1H-pyrazol-4-yl)-1H-pyrazolo[3,4-b]pyridine [731];

5-(1-methyl-1H-pyrazol-4-yl)-3-(4-(5-methylthiophen-2-yl)-1H-pyrrolo[2,3-b]pyridin-2-yl)-1H-pyrazolo[3,4-b]pyridine [732];

5-(1,2-dimethyl-1H-imidazol-5-yl)-3-(4-(5-methylthiophen-2-yl)-1H-pyrrolo[2,3-b]pyridin-2-yl)-1H-pyrazolo[3,4-b]pyridine [733];

1-(6-(3-(4-(5-methylthiophen-2-yl)-1H-pyrrolo[2,3-b]pyridin-2-yl)-1H-pyrazolo[3,4-b]pyridin-5-yl)pyrazin-2-yl)azetidin-3-amine [734];

5-(5-(cyclohexyloxy)pyridin-3-yl)-3-(4-(5-methylthiophen-2-yl)-1H-pyrrolo[2,3-b]pyridin-2-yl)-1H-pyrazolo[3,4-b]pyridine [735];

3-(4-(5-methylthiophen-2-yl)-1H-pyrrolo[2,3-b]pyridin-2-yl)-5-(5-(piperidin-4-yloxy)pyridin-3-yl)-1H-pyrazolo[3,4-b]pyridine [736];

N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)-2-(piperidin-4-yl)acetamide [737];

3-(4-(5-methylthiophen-2-yl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [738];

N,N-dimethyl-2-((5-(3-(4-(5-methylthiophen-2-yl)-1H-pyrrolo[2,3-b]pyridin-2-yl)-1H-pyrazolo[3,4-b]pyridin-5-yl)pyridin-3-yl)oxy)ethan-1-amine [739];

5-(5-methoxypyridin-3-yl)-3-(4-(5-methylthiophen-2-yl)-1H-pyrrolo[2,3-b]pyridin-2-yl)-1H-pyrazolo[3,4-b]pyridine [740];

5-(3-(4-(5-methylthiophen-2-yl)-1H-pyrrolo[2,3-b]pyridin-2-yl)-1H-pyrazolo[3,4-b]pyridin-5-yl)pyridin-3-ol [741];

5-(5-(benzyloxy)pyridin-3-yl)-3-(4-(5-methylthiophen-2-yl)-1H-pyrrolo[2,3-b]pyridin-2-yl)-1H-pyrazolo[3,4-b]pyridine [742];

2-cyclohexyl-N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)acetamide [743];

3-(4-(5-methylthiophen-2-yl)-1H-pyrrolo[2,3-b]pyridin-2-yl)-5-(pyrazin-2-yl)-1H-pyrazolo[3,4-b]pyridine [744];

1-(5-(2-(5-(piperidin-4-yl)-1H-pyrazolo[3,4-b]pyridin-3-yl)-1H-pyrrolo[2,3-b]pyridin-4-yl)thiophen-2-yl)ethan-1-one [745];

1-(5-(2-(5-(1,2,3,6-tetrahydropyridin-4-yl)-1H-pyrazolo[3,4-b]pyridin-3-yl)-1H-pyrrolo[2,3-b]pyridin-4-yl)thiophen-2-yl)ethan-1-one [746];

1-(5-(2-(5-(1H-pyrazol-4-yl)-1H-pyrazolo[3,4-b]pyridin-3-yl)-1H-pyrrolo[2,3-b]pyridin-4-yl)thiophen-2-yl)ethan-1-one [747];

1-(5-(2-(5-(1-methyl-1H-pyrazol-4-yl)-1H-pyrazolo[3,4-b]pyridin-3-yl)-1H-pyrrolo[2,3-b]pyridin-4-yl)thiophen-2-yl)ethan-1-one [748];

1-(5-(2-(5-(1,2-dimethyl-1H-imidazol-5-yl)-1H-pyrazolo[3,4-b]pyridin-3-yl)-1H-pyrrolo[2,3-b]pyridin-4-yl)thiophen-2-yl)ethan-1-one [749];

1-(5-(2-(5-(6-(3-aminoazetidin-1-yl)pyrazin-2-yl)-1H-pyrazolo[3,4-b]pyridin-3-yl)-1H-pyrrolo[2,3-b]pyridin-4-yl)thiophen-2-yl)ethan-1-one [750];

1-(5-(2-(5-(5-(cyclohexyloxy)pyridin-3-yl)-1H-pyrazolo[3,4-b]pyridin-3-yl)-1H-pyrrolo[2,3-b]pyridin-4-yl)thiophen-2-yl)ethan-1-one [751];

1-(5-(2-(5-(5-(piperidin-4-yloxy)pyridin-3-yl)-1H-pyrazolo[3,4-b]pyridin-3-yl)-1H-pyrrolo[2,3-b]pyridin-4-yl)thiophen-2-yl)ethan-1-one [752];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-2-(piperidin-4-yl)acetamide [753];

1-(5-(2-(5-(5-(2-(pyrrolidin-1-yl)ethoxy)pyridin-3-yl)-1H-pyrazolo[3,4-b]pyridin-3-yl)-1H-pyrrolo[2,3-b]pyridin-4-yl)thiophen-2-yl)ethan-1-one [754];

1-(5-(2-(5-(5-(2-(dimethylamino)ethoxy)pyridin-3-yl)-1H-pyrazolo[3,4-b]pyridin-3-yl)-1H-pyrrolo[2,3-b]pyridin-4-yl)thiophen-2-yl)ethan-1-one [755];

1-(5-(2-(5-(5-methoxypyridin-3-yl)-1H-pyrazolo[3,4-b]pyridin-3-yl)-1H-pyrrolo[2,3-b]pyridin-4-yl)thiophen-2-yl)ethan-1-one [756];

1-(5-(2-(5-(5-hydroxypyridin-3-yl)-1H-pyrazolo[3,4-b]pyridin-3-yl)-1H-pyrrolo[2,3-b]pyridin-4-yl)thiophen-2-yl)ethan-1-one [757];

1-(5-(2-(5-(5-(benzyloxy)pyridin-3-yl)-1H-pyrazolo[3,4-b]pyridin-3-yl)-1H-pyrrolo[2,3-b]pyridin-4-yl)thiophen-2-yl)ethan-1-one [758];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-2-cyclohexylacetamide [759];

1-(5-(2-(5-(pyrazin-2-yl)-1H-pyrazolo[3,4-b]pyridin-3-yl)-1H-pyrrolo[2,3-b]pyridin-4-yl)thiophen-2-yl)ethan-1-one [760];

N-(3-fluoro-5-(2-(5-(piperidin-4-yl)-1H-pyrazolo[3,4-b]pyridin-3-yl)-1H-pyrrolo[2,3-b]pyridin-4-yl)benzyl)methanesulfonamide [761];

N-(3-fluoro-5-(2-(5-(1,2,3,6-tetrahydropyridin-4-yl)-1H-pyrazolo[3,4-b]pyridin-3-yl)-1H-pyrrolo[2,3-b]pyridin-4-yl)benzyl)methanesulfonamide [762];

N-(3-(2-(5-(1H-pyrazol-4-yl)-1H-pyrazolo[3,4-b]pyridin-3-yl)-1H-pyrrolo[2,3-b]pyridin-4-yl)-5-fluorobenzyl)methanesulfonamide [763];

N-(3-fluoro-5-(2-(5-(1-methyl-1H-pyrazol-4-yl)-1H-pyrazolo[3,4-b]pyridin-3-yl)-1H-pyrrolo[2,3-b]pyridin-4-yl)benzyl)methanesulfonamide [764];

N-(3-(2-(5-(1,2-dimethyl-1H-imidazol-5-yl)-1H-pyrazolo[3,4-b]pyridin-3-yl)-1H-pyrrolo[2,3-b]pyridin-4-yl)-5-fluorobenzyl)methanesulfonamide [765];

N-(3-(2-(5-(6-(3-aminoazetidin-1-yl)pyrazin-2-yl)-1H-pyrazolo[3,4-b]pyridin-3-yl)-1H-pyrrolo[2,3-b]pyridin-4-yl)-5-fluorobenzyl)methanesulfonamide [766];

N-(3-(2-(5-(5-(cyclohexyloxy)pyridin-3-yl)-1H-pyrazolo[3,4-b]pyridin-3-yl)-1H-pyrrolo[2,3-b]pyridin-4-yl)-5-fluorobenzyl)methanesulfonamide [767];

N-(3-fluoro-5-(2-(5-(5-(piperidin-4-yloxy)pyridin-3-yl)-1H-pyrazolo[3,4-b]pyridin-3-yl)-1H-pyrrolo[2,3-b]pyridin-4-yl)benzyl)methanesulfonamide [768];

N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)-2-(piperidin-4-yl)acetamide [769];

N-(3-fluoro-5-(2-(5-(5-(2-(pyrrolidin-1-yl)ethoxy)pyridin-3-yl)-1H-pyrazolo[3,4-b]pyridin-3-yl)-1H-pyrrolo[2,3-b]pyridin-4-yl)benzyl)methanesulfonamide [770];

N-(3-(2-(5-(5-(2-(dimethylamino)ethoxy)pyridin-3-yl)-1H-pyrazolo[3,4-b]pyridin-3-yl)-1H-pyrrolo[2,3-b]pyridin-4-yl)-5-fluorobenzyl)methanesulfonamide [771];

N-(3-fluoro-5-(2-(5-(5-methoxypyridin-3-yl)-1H-pyrazolo[3,4-b]pyridin-3-yl)-1H-pyrrolo[2,3-b]pyridin-4-yl)benzyl)methanesulfonamide [772];

N-(3-fluoro-5-(2-(5-(5-hydroxypyridin-3-yl)-1H-pyrazolo[3,4-b]pyridin-3-yl)-1H-pyrrolo[2,3-b]pyridin-4-yl)benzyl)methanesulfonamide [773];

N-(3-(2-(5-(5-(benzyloxy)pyridin-3-yl)-1H-pyrazolo[3,4-b]pyridin-3-yl)-1H-pyrrolo[2,3-b]pyridin-4-yl)-5-fluorobenzyl)methanesulfonamide [774];

2-cyclohexyl-N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)acetamide [775];

N-(3-fluoro-5-(2-(5-(pyrazin-2-yl)-1H-pyrazolo[3,4-b]pyridin-3-yl)-1H-pyrrolo[2,3-b]pyridin-4-yl)benzyl)methanesulfonamide [776];

N1-(3-fluoro-5-(2-(5-(piperidin-4-yl)-1H-pyrazolo[3,4-b]pyridin-3-yl)-1H-pyrrolo[2,3-b]pyridin-4-yl)phenyl)-N2,N2-dimethylethane-1,2-diamine [777];

$N^1$-(3-fluoro-5-(2-(5-(1,2,3,6-tetrahydropyridin-4-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [778];

$N^1$-(3-(2-(5-(1H-pyrazol-4-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [779];

$N^1$-(3-fluoro-5-(2-(5-(1-methyl-1H-pyrazol-4-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [780];

$N^1$-(3-(2-(5-(1,2-dimethyl-1H-imidazol-5-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [781];

$N^1$-(3-(2-(5-(6-(3-aminoazetidin-1-yl)pyrazin-2-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [782];

$N^1$-(3-(2-(5-(5-(cyclohexyloxy)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [783];

$N^1$-(3-fluoro-5-(2-(5-(5-(piperidin-4-yloxy)pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [784];

N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)-2-(piperidin-4-yl)acetamide [785];

$N^1$-(3-fluoro-5-(2-(5-(5-(2-(pyrrolidin-1-yl)ethoxy)pyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [786];

$N^1$-(3-(2-(5-(5-(2-(dimethylamino)ethoxy)pyridin-3-yl)-1H-pyrazolo[3,4-b]pyridin-3-yl)-1H-pyrrolo[2,3-b]pyridin-4-yl)-5-fluorophenyl)-$N^2$,$N^2$-dimethylethane-1,2-diamine [787];

$N^1$-(3-fluoro-5-(2-(5-(5-methoxypyridin-3-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [788];

5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-ol [789];

$N^1$-(3-(2-(5-(5-(benzyloxy)pyridin-3-yl)-1H-pyrazolo[3,4-b]pyridin-3-yl)-1H-pyrrolo[2,3-b]pyridin-4-yl)-5-fluorophenyl)-$N^2$,N2-dimethylethane-1,2-diamine [790];

2-cyclohexyl-N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)acetamide [791];

$N^1$-(3-fluoro-5-(2-(5-(pyrazin-2-yl)-1H-pyrazolo[3,4-b]pyridin-3-yl)-1H-pyrrolo[2,3-b]pyridin-4-yl)phenyl)-$N^2$,$N^2$-dimethylethane-1,2-diamine [792];

N-(5-(3-(44342-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)propionamide [793];

N-(5-(3-(44342-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)-3-methylbutanamide [794];

5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-amine [795];

2-(3-fluoro-5-(2-(5-(pyridin-3-yl)-1H-pyrazolo[3,4-b]pyridin-3-yl)-1H-pyrrolo[2,3-b]pyridin-4-yl)phenoxy)-N,N-dimethylethan-1-amine [796];

2-(3-fluoro-5-(2-(5-(4-methylpyridin-3-yl)-1H-pyrazolo[3,4-b]pyridin-3-yl)-1H-pyrrolo[2,3-b]pyridin-4-yl)phenoxy)-N,N-dimethylethan-1-amine [797];

2-(3-(2-(5-(5-((ethylamino)methyl)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [798];

5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)-N,N-dimethylpyridin-3-amine [799];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)pivalamide [800];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)isobutyramide [801];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)-2-phenylacetamide [802];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)benzamide [803];

5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)-N-isopropylpyridin-3-amine [804];

2-(3-(2-(5-(5-((dimethylamino)methyl)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [805];

2-(3-fluoro-5-(2-(5-(5-(pyrrolidin-1-ylmethyl)pyridin-3-yl)-1H-pyrazolo[3,4-b]pyridin-3-yl)-1H-pyrrolo[2,3-b]pyridin-4-yl)phenoxy)-N,N-dimethylethan-1-amine [806];

2-(3-fluoro-5-(2-(5-(5-(piperidin-1-ylmethyl)pyridin-3-yl)-1H-pyrazolo[3,4-b]pyridin-3-yl)-1H-pyrrolo[2,3-b]pyridin-4-yl)phenoxy)-N,N-dimethylethan-1-amine [807];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)-3,3-dimethylbutanamide [808];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)butyramide [809];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)pentanamide [810];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)cyclopropanecarboxamide [811];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)cyclobutanecarboxamide [812];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)cyclopentanecarboxamide [813];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)cyclohexanecarboxamide [814];

2-(3-(2-(5-(5-((benzylamino)methyl)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [815];

2-(3-(2-(5-(5-(((cyclopentylmethyl)amino)methyl)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [816];

2-(3-(2-(5-(5-((3,3-difluoropyrrolidin-1-yl)methyl)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [817];

2-(3-fluoro-5-(2-(5-(pyrimidin-5-yl)-1H-pyrazolo[3,4-b]pyridin-3-yl)-1H-pyrrolo[2,3-b]pyridin-4-yl)phenoxy)-N,N-dimethylethan-1-amine [818];

2-(3-fluoro-5-(2-(5-(pyridin-2-yl)-1H-pyrazolo[3,4-b]pyridin-3-yl)-1H-pyrrolo[2,3-b]pyridin-4-yl)phenoxy)-N,N-dimethylethan-1-amine [819];

2-(3-fluoro-5-(2-(5-(piperidin-4-yl)-1H-pyrazolo[3,4-b]pyridin-3-yl)-1H-pyrrolo[2,3-b]pyridin-4-yl)phenoxy)-N,N-dimethylethan-1-amine [820];

2-(3-fluoro-5-(2-(5-(1,2,3,6-tetrahydropyridin-4-yl)-1H-pyrazolo[3,4-b]pyridin-3-yl)-1H-pyrrolo[2,3-b]pyridin-4-yl)phenoxy)-N,N-dimethylethan-1-amine [821];

2-(3-(2-(5-(1H-pyrazol-4-yl)-1H-pyrazolo[3,4-b]pyridin-3-yl)-1H-pyrrolo[2,3-b]pyridin-4-yl)-5-fluorophenoxy)-N,N-dimethylethan-1-amine [822];

2-(3-fluoro-5-(2-(5-(1-methyl-1H-pyrazol-4-yl)-1H-pyrazolo[3,4-b]pyridin-3-yl)-1H-pyrrolo[2,3-b]pyridin-4-yl)phenoxy)-N,N-dimethylethan-1-amine [823];

2-(3-(2-(5-(1,2-dimethyl-1H-imidazol-5-yl)-1H-pyrazolo[3,4-b]pyridin-3-yl)-1H-pyrrolo[2,3-b]pyridin-4-yl)-5-fluorophenoxy)-N,N-dimethylethan-1-amine [824];

14643-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyrazin-2-yl)azetidin-3-amine [825];

2-(3-(2-(5-(5-(cyclohexyloxy)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [826];

2-(3-fluoro-5-(2-(5-(5-(piperidin-4-yloxy)pyridin-3-yl)-1H-pyrazolo[3,4-b]pyridin-3-yl)-1H-pyrrolo[2,3-b]pyridin-4-yl)phenoxy)-N,N-dimethylethan-1-amine [827];

N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)-2-(piperidin-4-yl)acetamide [828];

2-(3-fluoro-5-(2-(5-(5-(2-(pyrrolidin-1-yl)ethoxy)pyridin-3-yl)-1H-pyrazolo[3,4-b]pyridin-3-yl)-1H-pyrrolo[2,3-b]pyridin-4-yl)phenoxy)-N,N-dimethylethan-1-amine [829];

2-((5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)oxy)-N,N-dimethylethan-1-amine [830];

2-(3-fluoro-5-(2-(5-(5-methoxypyridin-3-yl)-1H-pyrazolo[3,4-b]pyridin-3-yl)-1H-pyrrolo[2,3-b]pyridin-4-yl)phenoxy)-N,N-dimethylethan-1-amine [831];

5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-ol [832];

2-(3-(2-(5-(5-(benzyloxy)pyridin-3-yl)-1H-pyrazolo[3,4-b]pyridin-3-yl)-1H-pyrrolo[2,3-b]pyridin-4-yl)-5-fluorophenoxy)-N,N-dimethylethan-1-amine [833];

2-cyclohexyl-N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)acetamide [834];

2-(3-fluoro-5-(2-(5-(pyridin-4-yl)-1H-pyrazolo[3,4-b]pyridin-3-yl)-1H-pyrrolo[2,3-b]pyridin-4-yl)phenoxy)-N,N-dimethylethan-1-amine [835];

2-(3-fluoro-5-(2-(5-(pyrazin-2-yl)-1H-pyrazolo[3,4-b]pyridin-3-yl)-1H-pyrrolo[2,3-b]pyridin-4-yl)phenoxy)-N,N-dimethylethan-1-amine [836];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)propionamide [837];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)-3-methylbutanamide [838];

5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-amine [839];

3-(4-(3-fluoro-5-(2-(pyrrolidin-1-yl)ethoxy)phenyl)-1H-pyrrolo[2,3-b]pyridin-2-yl)-5-(pyridin-3-yl)-1H-pyrazolo[3,4-b]pyridine [840];

3-(4-(3-fluoro-5-(2-(pyrrolidin-1-yl)ethoxy)phenyl)-1H-pyrrolo[2,3-b]pyridin-2-yl)-5-(4-methylpyridin-3-yl)-1H-pyrazolo[3,4-b]pyridine [841];

N-((5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)methyl)ethanamine [842];

5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)-N,N-dimethylpyridin-3-amine [843];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)pivalamide [844];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)isobutyramide [845];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)-2-phenylacetamide [846];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)benzamide [847];

5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)-N-i sopropylpyridin-3-amine [848];

1-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)-N,N-dimethylmethanamine [849];

3-(4-(3-fluoro-5-(2-(pyrrolidin-1-yl)ethoxy)phenyl)-1H-pyrrolo[2,3-b]pyridin-2-yl)-5-(5-(pyrrolidin-1-ylmethyl)pyridin-3-yl)-1H-pyrazolo[3,4-b]pyridine [850];

3-(4-(3-fluoro-5-(2-(pyrrolidin-1-yl)ethoxy)phenyl)-1H-pyrrolo[2,3-b]pyridin-2-yl)-5-(5-(piperidin-1-ylmethyl)pyridin-3-yl)-1H-pyrazolo[3,4-b]pyridine [851];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)-3,3-dimethylbutanamide [852];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)butyramide [853];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)pentanamide [854];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)cyclopropanecarboxamide [855];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)cyclobutanecarboxamide [856];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)cyclopentanecarboxamide [857];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)cyclohexanecarboxamide [858];

N-benzyl-1-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)methanamine [859];

1-cyclopentyl-N-((5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)methyl)methanamine [860];

5-(5-(((3,3-difluoropyrrolidin-1-yl)methyl)pyridin-3-yl)-3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridine [861];

3-(4-(3-fluoro-5-(2-(pyrrolidin-1-yl)ethoxy)phenyl)-1H-pyrrolo[2,3-b]pyridin-2-yl)-5-(pyrimidin-5-yl)-1H-pyrazolo[3,4-b]pyridine [862];

3-(4-(3-fluoro-5-(2-(pyrrolidin-1-yl)ethoxy)phenyl)-1H-pyrrolo[2,3-b]pyridin-2-yl)-5-(pyridin-2-yl)-1H-pyrazolo[3,4-b]pyridine [863];

3-(4-(3-fluoro-5-(2-(pyrrolidin-1-yl)ethoxy)phenyl)-1H-pyrrolo[2,3-b]pyridin-2-yl)-5-(piperidin-4-yl)-1H-pyrazolo[3,4-b]pyridine [864];

3-(4-(3-fluoro-5-(2-(pyrrolidin-1-yl)ethoxy)phenyl)-1H-pyrrolo[2,3-b]pyridin-2-yl)-5-(1,2,3,6-tetrahydropyridin-4-yl)-1H-pyrazolo[3,4-b]pyridine [865];

3-(4-(3-fluoro-5-(2-(pyrrolidin-1-yl)ethoxy)phenyl)-1H-pyrrolo[2,3-b]pyridin-2-yl)-5-(1H-pyrazol -4-yl)-1H-pyrazolo[3,4-b]pyridine [866];

3-(4-(3-fluoro-5-(2-(pyrrolidin-1-yl)ethoxy)phenyl)-1H-pyrrolo[2,3-b]pyridin-2-yl)-5-(1-methyl -1H-pyrazol-4-yl)-1H-pyrazolo[3,4-b]pyridine [867];

5-(1,2-dimethyl-1H-imidazol-5-yl)-3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridine [868];

1-(6-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyrazin-2-yl)azetidin-3-amine [869];

5-(5-(cyclohexyloxy)pyridin-3-yl)-3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridine [870];

3-(4-(3-fluoro-5-(2-(pyrrolidin-1-yl)ethoxy)phenyl)-1H-pyrrolo[2,3-b]pyridin-2-yl)-5-(5-(piperidin-4-yloxy)pyridin-3-yl)-1H-pyrazolo[3,4-b]pyridine [871];

N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)-2-(piperidin-4-yl)acetamide [872];

3-(4-(3-fluoro-5-(2-(pyrrolidin-1-yl)ethoxy)phenyl)-1H-pyrrolo[2,3-b]pyridin-2-yl)-5-(5-(2-(pyrrolidin-1-yl)ethoxy)pyridin-3-yl)-1H-pyrazolo[3,4-b]pyridine [873];

2-((5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)oxy)-N,N-dimethylethan-1-amine [874];

3-(4-(3-fluoro-5-(2-(pyrrolidin-1-yl)ethoxy)phenyl)-1H-pyrrolo[2,3-b]pyridin-2-yl)-5-(5-methoxypyridin-3-yl)-1H-pyrazolo[3,4-b]pyridine [875];

5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-ol [876];

5-(5-(benzyloxy)pyridin-3-yl)-3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridine [877];

2-cyclohexyl-N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)acetamide [878];

3-(4-(3-fluoro-5-(2-(pyrrolidin-1-yl)ethoxy)phenyl)-1H-pyrrolo[2,3-b]pyridin-2-yl)-5-(pyridin-4-yl)-1H-pyrazolo[3,4-b]pyridine [879];

3-(4-(3-fluoro-5-(2-(pyrrolidin-1-yl)ethoxy)phenyl)-1H-pyrrolo[2,3-b]pyridin-2-yl)-5-(pyrazin-2-yl)-1H-pyrazolo[3,4-b]pyridine [880];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)propionamide [881];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)-3-methylbutanamide [882];

3-(2-(5-(5-aminopyridin-3-yl)-1H-pyrazolo[3,4-b]pyridin-3-yl)-1H-pyrrolo[2,3-b]pyridin-4-yl)-5-fluorophenol [883];

3-fluoro-5-(2-(5-(pyridin-3-yl)-1H-pyrazolo[3,4-b]pyridin-3-yl)-1H-pyrrolo[2,3-b]pyridin-4-yl)phenol [884];

3-fluoro-5-(2-(5-(4-methylpyridin-3-yl)-1H-pyrazolo[3,4-b]pyridin-3-yl)-1H-pyrrolo[2,3-b]pyridin-4-yl)phenol [885];

3-(2-(5-(5-((ethylamino)methyl)pyridin-3-yl)-1H-pyrazolo[3,4-b]pyridin-3-yl)-1H-pyrrolo[2,3-b]pyridin-4-yl)-5-fluorophenol [886];

3-(2-(5-(5-(dimethylamino)pyridin-3-yl)-1H-pyrazolo[3,4-b]pyridin-3-yl)-1H-pyrrolo[2,3-b]pyridin-4-yl)-5-fluorophenol [887];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)pivalamide [888];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)isobutyramide [889];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)-2-phenylacetamide [890];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)benzamide [891];

3-fluoro-5-(2-(5-(5-(isopropylamino)pyridin-3-yl)-1H-pyrazolo[3,4-b]pyridin-3-yl)-1H-pyrrolo[2,3-b]pyridin-4-yl)phenol [892];

3-(2-(5-(5-((dimethylamino)methyl)pyridin-3-yl)-1H-pyrazolo[3,4-b]pyridin-3-yl)-1H-pyrrolo[2,3-b]pyridin-4-yl)-5-fluorophenol [893];

3-fluoro-5-(2-(5-(5-(pyrrolidin-1-ylmethyl)pyridin-3-yl)-1H-pyrazolo[3,4-b]pyridin-3-yl)-1H-pyrrolo[2,3-b]pyridin-4-yl)phenol [894];

3-fluoro-5-(2-(5-(5-(piperidin-1-ylmethyl)pyridin-3-yl)-1H-pyrazolo[3,4-b]pyridin-3-yl)-1H-pyrrolo[2,3-b]pyridin-4-yl)phenol [895];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)-3,3-dimethylbutanamide [896];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)butyramide [897];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)pentanamide [898];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)cyclopropane carboxamide [899];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)cyclobutanecarboxamide [900];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)cyclopentanecarboxamide [901];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)cyclohexanecarboxamide [902];

3-(2-(5-(5-((benzylamino)methyl)pyridin-3-yl)-1H-pyrazolo[3,4-b]pyridin-3-yl)-1H-pyrrolo[2,3-b]pyridin-4-yl)-5-fluorophenol [903];

3-(2-(5-(5-(((cyclopentylmethyl)amino)methyl)pyridin-3-yl)-1H-pyrazolo[3,4-b]pyridin-3-yl)-1H-pyrrolo[2,3-b]pyridin-4-yl)-5-fluorophenol [904];

3-(2-(5-(5-((3,3-difluoropyrrolidin-1-yl)methyl)pyridin-3-yl)-1H-pyrazolo[3,4-b]pyridin-3-yl)-1H-pyrrolo[2,3-b]pyridin-4-yl)-5-fluorophenol [905];

3-fluoro-5-(2-(5-(pyrimidin-5-yl)-1H-pyrazolo[3,4-b]pyridin-3-yl)-1H-pyrrolo[2,3-b]pyridin-4-yl)phenol [906];

3-fluoro-5-(2-(5-(pyridin-2-yl)-1H-pyrazolo[3,4-b]pyridin-3-yl)-1H-pyrrolo[2,3-b]pyridin-4-yl)phenol [907];

3-fluoro-5-(2-(5-(piperidin-4-yl)-1H-pyrazolo[3,4-b]pyridin-3-yl)-1H-pyrrolo[2,3-b]pyridin-4-yl)phenol [908];

3-fluoro-5-(2-(5-(1,2,3,6-tetrahydropyridin-4-yl)-1H-pyrazolo[3,4-b]pyridin-3-yl)-1H-pyrrolo[2,3-b]pyridin-4-yl)phenol [909];

3-(2-(5-(1H-pyrazol-4-yl)-1H-pyrazolo[3,4-b]pyridin-3-yl)-1H-pyrrolo[2,3-b]pyridin-4-yl)-5-fluorophenol [910];

3-fluoro-5-(2-(5-(1-methyl-1H-pyrazol-4-yl)-1H-pyrazolo[3,4-b]pyridin-3-yl)-1H-pyrrolo[2,3-b]pyridin-4-yl)phenol [911];

3-(2-(5-(1,2-dimethyl-1H-imidazol-5-yl)-1H-pyrazolo[3,4-b]pyridin-3-yl)-1H-pyrrolo[2,3-b]pyridin-4-yl)-5-fluorophenol [912];

3-(2-(5-(6-(3-aminoazetidin-1-yl)pyrazin-2-yl)-1H-pyrazolo[3,4-b]pyridin-3-yl)-1H-pyrrolo[2,3-b]pyridin-4-yl)-5-fluorophenol [913];

3-(2-(5-(5-(cyclohexyloxy)pyridin-3-yl)-1H-pyrazolo[3,4-b]pyridin-3-yl)-1H-pyrrolo[2,3-b]pyridin-4-yl)-5-fluorophenol [914];

3-fluoro-5-(2-(5-(5-(piperidin-4-yloxy)pyridin-3-yl)-1H-pyrazolo[3,4-b]pyridin-3-yl)-1H-pyrrolo[2,3-b]pyridin-4-yl)phenol [915];

N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)-2-(piperidin-4-yl)acetamide [916];

3-fluoro-5-(2-(5-(5-(2-(pyrrolidin-1-yl)ethoxy)pyridin-3-yl)-1H-pyrazolo[3,4-b]pyridin-3-yl)-1H-pyrrolo[2,3-b]pyridin-4-yl)phenol [917];

3-(2-(5-(5-(2-(dimethylamino)ethoxy)pyridin-3-yl)-1H-pyrazolo[3,4-b]pyridin-3-yl)-1H-pyrrolo[2,3-b]pyridin-4-yl)-5-fluorophenol [918];

3-fluoro-5-(2-(5-(5-methoxypyridin-3-yl)-1H-pyrazolo[3,4-b]pyridin-3-yl)-1H-pyrrolo[2,3-b]pyridin-4-yl)phenol [919];

5-(3-(4-(3-fluoro-5-hydroxyphenyl)-1H-pyrrolo[2,3-b]pyridin-2-yl)-1H-pyrazolo[3,4-b]pyridin-5-yl)pyridin-3-ol [920];

3-(2-(5-(5-(benzyloxy)pyridin-3-yl)-1H-pyrazolo[3,4-b]pyridin-3-yl)-1H-pyrrolo[2,3-b]pyridin-4-yl)-5-fluorophenol [921];

2-cyclohexyl-N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)acetamide [922];

3-fluoro-5-(2-(5-(pyridin-4-yl)-1H-pyrazolo[3,4-b]pyridin-3-yl)-1H-pyrrolo[2,3-b]pyridin-4-yl)phenol [923];

3-fluoro-5-(2-(5-(pyrazin-2-yl)-1H-pyrazolo[3,4-b]pyridin-3-yl)-1H-pyrrolo[2,3-b]pyridin-4-yl)phenol [924];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)propionamide [925];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)-3-methylbutanamide [926];

5-(3-(4-(3-fluoro-5-methoxyphenyl)-1H-pyrrolo[2,3-b]pyridin-2-yl)-1H-pyrazolo[3,4-b]pyridin-5-yl)pyridin-3-amine [927];

3-(4-(3-fluoro-5-methoxyphenyl)-1H-pyrrolo[2,3-b]pyridin-2-yl)-5-(pyridin-3-yl)-1H-pyrazolo[3,4-b]pyridine [928];

3-(4-(3-fluoro-5-methoxyphenyl)-1H-pyrrolo[2,3-b]pyridin-2-yl)-5-(4-methylpyridin-3-yl)-1H-pyrazolo[3,4-b]pyridine [929];

N-((5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)methyl)ethanamine [930];

5-(3-(4-(3-fluoro-5-methoxyphenyl)-1H-pyrrolo[2,3-b]pyridin-2-yl)-1H-pyrazolo[3,4-b]pyridin-5-yl)-N,N-dimethylpyridin-3-amine [931];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)pival amide [932];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)isobutyramide [933];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)-2-phenylacetamide [934];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)benzamide [935];

5-(3-(4-(3-fluoro-5-methoxyphenyl)-1H-pyrrolo[2,3-b]pyridin-2-yl)-1H-pyrazolo[3,4-b]pyridin-5-yl)-N-isopropylpyridin-3-amine [936];

1-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)-N,N-dimethylmethanamine [937];

3-(4-(3-fluoro-5-methoxyphenyl)-1H-pyrrolo[2,3-b]pyridin-2-yl)-5-(5-(pyrrolidin-1-ylmethyl)pyridin-3-yl)-1H-pyrazolo[3,4-b]pyridine [938];

3-(4-(3-fluoro-5-methoxyphenyl)-1H-pyrrolo[2,3-b]pyridin-2-yl)-5-(5-(piperidin-1-ylmethyl)pyridin-3-yl)-1H-pyrazolo[3,4-b]pyridine [939];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)-3,3-dimethylbutanamide [940];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)butyramide [941];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)pentanamide [942];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)cyclopropanecarboxamide [943];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)cyclobutanecarboxamide [944];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)cyclopentanecarboxamide [945];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)cyclohexanecarboxamide [946];

N-benzyl-1-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)methanamine [947];

1-cyclopentyl-N-((5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)methyl)methanamine [948];

5-(5-((3,3-difluoropyrrolidin-1-yl)methyl)pyridin-3-yl)-3-(4-(3-fluoro-5-methoxyphenyl)-1H-pyrrolo[2,3-b]pyridin-2-yl)-1H-pyrazolo[3,4-b]pyridine [949];

3-(4-(3-fluoro-5-methoxyphenyl)-1H-pyrrolo[2,3-b]pyridin-2-yl)-5-(pyrimidin-5-yl)-1H-pyrazolo[3,4-b]pyridine [950];

3-(4-(3-fluoro-5-methoxyphenyl)-1H-pyrrolo[2,3-b]pyridin-2-yl)-5-(pyridin-2-yl)-1H-pyrazolo[3,4-b]pyridine [951];

3-(4-(3-fluoro-5-methoxyphenyl)-1H-pyrrolo[2,3-b]pyridin-2-yl)-5-(piperidin-4-yl)-1H-pyrazolo[3,4-b]pyridine [952];

3-(4-(3-fluoro-5-methoxyphenyl)-1H-pyrrolo[2,3-b]pyridin-2-yl)-5-(1,2,3,6-tetrahydropyridin-4-yl)-1H-pyrazolo[3,4-b]pyridine [953];

3-(4-(3-fluoro-5-methoxyphenyl)-1H-pyrrolo[2,3-b]pyridin-2-yl)-5-(1H-pyrazol-4-yl)-1H-pyrazolo[3,4-b]pyridine [954];

3-(4-(3-fluoro-5-methoxyphenyl)-1H-pyrrolo[2,3-b]pyridin-2-yl)-5-(1-methyl-1H-pyrazol-4-yl)-1H-pyrazolo[3,4-b]pyridine [955];

5-(1,2-dimethyl-1H-imidazol-5-yl)-3-(4-(3-fluoro-5-methoxyphenyl)-1H-pyrrolo[2,3-b]pyridin-2-yl)-1H-pyrazolo[3,4-b]pyridine [956];

1-(6-(3-(4-(3-fluoro-5-methoxyphenyl)-1H-pyrrolo[2,3-b]pyridin-2-yl)-1H-pyrazolo[3,4-b]pyridin-5-yl)pyrazin-2-yl)azetidin-3-amine [957];

5-(5-(cyclohexyloxy)pyridin-3-yl)-3-(4-(3-fluoro-5-methoxyphenyl)-1H-pyrrolo[2,3-b]pyridin-2-yl)-1H-pyrazolo[3,4-b]pyridine [958];

3-(4-(3-fluoro-5-methoxyphenyl)-1H-pyrrolo[2,3-b]pyridin-2-yl)-5-(5-(piperidin-4-yloxy)pyridin-3-yl)-1H-pyrazolo[3,4-b]pyridine [959];

N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)-2-(piperidin-4-yl)acetamide [960];

3-(4-(3-fluoro-5-methoxyphenyl)-1H-pyrrolo[2,3-b]pyridin-2-yl)-5-(5-(2-(pyrrolidin-1-yl)ethoxy)pyridin-3-yl)-1H-pyrrolo[3,4-b]pyridine [961];

2-((5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)oxy)-N,N-dimethylethan-1-amine [962];

3-(4-(3-fluoro-5-methoxyphenyl)-1H-pyrrolo[2,3-b]pyridin-2-yl)-5-(5-methoxypyridin-3-yl)-1H-pyrazolo[3,4-b]pyridine [963];

5-(3-(4-(3-fluoro-5-methoxyphenyl)-1H-pyrrolo[2,3-b]pyridin-2-yl)-1H-pyrazolo[3,4-b]pyridin-5-yl)pyridin-3-ol [964];

5-(5-(benzyloxy)pyridin-3-yl)-3-(4-(3-fluoro-5-methoxyphenyl)-1H-pyrrolo[2,3-b]pyridin-2-yl)-1H-pyrazolo[3,4-b]pyridine [965];

2-cyclohexyl-N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)acetamide [966];

3-(4-(3-fluoro-5-methoxyphenyl)-1H-pyrrolo[2,3-b]pyridin-2-yl)-5-(pyridin-4-yl)-1H-pyrazolo[3,4-b]pyridine [967];

3-(4-(3-fluoro-5-methoxyphenyl)-1H-pyrrolo[2,3-b]pyridin-2-yl)-5-(pyrazin-2-yl)-1H-pyrazolo[3,4-b]pyridine [968];

2-(dimethylamino)-N-(5-(3-(4-(3-fluorophenyl)-1H-pyrrolo[2,3-b]pyridin-2-yl)-1H-pyrazolo[3,4-b]pyridin-5-yl)pyridin-3-yl)acetamide [969];

2-(dimethylamino)-N-(5-(3-(4-(4-fluorophenyl)-1H-pyrrolo[2,3-b]pyridin-2-yl)-1H-pyrazolo[3,4-b]pyridin-5-yl)pyridin-3-yl)acetamide [970];

2-(dimethylamino)-N-(5-(3-(4-(2-fluorophenyl)-1H-pyrrolo[2,3-b]pyridin-2-yl)-1H-pyrazolo[3,4-b]pyridin-5-yl)pyridin-3-yl)acetamide [971];

2-(dimethylamino)-N-(5-(3-(4-(pyridin-3-yl)-1H-pyrrolo[2,3-b]pyridin-2-yl)-1H-pyrazolo[3,4-b]pyridin-5-yl)pyridin-3-yl)acetamide [972];

2-(dimethylamino)-N-(5-(3-(4-(pyridin-4-yl)-1H-pyrrolo[2,3-b]pyridin-2-yl)-1H-pyrazolo[3,4-b]pyridin-5-yl)pyridin-3-yl)acetamide [973];

2-(dimethylamino)-N-(5-(3-(4-(pyridin-2-yl)-1H-pyrrolo[2,3-b]pyridin-2-yl)-1H-pyrazolo[3,4-b]pyridin-5-yl)pyridin-3-yl)acetamide [974];

2-(dimethylamino)-N-(5-(3-(4-(piperidin-1-yl)-1H-pyrrolo[2,3-b]pyridin-2-yl)-1H-pyrazolo[3,4-b]pyridin-5-yl)pyridin-3-yl)acetamide [975];

2-(dimethylamino)-N-(5-(3-(4-(4-methyl-1H-imidazol-1-yl)-1H-pyrrolo[2,3-b]pyridin-2-yl)-1H-pyrazolo[3,4-b]pyridin-5-yl)pyridin-3-yl)acetamide [976];

2-(dimethylamino)-N-(5-(3-(4-(4-methylpiperazin-1-yl)-1H-pyrrolo[2,3-b]pyridin-2-yl)-1H-pyrazolo[3,4-b]pyridin-5-yl)pyridin-3-yl)acetamide [977];

N-(5-(3-(1H-pyrrolo[2,3-b]pyridin-2-yl)-1H-pyrazolo[3,4-b]pyridin-5-yl)pyridin-3-yl)-2-(dimethylamino)acetamide [978];

2-(dimethylamino)-N-(5-(3-(4-(thiophen-3-yl)-1H-pyrrolo[2,3-b]pyridin-2-yl)-1H-pyrazolo[3,4-b]pyridin-5-yl)pyridin-3-yl)acetamide [979];

2-(dimethylamino)-N-(5-(3-(4-(furan-3-yl)-1H-pyrrolo[2,3-b]pyridin-2-yl)-1H-pyrazolo[3,4-b]pyridin-5-yl)pyridin-3-yl)acetamide [980];

2-(dimethylamino)-N-(5-(3-(4-(thiophen-2-yl)-1H-pyrrolo[2,3-b]pyridin-2-yl)-1H-pyrazolo[3,4-b]pyridin-5-yl)pyridin-3-yl)acetamide [981];

2-(dimethylamino)-N-(5-(3-(4-(5-fluorothiophen-2-yl)-1H-pyrrolo[2,3-b]pyridin-2-yl)-1H-pyrazolo[3,4-b]pyridin-5-yl)pyridin-3-yl)acetamide [982];

2-(dimethylamino)-N-(5-(3-(4-(5-methylthiophen-2-yl)-1H-pyrrolo[2,3-b]pyridin-2-yl)-1H-pyrazolo[3,4-b]pyridin-5-yl)pyridin-3-yl)acetamide [983];

N-(5-(3-(4-(5-acetylthiophen-2-yl)-1H-pyrrolo[2,3-b]pyridin-2-yl)-1H-pyrazolo[3,4-b]pyridin-5-yl)pyridin-3-yl)-2-(dimethylamino)acetamide [984];

2-(dimethylamino)-N-(5-(3-(4-(3-fluoro-5-(methylsulfonamidomethyl)phenyl)-1H-pyrrolo[2,3-b]pyridin-2-yl)-1H-pyrazolo[3,4-b]pyridin-5-yl)pyridin-3-yl)acetamide [985];

2-(dimethylamino)-N-(5-(3-(4-(3-((2-(dimethylamino)ethyl)amino)-5-fluorophenyl)-1H-pyrrolo[2,3-b]pyridin-2-yl)-1H-pyrazolo[3,4-b]pyridin-5-yl)pyridin-3-yl)acetamide [986];

2-(dimethylamino)-N-(5-(3-(4-(3-(2-(dimethylamino)ethoxy)-5-fluorophenyl)-1H-pyrrolo[2,3-b]pyridin-2-yl)-1H-pyrazolo[3,4-b]pyridin-5-yl)pyridin-3-yl)acetamide [987];

2-(dimethylamino)-N-(5-(3-(4-(3-fluoro-5-(2-(pyrrolidin-1-yl)ethoxy)phenyl)-1H-pyrrolo[2,3-b]pyridin-2-yl)-1H-pyrazolo[3,4-b]pyridin-5-yl)pyridin-3-yl)acetamide [988];

2-(dimethylamino)-N-(5-(3-(4-(3-fluoro-5-hydroxyphenyl)-1H-pyrrolo[2,3-b]pyridin-2-yl)-1H-pyrazolo[3,4-b]pyridin-5-yl)pyridin-3-yl)acetamide [989]; and 2-(dimethylamino)-N-(5-(3-(4-(3-fluoro-5-methoxyphenyl)-1H-pyrrolo[2,3-b]pyridin-2-yl)-1H-pyrazolo[3,4-b]pyridin-5-yl)pyridin-3-yl)acetamide [990]; or a pharmaceutically acceptable salt thereof.

22. A pharmaceutical composition comprising a therapeutically effective amount of a compound according to claim 1, or a pharmaceutically acceptable salt thereof, and a pharmaceutically acceptable excipient.

23. A method of treating or ameliorating in a patient a disorder or disease selected from the group consisting of: colon cancer, colorectal cancer, pulmonary fibrosis, degenerative disc disease, and osteoarthritis, the method comprising administering to the patient a therapeutically effective amount of a compound according to claim 1, or a pharmaceutically acceptable salt thereof.

24. A method of claim 23, wherein the disorder or disease is colon cancer.

25. A method of claim 23, wherein the disorder or disease is colorectal cancer.

26. A method of claim 23, wherein the disorder or disease is pulmonary fibrosis.

27. A method of claim 26, wherein the pulmonary fibrosis is idiopathic pulmonary fibrosis (IPF).

28. A method of claim 23, wherein the disorder or disease is degenerative disc disease.

29. A method of claim 23, wherein the disorder or disease is osteoarthritis.

30. The method of claim 23, wherein the patient is a human.

* * * * *

UNITED STATES PATENT AND TRADEMARK OFFICE
CERTIFICATE OF CORRECTION

PATENT NO. : 10,285,983 B2
APPLICATION NO. : 15/749727
DATED : May 14, 2019
INVENTOR(S) : Sunil Kumar KC et al.

It is certified that error appears in the above-identified patent and that said Letters Patent is hereby corrected as shown below:

In the Claims

Column 367, Line 32, in Claim 1, delete "$R^{11}$ ," and insert -- $R^{11}$, --, therefor.

Column 367, Line 33, in Claim 1, delete "$R^{11}$ ," and insert -- $R^{11}$, --, therefor.

Column 367, Line 35, in Claim 1, delete "—C1-4" and insert -- —(C1-4 --, therefor.

Column 367, Line 41, in Claim 1, delete "$R^{13}$ ," and insert -- $R^{13}$, --, therefor.

Column 368, Line 2, in Claim 1, delete "$(C_{2-4}$" and insert -- —$(C_{2-4}$ --, therefor.

Column 368, Line 42, in Claim 1, delete "$(C_{2-4}$" and insert -- —$(C_{2-4}$ --, therefor.

Column 369, Line 45, in Claim 14, delete "$R^{10}$ ." and insert -- $R^{10}$. --, therefor.

Column 372, Line 59, in Claim 21, delete "1-(5-(344-" and insert -- 1-(5-(3-(4- --, therefor.

Column 373, Line 25, in Claim 21, delete "1-(5-(344-" and insert -- 1-(5-(3-(4- --, therefor.

Column 378, Line 11, in Claim 21, delete "[3 pyridin" and insert -- [3,4-b]pyridin --, therefor.

Column 378, Line 14, in Claim 21, delete "[3 pyridin" and insert -- [3,4-b]pyridin --, therefor.

Column 378, Line 24, in Claim 21, delete "[3 pyridin" and insert -- [3,4-b]pyridin --, therefor.

Column 378, Line 30, in Claim 21, delete "[3 pyridin" and insert -- [3,4-b]pyridin --, therefor.

Column 378, Line 45, in Claim 21, delete "[3 pyridin" and insert -- [3,4-b]pyridin --, therefor.

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,285,983 B2

Column 378, Line 48, in Claim 21, delete "[3 pyridin" and insert -- [3,4-b]pyridin --, therefor.

Column 379, Line 47, in Claim 21, delete "methylpipe razin" and insert -- methylpiperazin --, therefor.

Column 379, Line 56, in Claim 21, delete "methylpip erazin" and insert -- methylpiperazin --, therefor.

Column 380, Line 51, in Claim 21, delete "methylpip erazin" and insert -- methylpiperazin --, therefor.

Column 381, Line 18, in Claim 21, delete "N-i sopropylpyridin" and insert -- N-isopropylpyridin --, therefor.

Column 381, Line 19, in Claim 21, delete "145-(3-" and insert -- 1-(5-(3- --, therefor.

Column 381, Line 49, in Claim 21, delete "145-(3-" and insert -- 1-(5-(3- --, therefor.

Column 381, Line 52, in Claim 21, delete "145-(3-" and insert -- 1-(5-(3- --, therefor.

Column 383, Line 40, in Claim 21, delete "N-i sopropylpyridin" and insert -- N-isopropylpyridin --, therefor.

Column 387, Line 24, in Claim 21, delete "[3,4-1)]" and insert -- [3,4-b] --, therefor.

Column 387, Line 33, in Claim 21, delete "[3,4-1)]" and insert -- [3,4-b] --, therefor.

Column 388, Line 42, in Claim 21, delete "[3 pyridin" and insert -- [3,4-b]pyridin --, therefor.

Column 389, Approximately Line 12, in Claim 21, delete "[3 pyridin" and insert -- [3,4-b]pyridin --, therefor.

Column 389, Approximately Line 15, in Claim 21, delete "[3 pyridin" and insert -- [3,4-b]pyridin --, therefor.

Column 397, Approximately Line 10, in Claim 21, delete "[3 pyridin" and insert -- [3,4-b]pyridin --, therefor.

Column 398, Line 13, in Claim 21, delete "methylpipe razin" and insert -- methylpiperazin --, therefor.

Column 404, Line 40, in Claim 21, delete "pyridin-3-o1" and insert -- pyridin-3-ol --, therefor.

Column 404, Line 52, in Claim 21, delete "N-(5-(3-(44342-" and insert -- N-(5-(3-(4-(3-(2- --, therefor.

Column 404, Line 55, in Claim 21, delete "N-(5-(3-(44342-" and insert -- N-(5-(3-(4-(3-(2- --, therefor.

Column 404, Line 55, in Claim 21, delete "N-(5-(3-(44342-" and insert -- N-(5-(3-(4-(3-(2- --, therefor.

Column 406, Approximately Line 33, in Claim 21, delete "14643-" and insert -- 1-(6-(3- --, therefor.

Column 407, Line 43, in Claim 21, delete "N-i sopropylpyridin" and insert -- N-isopropylpyridin --, therefor.

Column 410, Approximately Line 9, in Claim 21, delete "cyclopropane carboxamide" and insert -- cyclopropanecarboxamide --, therefor.

Column 411, Line 40, in Claim 21, delete "pival amide" and insert -- pivalamide --, therefor.